United States Patent
Macherla et al.

(10) Patent No.: US 10,472,395 B2
(45) Date of Patent: Nov. 12, 2019

(54) CYCLIC PEPTIDE ANALOGS AND CONJUGATES THEREOF

(71) Applicant: Sirenas LLC, San Diego, CA (US)

(72) Inventors: Venkat Rami Reddy Macherla, San Diego, CA (US); Alexander Wayne Schammel, San Diego, CA (US); Ippei Usui, San Diego, CA (US); Elizabeth Paige Stout, San Diego, CA (US); Jacob Neal Beverage, La Jolla, CA (US); Bryan Junn Lee, San Diego, CA (US); Steven Bruce Cohen, San Diego, CA (US)

(73) Assignee: Sirenas LLC, San Diego, CA (US)

( * ) Notice: Subject to any disclaimer, the term of this patent is extended or adjusted under 35 U.S.C. 154(b) by 31 days.

(21) Appl. No.: 15/060,479

(22) Filed: Mar. 3, 2016

(65) Prior Publication Data

US 2017/0015710 A1    Jan. 19, 2017

Related U.S. Application Data

(60) Provisional application No. 62/213,588, filed on Sep. 2, 2015, provisional application No. 62/128,966, filed on Mar. 5, 2015.

(51) Int. Cl.
*C07K 11/02* (2006.01)
*A61K 38/15* (2006.01)
*C07K 16/32* (2006.01)

(52) U.S. Cl.
CPC .............. *C07K 11/02* (2013.01); *A61K 38/15* (2013.01); *C07K 16/32* (2013.01); *C07K 2317/24* (2013.01); *C07K 2317/76* (2013.01)

(58) Field of Classification Search
CPC combination set(s) only.
See application file for complete search history.

(56) References Cited

U.S. PATENT DOCUMENTS

| | | |
|---|---|---|
| 4,542,225 A | 9/1985 | Blattler |
| 4,569,789 A | 2/1986 | Blattler et al. |
| 4,625,014 A | 11/1986 | Senter et al. |
| 4,764,368 A | 8/1988 | Blattler et al. |
| 4,816,567 A | 3/1989 | Cabilly et al. |
| 5,122,368 A | 6/1992 | Greenfield et al. |
| 5,208,020 A | 5/1993 | Chari et al. |
| 5,595,756 A * | 1/1997 | Bally .................... A61K 9/1272 264/4.1 |
| 5,622,929 A | 4/1997 | Willner et al. |
| 5,824,805 A | 10/1998 | King et al. |
| 6,214,345 B1 | 4/2001 | Firestone et al. |
| 2003/0083263 A1 | 5/2003 | Doronina et al. |
| 2005/0009751 A1 | 1/2005 | Senter et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |

FOREIGN PATENT DOCUMENTS

| | | |
|---|---|---|
| JP | 2003-64052 A | 3/2003 |
| JP | 2003-64097 A2 | 3/2003 |
| JP | 2008-266282 A | 11/2008 |
| JP | 2010-174004 A | 8/2010 |
| JP | 2010-174005 A | 8/2010 |
| WO | WO-94/11026 A2 | 5/1994 |
| WO | WO-2004/010957 A2 | 2/2004 |
| WO | WO-2013/072813 A2 | 5/2013 |
| WO | WO-2015/095755 A1 | 6/2015 |

OTHER PUBLICATIONS

Sato et al., Chemistry & Biology, 2011, 18, 131-139.*
Cellular and Molecular Basis of Cancer—Merck Manual, pp. 1-5, from http://www.merckmanuals.com/professional/print/hematology_and_oncology/overview_of . . . .*
Sporn et at., "Chemoprevention of Cancer", Carcinogenesis, vol. 21 (2000), 525-530.*
Cancer Drug Design and Discovery, Neidle, Stephen, ed. (Elsevier/Academic Press, 2008) p. 427-431.*
Auerbach et al., Cancer and Metastasis Reviews, 2000, 19, pp. 167-172.*
Gura T, Science, 1997, 278(5340): 1041-1042.*
International Search Report and Written Opinion dated Jul. 19, 2016 for PCT/US2016/020763, filed on Mar. 3, 2016, seventeen pages.
Aboud-Pirak et al. (1989) "Cytotoxic Activity of a Daunorubicin or Vindesin Conjugated to a Monoclonal Antibody on Cultured MCF-7 Breast Carcinoma Cells," *Biochem. Pharmacol.* 38(4):641-648.
Blättler et al. (1985). "New Heterobifunctional Protein Cross-Linking Reagent That Forms an Acid-Labile Link," *Biochemistry* 24:1517-1524.
Clackson et al. (1991). "Making Antibody Fragments Using Phage Display Libraries," *Nature* 352:624-628.
De Groot et al. (2001). "Elongated Multiple Electronic Cascade and Cyclization Spacer Systems in Activatible Anticancer Prodrugs for Enhanced Drug Release," *J. Org. Chem* 66:8815-8830.
Dubowchik et al. (1999). "Receptor-Mediated and Enzyme-Dependent Targeting of Cytotoxic Anticancer Drugs," *Pharm. Therapeutics* 83:67-123.
Finniss et al. (2014). "A Versatile Acid-Labile Linker for Antibody-Drug Conjugates," *Medicinal Chemistry Communications* 5:1355-1358.
Han et al. (2006). "Aurilides B and C, Cancer Cell Toxins from a Papua New Guinea Collection of the Marine Cyanobacterium *Lyngbya majuscula,*" *J. Nat. Prod.* 69:572-575.
Hermanson, Greg T. (1996) "Introduction to Biconjugation," Chapter 1 in *Bioconjugate Techniques*, Academic Press, San Diego, CA, 125 pages.
Karton-Llfshin et al. (2012). "Exponential diagnostic signal amplification via dendritic chain reaction: the dendritic effect of a self-immolative amplifier component," *New J. Chem* 36:386-393.

(Continued)

*Primary Examiner* — James H Alstrum-Acevedo
*Assistant Examiner* — Kaipeen E Yang
(74) *Attorney, Agent, or Firm* — Morrison & Foerster LLP

(57) ABSTRACT

Provided are cyclic peptide analogs, conjugates comprising such compounds, and pharmaceutical compositions comprising such compounds and conjugates, and methods of treating cancer with such compounds and conjugates.

30 Claims, 59 Drawing Sheets

(56) References Cited

OTHER PUBLICATIONS

Kern et al. (2016). "Discovery of Pyrophosphate Diesters as Tunable, Soluble, and Bioorthogonal Linkers for Site-specific Antibody-Drug Conjugates," *J. Am. Chem. Soc.* 138:1430-1445.

Kohler et al. (1975). "Continuous Cultures of Fused Cells Secreting Antibody of Predefined Specificity," *Nature* 256:495-497.

Laguzza et al. (1989). "New Antitumor Monoclonal Antibody-Vinca Conjugates LY203725 and Related Compounds: Design, Preparation, and Representative in Vivo Activity," *J. Med. Chem.* 32:548-555.

Marks et al. (1991). "By-passing Immunization, Human Antibodies from V-gene Libraries Displayed on Phage," *J. Mol. Biol.* 222:581-597.

Nakao et al. (2004). "Kulokekahilide-2, a Cytotoxic Depsipeptide from a Cephalaspidean Mollusk *Philinopsis speciosa*," *J. Nat. Prod.* 67:1332-1340.

Neville et al. (1989). "Enhancement of Immunotoxin Efficacy by Acid-cleavable Cross-linking Agents Utilizing Diphtheria Toxin and Toxin Mutants," *J Biol. Chem.* 264(25):14653-14661.

Queen et al. (1989). "A Humanized Antibody that Binds to the Interleukin 2 Receptor," *Proc. Nat'l Acad. Sci. USA* 86:10029-10033.

Senter et al. (1985). "Novel Photocleavable Protein Crosslinking Reagents and their Use in the Preparation of Antibody-Toxin Conjugates," *Photochemistry and Photobiology* 42(3):231-237.

Suenaga et al. (2008). "Synthesis and Cytotoxicity of Aurilide Analogs," *Bioorganic & Medicinal Chemistry Letters* 18: 3902-3905.

Takada et al. (2012). "The Total Synthesis and Structure-Activity Relationships of a Highly Cytotoxic Depsipeptide Kulokekahilide-2 and its Analogs," *Tetrahedron* 68:659-669.

Tan, Lik Tong (2010). "Filamentous Tropical Marine Cyanobacteria: a Rich Source of Natural Products for Anticancer Drug Discovery," J. Appl. Phycol 22:659-676.

Tripathi et al. (2010). "Lagunamides A and B: Cytotoxic and Antimalarial Cyclodepsipeptides from the Marine Cyanobacterium *Lyngbya majuscula*," *J. Nat. Prod.* 73:1810-1814.

Tripathi et al. (2011). "Lagunamide C, a Cytotoxic Cyclodepsipeptide from the Marine Cyanobacterium Lyngbya Majuscula," *Phytochemistry* 72: 2369-2375.

Trouet et al. (1982). "A Covalent Linkage Between Daunorubicin and Proteins that is Stable in Serum and Reversible by Lysosomal Hydrolases, as Required for a Lysosomotropic Drug-carrier Conjugate: In vitro and in vivo studies," *Proc. Nat'l. Acad. Sci.* 79:626-629.

Umehara et al. (2012). "Structure-related cytotoxic activity of derivatives from kulokekahilide-2, a cyclodepsipeptide in Hawaiian marine mollusk," *Bioorganic & Medicinal Chemistry Letters* 22:7422-7425.

Umehara et al. (2013). "Stereochemical analysis and cytotoxicity of kulokekahilide-2 and its analogues," *Tetrahedron* 69:3045-3053.

Vitetta et al. (1987). "Redesigning Nature's Poisons to Create Anti-Tumor Reagents," *Science* 238:1098; 11 pages.

Widdison et al. (2015). "Development of Anilino-Maytansinoid ADCs that Efficiently Release Cytotoxic Metabolites in Cancer Cells and Induce High Levels of Bystander Killing," *Bioconjugate Chem* 26:2261-2278.

Williams et al. (2003). "The Structure of Palau'amide, a Potent Cytotoxin from a Species of the Marine Cyanobacterium *Lyngbya*," *J. Nat. Prod.* 66:1545-1549.

International Preliminary Report on Patentability dated Sep. 14, 2017 for PCT Application No. PCT/US2016/020763 filed on Mar. 3, 2016, twelve pages.

Badescu, G. et al. (May 3, 2014). "Bridging Disulfides for Stable and Defined Antibody Drug Conjugates," *Bioconjugate Chem.* 25(6):1124-1136.

Bryant, P. et al. (Apr. 20, 2015). "In Vitro and In Vivo Evaluation of Cysteine Rebridged Trastuzumab—MMAE Antibody Drug Conjugates with Defined Drug-to-Antibody Ratios," *Mol. Pharmaceuticals* 12(6):1872-1879.

Doronina, S.O. et al. (2008; e-pub. Sep. 20, 2008). "Novel Peptide Linkers for Highly Potent Antibody—Auristatin Conjugate," *Bioconjugate Chem.* 19(10):1960-1963.

Seiche, W. et al. (Oct. 2005). "Bidentate Ligands by Self-Assembly through Hydrogen Bonding: A General Room Temperature/Ambient Pressure Regioselective Hydroformylation of Terminal Alkenes," *Advanced Synthesis & Catalysis* 347:1488-1494.

Wang, G. et al. (2008; e-pub. Jul. 2, 2008). "Efficient and Selective Syntheses of (all-E)- and (6E,10Z)-2'-O-Methylmyxalamides D via Pd-Catalyzed Alkenylation—Carbonyl Olefination Synergy," *Organic Letters* 10(15):3223-3226.

International Search Report and Written Opinion dated Nov. 17, 2017, for PCT Application No. PCT/US2017/049764, filed on Aug. 31, 2017, 14 pages.

International Preliminary Report on Patentability dated Mar. 14, 2019 for PCT Application No. PCT/US2017/049764, filed on Aug. 31, 2017, 8 pages.

\* cited by examiner

CYCLIC PEPTIDE ANALOGS AND CONJUGATES THEREOF

CROSS REFERENCE TO RELATED APPLICATIONS

This application claims priority to U.S. Provisional Patent Application No. 62/213,588 filed Sep. 2, 2015 and U.S. Provisional Patent Application No. 62/128,966, filed Mar. 5, 2015, the disclosures of which are incorporated by reference herein in their entireties.

FIELD

Provided herein are cyclic peptide analogs, pharmaceutical compositions comprising such compounds, and methods of treating cancer with such compounds.

BACKGROUND

Cancer is a serious and debilitating disease brought on by abnormal and unchecked cell division in a patient. Current treatment strategies include chemotherapy, radiation therapy, and surgery. These treatment options may be singular treatments or combined for a more effective regimen. Unfortunately, many patients do not respond well to current chemotherapeutic regimens or develop resistance after prolonged treatment. In addition, for many chemotherapeutics, there is a maximal lifetime level of drug that a patient may be administered. In this case, new drugs must be tried. Thus, there is a need for development of new and varied chemotherapeutic compounds to assist in the treatment of cancer.

An important aspect of cancer, as opposed to infection caused by an exogenous pathogen for example, is that the disease is caused by cells already existing in the patient. These cells are similar in many ways to healthy tissue and reside among healthy cells in the patient. Thus, chemotherapeutic compounds, even if directly administered to a tumor, run the risk of entering and affecting healthy tissue in addition to cancerous tissue. This non-specific delivery can cause systemic and serious side effects in a patient including nausea, weakness, bleeding problems, infection, and hair loss. To avoid these systemic effects, chemotherapeutic compounds may be conjugated to a targeting molecule that assists with the specific and direct delivery of a chemotherapeutic compound to cancerous tissue only, preventing delivery to healthy tissue. These drugs may be associated with fewer and less severe side effects than traditional therapy, and so there is a need to develop chemotherapeutics that are effective in isolation, but are also suitable for conjugation to a targeting molecule.

Various types of agents have been described for use in treatment of cancer. Many of these compounds pose challenges. For instance, many compounds described for use in treatment of cancer have problems associated with toxicity. Some compounds present challenges related to their chemical synthesis. There are also challenges associated with finding appropriate permutations of therapeutic agents for combination therapy. Furthermore, only a minority of agents identified for use in treatment of cancer are suitable for conjugation to a targeting moiety. Accordingly, there remains a need for new compounds and conjugates for use in treatment of cancer.

SUMMARY

In one aspect, provided is a compound of Formula (I):

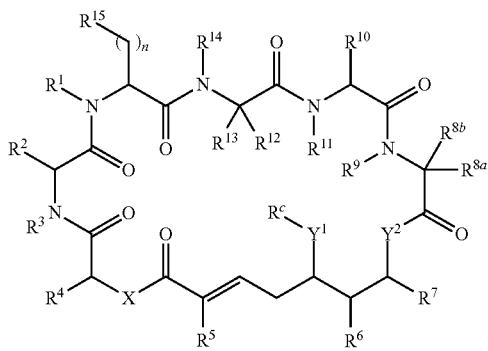

or a salt thereof, wherein
$R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;
X is —N($R^d$)— or —O—;
$Y^1$ is —N($R^d$)—, —O—, or —S—;
$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl, or —C(O)$R^e$;
or, alternatively, the (—$Y^1$—$R^c$) group is H or halo;
$Y^2$ is —N($R^d$)—, —O—, or —S—;
each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —$OR^d$, —$NR^d R^d$, or —$SR^d$;

provided that the compound is not a compound of Table 1x, or a salt thereof.

In another aspect, provided is a compound of Formula (II):

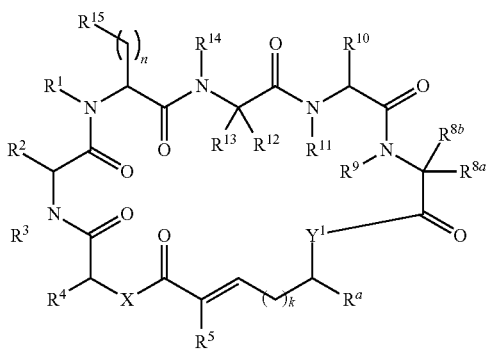

and salts thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

X is —$N(R^d)$— or —O—;

$Y^1$ is —$N(R^d)$—, —O—, or —S—;

k is 1, 2, or 3;

$R^a$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl; or $R^a$ is

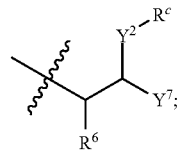

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$Y^2$ is —$N(R^d)$—, —O—, or —S—;

$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl or —$C(O)R^e$;

or, alternatively, the (—$Y^2$—$R^c$) group is halo;

each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —$OR^d$, —$NR^d R^d$, or —$SR^d$;

provided that the compound is not a compound of Table 1y, or a salt thereof.

In another aspect, provided is a compound of Formula (III):

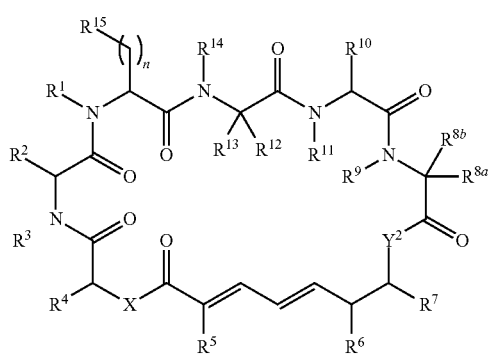

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

X is —N($R^d$)— or —O—;

$Y^2$ is —N($R^d$)—, —O—, or —S—; and each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl.

In another aspect, provided is a compound selected from the group consisting of compounds of Table 1, or a salt thereof.

In another aspect, provided is a conjugate comprising a compound of Formula (I), (II), or (III), or a salt thereof, bonded to a ligand, wherein the ligand is a polypeptide, a nucleic acid, or a targeting moiety. In some embodiments, compound of Formula (I), (II), or (III), or a salt thereof, is bonded to the ligand via a linker. In some embodiments, the linker is a cleavable linker. In some embodiments, the linker is a non-cleavable linker. In some embodiments, the ligand is an antibody.

In another aspect, provided is a conjugate comprising kulo-2 bonded to a ligand, wherein the ligand is a polypeptide, a nucleic acid, or a targeting moiety. In some embodiments, the kulo-2 is bonded to the ligand via a linker. In some embodiments, the linker is a cleavable linker. In some embodiments, the linker is a non-cleavable linker. In some embodiments, the ligand is an antibody.

In another aspect, provided is a conjugate comprising aurilide, aurilide B, or aurilide C bonded to a ligand, wherein the ligand is a polypeptide, a nucleic acid, or a targeting moiety. In some embodiments, the aurilide, aurilide B, or aurilide C is bonded to the ligand via a linker. In some embodiments, the linker is a cleavable linker. In some embodiments, the linker is a non-cleavable linker. In some embodiments, the ligand is an antibody.

In another aspect, provided is a pharmaceutical composition comprising a compound or conjugate as described herein, or a pharmaceutically acceptable salt thereof, and a pharmaceutically acceptable carrier.

In another aspect, provided is a method of treating cancer in an individual in need thereof comprising administering to the individual a therapeutically effective amount of a compound or conjugate described herein, or a pharmaceutically acceptable salt thereof.

In another aspect, provided is a kit comprising a compound or conjugate described herein and instructions for use in treatment of cancer in an individual in need thereof.

DETAILED DESCRIPTION

Definitions

Figure 1:
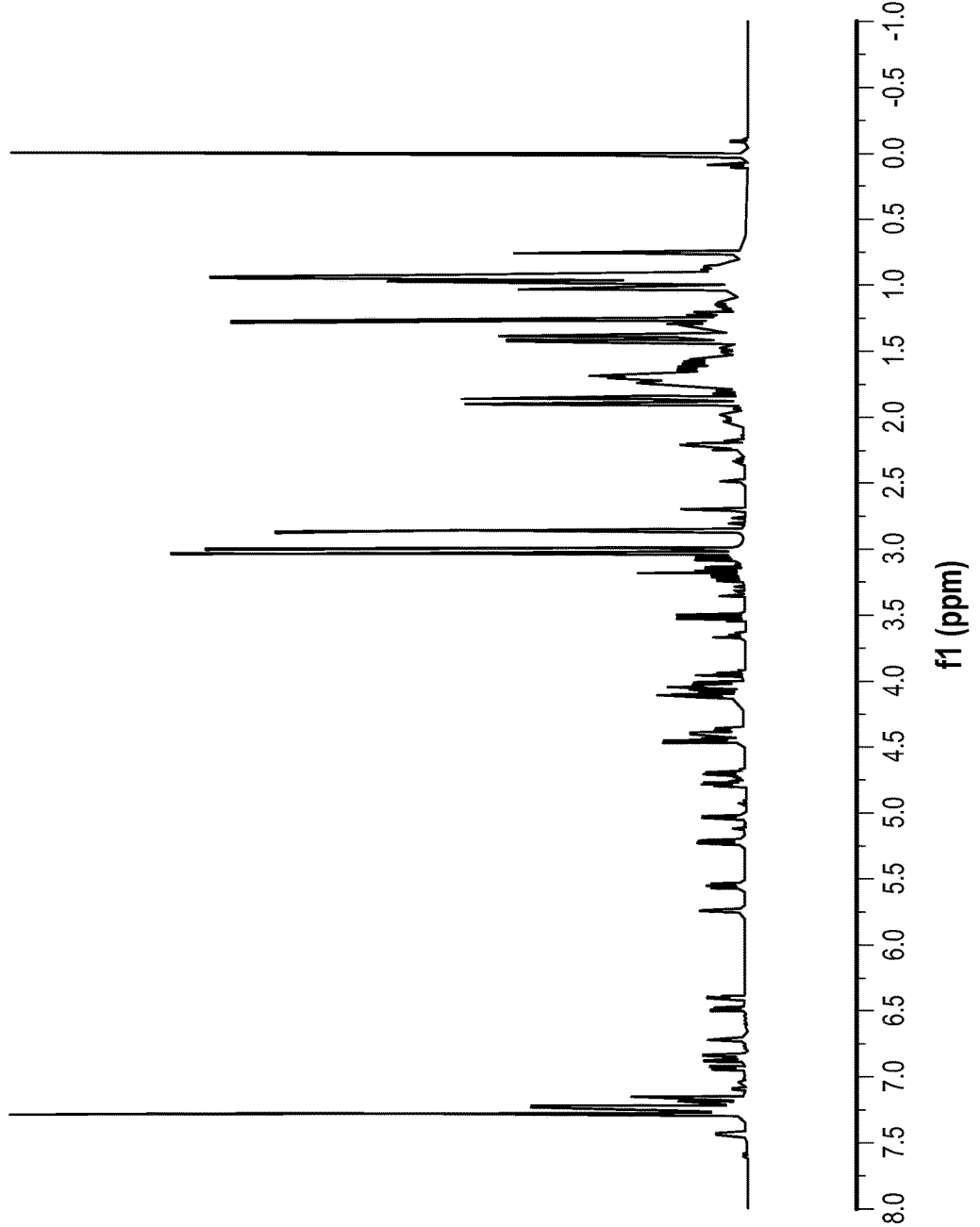
FIG. 1 is a $^1$H NMR spectrum of Compound 13 in $CDCl_3$.
Figure 2:
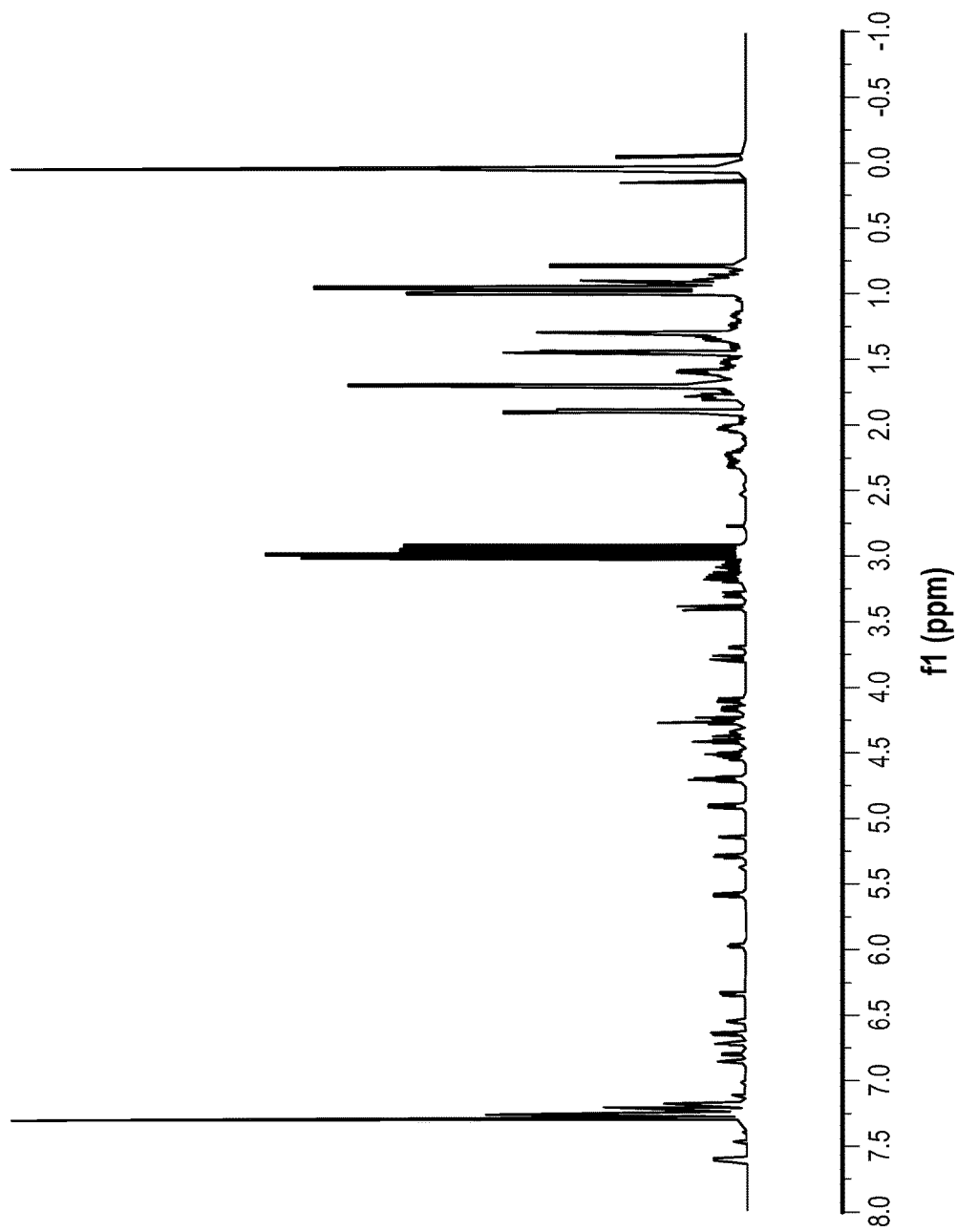
FIG. 2 is a $^1$H NMR spectrum of Compound 17 in $CDCl_3$.
Figure 3:
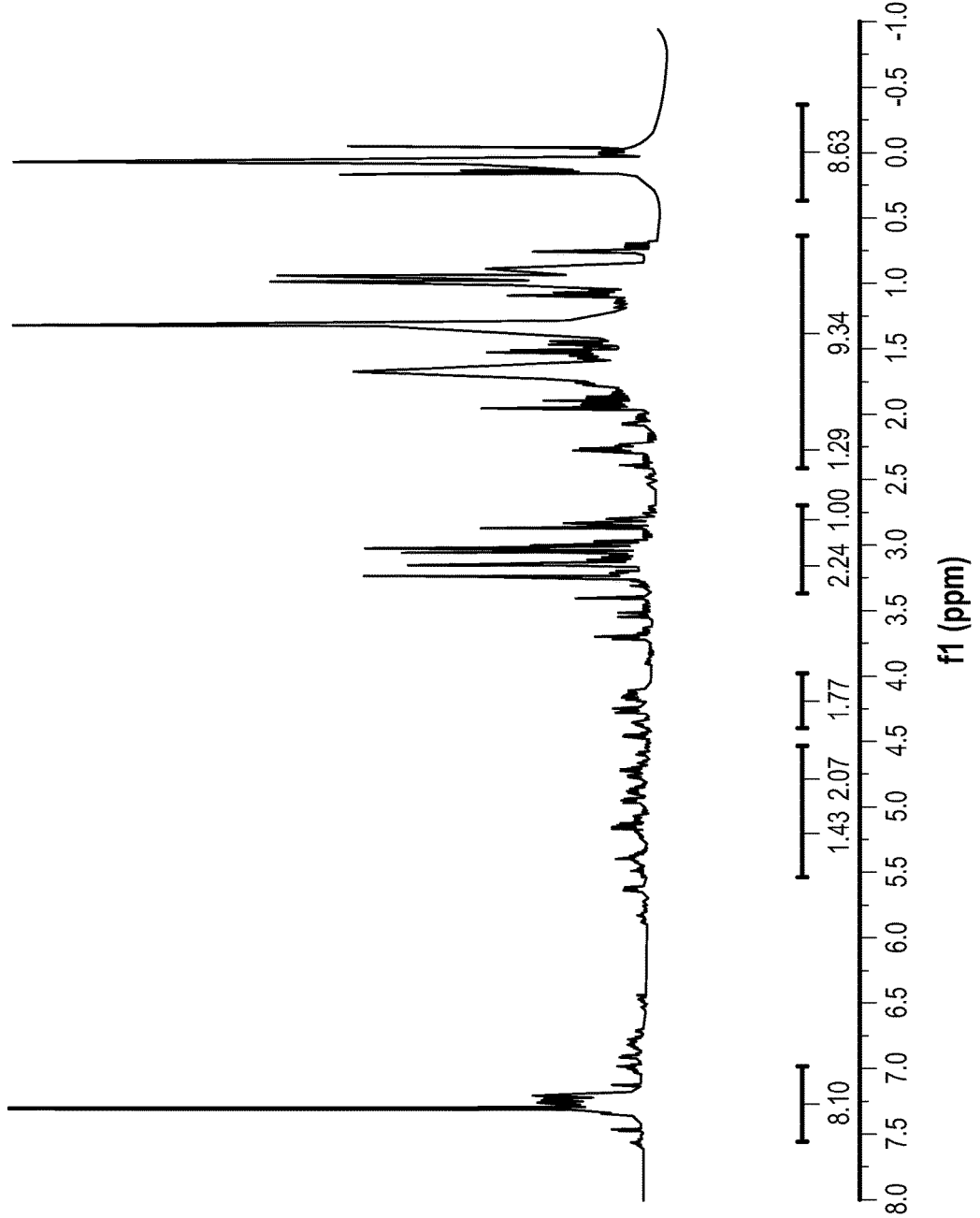
FIG. 3 is a $^1$H NMR spectrum of Compound 14 in $CDCl_3$.
Figure 4:
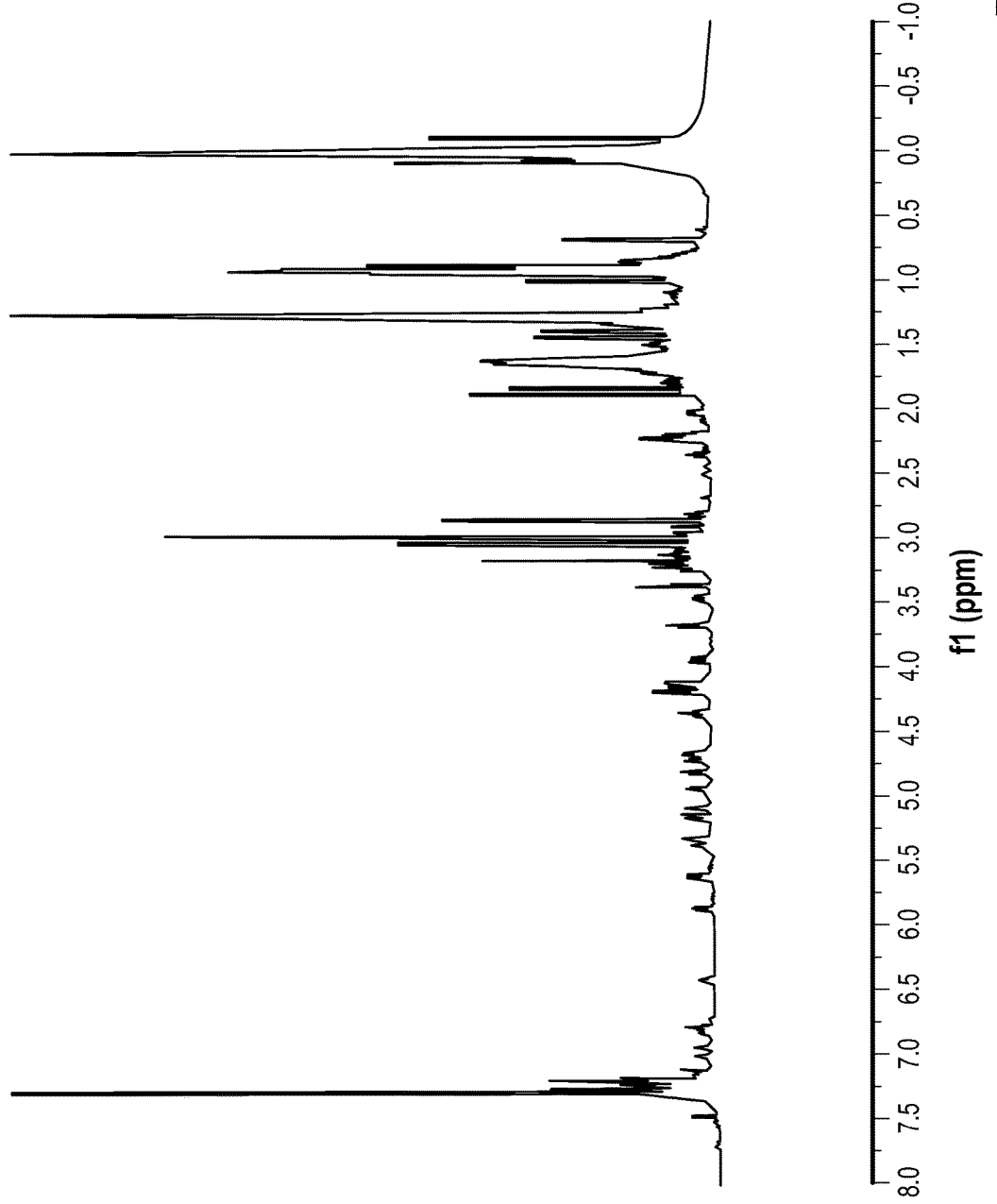
FIG. 4 is a $^1$H NMR spectrum of Compound 18 in $CDCl_3$.
Figure 5:
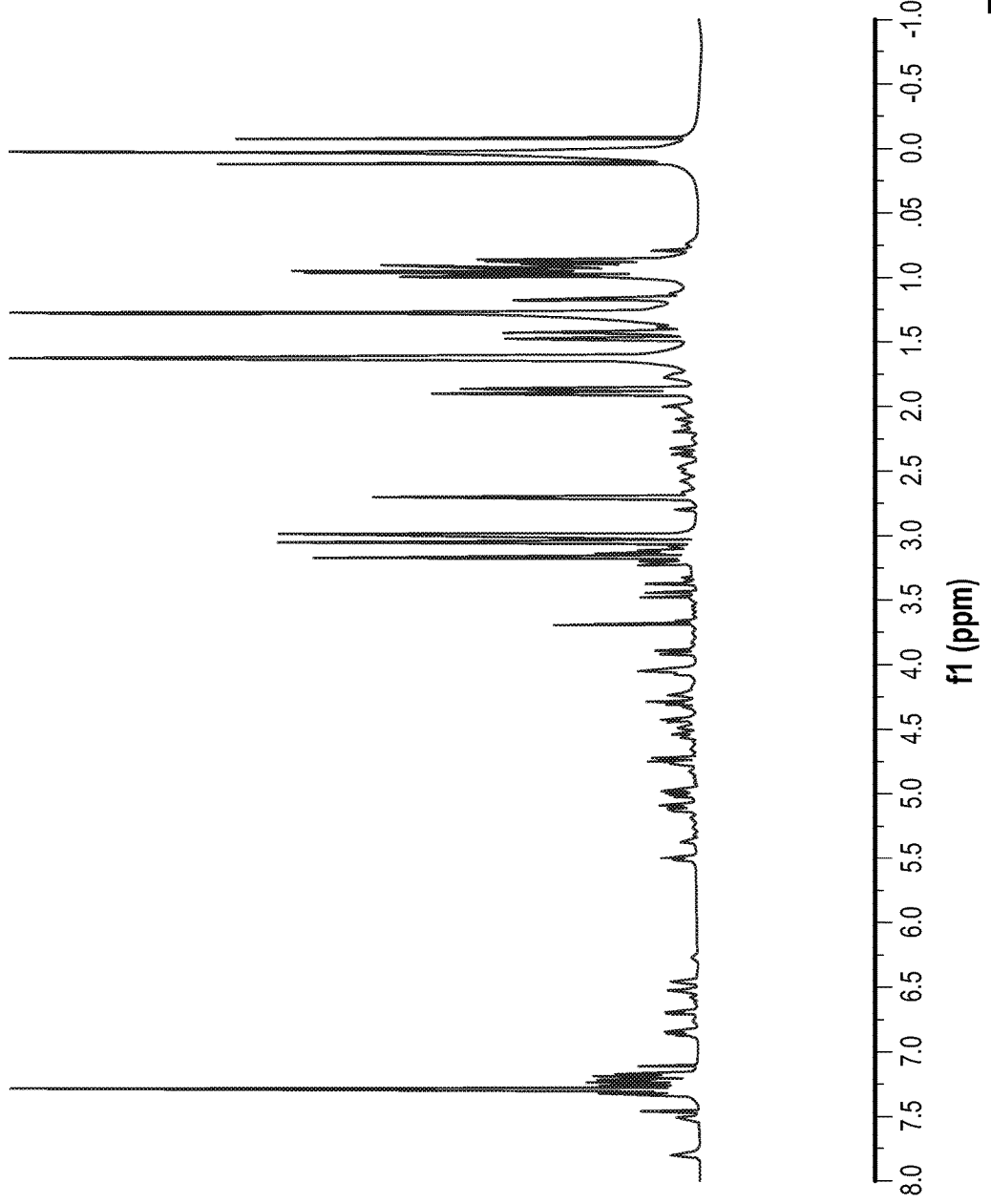
FIG. 5 is a $^1$H NMR spectrum of Compound 12 in $CDCl_3$.
Figure 6:
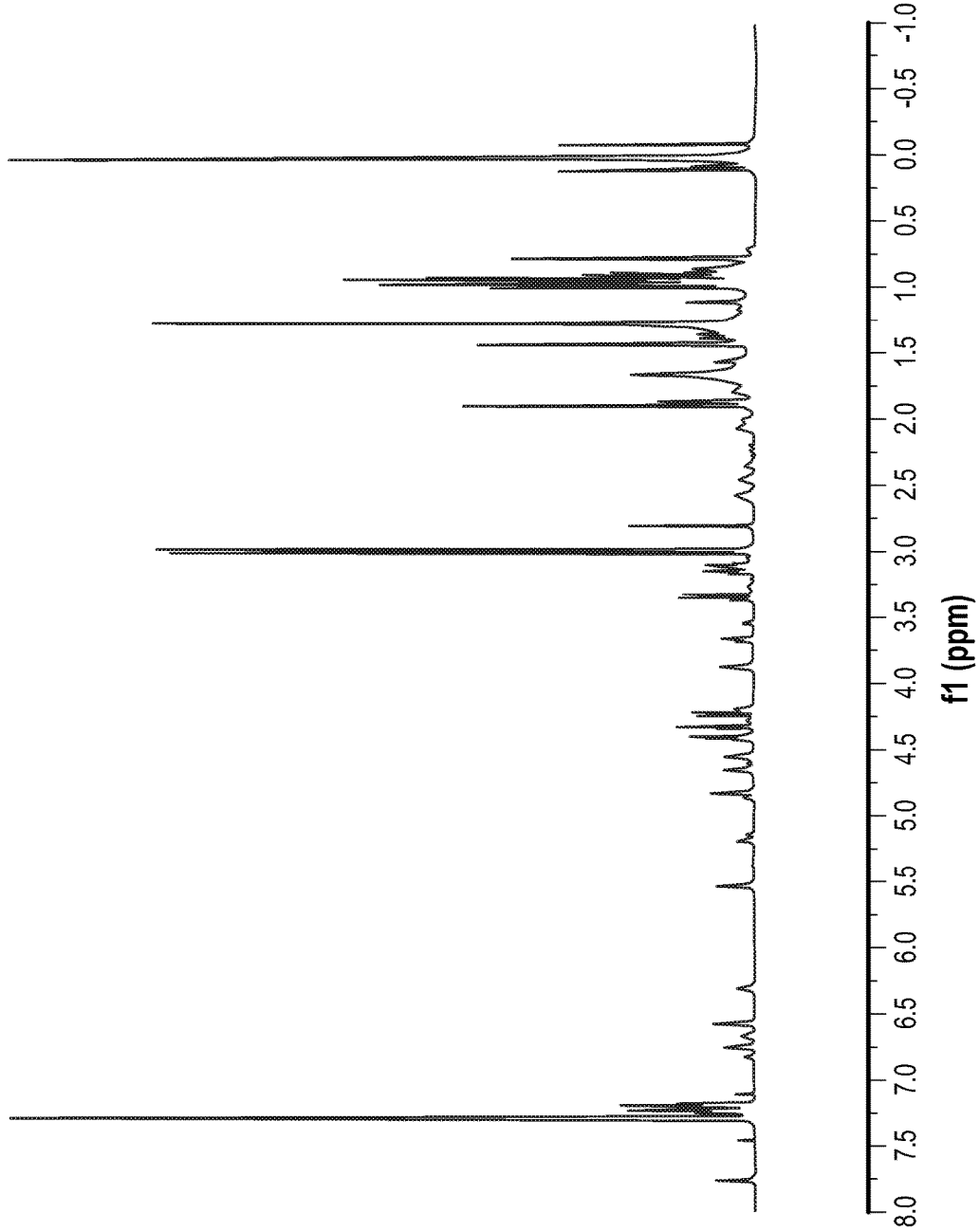
FIG. 6 is a $^1$H NMR spectrum of Compound 16 in $CDCl_3$.
Figure 7:
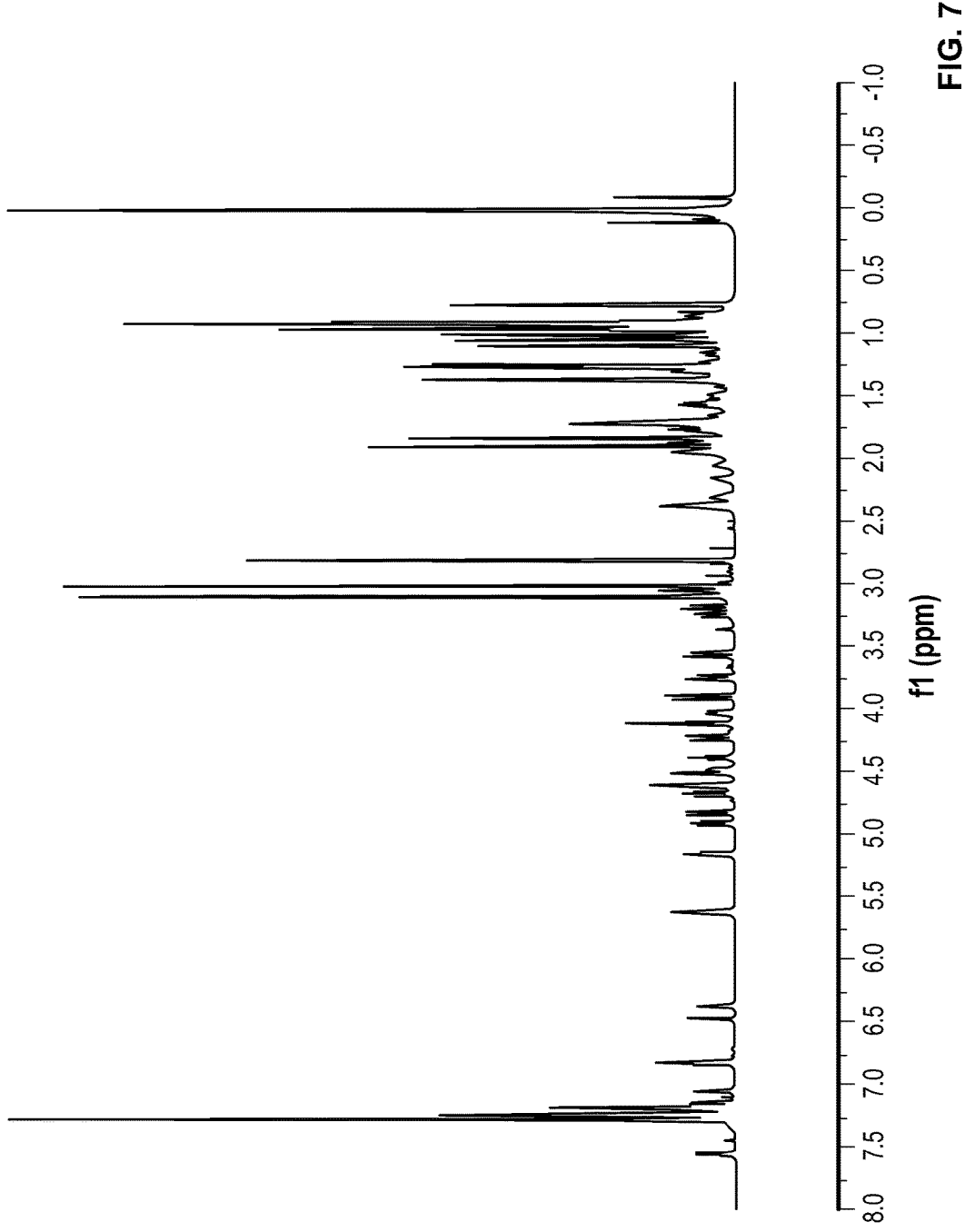
FIG. 7 is a $^1$H NMR spectrum of Compound 4 in $CDCl_3$.
Figure 8:
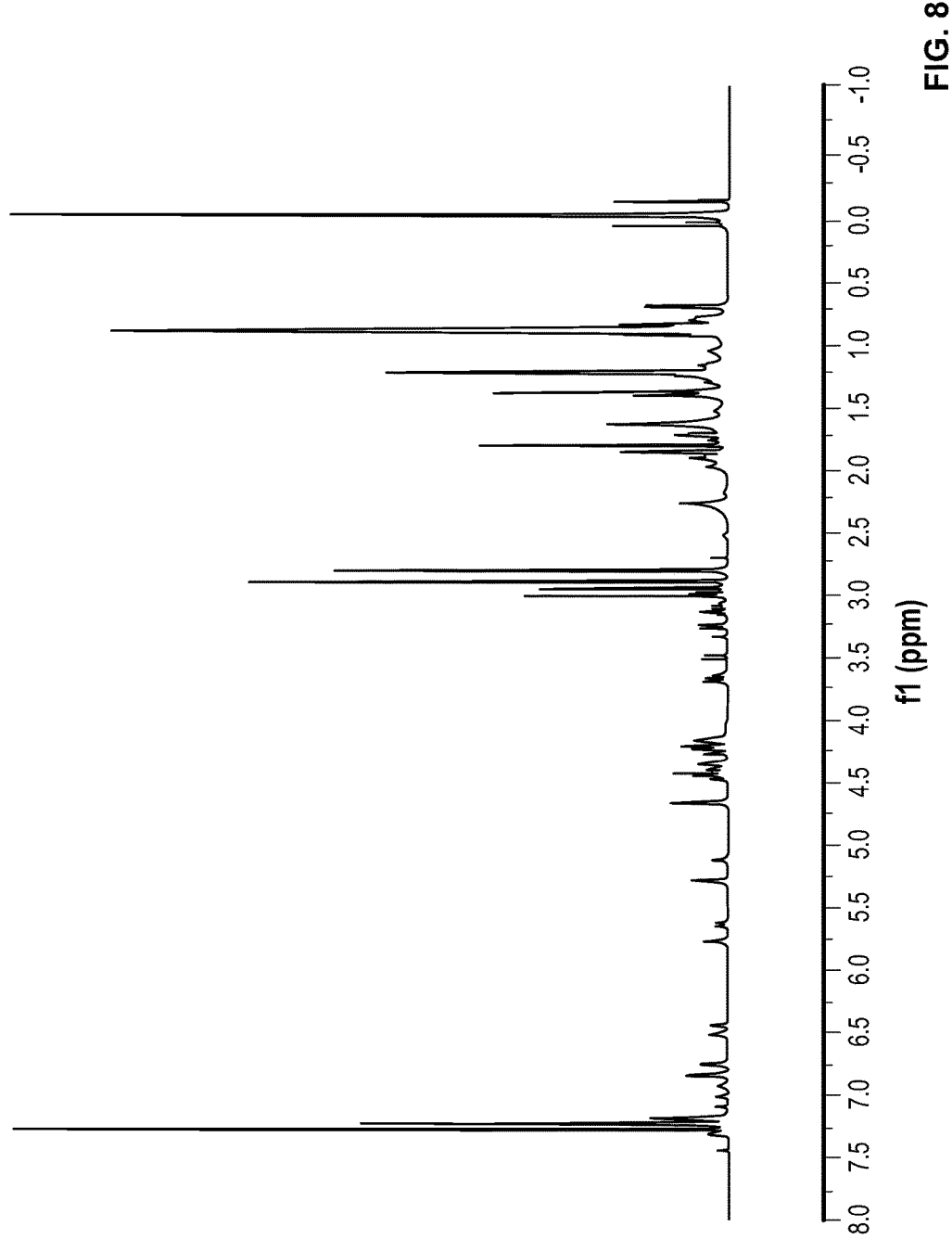
FIG. 8 is a $^1$H NMR spectrum of Compound 5 in $CDCl_3$.
Figure 9:
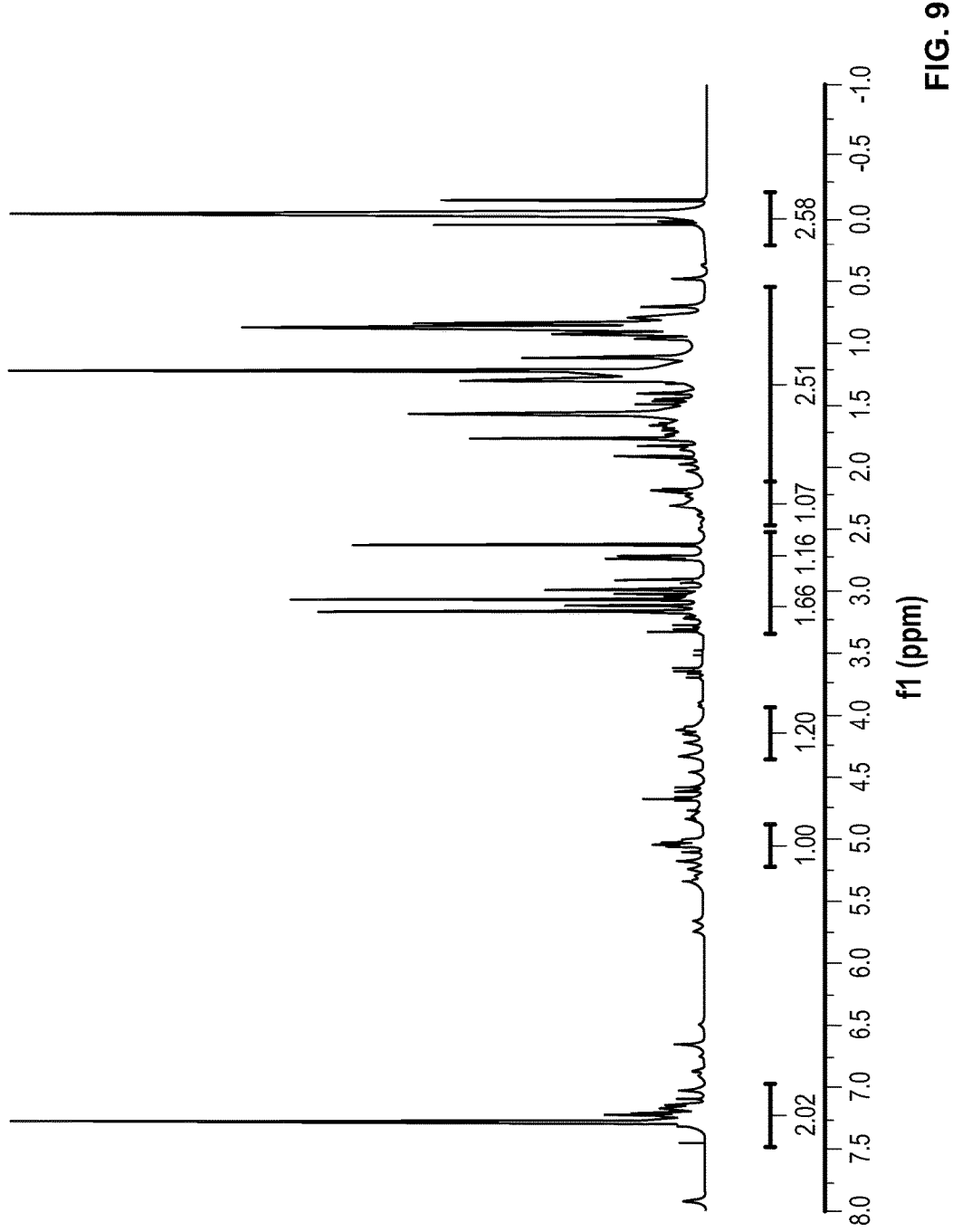
FIG. 9 is a $^1$H NMR spectrum of Compound 9 in $CDCl_3$.
Figure 10:
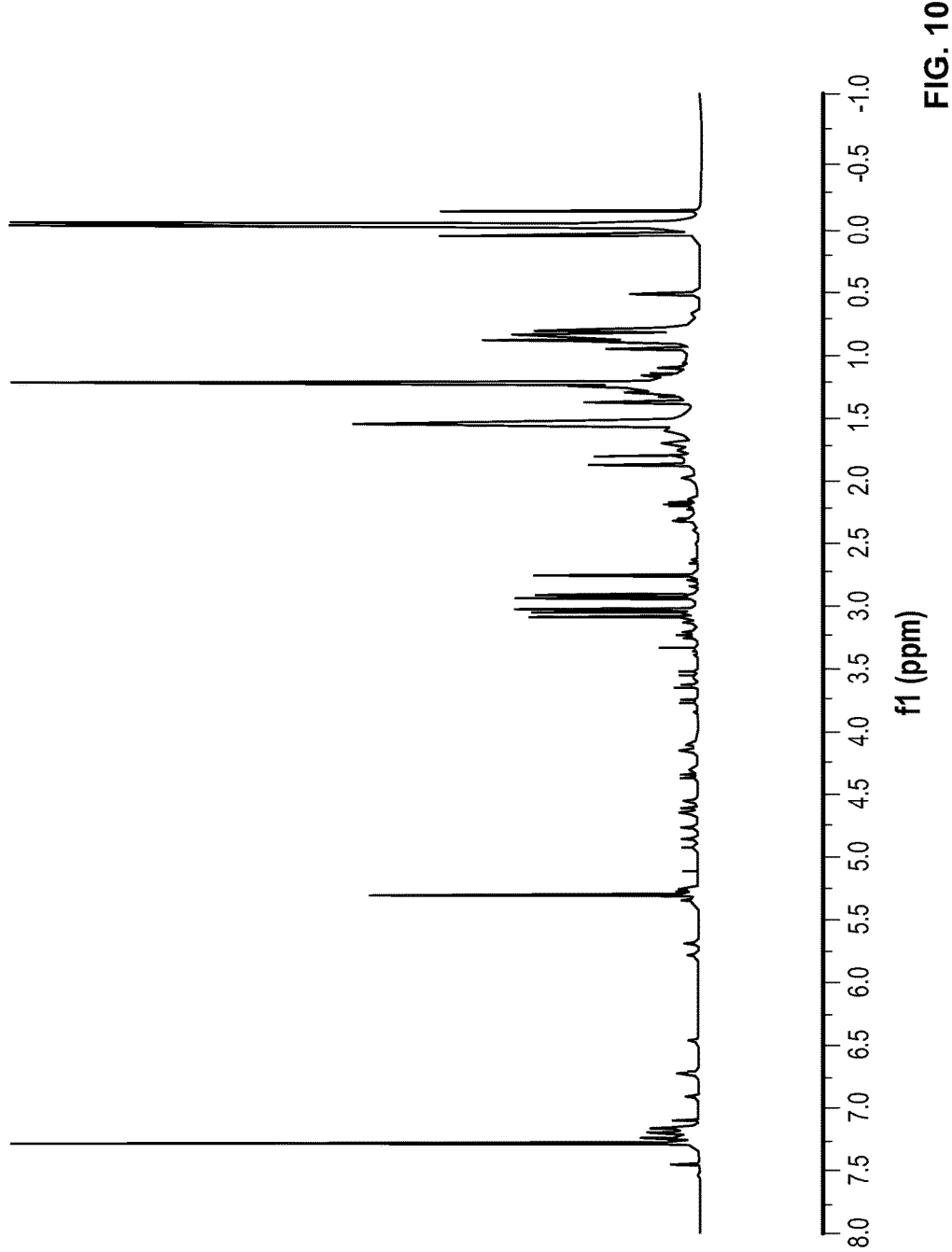
FIG. 10 is a $^1$H NMR spectrum of Compound 10 in $CDCl_3$.
Figure 11:
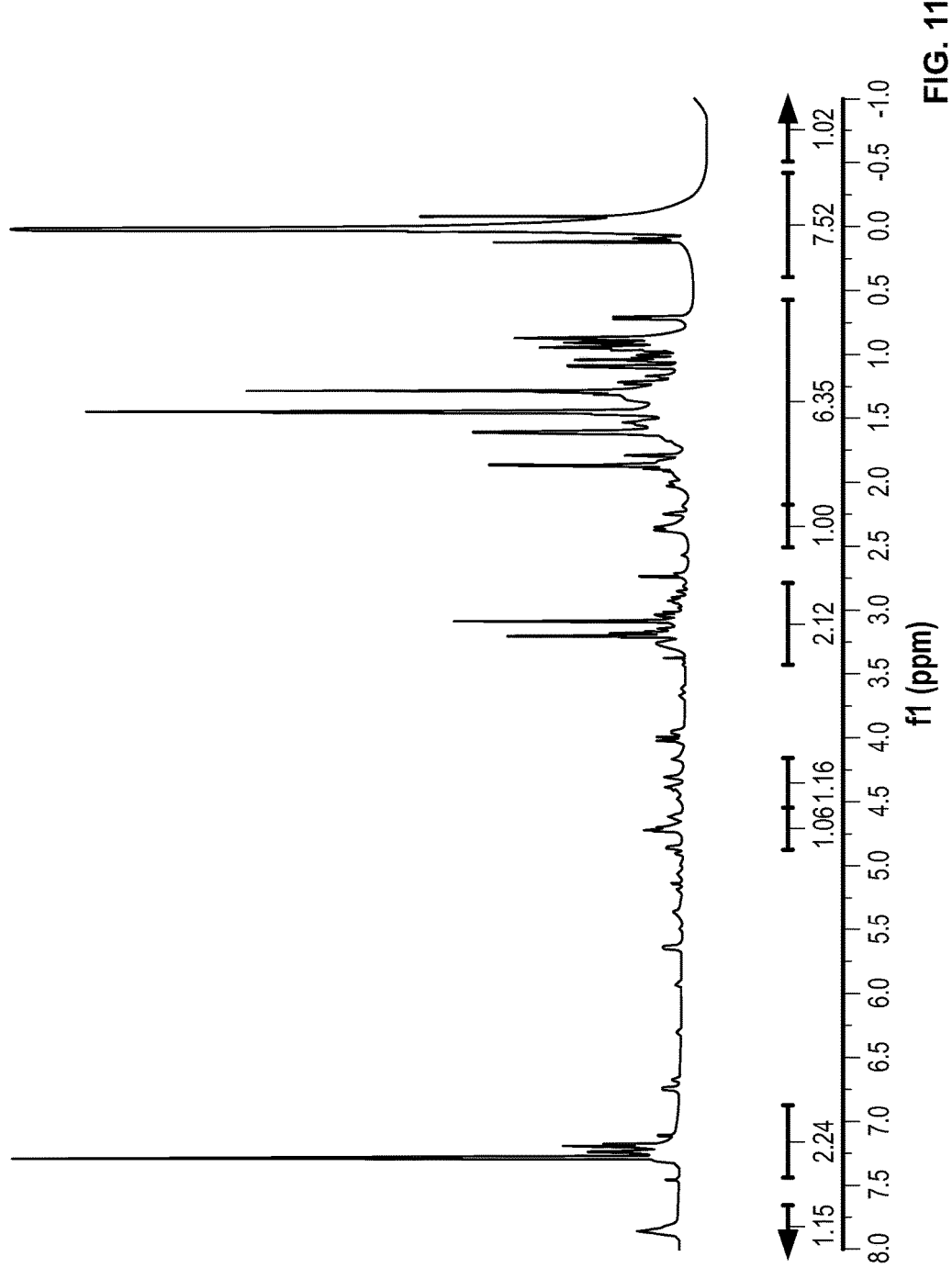
FIG. 11 is a $^1$H NMR spectrum of Compound 11 in $CDCl_3$.

As used herein, reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human, bovine, primate, equine, canine, feline, porcine, and ovine animals. Thus, the compositions and methods provided herein have use in both human medicine and in the veterinary context, including use in agricultural animals and domestic pets. The individual may be a human who has been diagnosed with or is suspected of having a condition described herein, such as cancer. The individual may be a human who exhibits one or more symptoms associated with a condition described herein, such as cancer. The individual may be a human who has a mutated or abnormal gene associated with a condition described herein, such as cancer. The individual may be a human who is genetically or otherwise predisposed to or at risk of developing a condition described herein, such as cancer.

As used herein, "treatment" or "treating" is an approach for obtaining beneficial or desired results including clinical results. For purposes of the compositions and methods provided herein, beneficial or desired clinical results include, but are not limited to, one or more of the following: decreasing one or more symptoms resulting from the condition, diminishing the extent of the condition, stabilizing the condition (e.g., preventing or delaying the worsening of the condition), preventing or delaying the spread (e.g., metastasis) of the condition, delaying or slowing the progression of the condition, ameliorating a disease state, providing a remission (whether partial or total) of a disease, decreasing the dose of one or more other medications required to treat the condition, enhancing the effect of another medication used to treat the condition, increasing the quality of life of an individual having the condition, and/or prolonging survival. A method of treating cancer encompasses a reduction of the pathological consequence of cancer. The methods described herein contemplate any one or more of these aspects of treatment.

As used herein, an "at risk" individual is an individual who is at risk of developing a disease or condition described herein, such as cancer. An individual "at risk" may or may not have detectable disease, and may or may not have displayed detectable disease prior to the treatment methods described herein. "At risk" denotes that an individual has one or more so-called risk factors, which are measurable parameters that correlate with development of a disease or condition described herein, such as cancer. An individual having one or more of these risk factors has a higher probability of developing the disease or condition than an individual without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound provided herein alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound provided herein which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of a disease or condition described herein, such as cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents, a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of a disease or condition described herein, such as cancer). For therapeutic use, beneficial or desired results include, e.g., decreasing one or more symptoms resulting from the disease (biochemical, histologic and/or behavioral), including its complications and intermediate pathological phenotypes presenting during development of the disease or condition, increasing the quality of life of those suffering from the disease or condition, decreasing the dose of other medications required to treat the disease or condition, enhancing effect of another medication, delaying the progression of the disease or condition, and/or prolonging survival of patients.

It is understood that an effective amount of a compound or pharmaceutically acceptable salt thereof, including a prophylactically effective amount, may be given to an individual in the adjuvant setting, which refers to a clinical setting in which an individual has had a history of cancer, and generally (but not necessarily) has been responsive to therapy, which includes, but is not limited to, surgery (e.g., surgical resection), radiotherapy, and chemotherapy. However, because of their history of cancer, these individuals are considered at risk of developing cancer. Treatment or administration in the "adjuvant setting" refers to a subsequent mode of treatment.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound provided herein in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound provided herein as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear or branched univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. This term is exemplified by groups such as methyl, t-butyl, n-heptyl, octyl, and the like.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl, and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —CH$_2$—CH=CH—CH$_3$ and —CH=CH—CH=CH$_2$.

"Cyclolkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl, and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

The term "alkoxy" refers to an —O-alkyl group, where the 0 is the point of attachment to the rest of the molecule, and alkyl is as defined above.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

The term "halogen" represents chlorine, fluorine, bromine, or iodine. The term "halo" represents chloro, fluoro, bromo, or iodo.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P $^{35}$S, $^{18}$F, $^{36}$Cl, and $^{125}$I, respectively. Substitution with heavier isotopes such as deuterium (i.e., $^2$H) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Chemical names were generated using ChemBioDraw Ultra Version 14.0.0.117. If there is a discrepancy between a chemical structure and the name listed for that structure, the structure prevails.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans) or E/Z isomers, salts and solvates of the compounds described herein, as well as methods of making such compounds. Any compound described herein may also be referred to as a drug.

In one aspect, provided are compounds of the Formula (I):

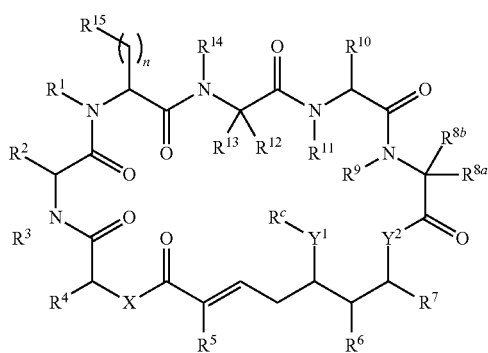

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

X is —N($R^d$)— or —O—;

$Y^1$ is —N($R^d$)—, —O—, or —S—;

$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl, or —C(O)$R^e$;

or, alternatively, the (—$Y^1$—$R^c$) group is H or halo;

$Y^2$ is —N($R^d$)—, —O—, or —S—;

each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —O$R^d$, —N$R^d R^d$, or —S$R^d$.

In some embodiments, the compound of Formula (I) is not a compound provided in Table 1x, or a salt or stereoisomer thereof.

TABLE 1x

| Compound No. | Name |
|---|---|
| X1 | (3R,6S,12R,15S,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X2 | (3R,6S,12R,15S,18R,24S,25S,26S,E)-26-((E)-but-2-en-2-yl)-6-((R)-sec-butyl)-12-(4-chlorobenzyl)-24-hydroxy-18-isobutyl-3,10,13,15,21,25- |

TABLE 1x-continued

| Compound No. | Name |
|---|---|
| | hexamethyl-1,19-dioxa-4,7,10,13,16-pentaazacyclohexacos-21-ene-2,5,8,11,14,17,20-heptaone |
| X3 | (3R,6S,12R,15R,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X4 | (3R,6S,12R,15S,18R,24S,25S,26S,E)-12-benzyl-26-((E)-but-2-en-2-yl)-6-((R)-sec-butyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone |
| X5 | (3R,6S,12S,15S,18R,24S,25S,26S,E)-12-benzyl-24-(benzyloxy)-26-((E)-but-2-en-2-yl)-6-((R)-sec-butyl)-18-isobutyl-3,10,13,15,21,25-hexamethyl-1,19-dioxa-4,7,10,13,16-pentaazacyclohexacos-21-ene-2,5,8,11,14,17,20-heptaone |
| X6 | (3R,6S,12R,15R,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X7 | (3R,6S,12R,15R,18R,24S,25S,26S,E)-12-benzyl-26-((E)-but-2-en-2-yl)-6-((R)-sec-butyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone |
| X8 | (3R,6S,12R,15S,18R,24S,25S,26S,E)-26-((E)-but-2-en-2-yl)-6-((R)-sec-butyl)-12-(4-chlorobenzyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X9 | (3R,6S,12R,15S,18R,24S,25S,26S,E)-26-((E)-but-2-en-2-yl)-6-((R)-sec-butyl)-12-(4-chlorobenzyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone |
| X10 | (3R,6S,12S,15R,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X11 | (3S,6S,12S,15R,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X12 | (3S,6S,12R,15S,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X13 | (3S,6S,12R,15S,18R,24S,25S,26S,E)-12-benzyl-26-((E)-but-2-en-2-yl)-6-((R)-sec-butyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone |
| X14 | (3R,6S,12S,15S,18R,24S,25S,26S,E)-12-benzyl-26-((E)-but-2-en-2-yl)-6-((R)-sec-butyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone |
| X15 | (3R,6S,12S,15S,18R,24S,25S,26S,E)-12-benzyl-26-((E)-but-2-en-2-yl)-6-((R)-sec-butyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone |
| X16 | (3R,6S,12R,15S,18R,24S,25S,26S,E)-12-benzyl-26-((E)-but-2-en-2-yl)-6-((R)-sec-butyl)-24-hydroxy-18-isobutyl-3,4,10,13,15,21,25-heptamethyl-1,19-dioxa-4,7,10,13,16-pentaazacyclohexacos-21-ene-2,5,8,11,14,17,20-heptaone |
| X17 | (3R,6S,12R,15S,18R,24S,25S,26S,E)-12-benzyl-26-((E)-but-2-en-2-yl)-6-((R)-sec-butyl)-18-isobutyl-3,4,10,13,15,21,25-heptamethyl-24-((methylthio)methoxy)-1,19-dioxa-4,7,10,13,16-pentaazacyclohexacos-21-ene-2,5,8,11,14,17,20-heptaone |
| X18 | (2R,5S,8R,14S,17R,20S,21S,22S,E)-8-benzyl-20-((E)-but-2-en-2-yl)-14-((R)-sec-butyl)-2-isobutyl-5,7,10,16,17,21,25-heptamethyl-3,6,9,12,15,18,26-heptaoxo-1,19-dioxa-4,7,10,13,16-pentaazacyclohexacos-24-en-22-yl (S)-3,3,3-trifluoro-2-methoxy-2-phenylpropanoate |
| X19 | (2R,5S,8R,14S,17R,20S,21S,22S,E)-8-benzyl-20-((E)-but-2-en-2-yl)-14-((R)-sec-butyl)-2-isobutyl-5,7,10,16,17,21,25-heptamethyl-3,6,9,12,15,18,26-heptaoxo-1,19-dioxa-4,7,10,13,16-pentaazacyclohexacos-24-en-22-yl (R)-3,3,3-trifluoro-2-methoxy-2-phenylpropanoate |
| X20 | (3R,6S,12S,15S,18R,24S,25S,26S,E)-3,12-dibenzyl-26-((E)-but-2-en-2-yl)-6-((R)-sec-butyl)-24-hydroxy-18-isobutyl-10,13,15,21,25-pentamethyl-1,19-dioxa-4,7,10,13,16-pentaazacyclohexacos-21-ene-2,5,8,11,14,17,20-heptaone |
| X21 | (3R,6S,12S,15S,18R,24S,25S,26S,E)-3,12-dibenzyl-26-((E)-but-2-en-2-yl)-6-((R)-sec-butyl)-18-isobutyl-10,13,15,21,25-pentamethyl-24-((methylthio)methoxy)-1,19-dioxa-4,7,10,13,16-pentaazacyclohexacos-21-ene-2,5,8,11,14,17,20-heptaone |
| X22 | (3S,6S,12R,15S,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X23 | (3S,6R,12R,15S,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |

TABLE 1x-continued

| Compound No. | Name |
|---|---|
| X24 | (3S,6S,12R,15S,18R,25S,26S,E)-18-((S)-sec-butyl)-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X25 | tert-butyl(4-((3S,6S,12R,15S,18R,24S,25S,26S,E)-18-((S)-sec-butyl)-24-hydroxy-12-isobutyl-6,15-diisopropyl-4,10,13,21,25-pentamethyl-2,5,8,11,14,17,20-heptaoxo-26-((E)-pent-2-en-2-yl)-1,19-dioxa-4,7,10,13,16-pentaazacyclohexacos-21-en-3-yl)butyl)carbamate |
| X26 | tert-butyl(4-((3S,6S,12R,15S,18R,24S,25S,26S,E)-18-((S)-sec-butyl)-24-hydroxy-12-isobutyl-15-isopropyl-3,4,10,13,21,25-hexamethyl-2,5,8,11,14,17,20-heptaoxo-26-((E)-pent-2-en-2-yl)-1,19-dioxa-4,7,10,13,16-pentaazacyclohexacos-21-en-6-yl)butyl)carbamate |
| X27 | tert-butyl(4-((2R,5S,8R,14S,17S,20S,21S,22S,E)-2-((S)-sec-butyl)-22-hydroxy-8-isobutyl-14-isopropyl-7,10,16,17,21,25-hexamethyl-3,6,9,12,15,18,26-heptaoxo-20-((E)-pent-2-en-2-yl)-1,19-dioxa-4,7,10,13,16-pentaazacyclohexacos-24-en-5-yl)butyl)carbamate |
| X28 | (2R,5S,8R,14S,17S,20S,21S,22S,E)-2-((S)-sec-butyl)-8-isobutyl-5,14-diisopropyl-7,10,16,17,21,25-hexamethyl-3,6,9,12,15,18,26-heptaoxo-20-((E)-pent-2-en-2-yl)-1,19-dioxa-4,7,10,13,16-pentaazacyclohexacos-24-en-22-yl 6-((((9H-fluoren-9-yl)methoxy)carbonyl)amino)hexanoate |
| X29 | 4-((6-(((2R,5S,8R,14S,17S,20S,21S,22S,E)-2-((S)-sec-butyl)-8-isobutyl-5,14-diisopropyl-7,10,16,17,21,25-hexamethyl-3,6,9,12,15,18,26-heptaoxo-20-((E)-pent-2-en-2-yl)-1,19-dioxa-4,7,10,13,16-pentaazacyclohexacos-24-en-22-yl)oxy)-6-oxohexyl)amino)-4-oxobutanoic acid |
| X30 | 4-((6-(((2R,5S,8R,14R,17S,20S,21S,22S,E)-2-((S)-sec-butyl)-8-isobutyl-5,14-diisopropyl-7,10,16,17,21,25-hexamethyl-3,6,9,12,15,18,26-heptaoxo-20-((E)-pent-2-en-2-yl)-1,19-dioxa-4,7,10,13,16-pentaazacyclohexacos-24-en-22-yl)oxy)-6-oxohexyl)amino)-4-oxobutanoic acid |
| X31 | (3S,6S,12S,15S,18R,24S,25S,26S,E)-12-((R)-sec-butyl)-18-((S)-sec-butyl)-24-hydroxy-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X32 | (3S,6S,12S,15S,18R,24S,25S,26S,E)-12-((R)-sec-butyl)-24-hydroxy-6,15,18-triisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X33 | (3S,6S,12S,15S,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X34 | (3S,6S,12S,15R,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X35 | (3S,6S,12R,15R,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X36 | (3S,6R,12S,15S,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X37 | (3S,6R,12S,15R,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X38 | (3S,6R,12R,15S,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X39 | (3S,6R,12R,15R,18R,24S,25S,26S,E)-18-((S)-sec-butyl)-24-hydroxy-12-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X40 | (3S,6S,12S,15S,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X41 | (3S,6S,12S,15R,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X42 | (3S,6S,12R,15S,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X43 | (3S,6S,12R,15R,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |

TABLE 1x-continued

| Compound No. | Name |
|---|---|
| X44 | (3S,6R,12S,15S,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X45 | (3S,6R,12S,15R,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X46 | (3S,6R,12R,15S,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X47 | (3S,6R,12R,15R,18R,24S,25S,26S,E)-18-((S)-sec-butyl)-24-hydroxy-12-isobutyl-6,15-diisopropyl-3,4,21,25-tetramethyl-26-((E)-pent-2-en-2-yl)-1,19-dioxa-4,7,10,13,16-pentaazacyclohexacos-21-ene-2,5,8,11,14,17,20-heptaone |
| X48 | (3S,6S,12S,15R,18R,24S,25S,26S,E)-18-((S)-sec-butyl)-24-hydroxy-15-isobutyl-6,12-diisopropyl-3,4,10,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X49 | (3S,6S,9R,15S,18R,24S,25S,26S,E)-18-((S)-sec-butyl)-24-hydroxy-9-isobutyl-6,15-diisopropyl-3,4,10,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X50 | (3S,6S,9R,12S,18R,24S,25S,26S,E)-18-((S)-sec-butyl)-24-hydroxy-9-isobutyl-6,12-diisopropyl-3,4,10,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X51 | (3S,6S,9S,15R,18R,24S,25S,26S,E)-18-((S)-sec-butyl)-24-hydroxy-15-isobutyl-6,9-diisopropyl-3,4,13,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X52 | (3S,6S,9S,12R,18R,24S,25S,26S,E)-18-((S)-sec-butyl)-24-hydroxy-12-isobutyl-6,9-diisopropyl-3,4,13,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X53 | (3S,9R,12S,15S,18R,24S,25S,26S,E)-18-((S)-sec-butyl)-24-hydroxy-9-isobutyl-12,15-diisopropyl-3,4,7,10,21,25-hexamethyl-26-((E)-pent-2-en-2-yl)-1,19-dioxa-4,7,10,13,16-pentaazacyclohexacos-21-ene-2,5,8,11,14,17,20-heptaone |
| X54 | (3S,9S,12R,15S,18R,24S,25S,26S,E)-18-((S)-sec-butyl)-24-hydroxy-12-isobutyl-9,15-diisopropyl-3,4,7,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X55 | (3S,9S,12S,15R,18R,24S,25S,26S,E)-18-((S)-sec-butyl)-24-hydroxy-15-isobutyl-9,12-diisopropyl-3,4,7,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X56 | (3S,6R,12S,15S,18R,24S,25S,26S,E)-18-((S)-sec-butyl)-24-hydroxy-6-isobutyl-12,15-diisopropyl-3,4,7,10,21,25-hexamethyl-26-((E)-pent-2-en-2-yl)-1,19-dioxa-4,7,10,13,16-pentaazacyclohexacos-21-ene-2,5,8,11,14,17,20-heptaone |
| X57 | (3S,6R,9S,15S,18R,24S,25S,26S,E)-18-((S)-sec-butyl)-24-hydroxy-6-isobutyl-9,15-diisopropyl-3,4,7,13,21,25-hexamethyl-26-((E)-pent-2-en-2-yl)-1,19-dioxa-4,7,10,13,16-pentaazacyclohexacos-21-ene-2,5,8,11,14,17,20-heptaone |
| X58 | (3S,6R,9S,12S,18R,24S,25S,26S,E)-18-((S)-sec-butyl)-24-hydroxy-6-isobutyl-9,12-diisopropyl-3,4,7,16,21,25-hexamethyl-26-((E)-pent-2-en-2-yl)-1,19-dioxa-4,7,10,13,16-pentaazacyclohexacos-21-ene-2,5,8,11,14,17,20-heptaone |
| X59 | (3S,6S,12R,15S,18R,24S,25S,26S,E)-12-benzyl-6-((R)-sec-butyl)-18,26-di((S)-sec-butyl)-24-hydroxy-3,4,10,13,15,21,25-heptamethyl-1,19-dioxa-4,7,10,13,16-pentaazacyclohexacos-21-ene-2,5,8,11,14,17,20-heptaone |
| X60 | (3S,6S,12R,15S,18R,24S,25S,26R,E)-12-benzyl-26-((E)-but-2-en-2-yl)-6-((R)-sec-butyl)-18-((S)-sec-butyl)-24-hydroxy-3,4,10,13,15,21,25-heptamethyl-1,19-dioxa-4,7,10,13,16-pentaazacyclohexacos-21-ene-2,5,8,11,14,17,20-heptaone |

In any variation of Formula (I) described herein, $R^{15}$ may be substituted or unsubstituted aryl, substituted or unsubstituted heteroaryl, substituted or unsubstituted cycloalkyl, or substituted or unsubstituted heterocyclyl. In any variation of Formula (I) described herein, $R^{15}$ may be substituted or unsubstituted aryl, substituted or unsubstituted heteroaryl, or substituted or unsubstituted heterocyclyl.

In some embodiments of Formula (I), X is —O—. In other embodiments of Formula (I), X is —$NR^d$—. In some of these embodiments, X is —NH—. In some of these embodiments X is where $R^d$ is H or substituted or unsubstituted alkyl. In some of these embodiments, X is —$NR^d$— where $R^d$ is $C_1$-$C_6$ unsubstituted alkyl, such as methyl or ethyl.

In some embodiments of Formula (I), $Y^1$ is —$NR^d$—, where $R^d$ is H or substituted or unsubstituted alkyl. In some of these embodiments, $Y^1$ is —$NR^d$—, where $R^d$ is H or $C_1$-$C_6$ alkyl, such as methyl or ethyl. In other embodiments of Formula (I), $Y^1$ is —O—. In yet other embodiments of Formula (I), $Y^1$ is —S—. In still other embodiments of Formula (I), the (—$Y^1$—$R^c$) group is halo. In a particular embodiment, the halo is fluoro. In another particular embodiment, the halo is chloro. In any of the forgoing embodiments of Formula (I), $R^c$ is H or substituted or unsubstituted alkyl. In a particular variation of any of the foregoing, $R^c$ is H or $C_1$-$C_6$ alkyl; such as methyl or ethyl. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $Y^2$ is —$NR^d$— where $R^d$ is H or substituted or unsubstituted alkyl. In some of these embodiments, $Y^2$ is —$NR^d$—, where $R^d$ is H or $C_1$-$C_6$ alkyl, such as methyl or ethyl. In some embodiments, $Y^2$ is —O—. In some embodiments, $Y^2$ is —S—. In any of the foregoing embodiments of Formula (I), $R^c$ is H or substituted or unsubstituted alkyl. In other such embodiment, $R^c$ is H or $C_1$-$C_6$ alkyl, such as methyl or ethyl. In yet other such embodiments, $R^c$ is H. In any of the foregoing embodiments of Formula (I), the carbon bearing $Y^2$ is in the (R) stereochemical configuration. In any of the foregoing embodiments of Formula (I), the carbon bearing $Y^2$ is in the (S) stereochemical configuration. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $Y^1$ and $Y^2$ are each —$NR^d$—, where each $R^d$ is independently H or substituted or unsubstituted alkyl. In one such embodiment, $R^c$ is H or substituted or unsubstituted alkyl. In some of these embodiments, $Y^1$ is —NH— or —$N(CH_3)$—. In some of these embodiments of Formula (I), $Y^2$ is —NH— or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In other embodiments of Formula (I), $Y^1$ is —O—, and $Y^2$ is —$N(R^d)$—, where $R^d$ is H or substituted or unsubstituted alkyl. In some such embodiments, $R^c$ is H or substituted or unsubstituted alkyl. In some variations of the foregoing, $R^c$ is H or methyl. In some variations, $R^c$ is an alkyl substituted with sulfane. In some embodiments, $R^c$ is methyl substituted with

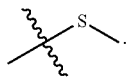

In some variations of the foregoing, $Y^2$ is —NH— or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In yet other embodiments of Formula (I), $Y^1$ is —S—, and $Y^2$ is —$N(R^d)$—, where $R^d$ is H or substituted or unsubstituted alkyl. In some such embodiments, $R^c$ is H or substituted or unsubstituted alkyl. In some variations of the foregoing, $R^c$ is H or methyl. In some variations of the foregoing, $Y^2$ is —NH— or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In yet other embodiments, of Formula (I), the (—$Y^1$—$R^c$) group is halo, and $Y^2$ is —$N(R^d)$—, where $R^d$ is H or substituted or unsubstituted alkyl. In some such embodiments, the (—$Y^1$—$R^c$) group is fluoro. In other such embodiments, the (—$Y^1$—$R^c$) group is chloro. In some variations of the foregoing, $Y^2$ is —NH or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some variations of Formula (I), $Y^1$ is —$NR^d$—, where $R^d$ is H or substituted or unsubstituted alkyl, and $Y^2$ is —O—. In some such variations, $R^c$ is H or substituted or unsubstituted alkyl. In particular variations, $R^c$ is H or $C_1$-$C_6$ alkyl, such as methyl or ethyl. In some of the foregoing variations, $Y^1$ is —NH— or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In other variations of Formula (I), $Y^1$ is —O—, and $Y^2$ is —O—. In some of these variations, $R^c$ is H or substituted or unsubstituted alkyl. In particular variations, $R^c$ is H or methyl. In some variations, $R^c$ is an alkyl substituted with sulfane. In some embodiments, $R^c$ is methyl substituted with

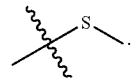

In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In other variations of Formula (I), $Y^1$ is —S—, and $Y^2$ is —O—. In some of these variations, $R^c$ is H or substituted or unsubstituted alkyl. In particular variations, $R^c$ is H or methyl. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In yet other variations, of Formula (I), the (—$Y^1$—$R^c$) group is halo, and $Y^2$ is —O—. In some such embodiments, the (—$Y^1$—$R^c$) group is fluoro. In other such embodiments, the (—$Y^1$—$R^c$) group is chloro. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $Y^1$ is —$NR^d$—, where $R^d$ is H or substituted or unsubstituted alkyl, and $Y^2$ is —S—. In some of these embodiments, $R^c$ is H or substituted or unsubstituted alkyl. In particular embodiments, $R^c$ is H. In other particular embodiments, $R^c$ is methyl. In any of the foregoing embodiments, $Y^1$ is —NH— or —$N(CH_3)$—. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $Y^1$ is —O—, and $Y^2$ is —S—. In some of these embodiments, $Y^1$ is —OH or —OCH$_3$. In some of these embodiments, $R^c$ is H or substituted or unsubstituted alkyl. In particular embodiments, $R^c$ is H. In other particular embodiments, $R^c$ is methyl. In some variations, $R^c$ is an alkyl substituted with sulfane. In some embodiments, $R^c$ is methyl substituted with

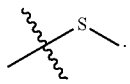

In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $Y^1$ is —S—, and $Y^2$ is —S—. In some of these embodiments, $R^c$ is H or substituted or unsubstituted alkyl. In particular embodiments, $R^c$ is H. In other particular embodiments, $R^c$ is methyl. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), the (—$Y^1$—$R^c$) group is halo, and $Y^2$ is —S—, where $R^d$ is H or substituted or unsubstituted alkyl. In some such embodiments, the (—$Y^1$—$R^c$) group is fluoro. In other such embodiments, the (—$Y^1$—$R^c$) group is chloro. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some embodiments of Formula (I), $R^1$, $R^2$, $R^3$, $R^4$, $R^{8a}$, $R^{8b}$, $R^9$, $R^{10}$, $R^{11}$, $R^{12}$, $R^{13}$, and $R^{14}$ are each independently H or substituted or unsubstituted alkyl, such as unsubstituted $C_1$-$C_6$ alkyl. In some embodiments, $R^3$ is H. In other embodiments, $R^1$ is $C_1$-$C_6$ alkyl, such as methyl. In some embodiments, $R^2$ is H. In some embodiments, $R^2$ is substituted or unsubstituted alkyl. In some embodiments, $R^2$ is $C_1$-$C_6$ alkyl, such as methyl. In yet other embodiments, $R^2$ is —(CH$_2$)$_4$NH$_2$ which is optionally substituted. In some embodiments, $R^3$ is H. In other embodiments, $R^3$ is $C_1$-$C_6$ alkyl, such as methyl. In some embodiments, $R^4$ is H. In other embodiments, $R^4$ is $C_1$-$C_6$ alkyl, such as methyl. In particular embodiments, $R^4$ is isobutyl. In some embodiments, $R^{8a}$ and $R^{8b}$ are both H. In other embodiments, $R^{8a}$ and $R^{8b}$ are each independently $C_1$-$C_6$ alkyl, such as methyl. In yet other embodiments, one of $R^{8a}$ and $R^{8b}$ is H and the other is $C_1$-$C_6$ alkyl, such as methyl. In yet other embodiments, one of $R^{8a}$ and $R^{8b}$ is H and the other is —(CH2)$_4$NH$_2$, which is optionally substituted. In some embodiments, $R^9$ is H. In other embodiments, $R^9$ is $C_1$-$C_6$ alkyl, such as methyl. In some embodiments, $R^{10}$ is H. In other embodiments, $R^{10}$ is $C_1$-$C_6$ alkyl, such as methyl. In particular embodiments, $R^{10}$ is sec-butyl. In some embodiments, $R^9$ is H. In other embodiments, $R^9$ is $C_1$-$C_6$ alkyl, such as methyl. In some embodiments, $R^{12}$ and $R^{13}$ are both H. In other embodiments, $R^{12}$ and $R^{13}$ are each independently $C_1$-$C_6$ alkyl, such as methyl. In yet other embodiments, one of $R^{12}$ and $R^{13}$ is H and the other is $C_1$-$C_6$ alkyl, such as methyl. In some embodiments, $R^{14}$ is H. In other embodiments, $R^{14}$ is $C_1$-$C_6$ alkyl, such as methyl.

In some embodiments of Formula (I), $R^1$ is methyl, $R^2$ is methyl, $R^3$ is H, and $R^4$ is isobutyl. In some of these embodiments, X is —O—. In some of these embodiments, $R^{15}$ is substituted or unsubstituted aryl and n is 1. In particular embodiments, $R^{15}$ is substituted or unsubstituted phenyl, and n is 1. The substituted phenyl may be a phenyl substituted at the para position. The substituted phenyl may be a phenyl substituted at the meta position. The substituted phenyl may be phenyl substituted with one or more fluoro, chloro, trifluoromethyl, or hydroxyl groups. In particular embodiments, the substituted phenyl is 4-fluorophenyl, 4-chlorophenyl, 4-(trifluoromethyl)phenyl, or 4-hydroxyphenyl. In any of the foregoing embodiments of Formula (I), n may be 0. In any of the foregoing embodiments of Formula (I), n may be 1. In any of the foregoing embodiments of Formula (I), n may be 2.

In some embodiments of Formula (I), $R^5$ is H or $C_1$-$C_6$ alkyl, such as methyl. In other embodiments of Formula (I), $R^5$ is halo. In some such embodiments, $R^5$ is fluoro. In other such embodiments, $R^5$ is chloro. In yet other embodiments of Formula (I), $R^5$ is perhaloalkyl. In some such embodiments, $R^5$ is trifluoromethyl.

In some embodiments of Formula (I), $R^6$ is H or $C_1$-$C_6$ alkyl. In some such embodiments, $R^6$ is H. In other such embodiments, $R^6$ is methyl. In other embodiments of Formula (I) embodiments, $R^6$ is halo. In some such embodiments, $R^6$ is fluoro. In some such embodiments, $R^6$ is chloro. In yet other embodiments of Formula (I), $R^6$ is substituted or unsubstituted aryl. In particular embodiments, $R^6$ is substituted phenyl. In other particular embodiments, $R^6$ is unsubstituted phenyl.

In some embodiments of Formula (I), $R^7$ is H or $C_1$-$C_6$ alkyl. In some such embodiments, $R^7$ is methyl. In other such embodiments, $R^7$ is H. In particular embodiments, $R^7$ is

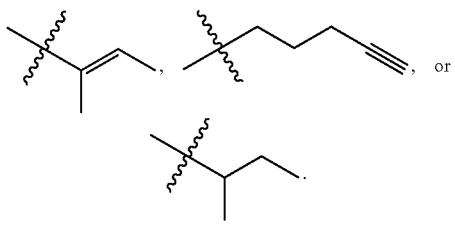

When $R^7$ is sec-butyl, it may be (S)-sec-butyl or (R)-sec-butyl. In some embodiments, $R^7$ is substituted or unsubstituted aryl, such as phenyl.

In some embodiments of Formula (I), $R^5$, $R^6$, and $R^7$ are all substituted or unsubstituted alkyl. In particular embodiments of Formula (I), $R^5$ and $R^6$ are both methyl, and $R^7$ is

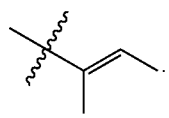 [SMILES: */C(C)=C/C]

In other particular embodiments of Formula (I), $R^5$ and $R^6$ are both methyl, and $R^7$ is

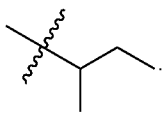 [SMILES: *C(C)CC]

In other particular embodiments of Formula (I), $R^5$ is methyl, and $R^6$ and $R^7$ are both hydrogen. In yet other particular embodiments of Formula (I), $R^5$ and $R^6$ are both methyl, and $R^7$ is hydrogen.

In some embodiments of Formula (I), $R^{15}$ is substituted or unsubstituted aryl, such as phenyl. In some embodiments, $R^{15}$ is phenyl substituted with halo, such as fluoro or chloro. In other embodiments, $R^{15}$ is phenyl substituted with hydroxyl. In other embodiments, $R^{15}$ is phenyl substituted with alkoxy. In other embodiments, $R^{15}$ is phenyl substituted with perhalomethyl. In some embodiments, $R^{15}$ is phenyl which is substituted at the para position. In yet other embodiments, $R^{15}$ is unsubstituted phenyl. In any of the foregoing embodiments, n may be 1. In any of the foregoing embodiments, n may be 2. In any of the foregoing embodiments, n may be 0.

In some embodiments, the carbon bearing $R^2$ is in the (S) stereochemical configuration. In some embodiments, the carbon bearing $R^2$ is in the (R) stereochemical configuration. In some embodiments, the carbon bearing $R^4$ is in the (S) stereochemical configuration. In some embodiments, the carbon bearing $R^4$ is in the (R) stereochemical configuration. In some embodiments, the carbon bearing $R^6$ is in the (S) stereochemical configuration. In some embodiments, the carbon bearing $R^6$ is in the (R) stereochemical configuration. In some embodiments, the carbon bearing $R^7$ is in the (S) stereochemical configuration. In some embodiments, the carbon bearing $R^7$ is in the (R) stereochemical configuration. In some embodiments, the carbon bearing $R^{8a}$ and $R^{8b}$ is in the (S) stereochemical configuration. In some embodiments, the carbon bearing $R^{8a}$ and $R^{8b}$ is in the (R) stereochemical configuration. In some embodiments, the carbon bearing $R^{10}$ is in the (S) stereochemical configuration. In some embodiments, the carbon bearing $R^{10}$ is in the (R) stereochemical configuration. In some embodiments, the carbon bearing $R^{12}$ and $R^{13}$ is in the (S) stereochemical configuration. In some embodiments, the carbon bearing $R^{12}$ and $R^{13}$ is in the (R) stereochemical configuration. In any of the foregoing embodiments of Formula (I), the carbon bearing $Y^1$ is in the (R) stereochemical configuration. In any of the foregoing embodiments of Formula (I), the carbon bearing $Y^1$ is in the (S) stereochemical configuration.

In some variations of any of the embodiments of Formula (I) provided herein, $R^c$ is —C(O)$R^e$. In some such variations, $R^e$ is —NR$^d$R$^d$. In some such variations, $R^e$ is —NR$^d$R$^d$, and each R$^d$ is independently substituted or unsubstituted alkyl. In some such variations, $R^e$ is —NR$^d$R$^d$, where one R$^d$ is substituted or unsubstituted alkyl and the other R$^d$ is methyl. In some such variations, $R^e$ is —NR$^d$R$^d$, where one R$^d$ is alkyl substituted with alkylamino and the other R$^d$ is optionally methyl. In particular variations, $R^e$ is —NR$^d$R$^d$ where one R$^d$ is —(CH$_2$)$_2$NHCH$_3$ and the other R$^d$ is methyl. In any of the aforementioned variations, $Y^1$ is —O—. In any of the aforementioned variations, $Y^1$ is —N(R$^d$)—, where R$^d$ is H or unsubstituted alkyl. In some variations of any of the embodiments of Formula (I) provided herein, —$Y^1$—$R^c$ taken together form the moiety —OC(O)N(CH$_3$)CH$_2$CH$_2$NHCH$_3$.

In some variations of any of the embodiments of Formula (I) provided herein, $Y^1$ is —O—, and $R^c$ is

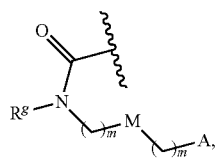

wherein

A is —OH, —NR$^f$R$^h$ or —N$_3$;

M is —(CH$_2$)$_k$— or —(OCH$_2$—CH$_2$)$_k$—, where k is an integer from 1-12, inclusive;

each m is independently an integer from 0 to 3,

R$^f$ is H, substituted or unsubstituted alkyl, or optionally substituted —C(O)O-alkyl;

R$^g$ is H or substituted or unsubstituted alkyl;

R$^h$ is H, substituted or unsubstituted alkyl, —C(O)R$^i$, or —S(O)$_2$R$^i$;

R$^i$ is H, OH, substituted or unsubstituted alkyl, substituted or unsubstituted aryl, substituted or unsubstituted heteroaryl, or

A$^1$ is —NR$^{f1}$R$^{h1}$;

M$^1$ is —(CH$_2$)$_j$— or —(OCH$_2$—CH$_2$)$_j$—, where j is an integer from 1-12, inclusive;

each m$^1$ is independently an integer from 0 to 3;

R$^{f1}$ is H, or substituted or unsubstituted alkyl;

R$^{h1}$ is H, substituted or unsubstituted alkyl, or —C(O)R$^{i1}$; and

R$^{i1}$ is H, OH, substituted or unsubstituted alkyl, substituted or unsubstituted aryl, or substituted or unsubstituted heteroaryl.

In some embodiments, R$^i$ is aryl substituted with nitro, formyl, or acetyl. In some embodiments, R$^i$ is

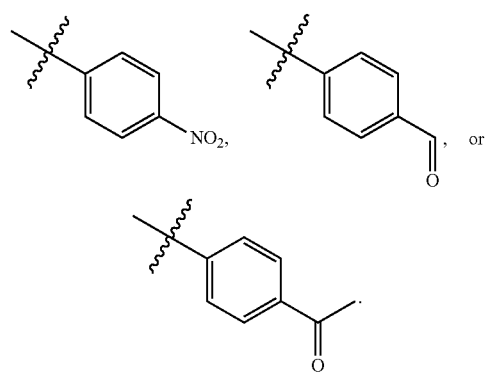

In some embodiments, R$^{i1}$ is aryl substituted with nitro, formyl, or acetyl. In some embodiments, R$^{i1}$ is

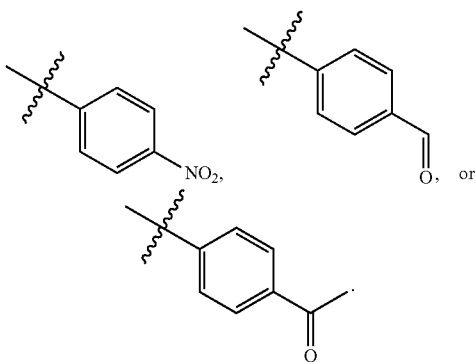

In some embodiments, $R^f$ is —C(O)O-alkyl, wherein the alkyl is substituted. In some embodiments, $R^f$ is —C(O)O-alkyl, wherein the alkyl is substituted with trimethylsilyl.

In some variations of any of the embodiments of Formula (I) provided herein, $Y^1$ is —O—, and $R^c$ is

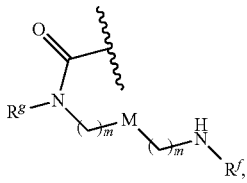

wherein $R^f$ is H, substituted or unsubstituted alkyl, or —C(O)O-alkyl;

$R^g$ is H or substituted or unsubstituted alkyl;

M is —(CH$_2$)$_k$— or —(OCH$_2$—CH$_2$)$_k$—, where k is an integer from 1-12, inclusive; and each m is independently an integer from 0 to 3.

In some variations of any of the embodiments of Formula (I) provided herein, the (—Y$^1$—R$^c$) group is H. In some embodiments, the (—Y$^1$—R$^c$) group is H, and $R^2$ is substituted or unsubstituted alkyl. In some embodiments, $R^2$ is $C_1$-$C_6$ alkyl, such as methyl. In some embodiments, $R^2$ is alkyl substituted with NR$^x$R$^y$, wherein R$^x$ and R$^y$ are independently H, —

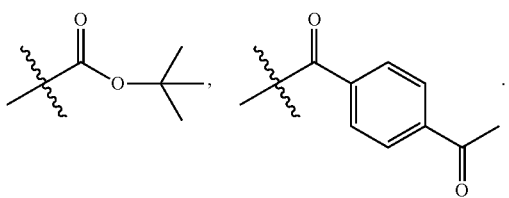

C(O)OR$^i$. or —C(O)R$^i$. In some embodiments, $R^i$ is H, OH, substituted or unsubstituted alkyl, substituted or unsubstituted aryl, substituted or unsubstituted heteroaryl, or

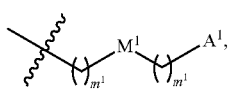

wherein $A^1$, $M^1$, and $m^1$ are as defined above. In some embodiments, $R^2$ is —(CH$_2$)$_4$NH$_2$ which is optionally substituted. In some embodiments, $R^2$ is —(CH$_2$)$_4$NR$^x$R$^y$, and one of R$^x$ and R$^y$ is

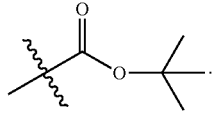 [SMILES: *C(=O)OC(C)(C)C]

In some embodiments, $R^2$ is —(CH$_2$)$_4$NR$^x$R$^y$, and one of R$^x$ and R$^y$ is

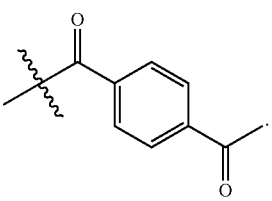 [SMILES: *C(=O)c1ccc(C(C)=O)cc1]

In some variations of any of the embodiments of Formula (I) provided herein, the (—Y$^1$—R$^c$) group is H, and $R^{15}$ is substituted or unsubstituted aryl. In some embodiments, $R^{15}$ is substituted or unsubstituted phenyl. In some embodiments, $R^{15}$ is phenyl which is substituted at the para position. In some embodiments, $R^{15}$ is phenyl substituted with —OR$^c$, wherein R$^c$ is

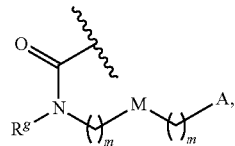

wherein M, A, m, and R$^g$ are as defined above. In some embodiments, $R^{15}$ is phenyl substituted with —OR$^c$, and A is NH$_2$.

In another aspect, the compound of Formula (I) is a compound of Formula (Ii):

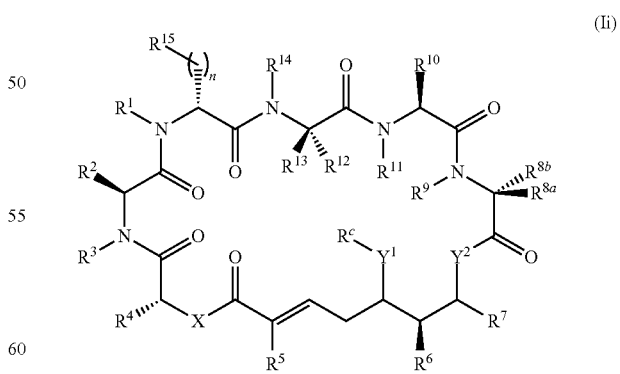

(Ii)

or a salt thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, $R^c$, n, X, $Y^1$, and $Y^2$ are as defined for Formula (I).

In another aspect, provided are compounds of Formula (II):

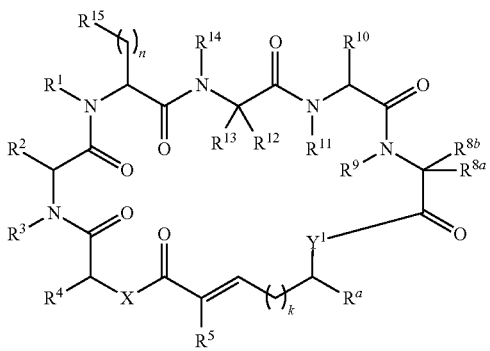

(II)

and salts thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

X is —N($R^d$)— or —O—;

$Y^1$ is —N($R^d$)—, —O—, or —S—;

k is 1, 2, or 3;

$R^a$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl; or $R^a$ is

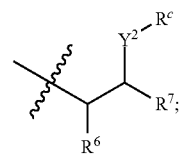

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$Y^2$ is —N($R^d$)—, —O—, or —S—;

$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl, or —C(O)$R^e$;

or, alternatively, the (—$Y^2$—$R^c$) group is halo;

each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —O$R^d$, —N$R^d R^d$, or —S$R^d$.

In some embodiments, the compound of Formula (I) is not a compound provided in Table 1y, or a salt or stereoisomer thereof.

TABLE 1y

| Compound No. | Name |
|---|---|
| Y1 | (3R,6S,12R,15S,18R,24S,E)-12-benzyl-6-((R)-sec-butyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |
| Y2 | (3R,6S,12R,15S,18R,24S,E)-6-((R)-sec-butyl)-12-(4-chlorobenzyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |
| Y3 | (3R,6S,12R,15R,18R,24S,E)-12-benzyl-6-((R)-sec-butyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |
| Y4 | (3R,6S,12R,15S,18R,24S,E)-12-benzyl-6-((R)-sec-butyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |
| Y5 | (3R,6S,12R,15S,18R,24S,E)-6-((R)-sec-butyl)-12-(4-chlorobenzyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |

TABLE 1y-continued

| Compound No. | Name |
|---|---|
| Y6 | (3R,6S,12S,15S,18R,24S,E)-12-benzyl-6-((R)-sec-butyl)-24-((2R,3S,E)-3-hydroxy-4-methylhex-4-en-2-yl)-18-isobutyl-3,10,13,15,21-pentamethyl-1,19-dioxa-4,7,10,13,16-pentaazacyclotetracos-21-ene-2,5,8,11,14,17,20-heptaone |
| Y7 | (3R,6S,12S,15S,18R,24S,E)-3,12-dibenzyl-6-((R)-sec-butyl)-24-((2R,3S,E)-3-hydroxy-4-methylhex-4-en-2-yl)-18-isobutyl-10,13,15,21-tetramethyl-1,19-dioxa-4,7,10,13,16-pentaazacyclotetracos-21-ene-2,5,8,11,14,17,20-heptaone |
| Y8 | (3S,6S,12R,15S,18R,24S,E)-12-benzyl-6-((R)-sec-butyl)-24-((2R,3R)-3-hydroxyoct-7-yn-2-yl)-18-isobutyl-3,4,10,13,15,21-hexamethyl-1,19-dioxa-4,7,10,13,16-pentaazacyclotetracos-21-ene-2,5,8,11,14,17,20-heptaone |

Any variation of Formula (II) described herein, $R^{15}$ may be substituted or unsubstituted aryl, substituted or unsubstituted heteroaryl, substituted or unsubstituted cycloalkyl, or substituted or unsubstituted heterocyclyl. Any variation of Formula (II) described herein, $R^{15}$ may be substituted or unsubstituted aryl, substituted or unsubstituted heteroaryl, or substituted or unsubstituted heterocyclyl.

In some embodiments of Formula (II), X is —O—. In other embodiments of Formula (II), X is —$NR^d$—. In some of these embodiments, X is —NH—. In some of these embodiments X is —$NR^d$—, where $R^d$ is H or substituted or unsubstituted alkyl. In some of these embodiments, X is —$NR^d$— where $R^d$ is $C_1$-$C_6$ unsubstituted alkyl, such as methyl or ethyl.

In some embodiments of Formula (II), $Y^1$ is —$NR^d$—, where $R^d$ is H or substituted or unsubstituted alkyl. In some of these embodiments, $Y^1$ is —$NR^d$—, where $R^d$ is H or $C_1$-$C_6$ alkyl, such as methyl or ethyl. In other embodiments of Formula (II), $Y^1$ is —O—. In yet other embodiments of Formula (II), $Y^1$ is —S—. In any of the foregoing embodiments of Formula (II), the carbon bearing $Y^1$ is in the (R) stereochemical configuration. In any of the foregoing embodiments of Formula (II), the carbon bearing $Y^1$ is in the (S) stereochemical configuration.

In some embodiments of Formula (II), $R^1$, $R^2$, $R^3$, $R^4$, $R^{8a}$, $R^{8b}$, $R^9$, $R^{10}$, $R^{11}$, $R^{12}$, $R^{13}$, and $R^{14}$ are each independently H or substituted or unsubstituted alkyl, such as unsubstituted $C_1$-$C_6$ alkyl. In some embodiments, $R^3$ is H. In other embodiments, $R^1$ is $C_1$-$C_6$ alkyl, such as methyl. In some embodiments, $R^2$ is H. In other embodiments, $R^2$ is $C_1$-$C_6$ alkyl, such as methyl. In some embodiments, $R^3$ is H. In other embodiments, $R^3$ is $C_1$-$C_6$ alkyl, such as methyl. In some embodiments, $R^4$ is H. In other embodiments, $R^4$ is $C_1$-$C_6$ alkyl, such as methyl. In particular embodiments, $R^4$ is isobutyl. In some embodiments, $R^{8a}$ and $R^{8b}$ are both H. In other embodiments, $R^{8a}$ and $R^{8b}$ are each independently $C_1$-$C_6$ alkyl, such as methyl. In yet other embodiments, one of $R^{8a}$ and $R^{8b}$ is H and the other is $C_1$-$C_6$ alkyl, such as methyl. In some embodiments, $R^9$ is H. In other embodiments, $R^9$ is $C_1$-$C_6$ alkyl, such as methyl. In some embodiments, le is H. In other embodiments, le is $C_1$-$C_6$ alkyl, such as methyl. In particular embodiments, le is sec-butyl. In some embodiments, $R^9$ is H. In other embodiments, $R^9$ is $C_1$-$C_6$ alkyl, such as methyl. In some embodiments, $R^{12}$ and $R^{13}$ are both H. In other embodiments, $R^{12}$ and $R^{13}$ are each independently $C_1$-$C_6$ alkyl, such as methyl. In yet other embodiments, one of $R^{12}$ and $R^{13}$ is H and the other is $C_1$-$C_6$ alkyl, such as methyl. In some embodiments, $R^{14}$ is H. In other embodiments, $R^{14}$ is $C_1$-$C_6$ alkyl, such as methyl.

In some embodiments of Formula (II), $R^1$ is methyl, $R^2$ is methyl, $R^3$ is H, and $R^4$ is isobutyl. In some of these embodiments, X is —O—. In some of these embodiments, le is substituted or unsubstituted aryl and n is 1. In particular embodiments, $R^{15}$ is substituted or unsubstituted phenyl, and n is 1. The substituted phenyl may be a phenyl substituted at the para position. The substituted phenyl may be a phenyl substituted at the meta position. The substituted phenyl may be phenyl substituted with one or more fluoro, chloro, trifluoromethyl, or hydroxyl groups. In particular embodiments, the substituted phenyl is 4-fluorophenyl, 4-chlorophenyl, 4-(trifluoromethyl)phenyl, or 4-hydroxyphenyl. In any of the foregoing embodiments of Formula (II), n may be 0. In any of the foregoing embodiments of Formula (II), n may be 1. In any of the foregoing embodiments of Formula (II), n may be 2.

In some embodiments of Formula (II), $R^5$ is H or $C_1$-$C_6$ alkyl, such as methyl. In other embodiments of Formula (II), $R^5$ is halo. In some such embodiments, $R^5$ is fluoro. In other such embodiments, $R^5$ is chloro. In yet other embodiments of Formula (II), $R^5$ is perhaloalkyl. In some such embodiments, $R^5$ is trifluoromethyl.

In some embodiments of Formula (II), $R^{15}$ is substituted or unsubstituted aryl, such as phenyl. In some embodiments, $R^{15}$ is phenyl substituted with halo, such as fluoro or chloro. In other embodiments, $R^{15}$ is phenyl substituted with hydroxyl. In some embodiments, $R^{15}$ is phenyl which is substituted at the para position. In yet other embodiments, $R^{15}$ is unsubstituted phenyl. In any of the foregoing embodiments, n may be 1. In any of the foregoing embodiments, n may be 2. In any of the foregoing embodiments, n may be 0.

In some embodiments, the carbon bearing $R^2$ is in the (S) stereochemical configuration. In some embodiments, the carbon bearing $R^2$ is in the (R) stereochemical configuration. In some embodiments, the carbon bearing $R^4$ is in the (S) stereochemical configuration. In some embodiments, the carbon bearing $R^4$ is in the (R) stereochemical configuration. In some embodiments, the carbon bearing $R^6$ is in the (S) stereochemical configuration. In some embodiments, the carbon bearing $R^6$ is in the (R) stereochemical configuration. In some embodiments, the carbon bearing $R^7$ is in the (S) stereochemical configuration. In some embodiments, the carbon bearing $R^7$ is in the (R) stereochemical configuration. In some embodiments, the carbon bearing $R^{8a}$ and $R^{8b}$ is in the (S) stereochemical configuration. In some embodiments, the carbon bearing $R^{8a}$ and $R^{8b}$ is in the (R) stereochemical configuration. In some embodiments, the carbon bearing $R^{10}$ is in the (S) stereochemical configuration. In some embodiments, the carbon bearing $R^{10}$ is in the (R) stereochemical configuration. In some embodiments, the carbon bearing $R^{12}$ and $R^{13}$ is in the (S) stereochemical configuration. In some embodiments, the carbon bearing $R^{12}$ and $R^{13}$ is in the (R) stereochemical configuration. In any of the foregoing embodiments of Formula (II), the carbon bearing $Y^1$ is in the (R) stereochemical configuration. In any of the foregoing embodiments of Formula (II), the carbon bearing $Y^1$ is in the (S) stereochemical configuration.

In some embodiments of Formula (II), $R^a$ is H. In some embodiments, $R^a$ is substituted or unsubstituted alkyl or substituted or unsubstituted alkenyl.

In some embodiments, $R^a$ is

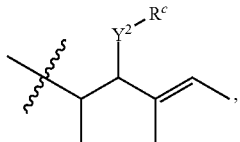

where $Y^2$ and $R^c$ are defined as for Formula (I). In some embodiments, $Y^2$ may be any of the substituents provided for group $Y^1$ in Formula (I), and $R^c$ is as defined for Formula (I).

In some embodiments of Formula (II), k is 1. In some embodiments, k is 2. In some embodiments, k is 3. In some embodiments of Formula (II), k is 2, and $Y^1$ is —O—. In particular embodiments of Formula (II), k is 2, $Y^1$ is —O—, and $R^a$ is H. In some embodiments of Formula (II), k is 3, and $Y^3$ is —O—. In particular embodiments of Formula (II), k is 3, $Y^3$ is —O—, and $R^a$ is H. In some embodiments of Formula (II), k is 1, and $Y^3$ is —O—. In particular embodiments of Formula (II), k is 1, $Y^3$ is —O—, and $R^a$ is H.

In another aspect, the compound of Formula (II) is a compound of Formula (B):

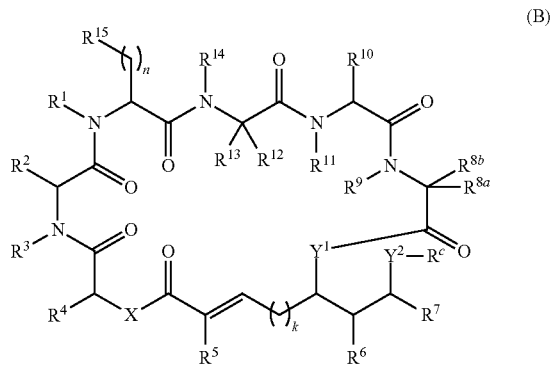

or a salt thereof, wherein
$R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, $R^c$, k, n, X, $Y^1$, and $Y^2$ are as defined for Formula (II).

In some embodiments, the compound of Formula (B) is not a compound of Table 1y, or a salt thereof.

Any variation of Formula (B) described herein, $R^{15}$ may be substituted or unsubstituted aryl, substituted or unsubstituted heteroaryl, substituted or unsubstituted cycloalkyl, or substituted or unsubstituted heterocyclyl. Any variation of Formula (B) described herein, $R^{15}$ may be substituted or unsubstituted aryl, substituted or unsubstituted heteroaryl, or substituted or unsubstituted heterocyclyl.

In some embodiments of Formula (B), X is —O—. In other embodiments of Formula (B), X is —NR$^d$—. In some of these embodiments, X is —NH—. In some of these embodiments X is —NR$^d$—, where R$^d$ is H or substituted or unsubstituted alkyl. In some of these embodiments, X is —NR$^d$— where R$^d$ is $C_1$-$C_6$ unsubstituted alkyl, such as methyl or ethyl.

In some embodiments of Formula (B), $Y^1$ is —NR$^d$—, where R$^d$ is H or substituted or unsubstituted alkyl. In some of these embodiments, $Y^1$ is —NR$^d$—, where R$^d$ is H or $C_1$-$C_6$ alkyl, such as methyl or ethyl. In other embodiments of Formula (B), $Y^1$ is —O—. In yet other embodiments of Formula (B), $Y^1$ is —S—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $Y^2$ is —N—. In some embodiments, $Y^2$ is —O—. In some embodiments, $Y^2$ is —S—. In any of the foregoing embodiments of Formula (B), $R^c$ is H or substituted or unsubstituted alkyl. In other such embodiment, $R^c$ is H or $C_1$-$C_6$ alkyl, such as methyl or ethyl. In yet other such embodiments, $R^c$ is H. In any of the foregoing embodiments of Formula (B), the carbon bearing $Y^2$ is in the (R) stereochemical configuration. In any of the foregoing embodiments of Formula (B), the carbon bearing $Y^2$ is in the (S) stereochemical configuration. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $Y^1$ and $Y^2$ are each —NR$^d$—, where each R$^d$ is independently H or substituted or unsubstituted alkyl. In one such embodiment, $R^c$ is H or substituted or unsubstituted alkyl. In some of these embodiments, $Y^1$ is —NH— or —N(CH$_3$)—. In some of these embodiments of Formula (B), $Y^2$ is —NH— or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In other embodiments of Formula (B), $Y^1$ is —O—, and $Y^2$ is —N(R$^d$)—, where R$^d$ is H or substituted or unsubstituted alkyl. In some such embodiments, $R^c$ is H or substituted or unsubstituted alkyl. In some variations of the foregoing, $R^c$ is H or methyl. In some variations of the foregoing, $Y^2$ is —NH— or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In yet other embodiments of Formula (B), $Y^1$ is —S—, and $Y^2$ is —N(R$^d$)—, where R$^d$ is H or substituted or unsubstituted alkyl. In some such embodiments, $R^c$ is H or substituted or unsubstituted alkyl. In some variations of the foregoing, $R^c$ is H or methyl. In some variations of the foregoing, $Y^2$ is —NH— or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In yet other embodiments, of Formula (B), the (—$Y^2$—$R^c$) group is halo, and $Y^1$ is —N(R$^d$)—, where R$^d$ is H or substituted or unsubstituted alkyl. In some such embodiments, the (—$Y^2$—$R^c$) group is fluoro. In other such embodiments, the (—$Y^2$—$R^c$) group is chloro. In some variations of the foregoing, $Y^1$ is —NH or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some variations of Formula (B), $Y^1$ is —NR$^d$—, where R$^d$ is H or substituted or unsubstituted alkyl, and $Y^2$ is —O—. In some such variations, $R^c$ is H or substituted or unsubstituted alkyl. In particular variations, $R^c$ is H or $C_1$-$C_6$ alkyl, such as methyl or ethyl. In some of the foregoing variations, $Y^1$ is —NH— or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In other variations of Formula (B), $Y^1$ is —O—, and $Y^2$ is —O—. In some of these variations, $R^c$ is H or substituted or unsubstituted alkyl. In particular variations, $R^c$ is H or methyl. In any of the foregoing embodiments of Formula (B), the carbon bearing $Y^1$ is in the (R) stereochemical configuration. In any of the foregoing embodiments of Formula (II), the carbon bearing $Y^1$ is in the (S) stereochemical configuration.

In other variations of Formula (B), $Y^1$ is S—, and $Y^2$ is —O—. In some of these variations, $R^c$ is H or substituted or unsubstituted alkyl. In particular variations, $R^c$ is H or methyl. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In yet other embodiments, of Formula (B), the (—$Y^2$—$R^c$) group is halo, and $Y^1$ is —O—, where $R^d$ is H or substituted or unsubstituted alkyl. In some such embodiments, the (—$Y^2$—$R^c$) group is fluoro. In other such embodiments, the (—$Y^2$—$R^c$) group is chloro. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $Y^1$ is —NR$^d$—, where $R^d$ is H or substituted or unsubstituted alkyl, and $Y^2$ is —S—. In some of these embodiments, $R^c$ is H or substituted or unsubstituted alkyl. In particular embodiments, $R^c$ is H. In other particular embodiments, $R^c$ is methyl. In any of the foregoing embodiments, $Y^1$ is —NH— or —N(CH$_3$)—. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $Y^1$ is —O—, and $Y^2$ is —S—. In some of these embodiments, $Y^1$ is —OH or —OCH$_3$. In some of these embodiments, $R^c$ is H or substituted or unsubstituted alkyl. In particular embodiments, $R^c$ is H. In other particular embodiments, $R^c$ is methyl. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $Y^1$ is —S—, and $Y^2$ is —S—. In some of these embodiments, $R^c$ is H or substituted or unsubstituted alkyl. In particular embodiments, $R^c$ is H. In other particular embodiments, $R^c$ is methyl. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), the (—$Y^2$—$R^c$) group is halo, and $Y^2$ is —S—, where $R^d$ is H or substituted or unsubstituted alkyl. In some such embodiments, the (—$Y^2$—$R^c$) group is fluoro. In other such embodiments, the (—$Y^2$—$R^c$) group is chloro. In any of the foregoing embodiments of Formula (B), the carbon bearing $Y^1$ is in the (R) stereochemical configuration. In any of the foregoing embodiments of Formula (B), the carbon bearing $Y^1$ is in the (S) stereochemical configuration.

In some embodiments of Formula (B), $R^1$, $R^2$, $R^3$, $R^4$, $R^{8a}$, $R^{8b}$, $R^9$, $R^{10}$, $R^{11}$, $R^{12}$, $R^{13}$, and $R^{14}$ are each independently H or substituted or unsubstituted alkyl, such as unsubstituted $C_1$-$C_6$ alkyl. In some embodiments, $R^3$ is H. In other embodiments, $R^1$ is $C_1$-$C_6$ alkyl, such as methyl. In some embodiments, $R^2$ is H. In other embodiments, $R^2$ is $C_1$-$C_6$ alkyl, such as methyl. In some embodiments, $R^3$ is H. In other embodiments, $R^3$ is $C_1$-$C_6$ alkyl, such as methyl. In some embodiments, $R^4$ is H. In other embodiments, $R^4$ is $C_1$-$C_6$ alkyl, such as methyl. In particular embodiments, $R^4$ is isobutyl. In some embodiments, $R^{8a}$ and $R^{8b}$ are both H. In other embodiments, $R^{8a}$ and $R^{8b}$ are each independently $C_1$-$C_6$ alkyl, such as methyl. In yet other embodiments, one of $R^{8a}$ and $R^{8b}$ is H and the other is $C_1$-$C_6$ alkyl, such as methyl. In yet other embodiments, one of $R^{8a}$ and $R^{8b}$ is H and the other is —(CH2)$_4$NH$_2$, which is optionally substituted. In some embodiments, $R^9$ is H. In other embodiments, $R^9$ is $C_1$-$C_6$ alkyl, such as methyl. In some embodiments, $R^{10}$ is H. In other embodiments, $R^{10}$ is $C_1$-$C_6$ alkyl, such as methyl. In particular embodiments, $R^{10}$ is sec-butyl. In some embodiments, $R^9$ is H. In other embodiments, $R^9$ is $C_1$-$C_6$ alkyl, such as methyl. In some embodiments, $R^{12}$ and $R^{13}$ are both H. In other embodiments, $R^{12}$ and $R^{13}$ are each independently $C_1$-$C_6$ alkyl, such as methyl. In yet other embodiments, one of $R^{12}$ and $R^{13}$ is H and the other is $C_1$-$C_6$ alkyl, such as methyl. In some embodiments, $R^{14}$ is H. In other embodiments, $R^{14}$ is $C_1$-$C_6$ alkyl, such as methyl.

In some embodiments of Formula (B), $R^1$ is methyl, $R^2$ is methyl, $R^3$ is H, and $R^4$ is isobutyl. In some of these embodiments, X is —O—. In some of these embodiments, $R^{15}$ is substituted or unsubstituted aryl and n is 1. In particular embodiments, $R^{15}$ is substituted or unsubstituted phenyl, and n is 1. The substituted phenyl may be a phenyl substituted at the para position. The substituted phenyl may be a phenyl substituted at the meta position. The substituted phenyl may be phenyl substituted with one or more fluoro, chloro, trifluoromethyl, or hydroxyl groups. In particular embodiments, the substituted phenyl is 4-fluorophenyl, 4-chlorophenyl, 4-(trifluoromethyl)phenyl, or 4-hydroxyphenyl. In any of the foregoing embodiments of Formula (B), n may be 0. In any of the foregoing embodiments of Formula (B), n may be 1. In any of the foregoing embodiments of Formula (B), n may be 2.

In some embodiments of Formula (B), $R^5$ is H or $C_1$-$C_6$ alkyl, such as methyl. In other embodiments of Formula (B), $R^5$ is halo. In some such embodiments, $R^5$ is fluoro. In other such embodiments, $R^5$ is chloro. In yet other embodiments of Formula (B), $R^5$ is perhaloalkyl. In some such embodiments, $R^5$ is trifluoromethyl.

In some embodiments of Formula (B), $R^6$ is H or $C_1$-$C_6$ alkyl. In some such embodiments, $R^6$ is H. In other such embodiments, $R^6$ is methyl. In other embodiments of Formula (B) embodiments, $R^6$ is halo. In some such embodiments, $R^6$ is fluoro. In some such embodiments, $R^6$ is chloro. In yet other embodiments of Formula (B), $R^6$ is substituted or unsubstituted aryl. In particular embodiments, $R^6$ is substituted phenyl. In other particular embodiments, $R^6$ is unsubstituted phenyl.

In some embodiments of Formula (B), $R^7$ is H or $C_1$-$C_6$ alkyl. In some such embodiments, $R^7$ is methyl. In other such embodiments, $R^7$ is H. In particular embodiments, $R^7$ is

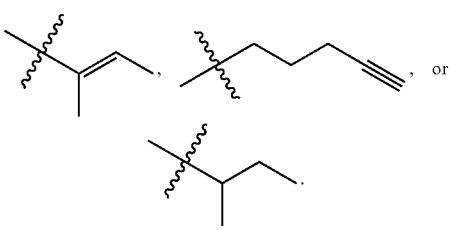

When R$^7$ is sec-butyl, it may be (S)-sec-butyl or (R)-sec-butyl. In some embodiments, R$^7$ is substituted or unsubstituted aryl, such as phenyl.

In some embodiments of Formula (B), R$^5$, R$^6$, and R$^7$ are all substituted or unsubstituted alkyl. In particular embodiments of Formula (B), R$^5$ and R$^6$ are both methyl, and R$^7$ is

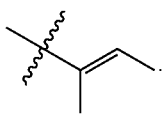 [SMILES: */C(C)=C/C]

In other particular embodiments of Formula (B), R$^5$ and R$^6$ are both methyl, and R$^7$ is

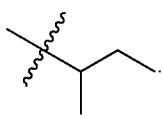 [SMILES: *C(C)CC]

In other particular embodiments of Formula (B), R$^5$ is methyl, and R$^6$ and R$^7$ are both hydrogen. In yet other particular embodiments of Formula (B), R$^5$ and R$^6$ are both methyl, and R$^7$ is hydrogen.

In some embodiments of Formula (B), R$^{15}$ is substituted or unsubstituted aryl, such as phenyl. In some embodiments, R$^{15}$ is phenyl substituted with halo, such as fluoro or chloro. In other embodiments, R$^{15}$ is phenyl substituted with hydroxyl. In other embodiments, R$^{15}$ is phenyl substituted with alkoxy. In other embodiments, R$^{15}$ is phenyl substituted with perhalomethyl. In some embodiments, R$^{15}$ is phenyl which is substituted at the para position. In yet other embodiments, R$^{15}$ is unsubstituted phenyl. In any of the foregoing embodiments, n may be 1. In any of the foregoing embodiments, n may be 2. In any of the foregoing embodiments, n may be 0.

In some embodiments, the carbon bearing R$^2$ is in the (S) stereochemical configuration. In some embodiments, the carbon bearing R$^2$ is in the (R) stereochemical configuration. In some embodiments, the carbon bearing R$^4$ is in the (S) stereochemical configuration. In some embodiments, the carbon bearing R$^4$ is in the (R) stereochemical configuration. In some embodiments, the carbon bearing R$^6$ is in the (S) stereochemical configuration. In some embodiments, the carbon bearing R$^6$ is in the (R) stereochemical configuration. In some embodiments, the carbon bearing R$^7$ is in the (S) stereochemical configuration. In some embodiments, the carbon bearing R$^7$ is in the (R) stereochemical configuration. In some embodiments, the carbon bearing R$^{8a}$ and R$^{8b}$ is in the (S) stereochemical configuration. In some embodiments, the carbon bearing R$^{8a}$ and R$^{8b}$ is in the (R) stereochemical configuration. In some embodiments, the carbon bearing R$^{10}$ is in the (S) stereochemical configuration. In some embodiments, the carbon bearing R$^{10}$ is in the (R) stereochemical configuration. In some embodiments, the carbon bearing R$^{12}$ and R$^{13}$ is in the (S) stereochemical configuration. In some embodiments, the carbon bearing R$^{12}$ and R$^{13}$ is in the (R) stereochemical configuration. In any of the foregoing embodiments of Formula (II), the carbon bearing Y$^1$ is in the (R) stereochemical configuration. In any of the foregoing embodiments of Formula (B), the carbon bearing Y$^1$ is in the (S) stereochemical configuration. In any of the foregoing embodiments of Formula (II), the carbon bearing Y$^2$ is in the (R) stereochemical configuration. In any of the foregoing embodiments of Formula (B), the carbon bearing Y$^2$ is in the (S) stereochemical configuration.

In some variations of any of the embodiments of Formula (B) provided herein, R$^c$ is —C(O)R$^e$. In some such variations, R$^e$ is —NR$^d$R$^d$. In some such variations, R$^e$ is —NR$^d$R$^d$, and each R$^d$ is independently substituted or unsubstituted alkyl. In some such variations, R$^e$ is —NR$^d$R$^d$, where one R$^d$ is substituted or unsubstituted alkyl and the other R$^d$ is methyl. In some such variations, R$^e$ is —NR$^d$R$^d$, where one R$^d$ is alkyl substituted with alkylamino and the other R$^d$ is optionally methyl. In particular variations, R$^e$ is —NR$^d$R$^d$ where one R$^d$ is —(CH$_2$)$_2$NHCH$_3$ and the other R$^d$ is methyl. In any of the aforementioned variations, Y$^2$ is —O—. In any of the aforementioned variations, Y$^2$ is —N(R$^d$)—, where R$^d$ is H or unsubstituted alkyl. In some variations of any of the embodiments of Formula (B) provided herein, —Y$^2$—R$^e$ taken together form the moiety —OC(O)N(CH$_3$)CH$_2$CH$_2$NHCH$_3$.

In some variations of any of the embodiments of Formula (B) provided herein, Y$^2$ is —O—, and R$^c$ is,

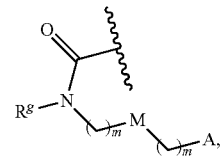

wherein
A is —OH, —NR$^f$R$^h$ or —N$_3$;
M is —(CH$_2$)$_k$— or —(OCH$_2$—CH$_2$)$_k$—, where k is an integer from 1-12, inclusive;
each m is independently an integer from 0 to 3,
R$^f$ is H, substituted or unsubstituted alkyl, or optionally substituted —C(O)O-alkyl;
R$^g$ is H or substituted or unsubstituted alkyl;
R$^h$ is H, substituted or unsubstituted alkyl, —C(O)R$^1$, or —S(O)$_2$R$^1$;
R$^i$ is H, OH, substituted or unsubstituted alkyl, substituted or unsubstituted aryl, substituted or unsubstituted heteroaryl, or

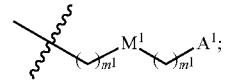

A$^1$ is —NR$^{f1}$R$^{h1}$;
M$^1$ is —(CH$_2$)$_j$— or —(OCH$_2$—CH$_2$)$_j$—, where j is an integer from 1-12, inclusive;
each m$^1$ is independently an integer from 0 to 3;
R$^{f1}$ is H, or substituted or unsubstituted alkyl;

$R^{h1}$ is H, substituted or unsubstituted alkyl, or —C(O)$R^{i1}$; and $R^{i1}$ is H, OH, substituted or unsubstituted alkyl, substituted or unsubstituted aryl, or substituted or unsubstituted heteroaryl.

In some embodiments, $R^i$ is aryl substituted with nitro, formyl, or acetyl. In some embodiments, $R^i$ is

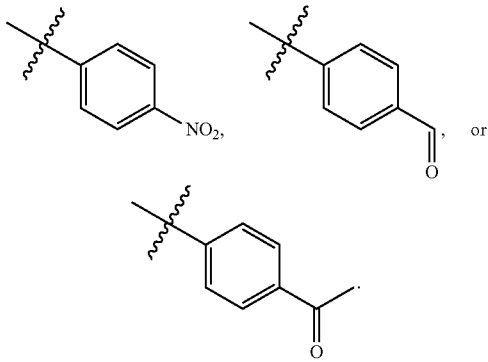

In some embodiments, $R^{i1}$ is aryl substituted with nitro, formyl, or acetyl. In some embodiments, $R^{i1}$ is

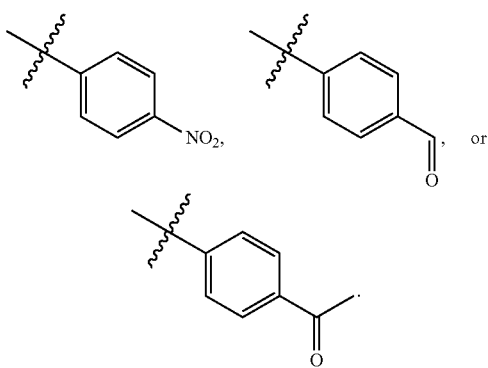

In some embodiments, $R^f$ is —C(O)O-alkyl, wherein the alkyl is substituted. In some embodiments, $R^f$ is —C(O)O-alkyl, wherein the alkyl is substituted with trimethylsilyl.

In some variations of any of the embodiments of Formula (B) provided herein, $Y^2$ is —O—, and $R^c$ is

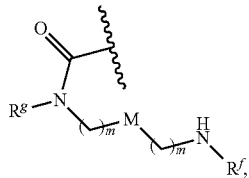

wherein
$R^f$ is H, substituted or unsubstituted alkyl, or —C(O)O-alkyl;
$R^g$ is H or substituted or unsubstituted alkyl;
M is —(CH$_2$)$_k$— or —(OCH$_2$—CH$_2$)$_k$—, where k is an integer from 1-12, inclusive; and
each m is independently an integer from 0 to 3.

In some variations of any of the embodiments of Formula (B) provided herein, the (—Y$^2$—R$^c$) group is H. In some embodiments, the (—Y$^2$—R$^c$) group is H, and $R^2$ is substituted or unsubstituted alkyl. In some embodiments, $R^2$ is $C_1$-$C_6$ alkyl, such as methyl. In some embodiments, $R^2$ is alkyl substituted with NR$^x$R$^y$, wherein R$^x$ and R$^y$ are independently H, —

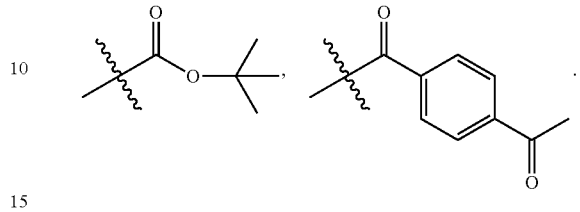

C(O)OR$^i$. or —C(O)R$^i$. In some embodiments, $R^i$ is H, OH, substituted or unsubstituted alkyl, substituted or unsubstituted aryl, substituted or unsubstituted heteroaryl, or

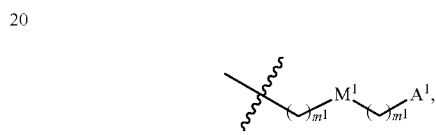

wherein A$^1$, M$^1$, and m$^1$ are as defined above. In some embodiments, $R^2$ is —(CH$_2$)$_4$NH$_2$ which is optionally substituted. In some embodiments, $R^2$ is —(CH$_2$)$_4$NR$^x$R$^y$, and one of R$^x$ and R$^y$ is

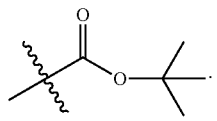

In some embodiments, $R^2$ is —(CH$_2$)$_4$NR$^x$R$^y$, and one of R$^x$ and R$^y$ is

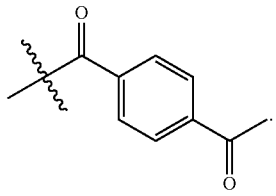 [SMILES: *C(=O)c1ccc(C(C)=O)cc1]

In some variations of any of the embodiments of Formula (B) provided herein, the (—Y$^2$—R$^c$) group is H, and R$^{15}$ is substituted or unsubstituted aryl. In some embodiments, R$^{15}$ is substituted or unsubstituted phenyl. In some embodiments, R$^{15}$ is phenyl which is substituted at the para position. In some embodiments, R$^{15}$ is phenyl substituted with —OR$^c$, wherein R$^c$ is

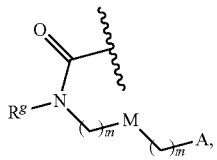

wherein M, A, m, and $R^g$ are as defined above. In some embodiments, $R^{15}$ is phenyl substituted with —$OR^c$, and A is $NH_2$.

In another aspect, the compound of Formula (B) is a compound of Formula (Bi):

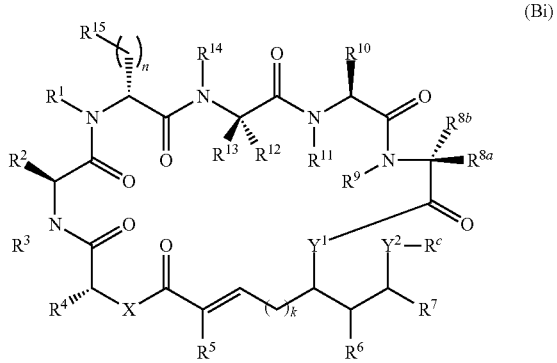

(Bi)

or a salt thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, $R^c$, k, n, X, $Y^1$, and $Y^2$ are as defined for Formula (B).

In another aspect, the compound of Formula (II) is a compound of Formula (IIi):

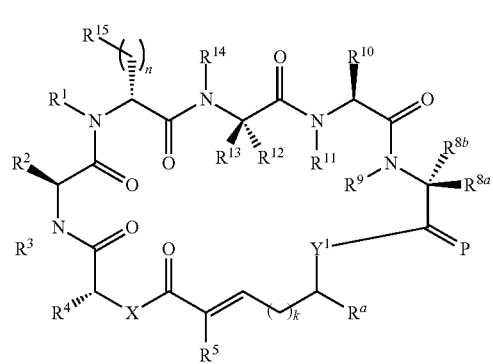

(IIi)

or a salt thereof, wherein $R^1$, $R^2$, $R^3$, $R^4$, $R^5$, $R^{8a}$, $R^{8b}$, $R^9$, $R^{10}$, $R^{11}$, $R^{12}$, $R^{13}$, $R^{14}$, $R^{15}$, k, n, X, $Y^1$, and $R^a$ are as defined for Formula (II).

In another aspect, provided is a compound of Formula (III):

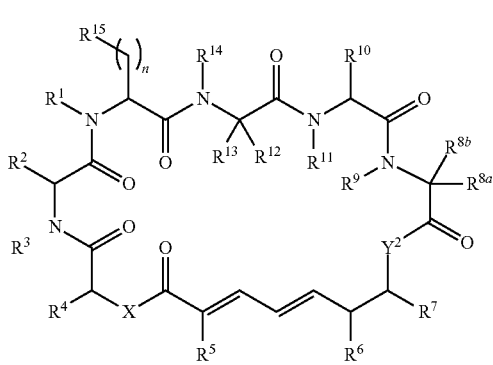

(III)

or a salt thereof, wherein
$R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

X is —$N(R^d)$— or —O—;

$Y^2$ is —$N(R^d)$—, —O—, or —S—; and each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl.

Any variation of Formula (III) described herein, le may be substituted or unsubstituted aryl, substituted or unsubstituted heteroaryl, substituted or unsubstituted cycloalkyl, or substituted or unsubstituted heterocyclyl. Any variation of Formula (III) described herein, $R^{15}$ may be substituted or unsubstituted aryl, substituted or unsubstituted heteroaryl, or substituted or unsubstituted heterocyclyl.

In some embodiments of Formula (III), X is —O—. In other embodiments of Formula (III), X is —$N(R^d)$—. In some of these embodiments, X is —NH—. In some of these embodiments X is —$N(R^d)$—, where $R^d$ is H or substituted or unsubstituted alkyl. In some of these embodiments, X is —$N(R^d)$— where $R^d$ is $C_1$-$C_6$ unsubstituted alkyl, such as methyl or ethyl.

In some embodiments of Formula (III), $Y^2$ is —$N(R^d)$— where $R^d$ is H or substituted or unsubstituted alkyl. In some of these embodiments, $Y^2$ is —$N(R^d)$—, where $R^d$ is H or $C_1$-$C_6$ alkyl, such as methyl or ethyl. In some embodiments, $Y^2$ is —O—. In some embodiments, $Y^2$ is —S—. In any of the foregoing embodiments of Formula (III), the carbon bearing $Y^2$ is in the (R) stereochemical configuration. In any of the foregoing embodiments of Formula (III), the carbon bearing $Y^2$ is in the (S) stereochemical configuration.

In some embodiments of Formula (III), $R^1$, $R^2$, $R^3$, $R^4$, $R^{8a}$, $R^{8b}$, $R^9$, $R^{10}$, $R^{11}$, $R^{12}$, $R^{13}$, and $R^{14}$ are each independently H or substituted or unsubstituted alkyl, such as unsubstituted $C_1$-$C_6$ alkyl. In some embodiments, $R^3$ is H. In other embodiments, $R^1$ is $C_1$-$C_6$ alkyl, such as methyl. In some embodiments, $R^2$ is H. In other embodiments, $R^2$ is $C_1$-$C_6$ alkyl, such as methyl. In some embodiments, $R^3$ is H. In other embodiments, $R^3$ is $C_1$-$C_6$ alkyl, such as methyl. In some embodiments, $R^4$ is H. In other embodiments, $R^4$ is $C_1$-$C_6$ alkyl, such as methyl. In particular embodiments, $R^4$ is isobutyl. In some embodiments, $R^{8a}$ and $R^{8b}$ are both H. In other embodiments, $R^{8a}$ and $R^{8b}$ are each independently $C_1$-$C_6$ alkyl, such as methyl. In yet other embodiments, one of $R^{8a}$ and $R^{8b}$ is H and the other is $C_1$-$C_6$ alkyl, such as methyl. In some embodiments, $R^9$ is H. In other embodiments, $R^9$ is $C_1$-$C_6$ alkyl, such as methyl. In some embodiments, $R^{10}$ is H. In other embodiments, $R^{10}$ is $C_1$-$C_6$ alkyl, such as methyl. In particular embodiments, $R^{10}$ is sec-butyl. In some embodiments, $R^9$ is H. In other embodiments, $R^9$ is $C_1$-$C_6$ alkyl, such as methyl. In some embodiments, $R^{12}$ and $R^{13}$ are both H. In other embodiments, $R^{12}$ and $R^{13}$ are each independently $C_1$-$C_6$ alkyl, such as methyl. In yet other embodiments, one of $R^{12}$ and $R^{13}$ is H and the other is $C_1$-$C_6$ alkyl, such as methyl. In some embodiments, $R^{14}$ is H. In other embodiments, $R^{14}$ is $C_1$-$C_6$ alkyl, such as methyl.

In some embodiments of Formula (III), $R^1$ is methyl, $R^2$ is methyl, $R^3$ is H, and $R^4$ is isobutyl. In some of these embodiments, X is —O—. In some of these embodiments, $R^{15}$ is substituted or unsubstituted aryl and n is 1. In particular embodiments, $R^{15}$ is substituted or unsubstituted phenyl, and n is 1. The substituted phenyl may be a phenyl substituted at the para position. The substituted phenyl may be a phenyl substituted at the meta position. The substituted phenyl may be phenyl substituted with one or more fluoro, chloro, trifluoromethyl, or hydroxyl groups. In particular embodiments, the substituted phenyl is 4-fluorophenyl, 4-chlorophenyl, 4-(trifluoromethyl)phenyl, or 4-hydroxyphenyl. In any of the foregoing embodiments of Formula (III), n may be 0. In any of the foregoing embodiments of Formula (III), n may be 1. In any of the foregoing embodiments of Formula (III), n may be 2.

In some embodiments of Formula (III), $R^5$ is H or $C_1$-$C_6$ alkyl, such as methyl. In other embodiments of Formula (III), $R^5$ is halo. In some such embodiments, $R^5$ is fluoro. In other such embodiments, $R^5$ is chloro. In yet other embodiments of Formula (III), $R^5$ is perhaloalkyl. In some such embodiments, $R^5$ is trifluoromethyl.

In some embodiments of Formula (III), $R^6$ is H or $C_1$-$C_6$ alkyl. In some such embodiments, $R^6$ is H. In other such embodiments, $R^6$ is methyl. In other embodiments of Formula (III), $R^6$ is halo. In some such embodiments, $R^6$ is fluoro. In some such embodiments, $R^6$ is chloro. In yet other embodiments of Formula (III), $R^6$ is substituted or unsubstituted aryl. In particular embodiments, $R^6$ is substituted phenyl. In other particular embodiments, $R^6$ is unsubstituted phenyl.

In some embodiments of Formula (III), $R^7$ is H or $C_1$-$C_6$ alkyl. In some such embodiments, $R^7$ is methyl. In other such embodiments, $R^7$ is H. In particular embodiments, $R^7$ is

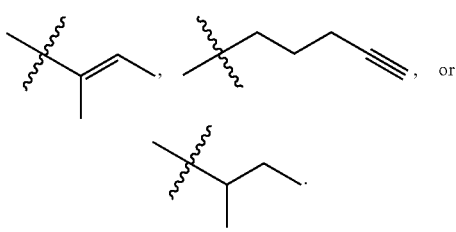

When $R^7$ is sec-butyl, it may be (S)-sec-butyl or (R)-sec-butyl. In some embodiments, $R^7$ is substituted or unsubstituted aryl, such as phenyl.

In some embodiments of Formula (III), $R^5$, $R^6$, and $R^7$ are all substituted or unsubstituted alkyl. In particular embodiments of Formula (III), $R^5$ and $R^6$ are both methyl, and $R^7$ is

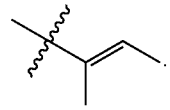 [SMILES: */C(C)=C/C]

In other particular embodiments of Formula (III), $R^5$ and $R^6$ are both methyl, and $R^7$ is

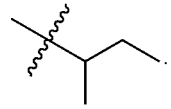 [SMILES: *C(C)CC]

In other particular embodiments of Formula (III), $R^5$ is methyl, and $R^6$ and $R^7$ are both hydrogen. In yet other particular embodiments of Formula (III), $R^5$ and $R^6$ are both methyl, and $R^7$ is hydrogen.

In some embodiments of Formula (III), $R^{15}$ is substituted or unsubstituted aryl, such as phenyl. In some embodiments, $R^{15}$ is phenyl substituted with halo, such as fluoro or chloro. In other embodiments, $R^{15}$ is phenyl substituted with hydroxyl. In other embodiments, $R^{15}$ is phenyl substituted with alkoxy. In other embodiments, $R^{15}$ is phenyl substituted with perhalomethyl. In some embodiments, $R^{15}$ is phenyl which is substituted at the para position. In yet other embodiments, $R^{15}$ is unsubstituted phenyl. In any of the foregoing embodiments, n may be 1. In any of the foregoing embodiments, n may be 2. In any of the foregoing embodiments, n may be 0.

In some variations of any of the embodiments of Formula (III) provided herein, $R^2$ is alkyl substituted with $NR^xR^y$, wherein $R^x$ and $R^y$ are independently H, —

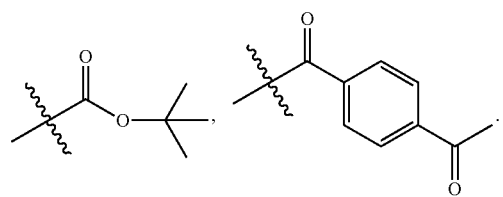

$C(O)OR^i$. or —$C(O)R^i$. In some embodiments, $R^i$ is H, OH, substituted or unsubstituted alkyl, substituted or unsubstituted aryl, substituted or unsubstituted heteroaryl, or

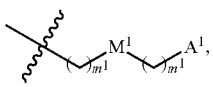

wherein $A^1$, $M^1$, and $m^1$ are as defined above. In some embodiments, $R^2$ is —$(CH_2)_4NH_2$ which is optionally substituted. In some embodiments, $R^2$ is —$(CH_2)_4NR^xR^y$, and one of $R^x$ and $R^y$ is

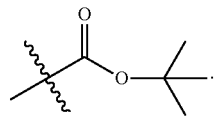

In some embodiments, $R^2$ is —$(CH_2)_4NR^xR^y$, and one of $R^x$ and $R^y$ is

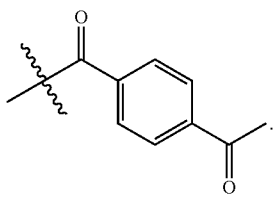

In some embodiments, the carbon bearing $R^2$ is in the (S) stereochemical configuration. In some embodiments, the carbon bearing $R^2$ is in the (R) stereochemical configuration. In some embodiments, the carbon bearing $R^4$ is in the (S) stereochemical configuration. In some embodiments, the carbon bearing $R^4$ is in the (R) stereochemical configuration. In some embodiments, the carbon bearing $R^6$ is in the (S) stereochemical configuration. In some embodiments, the carbon bearing $R^6$ is in the (R) stereochemical configuration. In some embodiments, the carbon bearing $R^7$ is in the (S) stereochemical configuration. In some embodiments, the carbon bearing $R^7$ is in the (R) stereochemical configuration. In some embodiments, the carbon bearing $R^{8a}$ and $R^{8b}$ is in the (S) stereochemical configuration. In some embodiments, the carbon bearing $R^{8a}$ and $R^{8b}$ is in the (R) stereochemical configuration. In some embodiments, the carbon bearing $R^{10}$ is in the (S) stereochemical configuration. In some embodiments, the carbon bearing $R^{10}$ is in the (R) stereochemical configuration. In some embodiments, the carbon bearing $R^{12}$ and $R^{13}$ is in the (S) stereochemical configuration. In some embodiments, the carbon bearing $R^{12}$ and $R^{13}$ is in the (R) stereochemical configuration.

In another aspect, the compound of Formula (III) is a compound of Formula (IIIi):

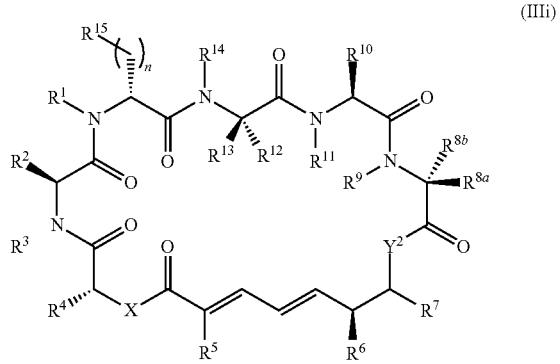

or a salt thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, X, and $Y^2$ are as defined for Formula (III).

In another aspect, the compound of Formula (I) is a compound of Formula (Ia):

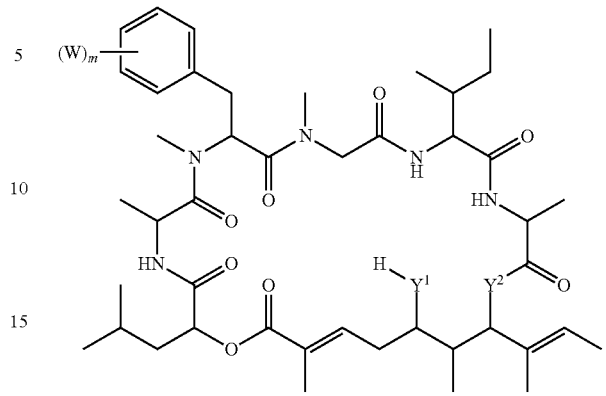

or a salt thereof, wherein $Y^1$ and $Y^2$ are defined as for Formula (I);

W is halo, perhalomethyl, cyano, nitro, amino, hydroxy, or alkoxy; and m is 0, 1, 2, 3, 4, or 5.

In some embodiments of Formula (Ia), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ia), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ia), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Ia), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ia), $Y^1$ is in the (R) stereochemical configuration. In any of the foregoing embodiments of Formula (Ia), $Y^1$ is in the (S) stereochemical configuration. In any of the foregoing embodiments of Formula (Ia), $Y^2$ is in the (R) stereochemical configuration. In any of the foregoing embodiments of Formula (Ia), $Y^2$ is in the (S) stereochemical configuration.

In some embodiments of Formula (Ia), m is 0. In some of these embodiments of Formula (Ia), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (Ia), the compound may contain one of the following features: i) $Y^1$ and $Y^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In some of these embodiments of Formula (Ia), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—. In any of the foregoing embodiments of Formula (Ia), Y$^1$ is in the (R) stereochemical configuration. In any of the foregoing embodiments of Formula (Ia), Y$^1$ is in the (S) stereochemical configuration. In any of the foregoing embodiments of Formula (Ia), Y$^2$ is in the (R) stereochemical configuration. In any of the foregoing embodiments of Formula (Ia), Y$^2$ is in the (S) stereochemical configuration.

In another aspect, the compound of Formula (I) is a compound of Formula (Iai):

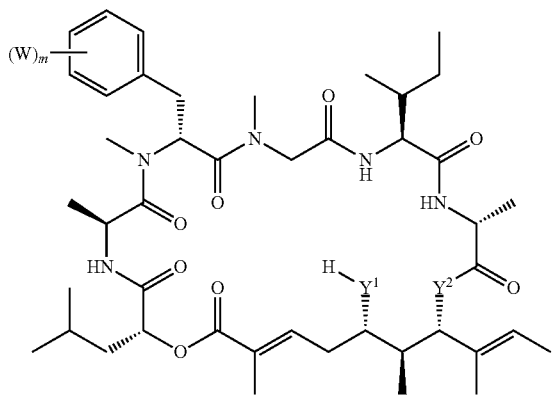

(Iai)

or a salt thereof, wherein Y$^1$, Y$^2$, W, and m are as defined for Formula (Ia).

In some embodiments of Formula (Iai), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Iai), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In any of the foregoing embodiments of Formula (Iai), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In any of the foregoing embodiments of Formula (Iai), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—.

In some embodiments of Formula (Iai), m is 0. In some of these embodiments of Formula (Iai), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In some of these embodiments of Formula (Iai), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In some of these embodiments of Formula (Iai), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—.

In another aspect, the compound of Formula (II) is a compound of Formula (IIa):

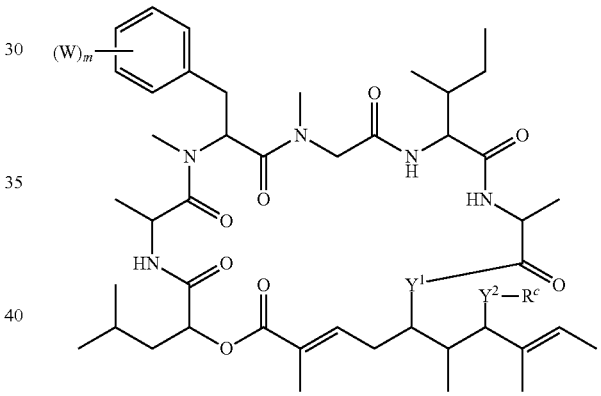

(IIa)

or a salt thereof, wherein Y$^1$, Y$^2$, and R$^e$ are as defined for Formula (II);

W is halo, perhalomethyl, cyano, nitro, amino, hydroxy, or alkoxy; and m is 0, 1, 2, 3, 4, or 5.

In some embodiments of Formula (IIa), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ia), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In any of the foregoing embodiments of Formula (IIa), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In any of the foregoing embodiments of Formula (IIa), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—. In any of the foregoing embodiments of Formula (IIa), R$^c$ is H. In any of the foregoing embodiments of Formula (IIa), R$^c$ is substituted or unsubstituted alkyl. In any of the foregoing embodiments of Formula (IIa), R$^c$ is methyl. In any of the foregoing embodiments of Formula (IIa), the (—Y$^2$—R$^c$) group is halo, such as fluoro or chloro. In any of the foregoing embodiments of Formula (IIa), Y$^1$ is in the (R) stereochemical configuration. In any of the foregoing embodiments of Formula (IIa), Y$^1$ is in the (S) stereochemical configuration. In any of the foregoing embodiments of Formula (IIa), Y$^2$ is in the (R) stereochemical configuration. In any of the foregoing embodiments of Formula (IIa), Y$^2$ is in the (S) stereochemical configuration.

In some embodiments of Formula (IIa), m is 0. In some of these embodiments of Formula (Ia), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In some of these embodiments of Formula (IIa), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In some of these embodiments of Formula (IIa), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—. In any of the foregoing embodiments of Formula (IIa), R$^c$ is H. In any of the foregoing embodiments of Formula (IIa), R$^c$ is substituted or unsubstituted alkyl. In any of the foregoing embodiments of Formula (IIa), R$^c$ is methyl. In any of the foregoing embodiments of Formula (IIa), the (—Y$^2$—R$^c$) group is halo, such as fluoro or chloro. In any of the foregoing embodiments of Formula (IIa), Y$^1$ is in the (R) stereochemical configuration. In any of the foregoing embodiments of Formula (IIa), Y$^1$ is in the (S) stereochemical configuration. In any of the foregoing embodiments of Formula (IIa), Y$^2$ is in the (R) stereochemical configuration. In any of the foregoing embodiments of Formula (IIa), Y$^2$ is in the (S) stereochemical configuration.

In another aspect, the compound of Formula (II) is a compound of Formula (IIai):

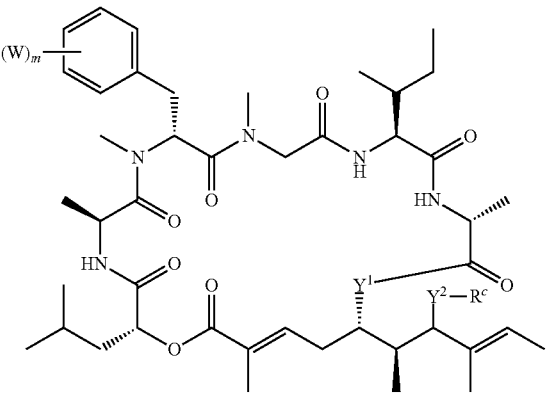

(IIai)

or a salt thereof, wherein Y$^1$, Y$^2$, W, and m are as defined for Formula (IIa).

In some embodiments of Formula (IIai), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIai), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In any of the foregoing embodiments of Formula (IIai), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In any of the foregoing embodiments of Formula (IIai), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—. In any of the foregoing embodiments of Formula (Ia), R$^c$ is H. In any of the foregoing embodiments of Formula (IIai), R$^c$ is substituted or unsubstituted alkyl. In any of the foregoing embodiments of Formula (IIai), R$^c$ is methyl. In any of the foregoing embodiments of Formula (IIai), the (—Y$^2$—R$^c$) group is halo, such as fluoro or chloro.

In some embodiments of Formula (IIai), m is 0. In some of these embodiments of Formula (IIai), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In some of these embodiments of Formula (IIai), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In some of these embodiments of Formula (IIai), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIai), $R^c$ is H. In any of the foregoing embodiments of Formula (IIai), $R^c$ is substituted or unsubstituted alkyl. In any of the foregoing embodiments of Formula (IIai), $R^c$ is methyl. In any of the foregoing embodiments of Formula (IIai), the (—$Y^2$—$R^c$) group is halo, such as fluoro or chloro.

In another aspect, the compound of Formula (I) is a compound of Formula (Ib):

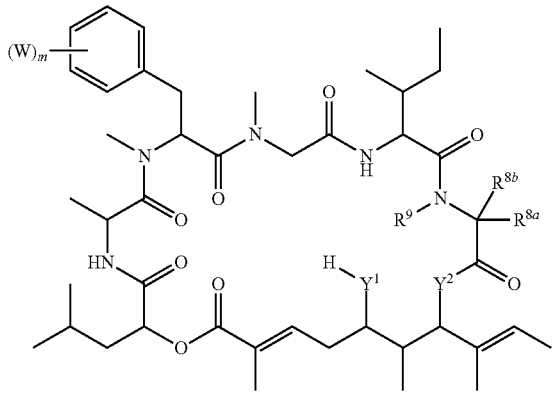

(Ib)

or a salt thereof, wherein $R^{8a}$, $R^{8b}$, $R^9$, $Y^1$, and $Y^2$ are defined as for Formula (I);

W is halo, perhalomethyl, cyano, nitro, amino, hydroxy, or alkoxy; and m is 0, 1, 2, 3, 4, or 5.

In some embodiments of Formula (Ib), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ib), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ib), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ib), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Ib), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ib), $R^c$ is H. In any of the foregoing embodiments of Formula (Ib), $R^c$ is substituted or unsubstituted alkyl. In any of the foregoing embodiments of Formula (Ib), $R^c$ is methyl. In any of the foregoing embodiments of Formula (Ib), $Y^1$ is in the (R) stereochemical configuration. In any of the foregoing embodiments of Formula (Ib), $Y^1$ is in the (S) stereochemical configuration. In any of the foregoing embodiments of Formula (Ib), $Y^2$ is in the (R) stereochemical configuration. In any of the foregoing embodiments of Formula (Ib), $Y^2$ is in the (S) stereochemical configuration.

In some embodiments of Formula (Ib), m is 0. In some of these embodiments of Formula (Ib), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (Ib), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (Ib), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ib), $R^c$ is H. In any of the foregoing embodiments of Formula (Ib), $R^c$ is substituted or unsubstituted alkyl. In any of the foregoing embodiments of Formula (Ib), $R^c$ is methyl. In any of the foregoing embodiments of Formula (Ib), $Y^1$ is in the (R) stereochemical configuration. In any of the foregoing embodiments of Formula (Ib), $Y^1$ is in the (S) stereochemical configuration. In any of the foregoing embodiments of Formula (Ib), $Y^2$ is in the (R) stereochemical configuration. In any of the foregoing embodiments of Formula (Ib), $Y^2$ is in the (S) stereochemical configuration.

In another aspect, the compound of Formula (I) is a compound of Formula (Ibi):

(Ibi)

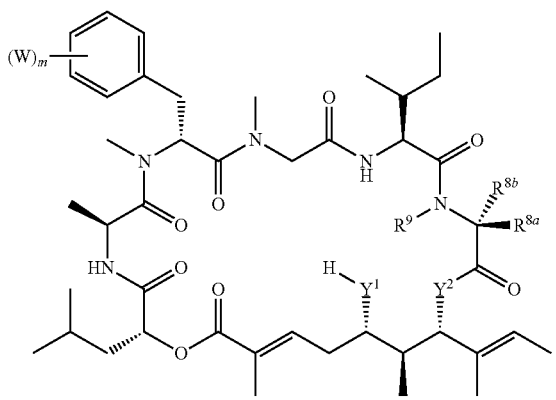

or a salt thereof, wherein $R^{8a}$, $R^{8b}$, $R^9$, $Y^1$, $Y^2$, W, and m are as defined for Formula (Ib).

In some embodiments of Formula (Ibi), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ibi), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ibi), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ibi), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Ibi), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—.

In some embodiments of Formula (Ibi), m is 0. In some of these embodiments of Formula (Ibi), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (Ibi), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (Ibi), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ibi), $R^c$ is H. In any of the foregoing embodiments of Formula (Ibi), $R^c$ is substituted or unsubstituted alkyl. In any of the foregoing embodiments of Formula (Ibi), $R^c$ is methyl.

In another aspect, the compound of Formula (II) is a compound of Formula (IIb):

(IIb)

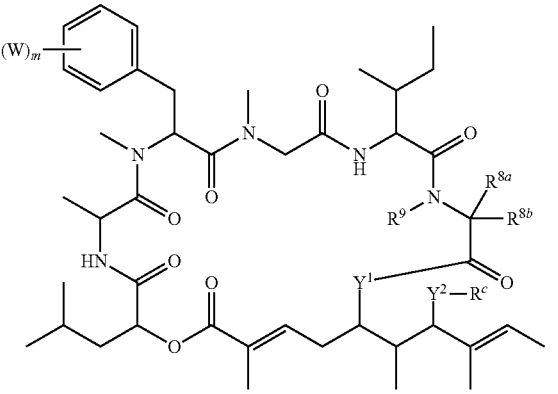

or a salt thereof, wherein $R^{8a}$, $R^{8b}$, $R^9$, $R^c$, $Y^1$, and $Y^2$ are defined as for Formula (II);

W is halo, perhalomethyl, cyano, nitro, amino, hydroxy, or alkoxy; and m is 0, 1, 2, 3, 4, or 5.

In some embodiments of Formula (IIb), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIb), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIb), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (IIb), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIb), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIb), $R^c$ is H. In any of the foregoing embodiments of Formula (IIb), $R^c$ is substituted or unsubstituted alkyl. In any of the foregoing embodiments of Formula (IIb), $R^c$ is methyl. In any of the foregoing embodiments of Formula (IIb), the (—$Y^2$—$R^c$) group is halo, such as fluoro or chloro. In any of the foregoing embodiments of Formula (IIb), $Y^1$ is in the (R) stereochemical configuration. In any of the foregoing embodiments of Formula (IIb), $Y^1$ is in the (S) stereochemical configuration. In any of the foregoing embodiments of Formula (IIb), $Y^2$ is in the (R) stereochemical configuration. In any of the foregoing embodiments of Formula (IIb), $Y^2$ is in the (S) stereochemical configuration.

In some embodiments of Formula (IIb), m is 0. In some of these embodiments of Formula (IIb), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (IIb), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (IIb), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIb), $R^c$ is H. In any of the foregoing embodiments of Formula (IIb), $R^c$ is substituted or unsubstituted alkyl. In any of the foregoing embodiments of Formula (IIb), $R^c$ is methyl. In any of the foregoing embodiments of Formula (IIb), the (—$Y^2$—$R^c$) group is halo, such as fluoro or chloro. In any of the foregoing embodiments of Formula (IIb), $Y^1$ is in the (R) stereochemical configuration. In any of the foregoing embodiments of Formula (IIb), $Y^1$ is in the (S) stereochemical configuration. In any of the foregoing embodiments of Formula (IIb), $Y^2$ is in the (R) stereochemical configuration. In any of the foregoing embodiments of Formula (IIb), $Y^2$ is in the (S) stereochemical configuration.

In another aspect, the compound of Formula (II) is a compound of Formula (IIbi):

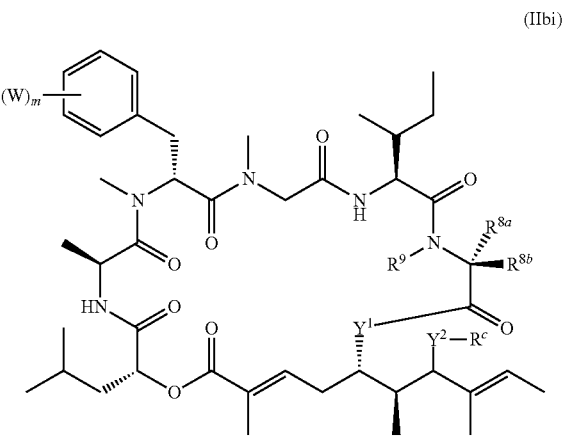

(IIbi)

or a salt thereof, wherein $R^{8a}$, $R^{8b}$, $R^9$, $R^c$, $Y^1$, $Y^2$, W, and m are as defined for Formula (IIb).

In some embodiments of Formula (IIbi), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIbi), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIbi), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (IIbi), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIbi), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIbi), $R^c$ is H. In any of the foregoing embodiments of Formula (IIbi), $R^c$ is substituted or unsubstituted alkyl. In any of the foregoing embodiments of Formula (IIbi), $R^c$ is methyl. In any of the foregoing embodiments of Formula (IIbi), the (—$Y^2$—$R^c$) group is halo, such as fluoro or chloro.

In some embodiments of Formula (IIbi), m is 0. In some of these embodiments of Formula (Ibi), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—;

and (v) $Y^1$ is —O—, and $Y^2$ is —N(CH$_3$)—. In some of these embodiments of Formula (IIbi), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N(R$^d$)—; (iv) $Y^1$ is —S—, and $Y^2$ is —NH—; and (v) $Y^1$ is —S—, and $Y^2$ is —N(CH$_3$)—. In some of these embodiments of Formula (IIbi), the compound may contain one of the following features: i) $Y^1$ and $Y^2$ are each —N(R$^d$)—; ii) $Y^1$ is —N(R$^d$)—, and $Y^2$ is —S—; iii) $Y^1$ is —N(R$^d$)—, and $Y^2$ is —O—; (iv) $Y^1$ is —N(R$^d$)—, and $Y^2$ is —NH—; (v) $Y^1$ is —N(R$^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIbi), $R^c$ is H. In any of the foregoing embodiments of Formula (IIbi), $R^c$ is substituted or unsubstituted alkyl. In any of the foregoing embodiments of Formula (IIbi), $R^c$ is methyl. In any of the foregoing embodiments of Formula (IIbi), the (—Y$^2$—R$^c$) group is halo, such as fluoro or chloro.

In another aspect, the compound of Formula (I) is a compound of Formula (Ic):

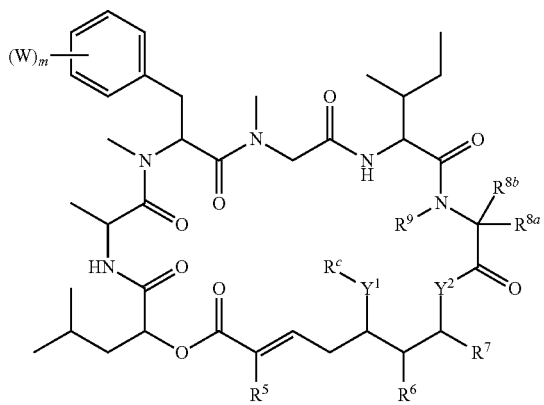

(Ic)

or a salt thereof, wherein $R^5$, $R^6$, $R^7$, $R^{8a}$, $R^{8b}$, $R^9$, $R^c$, $Y^1$, and $Y^2$ are defined as for Formula (I);

W is halo, perhalomethyl, cyano, nitro, amino, hydroxy, or alkoxy; and m is 0, 1, 2, 3, 4, or 5.

In some embodiments of Formula (Ic), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ic), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N(R$^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ic), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N(R$^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Ic), the compound may contain one of the following features: i) $Y^1$ and $Y^2$ are each —N(R$^d$)—; ii) $Y^1$ is —N(R$^d$)—, and $Y^2$ is —S—; iii) $Y^1$ is —N(R$^d$)—, and $Y^2$ is —O—; (iv) $Y^1$ is —N(R$^d$)—, and $Y^2$ is —NH—; (v) $Y^1$ is —N(R$^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ic), $R^c$ is H. In any of the foregoing embodiments of Formula (Ic), $R^e$ is substituted or unsubstituted alkyl. In any of the foregoing embodiments of Formula (Ic), $R^e$ is methyl. In any of the foregoing embodiments of Formula (Ic), the (—Y$^1$—R$^c$) group is halo, such as fluoro or chloro. In any of the foregoing embodiments of Formula (Ic), $Y^1$ is in the (R) stereochemical configuration. In any of the foregoing embodiments of Formula (Ic), $Y^1$ is in the (S) stereochemical configuration. In any of the foregoing embodiments of Formula (Ic), $Y^2$ is in the (R) stereochemical configuration. In any of the foregoing embodiments of Formula (Ic), $Y^2$ is in the (S) stereochemical configuration.

In some embodiments of Formula (Ic), $R^5$ is H or $C_1$-$C_6$ alkyl, such as methyl. In other embodiments of Formula (Ic), $R^5$ is halo. In some such embodiments, $R^5$ is fluoro. In other such embodiments, $R^5$ is chloro. In yet other embodiments of Formula (Ic), $R^5$ is perhaloalkyl. In some such embodiments, $R^5$ is trifluoromethyl.

In some embodiments of Formula (Ic), $R^6$ is H or $C_1$-$C_6$ alkyl. In some such embodiments, $R^6$ is H. In other such embodiments, $R^6$ is methyl. In other embodiments of Formula (Ic) embodiments, $R^6$ is halo. In some such embodiments, $R^6$ is fluoro. In some such embodiments, $R^6$ is chloro. In yet other embodiments of Formula (Ic), $R^6$ is substituted or unsubstituted aryl. In particular embodiments, $R^6$ is substituted phenyl. In other particular embodiments, $R^6$ is unsubstituted phenyl.

In some embodiments of Formula (Ic), $R^7$ is H or $C_1$-$C_6$ alkyl. In some such embodiments, $R^7$ is methyl. In other such embodiments, $R^7$ is H. In particular embodiments, $R^7$ is

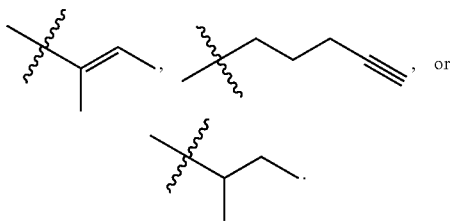

When $R^7$ is sec-butyl, it may be (S)-sec-butyl or (R)-sec-butyl. In some embodiments, $R^7$ is substituted or unsubstituted aryl, such as phenyl.

In some embodiments of Formula (Ic), $R^5$, $R^6$, and $R^7$ are all substituted or unsubstituted alkyl. In particular embodiments of Formula (Ic), $R^5$ and $R^6$ are both methyl, and $R^7$ is

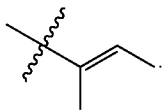 [SMILES: */C(C)=C/C]

In other particular embodiments of Formula (Ic), $R^5$ and $R^6$ are both methyl, and $R^7$ is

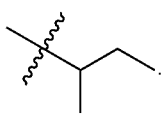 [SMILES: *C(C)CC]

In other particular embodiments of Formula (Ic), $R^5$ is methyl, and $R^6$ and $R^7$ are both hydrogen. In yet other particular embodiments of Formula (Ic), $R^5$ and $R^6$ are both methyl, and $R^7$ is hydrogen.

In some variations of Formula (Ic), $R^{8a}$ and $R^{8b}$ are independently selected from H and methyl, $R^9$ is H, $R^5$ and $R^6$ are both methyl. In some such variations, the compound of Formula (Ic) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^e$ is methyl, provided that i) and ii) do not both apply simultaneously and v) and vi) do not apply simultaneously. In any of the foregoing variations, the compound of Formula (Ic) is further defined by having m=1. In any of the foregoing variations, the compound of Formula (Ic) is further defined by having m=0.

In another aspect, the compound of Formula (I) is a compound of Formula (Ici):

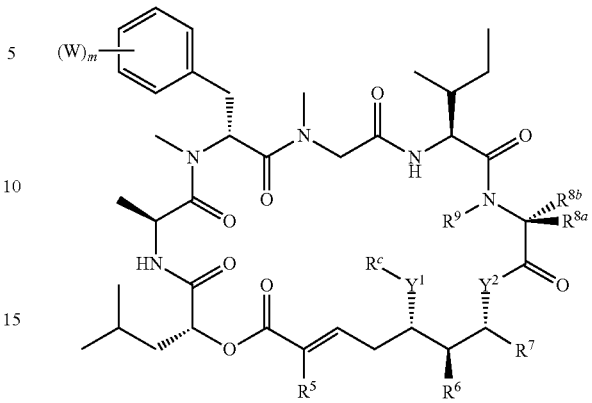

or a salt thereof, wherein $R^5$, $R^6$, $R^7$, $R^{8a}$, $R^{8b}$, $R^9$, $R^c$, $Y^1$, $Y^2$, W, and m are defined as for Formula (Ic).

In some embodiments of Formula (Ici), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ici), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ici), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ici), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Ici), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ici), $R^c$ is H. In any of the foregoing embodiments of Formula (Ici), $R^c$ is substituted or unsubstituted alkyl. In any of the foregoing embodiments of Formula (Ici), $R^c$ is methyl. In any of the foregoing embodiments of Formula (Ici), the (—$Y^1$—$R^c$) group is halo, such as fluoro or chloro.

In some embodiments of Formula (Ici), m is 0. In some of these embodiments of Formula (Ici), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (Ici), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (Ici), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Ic), $R^c$ is H. In any of the foregoing embodiments of Formula (Ici), $R^c$ is substituted or unsubstituted alkyl. In any of the foregoing embodiments of Formula (Ici), $R^c$ is methyl. In any of the foregoing embodiments of Formula (Ici), the (—$Y^1$—$R^c$) group is halo, such as fluoro or chloro.

In some embodiments of Formula (Ici), $R^5$ is H or $C_1$-$C_6$ alkyl, such as methyl. In other embodiments of Formula (Ici), $R^5$ is halo. In some such embodiments, $R^5$ is fluoro. In other such embodiments, $R^5$ is chloro. In yet other embodiments of Formula (Ici), $R^5$ is perhaloalkyl. In some such embodiments, $R^5$ is trifluoromethyl.

In some embodiments of Formula (Ici), $R^6$ is H or $C_1$-$C_6$ alkyl. In some such embodiments, $R^6$ is H. In other such embodiments, $R^6$ is methyl. In other embodiments of Formula (Ici) embodiments, $R^6$ is halo. In some such embodiments, $R^6$ is fluoro. In some such embodiments, $R^6$ is chloro. In yet other embodiments of Formula (Ici), $R^6$ is substituted or unsubstituted aryl. In particular embodiments, $R^6$ is substituted phenyl. In other particular embodiments, $R^6$ is unsubstituted phenyl.

In some embodiments of Formula (Ici), $R^7$ is H or $C_1$-$C_6$ alkyl. In some such embodiments, $R^7$ is methyl. In other such embodiments, $R^7$ is H. In particular embodiments, $R^7$ is

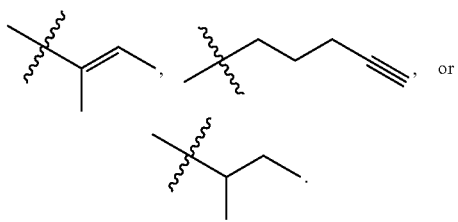

When $R^7$ is sec-butyl, it may be (S)-sec-butyl or (R)-sec-butyl. In some embodiments, $R^7$ is substituted or unsubstituted aryl, such as phenyl.

In some embodiments of Formula (Ici), $R^5$, $R^6$, and $R^7$ are all substituted or unsubstituted alkyl. In particular embodiments of Formula (Ici), $R^5$ and $R^6$ are both methyl, and $R^7$ is

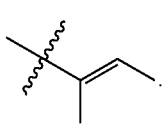 [SMILES: */C(C)=C/C]

In other particular embodiments of Formula (Ici), $R^5$ and $R^6$ are both methyl, and $R^7$ is

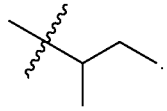 [SMILES: *C(C)CC]

In other particular embodiments of Formula (Ici), $R^5$ is methyl, and $R^6$ and $R^7$ are both hydrogen. In yet other particular embodiments of Formula (Ici), $R^5$ and $R^6$ are both methyl, and $R^7$ is hydrogen.

In some variations of Formula (Ici), $R^{8a}$ and $R^{8b}$ are independently selected from H and methyl, $R^9$ is H, $R^5$ and $R^6$ are both methyl. In some such variations, the compound of Formula (Ici) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^c$ is methyl, provided that i) and ii) do not both apply simultaneously and v) and vi) do not apply simultaneously. In any of the foregoing variations, the compound of Formula (Ici) is further defined by having m=1. In any of the foregoing variations, the compound of Formula (Ici) is further defined by having m=0.

In another aspect, the compound of Formula (II) is a compound of Formula (IIc):

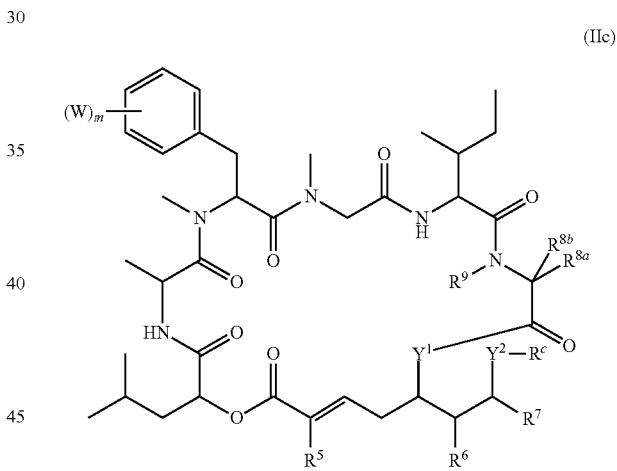

or a salt thereof, wherein $R^5$, $R^6$, $R^7$, $R^{8a}$, $R^{8b}$, $R^9$, $R^c$, $Y^1$, and $Y^2$ are defined as for Formula (II);

W is halo, perhalomethyl, cyano, nitro, amino, hydroxy, or alkoxy; and m is 0, 1, 2, 3, 4, or 5.

In some embodiments of Formula (IIc), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIc), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIc), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ic), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIc), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIc), $R^c$ is H. In any of the foregoing embodiments of Formula (IIc), $R^c$ is substituted or unsubstituted alkyl. In any of the foregoing embodiments of Formula (IIc), $R^c$ is methyl. In any of the foregoing embodiments of Formula (IIc), the (—$Y^2$—$R^c$) group is halo, such as fluoro or chloro. In any of the foregoing embodiments of Formula (IIc), $Y^1$ is in the (R) stereochemical configuration. In any of the foregoing embodiments of Formula (IIc), $Y^1$ is in the (S) stereochemical configuration. In any of the foregoing embodiments of Formula (IIc), $Y^2$ is in the (R) stereochemical configuration. In any of the foregoing embodiments of Formula (IIc), $Y^2$ is in the (S) stereochemical configuration.

In some embodiments of Formula (IIc), m is 0. In some of these embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (IIc), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (IIc), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIc), $R^c$ is H. In any of the foregoing embodiments of Formula (IIc), $R^c$ is substituted or unsubstituted alkyl. In any of the foregoing embodiments of Formula (IIc), $R^c$ is methyl. In any of the foregoing embodiments of Formula (IIc), the (—$Y^2$—$R^c$) group is halo, such as fluoro or chloro. In any of the foregoing embodiments of Formula (IIc), $Y^1$ is in the (R) stereochemical configuration. In any of the foregoing embodiments of Formula (IIc), $Y^1$ is in the (S) stereochemical configuration. In any of the foregoing embodiments of Formula (IIc), $Y^2$ is in the (R) stereochemical configuration. In any of the foregoing embodiments of Formula (IIc), $Y^2$ is in the (S) stereochemical configuration.

In some embodiments of Formula (IIc), $R^5$ is H or $C_1$-$C_6$ alkyl, such as methyl. In other embodiments of Formula (IIc), $R^5$ is halo. In some such embodiments, $R^5$ is fluoro. In other such embodiments, $R^5$ is chloro. In yet other embodiments of Formula (IIc), $R^5$ is perhaloalkyl. In some such embodiments, $R^5$ is trifluoromethyl.

In some embodiments of Formula (IIc), $R^6$ is H or $C_1$-$C_6$ alkyl. In some such embodiments, $R^6$ is H. In other such embodiments, $R^6$ is methyl. In other embodiments of Formula (IIc) embodiments, $R^6$ is halo. In some such embodiments, $R^6$ is fluoro. In some such embodiments, $R^6$ is chloro. In yet other embodiments of Formula (IIc), $R^6$ is substituted or unsubstituted aryl. In particular embodiments, $R^6$ is substituted phenyl. In other particular embodiments, $R^6$ is unsubstituted phenyl.

In some embodiments of Formula (IIc), $R^7$ is H or $C_1$-$C_6$ alkyl. In some such embodiments, $R^7$ is methyl. In other such embodiments, $R^7$ is H. In particular embodiments, $R^7$ is

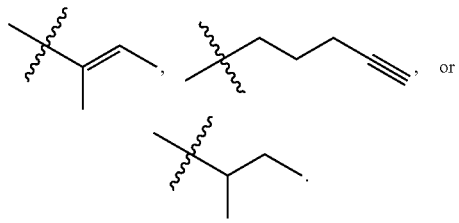

When $R^7$ is sec-butyl, it may be (S)-sec-butyl or (R)-sec-butyl. In some embodiments, $R^7$ is substituted or unsubstituted aryl, such as phenyl.

In some embodiments of Formula (IIc), $R^5$, $R^6$, and $R^7$ are all substituted or unsubstituted alkyl. In particular embodiments of Formula (IIc), $R^5$ and $R^6$ are both methyl, and $R^7$ is

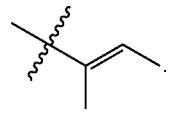 [SMILES: */C(C)=C/C]

In other particular embodiments of Formula (IIc), $R^5$ and $R^6$ are both methyl, and $R^7$ is

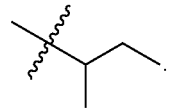 [SMILES: *C(C)CC]

In other particular embodiments of Formula (IIc), $R^5$ is methyl, and $R^6$ and $R^7$ are both hydrogen. In yet other particular embodiments of Formula (IIc), $R^5$ and $R^6$ are both methyl, and $R^7$ is hydrogen.

In some variations of Formula (IIc), $R^{8a}$ and $R^{8b}$ are independently selected from H and methyl, $R^9$ is H, $R^5$ and $R^6$ are both methyl. In some such variations, the compound of Formula (IIc) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^c$ is methyl, provided that i) and ii) do not both apply simultaneously and v) and vi) do not apply simultaneously. In any of the foregoing variations, the compound of Formula (IIc) is further defined by having m=1. In any of the foregoing variations, the compound of Formula (IIc) is further defined by having m=0.

In another aspect, the compound of Formula (II) is a compound of Formula (IIci):

(IIci)

or a salt thereof, wherein $R^5$, $R^6$, $R^7$, $R^{8a}$, $R^{8b}$, $R^9$, $R^c$, $Y^1$, $Y^2$, W, and m are defined as for Formula (IIc).

In some embodiments of Formula (IIci), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIci), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIci), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Ici), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIci), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIci), $R^c$ is H. In any of the foregoing embodiments of Formula (IIci), $R^c$ is substituted or unsubstituted alkyl. In any of the foregoing embodiments of Formula (IIci), $R^c$ is methyl. In any of the foregoing embodiments of Formula (IIci), the (—$Y^2$—$R^c$) group is halo, such as fluoro or chloro.

In some embodiments of Formula (IIci), m is 0. In some of these embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (IIci), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (IIci), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIci), $R^c$ is H. In any of the foregoing embodiments of Formula (IIci), $R^c$ is substituted or unsubstituted alkyl. In any of the foregoing embodiments of Formula (IIci), $R^c$ is methyl. In any of the foregoing embodiments of Formula (IIci), the (—$Y^2$—$R^c$) group is halo, such as fluoro or chloro.

In some embodiments of Formula (IIci), $R^5$ is H or $C_1$-$C_6$ alkyl, such as methyl. In other embodiments of Formula (IIci), $R^5$ is halo. In some such embodiments, $R^5$ is fluoro. In other such embodiments, $R^5$ is chloro. In yet other embodiments of Formula (IIci), $R^5$ is perhaloalkyl. In some such embodiments, $R^5$ is trifluoromethyl.

In some embodiments of Formula (IIci), $R^6$ is H or $C_1$-$C_6$ alkyl. In some such embodiments, $R^6$ is H. In other such embodiments, $R^6$ is methyl. In other embodiments of Formula (IIci) embodiments, $R^6$ is halo. In some such embodiments, $R^6$ is fluoro. In some such embodiments, $R^6$ is chloro. In yet other embodiments of Formula (IIci), $R^6$ is substituted or unsubstituted aryl. In particular embodiments, $R^6$ is substituted phenyl. In other particular embodiments, $R^6$ is unsubstituted phenyl.

In some embodiments of Formula (IIci), $R^7$ is H or $C_1$-$C_6$ alkyl. In some such embodiments, $R^7$ is methyl. In other such embodiments, $R^7$ is H. In particular embodiments, $R^7$ is

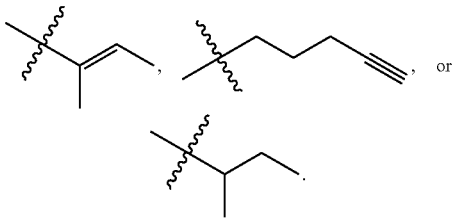

When $R^7$ is sec-butyl, it may be (S)-sec-butyl or (R)-sec-butyl. In some embodiments, $R^7$ is substituted or unsubstituted aryl, such as phenyl.

In some embodiments of Formula (IIci), $R^5$, $R^6$, and $R^7$ are all substituted or unsubstituted alkyl. In particular embodiments of Formula (IIci), $R^5$ and $R^6$ are both methyl, and $R^7$ is

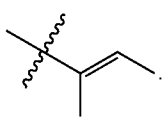 [SMILES: */C(C)=C/C]

In other particular embodiments of Formula (IIci), $R^5$ and $R^6$ are both methyl, and $R^7$ is

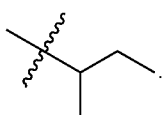 [SMILES: *C(C)CC]

In other particular embodiments of Formula (IIci), $R^5$ is methyl, and $R^6$ and $R^7$ are both hydrogen. In yet other particular embodiments of Formula (IIci), $R^5$ and $R^6$ are both methyl, and $R^7$ is hydrogen.

In some variations of Formula (IIci), $R^{8a}$ and $R^{8b}$ are independently selected from H and methyl, $R^9$ is H, $R^5$ and $R^6$ are both methyl. In some such variations, the compound of Formula (IIc) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^e$ is methyl, provided that i) and ii) do not both apply simultaneously and v) and vi) do not apply simultaneously. In any of the foregoing variations, the compound of Formula (IIci) is further defined by having m=1. In any of the foregoing variations, the compound of Formula (IIci) is further defined by having m=0.

In another aspect, the compound of Formula (II) is a compound of Formula (IId):

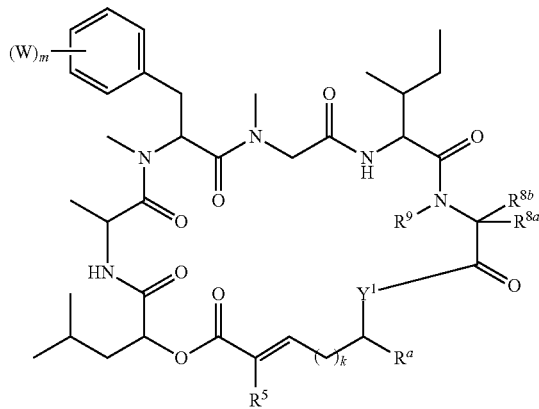

(IId)

or a salt thereof, wherein $R^5$, $R^{8a}$, $R^{8b}$, $R^9$, $R^a$, $Y^1$, and k, are defined as for Formula (II).

W is halo, perhalomethyl, cyano, nitro, amino, hydroxy, or alkoxy; and m is 0, 1, 2, 3, 4, or 5.

In some embodiments of Formula (IId), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some embodiments of Formula (IId), $Y^1$ is —N$R^d$—, where $R^d$ is H or substituted or unsubstituted alkyl. In some of these embodiments, $Y^1$ is —N$R^d$—, where $R^d$ is H or $C_1$-$C_6$ alkyl, such as methyl or ethyl. In other embodiments of Formula (IId), $Y^1$ is —O—. In yet other embodiments of Formula (IId), $Y^1$ is —S—. In any of the foregoing embodiments of Formula (II), the carbon bearing $Y^1$ is in the (R) stereochemical configuration. In any of the foregoing embodiments of Formula (IId), the carbon bearing $Y^1$ is in the (S) stereochemical configuration.

In some embodiments of Formula (IId), $R^5$ is H or $C_1$-$C_6$ alkyl, such as methyl. In other embodiments of Formula (IId), $R^5$ is halo. In some such embodiments, $R^5$ is fluoro. In other such embodiments, $R^5$ is chloro. In yet other embodiments of Formula (IId), $R^5$ is perhaloalkyl. In some such embodiments, $R^5$ is trifluoromethyl.

In some embodiments of Formula (IId), $R^a$ is H. In some embodiments, $R^a$ is substituted or unsubstituted alkyl or substituted or unsubstituted alkenyl.

In some embodiments, $R^a$ is

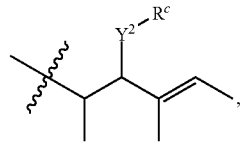

where $Y^2$ and $R^e$ are defined as for Formula (II) or any variation thereof.

In some embodiments of Formula (IId), k is 1. In some embodiments, k is 2. In some embodiments, k is 3. In some embodiments of Formula (IId), k is 2, and $Y^1$ is —O—. In particular embodiments of Formula (IId), k is 2, $Y^1$ is —O—, and $R^a$ is H. In some embodiments of Formula (IId), k is 3, and $Y^3$ is —O—. In particular embodiments of Formula (IId), k is 3, $Y^3$ is —O—, and $R^a$ is H. In some embodiments of Formula (IId), k is 1, and $Y^3$ is —O—. In particular embodiments of Formula (IId), k is 1, $Y^3$ is —O—, and $R^a$ is H.

In some variations of Formula (IId), $R^{8a}$ and $R^{8b}$ are independently selected from H and methyl, $R^9$ is H, and $R^5$ is methyl. In some such variations of Formula (IId), $Y^1$ is —N($R^d$)— or —O—. In any of the foregoing variations, the compound of Formula (IId) is further defined by having m=1. In any of the foregoing variations, the compound of Formula (IId) is further defined by having m=0.

In another aspect, the compound of Formula (II) is a compound of Formula (IIdi):

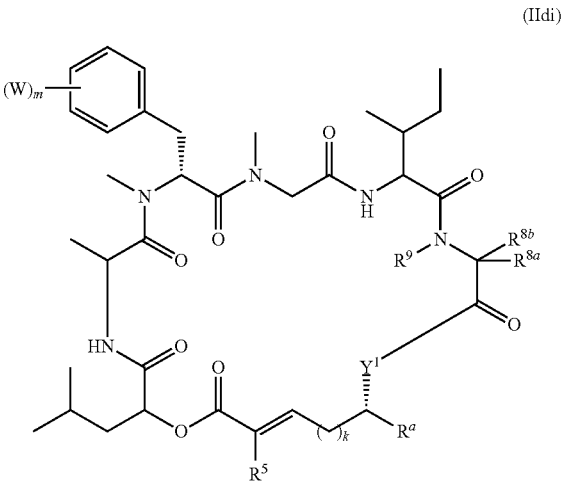

(IIdi)

or a salt thereof, wherein $R^5$, $R^{8a}$, $R^{8b}$, $R^9$, $R^a$, $Y^1$, W, m, and k, are defined as for Formula (IId).

In some embodiments of Formula (IIdi), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some embodiments of Formula (IIdi), $Y^1$ is —$NR^d$—, where $R^d$ is H or substituted or unsubstituted alkyl. In some of these embodiments, $Y^1$ is —$NR^d$—, where $R^d$ is H or $C_1$-$C_6$ alkyl, such as methyl or ethyl. In other embodiments of Formula (IIdi), $Y^1$ is —O—. In yet other embodiments of Formula (IIdi), $Y^1$ is —S—.

In some embodiments of Formula (IIdi), $R^5$ is H or $C_1$-$C_6$ alkyl, such as methyl. In other embodiments of Formula (IIdi), $R^5$ is halo. In some such embodiments, $R^5$ is fluoro. In other such embodiments, $R^5$ is chloro. In yet other embodiments of Formula (IIdi), $R^5$ is perhaloalkyl. In some such embodiments, $R^5$ is trifluoromethyl.

In some embodiments of Formula (IIdi), $R^a$ is H. In some embodiments, $R^a$ is substituted or unsubstituted alkyl or substituted or unsubstituted alkenyl.

In some embodiments, $R^a$ is

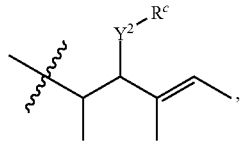

where $Y^2$ and $R^e$ are defined as for Formula (II) or any variation thereof.

In some embodiments of Formula (IIdi), k is 1. In some embodiments, k is 2. In some embodiments, k is 3. In some embodiments of Formula (IIdi), k is 2, and $Y^1$ is —O—. In particular embodiments of Formula (IIdi), k is 2, $Y^1$ is —O—, and $R^a$ is H. In some embodiments of Formula (IId), k is 3, and $Y^3$ is —O—. In particular embodiments of Formula (IIdi), k is 3, $Y^3$ is —O—, and $R^a$ is H. In some embodiments of Formula (IId), k is 1, and $Y^3$ is —O—. In particular embodiments of Formula (IIdi), k is 1, $Y^3$ is —O—, and $R^a$ is H.

In some variations of Formula (IIdi), $R^{8a}$ and $R^{8b}$ are independently selected from H and methyl, $R^9$ is H, and $R^5$ is methyl. In some such variations of Formula (IIdi), i) $Y^1$ is —$N(R^d)$— or O. In any of the foregoing variations, the compound of Formula (IIdi) is further defined by having m=1. In any of the foregoing variations, the compound of Formula (IIdi) is further defined by having m=0.

In another aspect, the compound of Formula (I) is a compound of Formula (Ie):

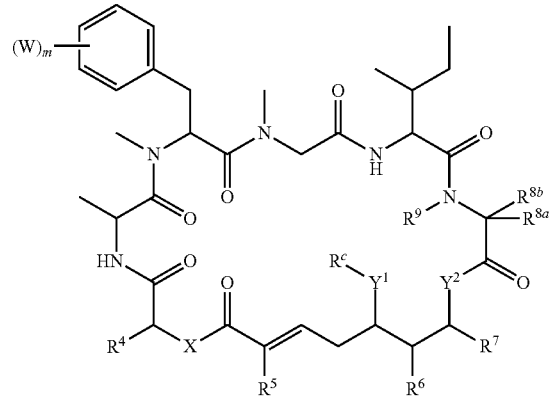

or a salt thereof, wherein
$R^4$, $R^5$, $R^6$, $R^7$, $R^{8a}$, $R^{8b}$, $R^9$, $R^c$, X, $Y^1$, and $Y^2$ are defined as for Formula (I);
W is halo, perhalomethyl, cyano, nitro, amino, hydroxy, or alkoxy; and
m is 0, 1, 2, 3, 4, or 5.

In some embodiments of Formula (Ie), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ie), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Ie), the compound may contain one of the following features: i) $Y^1$ and $Y^2$ are each —O—; ii) $Y^1$ is —O—, and $Y^2$ is —S—; iii) $Y^1$ is —O—, and $Y^2$ is —$N(R^d)$—; (iv) $Y^1$ is —O—, and $Y^2$ is —NH—; and (v) $Y^1$ is —O—, and $Y^2$ is —$N(CH_3)$—. In any of the foregoing embodiments of Formula (Ie), the compound may contain one of the following features: i) $Y^1$ and $Y^2$ are each —S—; ii) $Y^1$ is —S—, and $Y^2$ is —O—; iii) $Y^1$ is —S—, and $Y^2$ is —$N(R^d)$—; (iv) $Y^1$ is —S—, and $Y^2$ is —NH—; and (v) $Y^1$ is —S—, and $Y^2$ is —$N(CH_3)$—. In any of the foregoing embodiments of Formula (Ie), the compound may contain one of the following features: i) $Y^1$ and $Y^2$ are each —$N(R^d)$—; ii) $Y^1$ is —$N(R^d)$—, and $Y^2$ is —S—; iii) $Y^1$ is —$N(R^d)$—, and $Y^2$ is —O—; (iv) $Y^1$ is —$N(R^d)$—, and $Y^2$ is —NH—; (v) $Y^1$ is —$N(R^d)$—, and $Y^2$ is —$N(CH_3)$—; (vi) $Y^1$ is —$N(CH_3)$—, and $Y^2$ is —$N(CH_3)$—; (vii) $Y^1$ is —NH—, and $Y^2$ is —$N(CH_3)$—; (viii) $Y^1$ is —$N(CH_3)$—, and $Y^2$ is —NH—; and $Y^1$ is —NH—, and $Y^2$ is —NH—. In any of the foregoing embodiments of Formula (Ie), $R^c$ is H. In any of the foregoing embodiments of Formula (Ie), $R^c$ is substituted or unsubstituted alkyl. In any of the foregoing embodiments of Formula (Ie), $R^c$ is methyl. In any of the foregoing embodiments of Formula (Ie), the (—$Y^1$—$R^c$) group is halo, such as fluoro or chloro. In any of the foregoing embodiments, X is —O—. In any of the foregoing embodiments of Formula (Ie), X is —N(R$^d$)—. In any of the foregoing embodiments of Formula (Ie), X is —N(R$^d$)—, where R$^d$ is H. In any of the foregoing embodiments of Formula (Ie), X is —N(R$^d$)—, where R$^d$ is alkyl, such as methyl. In any of the foregoing embodiments of Formula (Ie), R$^4$ is alkyl. In any of the foregoing embodiments of Formula (Ie), R$^4$ is methyl. In any of the foregoing embodiments of Formula (Ie), R$^4$ is sec-butyl. In any of the foregoing embodiments of Formula (Ie), R$^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl. In any of the foregoing embodiments of Formula (Ie), Y$^1$ is in the (R) stereochemical configuration. In any of the foregoing embodiments of Formula (Ie), Y$^1$ is in the (S) stereochemical configuration. In any of the foregoing embodiments of Formula (Ie), Y$^2$ is in the (R) stereochemical configuration. In any of the foregoing embodiments of Formula (Ie), Y$^2$ is in the (S) stereochemical configuration.

In some embodiments of Formula (Ie), m is 0. In some of these embodiments of Formula (Ie), the compound may contain one of the following features: i) Y$^1$ and Y$^2$ are each —O—; ii) Y$^1$ is —O—, and Y$^2$ is —S—; iii) Y$^1$ is —O—, and Y$^2$ is —N(R$^d$)—; (iv) Y$^1$ is —O—, and Y$^2$ is —NH—; and (v) Y$^1$ is —O—, and Y$^2$ is —N(CH$_3$)—. In some of these embodiments of Formula (Ie), the compound may contain one of the following features: i) Y$^1$ and Y$^2$ are each —S—; ii) Y$^1$ is —S—, and Y$^2$ is —O—; iii) Y$^1$ is —S—, and Y$^2$ is —N(R$^d$)—; (iv) Y$^1$ is —S—, and Y$^2$ is —NH—; and (v) Y$^1$ is —S—, and Y$^2$ is —N(CH$_3$)—. In some of these embodiments of Formula (Ie), the compound may contain one of the following features: i) Y$^1$ and Y$^2$ are each —N(R$^d$)—; ii) Y$^1$ is —N(R$^d$)—, and Y$^2$ is —S—; iii) Y$^1$ is —N(R$^d$)—, and Y$^2$ is —O—; (iv) Y$^1$ is —N(R$^d$)—, and Y$^2$ is —NH—; (v) Y$^1$ is —N(R$^d$)—, and Y$^2$ is —N(CH$_3$)—; (vi) Y$^1$ is —N(CH$_3$)—, and Y$^2$ is —N(CH$_3$)—; (vii) Y$^1$ is —NH—, and Y$^2$ is —N(CH$_3$)—; (viii) Y$^1$ is —N(CH$_3$)—, and Y$^2$ is —NH—; and Y$^1$ is —NH—, and Y$^2$ is —NH—. In any of the foregoing embodiments of Formula (Ie), R$^e$ is H. In any of the foregoing embodiments of Formula (Ie), R$^e$ is substituted or unsubstituted alkyl. In any of the foregoing embodiments of Formula (Ie), R$^e$ is methyl. In any of the foregoing embodiments of Formula (Ie), the (—Y$^1$—R$^e$) group is halo, such as fluoro or chloro. In any of the foregoing embodiments of Formula (Ie), X is —O—. In any of the foregoing embodiments of Formula (Ie), X is —N(R$^d$)—. In any of the foregoing embodiments of Formula (Ie), X is —N(R$^d$)—, where R$^d$ is H. In any of the foregoing embodiments of Formula (Ie), X is —N(R$^d$)—, where R$^d$ is alkyl, such as methyl. In any of the foregoing embodiments of Formula (Ie), R$^4$ is alkyl. In any of the foregoing embodiments of Formula (Ie), R$^4$ is methyl. In any of the foregoing embodiments of Formula (Ie), R$^4$ is sec-butyl. In any of the foregoing embodiments of Formula (Ie), R$^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl. In any of the foregoing embodiments of Formula (Ie), Y$^1$ is in the (R) stereochemical configuration. In any of the foregoing embodiments of Formula (Ie), Y$^1$ is in the (S) stereochemical configuration. In any of the foregoing embodiments of Formula (Ie), Y$^2$ is in the (R) stereochemical configuration. In any of the foregoing embodiments of Formula (Ie), Y$^2$ is in the (S) stereochemical configuration.

In some embodiments of Formula (Ie), R$^5$ is H or C$_1$-C$_6$ alkyl, such as methyl. In other embodiments of Formula (Ie), R$^5$ is halo. In some such embodiments, R$^5$ is fluoro. In other such embodiments, R$^5$ is chloro. In yet other embodiments of Formula (Ie), R$^5$ is perhaloalkyl. In some such embodiments, R$^5$ is trifluoromethyl.

In some embodiments of Formula (Ie), R$^6$ is H or C$_1$-C$_6$ alkyl. In some such embodiments, R$^6$ is H. In other such embodiments, R$^6$ is methyl. In other embodiments of Formula (Ie), R$^6$ is halo. In some such embodiments, R$^6$ is fluoro. In some such embodiments, R$^6$ is chloro. In yet other embodiments of Formula (Ie), R$^6$ is substituted or unsubstituted aryl. In particular embodiments, R$^6$ is substituted phenyl. In other particular embodiments, R$^6$ is unsubstituted phenyl.

In some embodiments of Formula (Ie), R$^7$ is H or C$_1$-C$_6$ alkyl. In some such embodiments, R$^7$ is methyl. In other such embodiments, R$^7$ is H. In particular embodiments, R$^7$ is

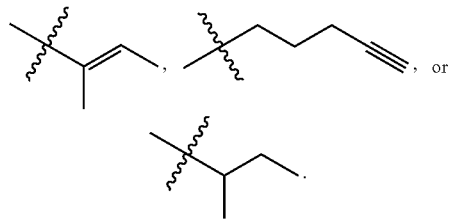

When R$^7$ is sec-butyl, it may be (S)-sec-butyl or (R)-sec-butyl. In some embodiments, R$^7$ is substituted or unsubstituted aryl, such as phenyl.

In some embodiments of Formula (Ie), R$^5$, R$^6$, and R$^7$ are all substituted or unsubstituted alkyl. In particular embodiments of Formula (Ie), R$^5$ and R$^6$ are both methyl, and R$^7$ is

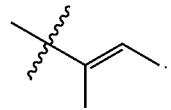

In other particular embodiments of Formula (Ie), R$^5$ and R$^6$ are both methyl, and R$^7$ is

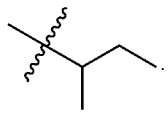

In other particular embodiments of Formula (Ie), R$^5$ is methyl, and R$^6$ and R$^7$ are both hydrogen. In yet other particular embodiments of Formula (Ie), R$^5$ and R$^6$ are both methyl, and R$^7$ is hydrogen.

In some variations of Formula (Ie), R$^{8a}$ and R$^{8b}$ are independently selected from H and methyl, R$^9$ is H, R$^5$ and R$^6$ are both methyl. In some such variations, the compound of Formula (Ie) additionally contains one or more of the following features: i) R$^7$ is H; ii) R$^7$ is C$_1$-C$_6$ alkyl or C$_1$-C$_6$ alkenyl; iii) Y$^1$ is —N(R$^d$)— or O; and iv) Y$^2$ is —N(R$^d$)— or —O—; v) R$^e$ is H; vi) R$^e$ is methyl; vii) X is —O—; viii) X is —N(R$^d$)—; ix) R$^4$ is alkyl; x) R$^4$ is alkyl substituted with phenyl or pyridyl, provided that i) and ii) do not both apply simultaneously, v) and vi) do not apply simultaneously, vii) and viii) do not apply simultaneously, and ix) and x) do not apply simultaneously. In any of the foregoing variations, the compound of Formula (Ie) is further defined by having m=1. In any of the foregoing variations, the compound of Formula (Ie) is further defined by having m=0.

In another aspect, the compound of Formula (I) is a compound of Formula (Iei):

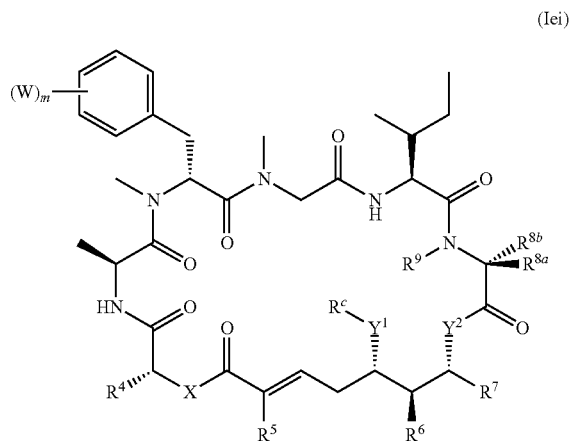

(Iei)

or a salt thereof, wherein $R^4$, $R^5$, $R^6$, $R^7$, $R^{8a}$, $R^{8b}$, $R^9$, $R^c$, X, $Y^1$, and $Y^2$ are defined as for Formula (Ie);

W is halo, perhalomethyl, cyano, nitro, amino, hydroxy, or alkoxy; and m is 0, 1, 2, 3, 4, or 5.

In some embodiments of Formula (Iei), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Iei), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (Iei), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (Iei), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (Iei), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Iei), $R^c$ is H. In any of the foregoing embodiments of Formula (Iei), $R^c$ is substituted or unsubstituted alkyl. In any of the foregoing embodiments of Formula (Iei), $R^c$ is methyl. In any of the foregoing embodiments of Formula (Iei), the (—$Y^1$—$R^c$) group is halo, such as fluoro or chloro. In any of the foregoing embodiments, X is —O—. In any of the foregoing embodiments of Formula (Iei), X is —N($R^d$)—. In any of the foregoing embodiments of Formula (Iei), X is —N($R^d$)—, where $R^d$ is H. In any of the foregoing embodiments of Formula (Iei), X is —N($R^d$)—, where $R^d$ is alkyl, such as methyl. In any of the foregoing embodiments of Formula (Iei), $R^4$ is alkyl. In any of the foregoing embodiments of Formula (Iei), $R^4$ is methyl. In any of the foregoing embodiments of Formula (Iei), $R^4$ is sec-butyl. In any of the foregoing embodiments of Formula (Iei), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl.

In some embodiments of Formula (Iei), m is 0. In some of these embodiments of Formula (Iei), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (Iei), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (Iei), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (Iei), $R^c$ is H. In any of the foregoing embodiments of Formula (Iei), $R^c$ is substituted or unsubstituted alkyl. In any of the foregoing embodiments of Formula (Ie), $R^c$ is methyl. In any of the foregoing embodiments of Formula (Iei), the (—$Y^1$—$R^c$) group is halo, such as fluoro or chloro. In any of the foregoing embodiments, X is —O—. In any of the foregoing embodiments of Formula (Iei), X is —N($R^d$)—. In any of the foregoing embodiments of Formula (Iei), X is —N($R^d$)—, where $R^d$ is H. In any of the foregoing embodiments of Formula (Iei), X is —N($R^d$)—, where $R^d$ is alkyl, such as methyl. In any of the foregoing embodiments of Formula (Iei), $R^4$ is alkyl. In any of the foregoing embodiments of Formula (Iei), $R^4$ is methyl. In any of the foregoing embodiments of Formula (Iei), $R^4$ is sec-butyl. In any of the foregoing embodiments of Formula (Iei), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl.

In some embodiments of Formula (Iei), $R^5$ is H or $C_1$-$C_6$ alkyl, such as methyl. In other embodiments of Formula (Iei), $R^5$ is halo. In some such embodiments, $R^5$ is fluoro. In other such embodiments, $R^5$ is chloro. In yet other embodiments of Formula (Iei), $R^5$ is perhaloalkyl. In some such embodiments, $R^5$ is trifluoromethyl.

In some embodiments of Formula (Iei), $R^6$ is H or $C_1$-$C_6$ alkyl. In some such embodiments, $R^6$ is H. In other such embodiments, $R^6$ is methyl. In other embodiments of Formula (Iei) embodiments, $R^6$ is halo. In some such embodiments, $R^6$ is fluoro. In some such embodiments, $R^6$ is chloro.

In yet other embodiments of Formula (Iei), $R^6$ is substituted or unsubstituted aryl. In particular embodiments, $R^6$ is substituted phenyl. In other particular embodiments, $R^6$ is unsubstituted phenyl.

In some embodiments of Formula (Iei), $R^7$ is H or $C_1$-$C_6$ alkyl. In some such embodiments, $R^7$ is methyl. In other such embodiments, $R^7$ is H. In particular embodiments, $R^7$ is

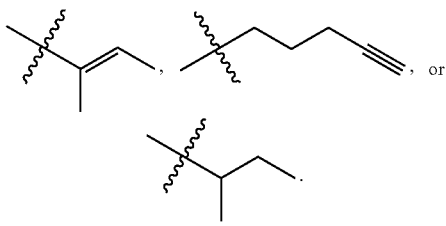

When $R^7$ is sec-butyl, it may be (S)-sec-butyl or (R)-sec-butyl. In some embodiments, $R^7$ is substituted or unsubstituted aryl, such as phenyl.

In some embodiments of Formula (Iei), $R^5$, $R^6$, and $R^7$ are all substituted or unsubstituted alkyl. In particular embodiments of Formula (Iei), $R^5$ and $R^6$ are both methyl, and $R^7$ is

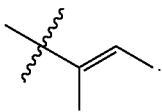 [SMILES: */C(C)=C/C]

In other particular embodiments of Formula (Iei), $R^5$ and $R^6$ are both methyl, and $R^7$ is

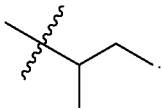 [SMILES: *C(C)CC]

In other particular embodiments of Formula (Iei), $R^5$ is methyl, and $R^6$ and $R^7$ are both hydrogen. In yet other particular embodiments of Formula (Iei), $R^5$ and $R^6$ are both methyl, and $R^7$ is hydrogen.

In some variations of Formula (Iei), $R^{8a}$ and $R^{8b}$ are independently selected from H and methyl, $R^9$ is H, $R^5$ and $R^6$ are both methyl. In some such variations, the compound of Formula (Ie) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^e$ is methyl; vii) X is —O—; viii) X is —N($R^d$)—; ix) $R^4$ is alkyl; x) $R^4$ is alkyl substituted with phenyl or pyridyl, provided that i) and ii) do not both apply simultaneously, v) and vi) do not apply simultaneously, vii) and viii) do not apply simultaneously, and ix) and x) do not apply simultaneously. In any of the foregoing variations, the compound of Formula (Iei) is further defined by having m=1. In any of the foregoing variations, the compound of Formula (Iei) is further defined by having m=0.

In another aspect, the compound of Formula (II) is a compound of Formula (IIe):

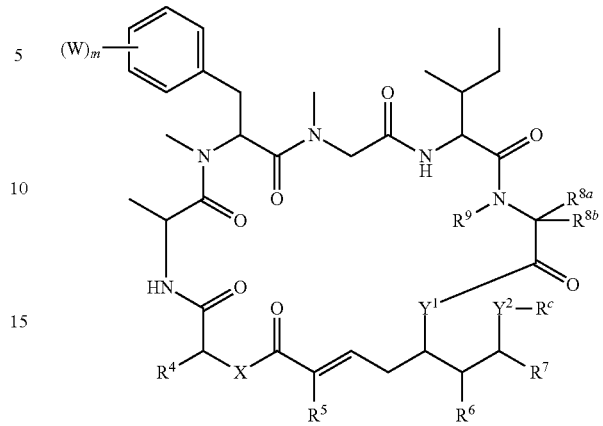

or a salt thereof, wherein
$R^4$, $R^5$, $R^6$, $R^7$, $R^{8a}$, $R^{8b}$, $R^9$, $R^c$, X, $Y^1$, and $Y^2$ are defined as for Formula (II);
W is halo, perhalomethyl, cyano, nitro, amino, hydroxy, or alkoxy; and
m is 0, 1, 2, 3, 4, or 5.

In some embodiments of Formula (IIe), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIe), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIe), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (IIe), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIe), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIe), $R^c$ is H. In any of the foregoing embodiments of Formula (IIe), $R^c$ is substituted or unsubstituted alkyl. In any of the foregoing embodiments of Formula (IIe), $R^c$ is methyl. In any of the foregoing embodiments of Formula (IIe), the (—$Y^2$—$R^c$) group is halo, such as fluoro or chloro. In any of the foregoing embodiments, X is —O—. In any of the foregoing embodiments of Formula (IIe), X is —N($R^d$)—. In any of the foregoing embodiments of Formula (IIe), X is —N($R^d$)—, where $R^d$ is H. In any of the foregoing embodiments of Formula (IIe), X is —N($R^d$)—, where $R^d$ is alkyl, such as methyl. In any of the foregoing embodiments of Formula (IIe), $R^4$ is alkyl. In any of the foregoing embodiments of Formula (IIe), $R^4$ is methyl. In any of the foregoing embodiments of Formula (IIe), $R^4$ is sec-butyl. In any of the foregoing embodiments of Formula (IIe), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl. In any of the foregoing embodiments of Formula (IIe), $Y^1$ is in the (R) stereochemical configuration. In any of the foregoing embodiments of Formula (IIe), $Y^1$ is in the (S) stereochemical configuration. In any of the foregoing embodiments of Formula (IIe), $Y^2$ is in the (R) stereochemical configuration. In any of the foregoing embodiments of Formula (IIe), $Y^2$ is in the (S) stereochemical configuration.

In some embodiments of Formula (IIe), m is 0. In some of these embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (IIe), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (IIe), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIe), $R^c$ is H. In any of the foregoing embodiments of Formula (IIe), $R^c$ is substituted or unsubstituted alkyl. In any of the foregoing embodiments of Formula (IIe), $R^c$ is methyl. In any of the foregoing embodiments of Formula (IIe), the (—$Y^2$—$R^c$) group is halo, such as fluoro or chloro. In any of the foregoing embodiments, X is —O—. In any of the foregoing embodiments of Formula (IIe), X is —N($R^d$)—. In any of the foregoing embodiments of Formula (IIe), X is —N($R^d$)—, where $R^d$ is H. In any of the foregoing embodiments of Formula (IIe), X is —N($R^d$)—, where $R^d$ is alkyl, such as methyl. In any of the foregoing embodiments of Formula (IIe), $R^4$ is alkyl. In any of the foregoing embodiments of Formula (IIe), $R^4$ is methyl. In any of the foregoing embodiments of Formula (IIe), $R^4$ is sec-butyl. In any of the foregoing embodiments of Formula (IIe), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl. In any of the foregoing embodiments of Formula (IIe), $Y^1$ is in the (R) stereochemical configuration. In any of the foregoing embodiments of Formula (IIe), $Y^1$ is in the (S) stereochemical configuration. In any of the foregoing embodiments of Formula (IIe), $Y^2$ is in the (R) stereochemical configuration. In any of the foregoing embodiments of Formula (IIe), $Y^2$ is in the (S) stereochemical configuration.

In some embodiments of Formula (IIe), $R^5$ is H or $C_1$-$C_6$ alkyl, such as methyl. In other embodiments of Formula (IIe), $R^5$ is halo. In some such embodiments, $R^5$ is fluoro. In other such embodiments, $R^5$ is chloro. In yet other embodiments of Formula (IIe), $R^5$ is perhaloalkyl. In some such embodiments, $R^5$ is trifluoromethyl.

In some embodiments of Formula (IIe), $R^6$ is H or $C_1$-$C_6$ alkyl. In some such embodiments, $R^6$ is H. In other such embodiments, $R^6$ is methyl. In other embodiments of Formula (IIe) embodiments, $R^6$ is halo. In some such embodiments, $R^6$ is fluoro. In some such embodiments, $R^6$ is chloro. In yet other embodiments of Formula (IIe), $R^6$ is substituted or unsubstituted aryl. In particular embodiments, $R^6$ is substituted phenyl. In other particular embodiments, $R^6$ is unsubstituted phenyl.

In some embodiments of Formula (IIe), $R^7$ is H or $C_1$-$C_6$ alkyl. In some such embodiments, $R^7$ is methyl. In other such embodiments, $R^7$ is H. In particular embodiments, $R^7$ is

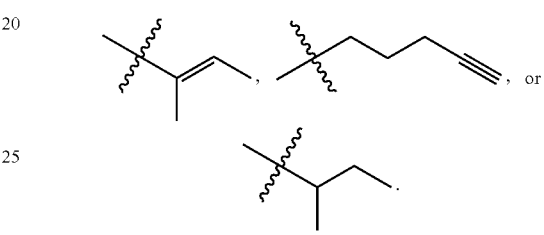

When $R^7$ is sec-butyl, it may be (S)-sec-butyl or (R)-sec-butyl. In some embodiments, $R^7$ is substituted or unsubstituted aryl, such as phenyl.

In some embodiments of Formula (IIe), $R^5$, $R^6$, and $R^7$ are all substituted or unsubstituted alkyl. In particular embodiments of Formula (IIe), $R^5$ and $R^6$ are both methyl, and $R^7$ is

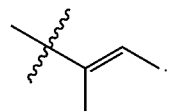

In other particular embodiments of Formula (IIe), $R^5$ and $R^6$ are both methyl, and $R^7$ is

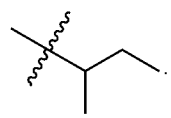

In other particular embodiments of Formula (IIe), $R^5$ is methyl, and $R^6$ and $R^7$ are both hydrogen. In yet other particular embodiments of Formula (IIe), $R^5$ and $R^6$ are both methyl, and $R^7$ is hydrogen.

In some variations of Formula (IIe), $R^{8a}$ and $R^{8b}$ are independently selected from H and methyl, $R^9$ is H, $R^5$ and $R^6$ are both methyl. In some such variations, the compound of Formula (IIe) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^e$ is methyl; vii) X is —O—; viii) X is —N($R^d$)—; ix) $R^4$ is alkyl; x) $R^4$ is alkyl substituted with phenyl or pyridyl, provided that i) and ii) do not both apply simultaneously, v) and vi) do not apply simultaneously, vii) and viii) do not apply simultaneously, and ix) and x) do not apply simultaneously. In any of the foregoing variations, the compound of Formula (IIe) is further defined by having m=1. In any of the foregoing variations, the compound of Formula (IIe) is further defined by having m=0.

In another aspect, the compound of Formula (II) is a compound of Formula (IIei):

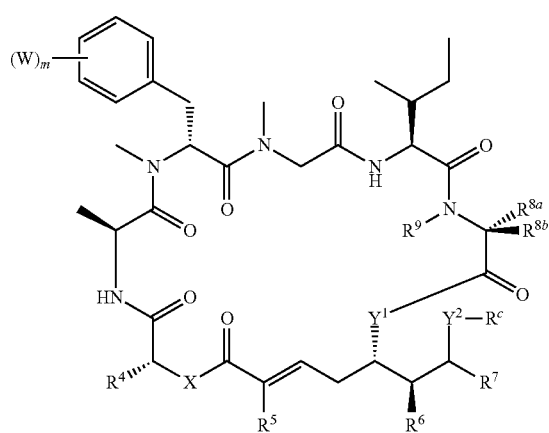

(IIei)

or a salt thereof, wherein $R^4$, $R^5$, $R^6$, $R^7$, $R^{8a}$, $R^{8b}$, $R^9$, $R^c$, $Y^1$, $Y^2$, W, and m are defined as for Formula (IIe).

In some embodiments of Formula (IIei), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (IIei), m is 1. In some such embodiments, W is halo. In some such embodiments, W is fluoro. In some such embodiments, W is chloro. In some such embodiments, W is trifluoromethyl. In some such embodiments, W is hydroxy. In particular embodiments where m is 1, W is fluoro, chloro, trifluoromethyl, or hydroxy and is attached at the para position on the phenyl ring. In other particular embodiments where m is 1, W is fluoro, chloro, trifluoromethyl, or hydroxy and is attached at the meta position on the phenyl ring. In any of the foregoing embodiments of Formula (IIei), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In any of the foregoing embodiments of Formula (IIei), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In any of the foregoing embodiments of Formula (IIei), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIei), $R^c$ is H. In any of the foregoing embodiments of Formula (IIei), $R^c$ is substituted or unsubstituted alkyl. In any of the foregoing embodiments of Formula (IIei), $R^c$ is methyl. In any of the foregoing embodiments of Formula (IIei), the (—Y$^2$—R$^c$) group is halo, such as fluoro or chloro. In any of the foregoing embodiments, X is —O—. In any of the foregoing embodiments of Formula (IIei), X is —N($R^d$)—. In any of the foregoing embodiments of Formula (IIei), X is —N($R^d$)—, where $R^d$ is H. In any of the foregoing embodiments of Formula (IIei), X is —N($R^d$)—, where $R^d$ is alkyl, such as methyl. In any of the foregoing embodiments of Formula (IIei), $R^4$ is alkyl. In any of the foregoing embodiments of Formula (IIei), $R^4$ is methyl. In any of the foregoing embodiments of Formula (Ie), $R^4$ is sec-butyl. In any of the foregoing embodiments of Formula (IIei), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl.

In some embodiments of Formula (IIei), m is 0. In some of these embodiments of Formula (IIei), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N(CH$_3$)—. In some of these embodiments of Formula (IIci), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N(CH$_3$)—. In some of these embodiments of Formula (IIei), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N(CH$_3$)—; (vi) $Y^1$ is —N(CH$_3$)—, and $Y^2$ is —N(CH$_3$)—; (vii) $Y^1$ is —NH—, and $Y^2$ is —N(CH$_3$)—; (viii) $Y^1$ is —N(CH$_3$)—, and $Y^2$ is —NH—; and $Y^1$ is —NH—, and $Y^2$ is —NH—. In any of the foregoing embodiments of Formula (IIei), $R^c$ is H. In any of the foregoing embodiments of Formula (IIei), $R^c$ is substituted or unsubstituted alkyl. In any of the foregoing embodiments of Formula (IIei), $R^c$ is methyl. In any of the foregoing embodiments of Formula (IIei), the (—Y$^2$—R$^c$) group is halo, such as fluoro or chloro. In any of the foregoing embodiments, X is —O—. In any of the foregoing embodiments of Formula (IIei), X is —N($R^d$)—. In any of the foregoing embodiments of Formula (Ie), X is —N($R^d$)—, where $R^d$ is H. In any of the foregoing embodiments of Formula (IIei), X is —N($R^d$)—, where $R^d$ is alkyl, such as methyl. In any of the foregoing embodiments of Formula (IIei), $R^4$ is alkyl. In any of the foregoing embodiments of Formula (IIei), $R^4$ is methyl. In any of the foregoing embodiments of Formula (IIei), $R^4$ is sec-butyl. In any of the foregoing embodiments of Formula (IIei), $R^4$ is alkyl substituted with aryl or heteroaryl. In particular embodiments, the aryl is phenyl. In other particular embodiments, the aryl is pyridyl, such as 2-pyridyl, 3-pyridyl, or 4-pyridyl.

In some embodiments of Formula (IIei), $R^5$ is H or $C_1$-$C_6$ alkyl, such as methyl. In other embodiments of Formula (IIei), $R^5$ is halo. In some such embodiments, $R^5$ is fluoro. In other such embodiments, $R^5$ is chloro. In yet other embodiments of Formula (IIei), $R^5$ is perhaloalkyl. In some such embodiments, $R^5$ is trifluoromethyl.

In some embodiments of Formula (IIei), $R^6$ is H or $C_1$-$C_6$ alkyl. In some such embodiments, $R^6$ is H. In other such embodiments, $R^6$ is methyl. In other embodiments of Formula (IIei) embodiments, $R^6$ is halo. In some such embodiments, $R^6$ is fluoro. In some such embodiments, $R^6$ is chloro.

In yet other embodiments of Formula (IIei), $R^6$ is substituted or unsubstituted aryl. In particular embodiments, $R^6$ is substituted phenyl. In other particular embodiments, $R^6$ is unsubstituted phenyl.

In some embodiments of Formula (IIei), $R^7$ is H or $C_1$-$C_6$ alkyl. In some such embodiments, $R^7$ is methyl. In other such embodiments, $R^7$ is H. In particular embodiments, $R^7$ is

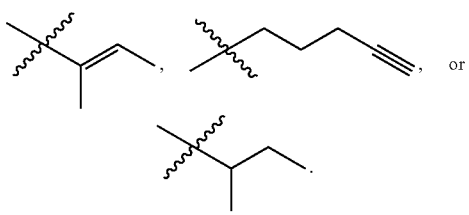

When $R^7$ is sec-butyl, it may be (S)-sec-butyl or (R)-sec-butyl. In some embodiments, $R^7$ is substituted or unsubstituted aryl, such as phenyl.

In some embodiments of Formula (IIei), $R^5$, $R^6$, and $R^7$ are all substituted or unsubstituted alkyl. In particular embodiments of Formula (IIei), $R^5$ and $R^6$ are both methyl, and $R^7$ is

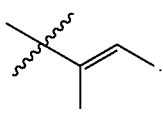

In other particular embodiments of Formula (IIei), $R^5$ and $R^6$ are both methyl, and $R^7$ is

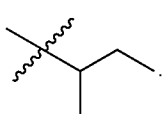 [SMILES: *C(C)CC]

In other particular embodiments of Formula (IIei), $R^5$ is methyl, and $R^6$ and $R^7$ are both hydrogen. In yet other particular embodiments of Formula (IIei), $R^5$ and $R^6$ are both methyl, and $R^7$ is hydrogen.

In some variations of Formula (IIei), $R^{8a}$ and $R^{8b}$ are independently selected from H and methyl, $R^9$ is H, $R^5$ and $R^6$ are both methyl. In some such variations, the compound of Formula (Ie) additionally contains one or more of the following features: i) $R^7$ is H; ii) $R^7$ is $C_1$-$C_6$ alkyl or $C_1$-$C_6$ alkenyl; iii) $Y^1$ is —N($R^d$)— or O; and iv) $Y^2$ is —N($R^d$)— or —O—; v) $R^c$ is H; vi) $R^e$ is methyl; vii) X is —O—; viii) X is —N($R^d$)—; ix) $R^4$ is alkyl; x) $R^4$ is alkyl substituted with phenyl or pyridyl, provided that i) and ii) do not both apply simultaneously, v) and vi) do not apply simultaneously, vii) and viii) do not apply simultaneously, and ix) and x) do not apply simultaneously. In any of the foregoing variations, the compound of Formula (IIei) is further defined by having m=1. In any of the foregoing variations, the compound of Formula (IIei) is further defined by having m=0.

In some variations of Formula (I), the compound is of Formula (If):

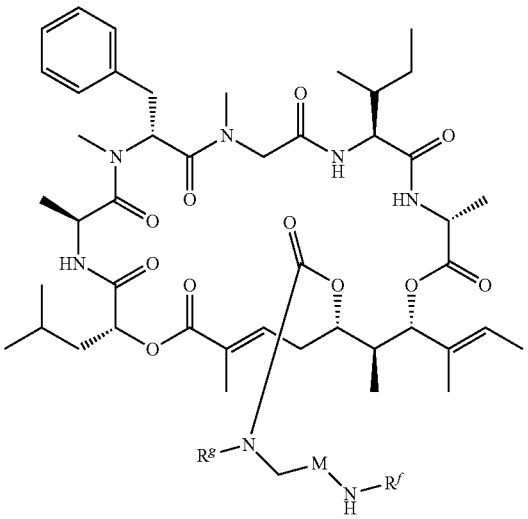

or a salt thereof, wherein
$R^f$ is H, substituted or unsubstituted alkyl, or —C(O)O-alkyl;
$R^g$ is H or substituted or unsubstituted alkyl; and
M is —(CH$_2$)$_k$— or —(OCH$_2$—CH$_2$)$_k$—, where k is an integer from 1-12, inclusive.

In some variations of Formula (I), the compound is of Formula (Ig):

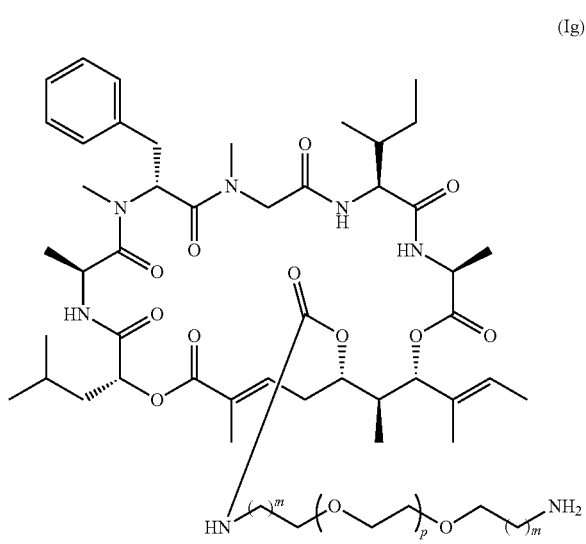

or a salt thereof, wherein
each m is independently 1 or 2; and
p is an integer from 0 to 10, inclusive.

It is to be understood that any variable group definition provided herein can be used in combination with any other variable group definition provided herein, such that all possible combinations and permutations of variable groups provided herein, where chemically feasible, are contemplated.

Variations of Formulae (I), (II), and (III), apply to Formulae (B), (Bi), (Ii), (IIi), (IIIi), (Ia), (Iai), (IIa), (IIai), (Ib), (Ibi), (IIb), (IIbi), (IIc), (IIei), (IId), (IIdi), (Ie), (Iei), (IIe), (IIei), (If), or (Ig) the same as if each and every variation were specifically and individually listed for Formulae (B), (Bi), (Ii), (IIi), (IIIi), (Ia), (Iai), (IIa), (IIai), (Ib), (Ibi), (IIb), (IIbi), (IIc), (IIei), (IId), (IIdi), (Ie), (Iei), (IIe), (IIei), (If), or (Ig).

Also provided are methods of using compounds described herein, including any formula detailed herein or specific compound detailed herein, in various therapeutic applications.

In some embodiments, provided herein are compounds and salts thereof described in Table 1, and uses thereof.

TABLE 1

| Compound No. | Structure |
| --- | --- |
| 1 | 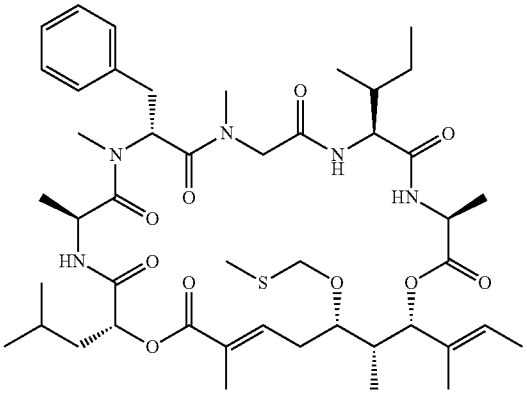 |
| 2 | 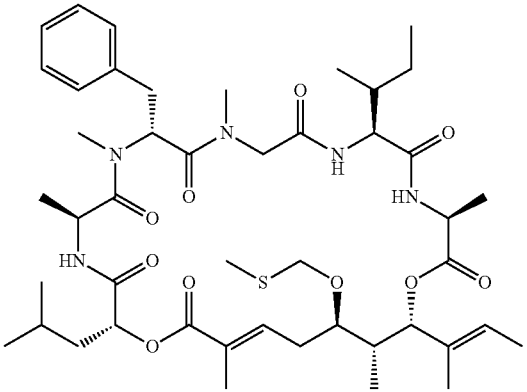 |
| 3 | 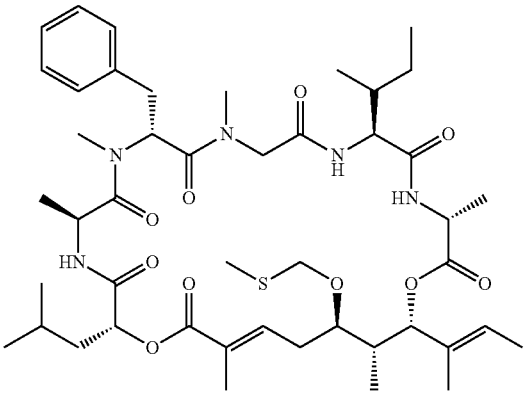 |

TABLE 1-continued

| Compound No. | Structure |
|---|---|
| 4 | 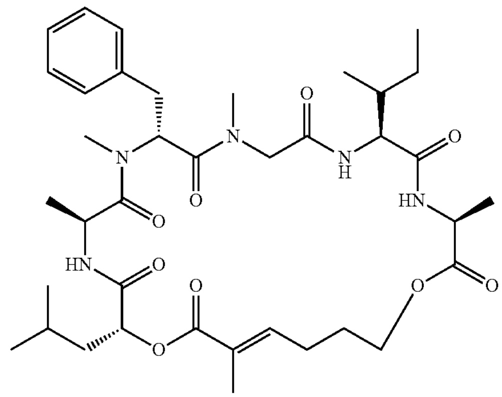 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCOC(=O)[C@H](C)NC1=O] |
| 5 | 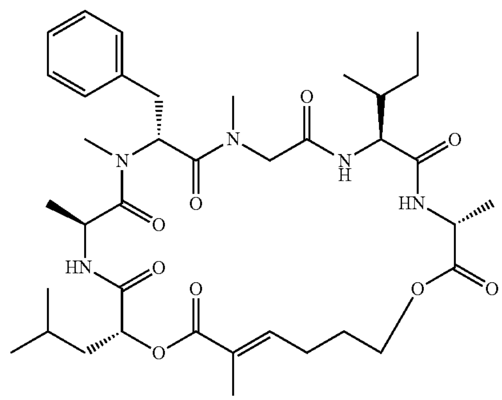 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCOC(=O)[C@@H](C)NC1=O] |
| 6 | 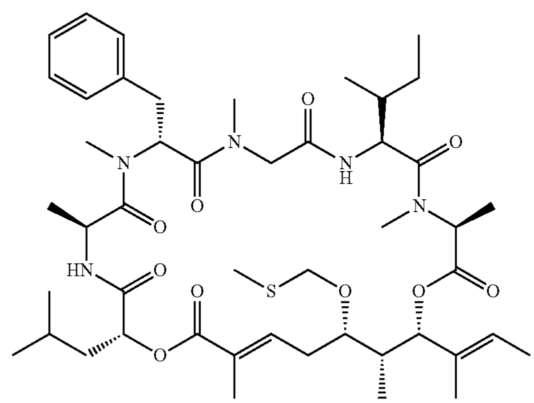 [SMILES: C/C=C(\C)[C@H]1OC(=O)[C@H](C)N(C)C(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@H]1C] |
| 7 | 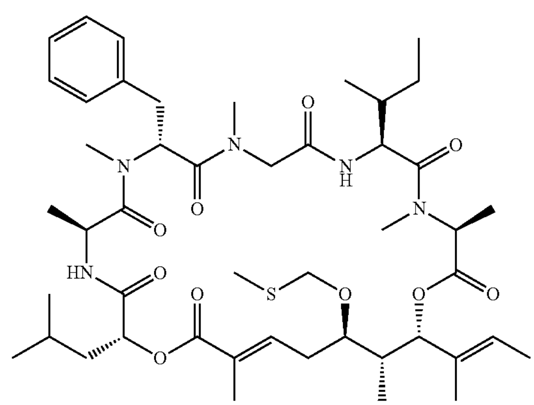 |

TABLE 1-continued
| Compound No. | Structure |
|---|---|
| 8 | 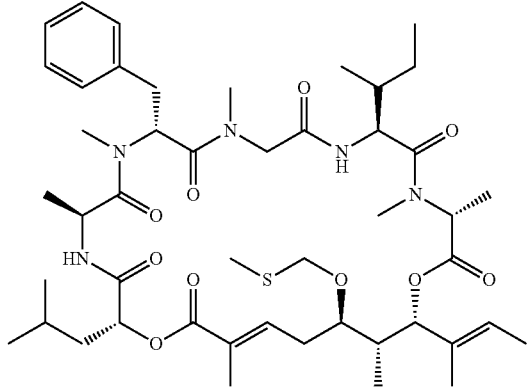 |
| 9 | 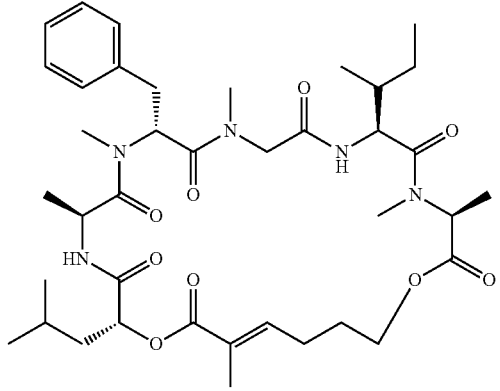 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCOC(=O)[C@H](C)N(C)C1=O] |
| 10 | 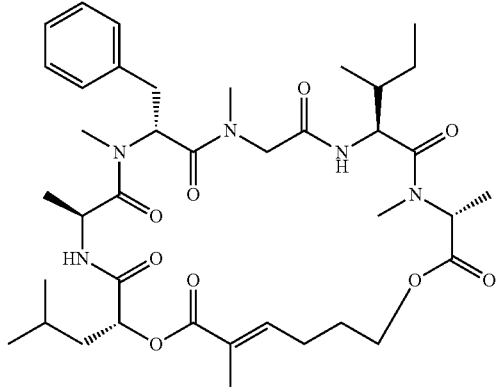 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCOC(=O)[C@@H](C)N(C)C1=O] |

TABLE 1-continued
| Compound No. | Structure |
|---|---|
| 11 | 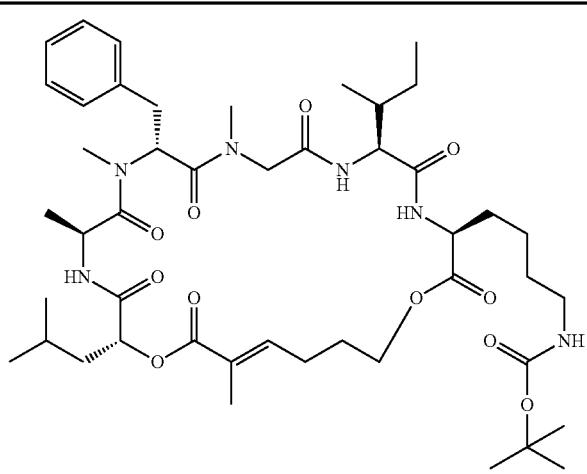 |
| 12 | 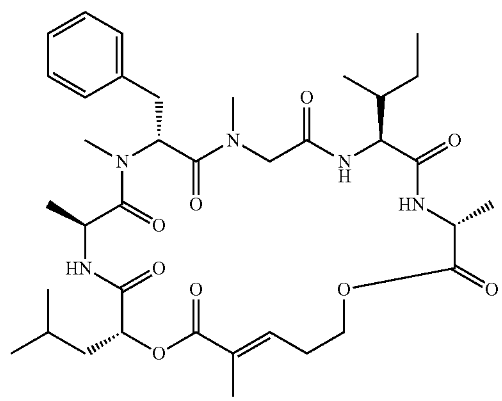 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCOC(=O)[C@@H](C)NC1=O] |
| 13 | 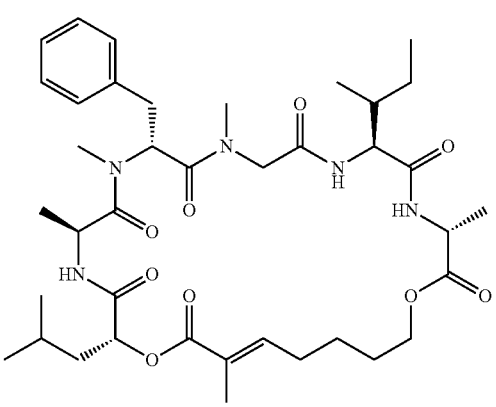 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@@H](C)NC1=O] |

TABLE 1-continued
| Compound No. | Structure |
|---|---|
| 14 | 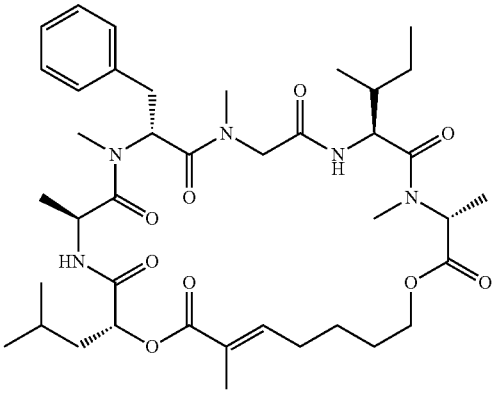 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@@H](C)N(C)C1=O] |
| 15 | 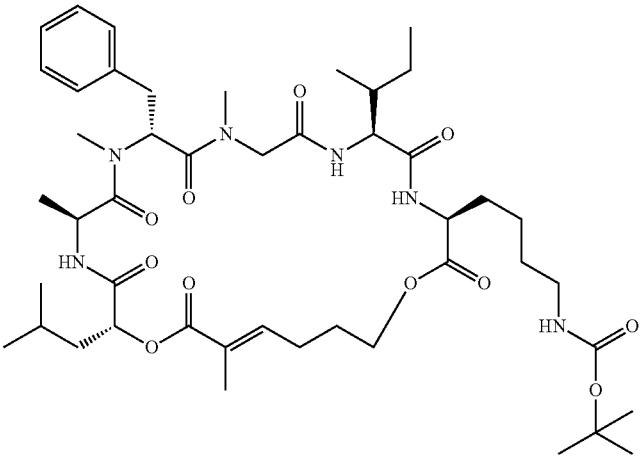 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCOC(=O)[C@H](CCCCNC(=O)OC(C)(C)C)NC1=O] |
| 16 | 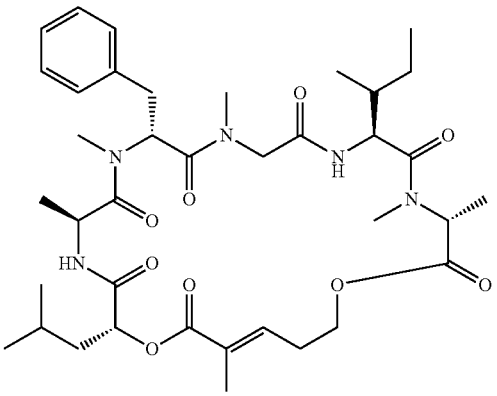 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCOC(=O)[C@@H](C)N(C)C1=O] |

TABLE 1-continued

| Compound No. | Structure |
|---|---|
| 17 | 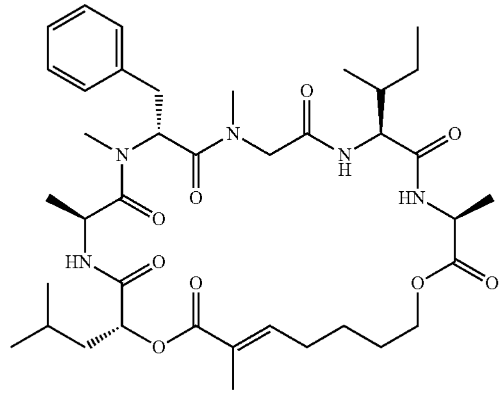 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@H](C)NC1=O] |
| 18 | 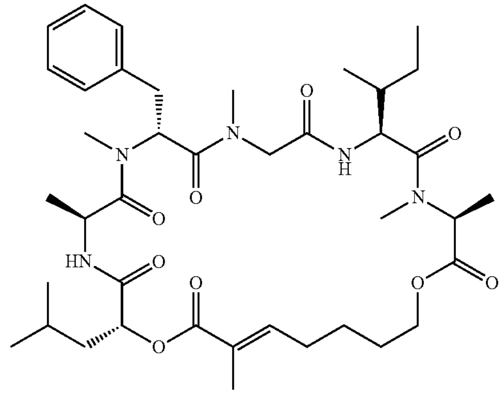 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@H](C)N(C)C1=O] |
| 19 | 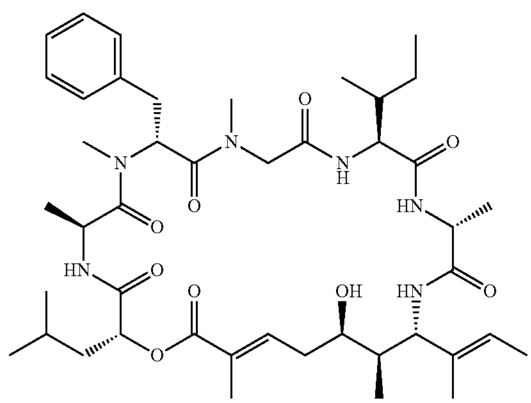 [SMILES: C/C=C(\C)[C@H]1NC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@@H](O)[C@@H]1C] |
| 20 | 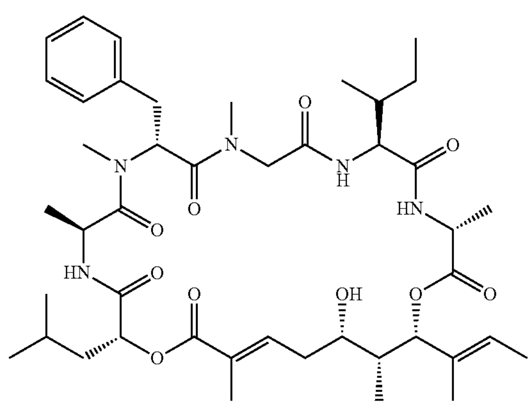 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@H]1C] |

TABLE 1-continued

| Compound No. | Structure |
| --- | --- |
| 21 | *(cyclic depsipeptide structure with 4-chlorobenzyl substituent)* |
| 22 | *(cyclic depsipeptide structure with 4-fluorobenzyl substituent)* |
| 23 | *(cyclic depsipeptide structure with 4-trifluoromethylbenzyl substituent)* |
| 24 | *(cyclic depsipeptide structure with 4-hydroxybenzyl substituent)* |

TABLE 1-continued
| Compound No. | Structure |
|---|---|
| 25 | 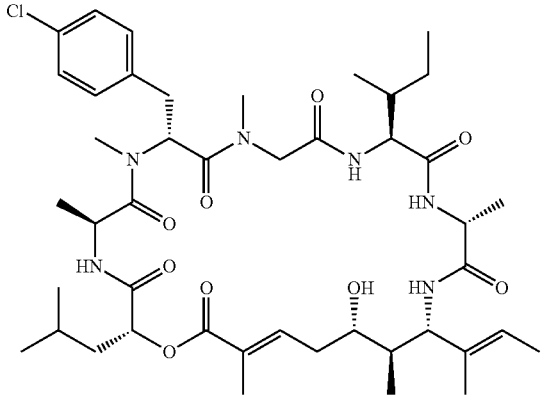 [SMILES: C/C=C(\C)[C@H]1NC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](O)[C@@H]1C] |
| 26 | 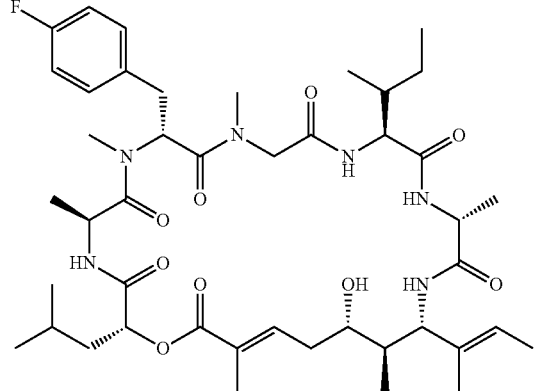 [SMILES: C/C=C(\C)[C@H]1NC(=O)[C@@H](C)NC(=O)[C@H](C(C)CC)NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@@H]1C] |
| 27 | 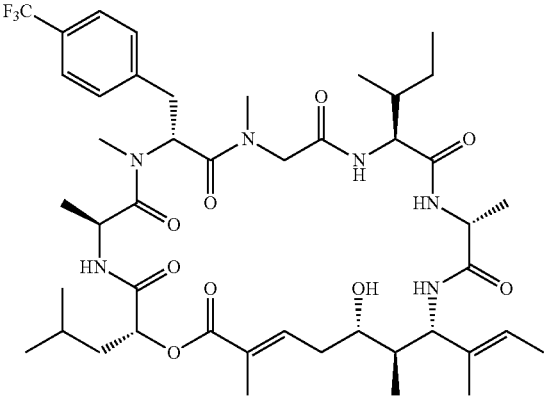 [SMILES: C/C=C(\C)[C@H]1NC(=O)[C@@H](C)NC(=O)[C@H](C(C)CC)NC(=O)CN(C)C(=O)[C@@H](Cc2ccc(C(F)(F)F)cc2)N(C)C(=O)[C@H](C)NC(=O)[C@@H](CC(C)C)OC(=O)/C(C)=C/C[C@H](O)[C@@H]1C] |

TABLE 1-continued

| Compound No. | Structure |
|---|---|
| 28 | 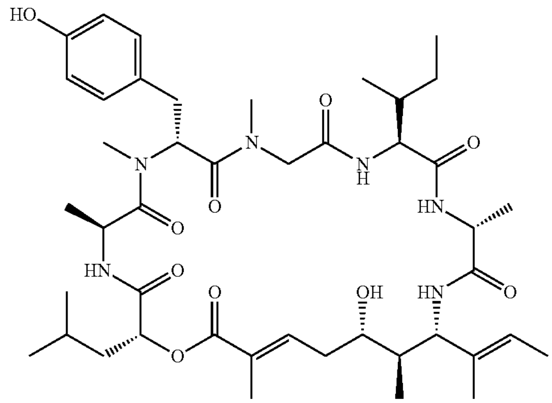 [SMILES: C/C=C(\C)[C@H]1NC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](O)[C@@H]1C] |
| 29 | 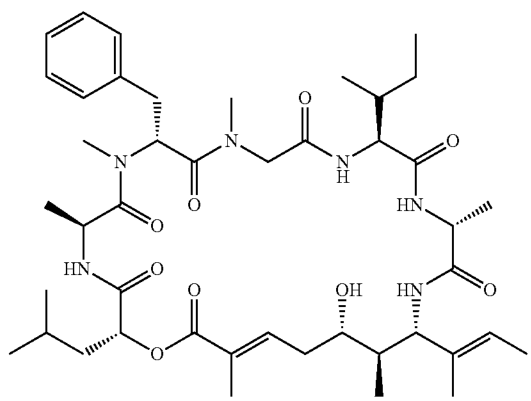 |
| 30 | 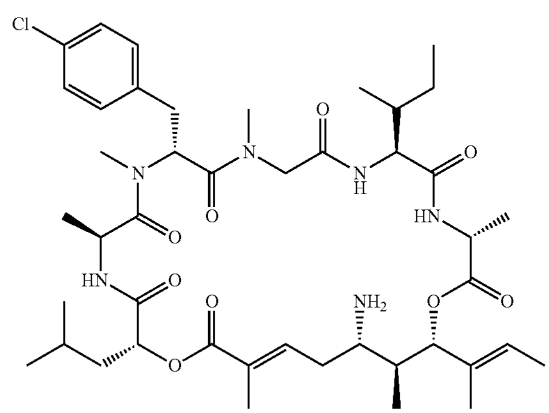 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](N)[C@@H]1C] |
| 31 | 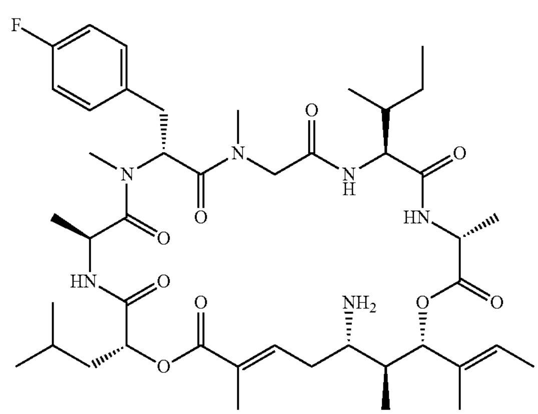 |

TABLE 1-continued

| Compound No. | Structure |
| --- | --- |
| 32 | 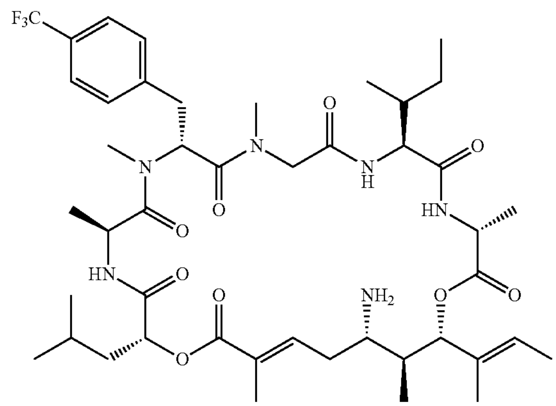 [SMILES: C/C=C(\C)[C@H]1OC(=O)[C@@H](C)NC(=O)[C@H](C(C)CC)NC(=O)CN(C)C(=O)[C@@H](Cc2ccc(C(F)(F)F)cc2)N(C)C(=O)[C@H](C)NC(=O)[C@@H](CC(C)C)OC(=O)/C(C)=C/C[C@H](N)[C@@H]1C] |
| 33 | 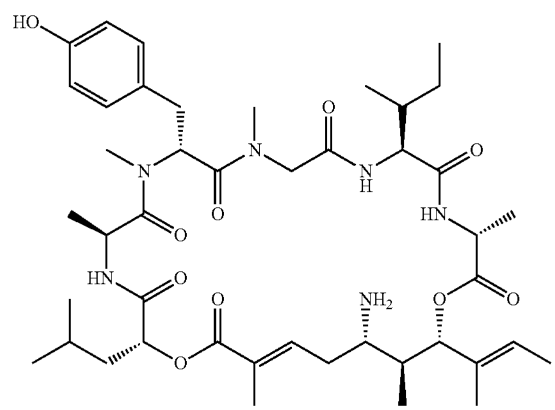 |
| 34 | 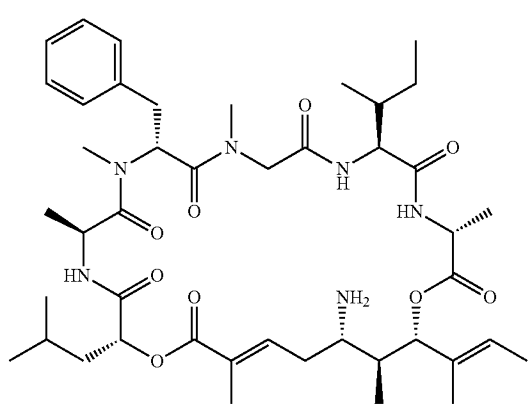 |

TABLE 1-continued

| Compound No. | Structure |
|---|---|
| 35 | 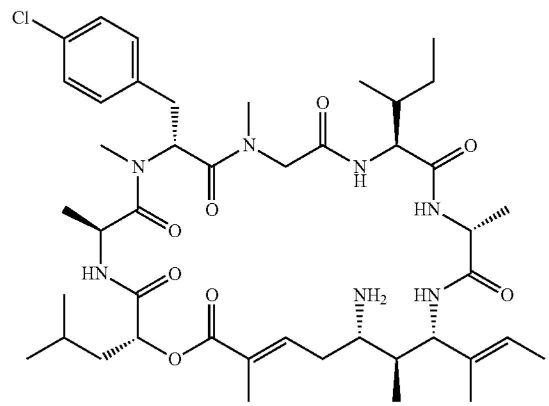 |
| 36 | 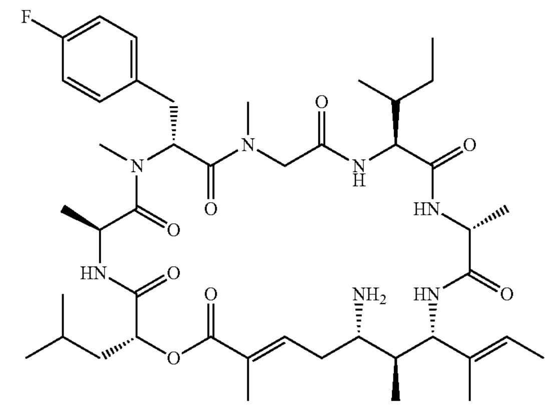 |
| 37 | 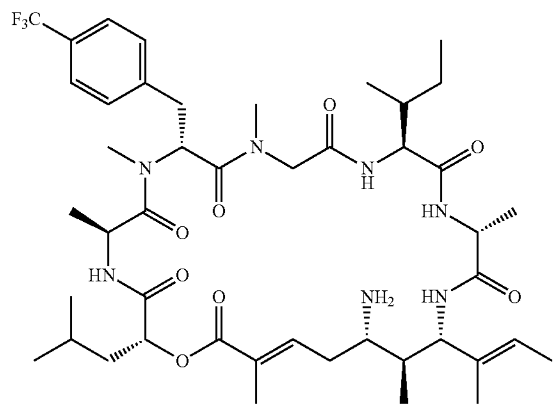 |
| 38 | 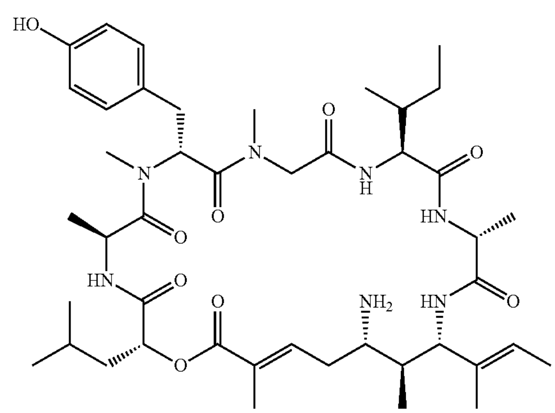 |

TABLE 1-continued
| Compound No. | Structure |
|---|---|
| 39 | 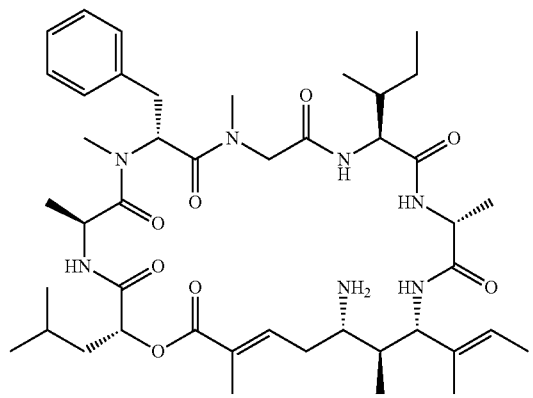 |
| 40 | 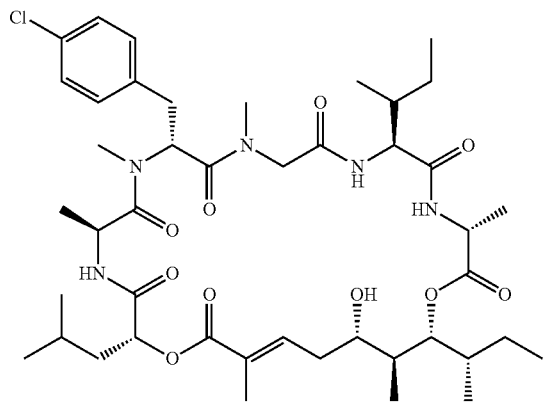 |
| 41 | 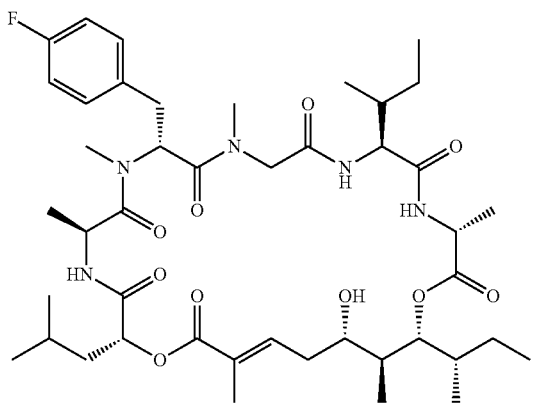 [SMILES: CCC(C)[C@@H]1NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@H](C)[C@@H]([C@@H](C)CC)OC(=O)[C@@H](C)NC1=O] |

TABLE 1-continued

| Compound No. | Structure |
|---|---|
| 42 | (macrocyclic structure with 4-CF₃-phenyl group) |
| 43 | (macrocyclic structure with 4-OH-phenyl group) |
| 44 | (macrocyclic structure with phenyl group) |
| 45 | (macrocyclic structure with 4-Cl-phenyl group) |

TABLE 1-continued

| Compound No. | Structure |
|---|---|
| 46 | 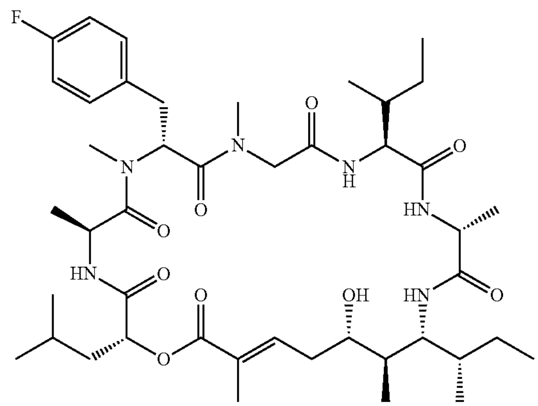 [SMILES: CCC(C)[C@@H]1NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@H](C)[C@@H]([C@@H](C)CC)NC(=O)[C@@H](C)NC1=O] |
| 47 | 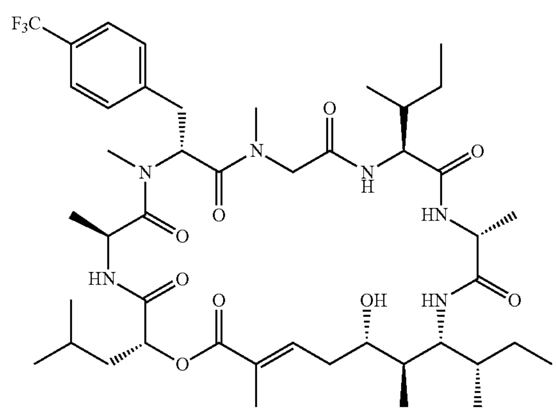 [SMILES: CCC(C)[C@@H]1NC(=O)CN(C)C(=O)[C@@H](Cc2ccc(C(F)(F)F)cc2)N(C)C(=O)[C@H](C)NC(=O)[C@@H](CC(C)C)OC(=O)/C(C)=C/C[C@H](O)[C@H](C)[C@@H]([C@@H](C)CC)NC(=O)[C@@H](C)NC1=O] |
| 48 | 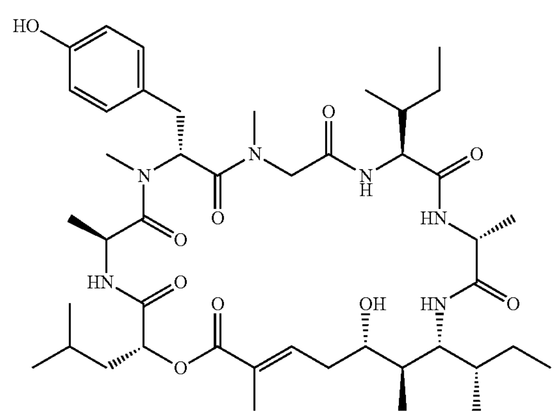 |

TABLE 1-continued

| Compound No. | Structure |
|---|---|
| 49 | (structure) |
| 50 | (structure) |
| 51 | (structure) |
| 52 | (structure) |

TABLE 1-continued
| Compound No. | Structure |
|---|---|
| 53 | 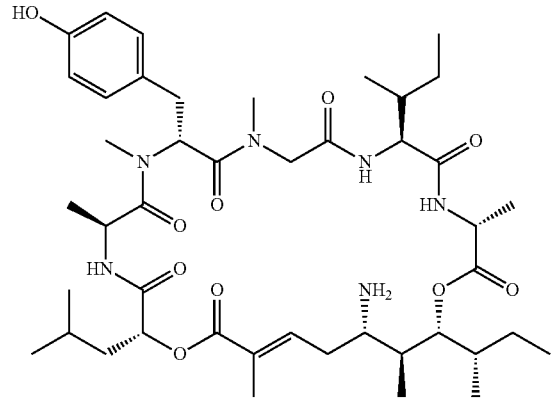 |
| 54 | 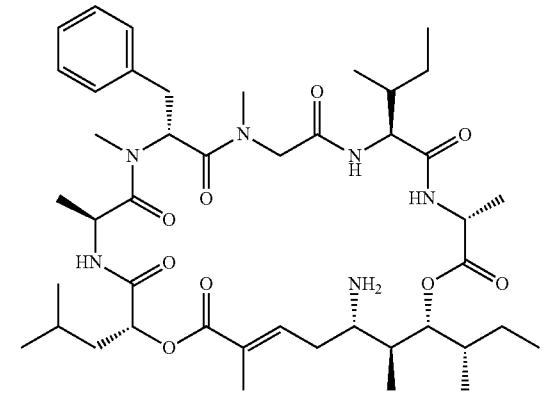 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/C[C@H](N)[C@H](C)[C@@H]([C@@H](C)CC)OC(=O)[C@@H](C)NC1=O] |
| 55 | 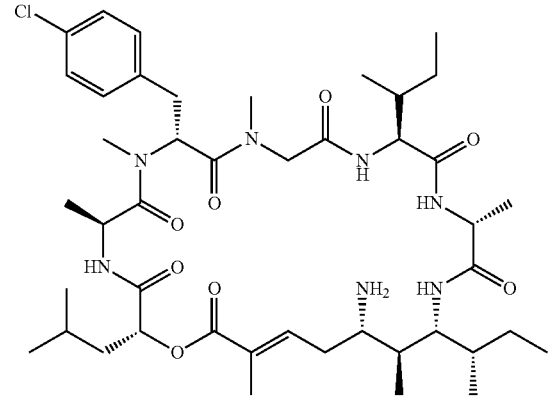 |

TABLE 1-continued

| Compound No. | Structure |
|---|---|
| 56 | *(structure)* |
| 57 | *(structure)* |
| 58 | *(structure)* |
| 59 | *(structure)* |

TABLE 1-continued
| Compound No. | Structure |
|---|---|
| 60 | 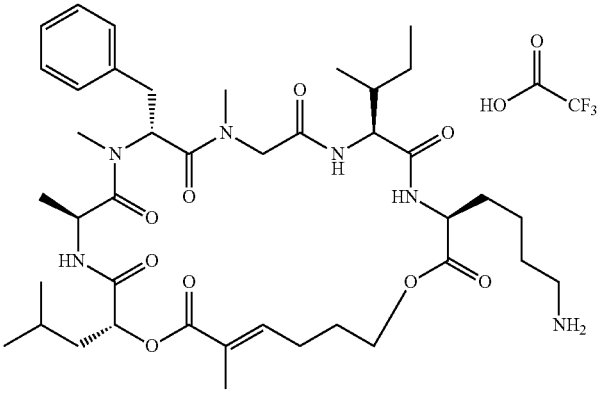 |
| 61 | 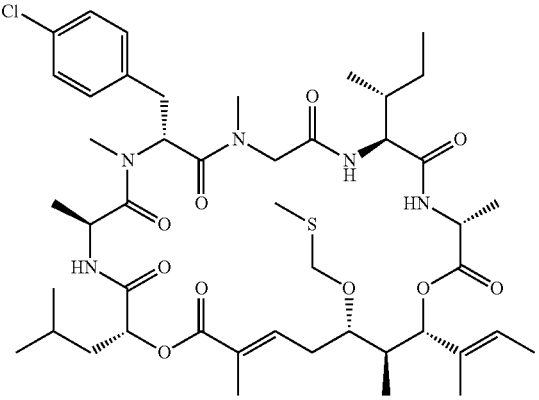 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OCSC)[C@@H]1C] |
| 62 | 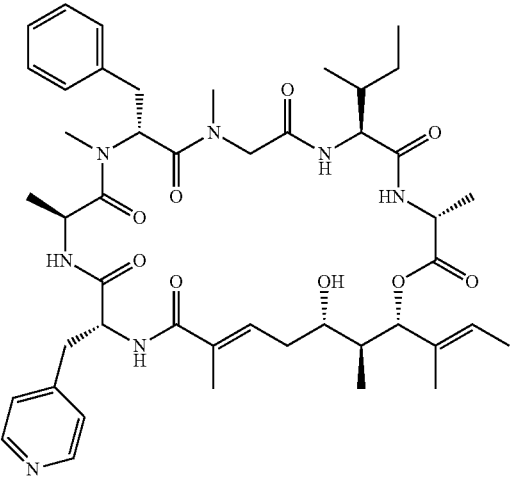 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](Cc2ccncc2)NC(=O)/C(C)=C/C[C@H](O)[C@@H]1C] |

TABLE 1-continued
| Compound No. | Structure |
|---|---|
| 63 | 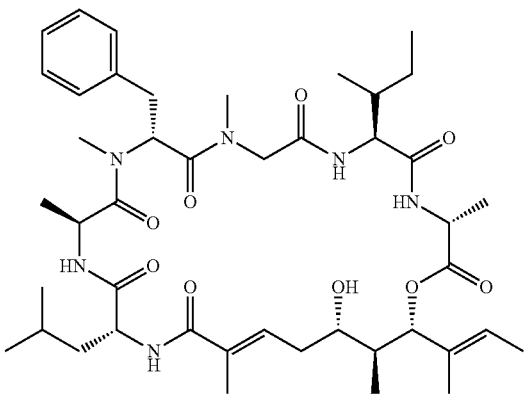 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)NC(=O)/C(C)=C/C[C@H](O)[C@@H]1C] |
| 64 | 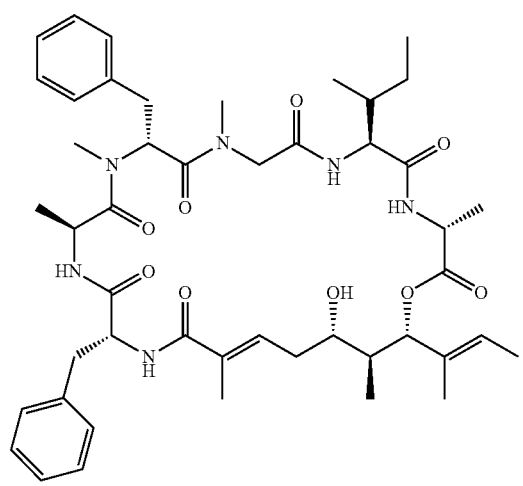 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](Cc2ccccc2)NC(=O)/C(C)=C/C[C@H](O)[C@@H]1C] |
| 65 | 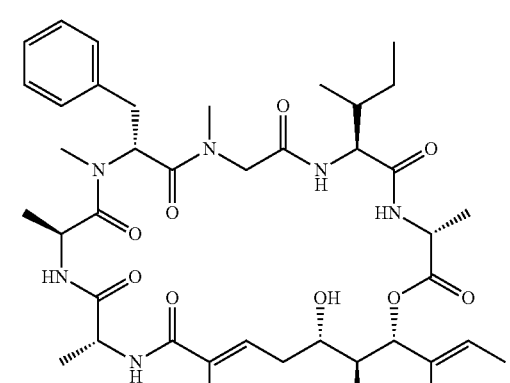 |

TABLE 1-continued
| Compound No. | Structure |
|---|---|
| 66 | 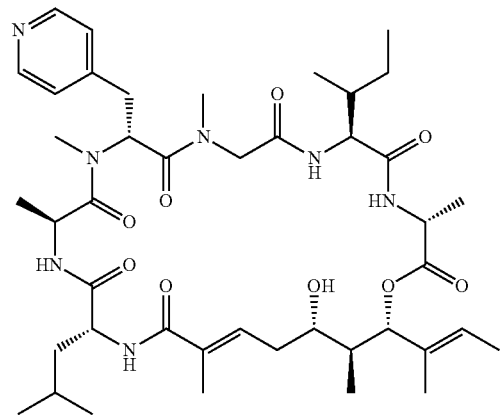 [SMILES: C/C=C(\C)[C@H]1OC(=O)[C@@H](C)NC(=O)[C@H](C(C)CC)NC(=O)CN(C)C(=O)[C@@H](Cc2ccncc2)N(C)C(=O)[C@H](C)NC(=O)[C@@H](CC(C)C)NC(=O)/C(C)=C/C[C@H](O)[C@@H]1C] |
| 67 | 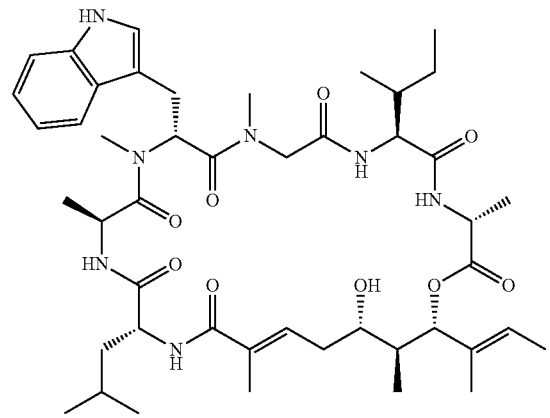 [SMILES: C/C=C(\C)[C@H]1OC(=O)[C@@H](C)NC(=O)[C@H](C(C)CC)NC(=O)CN(C)C(=O)[C@@H](Cc2c[nH]c3ccccc23)N(C)C(=O)[C@H](C)NC(=O)[C@@H](CC(C)C)NC(=O)/C(C)=C/C[C@H](O)[C@@H]1C] |
| 68 | 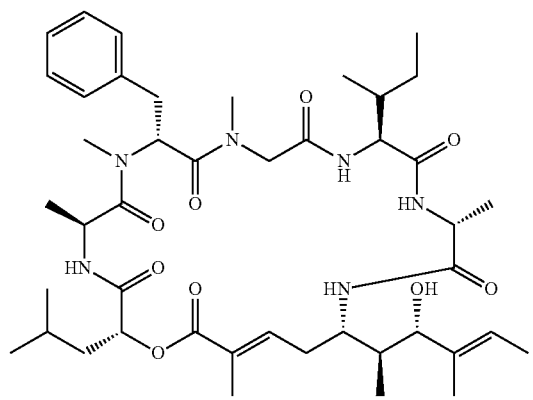 [SMILES: C/C=C(\C)[C@@H](O)[C@@H](C)[C@@H]1C/C=C(\C)C(=O)O[C@H](CC(C)C)C(=O)N[C@@H](C)C(=O)N(C)[C@H](Cc2ccccc2)C(=O)N(C)CC(=O)N[C@@H](C(C)CC)C(=O)N[C@H](C)C(=O)N1] |

… TABLE 1-continued
| Compound No. | Structure |
| --- | --- |
| 69 | 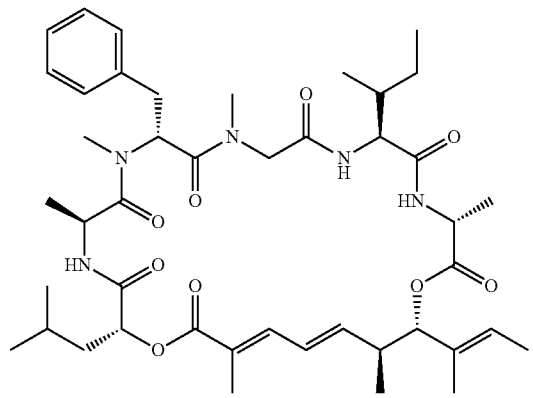 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C=C/[C@@H]1C] |
| 70 | 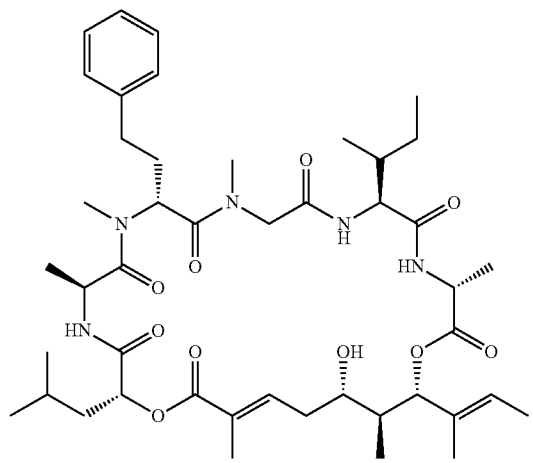 [SMILES: C/C=C(\C)[C@H]1OC(=O)[C@@H](C)NC(=O)[C@H](C(C)CC)NC(=O)CN(C)C(=O)[C@@H](CCc2ccccc2)N(C)C(=O)[C@H](C)NC(=O)[C@@H](CC(C)C)OC(=O)/C(C)=C/C[C@H](O)[C@@H]1C] |
| 71 | 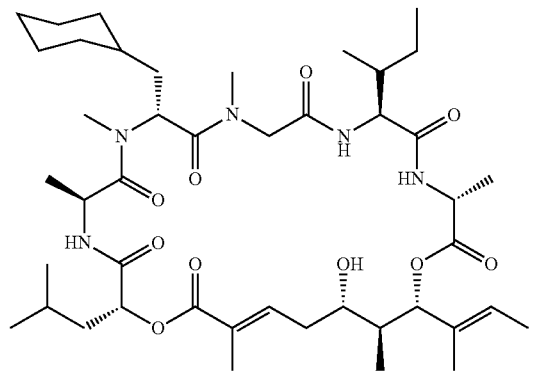 [SMILES: C/C=C(\C)[C@H]1OC(=O)[C@@H](C)NC(=O)[C@H](C(C)CC)NC(=O)CN(C)C(=O)[C@@H](CC2CCCCC2)N(C)C(=O)[C@H](C)NC(=O)[C@@H](CC(C)C)OC(=O)/C(C)=C/C[C@H](O)[C@@H]1C] |

TABLE 1-continued

| Compound No. | Structure |
| --- | --- |
| 72 | 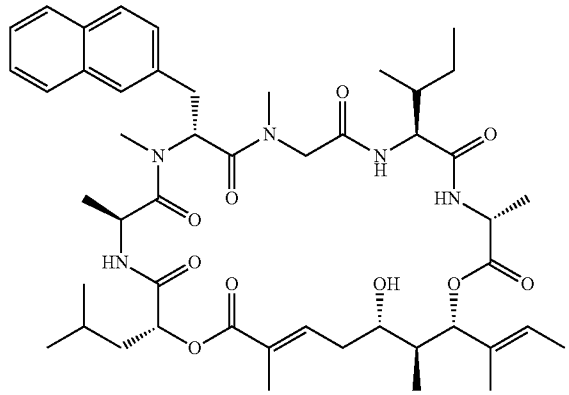 [SMILES: C/C=C(\C)[C@H]1OC(=O)[C@@H](C)NC(=O)[C@H](C(C)CC)NC(=O)CN(C)C(=O)[C@@H](Cc2ccc3ccccc3c2)N(C)C(=O)[C@H](C)NC(=O)[C@@H](CC(C)C)OC(=O)/C(C)=C/C[C@H](O)[C@@H]1C] |
| 73 | 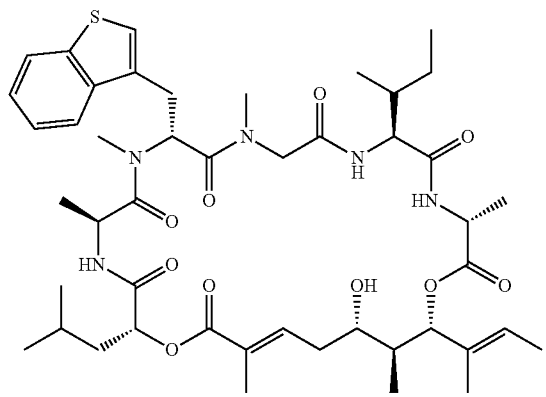 [SMILES: C/C=C(\C)[C@H]1OC(=O)[C@@H](C)NC(=O)[C@H](C(C)CC)NC(=O)CN(C)C(=O)[C@@H](Cc2csc3ccccc23)N(C)C(=O)[C@H](C)NC(=O)[C@@H](CC(C)C)OC(=O)/C(C)=C/C[C@H](O)[C@@H]1C] |
| 74 | 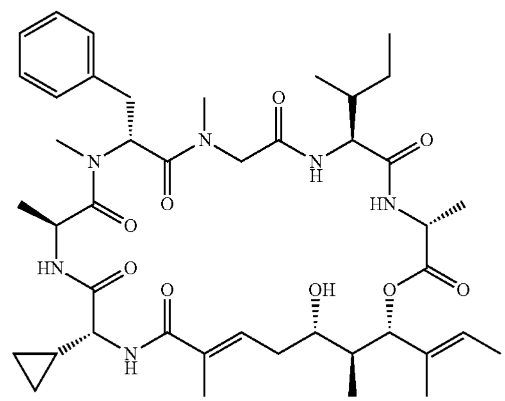 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](C2CC2)NC(=O)/C(C)=C/C[C@H](O)[C@@H]1C] |
| 75 | 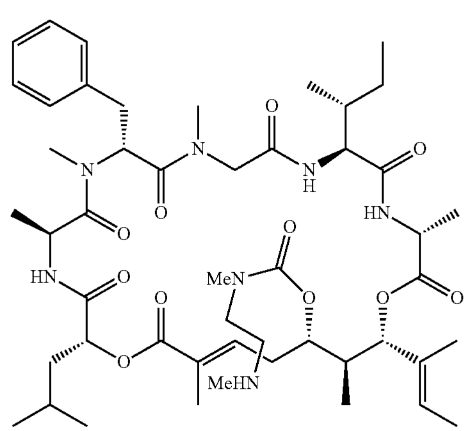 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCNC)[C@@H]1C] |

TABLE 1-continued

| Compound No. | Structure |
| --- | --- |
| 76 | 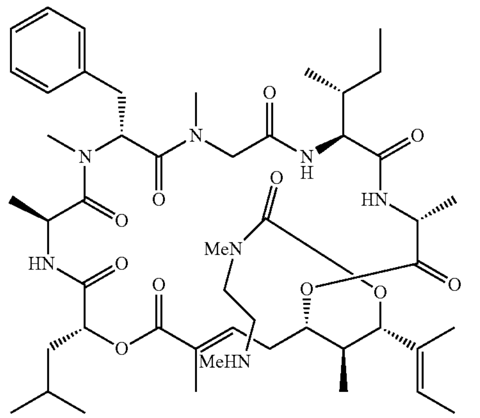 [SMILES: C/C=C(\C)[C@@H](OC(=O)N(C)CCNC)[C@@H](C)[C@@H]1C/C=C(\C)C(=O)O[C@H](CC(C)C)C(=O)N[C@@H](C)C(=O)N(C)[C@H](Cc2ccccc2)C(=O)N(C)CC(=O)N[C@@H]([C@H](C)CC)C(=O)N[C@H](C)C(=O)O1] |
| 77 | 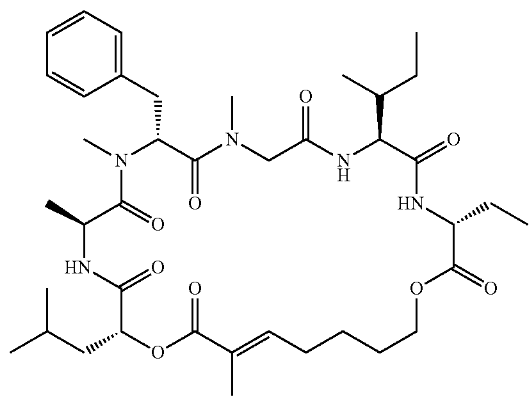 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@@H](CC)NC1=O] |
| 78 | | ns
TABLE 1-continued

| Compound No. | Structure |
|---|---|
| 79 | 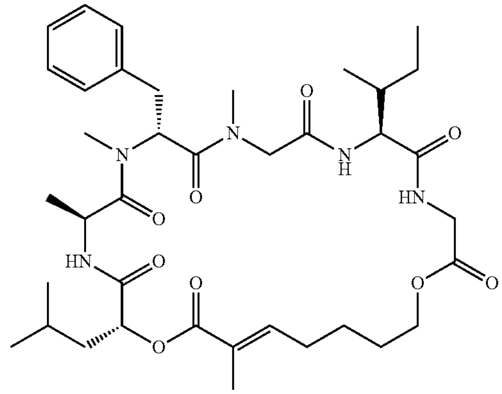 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)CNC1=O] |
| 80 | 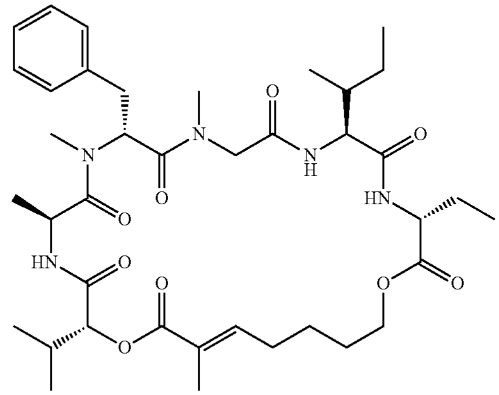 [SMILES: CCC(C)[C@@H]1NC(=O)CN(C)C(=O)[C@@H](Cc2ccccc2)N(C)C(=O)[C@H](C)NC(=O)[C@@H](C(C)C)OC(=O)/C(C)=C/CCCCOC(=O)[C@@H](CC)NC1=O] |
| 81 | 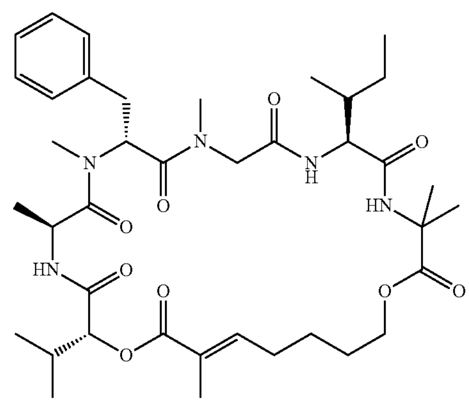 [SMILES: CCC(C)[C@@H]1NC(=O)CN(C)C(=O)[C@@H](Cc2ccccc2)N(C)C(=O)[C@H](C)NC(=O)[C@@H](C(C)C)OC(=O)/C(C)=C/CCCCOC(=O)C(C)(C)NC1=O] |
| 82 | 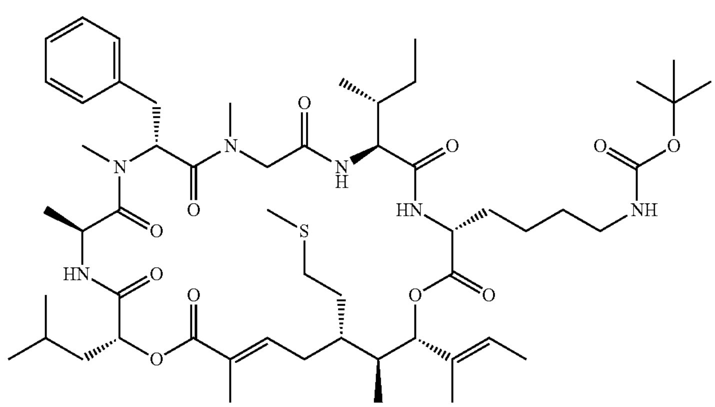 |

TABLE 1-continued
| Compound No. | Structure |
| --- | --- |
| 83 | 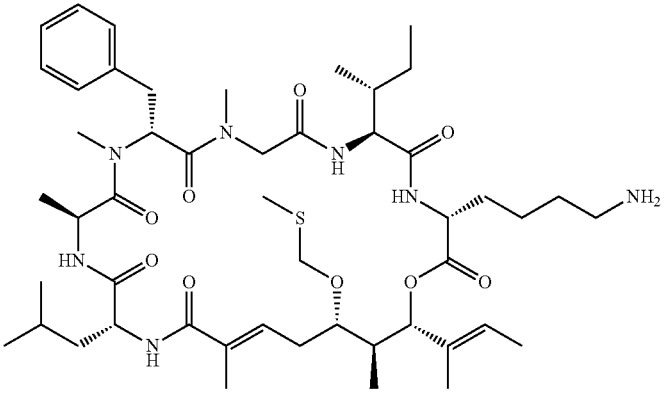 |
| 84 | 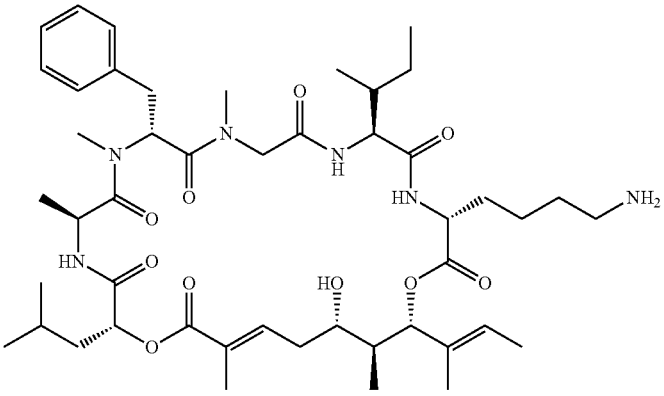 [SMILES: C/C=C(\C)[C@H]1OC(=O)[C@@H](CCCCN)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@@H]1C] |
| 85 | 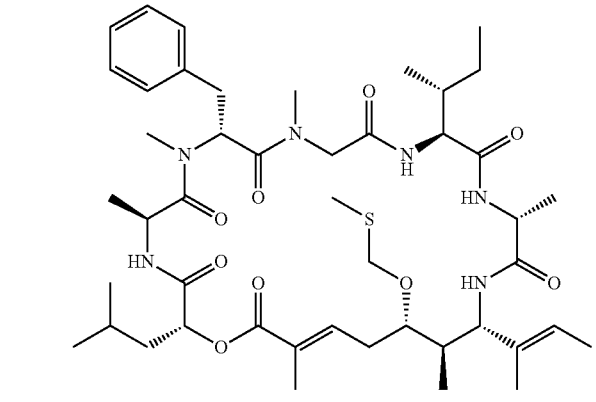 [SMILES: C/C=C(\C)[C@H]1NC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@@H]1C] |
| 86 | 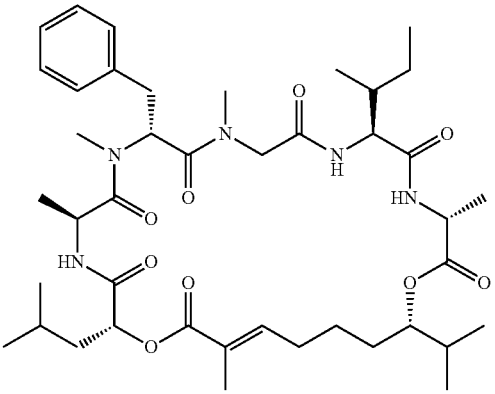 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@@H](C(C)C)OC(=O)[C@@H](C)NC1=O] |

TABLE 1-continued
| Compound No. | Structure |
|---|---|
| 87 | 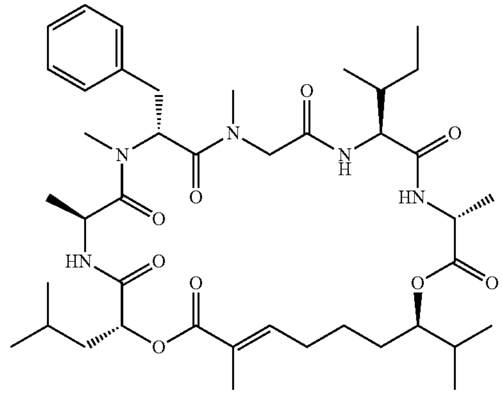 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@H](C(C)C)OC(=O)[C@@H](C)NC1=O] |
| 88 | 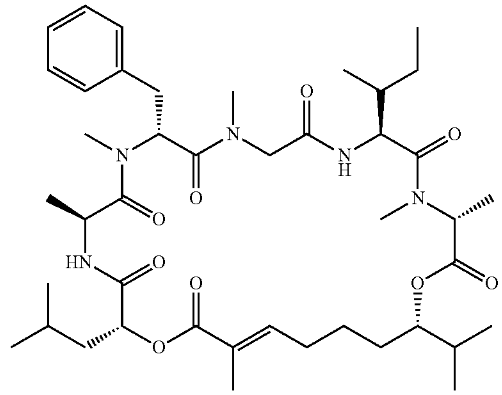 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@@H](C(C)C)OC(=O)[C@@H](C)N(C)C1=O] |
| 89 | 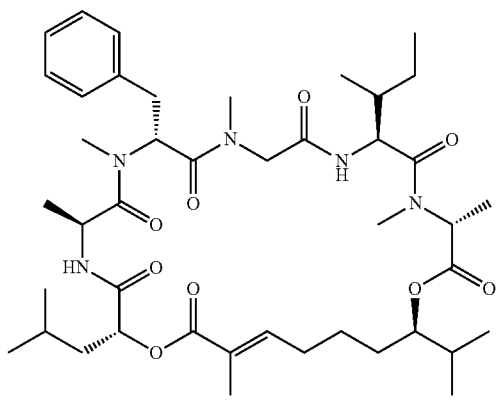 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@H](C(C)C)OC(=O)[C@@H](C)N(C)C1=O] |
| 90 | 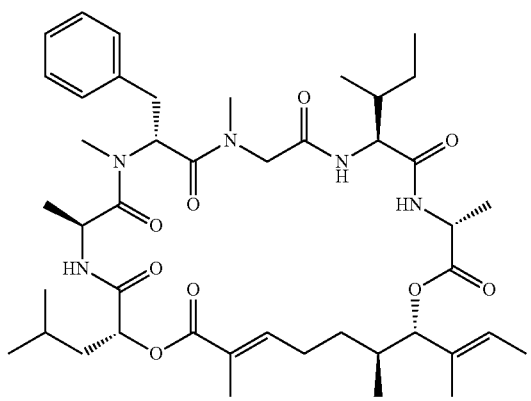 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/CC[C@@H]1C] |

TABLE 1-continued
| Compound No. | Structure |
|---|---|
| 91 | 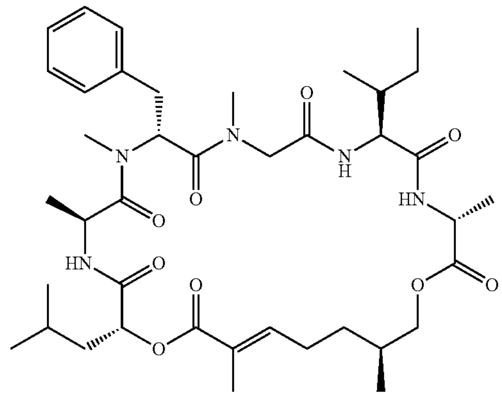 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CC[C@H](C)COC(=O)[C@@H](C)NC1=O] |
| 92 | 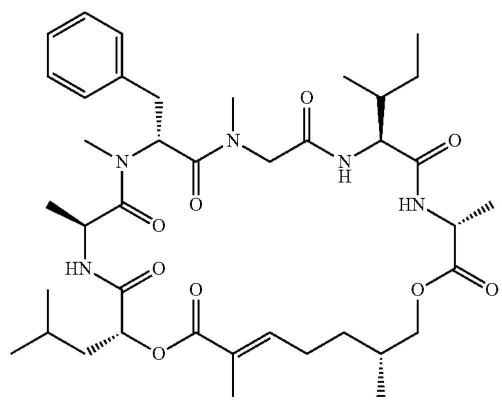 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CC[C@@H](C)COC(=O)[C@@H](C)NC1=O] |
| 93 | 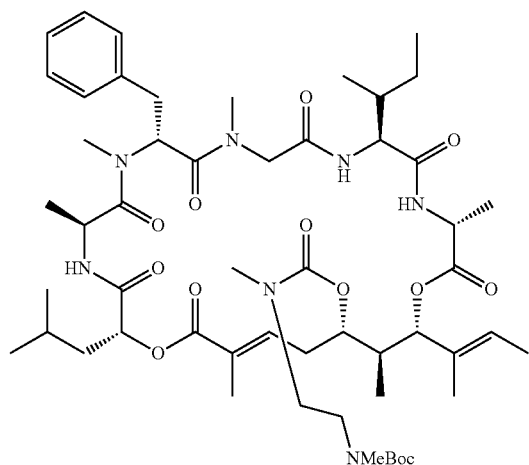 |

TABLE 1-continued
| Compound No. | Structure |
|---|---|
| 94 | 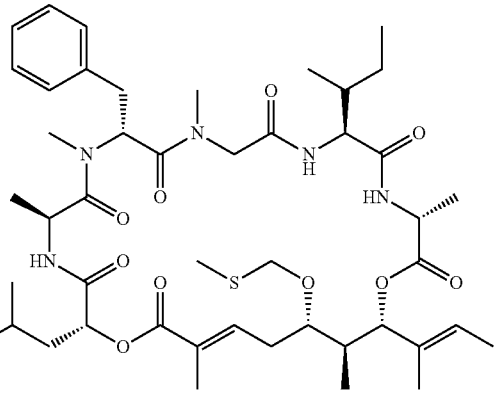 |
| 95 | 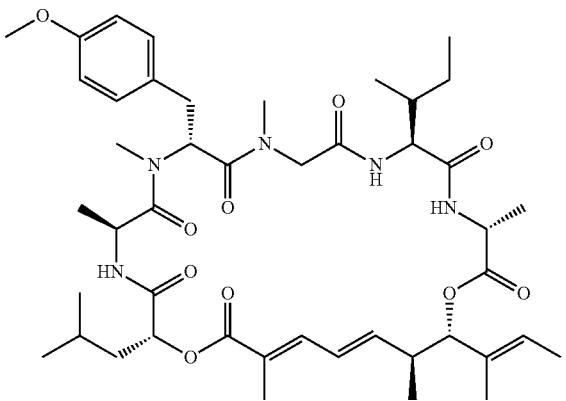 [SMILES: C/C=C(\C)[C@H]1OC(=O)[C@@H](C)NC(=O)[C@H](C(C)CC)NC(=O)CN(C)C(=O)[C@@H](Cc2ccc(OC)cc2)N(C)C(=O)[C@H](C)NC(=O)[C@@H](CC(C)C)OC(=O)/C(C)=C/C=C/[C@@H]1C] |
| 96 | 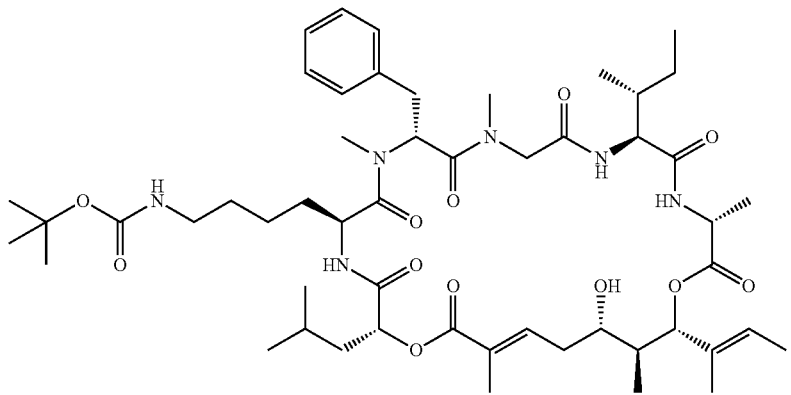 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](CCCCNC(=O)OC(C)(C)C)NC(=O)[C@@H](CC(C)C)OC(=O)/C(C)=C/C[C@H](O)[C@@H]1C] |
| 97 | 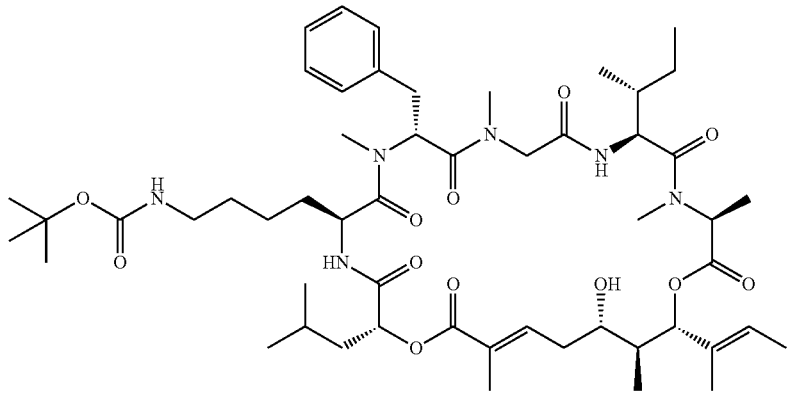 [SMILES: C/C=C(\C)[C@H]1OC(=O)[C@H](C)N(C)C(=O)[C@H]([C@H](C)CC)NC(=O)CN(C)C(=O)[C@@H](Cc2ccccc2)N(C)C(=O)[C@H](CCCCNC(=O)OC(C)(C)C)NC(=O)[C@@H](CC(C)C)OC(=O)/C(C)=C/C[C@H](O)[C@@H]1C] |

TABLE 1-continued

| Compound No. | Structure |
|---|---|
| 98 | 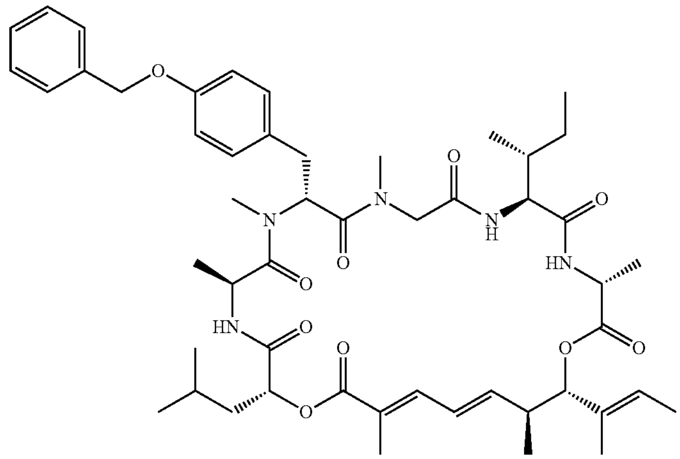 [SMILES: C/C=C(\C)[C@H]1OC(=O)[C@@H](C)NC(=O)[C@H]([C@H](C)CC)NC(=O)CN(C)C(=O)[C@@H](Cc2ccc(OCc3ccccc3)cc2)N(C)C(=O)[C@H](C)NC(=O)[C@@H](CC(C)C)OC(=O)/C(C)=C/C=C/[C@@H]1C] |
| 99 | 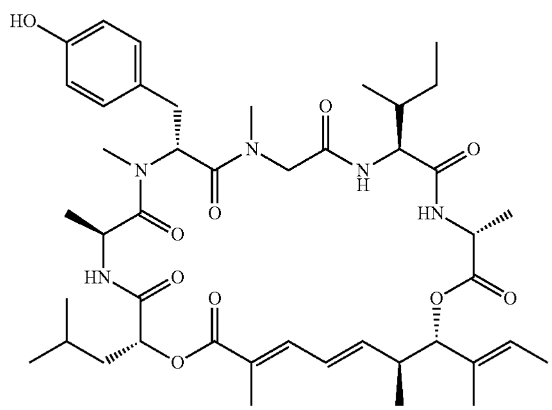 [SMILES: C/C=C(\C)[C@H]1OC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/C=C/[C@@H]1C] |
| 100 | 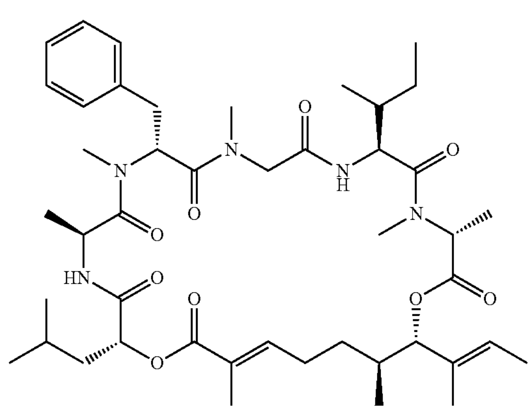 [SMILES: C/C=C(\C)[C@H]1OC(=O)[C@@H](C)N(C)C(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/CC[C@@H]1C] |

TABLE 1-continued

| Compound No. | Structure |
|---|---|
| 101 | 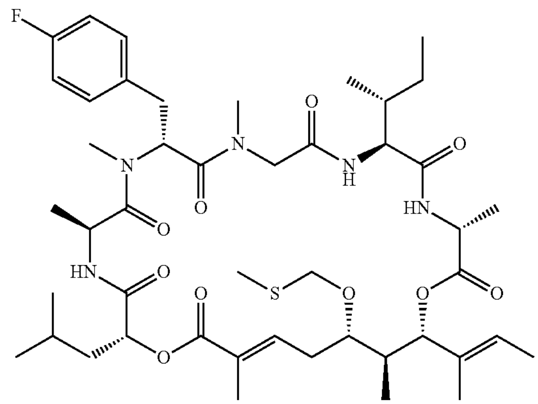 [SMILES: C/C=C(\C)[C@H]1OC(=O)[C@@H](C)NC(=O)[C@H]([C@H](C)CC)NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](OCSC)[C@@H]1C] |
| 102 | 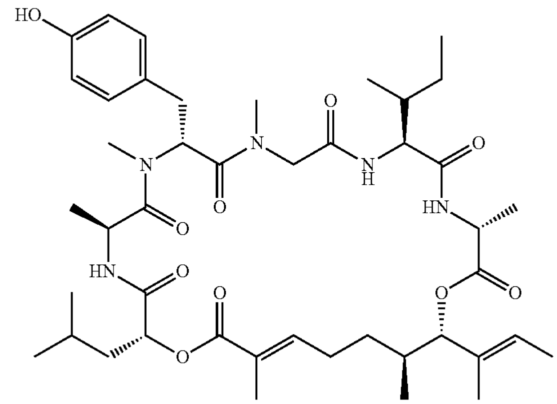 [SMILES: C/C=C(\C)[C@H]1OC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/CC[C@@H]1C] |
| 103 | 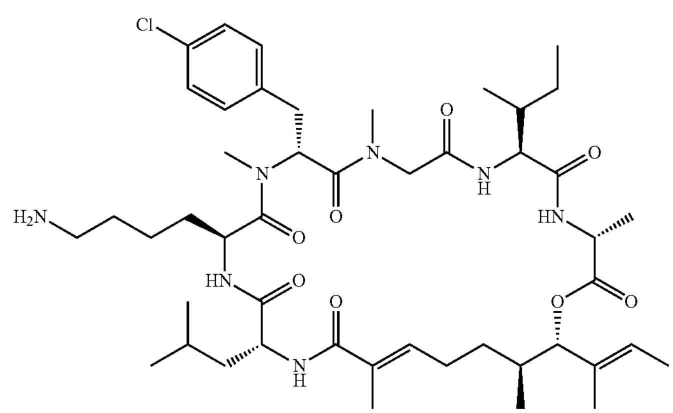 |
| 104 | 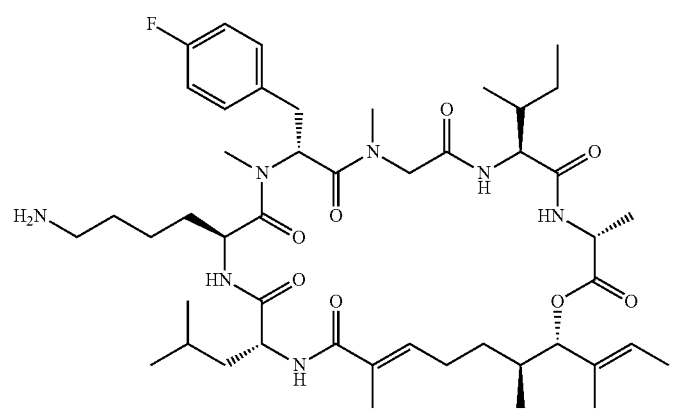 [SMILES: C/C=C(\C)[C@H]1OC(=O)[C@@H](C)NC(=O)[C@H](C(C)CC)NC(=O)CN(C)C(=O)[C@@H](Cc2ccc(F)cc2)N(C)C(=O)[C@H](CCCCN)NC(=O)[C@@H](CC(C)C)NC(=O)/C(C)=C/CC[C@@H]1C] |

TABLE 1-continued
| Compound No. | Structure |
|---|---|
| 105 | 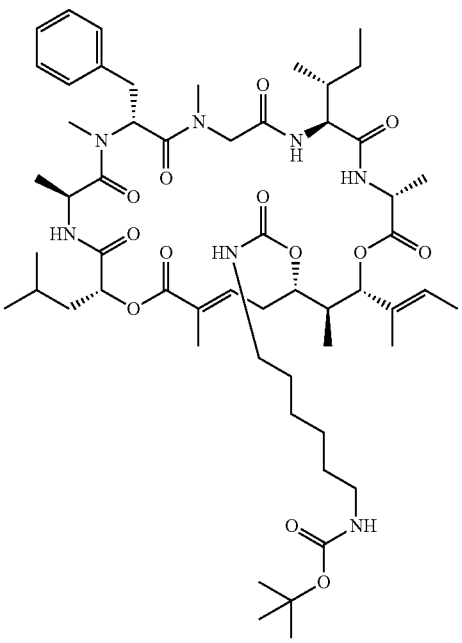 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCNC(=O)OC(C)(C)C)[C@@H]1C] |
| 106 | 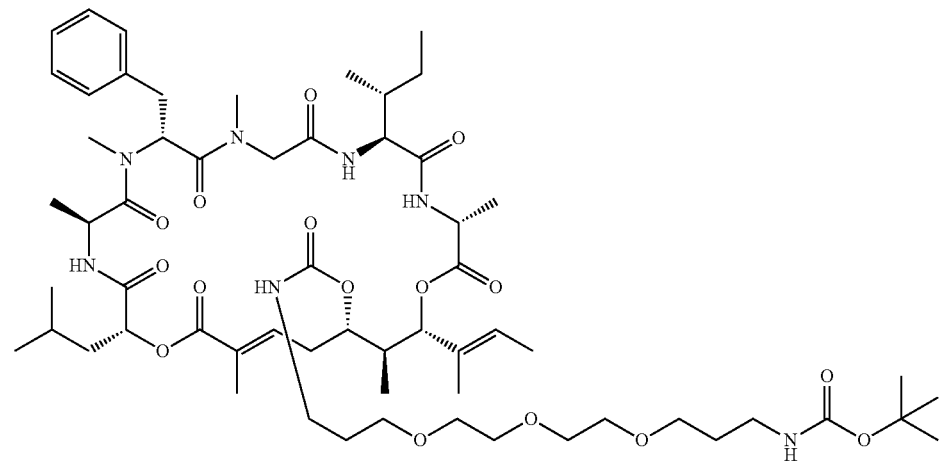 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCNC(=O)OC(C)(C)C)[C@@H]1C] |
| 107 | 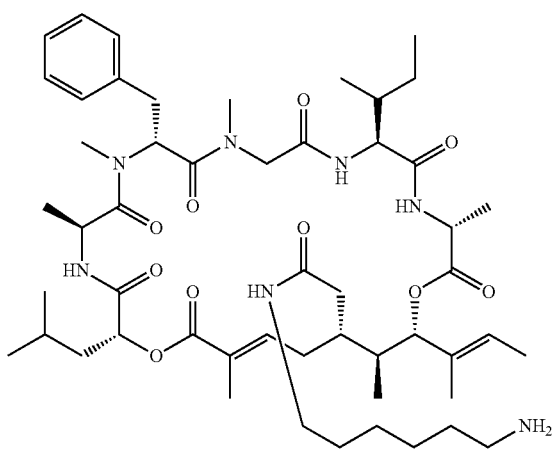 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](CC(=O)NCCCCCCN)[C@@H]1C] |

TABLE 1-continued
| Compound No. | Structure |
|---|---|
| 108 | 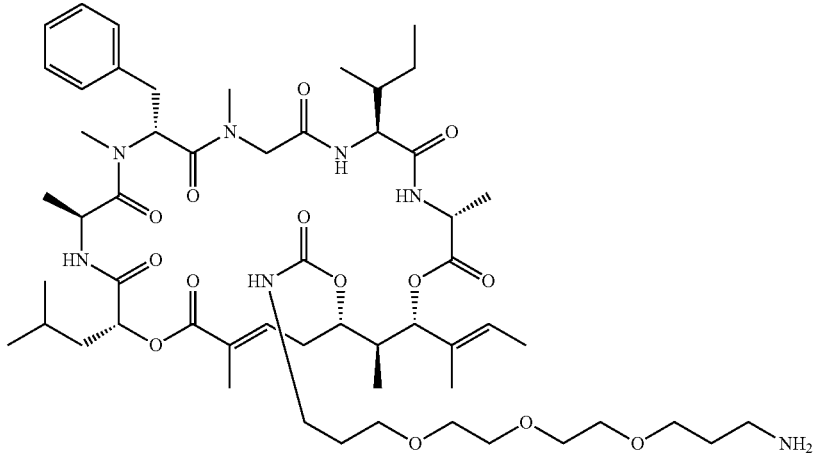 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCN)[C@@H]1C] |
| 109 | 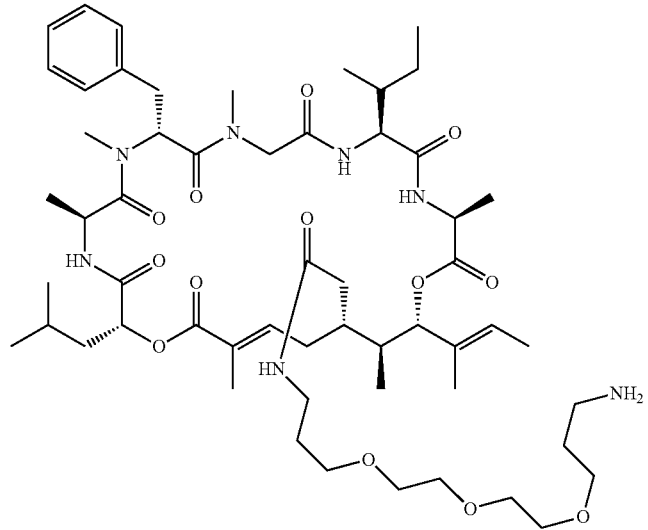 [SMILES: C/C=C(\C)[C@H]1OC(=O)[C@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](CC(=O)NCCCOCCOCCOCCCN)[C@@H]1C] |
| 110 | 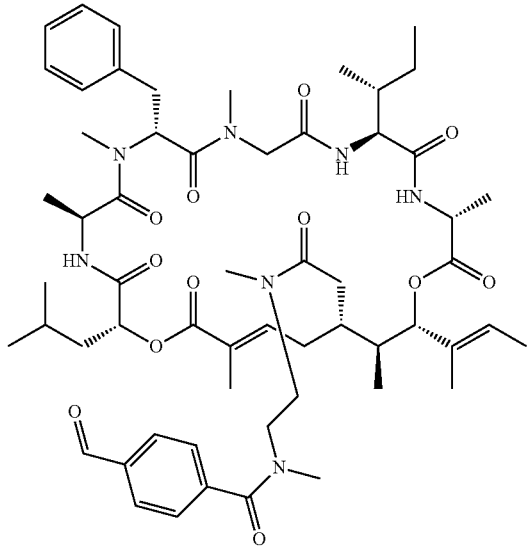 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](CC(=O)N(C)CCN(C)C(=O)c2ccc(C=O)cc2)[C@@H]1C] |

TABLE 1-continued
| Compound No. | Structure |
|---|---|
| 111 | 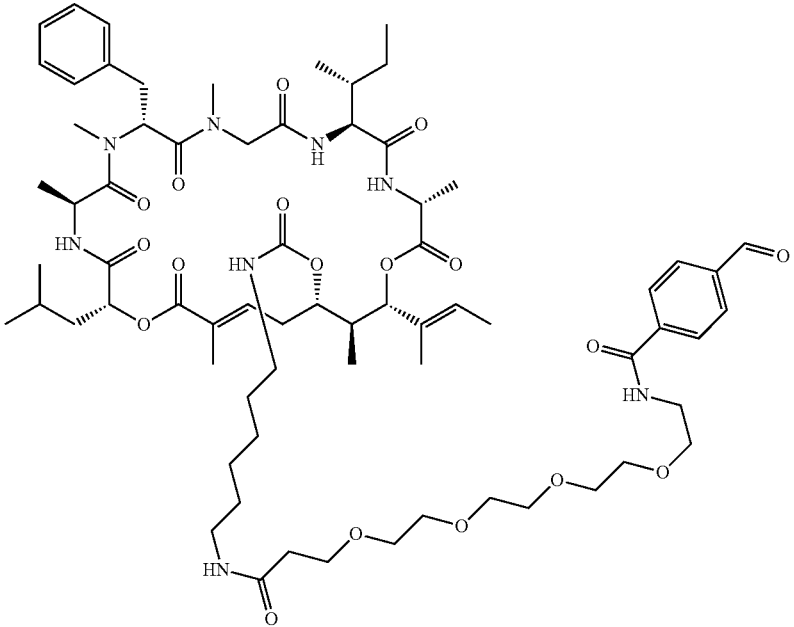 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCNC(=O)CCOCCOCCOCCOCCNC(=O)c2ccc(C=O)cc2)[C@@H]1C] |
| 112 | 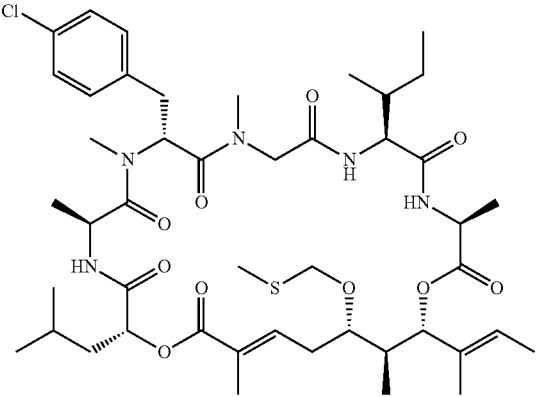 [SMILES: C/C=C(\C)[C@H]1OC(=O)[C@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OCSC)[C@@H]1C] |
| 113 | 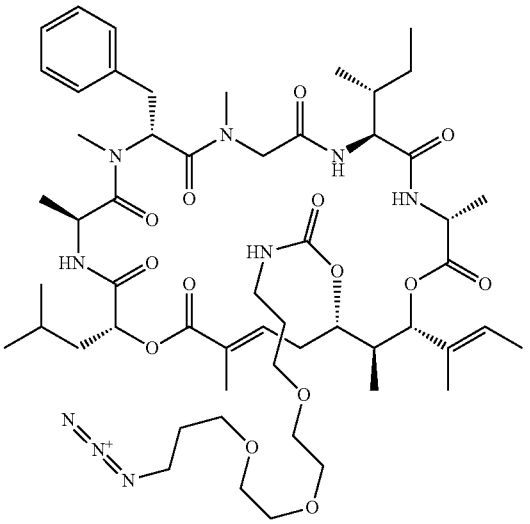 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCN=[N+]=N)[C@@H]1C] |

… 149 …
TABLE 1-continued
| Compound No. | Structure |
|---|---|
| 114 | 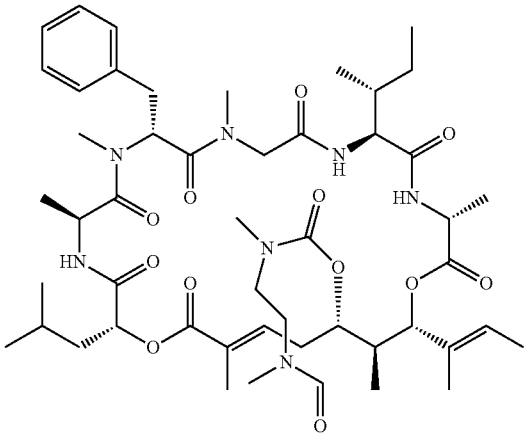 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)C=O)[C@@H]1C] |
| 115 | 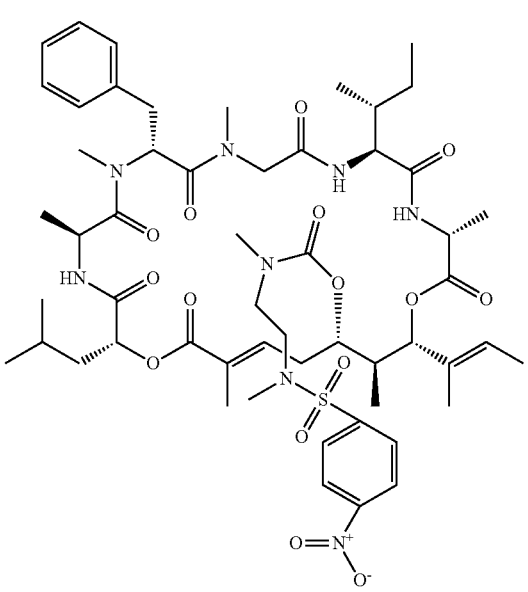 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)S(=O)(=O)c2ccc([N+](=O)[O-])cc2)[C@@H]1C] |

TABLE 1-continued
| Compound No. | Structure |
|---|---|
| 116 | 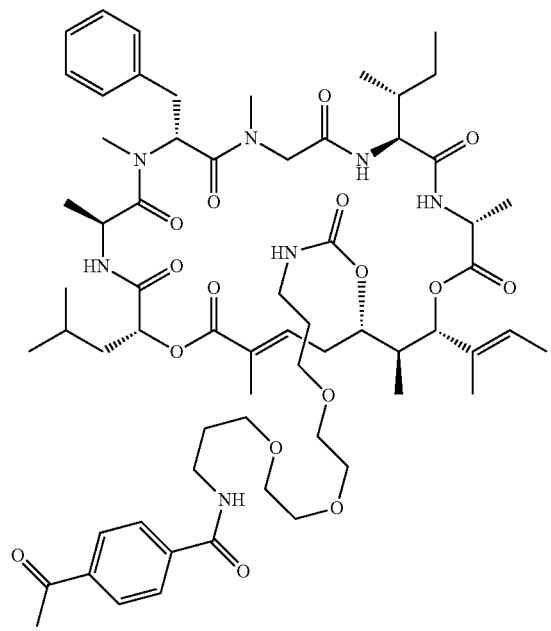 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCNC(=O)c2ccc(C(C)=O)cc2)[C@@H]1C] |
| 117 | 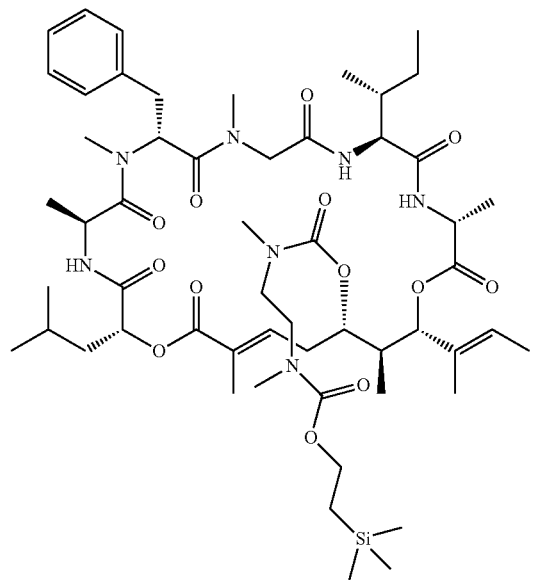 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)C(=O)OCC[Si](C)(C)C)[C@@H]1C] |
| 118 | 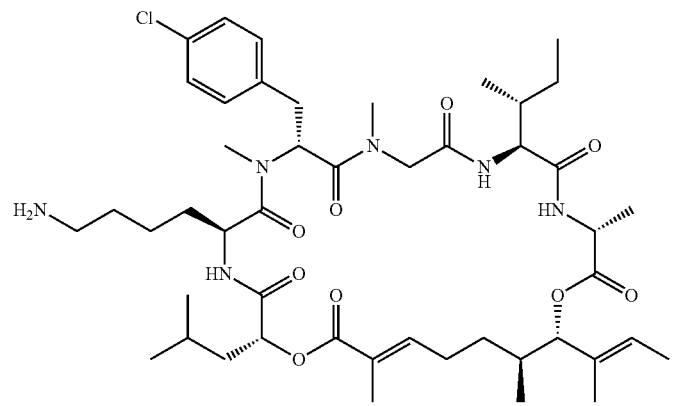 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCN)NC(=O)[C@@H](CC(C)C)OC(=O)/C(C)=C/CC[C@@H]1C] |

TABLE 1-continued
| Compound No. | Structure |
| --- | --- |
| 119 | 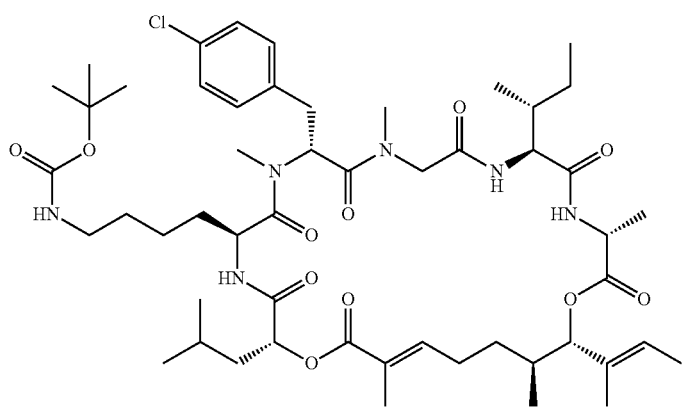 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCNC(=O)OC(C)(C)C)NC(=O)[C@@H](CC(C)C)OC(=O)/C(C)=C/CC[C@@H]1C] |
| 120 | 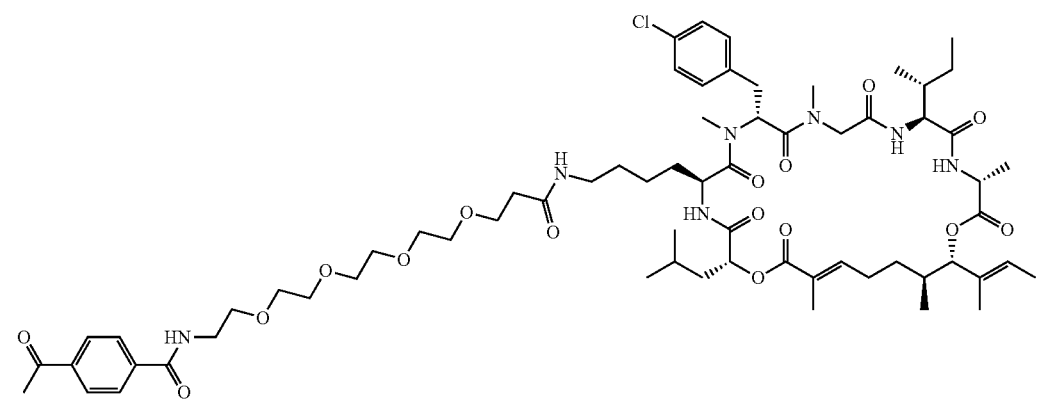 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCNC(=O)CCOCCOCCOCCOCCNC(=O)c2ccc(C(C)=O)cc2)NC(=O)[C@@H](CC(C)C)OC(=O)/C(C)=C/CC[C@@H]1C] |
| 121 | 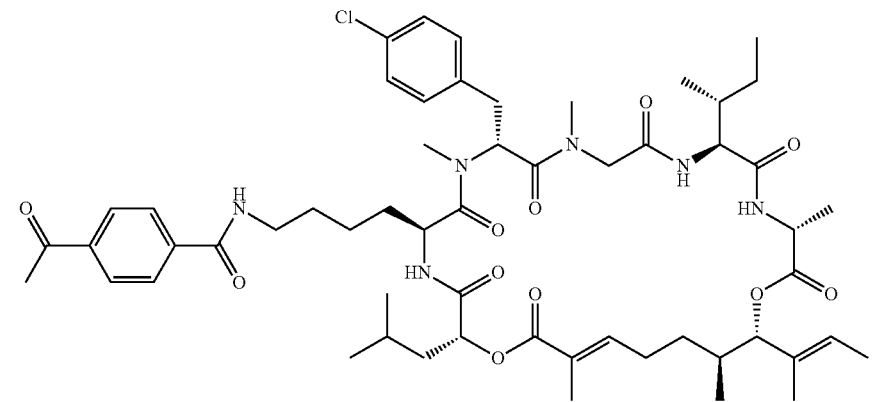 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCNC(=O)c2ccc(C(C)=O)cc2)NC(=O)[C@@H](CC(C)C)OC(=O)/C(C)=C/CC[C@@H]1C] |

TABLE 1-continued
| Compound No. | Structure |
|---|---|
| 122 | 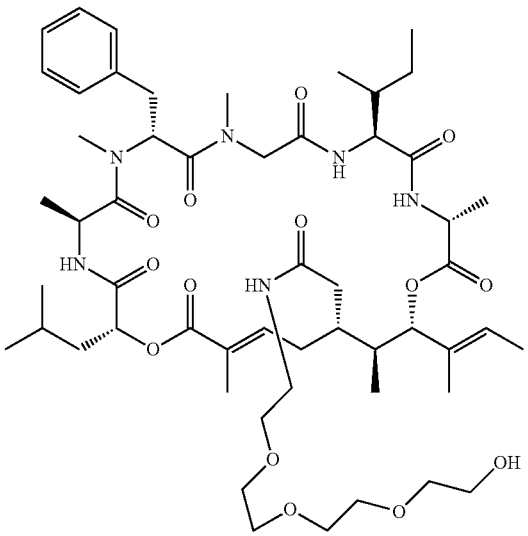 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](CC(=O)NCCOCCOCCOCCO)[C@@H]1C] |
| 123 | 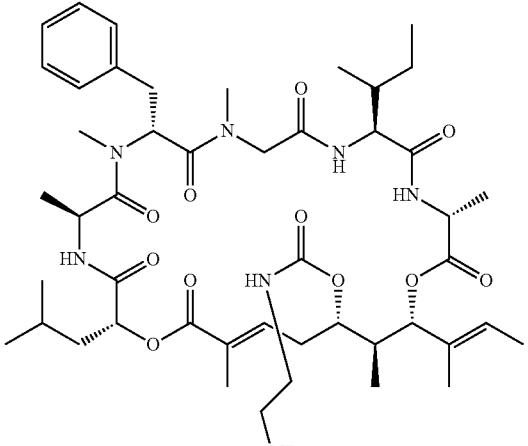 |
| 124 | 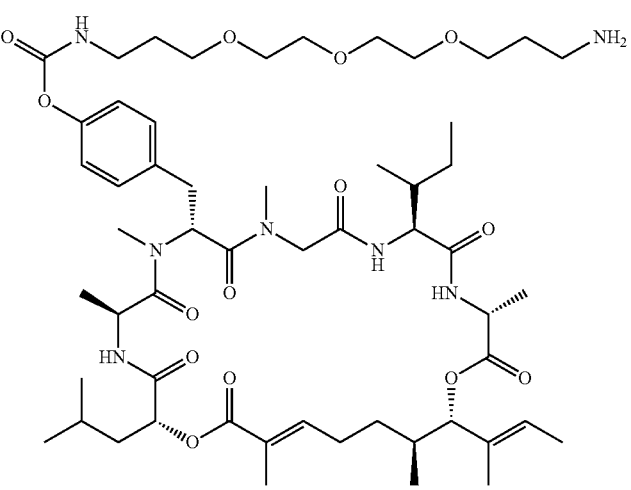 [SMILES: C/C=C(\C)[C@H]1OC(=O)[C@@H](C)NC(=O)[C@H](C(C)CC)NC(=O)CN(C)C(=O)[C@@H](Cc2ccc(OC(=O)NCCCOCCOCCOCCCN)cc2)N(C)C(=O)[C@H](C)NC(=O)[C@@H](CC(C)C)OC(=O)/C(C)=C/CC[C@@H]1C] |

TABLE 1-continued

| Compound No. | Structure |
|---|---|
| 125 | 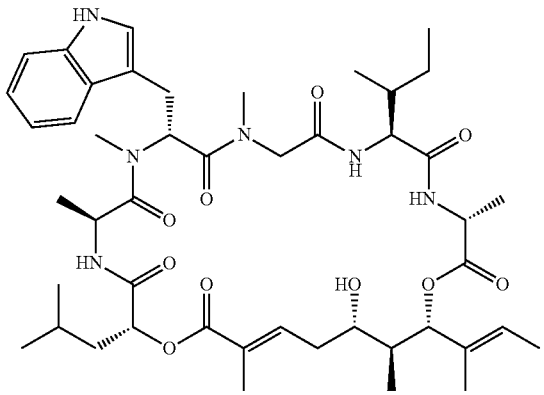 [SMILES: C/C=C(\C)[C@H]1OC(=O)[C@@H](C)NC(=O)[C@H](C(C)CC)NC(=O)CN(C)C(=O)[C@@H](Cc2c[nH]c3ccccc23)N(C)C(=O)[C@H](C)NC(=O)[C@@H](CC(C)C)OC(=O)/C(C)=C/C[C@H](O)[C@@H]1C] |

In some variations, any of the compounds described herein, such as a compound of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or a compound of Table 1, may be deuterated (e.g., a hydrogen atom is replaced by a deuterium atom). In some of these variations, the compound is deuterated at a single site. In other variations, the compound is deuterated at multiple site. Deuterated compounds can be prepared from deuterated starting materials in a manner similar to the preparation of the corresponding non-deuterated compounds. Hydrogen atoms may also be replaced with deuterium atoms using other methods known in the art.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Conjugates

The compounds described herein may be conjugated to one or more linkers and/or ligands. A ligand may be directly bound to a compound of Formula (I), (II), or (III) or any variation thereof, including any compound listed in Table 1. Alternatively, a ligand may be bound to a compound of Formula (I), (II), or (III) or any variation thereof, including any compound listed in Table 1, via one or more linkers. In some variations, the ligand is a polypeptide. In some variations, the ligand is a nucleic acid. In some variations, the ligand is a targeting moiety. In some variations, the ligand is an antibody. In some variations, the antibody binds to a receptor. In some variations, the antibody binds to a receptor on the surface of a cell.

Accordingly, in one aspect, provided herein are conjugates of the compounds described herein. In some variations, provided is a conjugate containing a compound of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, bonded to a ligand. In some variations, the compound of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, is directly bonded to the ligand (i.e., no linker is present). In other variations, the compound of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, is bonded to the ligand via a linker. Any suitable ligand and/or linker can be used in the foregoing compositions, including, but not limited to, any of the linkers or ligands described herein.

In any of the conjugates provided herein, the ratio of compound to ligand may be 1:1, 2:1, 3:1, 4:1, 5:1, 6:1, 7:1, 8:1, 9:1, 10:1, 11:1, or 12:1. In any of the conjugates provided herein, the ratio of compound to ligand may be 1:1 or 1:2. In any of the conjugates provided herein, the ratio of linker to ligand may be 1:1, 2:1, 3:1, 4:1, 5:1, 6:1, 7:1, 8:1, 9:1, 10:1, 11:1, or 12:1.

Also provided herein are conjugates containing a compound described herein bonded to a linker. The ratio of compound to linker may be 1:1, 2:1, 3:1, 1:2, or 1:3. In some embodiments, the linker is additionally bonded to a ligand. In other embodiments, the linker is not bonded to a ligand. In some such embodiments, the linker contains one or more functional groups suitable for bonding to a ligand. As used herein, the term "drug-linker conjugate" refers to a compound provided herein bonded to a linker, wherein the linker is not further bonded to a ligand.

In some variations, provided is a conjugate containing a compound of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, bonded to a linker. Any suitable linker can be used in the foregoing compositions, including, but not limited to, any of the linkers described herein. The linker may be suitable for attachment to a ligand.

One or more linkers and/or ligands may be bonded to a compound described herein via a functional group including, but not limited to —NHR, —NHNH$_2$, —ONH$_2$, —N$_3$, —OH, —SH, or CO$_2$H located at any chemically feasible position on the compound. In some embodiments, the conjugation site on the compound is an —OH or —NH$_2$ group. In particular embodiments, the conjugation site on the compound is an —OH or —NH$_2$ group located at the position corresponding —Y$^1$—R$^c$ or Y$^2$—R$^c$. In other embodiments, the conjugation site on the compound is a phenyl ring substituted with —NHR, —NH$_2$, or OH. In particular embodiments, the functional group for conjugation is at the para position on the phenyl ring. In yet other embodiments, an amino acid unit of the compound has been replaced with a lysine unit as a site for conjugation.

Provided herein are compounds of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, or a salt thereof, wherein the compound is substituted at any chemically feasible position with a moiety suitable for attachment to a linker and/or ligand. In some variations, provided are compounds of Formula (I), (II), (III), (B), (Ii), (IIi), (IIIi), (Bi), (Ia), (Iai), (IIa), (IIai), (Ib), (Ibi), (IIb), (IIbi), (IIc), (IIci), (IId), (IIdi), (Ie), (Iei), (IIe), (IIei), (If), or (Ig), or any variation thereof, or any compound listed in Table 1, or a salt thereof, wherein the compound is substituted at any chemically feasible position with a functional group which is —NHR, —NHNH$_2$, —ONH$_2$, —N$_3$, —OH, —SH, or —CO$_2$H. In any of the foregoing embodiments, the functional group suitable for attachment to a linker and/or ligand is bonded to a protecting group, which may be removed prior to reaction with a linker and/or ligand.

In some aspects, provided herein are conjugates having Formula (C):

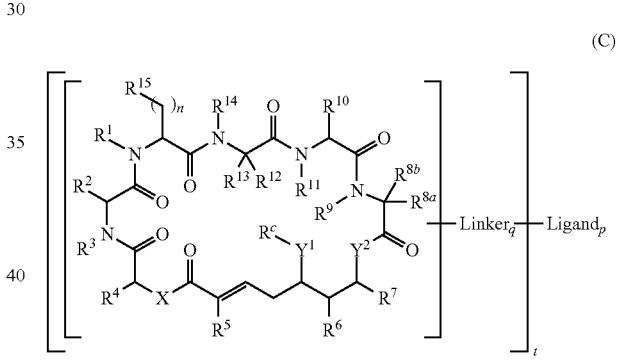

(C)

and salts thereof, wherein R$^1$, R$^2$, R$^3$, R$^4$, R$^5$, R$^6$, R$^7$, R$^{8a}$, R$^{8b}$, R$^9$, R$^{10}$, R$^{11}$, R$^{12}$, R$^{13}$, R$^{14}$, R$^{15}$, R$^c$, n, X, Y$^1$, and Y$^2$ are as defined for Formula (I) or any variation thereof;
q is 0, 1, or 2;
p is 0, 1, or 2; and
t is an integer from 1-12, inclusive.

In other aspects, provided herein are conjugates having Formula (D):

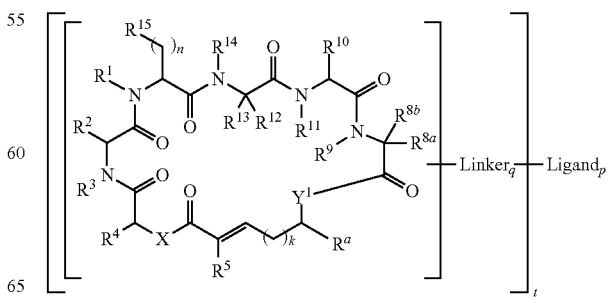

and salts thereof, wherein $R^1$, $R^2$, $R^3$, $R^4$, $R^5$, $R^{8a}$, $R^{8b}$, $R^9$, $R^{10}$, $R^{11}$, $R^{12}$, $R^{13}$, $R^{14}$, $R^{15}$, $R^a$, k, n, X, and $Y^1$ are as defined for Formula (II) or any variation thereof;

q is 0, 1, or 2;

p is 0, 1, or 2; and t is an integer from 1-12, inclusive.

In other aspects, provided herein are conjugates having Formula (E):

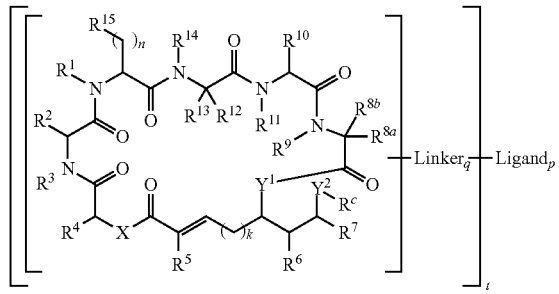

and salts thereof, wherein $R^1$, $R^2$, $R^3$, $R^4$, $R^5$, $R^{8a}$, $R^{8b}$, $R^9$, $R^{10}$, $R^{11}$, $R^{12}$, $R^{13}$, $R^{14}$, $R^{15}$, $R^a$, $R^c$, k, n, X, $Y^1$, and $Y^2$ are as defined for Formula (B) or any variation thereof;

q is 0, 1, or 2;

p is 0, 1, or 2; and t is an integer from 1-12, inclusive.

In any variations of conjugates having Formulas (C), (D), and (E), chemically appropriate valences and chemical bonding are present in the compound at the site of conjugation to the linker and/or ligand. For example, an atom on the compound is replaced by the linker or ligand such that a chemically appropriate number of bonds is maintained for all atoms. In particular examples, an —OH moiety on the compound is replaced with an —O-linker-ligand moiety in the conjugate, or an —NH₂— moiety on the compound is replaced with an —NH— linker-ligand moiety in the conjugate.

In some variations of any of the conjugates of Formula (C), (D), and (E), one or more linkers and/or ligands may be bonded to a compound described herein via a functional group including, but not limited to —NHR, —NHNH₂, —ONH₂, —N₃, —OH, —SH, or —CO₂H located at any chemically feasible position on the compound. In some embodiments, the conjugation site on the compound is an —OH or —NH₂ group. In particular embodiments, the conjugation site on the compound is an —OH or —NH₂ group located at the position corresponding to —$Y^1$—$R^c$ or $Y^2$—$R^c$. In other embodiments, the conjugation site on the compound is a phenyl ring substituted with —NHR, —NH₂, or OH. In particular embodiments, the substitution is at the para position on the phenyl ring. In yet other embodiments, an amino acid unit of the compound has been replaced with a lysine unit as a site for conjugation.

In a particular linker configuration, a compound of Formula (I) or any variation thereof is modified at position $Y^1$ to contain an amine linker according to Formula (L):

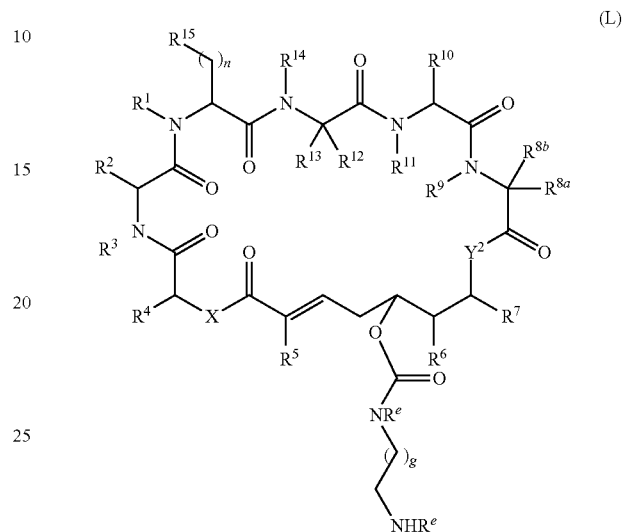

or a salt thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, X, and $Y^2$ are as defined for Formula (I) or any variation thereof;

each $R^e$ is independently H or substituted or unsubstituted alkyl; and g is 1, 2, 3, 4, or 5.

In some variations of any of the conjugates of Formula (C), (D), and (E), one or more linkers and/or ligands may be bonded to a compound described herein via a hydroxyl group. In some variations, the linkers can be carbamate linkers, silyl linkers, pyrophosphate linkers, p-aminobenzyl (PAB) linkers, denditric-type linkers or any combinations of such linkers thereof. In some embodiments, the linkers and/or ligands may be conjugated to a compound described herein via a primary or secondary hydroxyl group. In particular embodiments, the conjugation site on the compound is a primary or secondary hydroxyl group located at the position corresponding to —$Y^1$—$R^c$ or $Y^2$—$R^c$. In some embodiments, the conjugation site on the compound is a primary or secondary hydroxyl group located at the position corresponding to $R^2$. In some embodiments, the conjugation site on the compound is a primary or secondary hydroxyl group located at the position corresponding to $R^{8a}$ or $R^{8b}$. In some embodiments, the conjugation site on the compound is a primary or secondary hydroxyl group located at the position corresponding to $R^{15}$. In other embodiments, the conjugation site on the compound is a primary or secondary hydroxyl group located at the position corresponding to $R^4$. In some embodiments, the conjugation site on the compound is a phenyl ring substituted with —OH. In particular embodiments, the substitution is at the para position on the phenyl ring.

In one aspect, provided herein are conjugates containing kulo-2 or its 24-membered ring analog, Compound A:

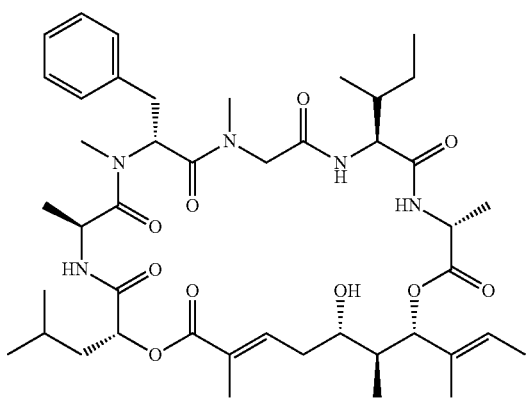

Kulo-2

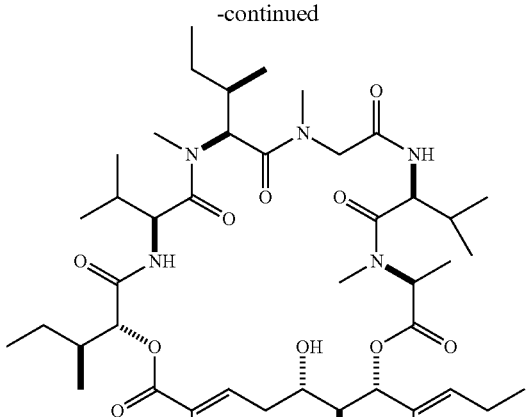

Aurilide B

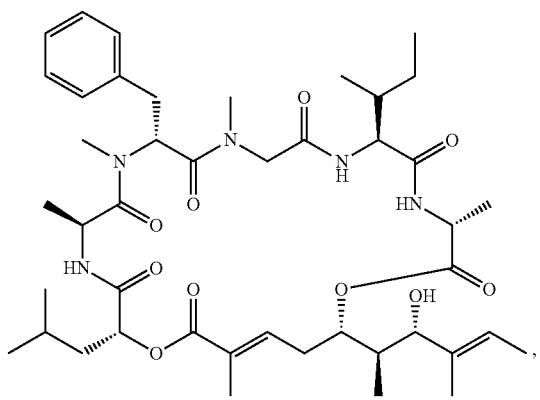

Compound A

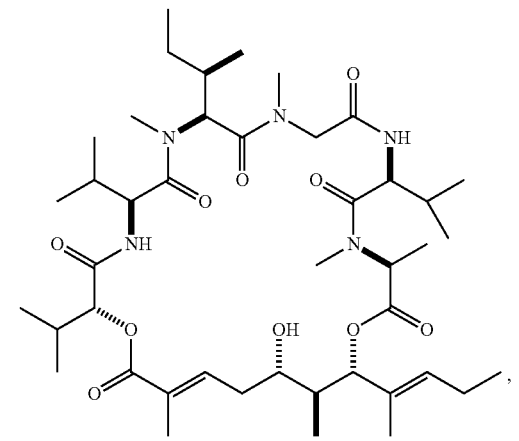

Aurilide C or a salt thereof.

Kulo-2 is a marine natural product that has been isolated from a cephalaspidean mollusk, *Philinosis speciose*. Kulo-2 exhibits potent cytotoxicity against several cancer cell lines (Y. Nakao et al., *J. Nat. Prod.* 2004, 67, 1332-1340). Accordingly, kulo-2 is particularly well suited for modification to enhance its chemotherapeutic activity and provide a means to create chemotherapeutic conjugates for targeted delivery.

In another aspect, provided herein are conjugates containing aurilide, aurilide B, or aurilide C:

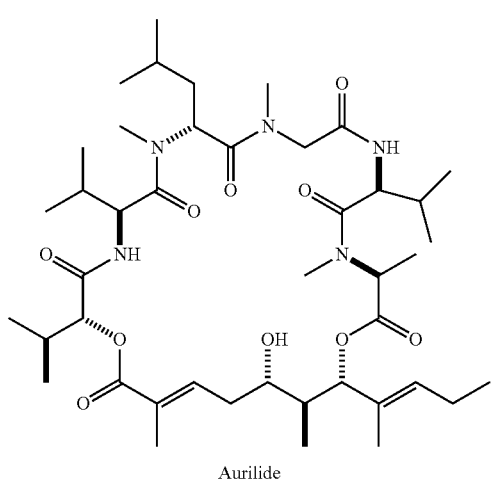

Aurilide or a salt thereof.

Aurlide, aurilide B, and aurilide C are marine natural products. Aurilide has been isolated from the sear hare *Dolabella auricularia*, and aurilides B and C have been isolated from the cyanobacterium *Lyngbya majuscula*. Aurilide exhibits potent cytotoxicity against HeLa $S_3$ cells (K. Suenaga et al., *Bioorg. Med. Chem. Lett.* 2008, 18, 3902-3905). Accordingly, aurilide is particularly well suited for modification to enhance its chemotherapeutic activity and provide a means to create chemotherapeutic conjugates for targeted delivery.

Accordingly, in one aspect, provided herein are conjugates of kulo-2, Compound A, aurilide, aurilide B, or aurilide C bonded to a ligand. In some variations, kulo-2, Compound A, aurilide, aurilide B, or aurilide C is directly bonded to the ligand. In other variations, kulo-2, Compound A, aurilide, aurilide B, or aurilide C is bonded to the ligand via a linker. Any suitable ligand and/or linker can be used in the foregoing compositions, including, but not limited to, any of the linkers or ligands described herein.

In any of the conjugates containing kulo-2, Compound A, aurilide, aurilide B, or aurilide C provided herein, the ratio of compound to ligand in the composition may be 1:1, 2:1, 3:1, 4:1, 5:1, 6:1, 7:1, 8:1, 9:1, 10:1, 11:1, or 12:1. In any of the conjugates provided herein, the ratio of compound to ligand may be 1:1 or 1:2. In any of the conjugates provided herein, the ratio of linker to ligand may be 1:1, 2:1, 3:1, 4:1, 5:1, 6:1, 7:1, 8:1, 9:1, 10:1, 11:1, or 12:1.

Also provided herein are conjugates containing kulo-2, Compound A, aurilide, aurilide B, or aurilide C bonded to a linker. The ratio of compound to linker may be 1:1, 2:1, 3:1, 1:2, or 1:3. In some embodiments, the linker is additionally bonded to a ligand. In other embodiments, the linker is not bonded to a ligand. In some such embodiments, the linker contains one or more functional groups suitable for bonding to a ligand.

In some variations, provided is a conjugate containing kulo-2, Compound A, aurilide, aurilide B, or aurilide C bonded to a linker. Any suitable linker can be used in the foregoing compositions, including, but not limited to, any of the linkers described herein. The linker may be suitable for attachment to a ligand.

Provided herein are compounds containing kulo-2, Compound A, aurilide, aurilide B, or aurilide C substituted at any chemically feasible position with a moiety suitable for attachment to a linker and/or ligand. In some variations, the kulo-2, Compound A, aurilide, aurilide B, or aurilide C is substituted at any chemically feasible position with a function group which is —NHR, —NHNH$_2$, —ONH$_2$, —N$_3$, —OH, —SH, or —CO$_2$H. In any of the foregoing embodiments, the functional group suitable for attachment to a linker and/or ligand is bonded to a protecting group, which may be removed prior to reaction with a linker and/or ligand.

One or more linkers and/or ligands may be bonded to kulo-2, Compound A, aurilide, aurilide B, or aurilide C via a functional group including, but not limited to —NHR, —NHNH$_2$, —ONH$_2$, —N$_3$, —OH, —SH, or —CO$_2$H located at any chemically feasible position on the kulo-2, Compound A, aurilide, aurilide B, or aurilide C. In some embodiments, the conjugation site on the kulo-2, Compound A, aurilide, aurilide B, or aurilide C is an —OH or —NH$_2$ group. In some embodiments, the free hydroxyl group of kulo-2, Compound A, aurilide, aurilide B, or aurilide C has been replaced with —NHR or —NH$_2$ as a site for conjugation. In other embodiments, the phenyl ring of kulo-2 or Compound A is been substituted with —NHR, —NH$_2$, or OH as a site for conjugation. In particular embodiments, the functional group for conjugation is at the para position on the phenyl ring. In yet other embodiments, an amino acid unit of kulo-2, Compound A, aurilide, aurilide B, or aurilide C has been replaced with a lysine unit as a handle for conjugation.

In certain aspects, provided herein are conjugates of kulo-2, Compound A, aurilide, aurilide B, or aurilide C having the following structures:

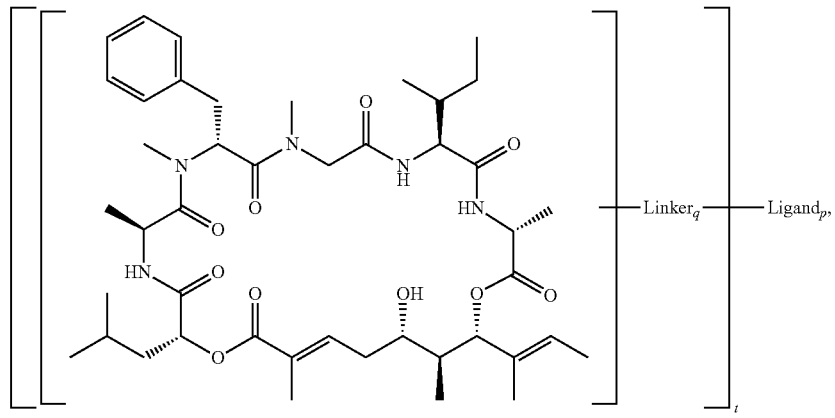

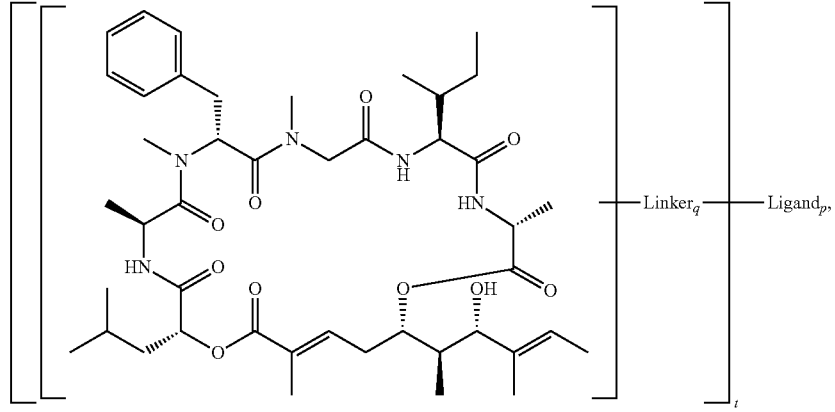

-continued
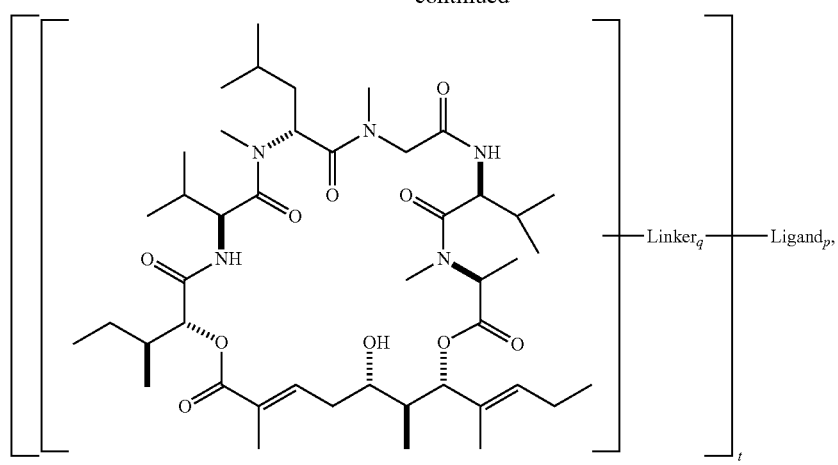
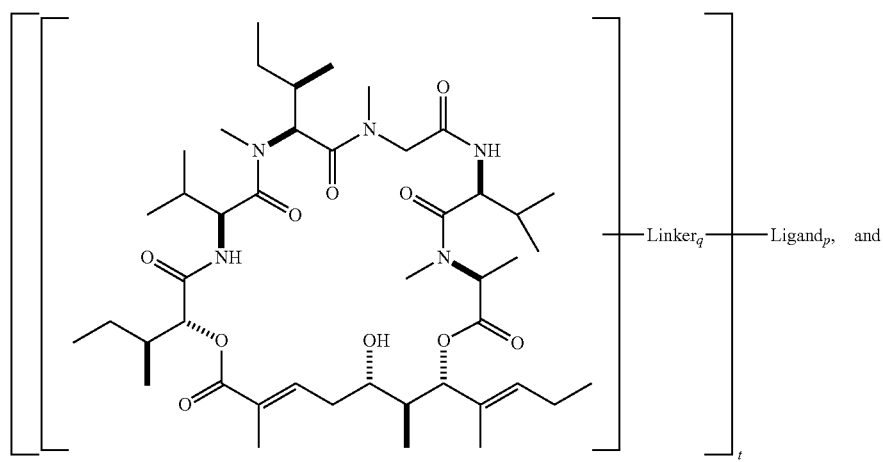
and
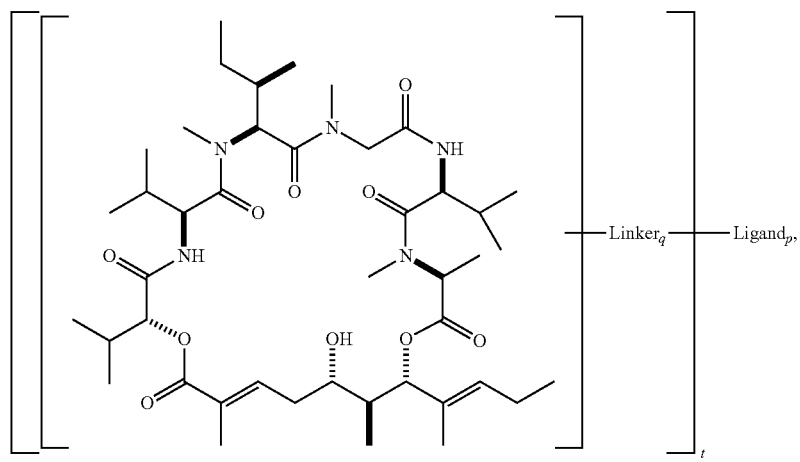

and salts thereof, wherein q, t, and p are as defined for Formulae (C), and where chemically appropriate valences and chemical bonding are present at the site of conjugation to the linker and/or ligand. For example, an atom on the compound is replaced by the linker or ligand such that a chemically appropriate number of bonds is maintained for all atoms. In particular examples, an —OH moiety on the compound is replaced with an —O-linker-ligand moiety in the conjugate, or an —NH₂— moiety on the compound is replaced with an —NH-linker-ligand moiety in the conjugate.

In a particular linker configuration, kulo-2 is modified to contain an amine linker according to Formula (L1):

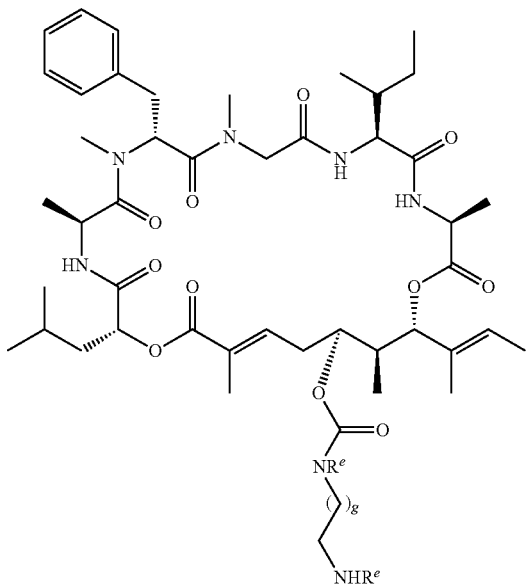

(L1)

or a salt thereof, wherein each $R^e$ is independently H or substituted or unsubstituted alkyl; and g is 1, 2, 3, 4, or 5.

Ligands

The term "ligand" as used herein refers to any molecule or moiety connected to the compounds described herein. "Ligand" may refer to one or more ligands attached to a compound. Likewise, multiple compounds may be attached to a single ligand.

Ligands may serve a number of purposes including facilitating uptake of the conjugate into a target cell or tissue and directing the conjugate to a particular cell or tissue (also referred to as conjugate targeting). A ligand may also serve to enhance the efficacy of the compounds by, for example, inhibiting or interacting with cellular factors that may inhibit or reduce the efficacy of the compounds described herein. The compound as described herein may be conjugated to one or more ligands. The term "ligand" as used herein refers to one or more ligands.

In some embodiments, a ligand is an antibody, or fragment thereof. In other embodiments, the ligand is a peptide or protein. In yet other embodiments, the ligand is another moiety useful for directing the compounds described herein to a target cell or tissue.

Antibody ligands include monoclonal antibodies, polyclonal antibodies, multispecific antibodies (e.g. bispecific antibodies) formed from at least two intact antibodies, multivalent antibodies, humanized antibodies, and antibody fragments. Examples of antibody fragments include Fab, Fab', F(ab')₂ and Fv fragments; diabodies; linear antibodies; single chain antibody molecules; and multispecific antibodies formed from antibody fragment(s). In one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is an IgG1, IgG2, IgG3, or IgG4 antibody.

The term "monoclonal antibody," as used herein, refers to an antibody obtained from a population of substantially homogeneous antibodies. A monoclonal antibody composition typically displays a single binding specificity and affinity for a particular epitope. In contrast, polyclonal antibody compositions typically include a multitude of antibodies that may be directed against different epitopes of the same target molecule. A polyclonal antibody composition may contain a plurality of monoclonal antibodies with different epitope specificities, affinities, or avidities within a single antigen that contains multiple antigenic epitopes. The term "monoclonal" indicates the character of the antibody as being obtained from a substantially homogeneous population of antibodies, and is not to be construed as requiring production of the antibody by any particular method. For example, the monoclonal antibodies to be used in accordance with any of the compositions, uses, or methods described herein may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example.

As used herein, the term "humanized antibody" refers to forms of antibodies that contain sequences from non-human (e.g., murine) antibodies as well as human antibodies. These antibodies retain the activity of a non-human antibody while being less immunogenic in humans. Humanized antibodies are chimeric antibodies which contain at least part of its sequence derived from non-human immunoglobulin. In general, the humanized antibody will comprise substantially all the non-human CDR regions, while the remaining parts of the antibody may be replaced by the corresponding human counterparts. In some embodiments, the humanized antibody retains at least one complete non-human variable domain. The humanized antibody optionally also will comprise at least a portion of an immunoglobulin constant region (Fc), typically that of a human immunoglobulin. See e.g., Cabilly, U.S. Pat. No. 4,816,567; Queen et al. (1989) Proc. Nat'l Acad. Sci. USA 86:10029-10033; and Antibody Engineering: A Practical Approach (Oxford University Press 1996).

The term "recombinant antibody", as used herein, includes all human and non-human antibodies that are prepared, expressed, created or isolated by recombinant means, such as antibodies isolated from an animal (e.g., a mouse) or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of all or a portion of a human immunoglobulin gene, sequences to other DNA sequences.

Exemplary peptide or protein ligands include receptor ligands for targeting delivery of the conjugate to a particular cell. Receptor ligands may engage with their target receptor and provide specific targeting to a tissue or cell type that expresses that receptor. This receptor engagement may also facilitate cellular uptake of the conjugate. Exemplary peptides may also include targeting peptides to facilitate passage across the cell membrane or intracellular targeting including, but not limited to, targeting to organelles such as the nucleus, Golgi apparatus, lysosome, and mitochondria.

In some embodiments, the ligand is an antibody that is specific for a cancer cell antigen. A "cancer cell antigen" is a peptide or molecular moiety expressed by a cancer cell that is recognized by an antibody. Antibodies specific for a cancer cell antigen can be obtained commercially or produced by any method known to one of skill in the art such as, e.g., chemical synthesis or recombinant expression techniques.

In additional embodiments, the peptide ligand is an interferon, a lymphokine, or a hormone.

Additional exemplary ligands include nucleic acids (e.g. DNA, RNA, PNA, etc.) or other molecules known in the art that would be useful for conjugation to the presently described compounds.

Linkers

In one embodiment, the compounds described herein comprise one or more linker or linking group. The term "linker", "linker molecule", "linking group", or "linker moiety" as used herein refers to a chemical moiety comprising a covalent bond and/or a chain of atoms that covalently attaches a ligand to a drug moiety or other molecule. For example, exemplary linkers, including their structure and synthesis, are described in WO 2004/010957, U.S. Pat. Publ. No. 2006/0074008, U.S. Pat. Publ. No. 2005/0238649, and U.S. Pat. Publ. No. 2006/0024317, U.S. Pat. Publ. Nos. 2003/0083263, 2005/0238649 and 2005/0009751, WO 2015/095755, W. C. Widdison et al., *Bioconjugate Chem.*, 2015, 26, 2261; D. Shabat et al., *New J. Chem.*, 2012, 36, 386; F. M. H. de Groot et al., *J. Org. Chem.*, 2001, 66, 8815; J. M. DeSimone et al., *Med. Chem. Comm.*, 2014, 5, 1355; and R. M. Garbaccio et al., *J. Amer. Chem. Soc.*, 2016, 138(4), 1430, each of which is incorporated herein by reference in its entirety and for all purposes.

The linker may be cleavable or non-cleavable. Cleavable linkers are typically cleavable under intracellular conditions, such that the linker itself is degraded and releases the compound from the ligand. Non-cleavable linkers do not degrade intracellularly and in this embodiment, the compound is released from the ligand via degradation of the ligand.

A conjugate as described herein may or may not comprise a linker molecule or moiety. A person of skill in the art could determine the appropriate type of linker based on the type of treatment or tissue being targeted by the conjugate. Exemplary linking moieties include hydrazones, peptides, chelating agents, maleimides, disufide groups, thioether groups, acid labile groups, photolabile groups, peptidase labile groups, or esterase labile groups, as known to one of skill in the art. Linker moieties may comprise a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cleavable linkers may be cleaved or degraded by a cleaving agent (e.g. a protease or reducing agent) present in the intracellular environment. In some embodiments, the linker is a peptidyl linker that is cleaved by an intracellular peptidase or protease enzyme, including, but not limited to, a lysosomal or endosomal protease. In some embodiments, the peptidyl linker is at least two amino acids long. Protein and peptide cleaving agents can include cathepsins B and D and plasmin, all of which are known to cleave dipeptides resulting in the release of active drug inside target cells (see, e.g., Dubowchik and Walker (1999) *Pharm. Therapeutics* 83:67-123). For example, a peptidyl linker that is cleavable by the thiol-dependent protease cathepsin-B, which is highly expressed in cancerous tissue, can be used (e.g., a Phe-Leu containing linker). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

A cleavable linker may be fully cleaved by a cleaving agent to release the compound to which it is bound. Alternatively, a cleavable linker may be partially cleaved, such that a portion of the linker remains bound to the compound. For example, if a linker is bound to a compound via a group —C(O)N(CH$_3$)CH$_2$CH$_2$N(CH$_3$)—, the linker may be partially cleaved such that group —C(O)N(CH$_3$)CH$_2$CH$_2$NHCH$_3$ remains bound to the compound.

In other embodiments, the cleavable linker is pH-sensitive. Typically, the pH-sensitive linker is unstable and degrades under acidic conditions. For example, an acid-labile linker that is cleavable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker (1999) *Pharm. Therapeutics* 83:67-123; Neville et al. (1989) *Biol. Chem.* 264:14653-14661.) Such linkers are relatively stable under neutral pH conditions, such as those in the blood, but are unstable at below pH 5.5 or 5.0, the approximate pH of the lysosome.

Typically, the linker is not substantially sensitive to the extracellular environment. As used herein, "not substantially sensitive to the extracellular environment," in the context of a linker, means that no more than about 20%, 15%, 10%, 5%, or 1% of the linkers, in a sample of compound-ligand conjugate compound, are cleaved when the antibody-drug conjugate compound is in an extracellular environment. Whether a linker is not substantially sensitive to the extracellular environment can be determined using methods known to those of skill in the relevant art.

In some embodiments, the linker contains a spacer unit. In some embodiments, the spacer unit contains a para-aminobenzoate (PAB) moiety. In some embodiments, the linker contains a stretcher unit. In some embodiments, the stretcher unit contains a maleimide moiety.

In some embodiments, the linking groups will be bifunctional, meaning they comprise two reactive sites, wherein a first reactive site may be bound to the compounds described herein and the second reactive site may be bound to the ligand. The linker may be hetero-bifunctional, indicating that the binding moieties on either end of the linker moiety are different.

In some embodiments, conjugates of the ligand and compound are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238: 1098. Carbon-14-labeled 1-isothiocyanatobenzyl-3-methyl-diethylene triaminepentaacetic acid (MX-DTPA) is an exemplary chelating agent for conjugation of radionucleotide to the compound or ligand (WO94/11026).

The compounds described herein can be linked to ligands via an acid labile linker as previously described (Blattler et al, 24 Biochemistry, 1517-1524 (1985), U.S. Pat. Nos. 4,542,225, 4,569,789 and 4,764,368).

The compounds described herein can be linked to ligands via a photolabile linker as previously described (Senter et al, 42 Photochemistry and Photobiology, 231-237 (1985), U.S. Pat. No. 4,625,014).

The compounds described herein can be linked to a ligand to produce a conjugate that can be cleaved by intracellular esterases to liberate free drug. (For examples see: U.S. Pat. No. 5,208,020 and Aboud-Pirak et al, 38 Biochem. Pharmacol., 641-648 (1989), Laguzza et al, 32 J. Med. Chem., 549-555 (1989)).

The compounds described herein can also be linked to ligands via peptide spacer linkers. It has been previously shown that short peptide spacers between drugs and macromolecular carriers are stable in serum but are readily hydrolyzed by intracellular lysosomal peptidases (Trouet et al, 79 Proc. Nat'l. Acad. Sci. 626-629 (1982)).

Functional groups on the compound that can serve as a handle for attachment of a linker or ligand using the coupling methods described herein include, without limitation, —NHR, —NHNH$_2$, —ONH$_2$, —N$_3$, —OH, —SH, —CO$_2$H, and other functional groups. In any of the variations of Formulae (I), (II), (III), and (B) described herein, the compound may be modified to contain one or more functional groups that can serve as a handle for attachment of a linker or ligand at any chemically feasible position. In some embodiments, any of the variations of Formula (I), (II), (III), and (B) may contain one or more moieties selected from the group consisting of —NHR, —NHNH$_2$, —ONH$_2$, —N$_3$, —OH, —SH, —CO$_2$H at any chemically feasible position. In some embodiments, a handle for attachment of a linker or ligand can be located on an amino acid side chain. In other embodiments, a handle for attachment of a linker or ligand can be located at position Y$^1$ or Y$^2$. In other embodiments, a handle for attachment of a linker or ligand can be located at position R$^c$. In yet other embodiments, an amino acid side chain of a compound of Formula (I), (II), (III), or (B) contains a lysine (—(CH$_2$)$_4$NH$_2$)) side chain as a handle for attachment of a linker or ligand.

In some variations the linker is of formula (La1), where the linker is bonded to a compound provided herein via the bond shown as

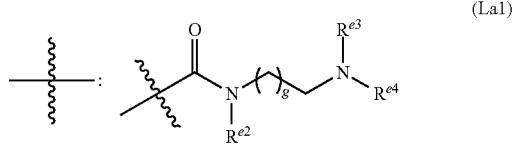

(La1)

wherein R$^{e2}$, R$^{e3}$ and R$^{e4}$ are each independently H or substituted or unsubstituted alkyl; and g is 1, 2, 3, 4, or 5.

In some variations of formula (La1), R$^{e4}$ is

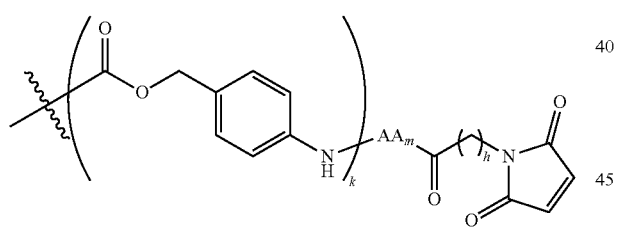

wherein AA is an amino acid, m is an integer from 0-12, h is an integer from 0-12, and k is 0 or 1. In some embodiments, m is 2. In some embodiments, m is 0. In some embodiments AA$_m$ is -Cit-Val-. In some embodiments, AA$_m$ is -Ala-Val-. In some embodiments h is 2, 3, 4, 5, or 6. In some embodiments, k is 1. In some embodiments, k is 0.

In some variations of formula (La1), R$^{e4}$ is

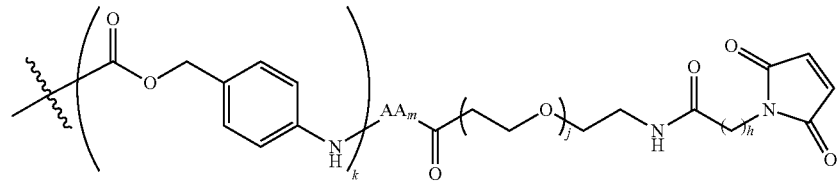

wherein AA is an amino acid; m, h, and j are each independently an integer from 0-12; and k is 0 or 1. In some embodiments, m is 2. In some embodiments, m is 0. In some embodiments AA$_m$ is -Cit-Val-. In some embodiments, AA$_m$ is -Ala-Val-. In some embodiments, h is 2, 3, 4, 5, or 6. In some embodiments, j is 3, 4, 5, 6, 7, or 8. In some embodiments, k is 1. In some embodiments, k is 0.

In some variations the linker is of formula (La2), where the linker is bonded to a compound provided herein via the bond shown as

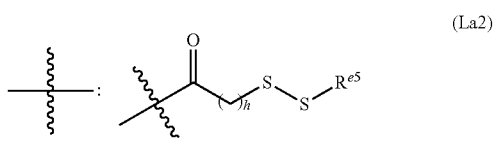

(La2)

wherein R$^{e5}$ is aryl or heteroaryl, and h is an integer from 1-12. In some embodiments, R$^{e5}$ is pyridyl (e.g., 2-pyridyl). In some embodiments, h is 2, 3, 4, 5, or 6.

In some variations the linker is of formula (La3), where the linker is bonded to a compound provided herein via the bond shown as

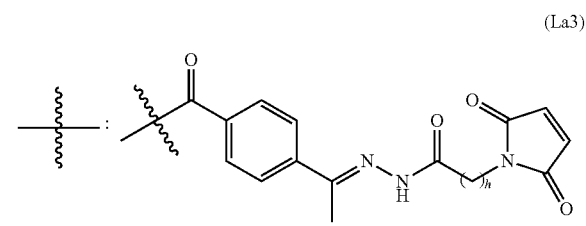

(La3)

wherein h is an integer from 1-12. In some embodiments, h is 2, 3, 4, 5, or 6.

In some variations the linker is of formula (La4), where the linker is bonded to a compound provided herein via the bond shown as

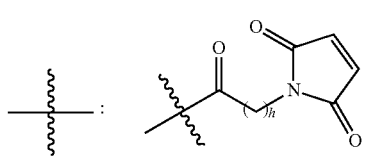
(La4)

wherein h is an integer from 0-12. In some embodiments, h is 2, 3, 4, 5, or 6.

In some variations the linker is of formula (La5), where the linker is bonded to a compound provided herein via the bond shown as

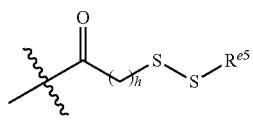
(La5)

wherein j is an integer from 1-12, and $R^{e6}$ is substituted or unsubstituted alkyl. In some variations of formula (La5), $R^{e6}$ is

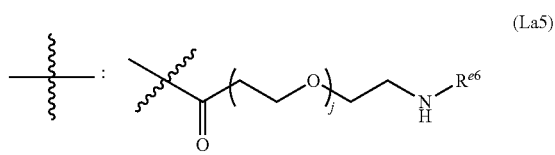

wherein $R^{e5}$ is aryl or heteroaryl, and h is an integer from 1-12. In some embodiments, $R^{e5}$ is pyridyl (e.g., 2-pyridyl). In some embodiments, h is 2, 3, 4, 5, or 6. In some variation of (La5), $R^{e6}$ is

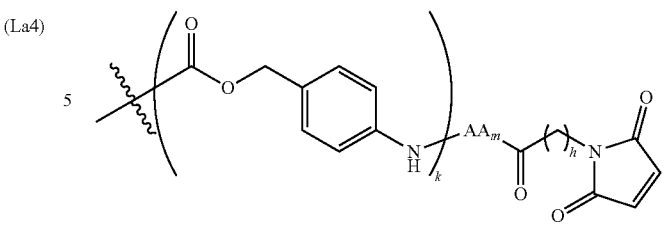

wherein AA is an amino acid, m is an integer from 0-12, h is an integer from 0-12, and k is 0 or 1. In some embodiments, m is 2. In some embodiments, m is 0. In some embodiments $AA_m$ is -Cit-Val-. In some embodiments, $AA_m$ is -Ala-Val-. In some embodiments h is 2, 3, 4, 5, or 6.

In some variations, the linker is of formula (La6), where the linker is bonded to a compound provided herein via the bond shown as (La6)

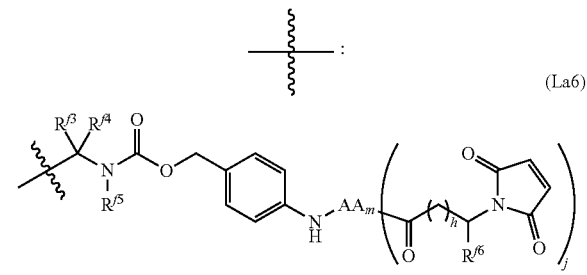

wherein $R^{f3}$, $R^{f4}$, $R^{f5}$, and $R^{f6}$ are each independently H or substituted or unsubstituted alkyl; AA is an amino acid; m and h are each independently an integer from 0-12; and j is 0 or 1. In some embodiments, j is 0. In some embodiments, j is 1. In some embodiments, m is 2. In some embodiments, linker (La6) is bonded to a compound provided herein at a primary or secondary alcohol site on the compound. Exemplary conjugates containing linker (La6) and general schemes for their preparation include the following:

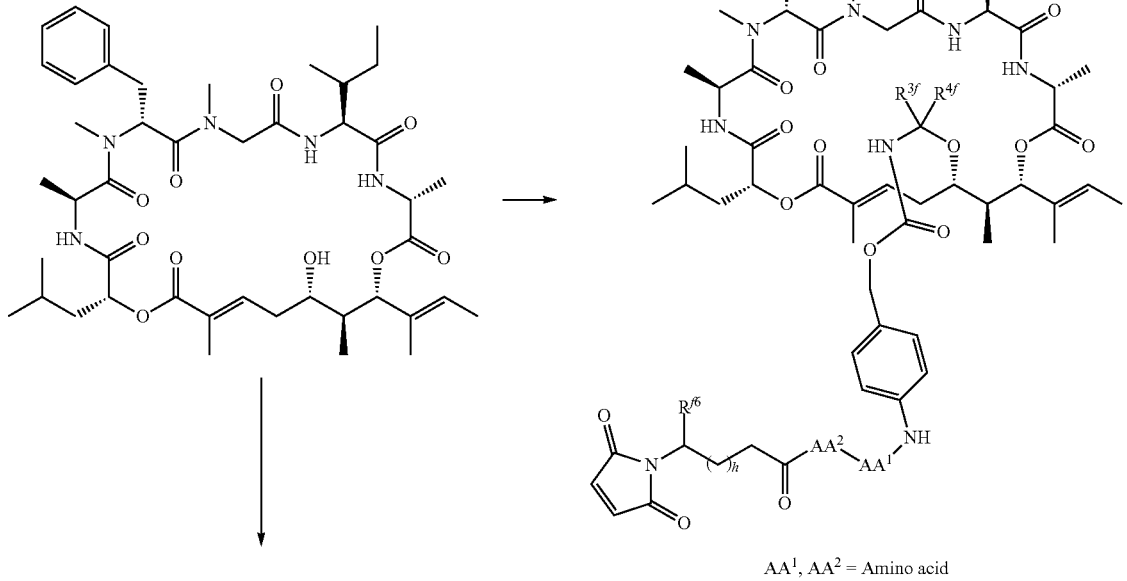

$AA^1$, $AA^2$ = Amino acid

-continued

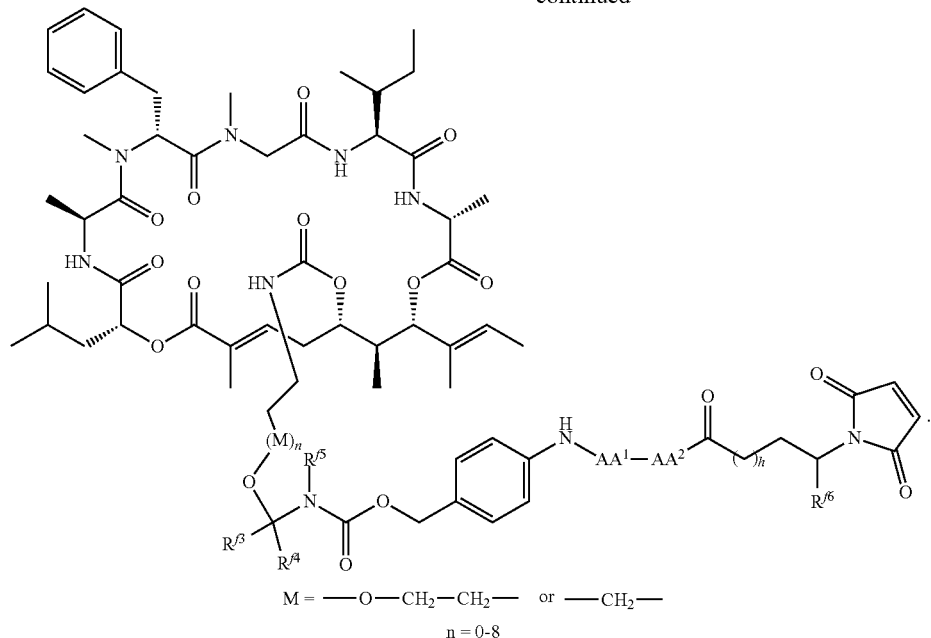

M = —O—CH₂—CH₂— or —CH₂—
n = 0-8

In some variations, the linker is of formula (La7), where the linker is bonded to a compound provided herein via the bond shown as

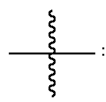

-continued

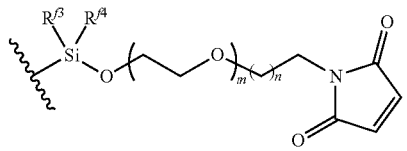 (La7)

wherein $R^{f3}$ and $R^{f4}$ are each independently H or substituted or unsubstituted alkyl; and m and n are each independently an integer from 0-12. In some embodiments, linker (La7) is bonded to a compound provided herein at a primary or secondary alcohol site on the compound. Exemplary conjugates containing linker (La7) and general schemes for their preparation include the following:

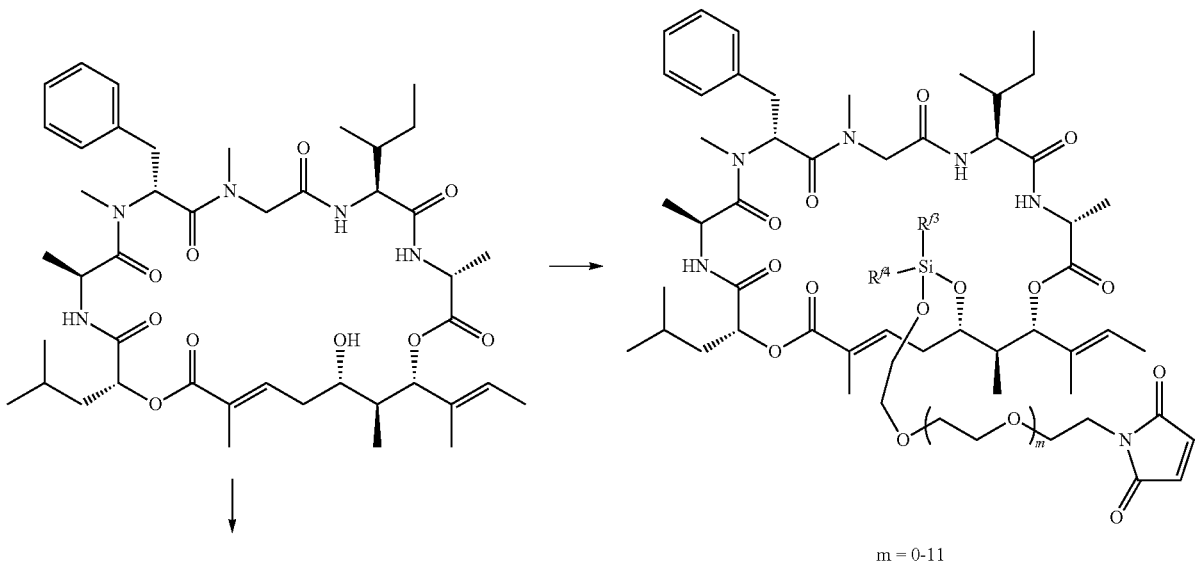

m = 0-11

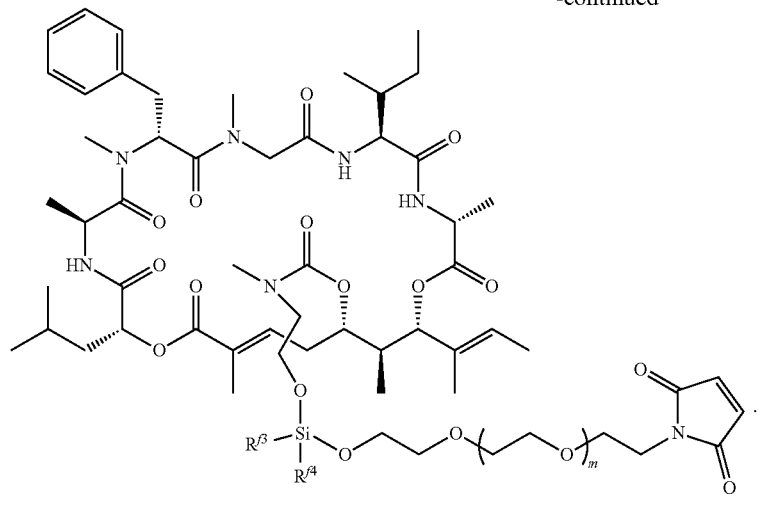

m = 0-8

In some variations the linker is of formula (La8), where the linker is bonded to a compound provided herein via the bond shown as

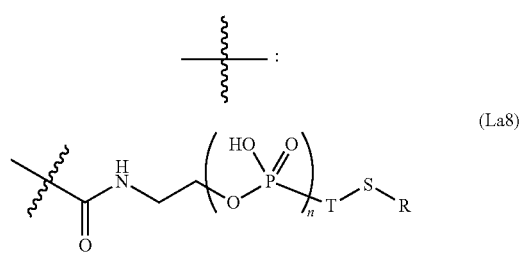

(La8)

wherein n is an integer from 1-4; T is —O— or —NH—; S is aryl or —(CH$_2$)$_m$NH— where m is an integer from 1-6; and R is

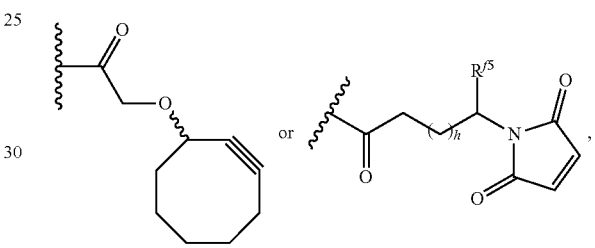

where R$^{f5}$ is H or substituted or unsubstituted alkyl, and h is an integer from 0-6. In some embodiments, linker (La8) is bonded to a compound provided herein at a primary or secondary alcohol site on the compound. Exemplary conjugates containing linker (La8) and general schemes for their preparation include the following:

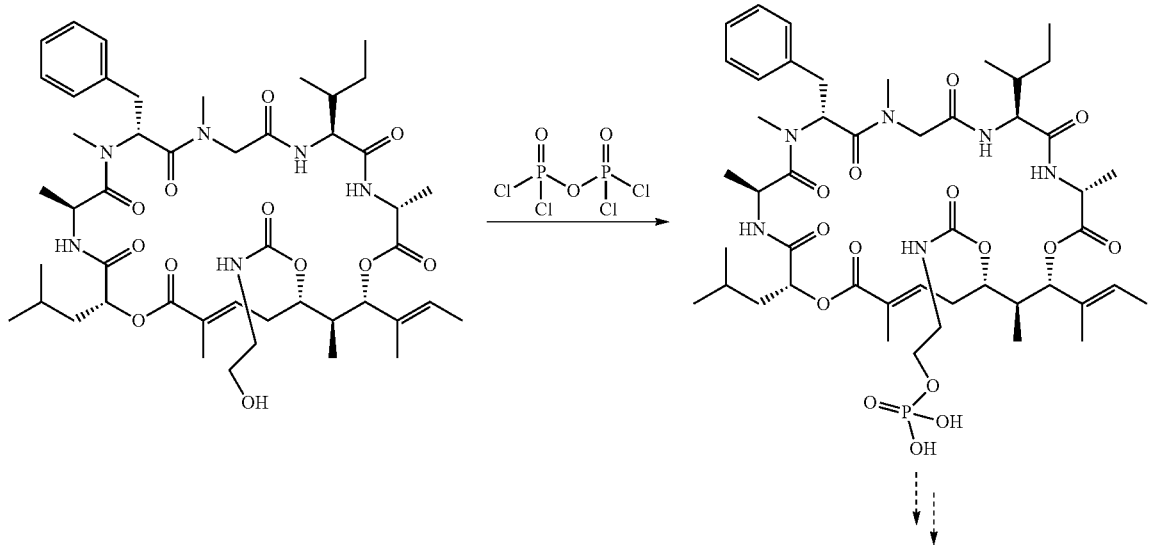

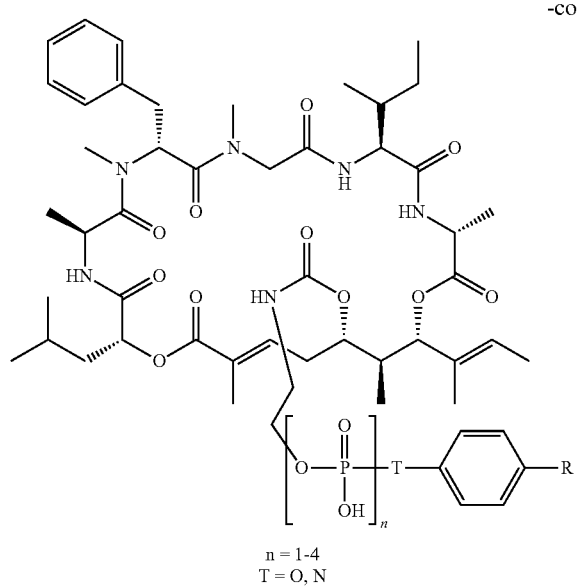

n = 1-4
T = O, N or

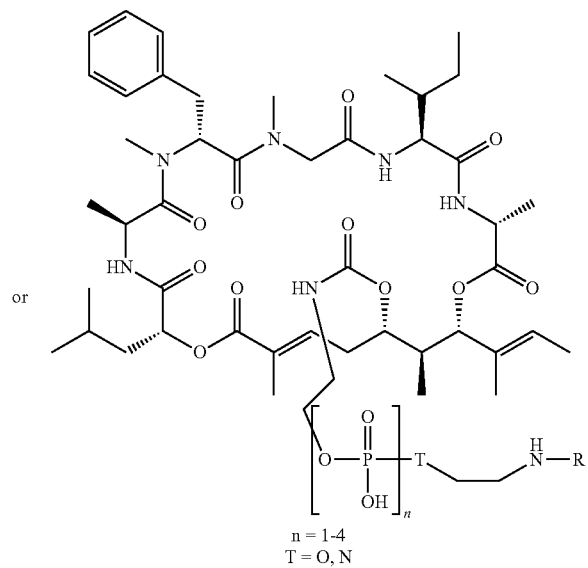

n = 1-4
T = O, N

R = 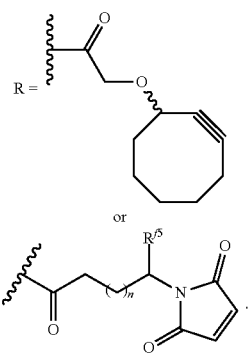

or

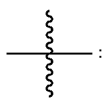

In some variations the linker is of formula (La9) or (La10), where the linker is bonded to a compound provided herein via the bond shown as

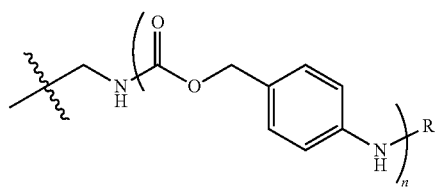

(La9)

-continued

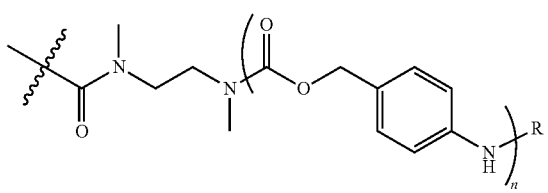

(La10)

wherein n is and integer from 2-4, and R is substituted or unsubstituted alkyl. In some embodiments, linker (La9) or (La10) is bonded to a compound provided herein at a primary or secondary alcohol site on the compound. Exemplary conjugates containing linker (La10) include the following:

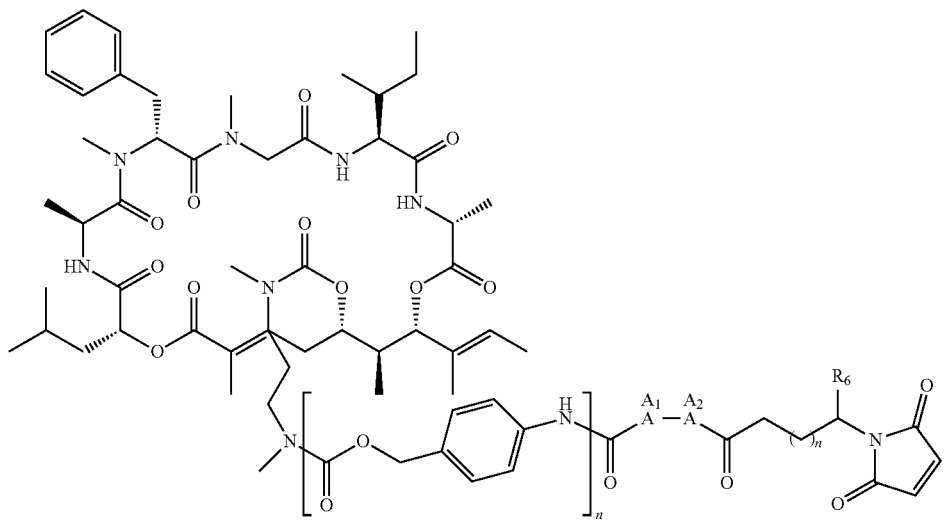

Analogous conjugates for (La9) are also provided herein.

In some variations the linker is of formula (La11), where the linker has two bonds to compounds provided herein via the bonds shown as

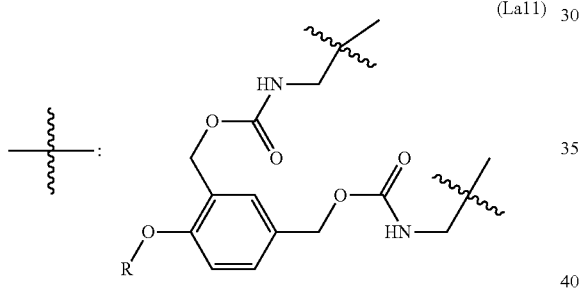
(La11)

wherein R is a moiety capable of forming a bond with a ligand. In some embodiments, linker (La11) is bonded to one or more compounds provided herein at a primary or secondary alcohol site on the compound(s).

In some variations the linker is of formula (La12), where the linker is bonded to a compound provided herein via the bond shown as

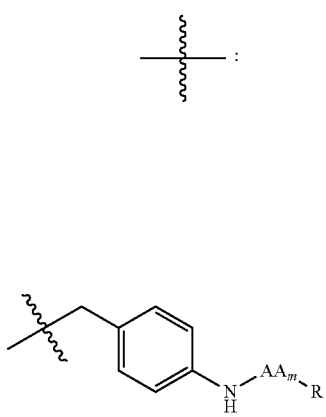
(La12)

wherein AA is an amino acid, m is an integer from 1-12, and R is a moiety capable of forming a bond with a ligand. In some embodiments, linker (La12) is bonded to a compound provided herein at a primary or secondary alcohol site on the compound.

In some variations the linker is of formula (La13), where the linker is bonded to a compound provided herein via the bond shown as

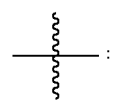

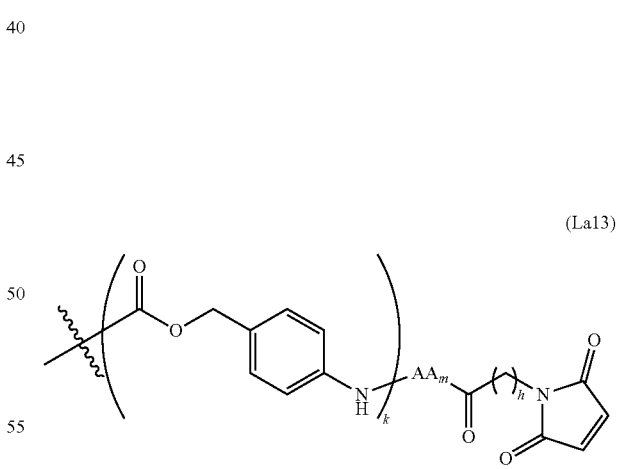
(La13)

wherein AA is an amino acid, m is an integer from 0-12, h is an integer from 0-12, and k is 0 or 1. In some embodiments, m is 2. In some embodiments, m is 0. In some embodiments $AA_m$ is -Cit-Val-. In some embodiments, $AA_m$ is -Ala-Val-. In some embodiments h is 2, 3, 4, 5, or 6. In some embodiments, k is 1. In some embodiments, k is 0.

In some variations the linker is of formula (La14), where the linker is bonded to a compound provided herein via the bond shown as

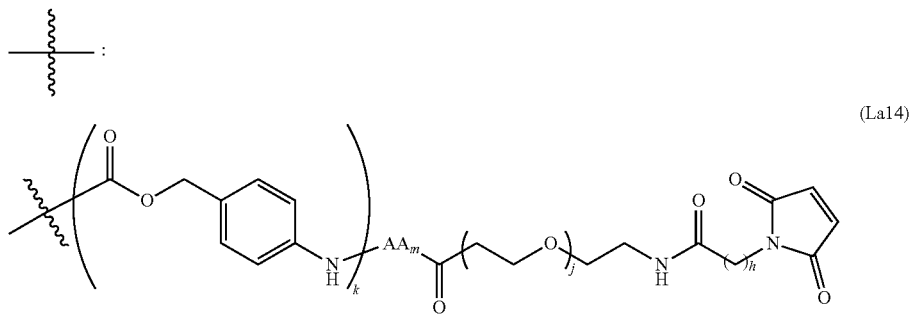

(La14)

wherein AA is an amino acid; m, h, and j are each independently an integer from 0-12; and k is 0 or 1. In some embodiments, m is 2. In some embodiments, m is 0. In some embodiments $AA_m$ is -Cit-Val-. In some embodiments, $AA_m$ is -Ala-Val-. In some embodiments, h is 2, 3, 4, 5, or 6. In some embodiments, j is 3, 4, 5, 6, 7, or 8. In some embodiments, k is 1. In some embodiments, k is 0.

Exemplary conjugates containing kulo-2 bonded to a linker are shown in Table 2. In some variations of any of the conjugates of Table 2, the kulo-2 portion of the conjugate can be replaced with any compound described herein. Also provided herein are salts of any of the conjugates shown in Table 2. In some embodiments, a conjugate shown in Table 2, or a salt thereof, is a precursor compound in which the linker portion may be further modified, e.g., to insert a functional group suitable for bonding to a ligand.

TABLE 2
| Conjugate | Structure |
|---|---|
| L1 | 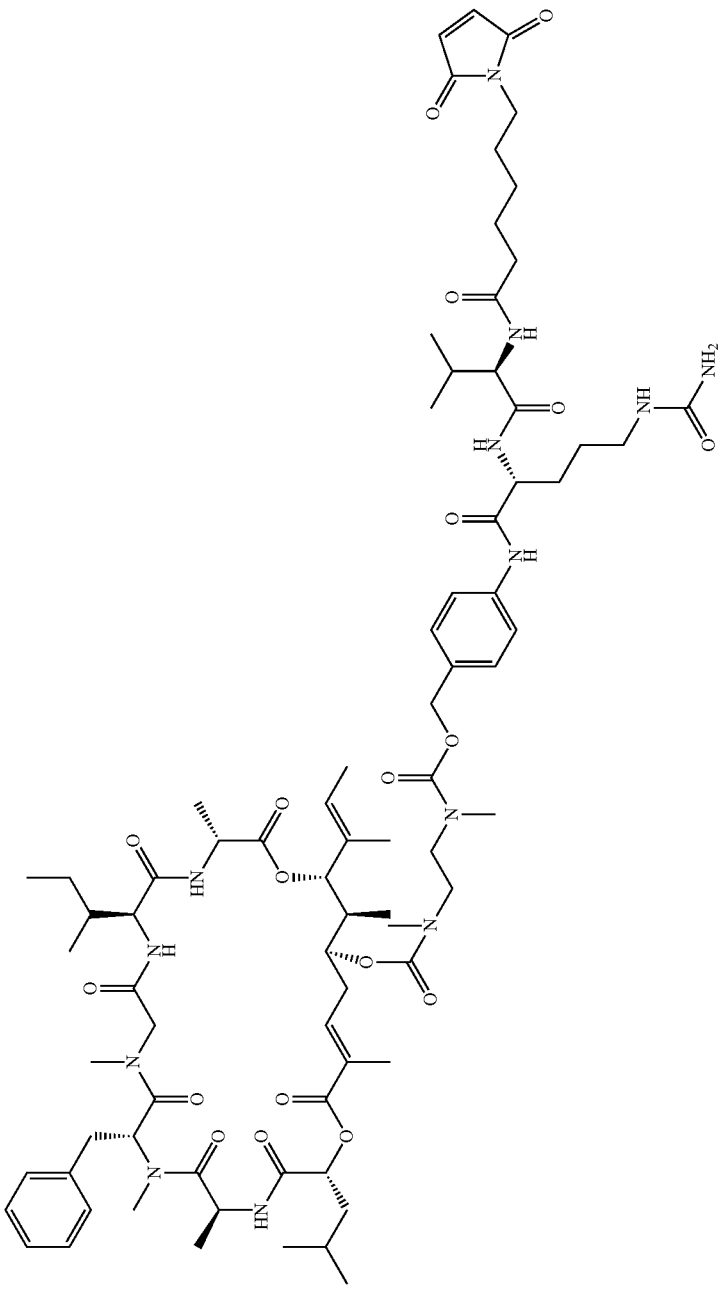 |

TABLE 2-continued
| Conjugate | Structure |
|---|---|
| L2 | 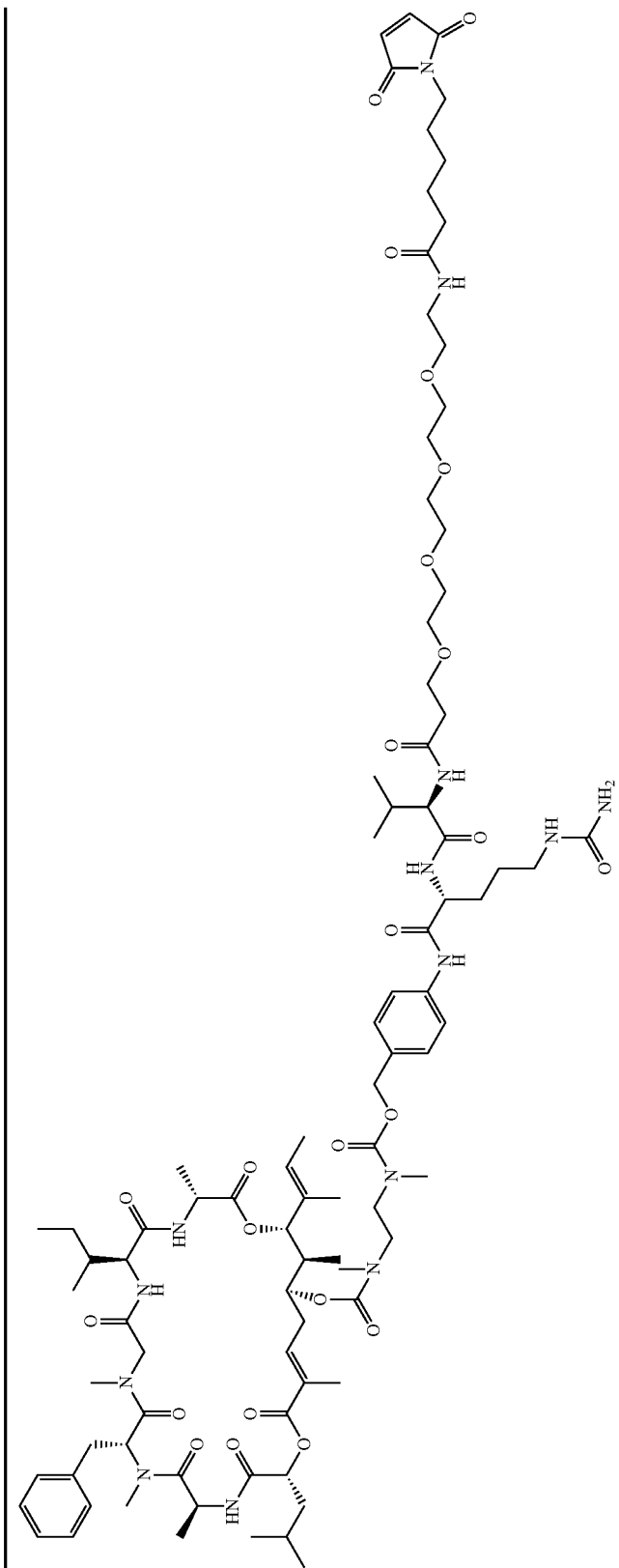 |

TABLE 2-continued
| Conjugate | Structure |
|---|---|
| L3 | 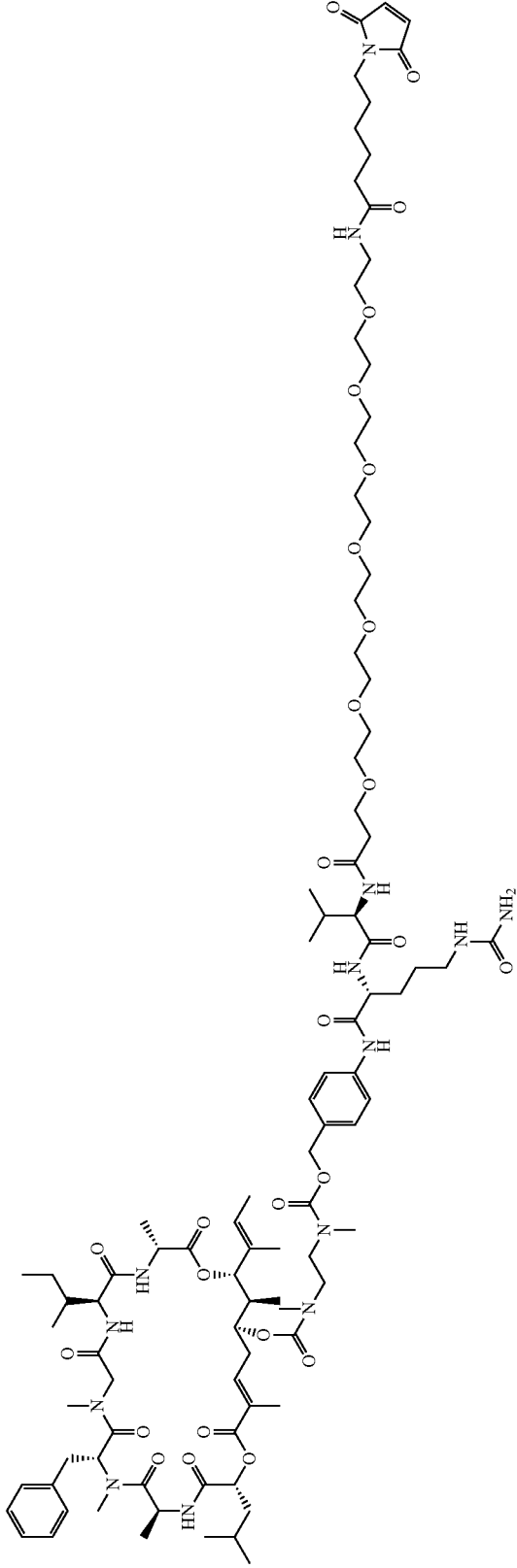 |

TABLE 2-continued
| Conjugate | Structure |
|---|---|
| L4 | 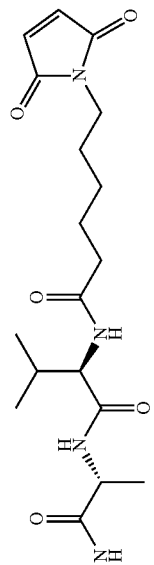 |

TABLE 2-continued
| Conjugate | Structure |
|---|---|
| L5 | 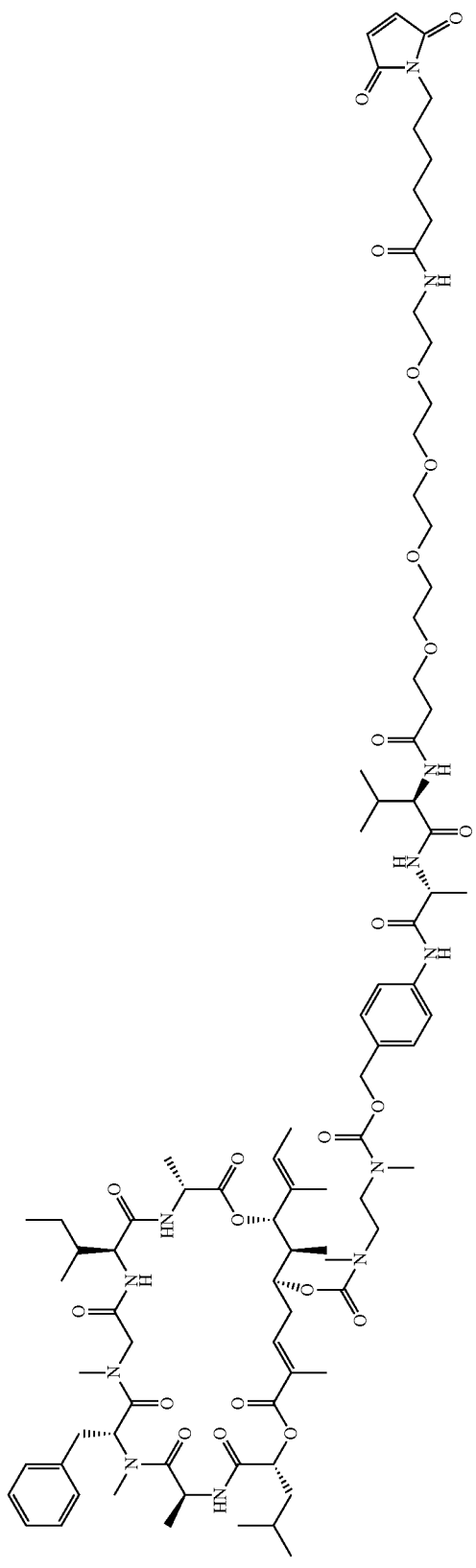 |
| L6 | 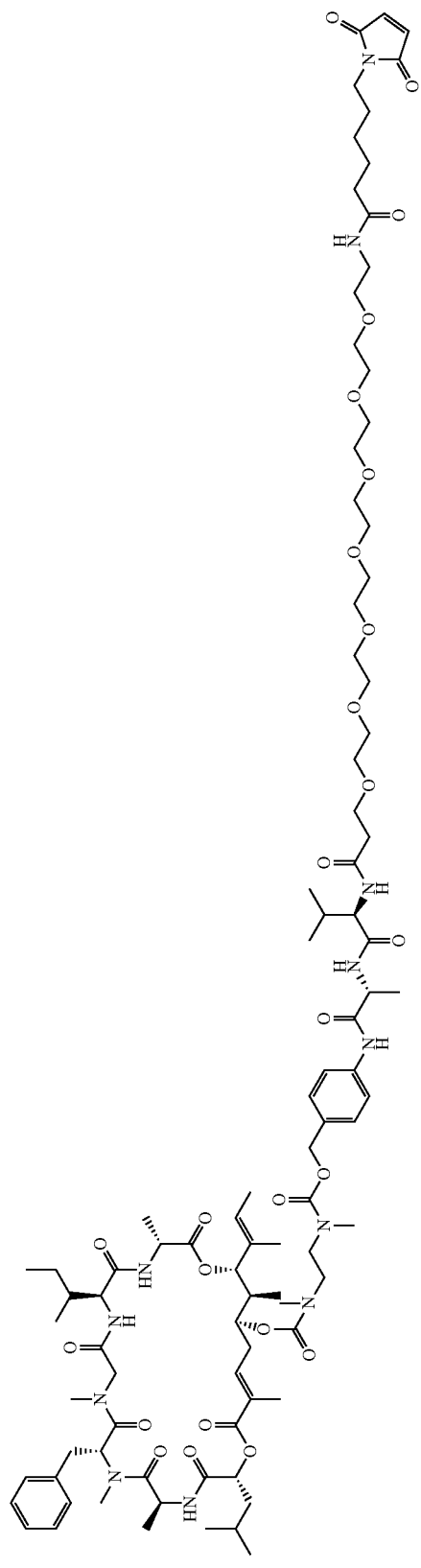 |

TABLE 2-continued

| Conjugate | Structure |
|---|---|
| L7 | 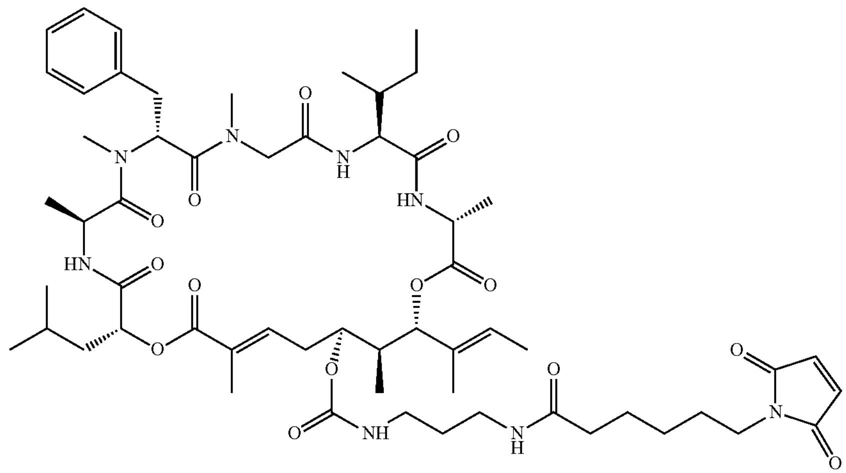 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCNC(=O)CCCCCN2C(=O)C=CC2=O)[C@@H]1C] |
| L8 | 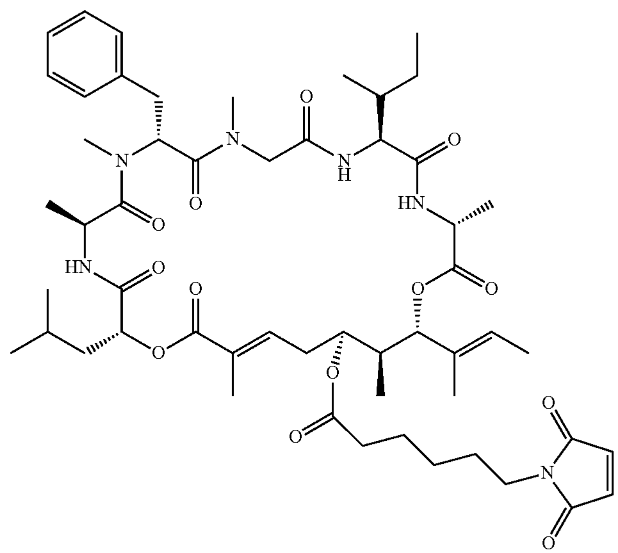 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)CCCCCN2C(=O)C=CC2=O)[C@@H]1C] |

TABLE 2-continued
| Conjugate | Structure |
|---|---|
| L9 | 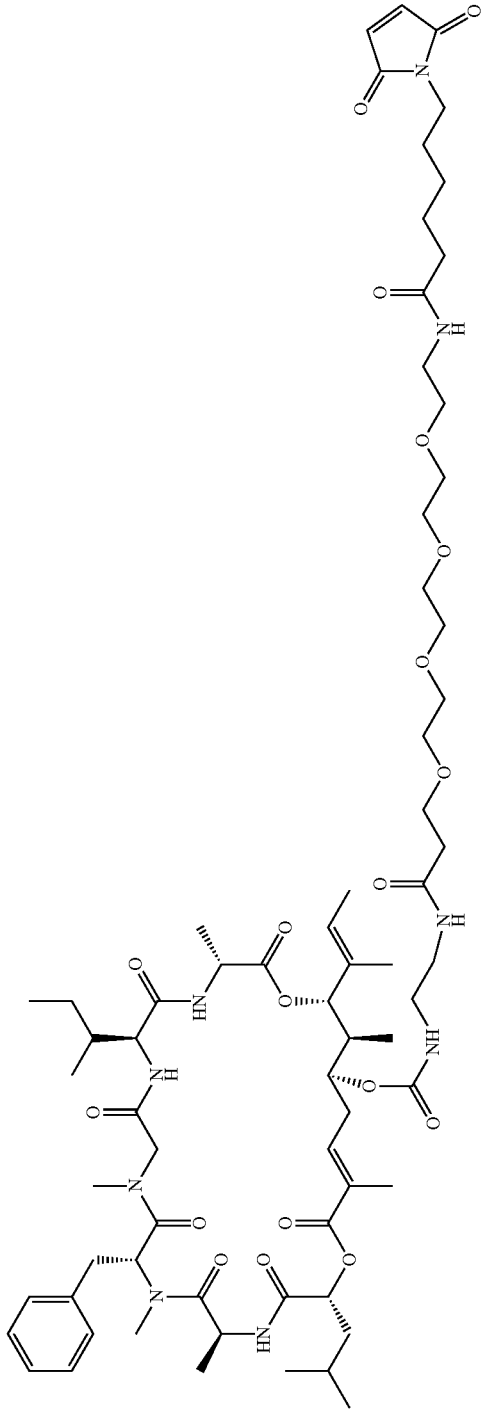 |

TABLE 2-continued
| Conjugate | Structure |
|---|---|
| L10 | 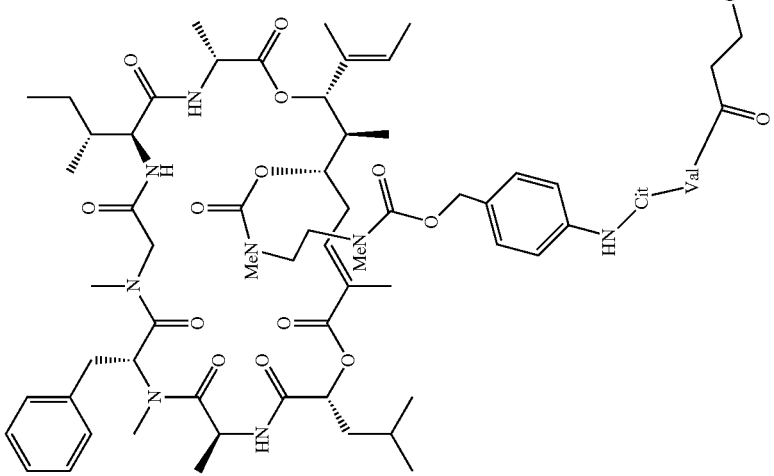 |

TABLE 2-continued
| Conjugate | Structure |
|---|---|
| L11 | 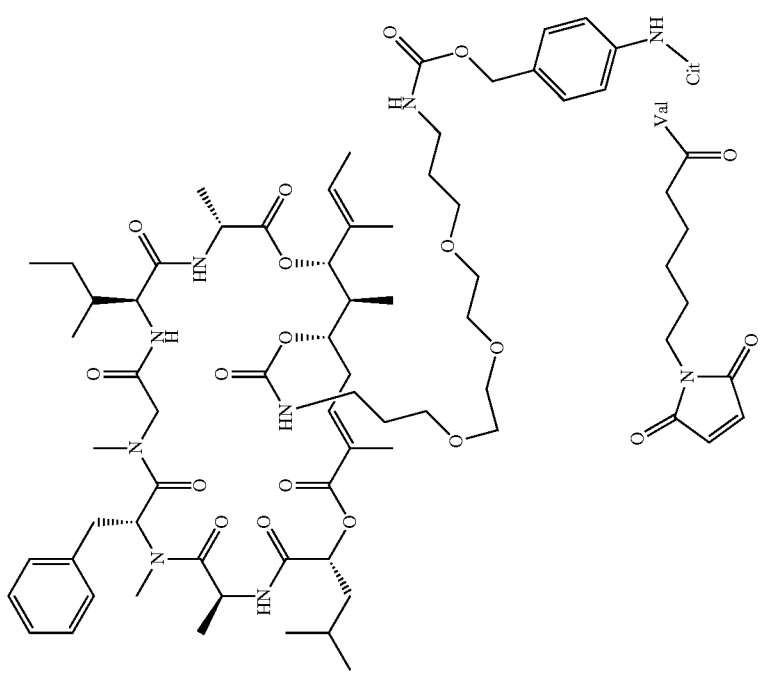 |

| Conjugate | Structure |
|---|---|
| L12 | 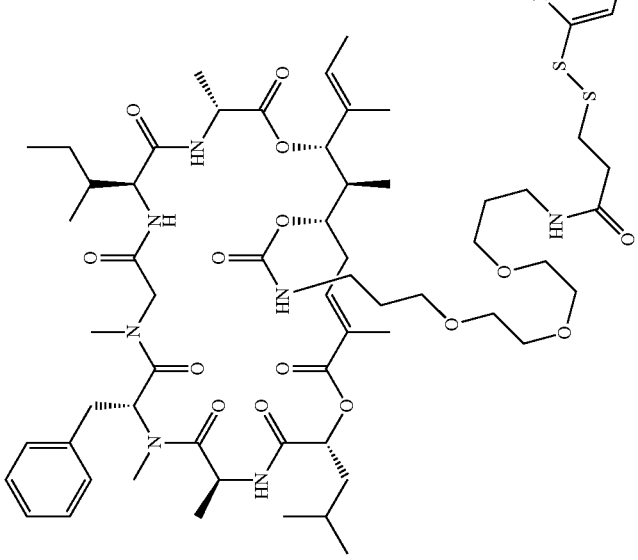 |

| Conjugate | Structure |
|---|---|
| L13 | 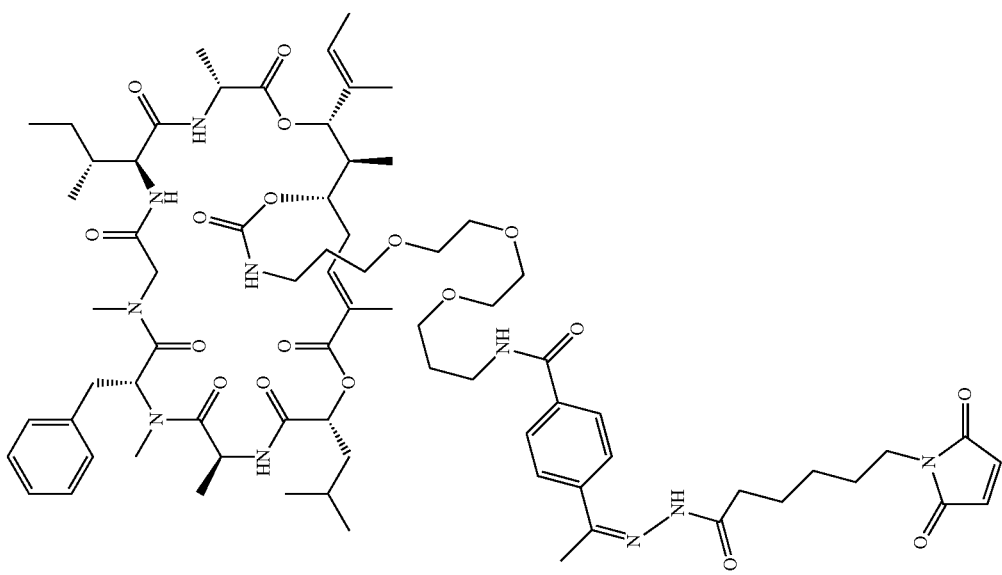 |

TABLE 2-continued
| Conjugate | Structure |
|---|---|
| L14 | 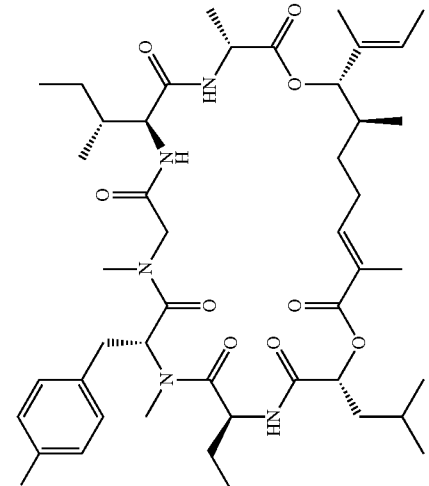 |
| L15 | 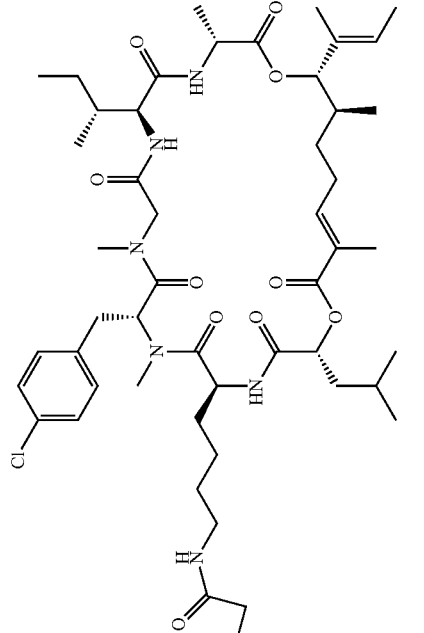 |

TABLE 2-continued
| Conjugate | Structure |
|---|---|
| L16 | 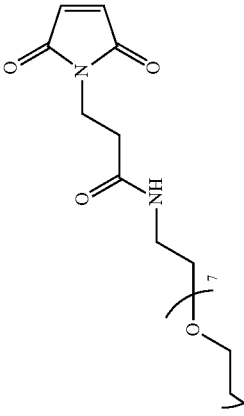 |

TABLE 2-continued
| Conjugate | Structure |
|---|---|
| L17 | 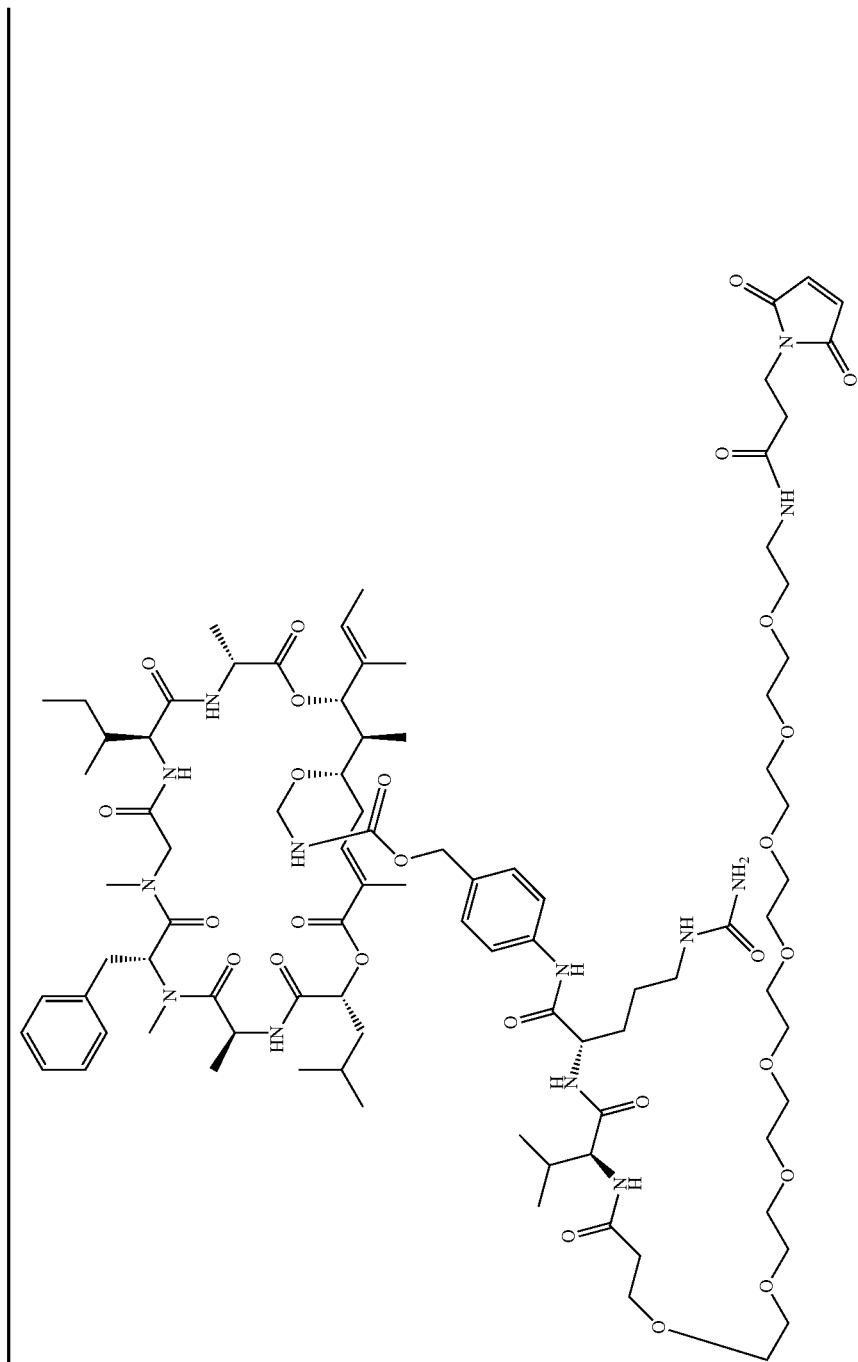 |

TABLE 2-continued
| Conjugate | Structure |
|---|---|
| L18 | 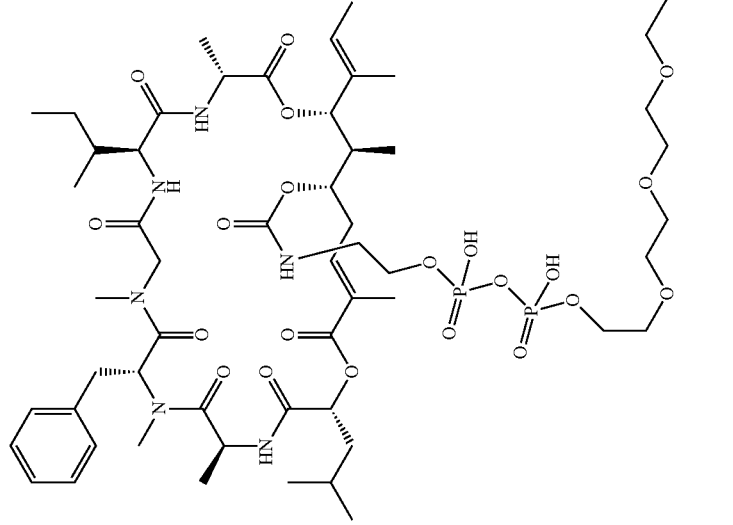 |

TABLE 2-continued
| Conjugate | Structure |
|---|---|
| L19 | 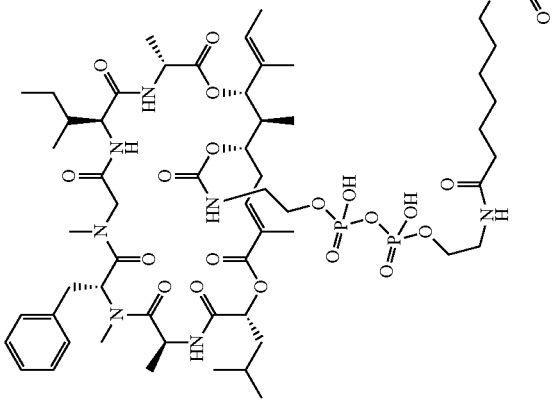 |
| L20 | 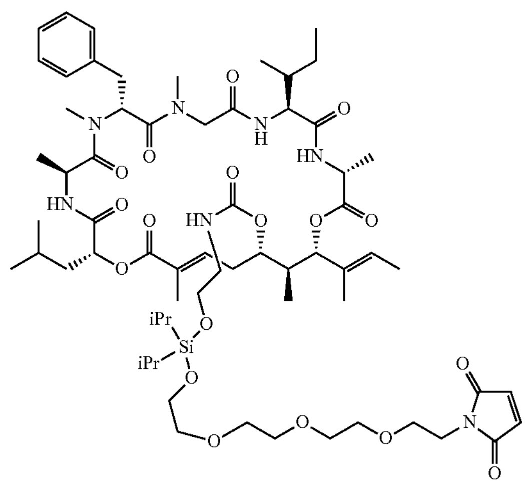 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCO[Si](OCCOCCOCCOCCN2C(=O)C=CC2=O)(C(C)C)C(C)C)[C@@H]1C] |

TABLE 2-continued
| Conjugate | Structure |
|---|---|
| L21 | 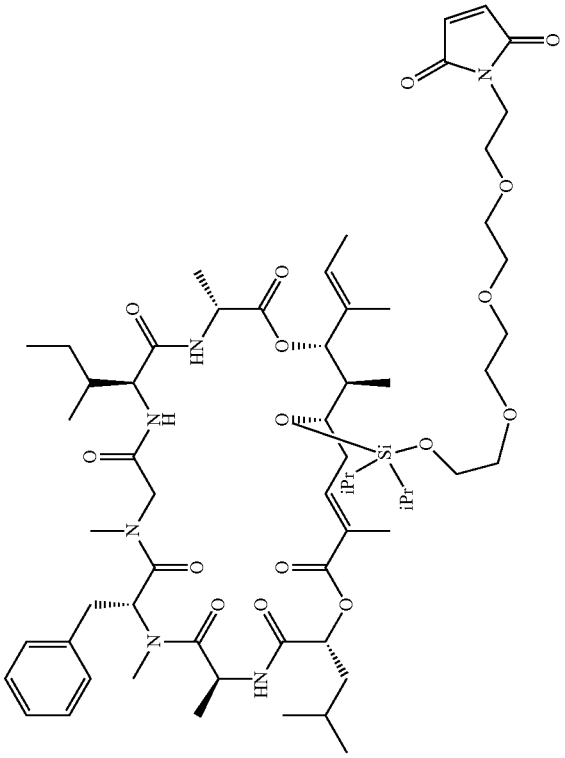 |

TABLE 2-continued
| Conjugate | Structure |
|---|---|
| L22 | 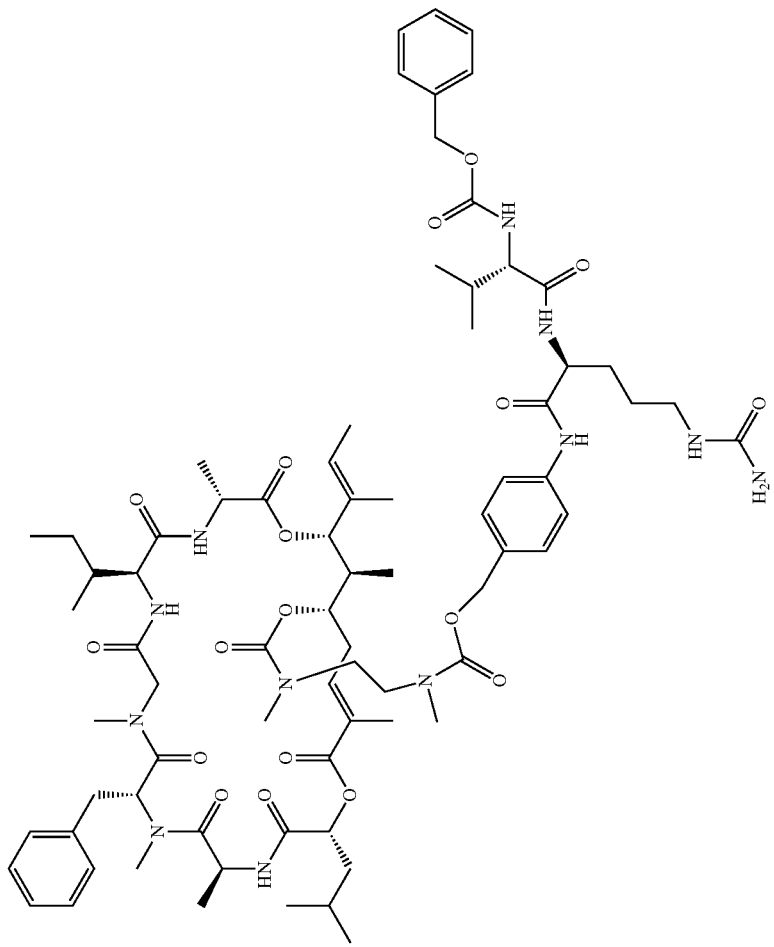 |

TABLE 2-continued
| Conjugate | Structure |
|---|---|
| L23 | 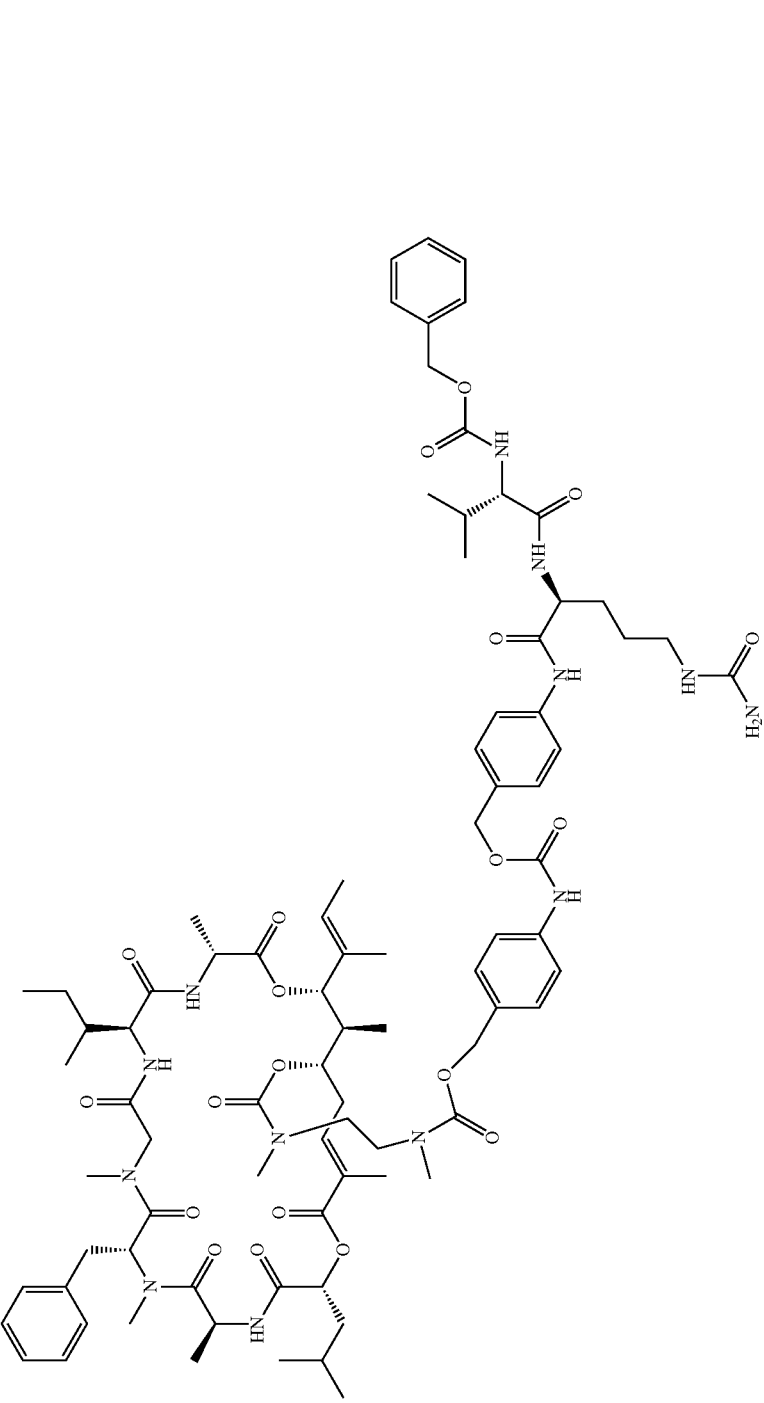 |

TABLE 2-continued
| Conjugate | Structure |
|---|---|
| L24 | 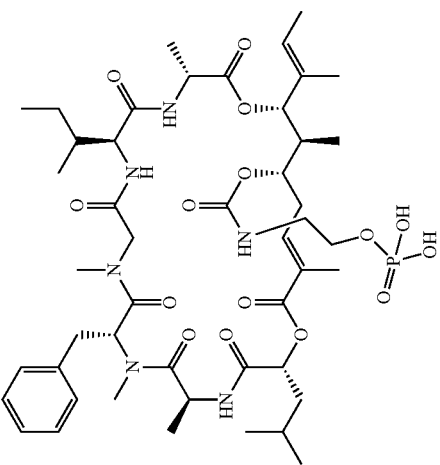 |
| L25 | 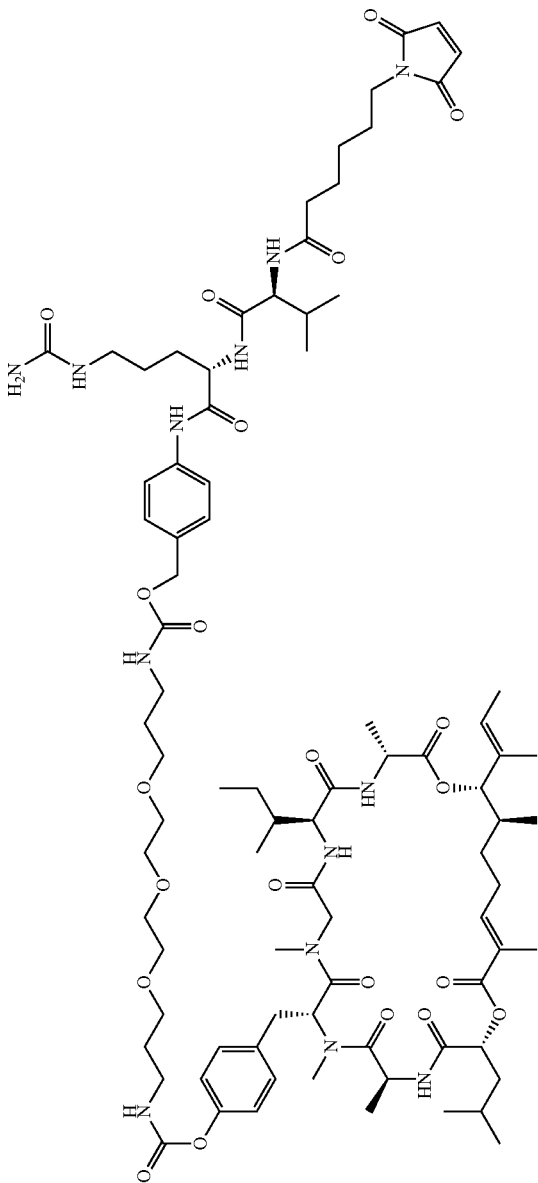 |

TABLE 2-continued
| Conjugate | Structure |
|---|---|
| L26 | 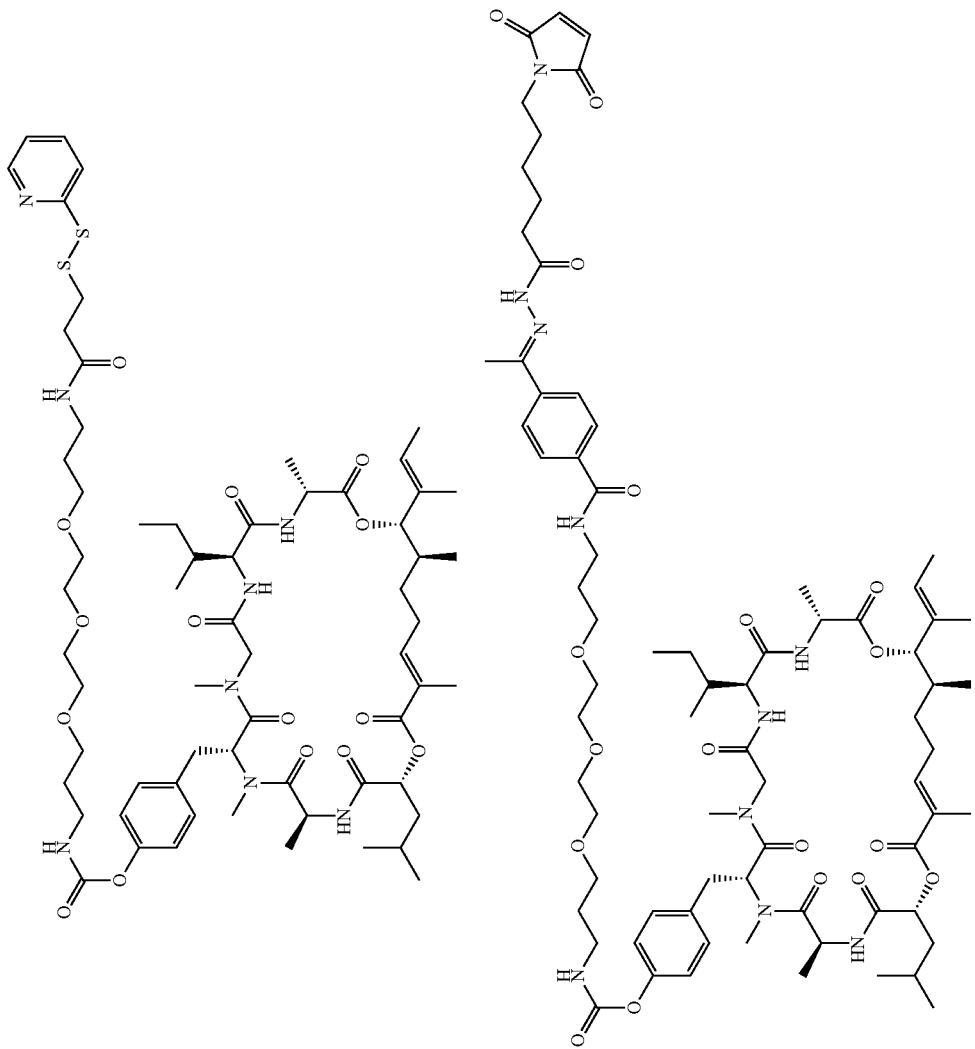 |
| L27 | 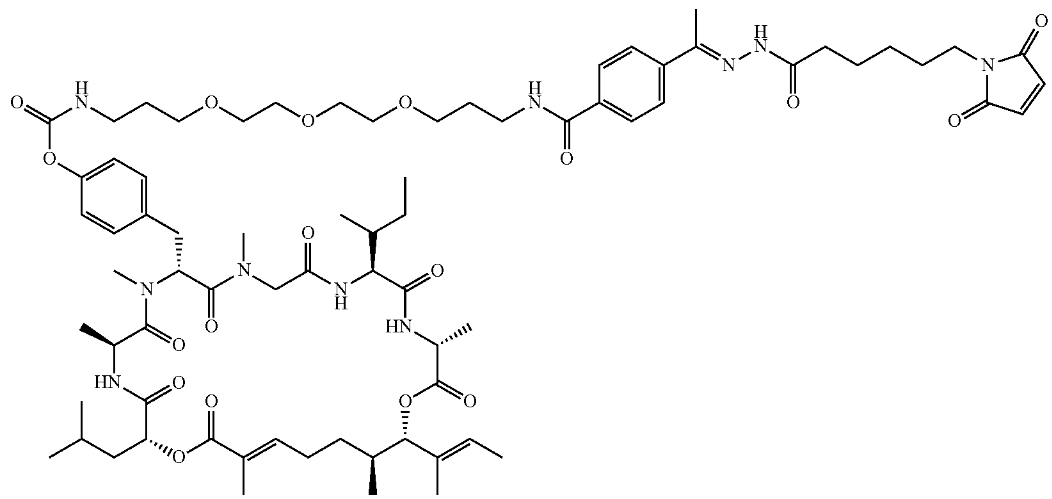 [SMILES: C/C=C(\C)[C@H]1OC(=O)[C@@H](C)NC(=O)[C@H](C(C)CC)NC(=O)CN(C)C(=O)[C@@H](Cc2ccc(OC(=O)NCCCOCCOCCOCCCNC(=O)c3ccc(/C(C)=N/NC(=O)CCCCCN4C(=O)C=CC4=O)cc3)cc2)N(C)C(=O)[C@H](C)NC(=O)[C@@H](CC(C)C)OC(=O)/C(C)=C/CC[C@@H]1C] |

TABLE 2-continued
| Conjugate | Structure |
|---|---|
| L28 | 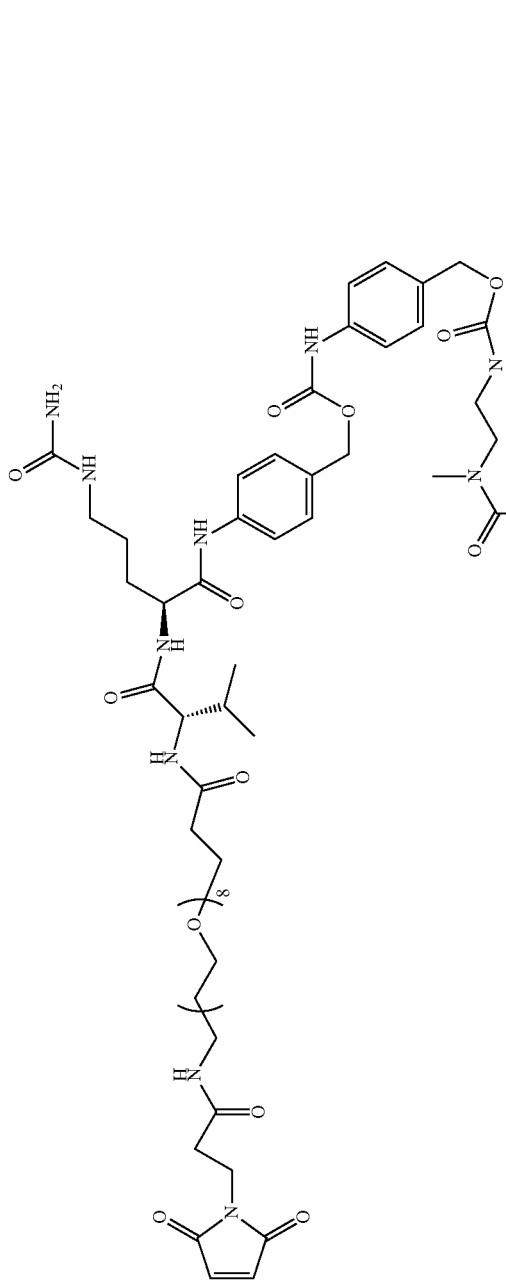 |

TABLE 2-continued
| Conjugate | Structure |
|---|---|
| L29 | 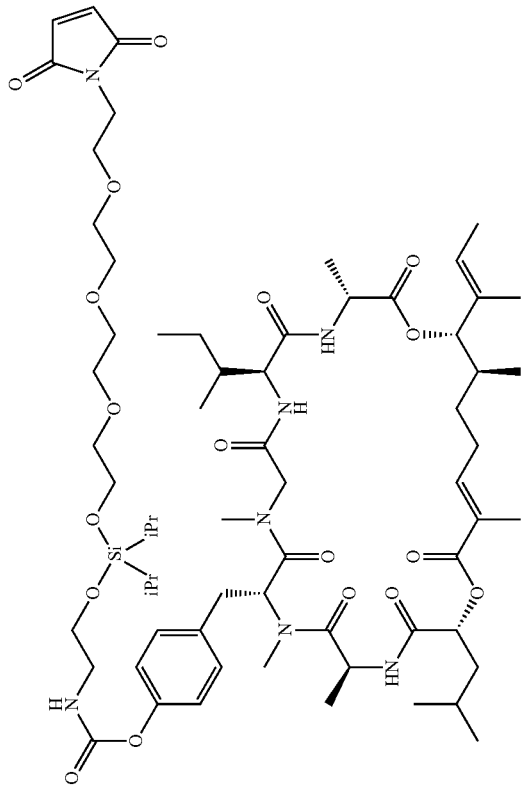 |
| L30 | 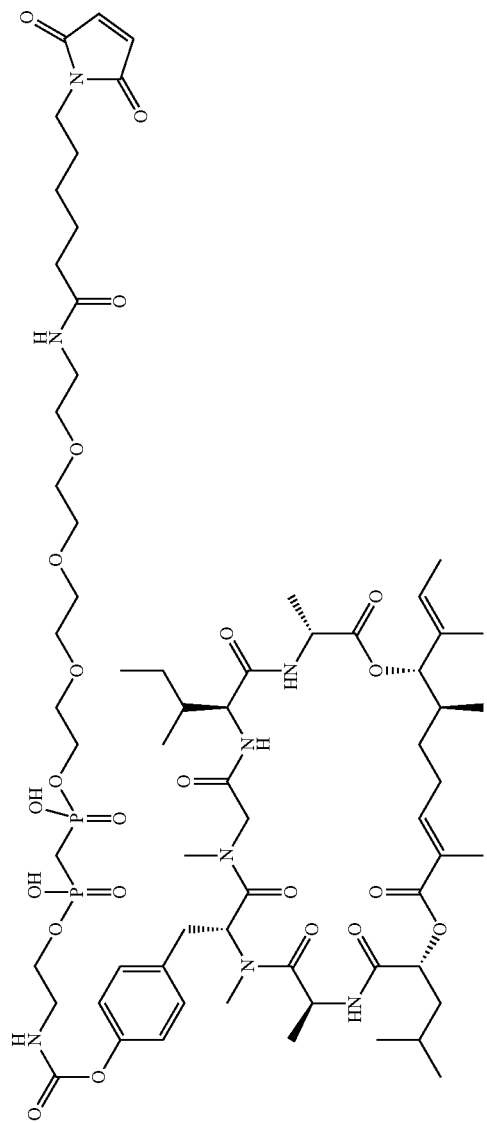 |

TABLE 2-continued
| Conjugate | Structure |
|---|---|
| L31 | 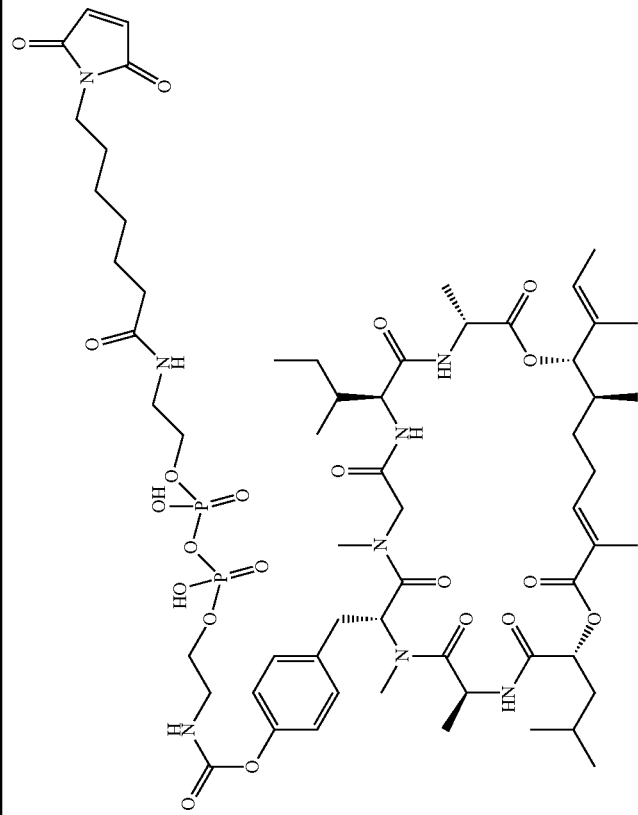 |

TABLE 2-continued
| Conjugate | Structure |
|---|---|
| L32 | 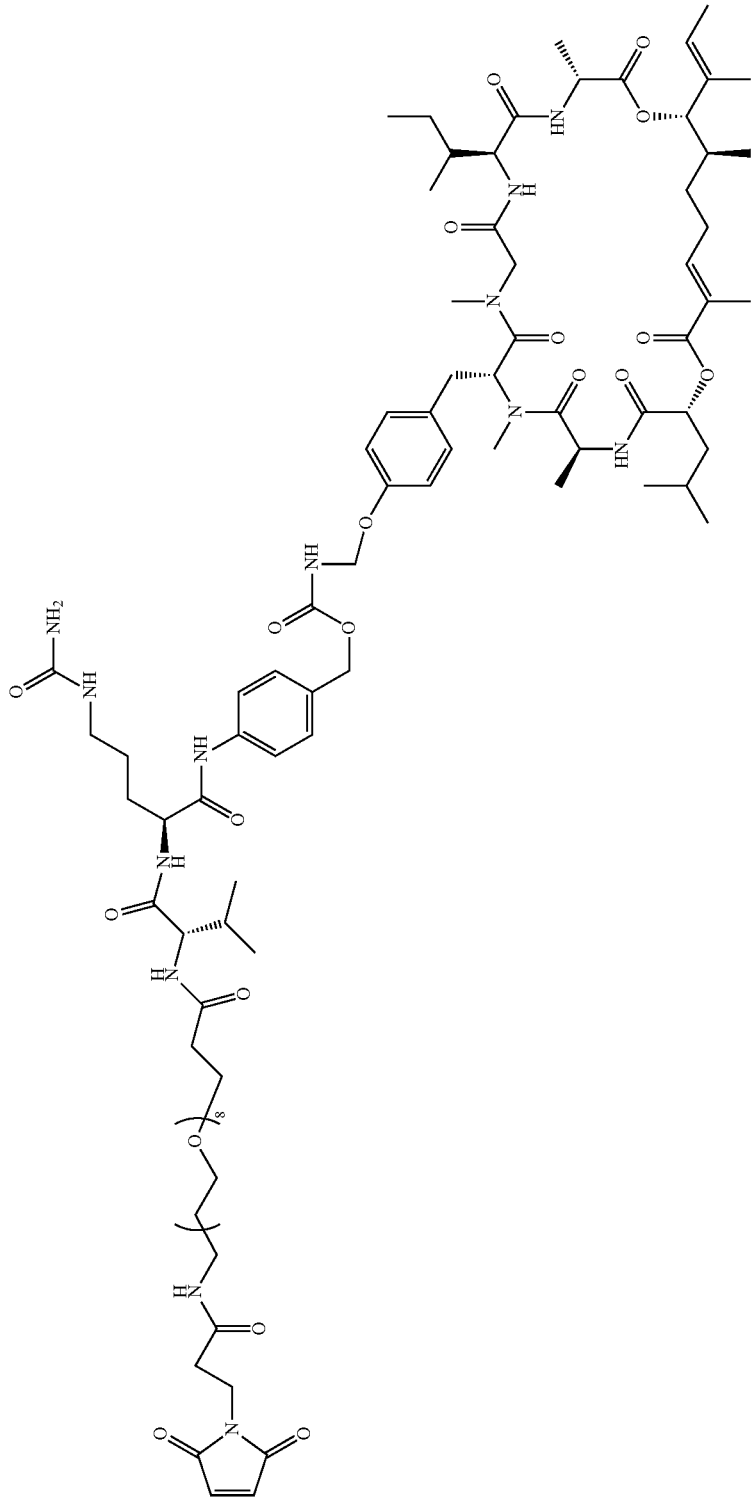 |

TABLE 2-continued
| Conjugate | Structure |
|---|---|
| L33 | 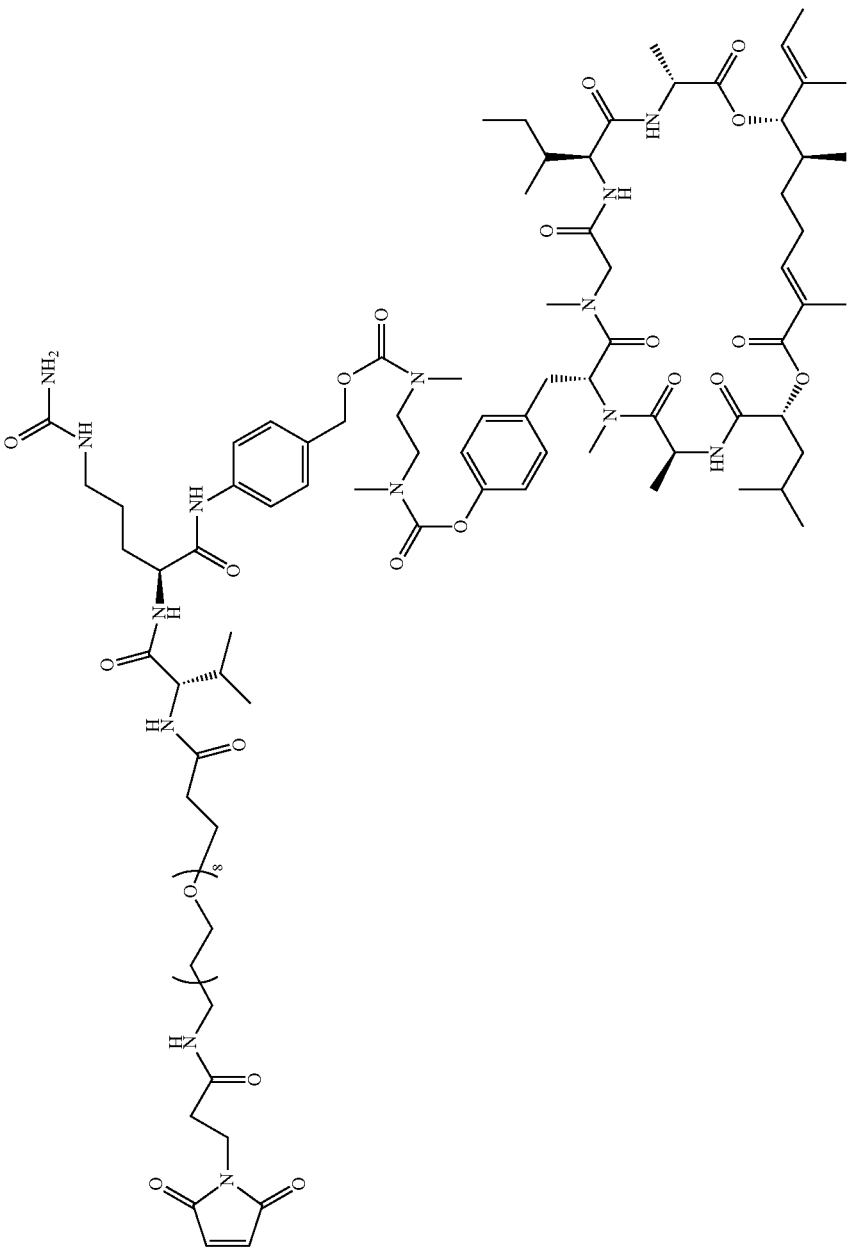 |

In some variations, a conjugate of Table 2 is further bonded to a ligand, such as an antibody. In particular variations, the ligand is bonded to the maleimide moiety on the linker. Exemplary conjugates containing an antibody are shown in Table 3. In any of the conjugates of Table 3, b is an integer from 1-12, inclusive, and Ab is an antibody. In some variations, the antibody binds to a receptor. In some variations, the antibody binds to a receptor on the surface of a cell. In some embodiments, b is 1. In some embodiments, b is 2. In some embodiments, b is 3. In some embodiments, b is 4. In some embodiments, b is 5 in some embodiments, b is 6. In some embodiments, b is 7. In some embodiments, b is 8. In some embodiments, b is 9. In some embodiments, b is 10. In some embodiments, b is 11. In some embodiments, b is 12. In some variations, the antibody in any of the conjugates of Table 3 is replaced with any other suitable ligand. Also provided are salts of any of the conjugates shown in Table 3 or any variation thereof.

TABLE 3
| Con-ju-gate | Structure |
|---|---|
| C1 | 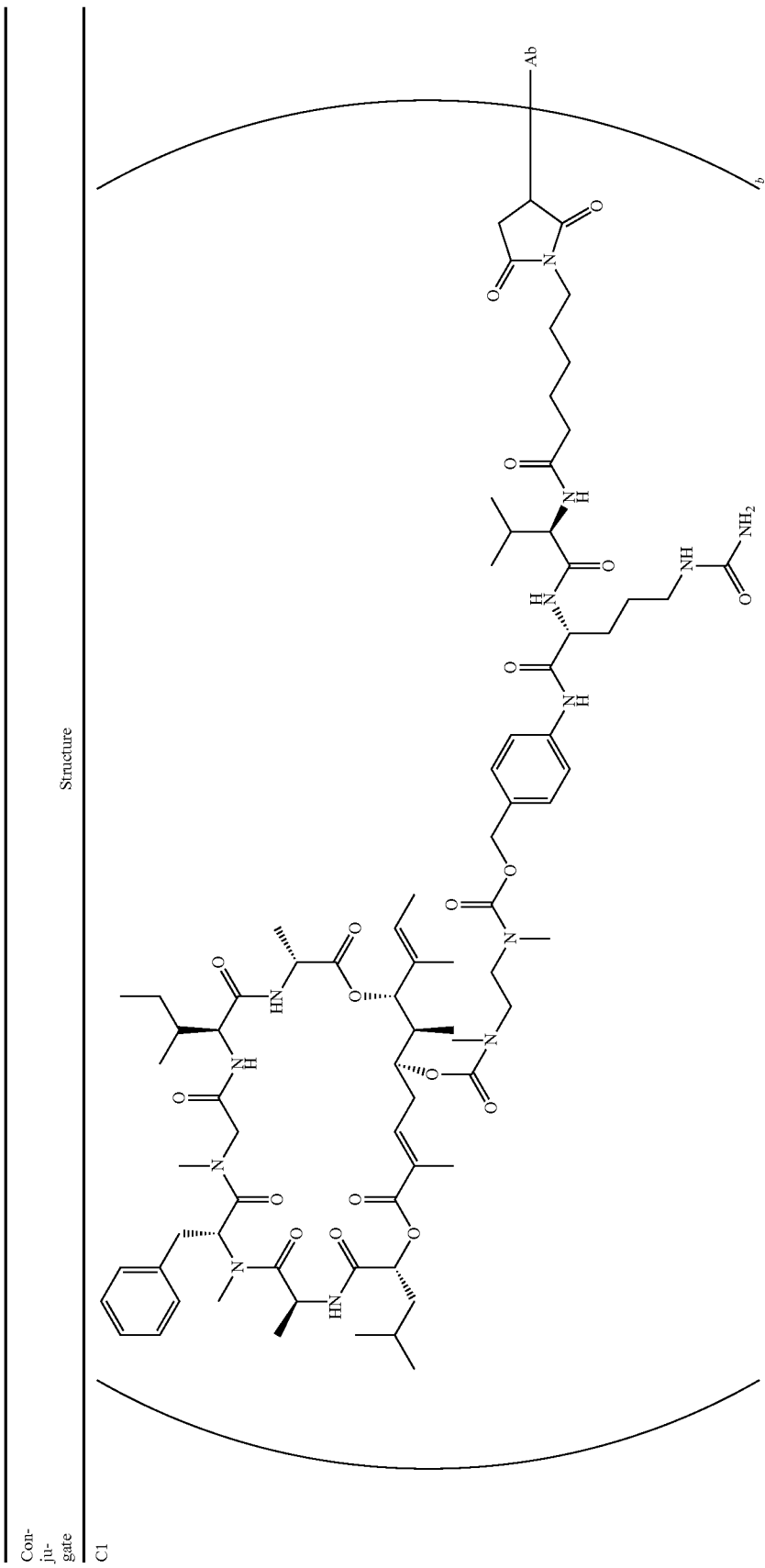 |

TABLE 3-continued
| Conjugate | Structure |
|---|---|
| C2 | 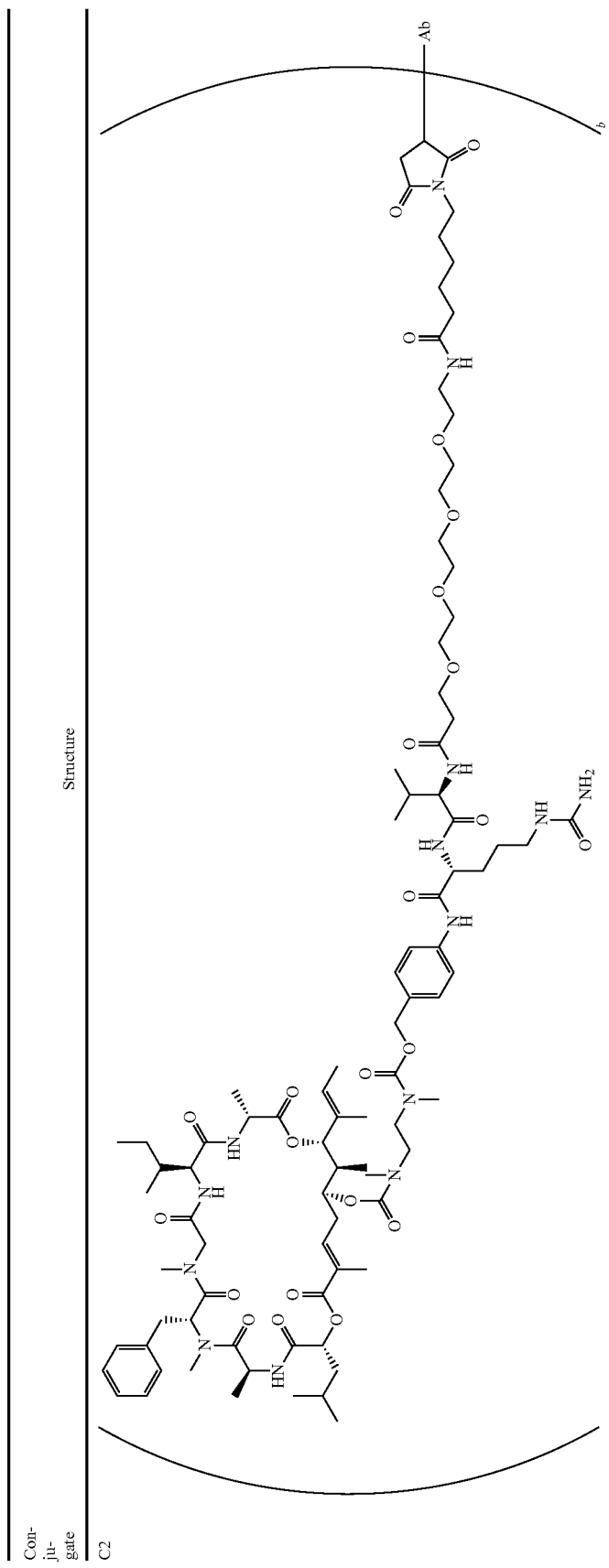 |

TABLE 3-continued
| Conjugate | Structure |
|---|---|
| C3 | 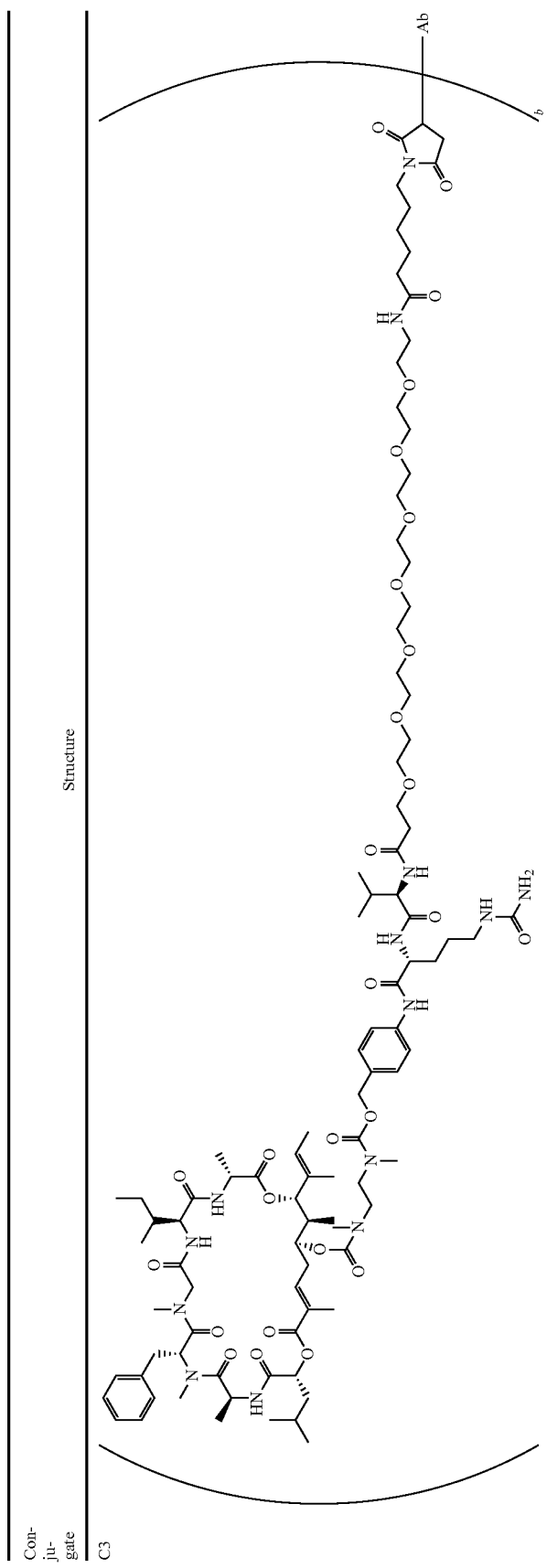 |

TABLE 3-continued
| Conjugate | Structure |
|---|---|
| C4 | 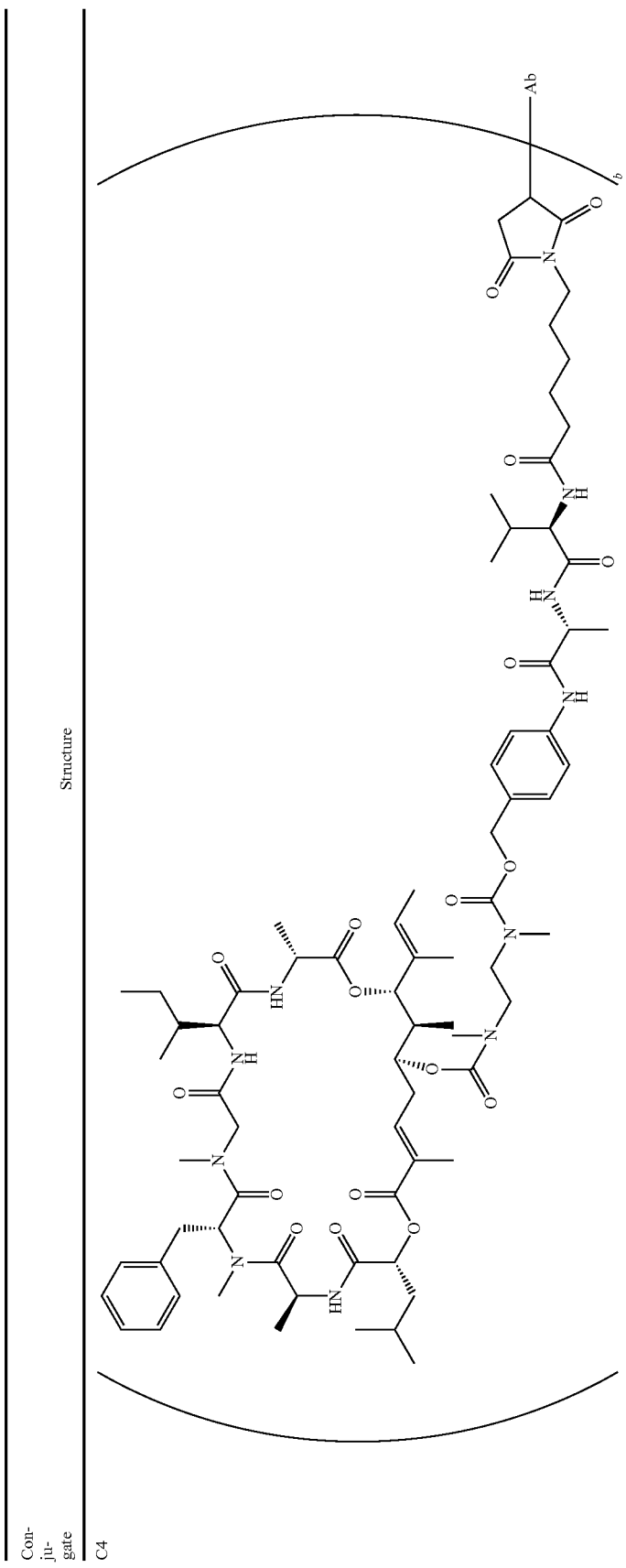 |

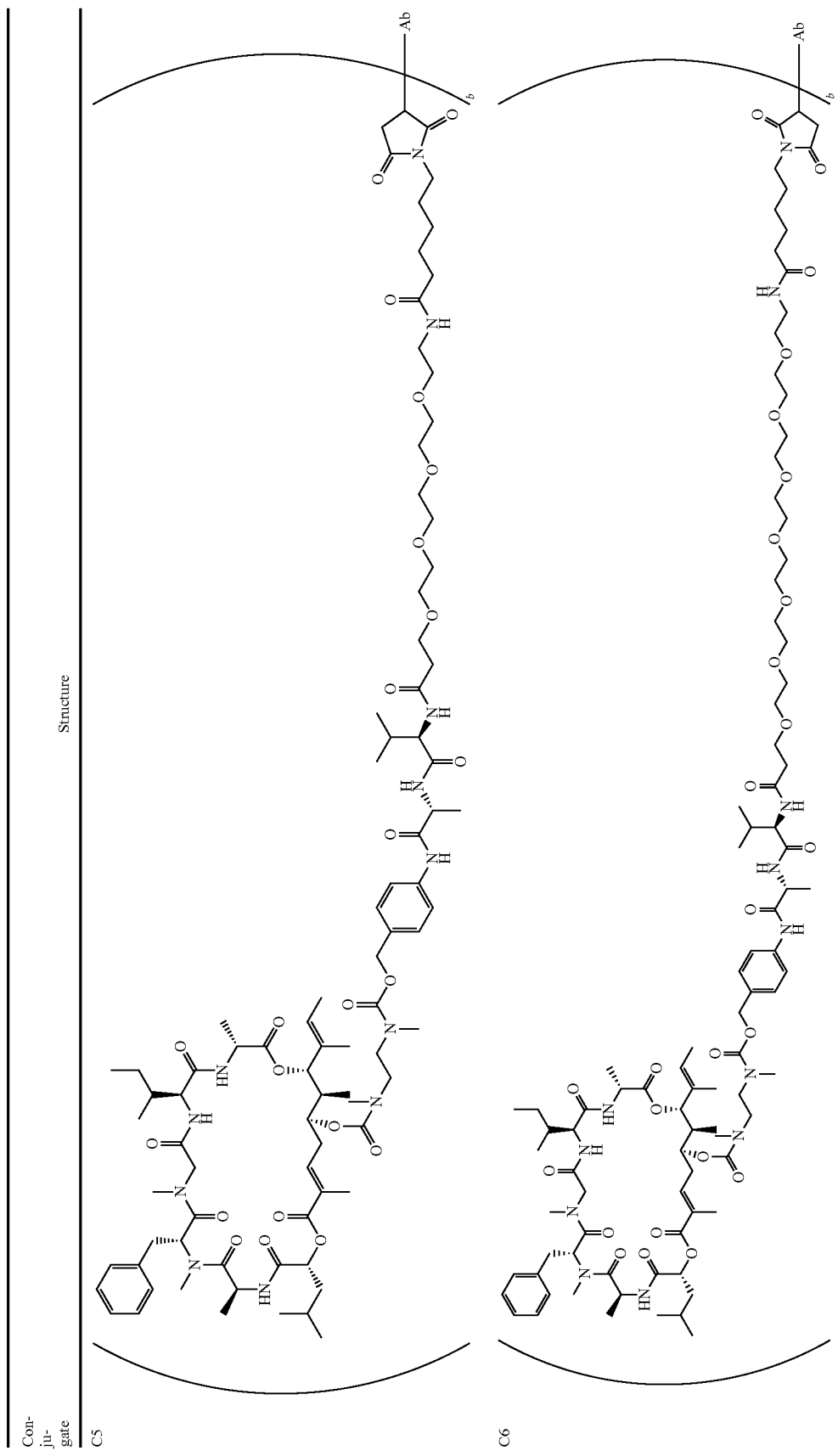

TABLE 3-continued
| Conjugate | Structure |
|---|---|
| C7 | 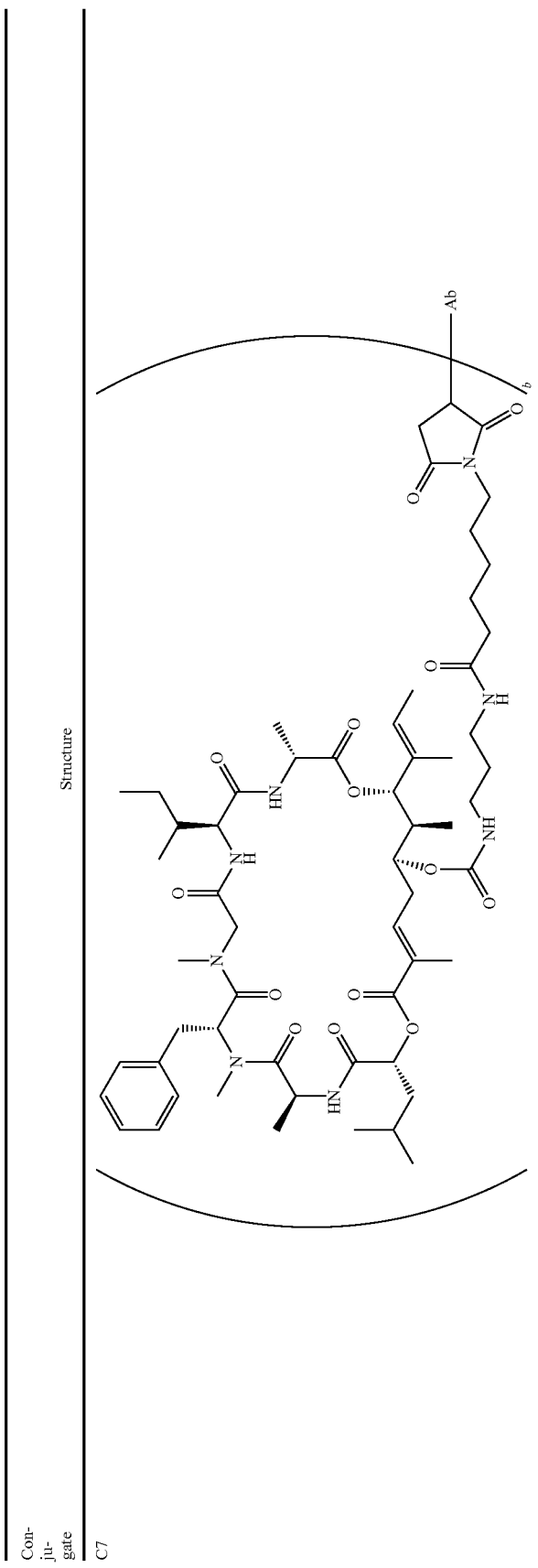 |

TABLE 3-continued
Conjugate: C8
Structure:
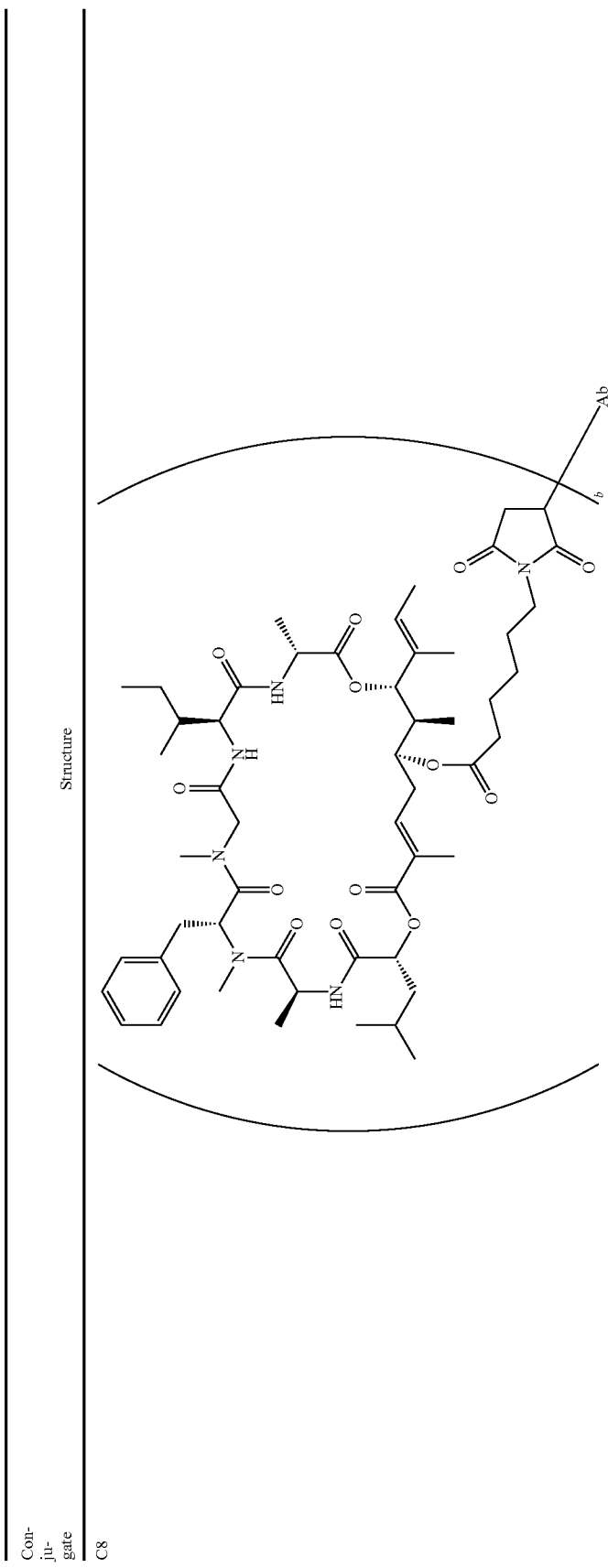

TABLE 3-continued
Structure
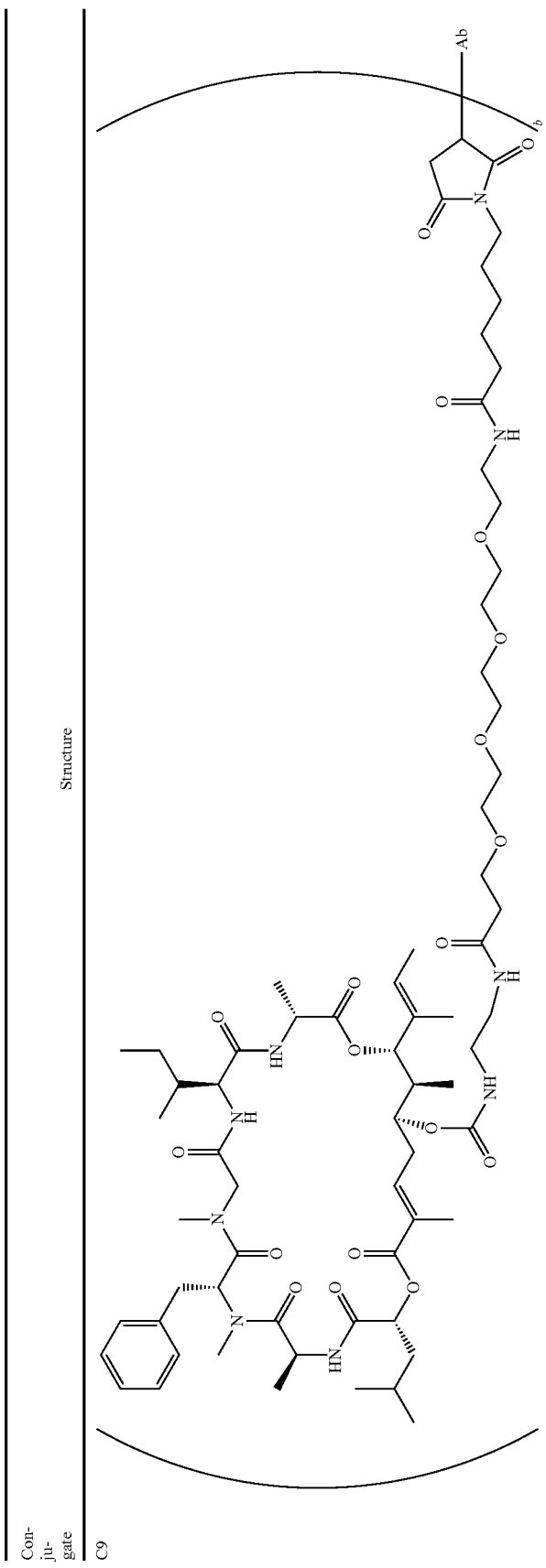
Conjugate: C9

TABLE 3-continued
| Conjugate | Structure |
|---|---|
| C10 | 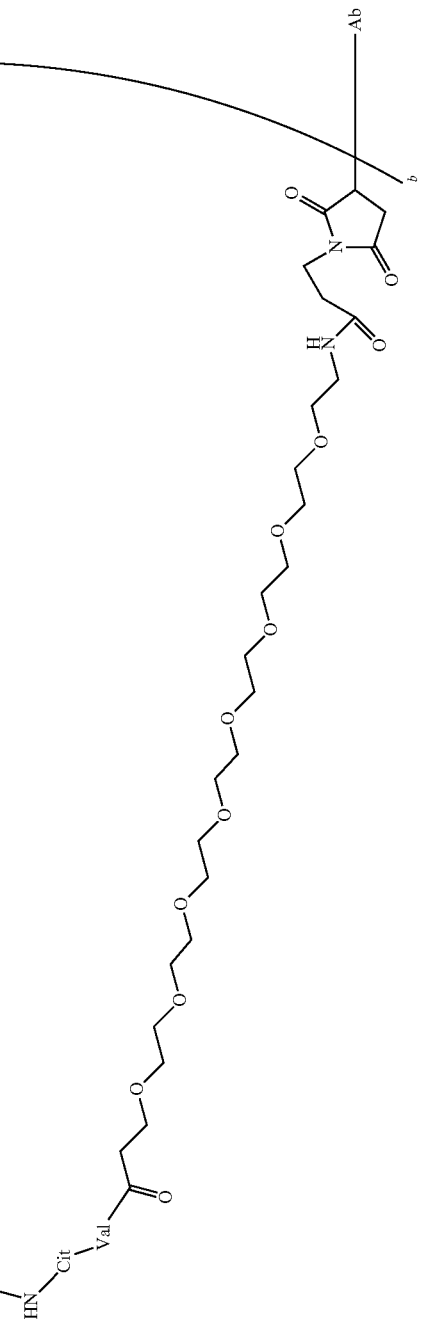 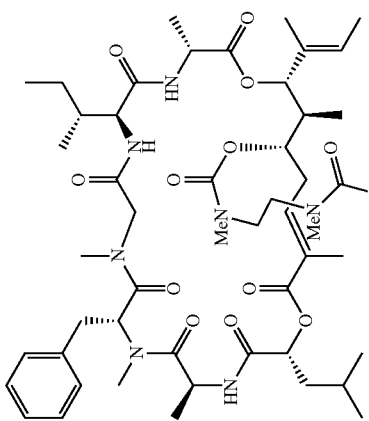 |

TABLE 3-continued
| Conjugate | Structure |
|---|---|
| C11 | 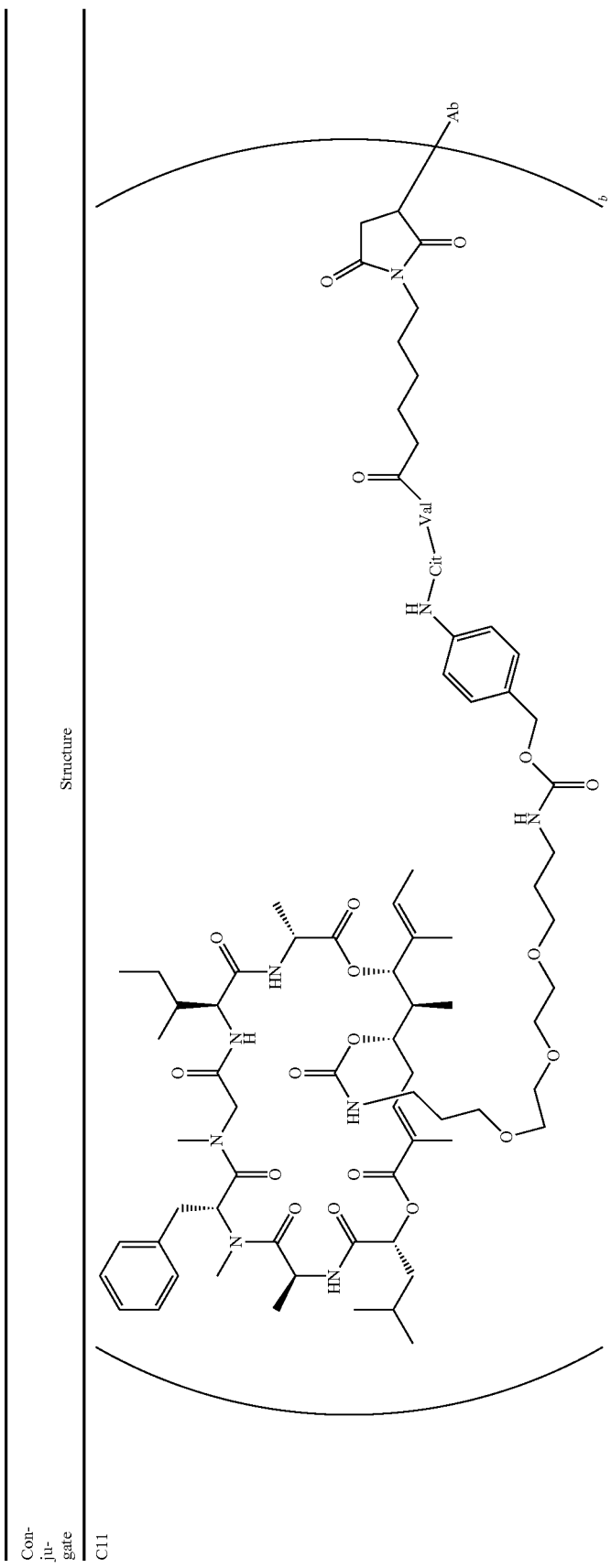 |

TABLE 3-continued
| Conjugate | Structure |
|---|---|
| C12 | 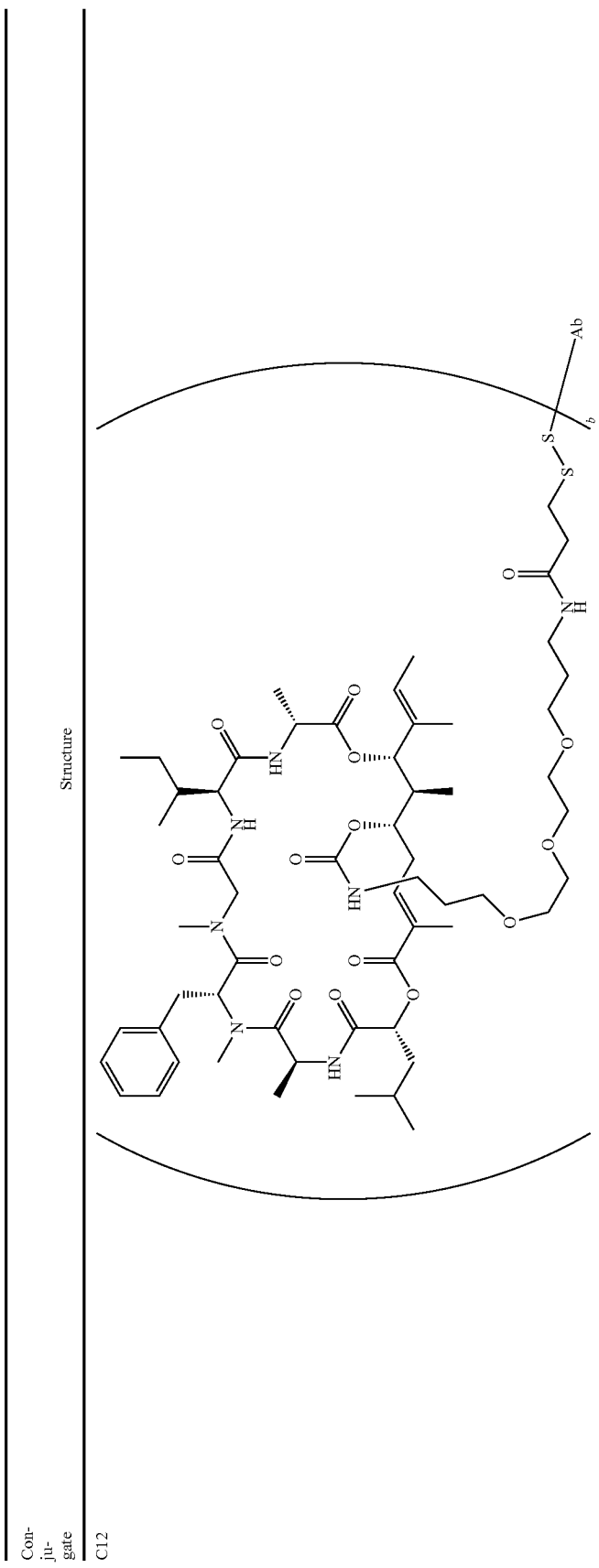 |

TABLE 3-continued
| Conjugate | Structure |
|---|---|
| C13 | 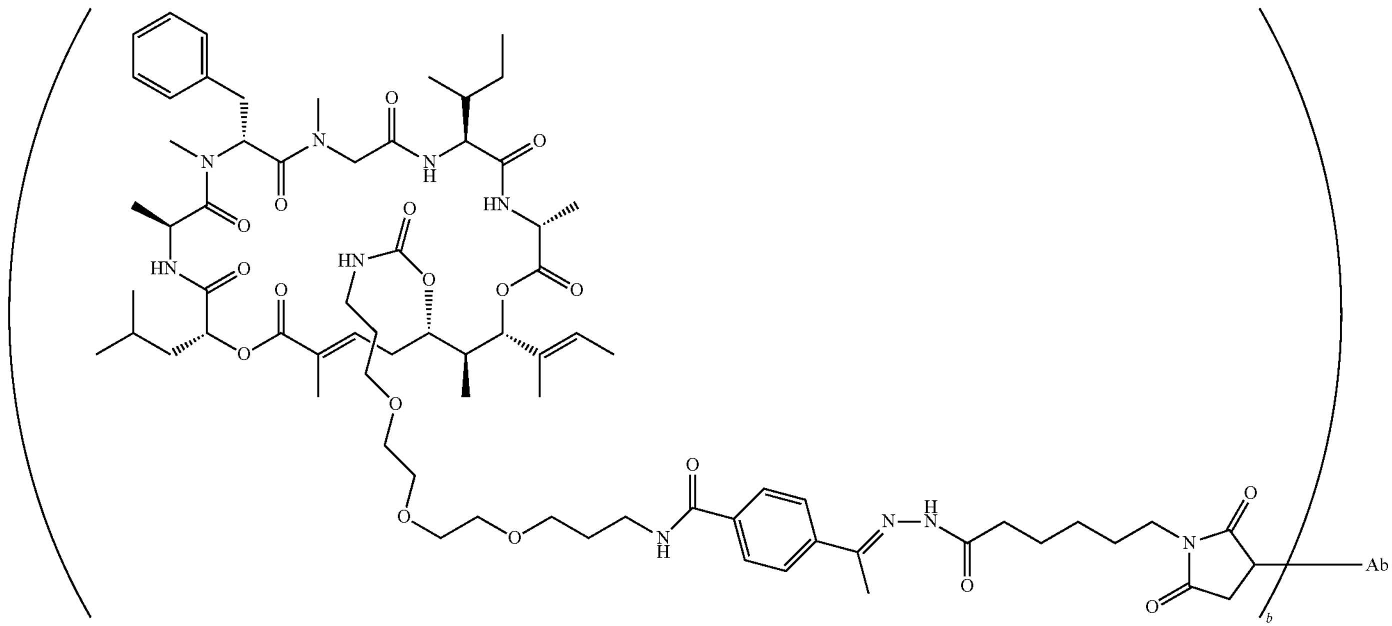 |

TABLE 3-continued
| Conjugate | Structure |
|---|---|
| C14 | 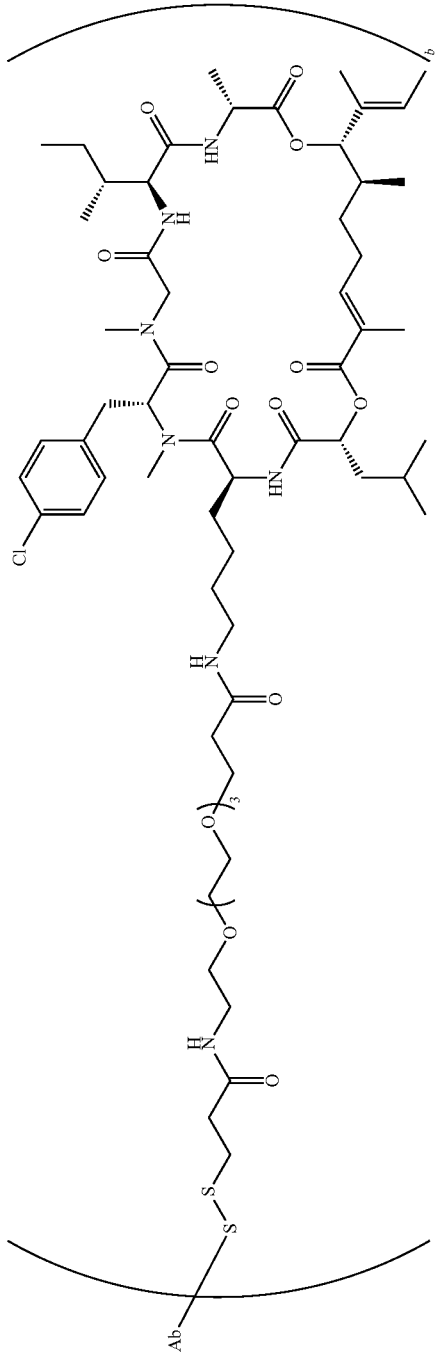 |
| C15 | 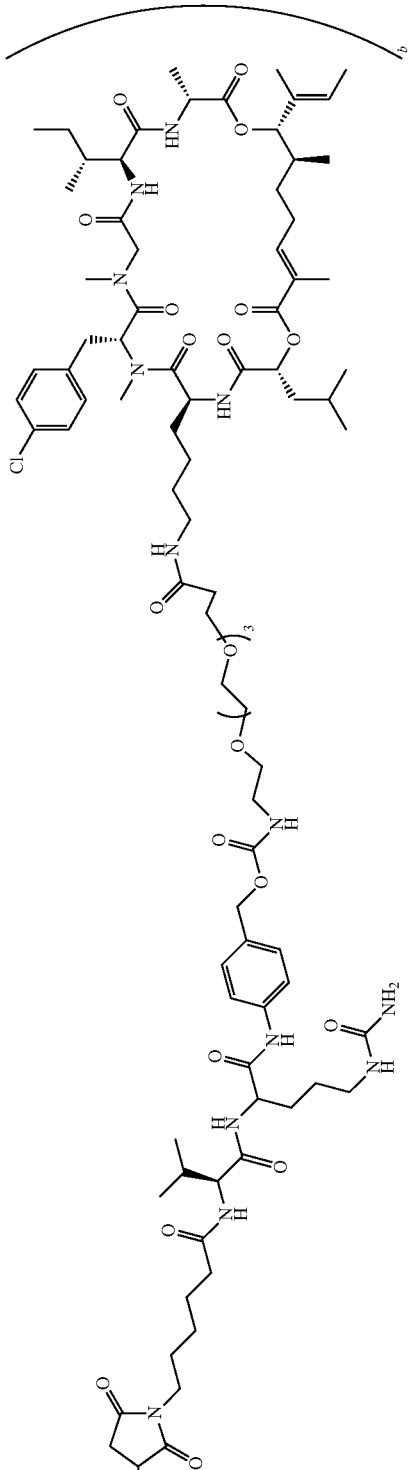 |

TABLE 3-continued
| Conjugate | Structure |
|---|---|
| C16 | 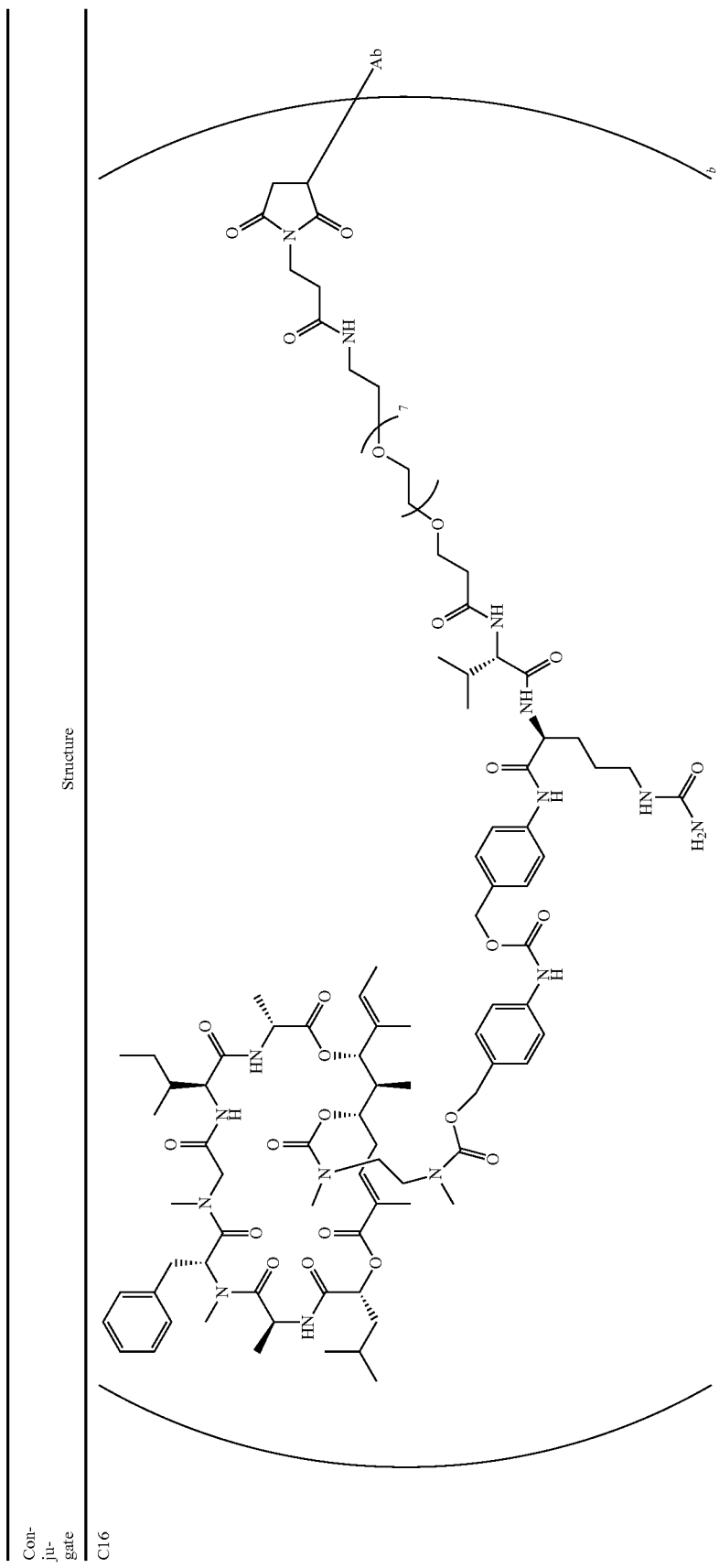 |

TABLE 3-continued
| Conjugate | Structure |
|---|---|
| C17 | 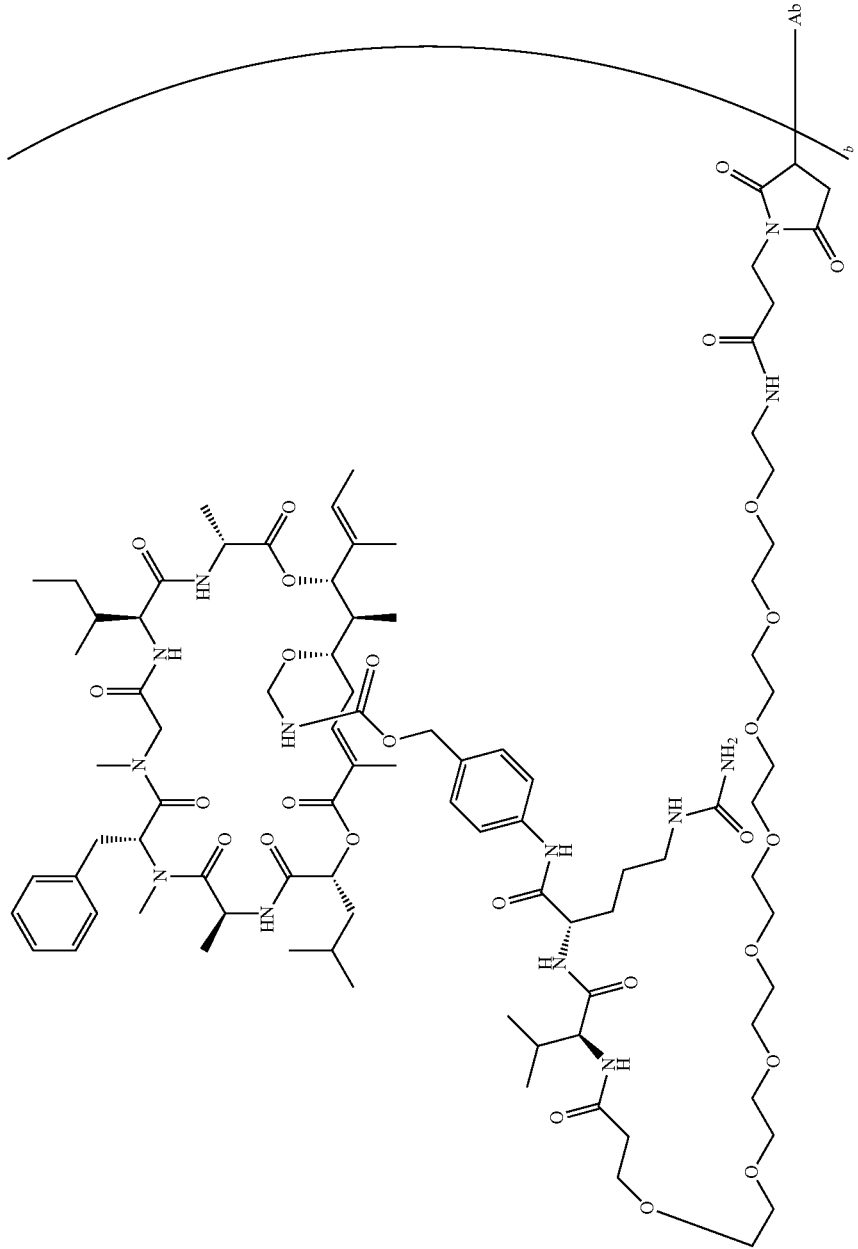 |

TABLE 3-continued
| Conjugate | Structure |
|---|---|
| C18 | 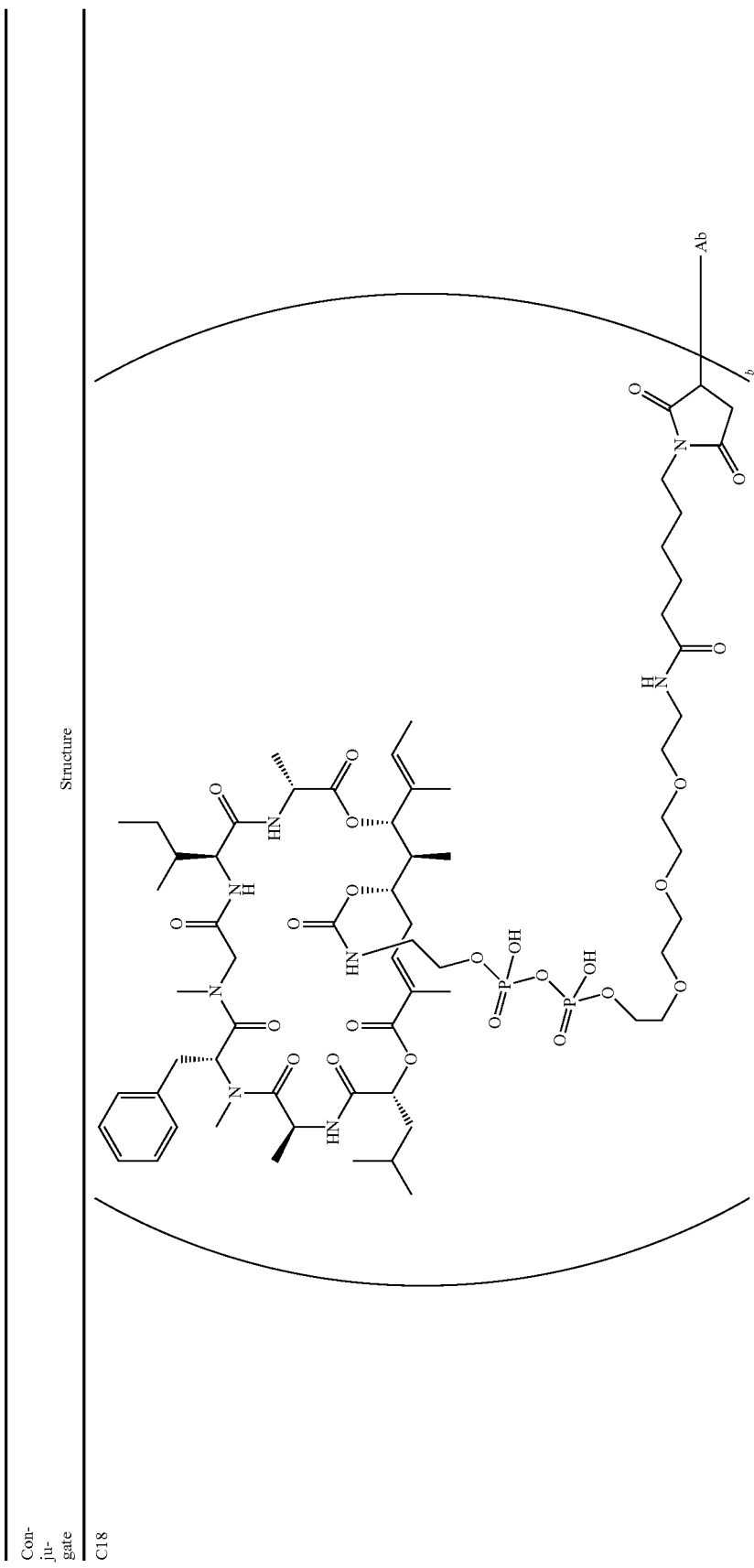 |

TABLE 3-continued
| Conjugate | Structure |
|---|---|
| C19 | 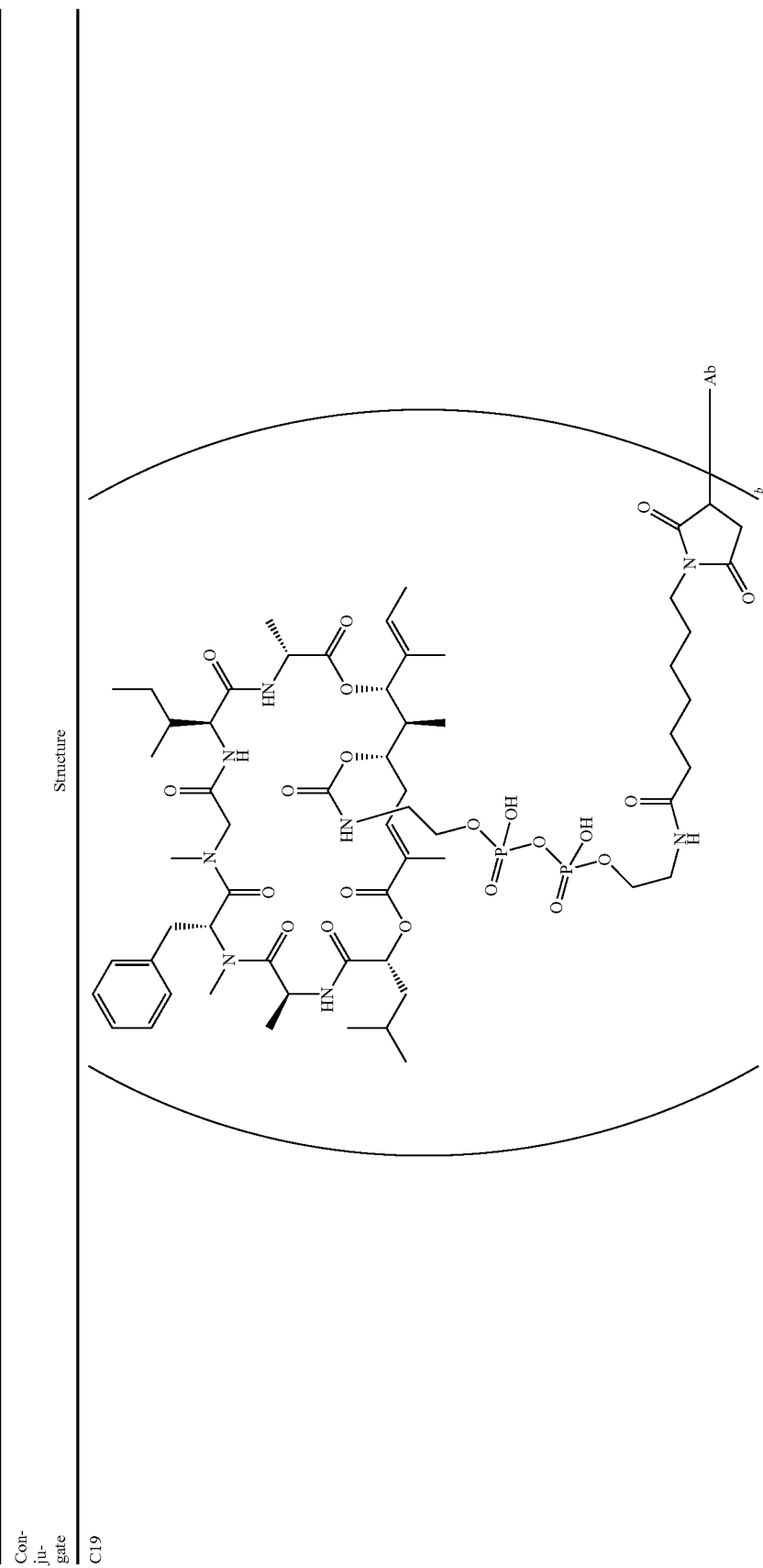 |

TABLE 3-continued
| Conjugate | Structure |
|---|---|
| C20 | 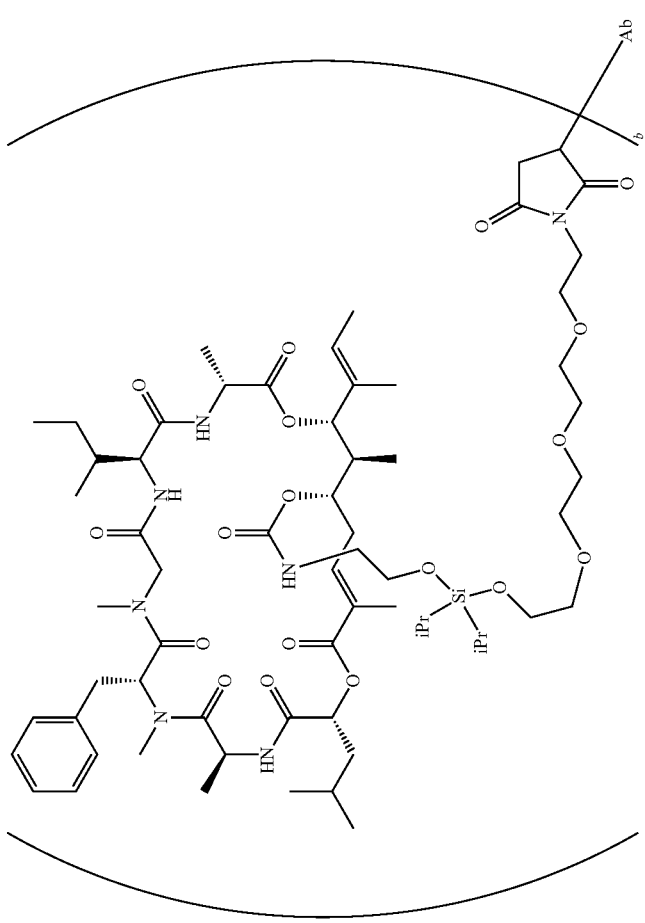 |

TABLE 3-continued

| Conjugate | Structure |
|---|---|
| C21 | (chemical structure) |

TABLE 3-continued
| Conjugate | Structure |
|---|---|
| C25 | 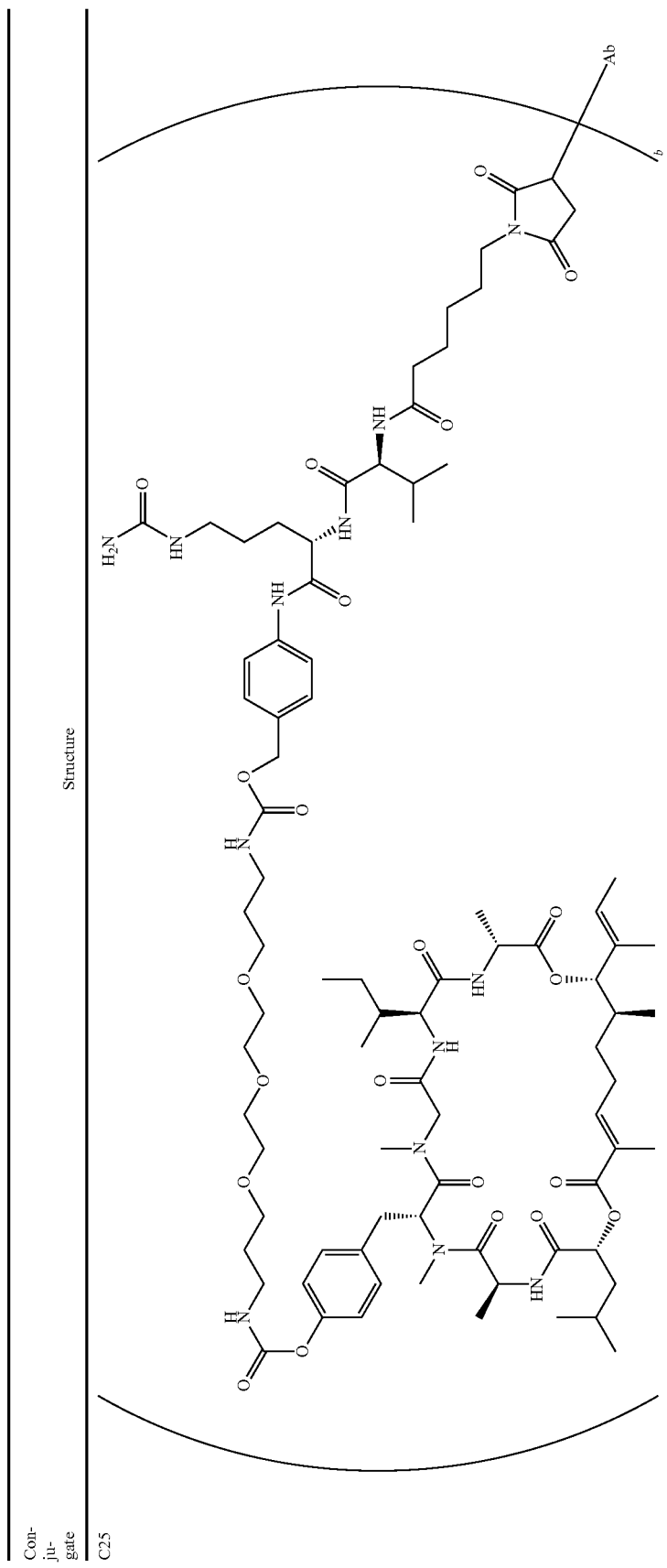 |

TABLE 3-continued
| Conjugate | Structure |
|---|---|
| C26 | 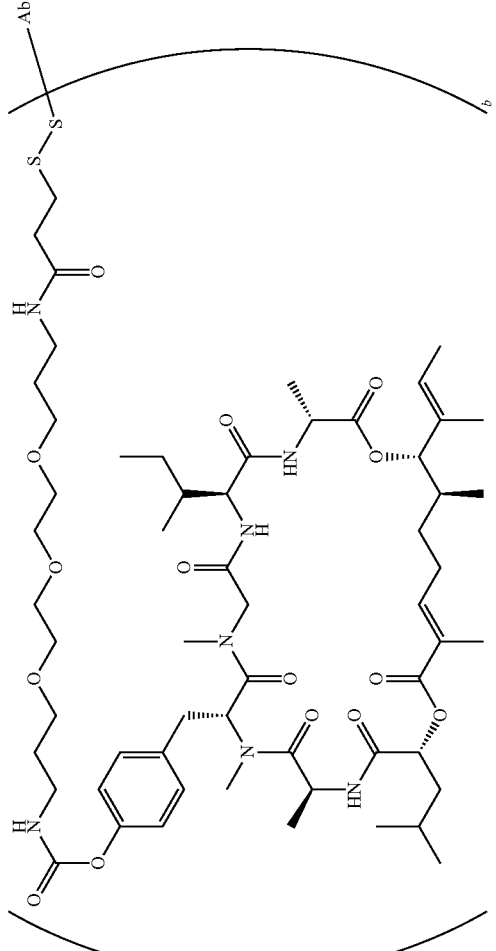 |

TABLE 3-continued
Conjugate: C27
Structure:
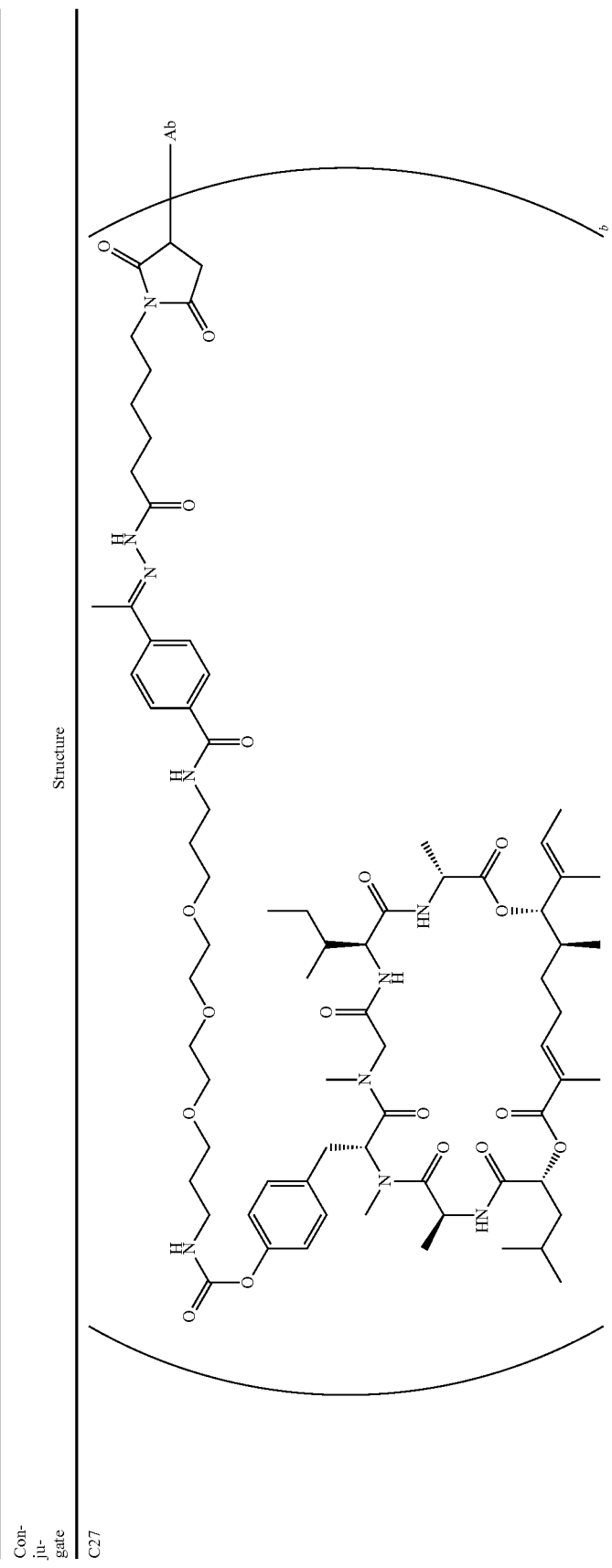

TABLE 3-continued
| Conjugate | Structure |
|---|---|
| C28 | 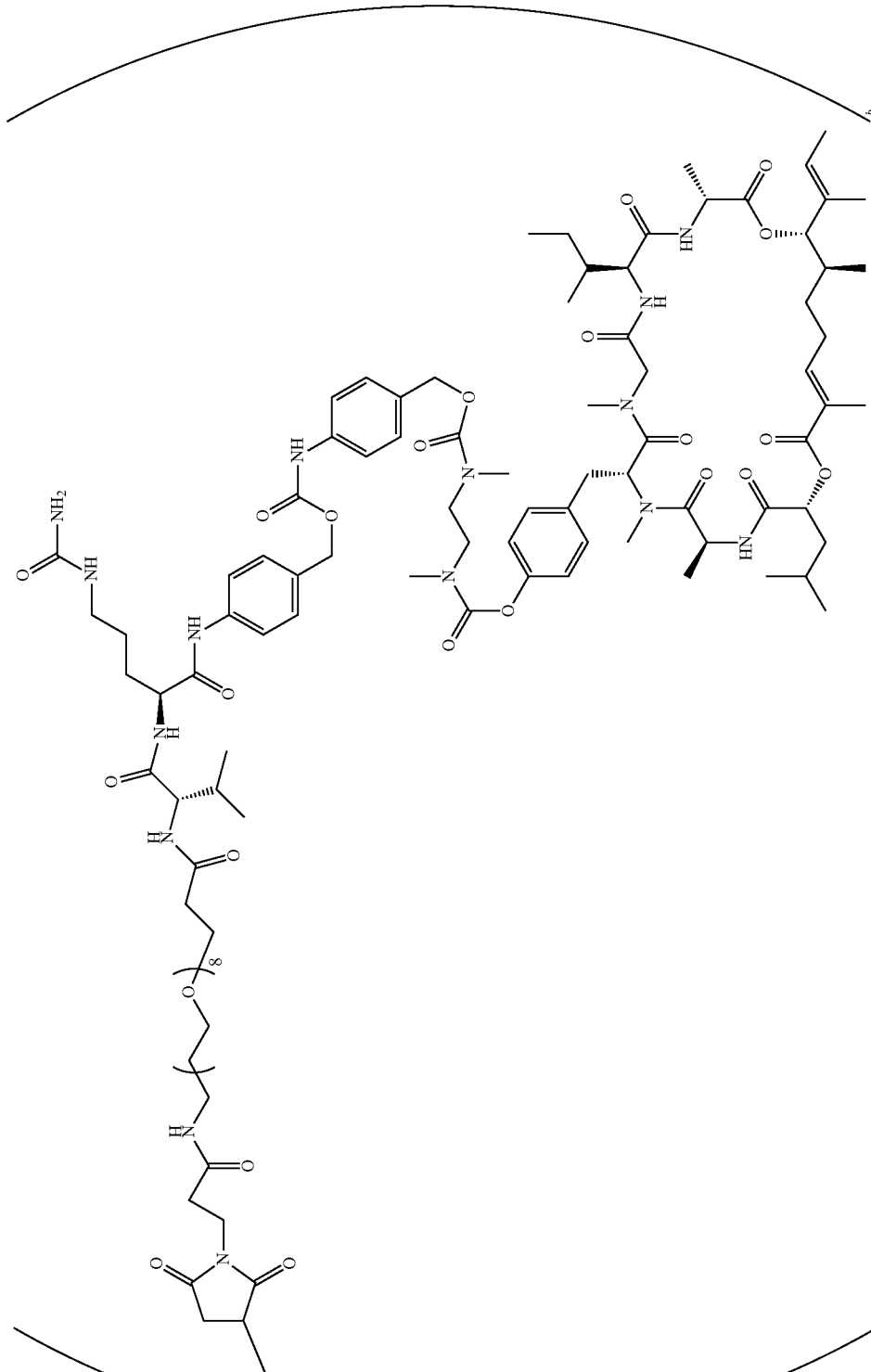 |

TABLE 3-continued
| Conjugate | Structure |
|---|---|
| C29 | 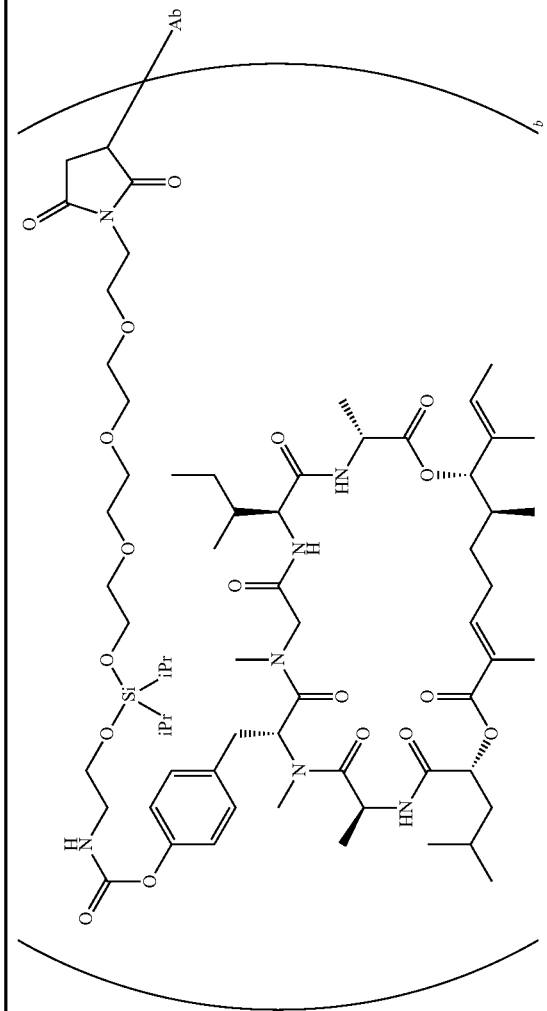 |
| C30 | 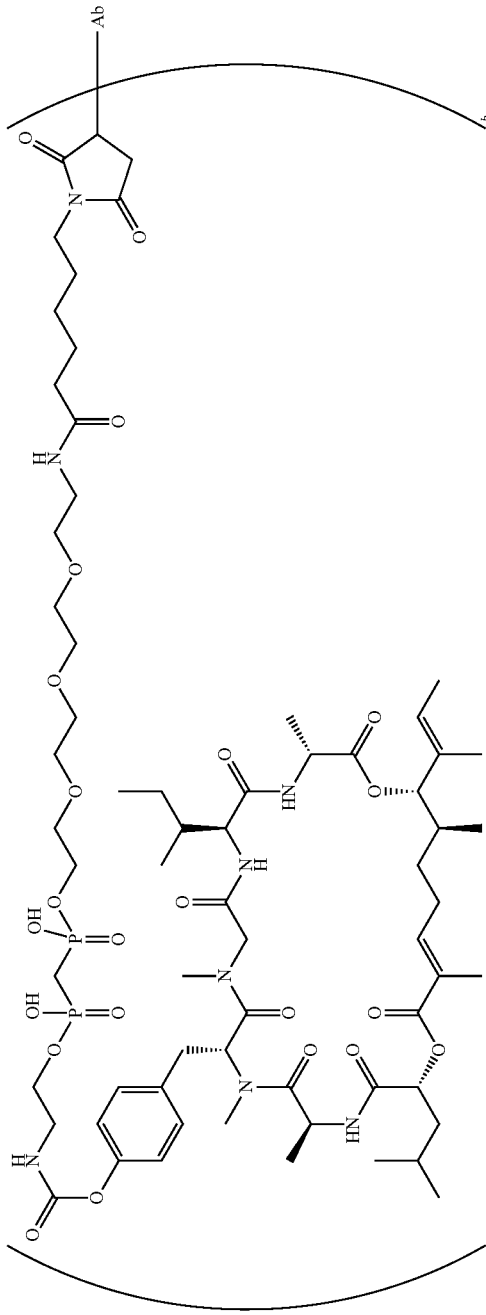 |

TABLE 3-continued
| Conjugate | Structure |
|---|---|
| C31 | 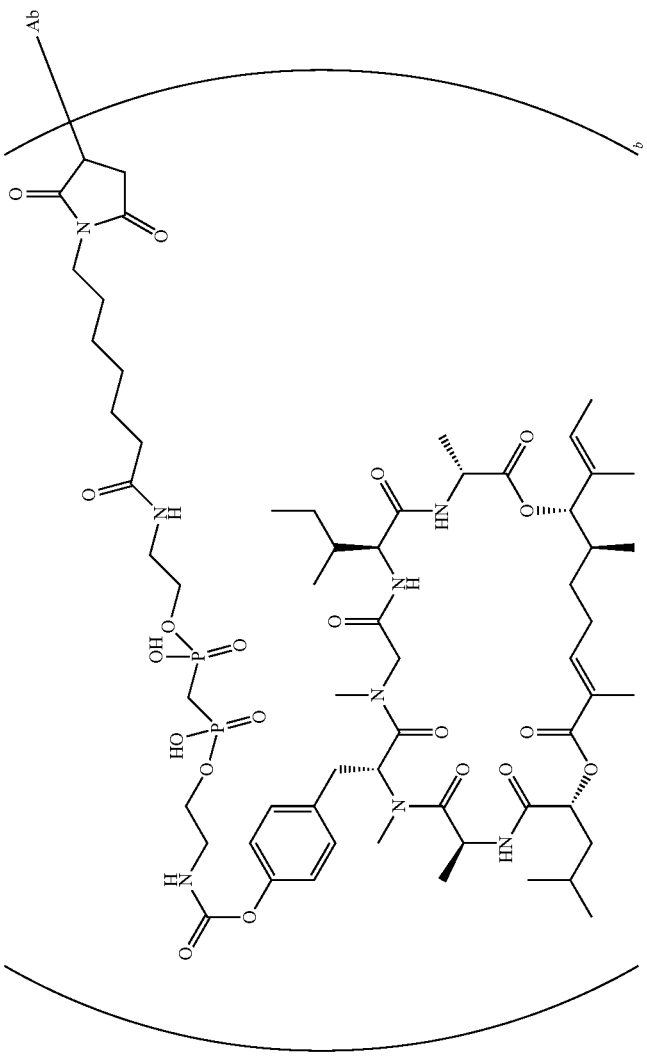 |

TABLE 3-continued
| Conjugate | Structure |
|---|---|
| C32 | 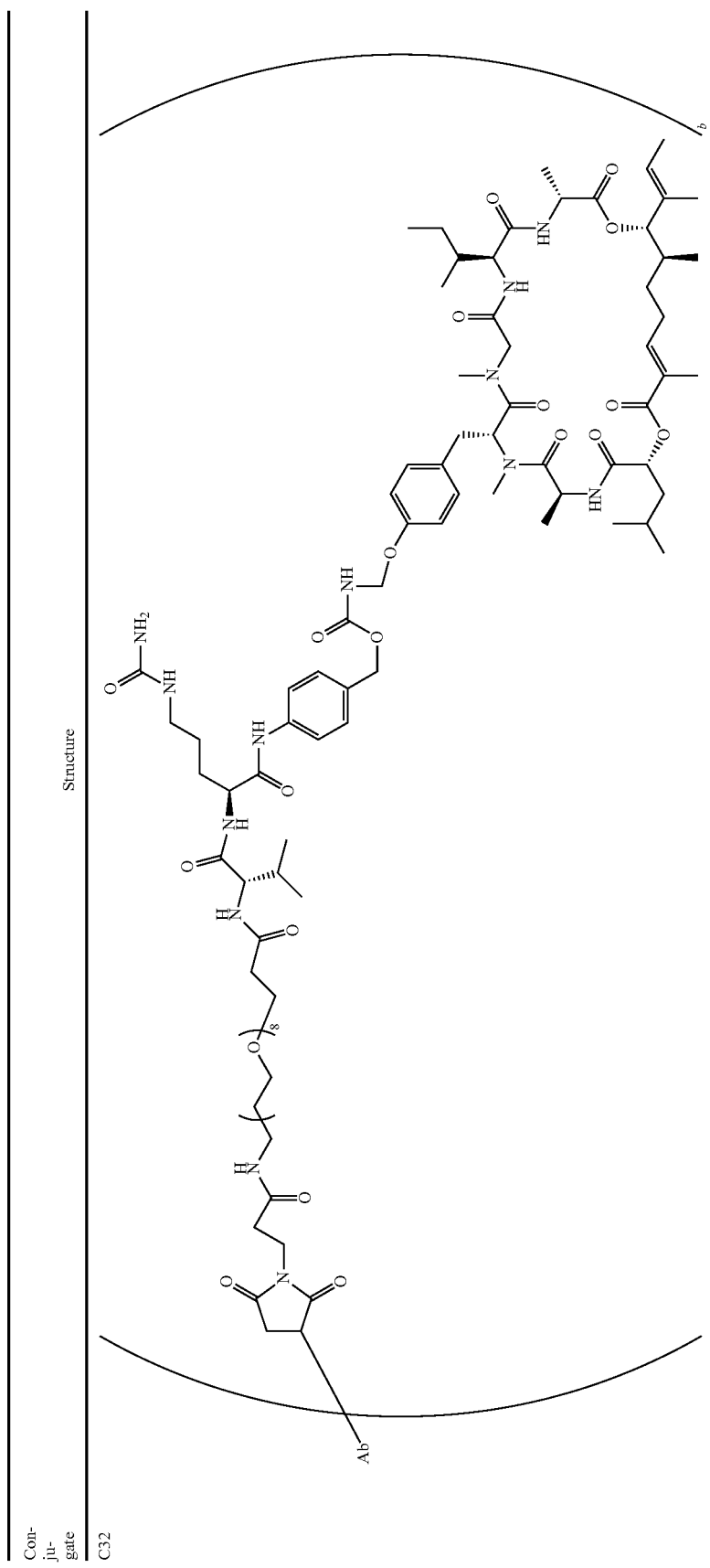 |

TABLE 3-continued
Conjugate: C33
Structure:
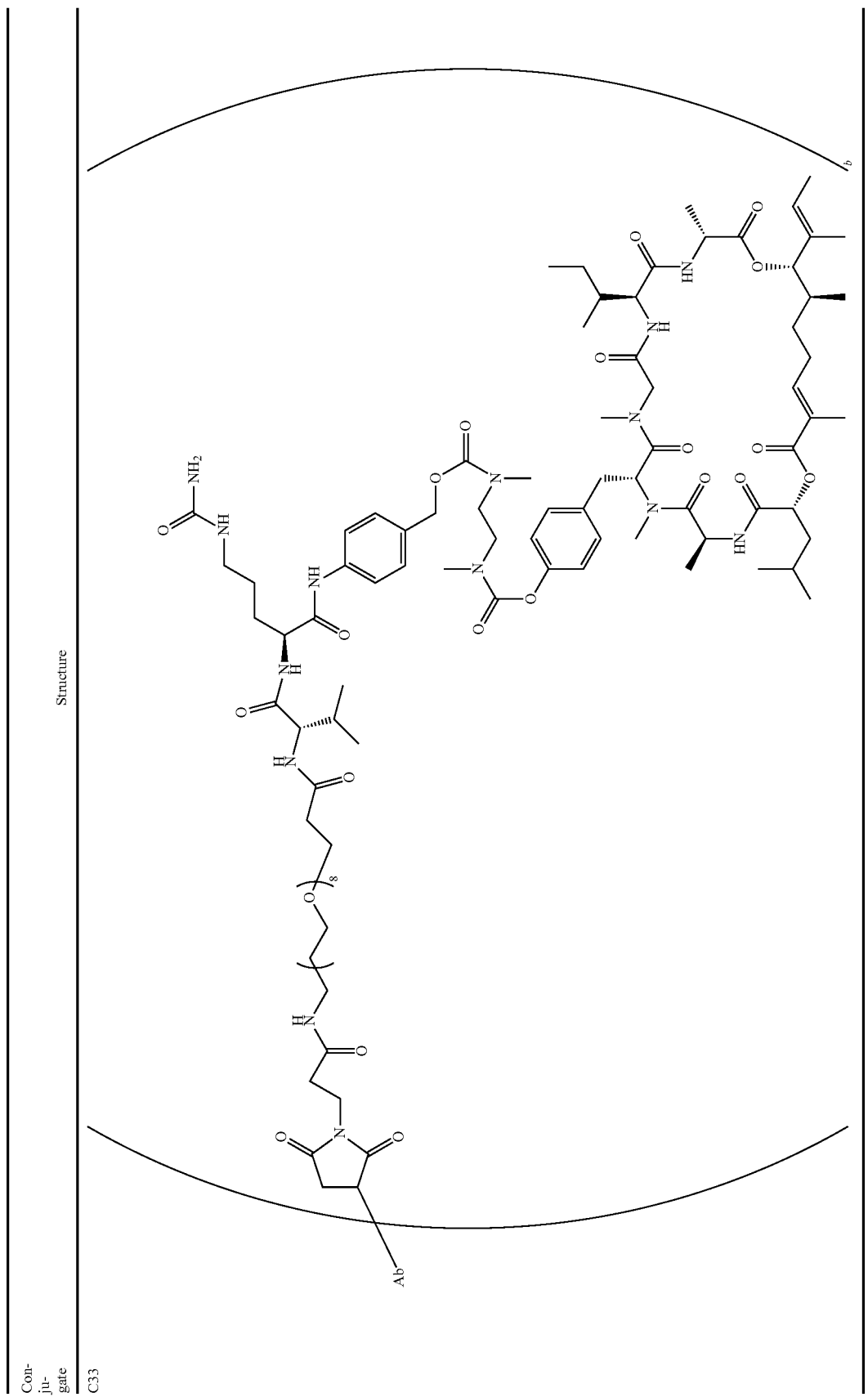

Compositions

The present disclosure also provides a composition, e.g., a pharmaceutical composition, containing one or more of the compounds or conjugates described herein. The composition may be a pharmaceutical composition. The composition may be an intermediate for use in preparation of a pharmaceutical compositions. Compositions may contain one or more compounds or conjugates described herein. In some aspects, a composition may contain a synthetic intermediate that may be used in the preparation of a compound or conjugate described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

In any composition containing a conjugate, wherein the conjugate comprises a ligand, the average ratio of drug to ligand in the composition is from 1 to 12, inclusive, where the ratio may be an integral or non-integral value. In some such compositions, the conjugate comprises an antibody, and the average drug to antibody ratio (DAR) is from 1 to 12, inclusive, where the ratio may be an integral or non-integral value.

Pharmaceutical Formulations

The present disclosure also provides a composition, e.g., a pharmaceutical composition, containing one or more of the compounds described herein, formulated together with a pharmaceutically acceptable carrier. Pharmaceutical compositions of the invention also can be administered in combination therapy, i.e., combined with other agents. For example, the combination therapy can include a conjugate as described herein combined with at least one other active agent.

Pharmaceutically acceptable carriers may include any and all carriers, excipients, stabilizers, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the conjugate described herein, may be coated in a material to protect the compound from the action of acids and other natural conditions that may inactivate the compound.

Acceptable carriers, excipients, or stabilizers are nontoxic to recipients at standard dosages and concentrations to be administered, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ or polyethylene glycol (PEG).

The pharmaceutical compositions of the invention may include one or more pharmaceutically acceptable salts. A pharmaceutically acceptable salt retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Dosages and Dosage Forms

For the prevention or treatment of disease, the appropriate dosage of conjugates and compounds described herein will depend on the type of disease to be treated, the severity and course of the disease, whether the compound or conjugate is administered for preventive or therapeutic purposes, mode of delivery, previous therapy, and the subject's clinical history. The compounds and conjugates described herein are suitably administered to a subject at one time or over a series of treatments. Depending on the type and severity of the disease, a typical daily dosage might range from about 0.0001 mg/kg to 100 mg/kg or more, depending on the factors mentioned above. For repeated administrations over several days or longer, depending on the condition, the treatment is sustained until a desired suppression of disease symptoms occurs.

For example dosages can be 0.3 mg/kg body weight, 1 mg/kg body weight, 3 mg/kg body weight, 5 mg/kg body weight or 10 mg/kg body weight or within the range of 1-10 mg/kg. Treatment regimens may comprise administration once per week, once every two weeks, once every three weeks, once every four weeks, once per month, once every 3 months or once every three to 6 months. In other embodiments, sustained release formulations are administered, which would result in less frequent administration compared to non-sustained release formulations.

The amount of active ingredient which can be combined with a carrier material to produce a single dosage form will generally be that amount of the composition which produces a therapeutic effect, without being toxic to the subject. Generally, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Administration

A composition described herein can be administered via one or more routes of administration using one or more of a variety of methods known in the art. As will be appreciated by the skilled artisan, the route and/or mode of administration will vary depending upon the desired results. Routes of administration for the compounds and compositions described herein include oral, sublingual, buccal, intranasal, topical, rectal, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Methods of Treatment

In one embodiment, the disease or condition to be treated or prevented is cancer. The term "cancer" refers to precancerous conditions, non-malignant, low-grade, high-grade, and malignant cancer. Cancer of any tissue type is contemplated for treatment or prevention by the compounds disclosed herein. Exemplary types of cancer include carcinoma, lymphoma, blastoma, sarcoma, leukemia, and lymphoid malignancies. More specifically, in certain embodiments the cancer is squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Provided herein is a method of treating cancer in an individual in need thereof by administering to the individual a therapeutically effective amount of a compound, conjugate, or composition described herein. Also provided herein is the use of a compound, conjugate, or composition described herein in the manufacture of a medicament for treatment of cancer in an individual in need thereof. Also provided herein is the use of a compound, conjugate, or composition described herein for treatment of cancer in an individual in need thereof. Also provided herein is a compound, conjugate, or composition described herein for use in treatment of cancer in an individual in need thereof.

In one aspect, provided herein are kits containing a compound, conjugate, or composition described herein and instructions for use. The kits may contain instructions for use in the treatment of cancer in an individual in need thereof. A kit may additionally contain any materials or equipment that may be used in the administration of the compound, conjugate, or composition, such as vials, syringes, or IV bags. A kit may also contain sterile packaging.

General Synthetic Methods

Compounds of Formula (I) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (II), (III), or any variation thereof. Other compounds described herein may be prepared by similar methods. For example, Scheme 1b is an exemplified synthesis of the method detailed in Scheme 1a, but other compounds described herein may be prepared by similar methods.

Peptide coupling, esterification, and deprotection reactions referred to herein can be carried out using methods known in the art.

Scheme 1a.

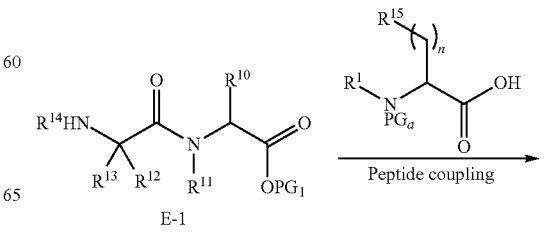

-continued

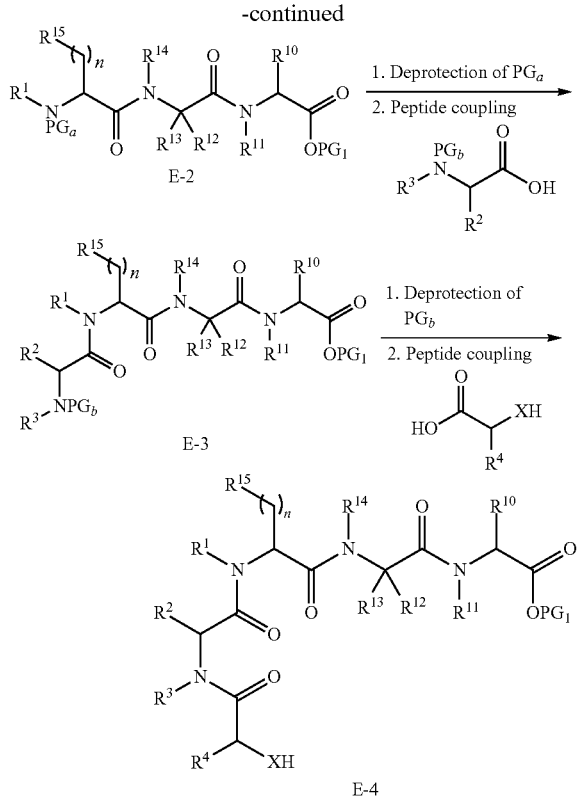

Protected di-peptide E-1 is subjected to a peptide coupling reaction to form protected tri-peptide E-2. Protecting group $PG_a$ is removed, followed by a further peptide coupling reaction to afford compound E-3. Protecting group $PG_b$ is then removed, followed by a further peptide coupling reaction to afford compound E-4.

Scheme 2a.

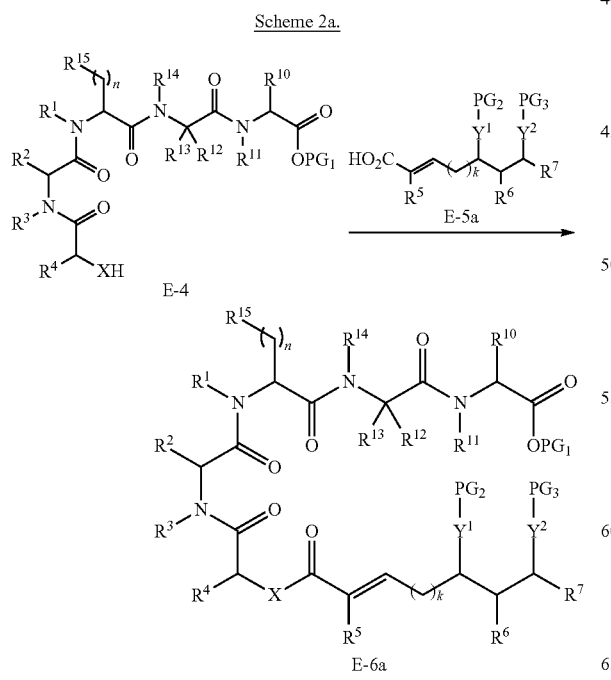

Compound E-4 is reacted with compound E-5a under suitable conditions to afford compound E-6a.

Scheme 3a.

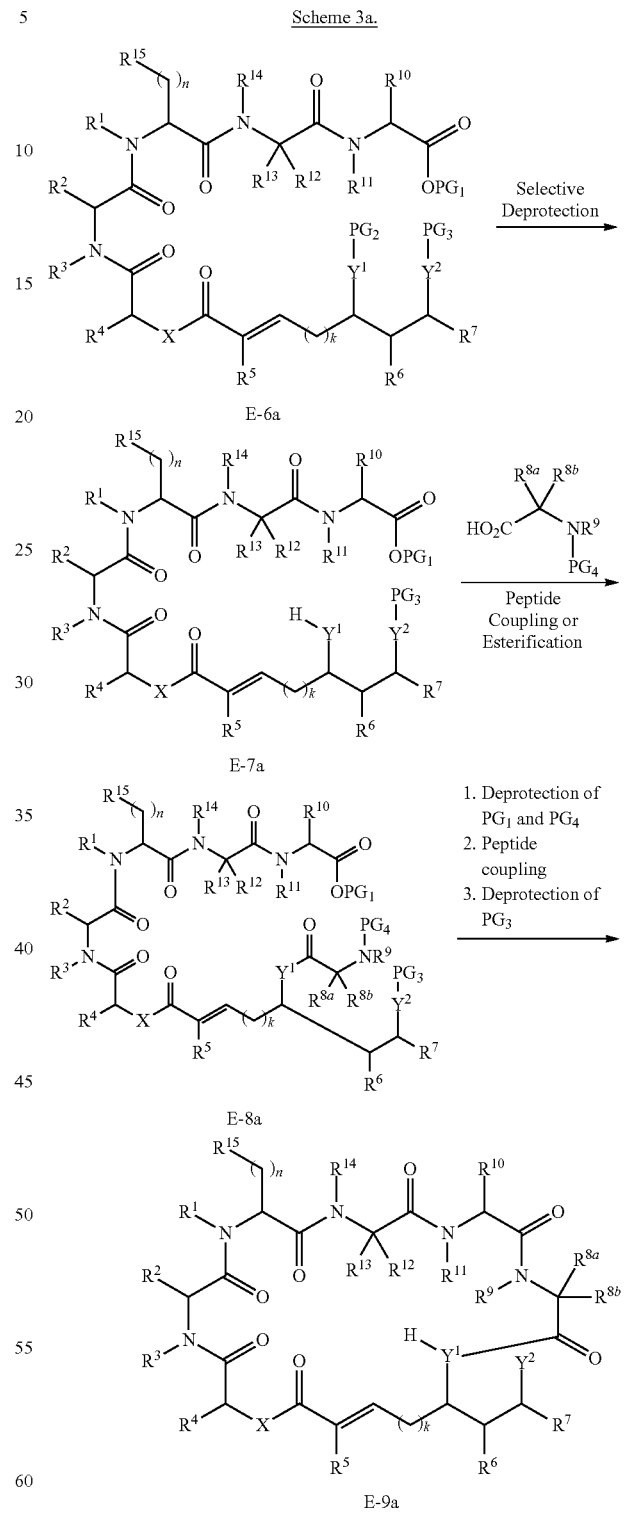

Selective deprotection of compound E-6a to remove protecting group $PG_2$ affords compound E-7a. A peptide coupling or esterification reaction is produces compound E-8a. E-8a can be selectively deprotected to remove $PG_1$ and $PG_4$, cyclized via a peptide coupling reaction, and then deprotected to remove PG$_3$, resulting in compound E-9a.

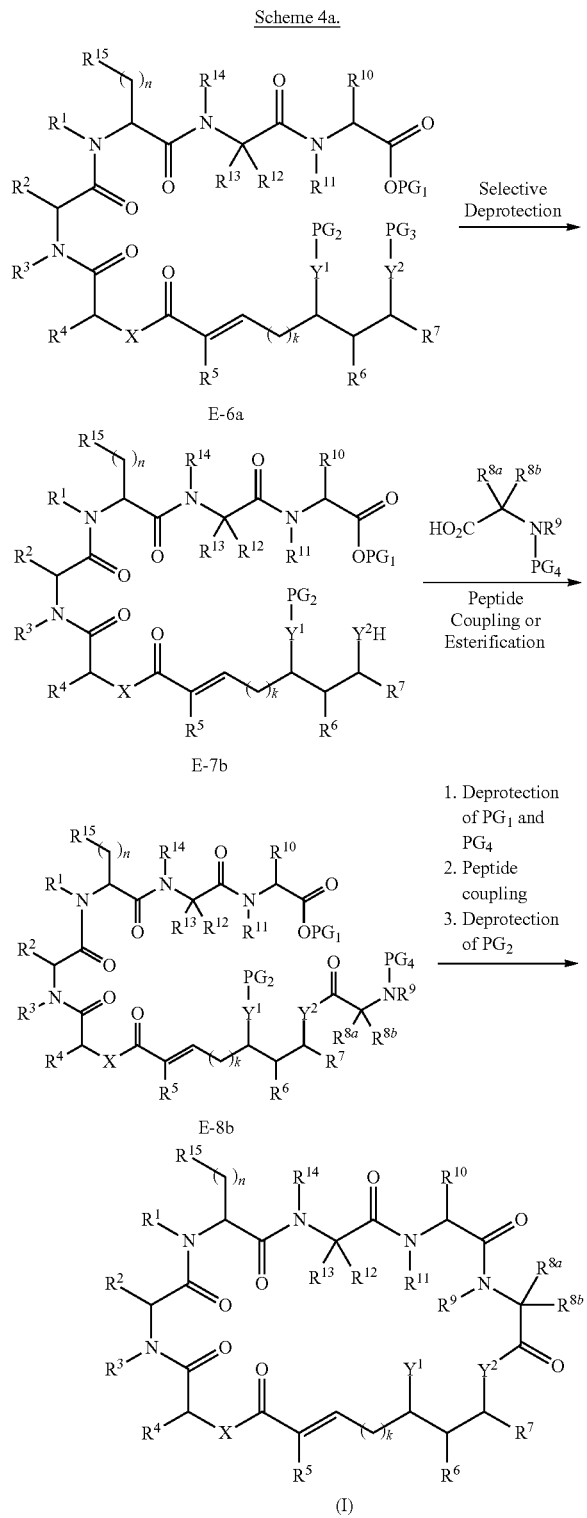

In an alternative synthetic route, compound E-6a is selectively deprotected to remove PG$_3$, resulting in compound E-7b. This compound is subject to peptide coupling or esterification to afford compound E-8b. Removal of protecting groups PG$_1$ and PG$_4$, cyclization via a peptide coupling reaction, and removal of protecting group PG$_2$ afford compounds of Formula (I).

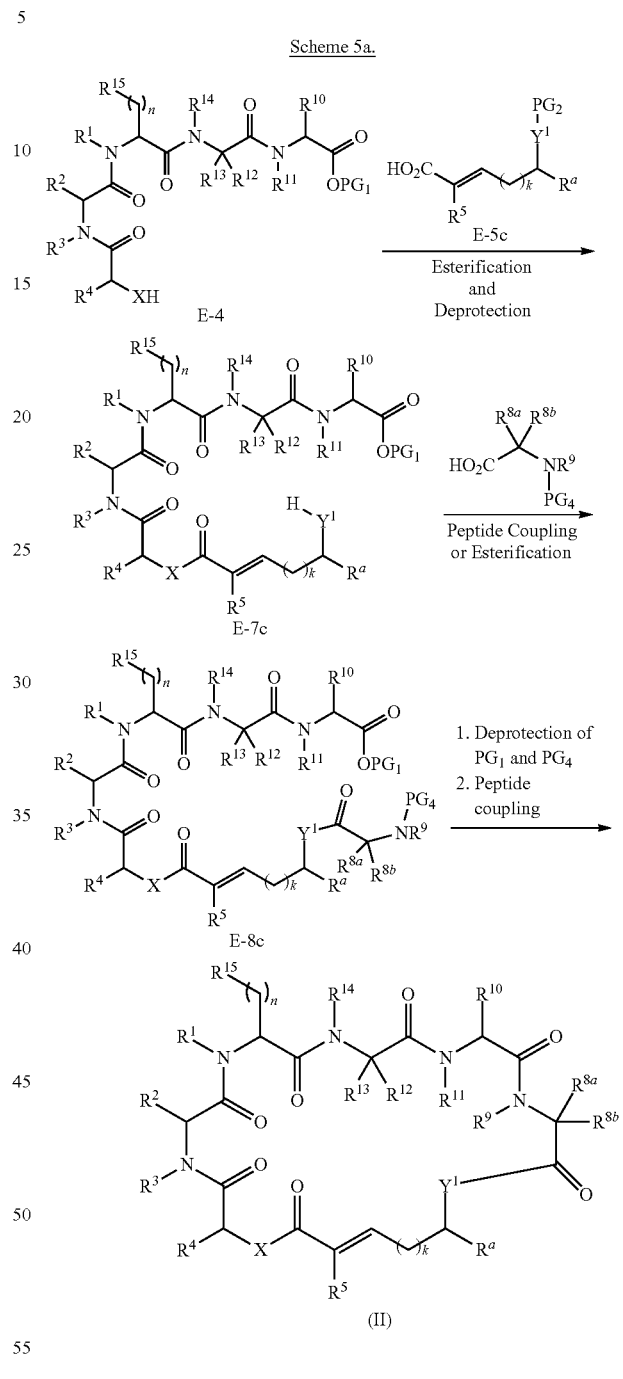

In yet another alternative synthetic route, compound E-4 is subjected to an esterification reaction with compound E-5c, following by deprotection to remove PG$_2$, resulting in compound E-7c. Peptide coupling or esterification of compound E-7c affords compound E-8c. Deprotection of E-8c to remove PG$_1$ and PG$_4$ followed by cyclization via peptide coupling affords compounds of Formula (II).

Exemplified syntheses according to Schemes 1a through 5a are described in Schemes 1b through 5b.

Scheme 1b.

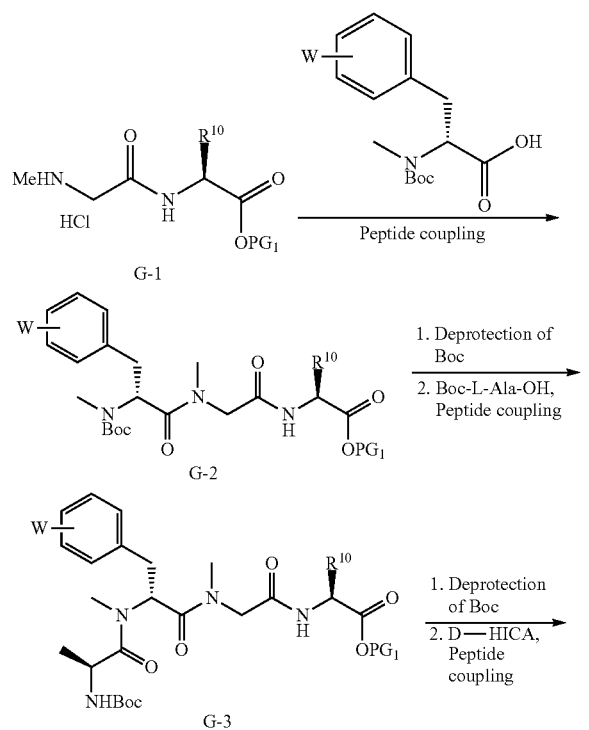

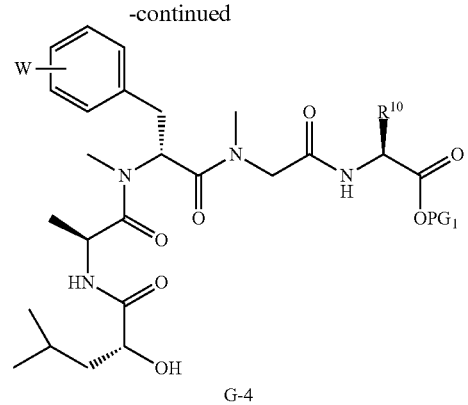

In an exemplified synthesis, the hydrochloride salt of protected di-peptide G-1 is subjected to a peptide coupling reaction to a Boc-protected phenylalanine or substituted phenylalanine to afford tri-peptide G-2. The Boc group is removed, followed by a peptide coupling reaction to Boc-protected alanine to afford compound G-3. The Boc-group is removed, and the compound is further reacted with D-2-hydroxyisocaproic acid (D-HICA) via a peptide coupling reaction to afford compound G-4.

Scheme 2b.

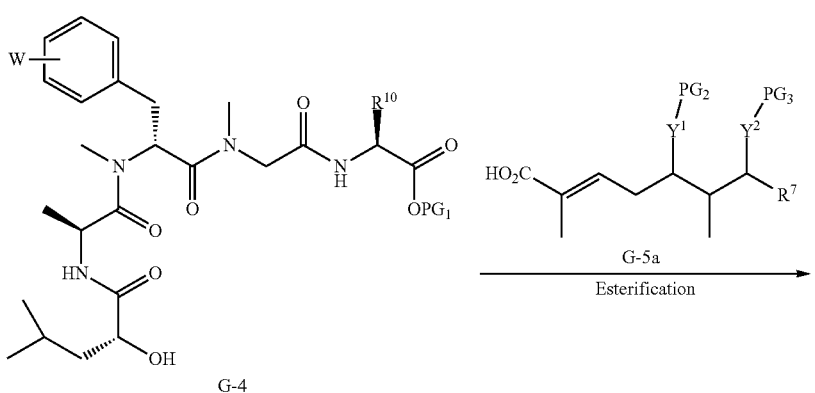

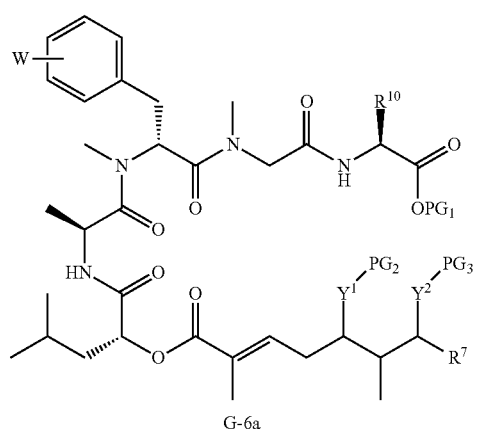

Compound G-4 is reacted with compound G-5a under suitable esterification conditions to afford compound G-6a.

Scheme 3b.

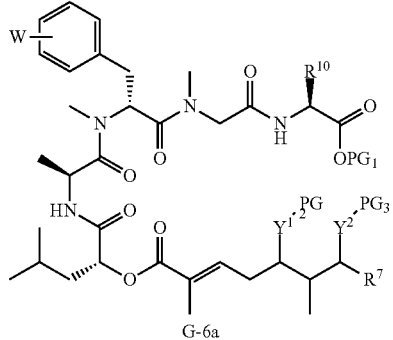
G-6a

Scheme 4b.

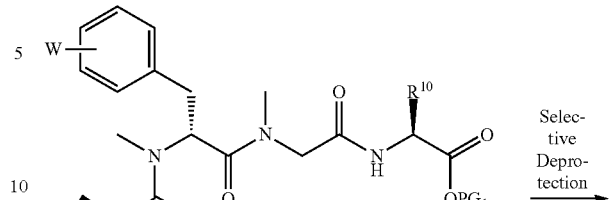
G-6a

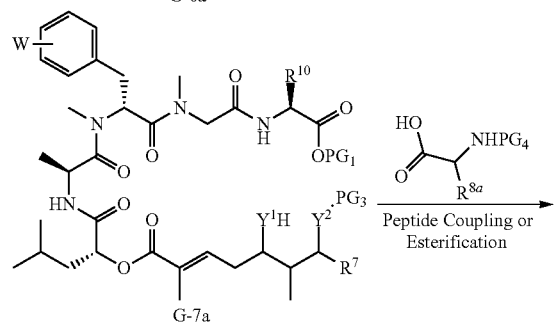
G-7a

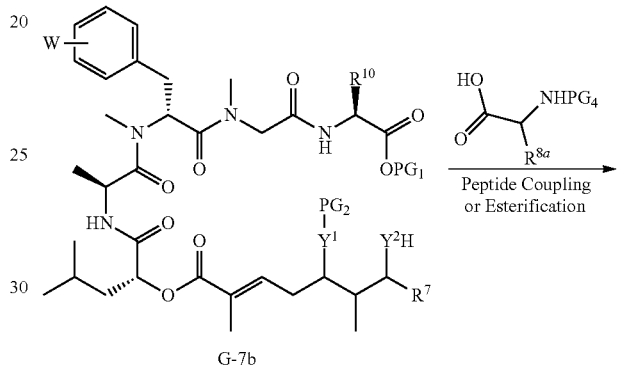
G-7b

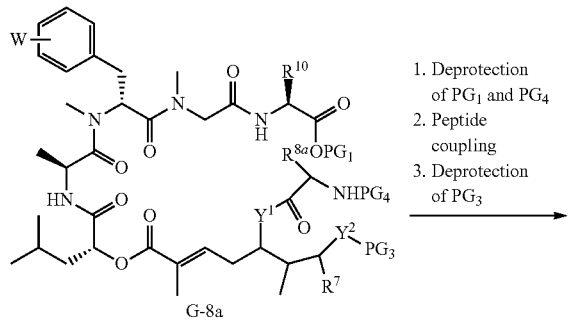
G-8a

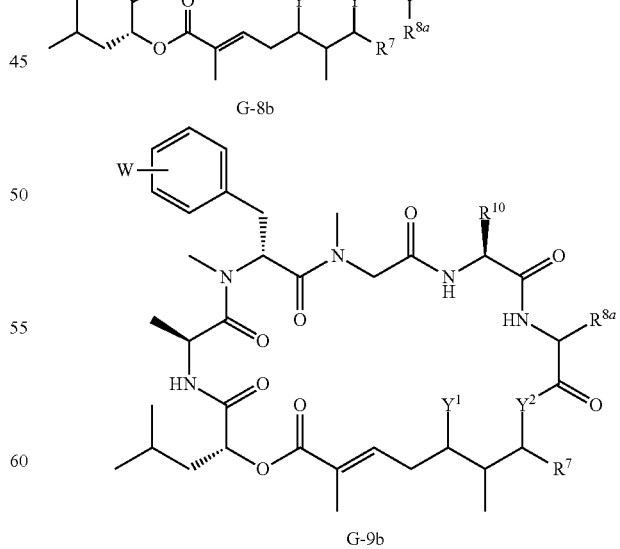

In one variation, compound G-6a is selectively deprotected to remove $PG_2$, resulting in compound G-7a. G-7a is subject to a peptide coupling or esterification reaction to afford compound G-8a. Removal of protecting groups $PG_1$ and $PG_4$, cyclization via a peptide coupling reaction, and removal of protecting group $PG_3$ affords compound G-9a.

In another variation, compound G-6a is selectively deprotected to remove $PG_3$, resulting in compound G-7b. G-7b is subject to peptide coupling or esterification to afford compound G-8b. Removal of protecting groups PG₁ and PG₄, cyclization via a peptide coupling reaction, and removal of protecting group PG₂ affords compound G-9a.

In yet another variation, compound G-4 is subjected to an esterification reaction with compound G-5c, following by deprotection to remove PG₂, resulting in compound G-7c. Peptide coupling or esterification of compound G-7c affords compound G-8c. Deprotection of G-8c followed by cyclization via peptide coupling affords compound G-9c.

Certain intermediates useful in the preparation of the compounds and conjugates described herein may be synthesized according to any of the following schemes or variations thereof.

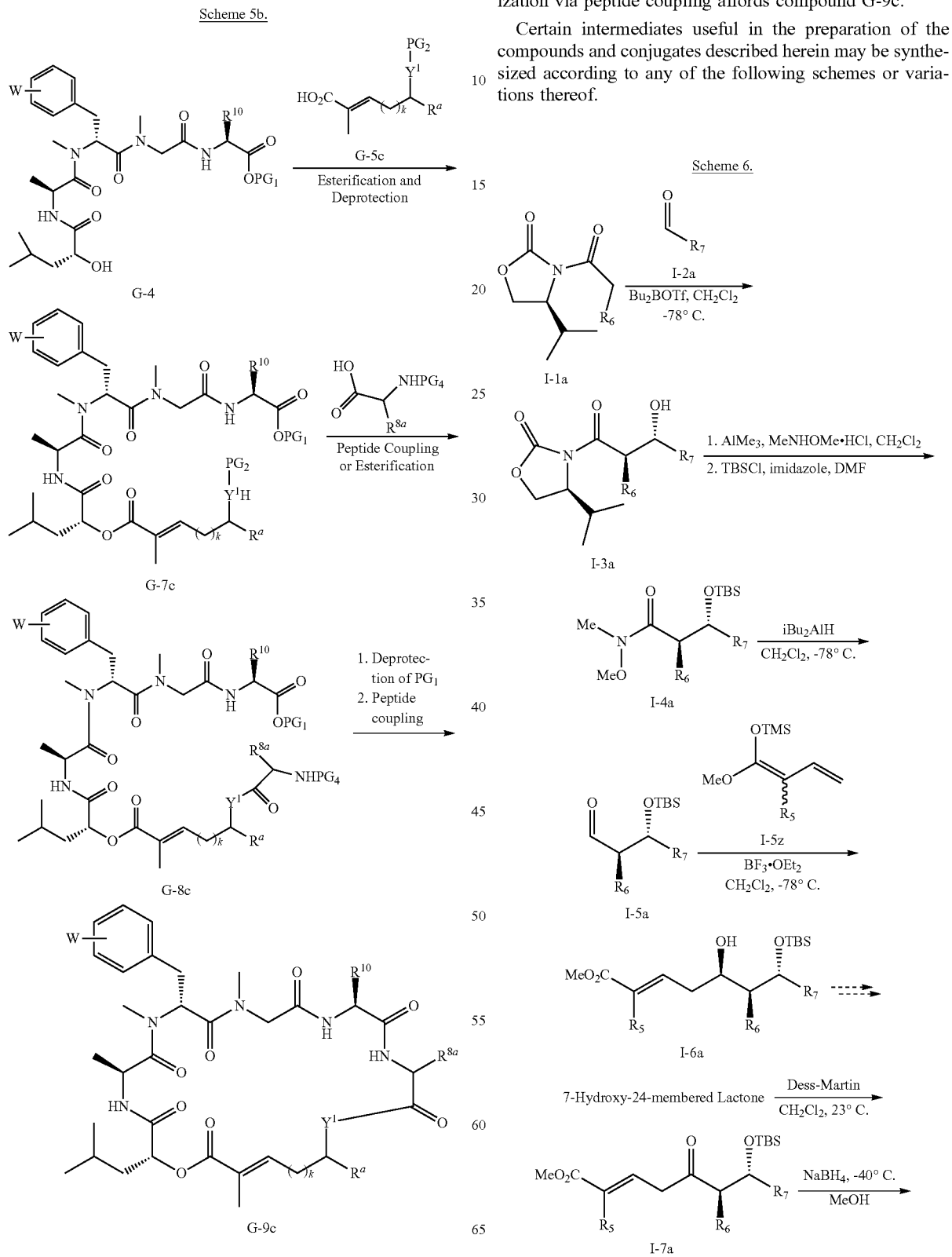

-continued

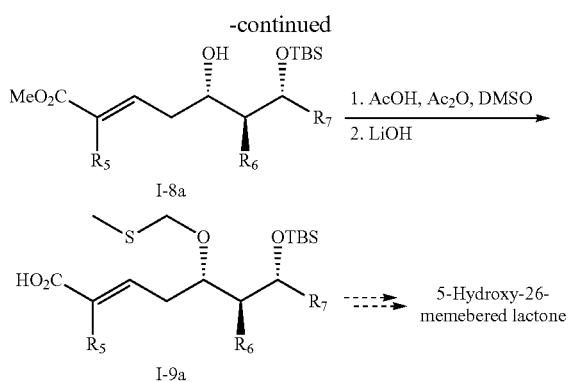

Compound I-1a is reacted with aldehyde I-2a in the presence of Bu$_2$BOTf in methylene chloride at −78° C. to form compound I-3a. Reaction with trimethylaluminum and MeNHOMe HCl in methylene chloride followed by treatment with TBSCl and imidazole in DMF affords compound I-4a. Compound I-4a is treated with diisobutylaluminum hydride in methylene chloride at −78° C. to afford aldehyde I-5a. Compound I-5a is reacted with compound I-5z in the presence of boron trifluoride diethyl etherate in methylene chloride at −78° C. to afford compound I-6a. Compound I-6a can be further reacted as described herein to afford a 7-hydroxy-24-membered lactone compound provided herein.

Alternatively, compound I-6a can be subjected to a Dess-Martin reaction in methylene chloride at 23° C. to afford ketone I-7a. Further reaction with sodium borohydride in methanol at −40° C. affords compound I-8a. Compound I-8a is treated with acetic acid, acetic anhydride, and DMSO, followed by treatment with lithium hydroxide to afford compound I-9a. Compound I-9a can be further reacted as described herein to afford a 5-hydroxy-26-membered lactone compound provided herein.

Scheme 7.

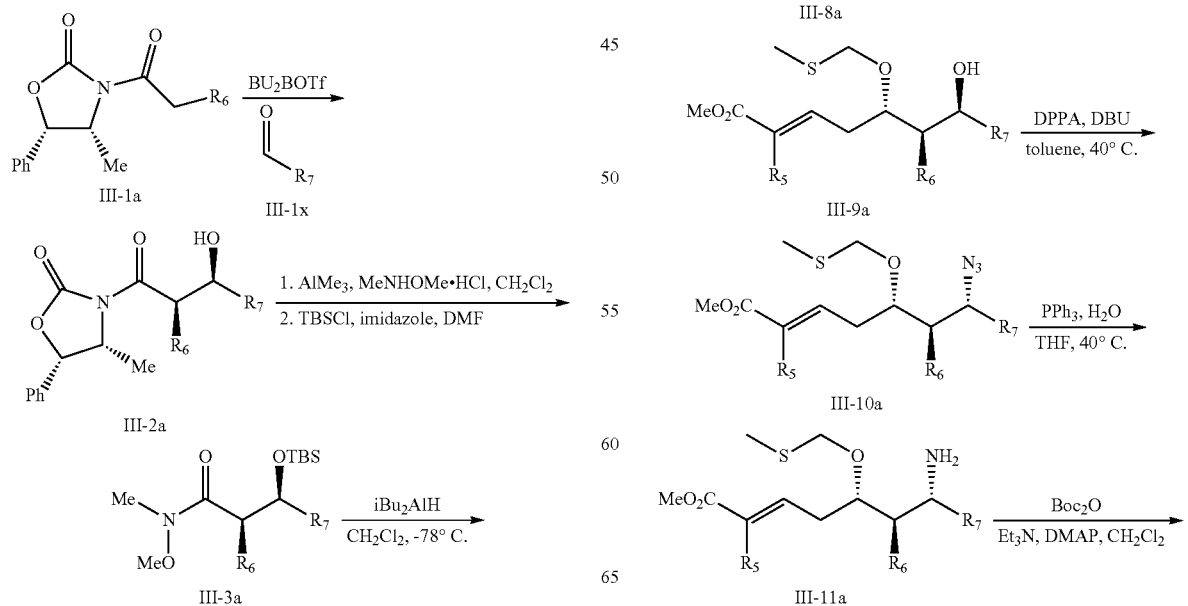

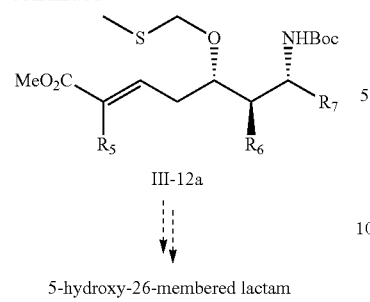

III-12a

↓↓

5-hydroxy-26-membered lactam

Compound III-1a is reacted with aldehyde III-1x in the presence of Bu₂BOTf to form compound III-2a. Reaction with trimethylaluminum and MeNHOMe.HCl in methylene chloride followed by treatment with TBSCl and imidazole in DMF affords compound III-3a. Compound III-3a is treated with diisobutylaluminum hydride in methylene chloride at −78° C. to afford aldehyde III-4a. Compound III-4a is reacted with compound III-1z in the presence of boron trifluoride diethyl etherate in methylene chloride at −78° C. to afford compound III-5a. Compound III-5a can be subjected to a Dess-Martin reaction in methylene chloride at 23° C. to afford ketone III-6a. Further reaction with (R)—CBS and sodium borohydride in THF at −40° C. affords compound III-7a. Compound III-7a is treated with acetic acid, acetic anhydride, and DMSO to afford compound III-8a. Treatment with HF pyridine in pyridine and THF at 40° C. affords compound III-9a. Compound III-9a is reacted with DPPA and DBU in toluene at 40° C. to afford compound 111-10a. Further reaction with triphenylphosphine in water and THF at 40° C. results in compound III-11a. Treatment with Boc anhydride, trimethylamine, and DMAP in methylene chloride affords compound III-12a. Compound III-12a can be further reacted as described herein to afford a 5-hydroxy-26-membered lactam compound provided herein.

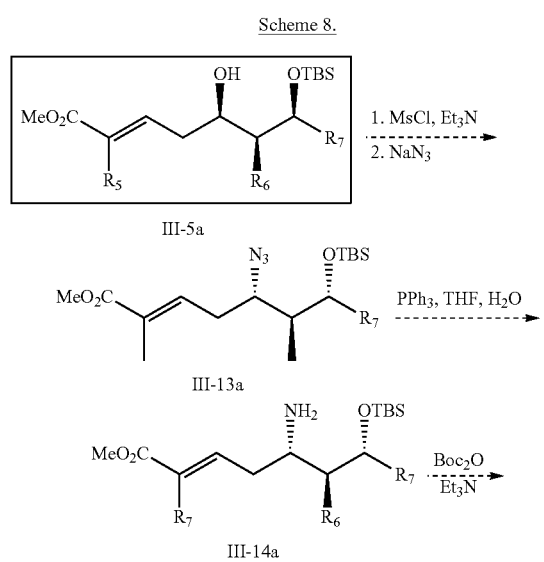

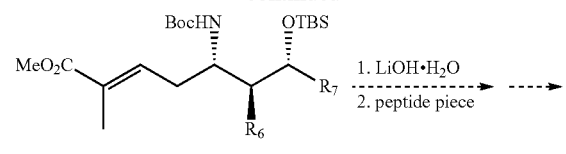

III-15a

7-Hydroxy-24-membered lactam

Alternatively, compound III-5a can be treated with MsCl and trimethylamine followed by reaction with sodium azide to afford compound III-13a. Further treatment with triphenylphosphine in THF and water results in compound III-14a. Compound III-14a is treated with Boc anhydride and trimethylamine to afford compound III-15a. Compound III-15a is reacted with LiOH H₂O followed by reaction with an appropriate peptide as described herein to afford a 7-hydroxy-24-membered lactam provided herein.

An exemplary method for synthesizing 5-amino-26-membered lactam compounds is provided in Scheme 9. Other compound described herein can be prepared using a similar method.

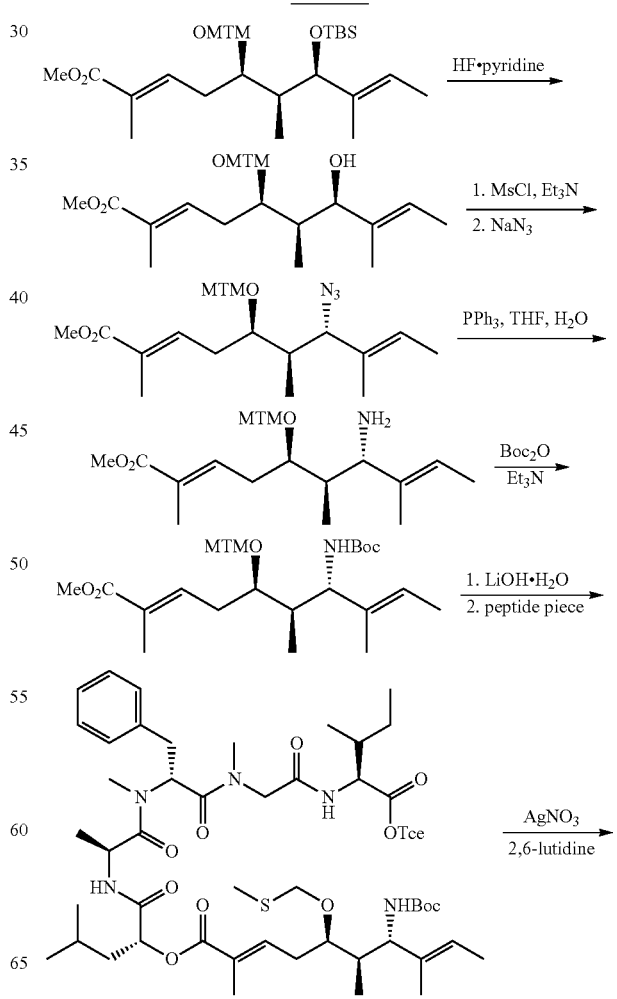

315
-continued
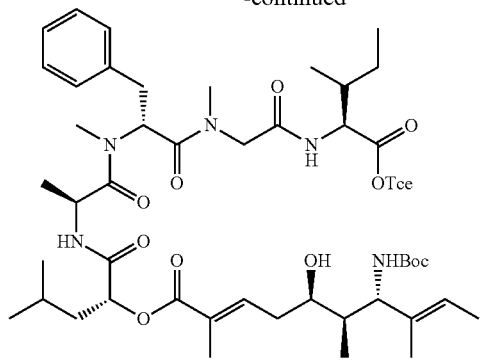
316
-continued
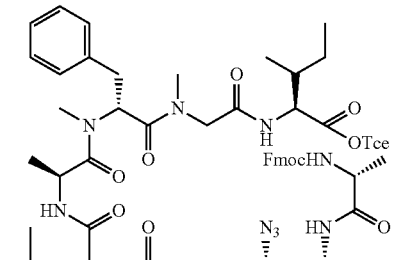
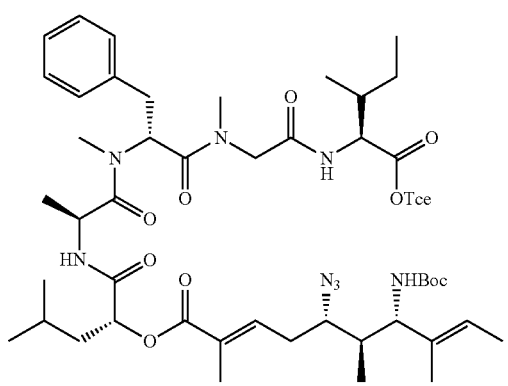
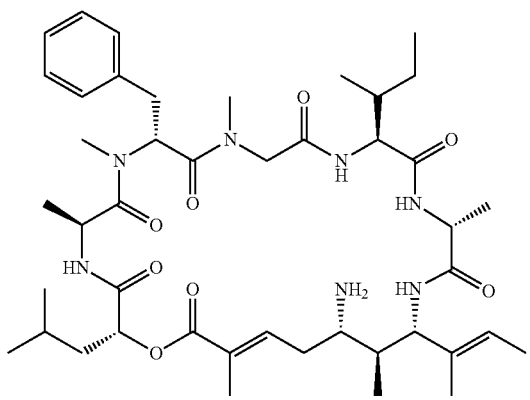
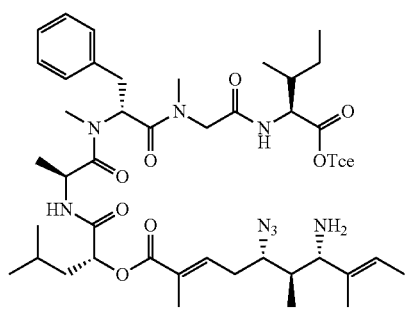
An exemplary method for synthesizing 7-amino-24-membered lactam compounds is provided in Scheme 10. Other compound described herein can be prepared using a similar method.
Scheme 10.
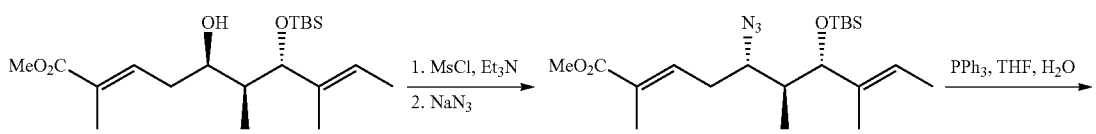
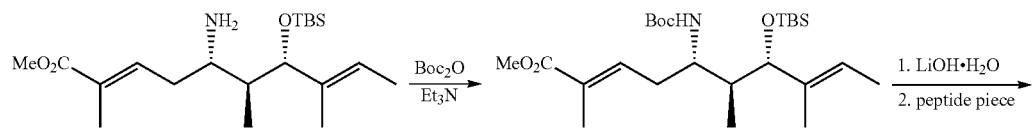

317
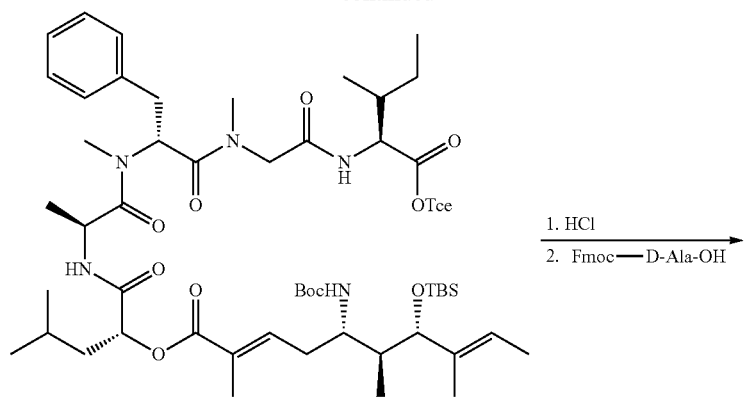
1. HCl
2. Fmoc—D-Ala-OH
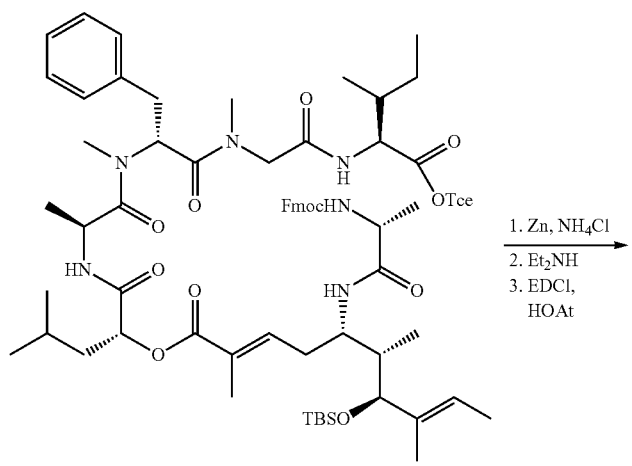
1. Zn, NH₄Cl
2. Et₂NH
3. EDCl, HOAt
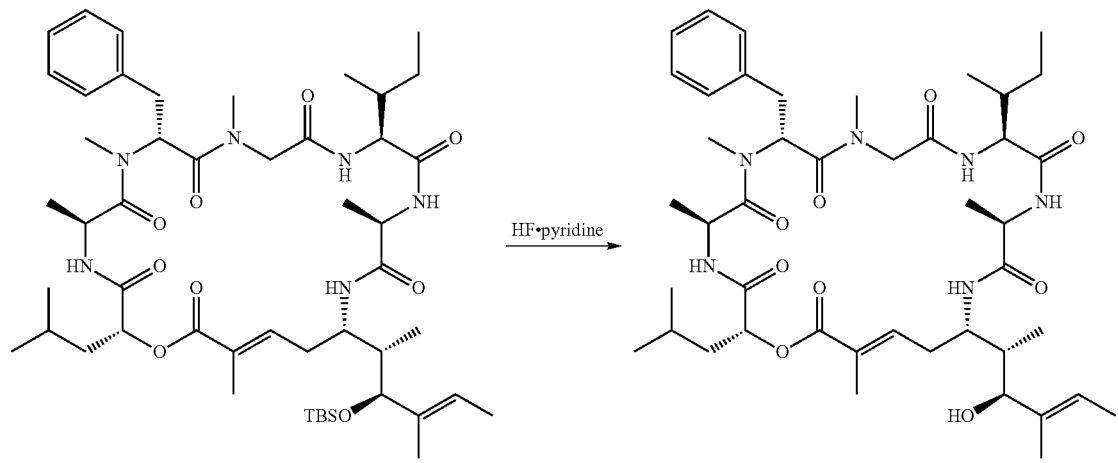
HF·pyridine
318

Compounds containing linkers as described herein can be obtain from appropriate precursor compounds and may be prepared using methods known in the art. In some variations, linker-containing compounds of Formula (L) may be prepared in accordance with Schemes 11-14.

Scheme 11.

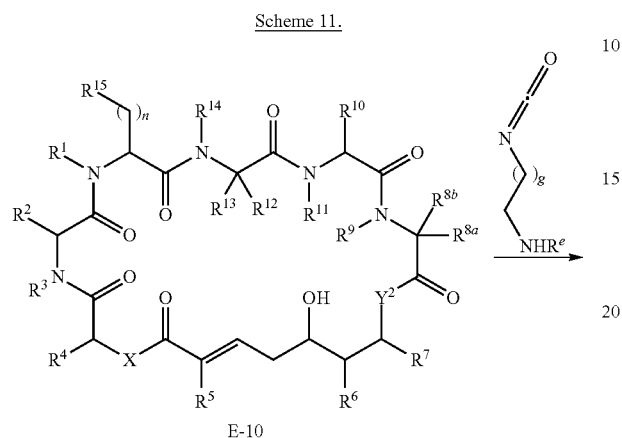

E-10

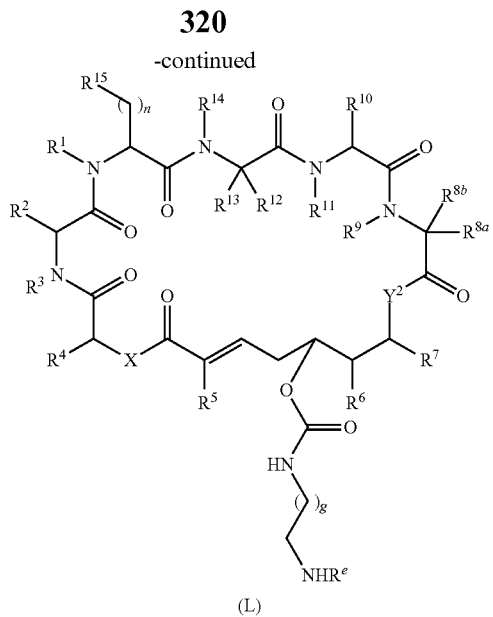

(L)

Compound E-10 is reacted with an isocyanato amine under suitable conditions to afford a compound of Formula (L).

Scheme 12.

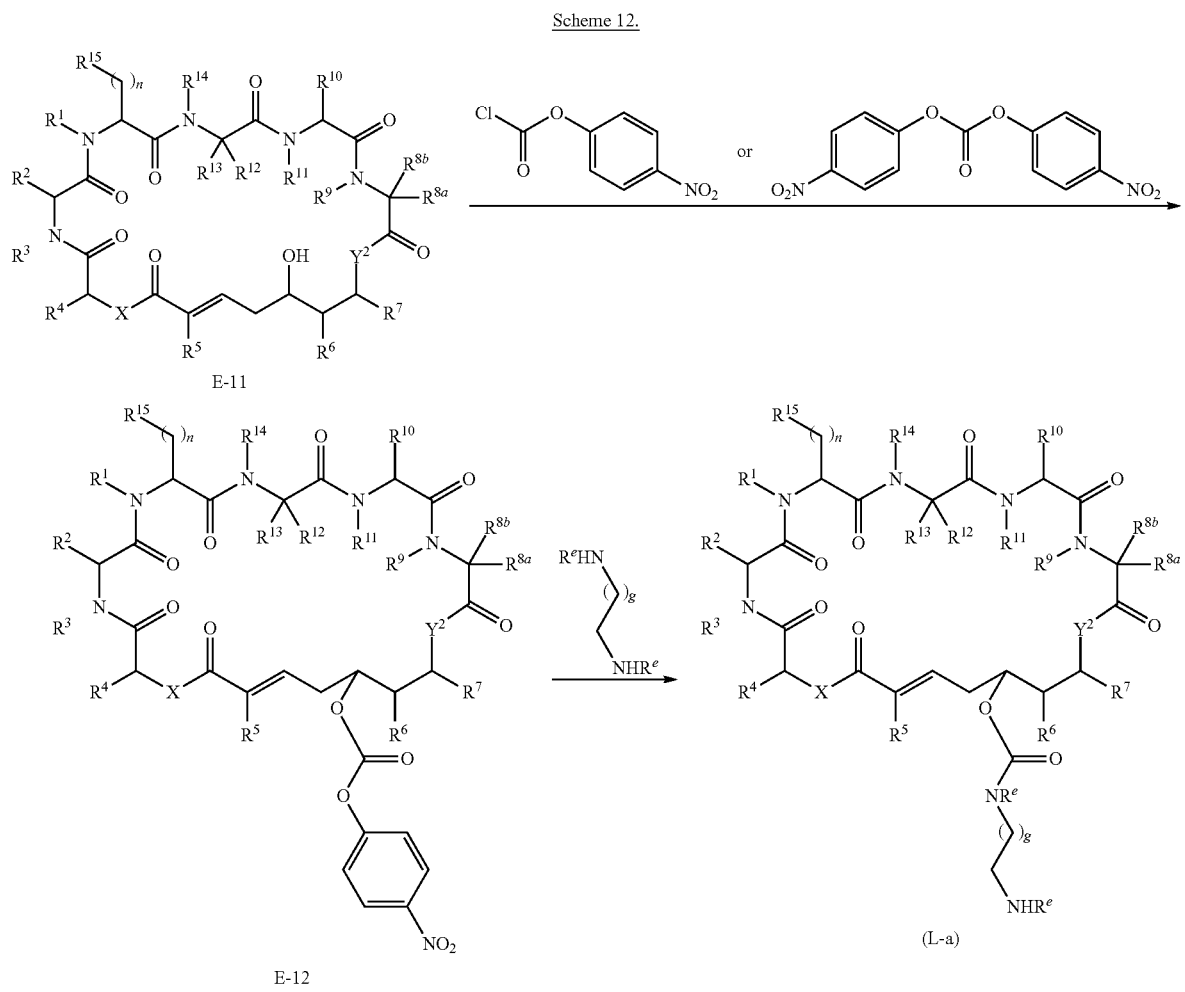

E-11

E-12

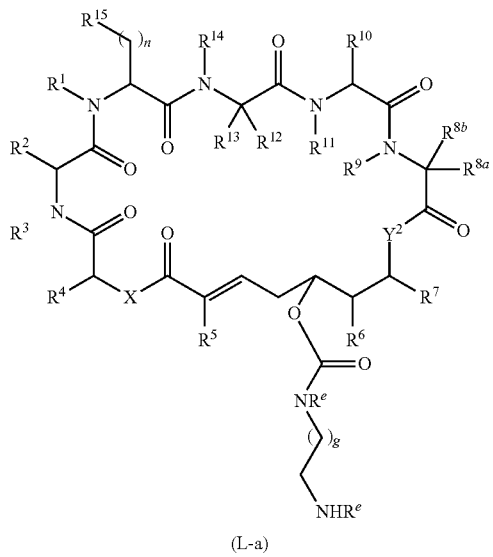

(L-a)

Compound E-11 is reacted with acyl chloride or anyhydride under suitable conditions to form Compound E-12. Compound E-12 is reacted with a diamine under suitable conditions to afford a compound of Formula (L-a). Compounds of Formula (L-b) and variations thereof can be prepared in a similar manner Scheme 13.

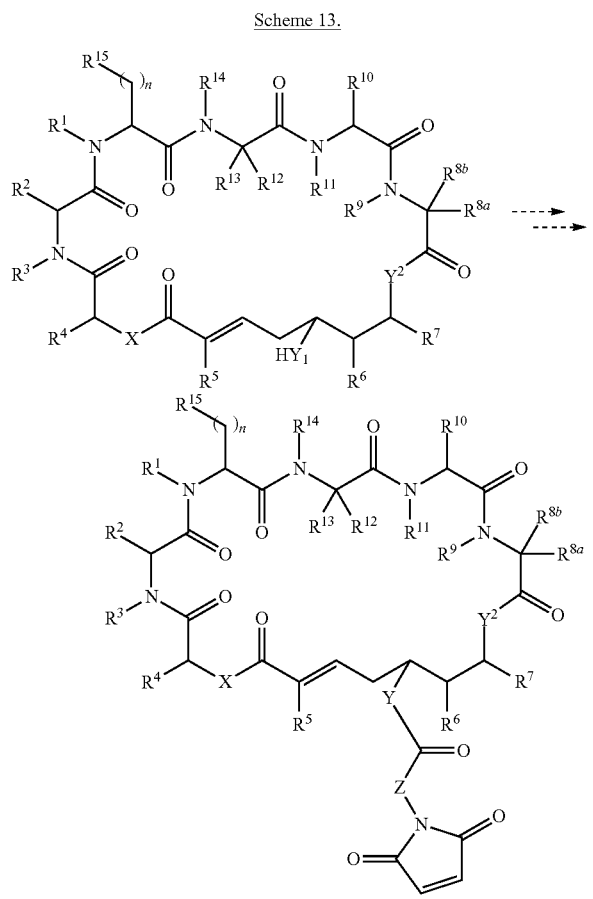

A compound of Formula (I), wherein Rc is H, is reacted using suitable methods to produce a conjugate containing the compound of Formula (I) bonded to a maleimide-containing linker, wherein Z represents any suitable portion of a linker moiety.

More generally, any of the compounds described herein can be coupled to a maleimide-containing linker at an available $Y^1$ or $Y^2$ position according the following general scheme:

Scheme 14.

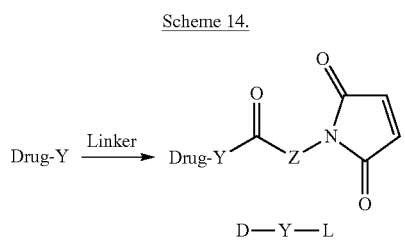

As shown in Scheme 14, Drug-Y may be reacted with a linker to produce the drug-linker conjugate D-Y-L using suitable methods known in the art. In Scheme 14, Drug-Y may be any compound described herein, where Y is any position on the compound suitable for reaction with a linker, and Z is a suitable portion of any linker moiety. In some embodiments, Y is the $Y^1$—$R^c$ or $Y^2$—$R^c$ group of the compound.

Compounds or drug-linker conjugates provided herein can be conjugated to an antibody using methods known in the art, such as those described in Greg T. Hermanson, *Bioconjugate Techniques*, Academic Press 19, page 60. An exemplary method is provided in Scheme 15.

Scheme 15.

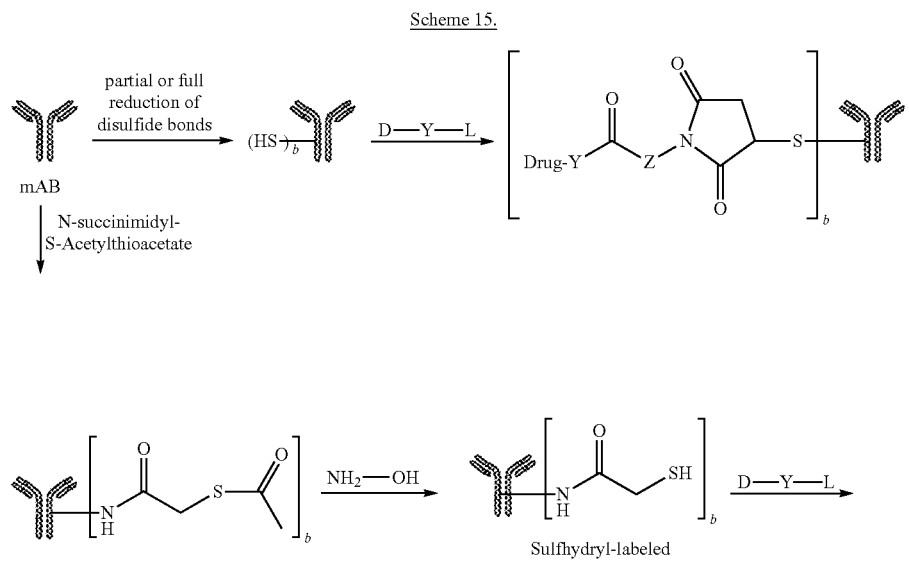

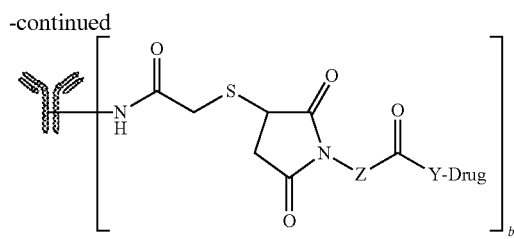

A monoclonal antibody is treated to partially or fully reduce any disulfide bonds. The reduced mAb is treated with D-Y-L under suitable conditions to afford a conjugate as shown in Scheme 15.

Alternatively, a monoclonal antibody is treated with SATA (N-succinimidyl-S-acetylthioacetate), reduced, and reacted with D-Y-L under suitable conditions to afford a conjugate as shown in Scheme 15.

EXAMPLES

The following examples are offered to illustrate but not to limit the compositions, uses, and methods provided herein. The compounds are prepared using the general methods described above.

The following chemical abbreviations are used throughout the Examples: (R)—CBS ((R)-1-Methyl,3,3-diphenyl-tetrahydro-pyrrolo(1,2-c)(1,3,2)oxazaborole), Ac (acetyl), Boc (tert-butlyoxycarbonyl), Bu (butyl), DBU (1,8-Diazabicyclo[5.4.0]undec-7-ene), DCM (dichloromethane), DEPBT (3-(Diethoxyphosphoryloxy)-1,2,3-benzotriazin-4 (3H)-one), D-HICA (D-2-hydroxyisocaproic acid), DMAP (4-dimethylaminopyridine), DMF (dimethylformamide), DMSO (dimethylsulfoxide), DPPA (diphenyl phosphorazidate), EDC (1,2-dichloroethane), EDCI (1-Ethyl-3-(3-dimethylaminopropyl)carbodiimide), ESI (electrospray ionization), Et (ethyl), EtOAc (ethyl acetate), Fmoc (9-fluorenylmethyloxycarbonyl), $^1$H NMR (Proton Nuclear Magnetic Resonance), HATU (1-[Bis(dimethylamino)methylene]-1H-1,2,3-triazolo[4,5-b]pyridinium 3-oxid hexafluorophosphate), HBTU (N,N,N',N'-Tetramethyl-O-(1H-benzotriazol-1-yl)uronium hexafluorophosphate), HOAt (1-hydroxy-7-azabenzotriazole), HPLC (High Performance Liquid Chromatography), HRMS (High Resolution Mass Spectrometry), LCMS (Liquid Chromatography-Mass Spectrometry), Me (methyl), Ms (methansulfinyl), MS (Mass Spectrometry), MTM (methylthiomethyl), MW (molecular weight), PBS (phosphate-buffered saline), Ph (phenyl), Pr (propyl), RP (Reversed Phase), TCEP (tris(2-carboxyethyl) phosphine), TBS (tert-butyldimethylsilyl), Tce/tce/TCE (trichloroethylene), Tf (trifluoromethanesulfinyl), TFA (Trifluoroacetic acid), THF (tetrahydrofuran), TLC (Thin Layer Chromatography), TMS (trimethylsilyl).

Example 1

Synthesis of Intermediate I-9

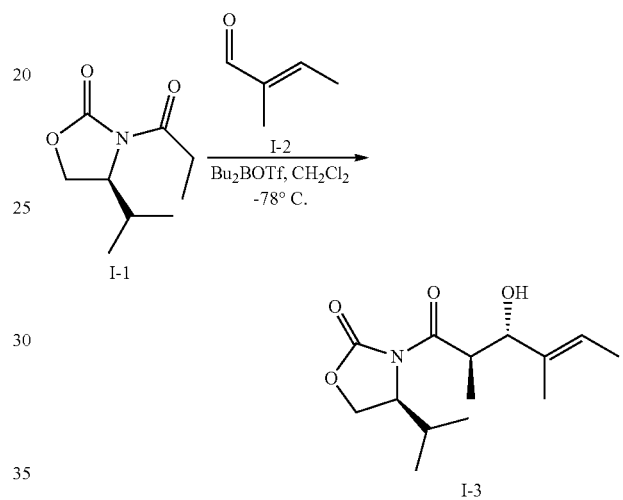

To a stirred solution of N-propionyl oxazolidinone, I-1 (1.0 mL, 5.0 mmol) in dry $CH_2Cl_2$ (15 mL) under argon was treated with 1 M dibutylboron triflate in $CH_2Cl_2$ (5.5 mL, 5.5 mmol) and diisopropylethylamine (1.1 mL, 6.0 mmol) at 0° C. After 30 min, the reaction mixture was cooled to −78° C. and trans-2-methyl-2-butenal (530 µL, 5.5 mmol) was added dropwise. The resulting mixture was stirred at −78° C. for 30 min and then 90 min at room temperature. The reaction was quenched by addition of pH 7 aqueous phosphate buffer (10 mL) and oxidized with 30% hydrogen peroxide/methanol (1:1, 20 mL). The resulting solution was stirred at 0° C. for 1 h. The solvent was evaporated under reduced pressure. The residue was dissolved in water (30 mL) and extracted with EtOAc (25 mL×3). The combined organic layer was washed with 5% $NaHCO_3$ (25 mL) and brine (25 mL), dried over $MgSO_4$, and concentrated under reduced pressure, yielding a viscous yellow oil. The crude oil was purified by flash chromatography (EtOAc/n-hexane, 25:75), and the aldol, I-3 was obtained as a colorless oil.

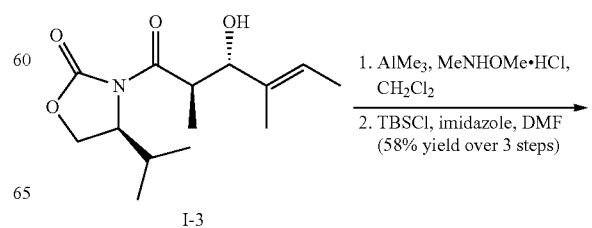

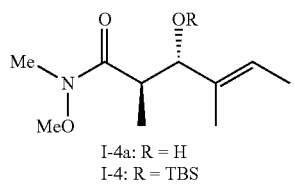

I-4a: R = H
I-4: R = TBS

To a stirred suspension of N,O-dimethylhydroxylamine hydrochloride (317.5 mg, 3.25 mmol) in CH$_2$Cl$_2$ (6 mL) at 0° C. under argon was slowly added 15% trimethylaluminum in toluene (1.6 mL, 3.2 mmol) with concomitant evolution of gas. The resulting homogeneous solution was stirred for 40 min at room temperature and then recooled to 0° C., and a solution of aldol I-3 (516 mg, 1.6 mmol) in CH$_2$Cl$_2$ (5 mL) was added over a period of 5 min. The solution was stirred for 1.5 h at 0° C., and then ice-cooled 0.5 M aqueous HCl (30 mL) and CH$_2$Cl$_2$ (10 mL) were added. The layers were separated, and the aqueous layer was extracted with CH$_2$Cl$_2$ (10 mL×3). The combined organic layers were dried over anhydrous Na$_2$SO$_4$ and concentrated under reduced pressure. The residue was purified by flash chromatography EtOAc/n-hexane, 50:50), and amide I-4a was obtained as a colorless solid.

A mixture of I-4a (265 mg, 1.3 mmol), TBSCl (600 mg, 4.0 mmol), and imidazole (540 mg, 7.9 mmol) in DMF (6 mL) was stirred overnight at room temperature. The reaction mixture was quenched with water and extracted with EtOAc (15 mL×3). The combined organic layers were dried over anhydrous MgSO$_4$ and concentrated under reduced pressure, yielding a colorless oil. The resulting oil was purified by column chromatography (EtOAc/n-hexane, 50:50), and protected amide I-4 was obtained as a colorless oil.

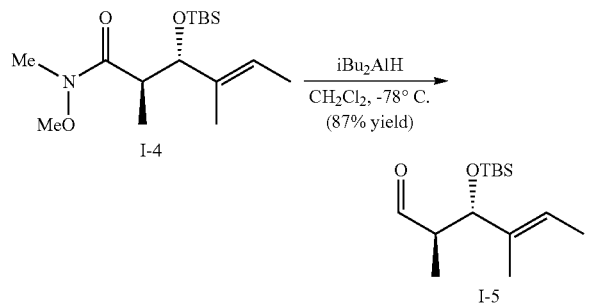

To a stirred solution of silyl ether I-4 (633 mg, 1.92 mmol) in THF (6.5 mL) cooled at −78° C. was added a 0.98M solution of diisobutylaluminum hydride in hexane (3.9 mL, 3.8 mmol) dropwise. The solution was stirred at −78° C. for 1.5 h, and the reaction was quenched by addition of acetone (0.4 mL). The solution was stirred at −78° C. for 10 min and then transferred into a vigorously stirred mixture of CH$_2$Cl$_2$ (30 mL) and 0.5 M tartaric acid (30 mL) at room temperature. The resulting two-phase mixture was stirred at room temperature for 30 min. The layers were separated, and the aqueous layer was extracted with CH$_2$Cl$_2$ (3×30 mL). The organic layer and the extracts were combined, washed with brine (10 mL), dried (Na$_2$SO$_4$), and concentrated. The residual oil was purified by column chromatography on silica gel (hexanes/EtOAc 10:1/7:1) to yield aldehyde I-5.

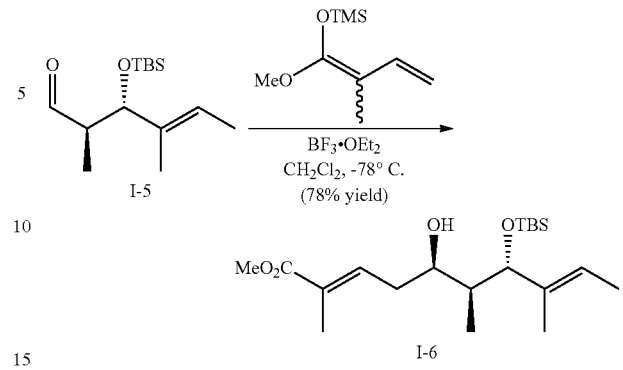

To a stirred solution of aldehyde I-5 (83.9 mg, 0.31 mmol) in CH$_2$CL$_2$ (2.4 mL) and ether (0.24 mL) cooled at −78° C. were added 2-methyl-1-trimethylsiloxy-1-methoxy-1,3-butadiene (0.2 mL, 1.01 mmol) and boron trifluoride diethyl etherate (0.06 mL, 0.49 mmol), successively. The reaction mixture was stirred at −78° C. for 2 h and diluted with THF-H$_2$O-0.3 M HCl (5:1:0.4, 4 mL). The mixture was stirred at room temperature for 15 min and then transferred into saturated aqueous NaHCO$_3$ (5 mL) at 0° C. The layers were separated, and the aqueous layer was extracted with hexane (3×7 mL). The organic layer and the extracts were combined, washed with brine (2 mL), dried (Na$_2$SO$_4$). Flash chromatography (4:1 hexanes/EtOAc) gave I-6 (92 mg, 83% yield).

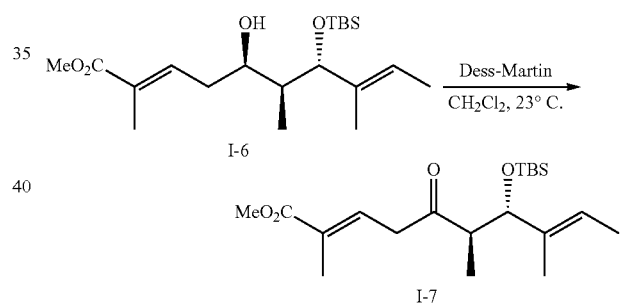

To a stirred solution of methyl ester I-6 (1.32 g, 3.44 mmol) in CH$_2$Cl$_2$ (25 mL) was added Dess-Martin periodinane (2.29 g, 5.41 mmol). The mixture was stirred at room temperature for 1 h and diluted with ether (30 mL), saturated aqueous Na$_2$S$_2$O$_3$ (40 mL), and 0.5 M phosphate buffer (pH 7, 40 mL). The resulting mixture was stirred at room temperature for 30 min and extracted with ether (3×50 mL). The combined extracts were washed with H$_2$O (2×50 mL) and brine (25 mL), dried (Na$_2$SO$_4$) and concentrated. The residual oil was purified by column chromatography on silica gel (35 g, hexane-ether 15:1/8:1) to give I-7 (1.23 g, 94%) as a colorless oil.

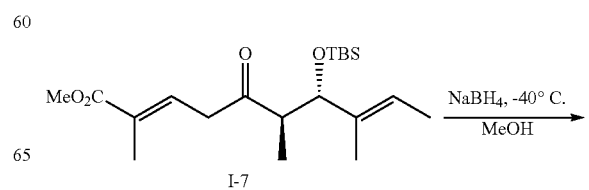

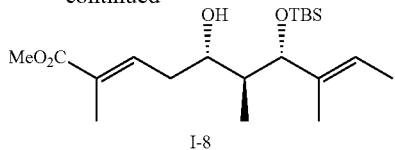

To a stirred solution of ketone I-7 (234 mg, 0.613 mmol) in methanol (6 mL) cooled at −23° C. was added sodium borohydride (119 mg, 3.15 mmol). The mixture was stirred at −23° C. for 50 min, diluted with saturated aqueous ammonium chloride (20 mL), and extracted with hexane (4×20 mL). The combined extracts were washed with brine (15 mL), dried ($Na_2SO_4$), and concentrated. The residual oil was purified by column chromatography on silica gel using hexanes:EtOAc (10:1 to 4:1) gradient to yield alcohol I-8.

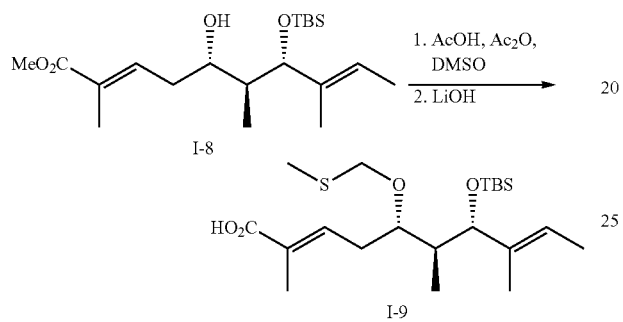

To a stirred solution of alcohol I-8 (1.47 g, 3.83 mmol) in DMSO (28 mL) was added a 1:5.6 mixture of acetic acid and acetic anhydride (23 mL) at room temperature. The mixture was stirred at 40° C. for 3 h and diluted with hexane (54 mL) and 0.5 M phosphate buffer (pH 7, 90 mL). The layers were separated, and the aqueous layer was extracted with hexane (3×30 mL). The organic layer and the extracts were combined, washed with $H_2O$ (20 mL) and brine (20 mL), dried ($Na_2SO_4$), and concentrated. The residual oil was purified by column chromatography on silica gel (9:1 hexanes:EtOAc).

To a stirred solution of (methylthio)methyl ether above (806 mg, 1.82 mmol) in MeOH (20 mL) was added 5 M LiOH (5 mL) at room temperature. The mixture was stirred at 30° C. for 11.5 h, acidified with 10% aqueous citric acid (60 mL), and extracted with ether (3×50 mL). The combined extracts were washed with $H_2O$ (25 mL) and brine (25 mL), dried ($Na_2SO_4$), and concentrated. The residual oil was purified by column chromatography to yield pure compound I-9.

Example 2

Synthesis of Kulo-2

Kulo-2 was synthesized according to the following scheme, as described in *Tetrahedron*, 68, 2012, 659-669.

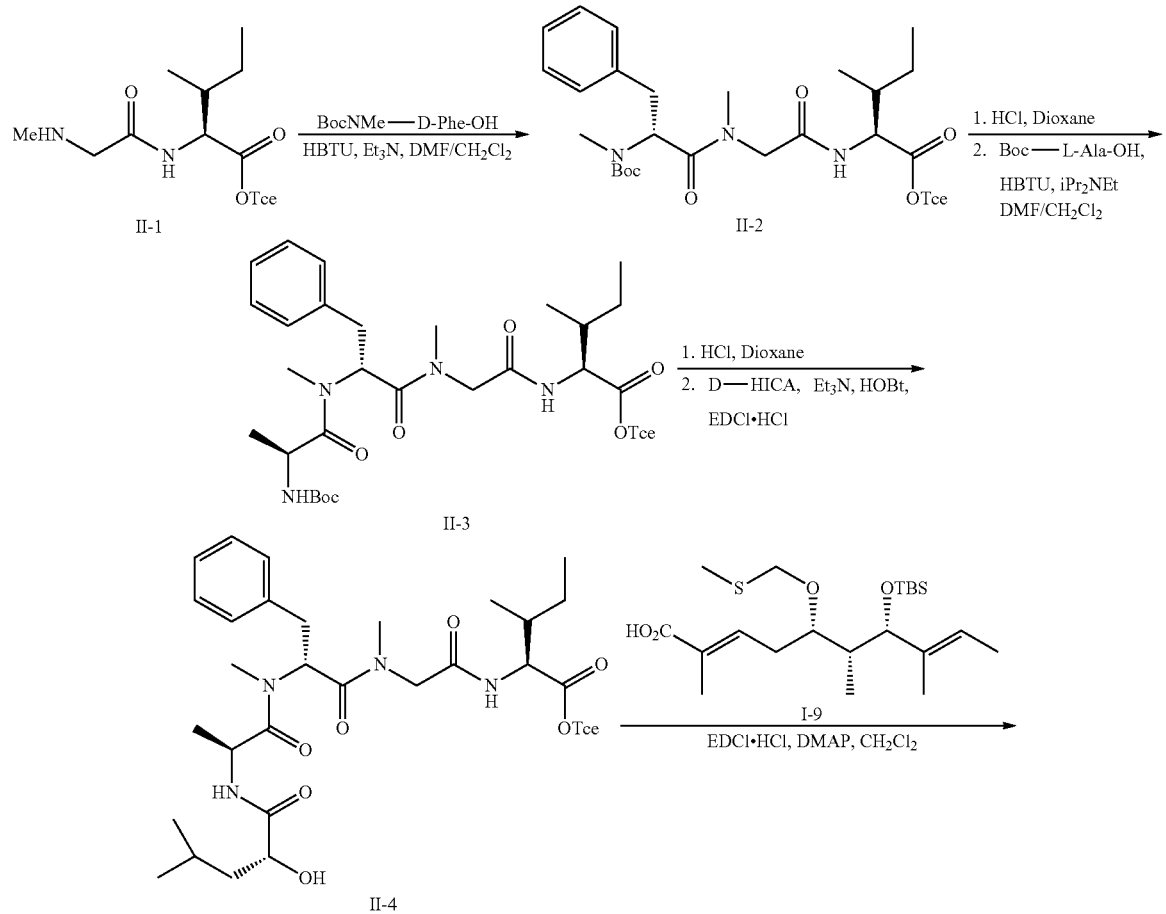

-continued
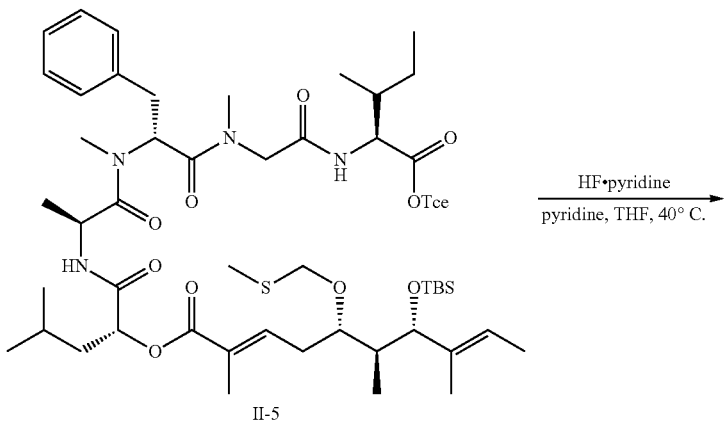
II-5
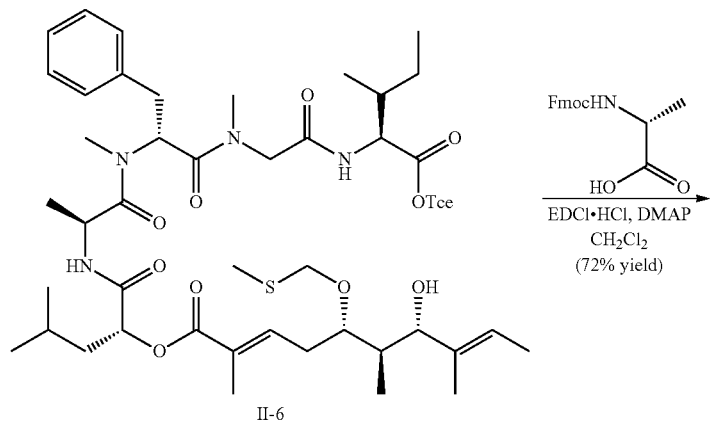
II-6
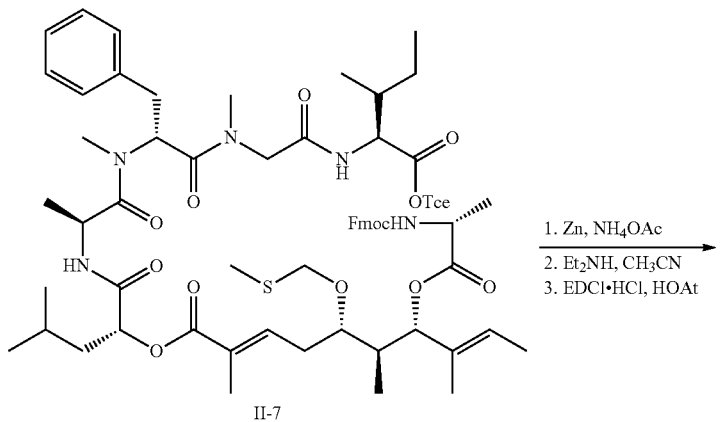
II-7
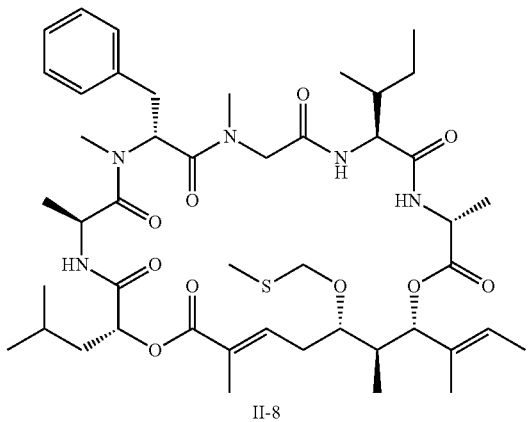
II-8

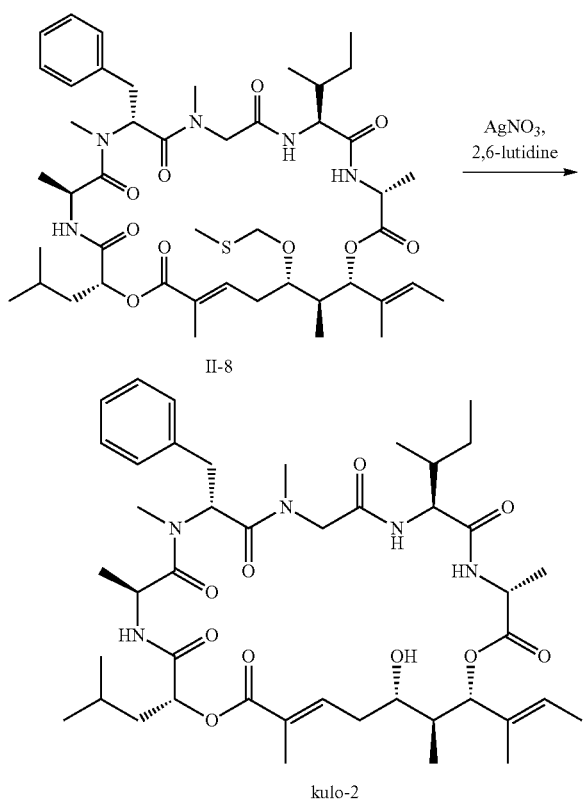

In the final step, 1 mg of compound 11-8 was dissolved in THF/H$_2$O (40 μL/10 μL). AgNO$_3$ was added followed by 2.2 μL and the reaction was heated to 65° C. After 1 h the reaction was cooled to 23° C. and the reaction was filtered over celite and concentrated. The residue was taken up in EtOAc and the organic layer was then washed with 1 M HCl (10 mL), sat. Aq. NaHCO$_3$ (10 mL), and brine (10 mL), dried over Na$_2$SO$_4$. The product was purified by Prep TLC using 100% EtOAc to afford compound kulo-2 as a pure compound. ESI HRMS: m/z 848.4612 [M+Na]$^+$.

Example 3

Synthesis of Intermediate III-12

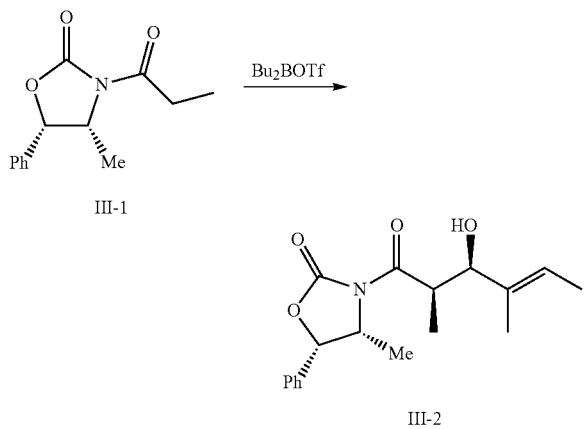

To a stirred solution of N-propionyl oxazolidinone, III-1 (1.0 mL, 5.0 mmol) in dry CH$_2$Cl$_2$ (15 mL) under argon was treated with 1 M dibutylboron triflate in CH$_2$Cl$_2$ (5.5 mL, 5.5 mmol) and diisopropylethylamine (1.1 mL, 6.0 mmol) at 0° C. After 30 min, the reaction mixture was cooled to −78° C. and trans-2-methyl-2-butenal (530 μL, 5.5 mmol) was added dropwise. The resulting mixture was stirred at −78° C. for 30 min and then 90 min at room temperature. The reaction was quenched by addition of pH 7 aqueous phosphate buffer (10 mL) and oxidized with 30% hydrogen peroxide/methanol (1:1, 20 mL). The resulting solution was stirred at 0° C. for 1 h. The solvent was evaporated under reduced pressure. The residue was dissolved in water (30 mL) and extracted with EtOAc (25 mL×3). The combined organic layer was washed with 5% NaHCO$_3$ (25 mL) and brine (25 mL), dried over MgSO$_4$, and concentrated under reduced pressure, yielding a viscous yellow oil. The crude oil was purified by flash chromatography (EtOAc/n-hexane, 25:75), and the aldol, III-2 was obtained as a colorless oil.

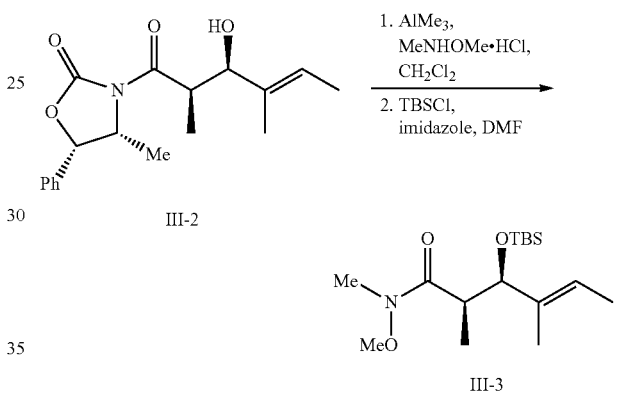

To a stirred suspension of N,O-dimethylhydroxylamine hydrochloride (317.5 mg, 3.25 mmol) in CH$_2$Cl$_2$ (6 mL) at 0° C. under argon was slowly added 15% trimethylaluminum in toluene (1.6 mL, 3.2 mmol) with concomitant evolution of gas. The resulting homogeneous solution was stirred for 40 min at room temperature and then recooled to 0° C., and a solution of aldol 6a (516 mg, 1.6 mmol) in CH$_2$Cl$_2$ (5 mL) was added over a period of 5 min. The solution was stirred for 1.5 h at 0° C., and then ice-cooled 0.5 M aqueous HCl (30 mL) and CH$_2$Cl$_2$ (10 mL) were added. The layers were separated, and the aqueous layer was extracted with CH$_2$Cl$_2$ (10 mL×3). The combined organic layers were dried over anhydrous Na$_2$SO$_4$ and concentrated under reduced pressure. The residue was purified by flash chromatography EtOAc/n-hexane, 50:50), to yield an amide as a colorless solid.

A mixture of amide (265 mg, 1.3 mmol), TBSCl (600 mg, 4.0 mmol), and imidazole (540 mg, 7.9 mmol) in DMF (6 mL) was stirred overnight at room temperature. The reaction mixture was quenched with water and extracted with EtOAc (15 mL×3). The combined organic layers were dried over anhydrous MgSO$_4$ and concentrated under reduced pressure, yielding a colorless oil. The resulting oil was purified by column chromatography (EtOAc/n-hexane, 50:50), and protected amide III-3 was obtained as a colorless oil.

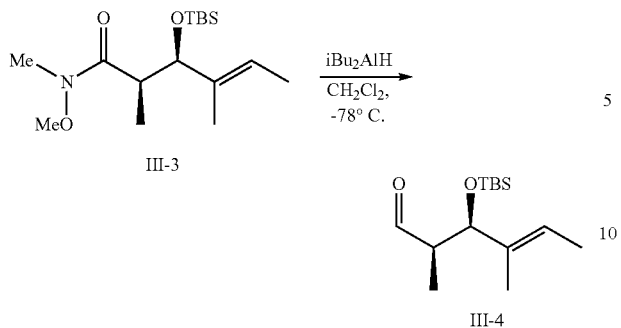

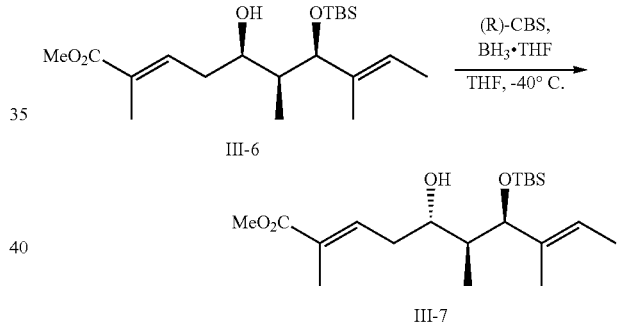

To a stirred solution of silyl ether III-3 (633 mg, 1.92 mmol) in THF (6.5 mL) cooled at −78° C. was added a 0.98 M solution of diisobutylaluminum hydride in hexane (3.9 mL, 3.8 mmol) dropwise. The solution was stirred at −78° C. for 1.5 h, and the reaction was quenched by addition of acetone (0.4 mL). The solution was stirred at −78° C. for 10 min and then transferred into a vigorously stirred mixture of $CH_2Cl_2$ (30 mL) and 0.5 M tartaric acid (30 mL) at room temperature. The resulting two-phase mixture was stirred at room temperature for 30 min. The layers were separated, and the aqueous layer was extracted with $CH_2Cl_2$ (3×30 mL). The organic layer and the extracts were combined, washed with brine (10 mL), dried ($Na_2SO_4$), and concentrated. The residual oil was purified by column chromatography on silica gel (hexanes/EtOAc 10:1/7:1) to yield aldehyde III-4.

To a stirred solution of methyl ester III-5 (1.32 g, 3.44 mmol) in $CH_2Cl_2$ (25 mL) was added Dess-Martin periodinane (2.29 g, 5.41 mmol). The mixture was stirred at room temperature for 1 h and diluted with ether (30 mL), saturated aqueous $Na_2S_2O_3$ (40 mL), and 0.5 M phosphate buffer (pH 7, 40 mL). The resulting mixture was stirred at room temperature for 30 min and extracted with ether (3×50 mL). The combined extracts were washed with $H_2O$ (2×50 mL) and brine (25 mL), dried ($Na_2SO_4$) and concentrated. The residual oil was purified by column chromatography on silica gel (35 g, hexane/ether 15:1/8:1) to yield III-6 (1.23 g, 94%) as a colorless oil.

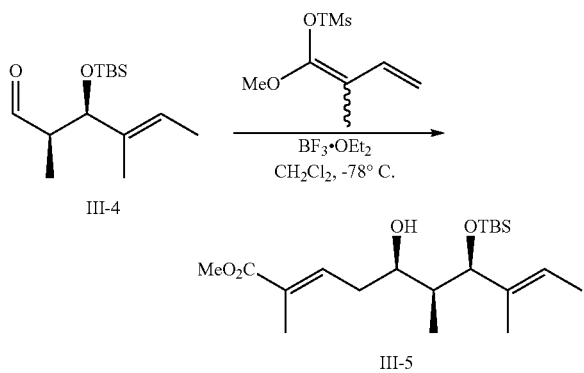

To a stirred solution of aldehyde III-4 (83.9 mg, 0.31 mmol) in $CH_2CL_2$ (2.4 mL) and ether (0.24 mL) cooled at −78° C. were added 2-methyl-1-trimethylsiloxy-1-methoxy-1,3-butadiene (0.2 mL, 1.01 mmol) and boron trifluoride diethyl etherate (0.06 mL, 0.49 mmol), successively. The reaction mixture was stirred at −78° C. for 2 h and diluted with THF-$H_2O$-0.3 M HCl (5:1:0.4, 4 mL). The mixture was stirred at room temperature for 15 min and then transferred into saturated aqueous $NaHCO_3$ (5 mL) at 0° C. The layers were separated, and the aqueous layer was extracted with hexane (3×7 mL). The organic layer and the extracts were combined, washed with brine (2 mL), dried ($Na_2SO_4$). Flash chromatography (4:1 hexanes/EtOAc) gave III-5.

To a solution of ketone III-6 (212.5 mg, 0.2148 mmol) and (R)-2-methyl-CBS-oxazaborolidine (1.0 M solution in toluene, 1.08 mL, 1.08 mmol) in THF (2.2 mL) at −40° C. was added BH3.THF (0.95 M solution in THF, 2.26 mL, 2.15 mmol), and the resultant solution was stirred at −40° C. for 7 h 20 min. The reaction was quenched with MeOH. The resultant mixture was diluted with EtOAc, washed with $H_2O$ and brine, dried (Na2SO4), filtered, and concentrated under reduced pressure. Purification of the residue by flash column chromatography (silica gel, 5% $Et_2O$/benzene then 20% EtOAc/hexanes) gave alcohol III-7.

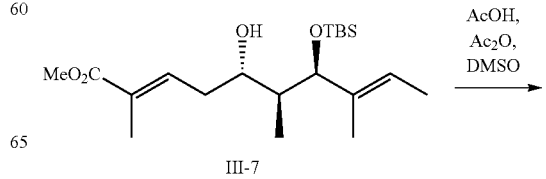

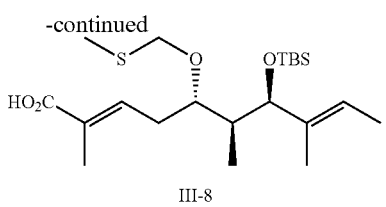

To a stirred solution of alcohol III-7 (1.47 g, 3.83 mmol) in DMSO (28 mL) was added a 1:5.6 mixture of acetic acid and acetic anhydride (23 mL) at room temperature. The mixture was stirred at 40° C. for 3 h and diluted with hexane (54 mL) and 0.5 M phosphate buffer (pH 7, 90 mL). The layers were separated, and the aqueous layer was extracted with hexane (3×30 mL). The organic layer and the extracts were combined, washed with $H_2O$ (20 mL) and brine (20 mL), dried ($Na_2SO_4$), and concentrated. The residual oil was purified by column chromatography on silica gel (9:1 hexanes:EtOAc) to yield silyl ether III-8.

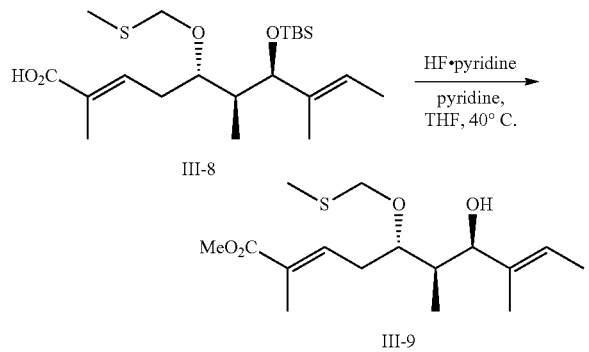

Silyl ether III-8 (487 mg, 0.451 mmol) was dissolved in HF-pyridine/pyridine/THF (1:1:4, 27 mL). The solution was stirred at 40° C. for 12 h. After cooling, the reaction mixture was diluted with EtOAc (100 mL) and poured into saturated $NaHCO_3$ (160 mL). The mixture was separated and extracted with EtOAc (20 mL). The combined extracts were washed with 1 M HCl (20 mL), dried over $Na_2SO_4$, and evaporated to dryness. The residue was subjected to flash column chromatography on silica gel [n-hexane/EtOAc, (7:3) to (3:7)] to give alcohol III-9.

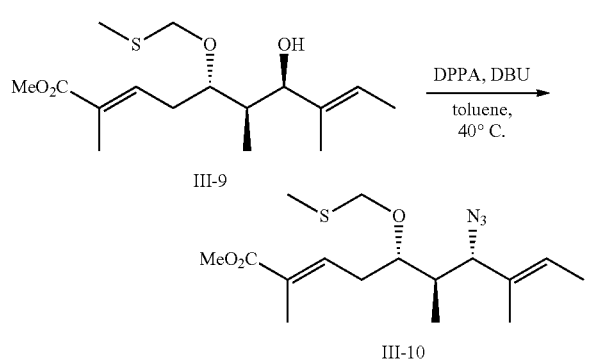

A mixture of alcohol III-9 (2.0 g) and diphenyl phosphorazidate (3.6 g) was dissolved in dry toluene (18 mL). The mixture was cooled to 0° C. under $N_2$, and neat DBU (1.9 mL, 12.7 mmol) was added. The reaction was stirred for 2 h at 0° C. and then at 20° C. for 16 h. The resulting two-phase mixture was washed with $H_2O$ (2×10 mL) and 5% HCl (10 mL). The organic layer was concentrated in vacuo and purified by silica gel chromatography using 90/10 hexane/ethyl acetate to afford 2.07 g (91%) of azide III-10 as a clear oil. 1H NMR ($CDCl_3$): δ 6.81 (ddq, J=6.9, 1H), 5.47 (d, J=7.0 Hz, 1H), 4.67 (q, J=7.0, 7.0, 7.0), 3.75 (s, 3H), 3.71 (t, 1H J=7.0), 2.41-2.66 (m, 1H), 2.33-2.41 (m, 1H), 2.14 (s, 3H), 1.85 (d, J=1.3 Hz, 3H), 1.54 (s, 3H), 1.40 (d, J=1.3 Hz, 3H), 1.03 (d, 1.3 Hz, 3H).

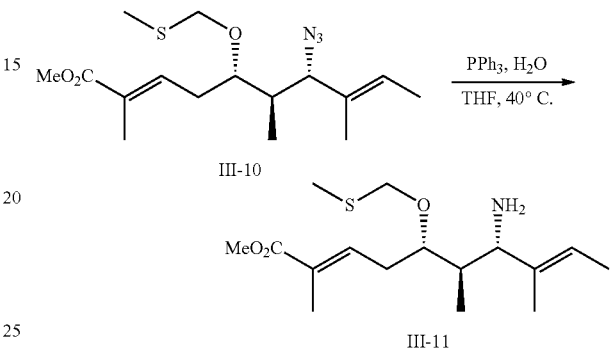

12 mg of azide III-10 was dissolved in THF (0.29 mL) and water (0.14 mL) and 18 mg of $PPh_3$ was added. The reaction was heated to 50° C. for 18 h. The reaction was then cooled to 23° C., diluted with EtOAc and $H_2O$ and the layers separated. The aqueous layer was extracted with EtOAc (3×15 mL). The combined organic layers were washed with brine (30 mL), dried over $Na_2SO_4$. Purified by flash chromatography (10% $MeOH/CH_2Cl_2$) to afford 10 mg of amine III-11. $^1H$ NMR ($CDCl_3$): δ 6.81 (ddq, J=6.9, 1H), 5.47 (d, J=7.0 Hz, 1H), 4.67 (q, J=7.0, 7.0, 7.0), 3.75 (s, 3H), 3.71 (t, 1H J=7.0), 2.41-2.66 (m, 1H), 2.33-2.41 (m, 1H), 2.14 (s, 3H), 1.85 (d, J=1.3 Hz, 3H), 1.54 (s, 3H), 1.40 (d, J=1.3 Hz, 3H), 1.03 (d, 1.3 Hz, 3H).

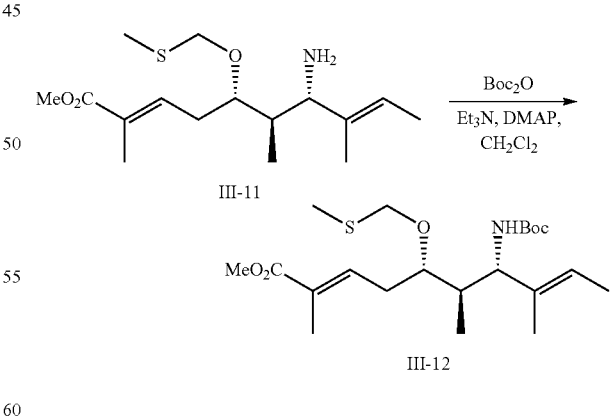

9 mg of amine III-11 was dissolved in 0.28 mL of $CH_2Cl_2$. To the mixture was added 0.1 mg of DMAP and 6.8 mg of $Boc_2O$, followed by 4.4 μL of $Et_3N$. After 2 hours the reaction was quenched with sat. Aq. $NH_4Cl$. The aqueous layer was extracted with EtOAc (3×5 mL). The combined organics were washed with brine, dried over $Na_2SO_4$ to afford carbamate III-12.

Example 4

Synthesis of Compound 19

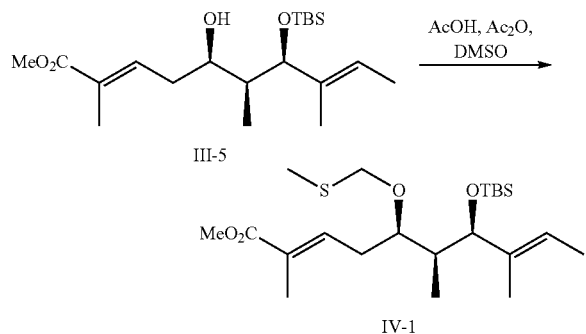

To a stirred solution of alcohol III-5 (1.47 g, 3.83 mmol) in DMSO (28 mL) was added a 1:5.6 mixture of acetic acid and acetic anhydride (23 mL) at room temperature. The mixture was stirred at 40° C. for 3 h and diluted with hexane (54 mL) and 0.5 M phosphate buffer (pH 7, 90 mL). The layers were separated, and the aqueous layer was extracted with hexane (3×30 mL). The organic layer and the extracts were combined, washed with H$_2$O (20 mL) and brine (20 mL), dried (Na$_2$SO$_4$), and concentrated. The residual oil was purified by column chromatography on silica gel (9:1 hexanes:EtOAc) to afford compound IV-1.

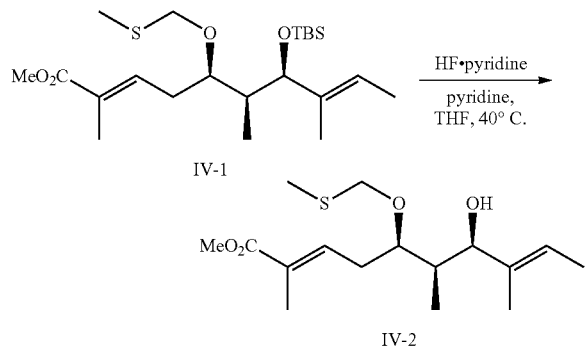

Silyl ether IV-1 (487 mg, 0.451 mmol) was dissolved in HF-pyridine/pyridine/THF (1:1:4, 27 mL). The solution was stirred at 40° C. for 12 h. After cooling, the reaction mixture was diluted with EtOAc (100 mL) and poured into saturated NaHCO3 (160 mL). The mixture was separated and extracted with EtOAc (20 mL). The combined extracts were washed with 1 M HCl (20 mL), dried over Na$_2$SO$_4$, and evaporated to dryness. The residue was subjected to flash column chromatography on silica gel [n-hexane/EtOAc, (7:3) to (3:7)] to give alcohol IV-2.

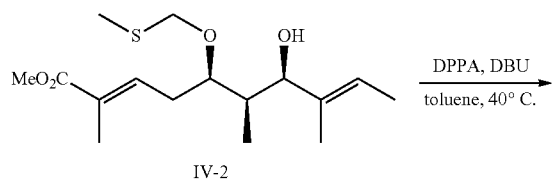

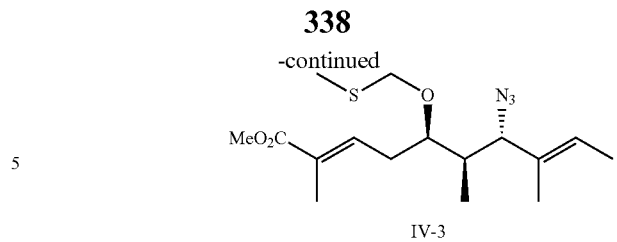

A mixture of alcohol IV-2 (2.0 g) and diphenyl phosphorazidate (3.6 g) was dissolved in dry toluene (18 mL). The mixture wan cooled to 0° C. under N$_2$, and neat DBU (1.9 mL, 12.7 mmol) was added. The reaction was stirred for 2 h at 0° C. and then at 20° C. for 16 h. The resulting two-phase mixture was washed with H$_2$O (2×10 mL) and 5% HCl (10 mL). The organic layer was concentrated in vacuo and purified by silica gel chromatography using 90/10 hexane/ethyl acetate to afford 2.07 g (91%) compound IV-3 as a clear oil.

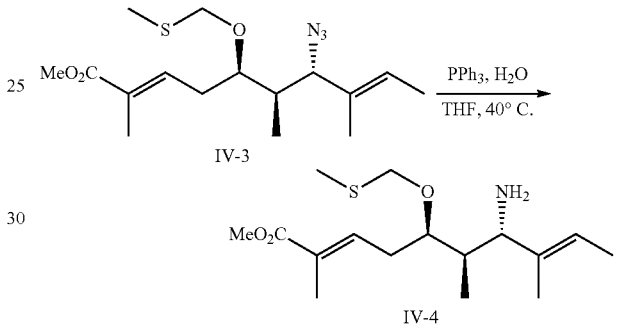

12 mg of Azide IV-3 was dissolved in THF (0.29 mL) and water (0.14 mL) and 18 mg of PPh$_3$ was added. The reaction was heated to 50° C. for 18 h. The reaction was then cooled to 23° C., diluted with EtOAc and H$_2$O and the layers separated. The aqueous layer was extracted with EtOAc (3×15 mL). The combined organic layers were washed with brine (30 mL), dried over Na$_2$SO$_4$. Purified by flash chromatography (10% MeOH/CH$_2$Cl$_2$) to afford 10 mg of amine IV-4.

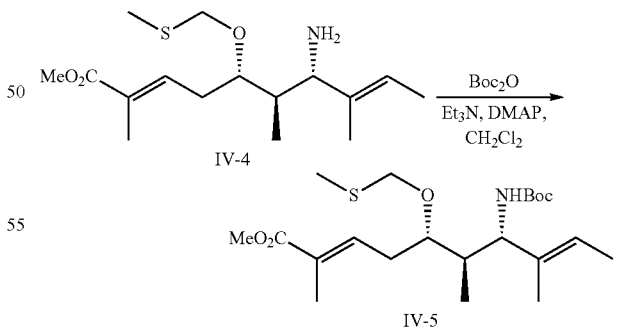

9 mg of amine IV-4 was dissolved in 0.28 mL of CH$_2$Cl$_2$. To the mixture was added 0.1 mg of DMAP and 6.8 mg of Boc$_2$O, followed by 4.4 μL of Et$_3$N. After 2 hours the reaction was quenched with sat. Aq. NH$_4$Cl. The aqueous layer was extracted with EtOAc (3×5 mL). The combined organics were washed with brine, dried over Na$_2$SO$_4$ to afford carbamate IV-5.

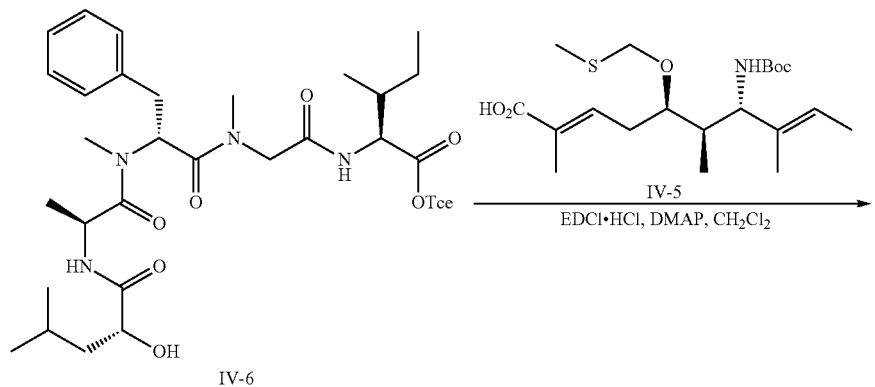
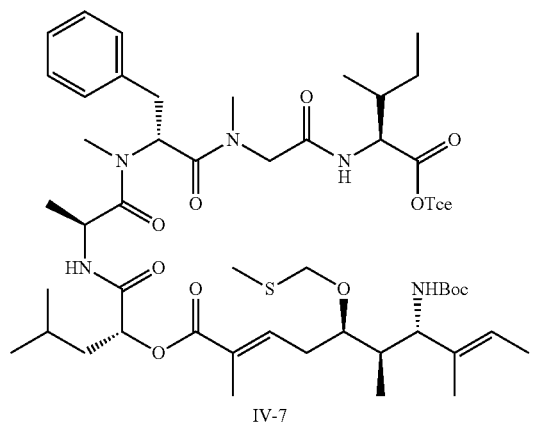
Carbamate IV-5 was reacted with compound IV-6 in accordance with the procedure described in *Tetrahedron* 68 (2012) 659-669 to afford compound IV-7.
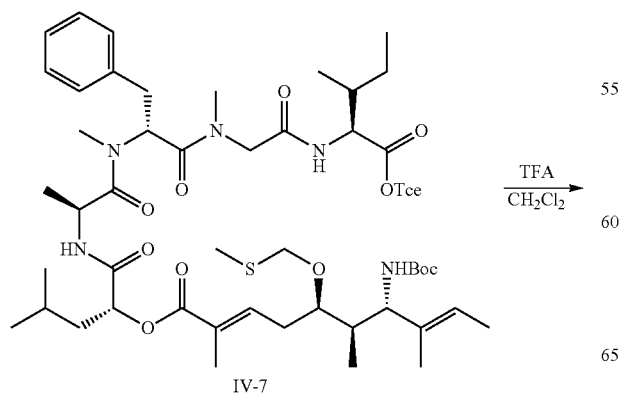
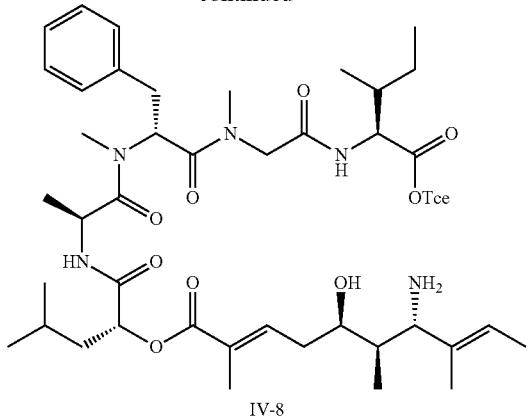
23.9 mg of Boc-carbamate IV-7 was dissolved in $CH_2Cl_2$ and TFA (0.17 mL and 0.08 mL). The reaction was stirred for 90 minutes then concentrated to afford IV-8 (22 mg, 95% yield).

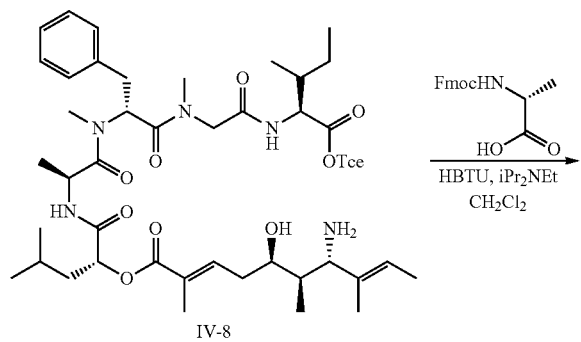

IV-8

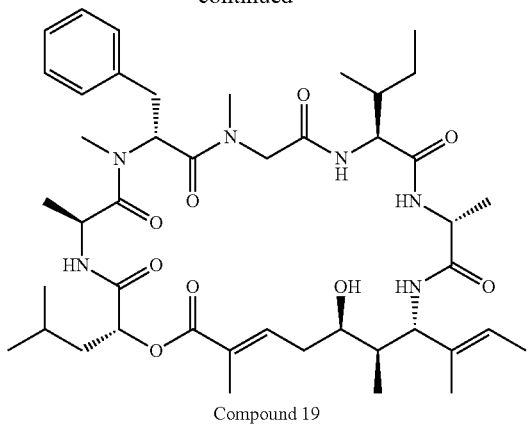

Compound 19

7.8 mg of TCE ester IV-9 was dissolved in THF 0.32 mL and 0.07 mL of 1 M NH$_4$Ac. 30 mg of Zn was then added and the reaction was stirred for 12 hours. The reaction was filtered over celite, and the organics washed with 10% citric acid, water and brine, and dried over Na$_2$SO$_4$.

The resulting residue was dissolved in CH$_3$CN (0.3 mL) and diethyl amine was added (0.03 mL). After three hours the reaction was concentrated and the non-polar compounds were washed away with penatanes. The resulting residue was then dissolved in 6 mL of THF. 6.4 µL of iPr$_2$NEt was added followed by 5.5 mg of DEPBT. The reaction was stirred for 22 hours and quenched with NH$_4$Cl. The aqueous layer was extracted with EtOAC and the combined organics were washed with brine, dried over Na$_2$SO$_4$. The product was purified by Prep TLC using EtOAC to afford 1 mg of Compound 19. ESI HRMS: m/z 825.5258 [M+H]$^+$.

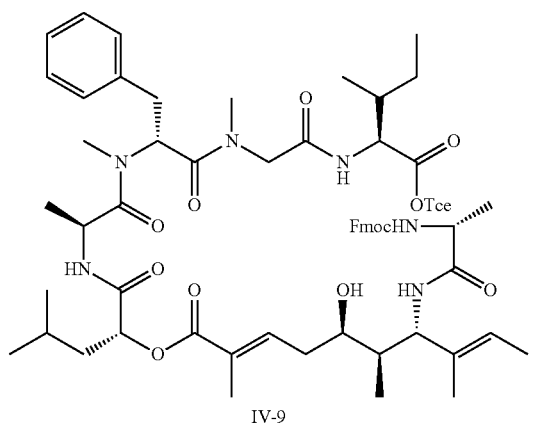

IV-9

19.8 mg of amino alcohol IV-8 was dissolved in 0.22 mL of CH$_2$Cl$_2$. The solution was cooled to 0° C. and Fmoc-D-Ala-OH (8.2 mg) was added followed by 4.6 µL of iPr$_2$NEt and 12.5 mg of HBTU. After 12 h, the reaction was diluted with EtOAc and quenched with 10% citric acid. The aqueous layer was extracted with EtOAc (3×10 mL) and the combined organic layers were washed with brine (10 mL), dried over Na$_2$SO$_4$. Purified by Prep TLC (7:3 EtOAc: hexanes) to afford 7.8 mg (30% yield) of Fmoc amine IV-9.

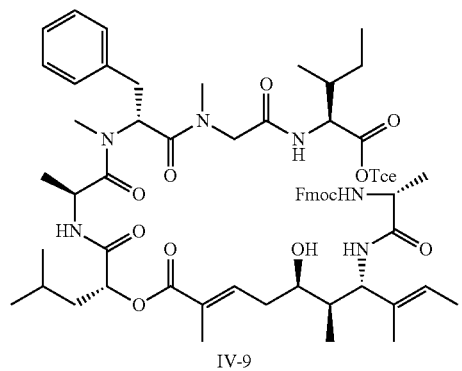

IV-9

Example 5

Synthesis of Compound 20

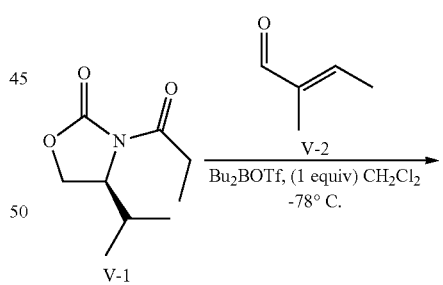

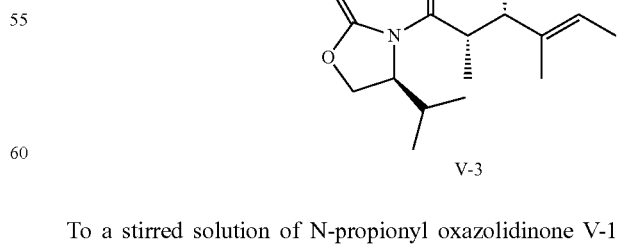

To a stirred solution of N-propionyl oxazolidinone V-1 (1.0 mL, 5.0 mmol) in dry Et$_2$O (15 mL) under argon was treated with dibutylboron triflate in CH$_2$Cl$_2$ (5.5 mL, 5.0 mmol) and diisopropylethylamine (1.1 mL, 6.0 mmol) at 0° C. After 30 min, the reaction mixture was cooled to −78° C.

and trans-2-methyl-2-butenal V-2 (530 μL, 5.5 mmol) was added dropwise. The resulting mixture was stirred at −78° C. for 30 min and then 90 min at room temperature. The reaction was quenched by addition of pH 7 aqueous phosphate buffer (10 mL) and oxidized with 30% hydrogen peroxide/methanol (1:1, 20 mL). The resulting solution was stirred at 0° C. for 1 h. The solvent was evaporated under reduced pressure. The residue was dissolved in water (30 mL) and extracted with EtOAc (25 mL×3). The combined organic layer was washed with 5% NaHCO3 (25 mL) and brine (25 mL), dried over MgSO₄, and concentrated under reduced pressure, yielding a viscous yellow oil. The crude oil was purified by flash chromatography (EtOAc/n-hexane, 25:75), and the aldol V-3 was obtained as a colorless oil.

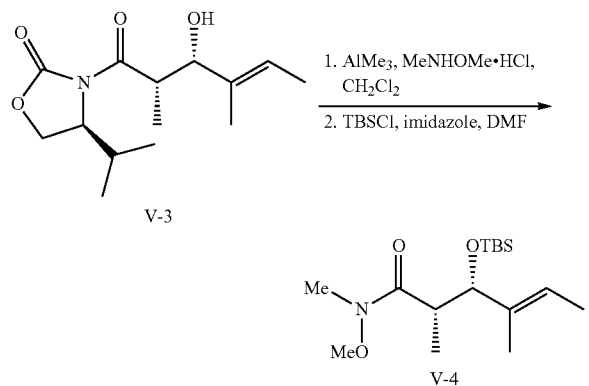

Compound V-3 was treated in accordance with the procedure described in *Tetrahedron* 68 (2012) 659-669 to afford compound V-4.

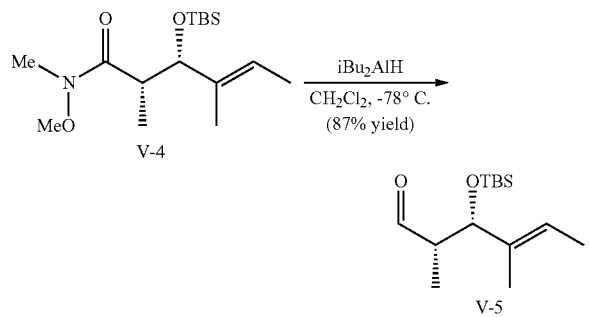

Compound V-4 was treated in accordance with the procedure described in *Tetrahedron* 68 (2012) 659-669 to afford compound V-5.

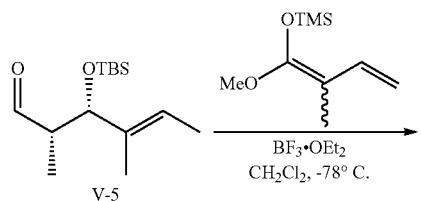

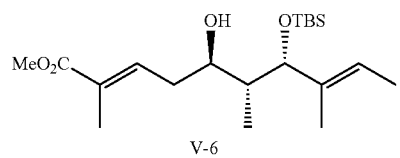

Compound V-5 was treated in accordance with the procedure described in *Tetrahedron* 68 (2012) 659-669 to afford compound V-6.

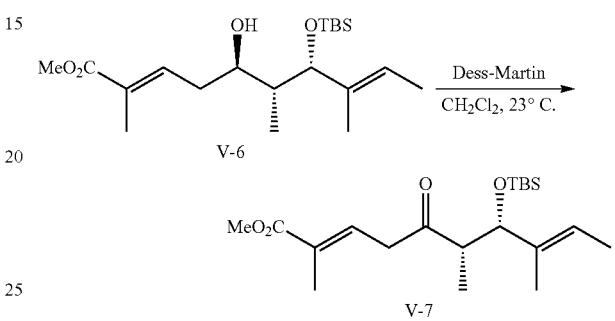

To a stirred solution of methyl ester V-6 (1.32 g, 3.44 mmol) in CH₂Cl₂ (25 mL) was added Dess-Martin periodinane (2.29 g, 5.41 mmol). The mixture was stirred at room temperature for 1 h and diluted with ether (30 mL), saturated aqueous Na₂S₂O₃ (40 mL), and 0.5 M phosphate buffer (pH 7, 40 mL). The resulting mixture was stirred at room temperature for 30 min and extracted with ether (3×50 mL). The combined extracts were washed with H₂O (2×50 mL) and brine (25 mL), dried (Na₂SO₄) and concentrated. The residual oil was purified by column chromatography on silica gel (35 g, hexane/ether 15:1/8:1) to give compound V-7 (1.23 g, 94%) as a colorless oil.

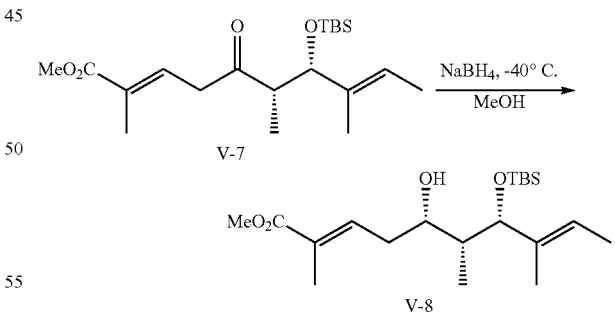

To a stirred solution of ketone V-7 (234 mg, 0.613 mmol) in methanol (6 mL) cooled at −23° C. was added sodium borohydride (119 mg, 3.15 mmol). The mixture was stirred at −40° C. for 50 min, diluted with saturated aqueous ammonium chloride (20 mL), and extracted with hexane (4×20 mL). The combined extracts were washed with brine (15 mL), dried (Na₂SO₄), and concentrated. The residual oil was purified by column chromatography on silica gel, hexanes:EtOAc (10:1 to 4:1) to afford compound V-8.

345
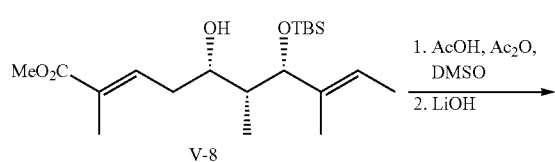
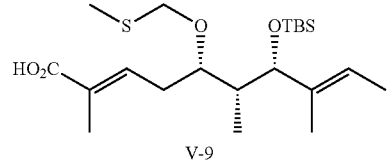
Compound V-8 was treated in accordance with the procedure described in *Tetrahedron* 68 (2012) 659-669 to afford compound V-9.
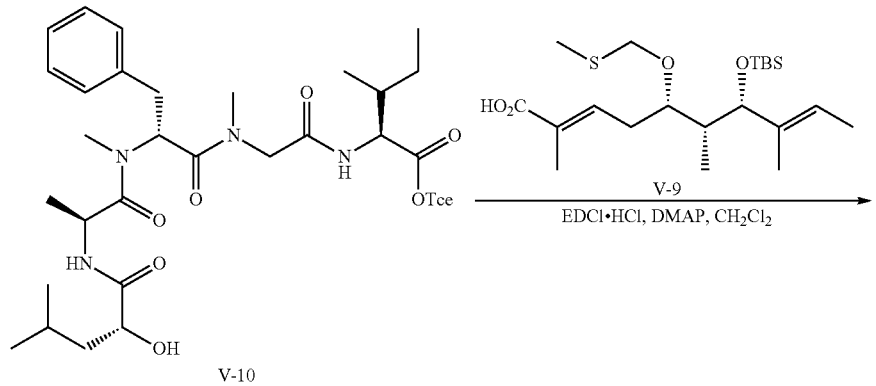
346
Compound V-9 was reacted with compound V-10 in accordance with the procedure described in *Tetrahedron* 68 (2012) 659-669 to afford compound V-11.
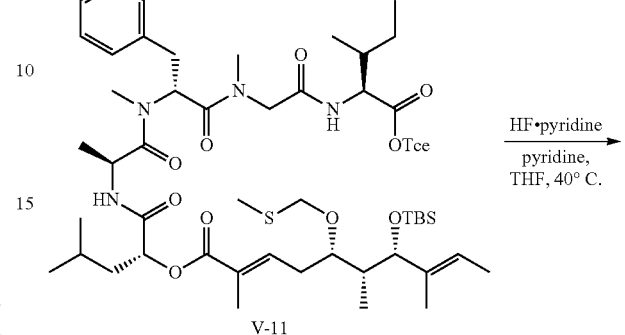
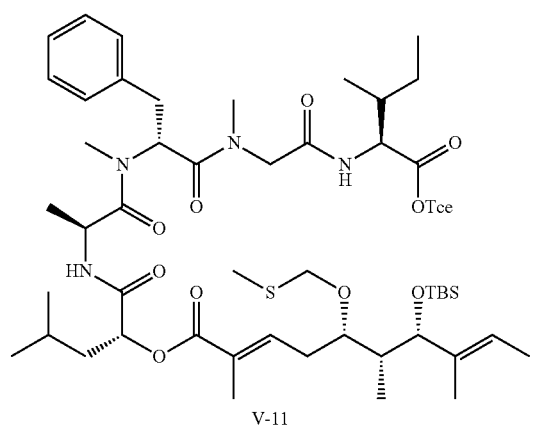

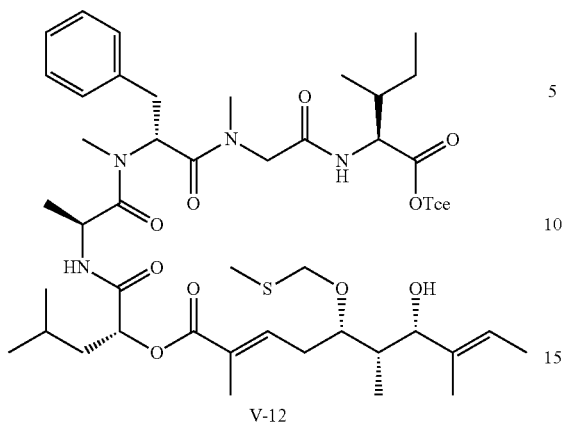
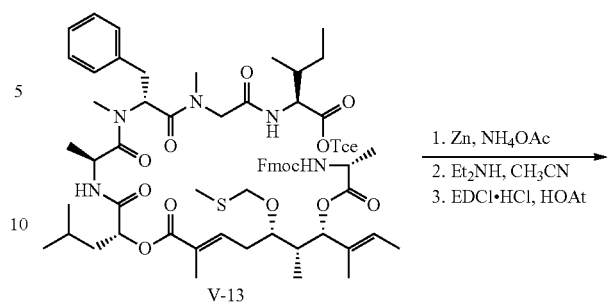
Compound V-11 was treated in accordance with the procedure described in *Tetrahedron* 68 (2012) 659-669 to afford compound V-12.
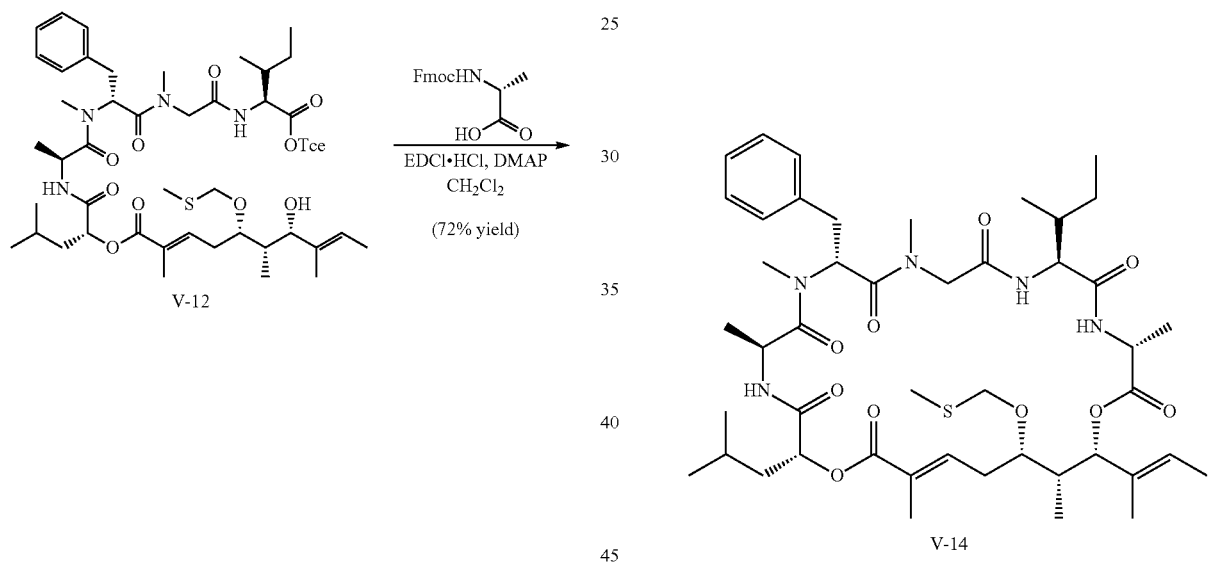
Compound V-12 was treated in accordance with the procedure described in *Tetrahedron* 68 (2012) 659-669 to afford compound V-13.
Compound V-13 was treated in accordance with the procedure described in *Tetrahedron* 68 (2012) 659-669 to afford compound V-14.
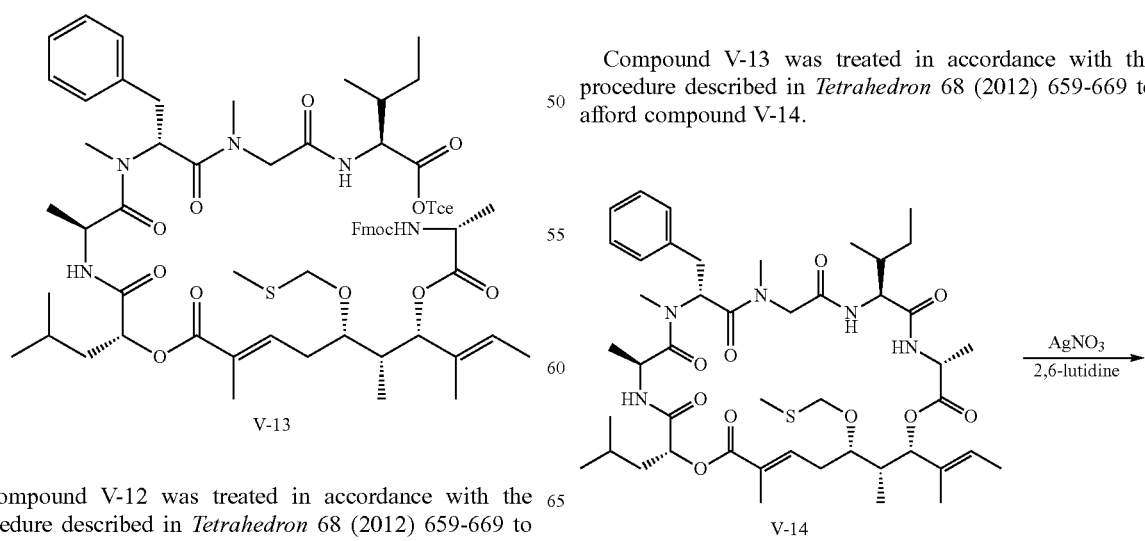

349
-continued

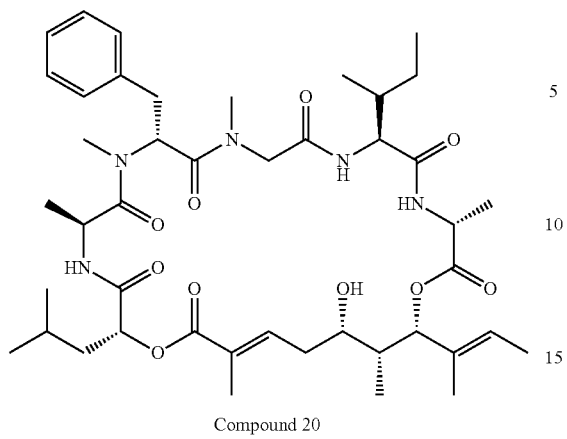

Compound 20

1 mg of MTM-alcohol V-14 was dissolved in THF/H$_2$O (40 μL/10 μL). AgNO$_3$ was added followed by 2.2 μL and the reaction was heated to 65° C. After 1 h the reaction was cooled to 23° C. and the reaction was filtered over celite and concentrated. The residue was taken up in EtOAc and the organic layer was then washed with 1 M HCl (10 mL), sat. Aq. NaHCO$_3$ (10 mL), and brine (10 mL), dried over Na$_2$SO$_4$. The product was purified by prep TLC plate using 100% EtOAc to afford Compound 20 as pure compound. Observed ESI HRMS: m/z 826.4976 [M+H]$^+$.

Example 6

Synthesis of Various Compounds

Certain compounds were synthesized using a procedure similar to that described in Example 2.

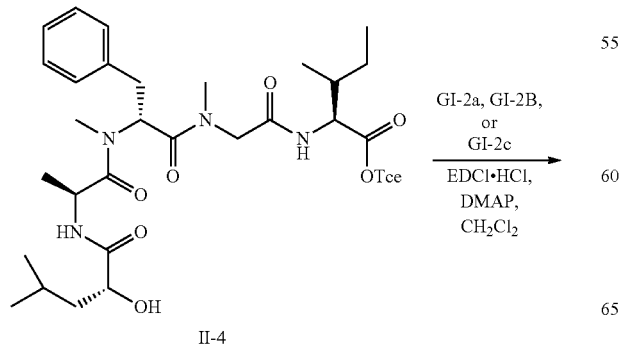

II-4

350
-continued

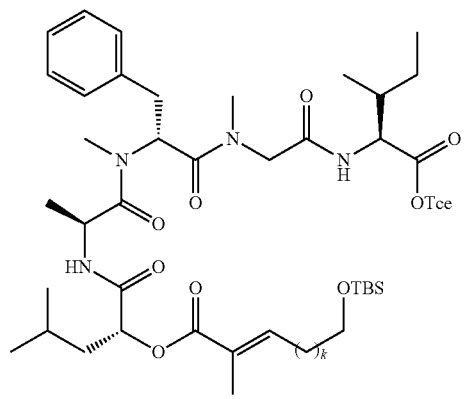

k = 1, 2, or 3
II-5a

Approximately 7 mg of depsipeptide 11-4 was reacted with protected hydroxyl acid GI-2a, GI-2b, or GI-2c to afford compounds of structure II-5a. For some compounds the protected D-alanine amino acid used in Example 2 was replaced with an alternative amino acid. The general synthetic schemes for certain steps in the synthesis are shown below.

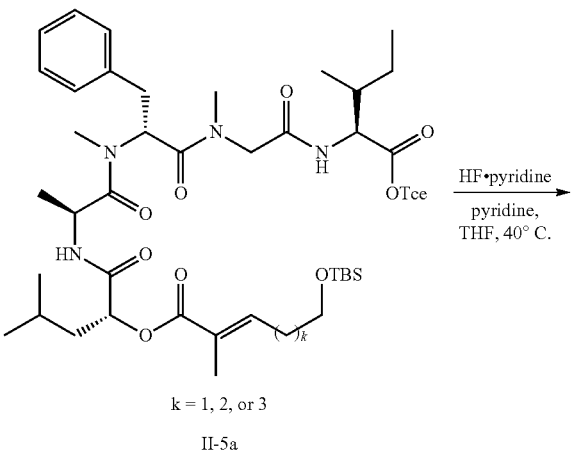

k = 1, 2, or 3
II-5a

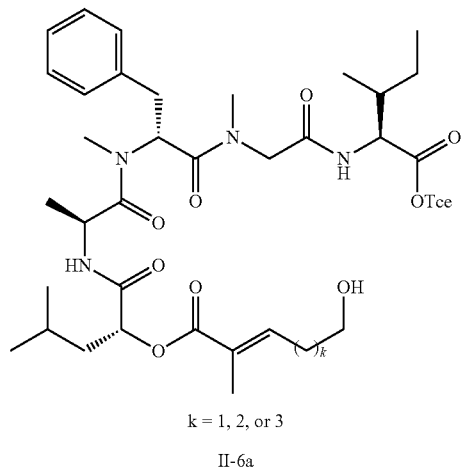

k = 1, 2, or 3
II-6a

351
-continued

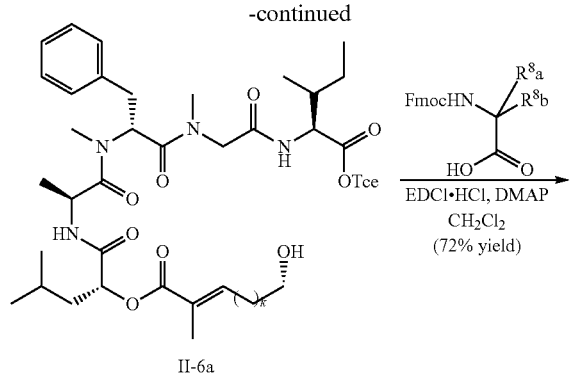

352
-continued

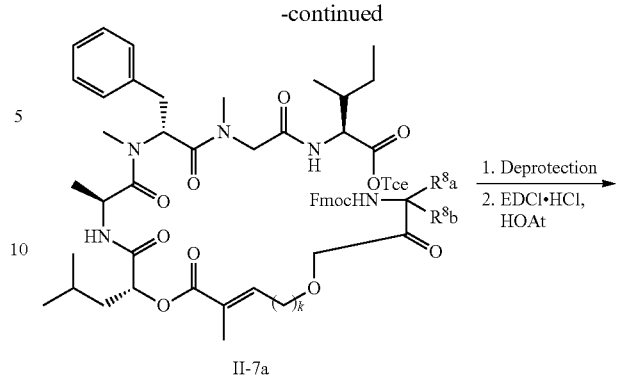

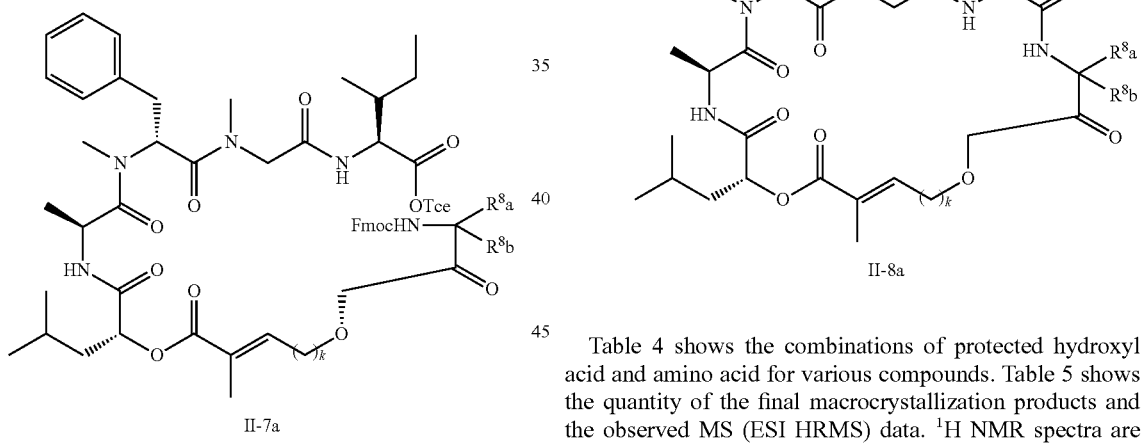

Table 4 shows the combinations of protected hydroxyl acid and amino acid for various compounds. Table 5 shows the quantity of the final macrocrystallization products and the observed MS (ESI HRMS) data. $^1$H NMR spectra are provided in FIGS. 1-11.

TABLE 4

| Amino Acids | GI-2a | GI-2b | GI-2c |
|---|---|---|---|
| L-Ala | Compound 13 | Compound 12 | Compound 4 |
| D-Ala | Compound 17 | Compound 16 | Compound 5 |
| N-Me-L-Ala | Compound 14 | | Compound 9 |
| N-Me-D-Ala | Compound 18 | | Compound 10 |
| γ-Boc-L-Lys | | | Compound 11 |

TABLE 5

| Compound | Quantity (mg) | ESI HRMS m/z ([M + H]$^+$) |
|---|---|---|
| 4 | 1.98 | 728.4054 |
| 5 | 1.20 | 728.4112 |
| 9 | 0.67 | 742.4112 |
| 10 | 0.27 | 742.4415 |
| 11 | 0.90 | 885.5080 |
| 12 | 0.15 | 714.3947 |
| 13 | 1.15 | 742.4270 |
| 14 | 0.24 | 756.4306 |
| 16 | 0.62 | 714.3949 |
| 17 | 1.35 | 742.4323 |
| 18 | 0.45 | 753.4450 |

Example 7

Synthesis of Compound 60

Figure 12:
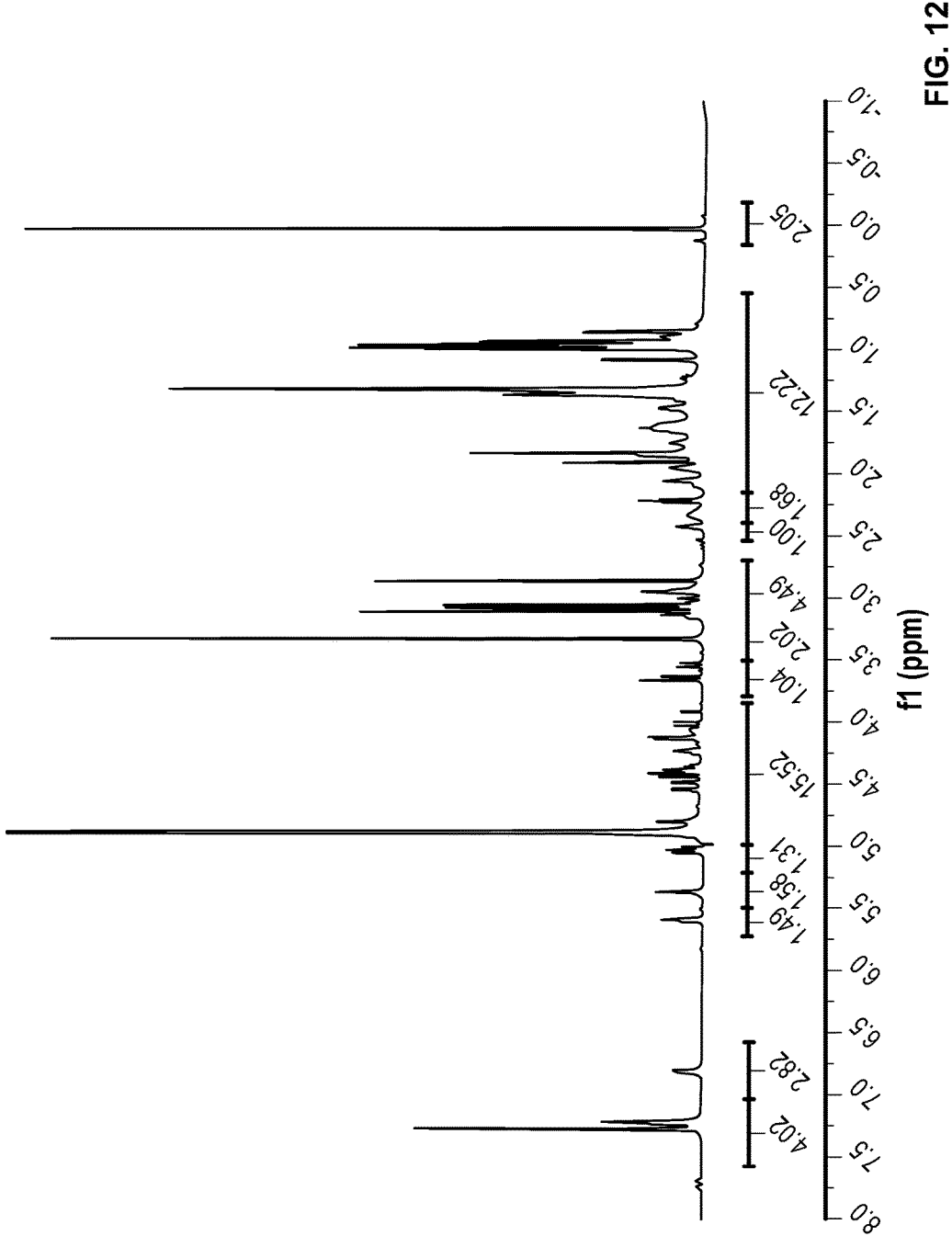
FIG. 12 is a $^1$H NMR spectrum of Compound 60 in $CD_3OD$.

Boc deprotection of Compound 11 (1.3 mg) was performed by treating with TFA (0.1 mL) in DCM (1 mL) for 2 h. The consumption of Compound 11 was confirmed by LCMS and the volatile was removed in vacuo to provide 1.4 mg of Compound 60. Observed ESI HRMS: m/z 785.4888 [M+H]$^+$. The $^1$H NMR spectrum is shown in FIG. 12.

Example 8

Synthesis of Compound 61

Figure 13:
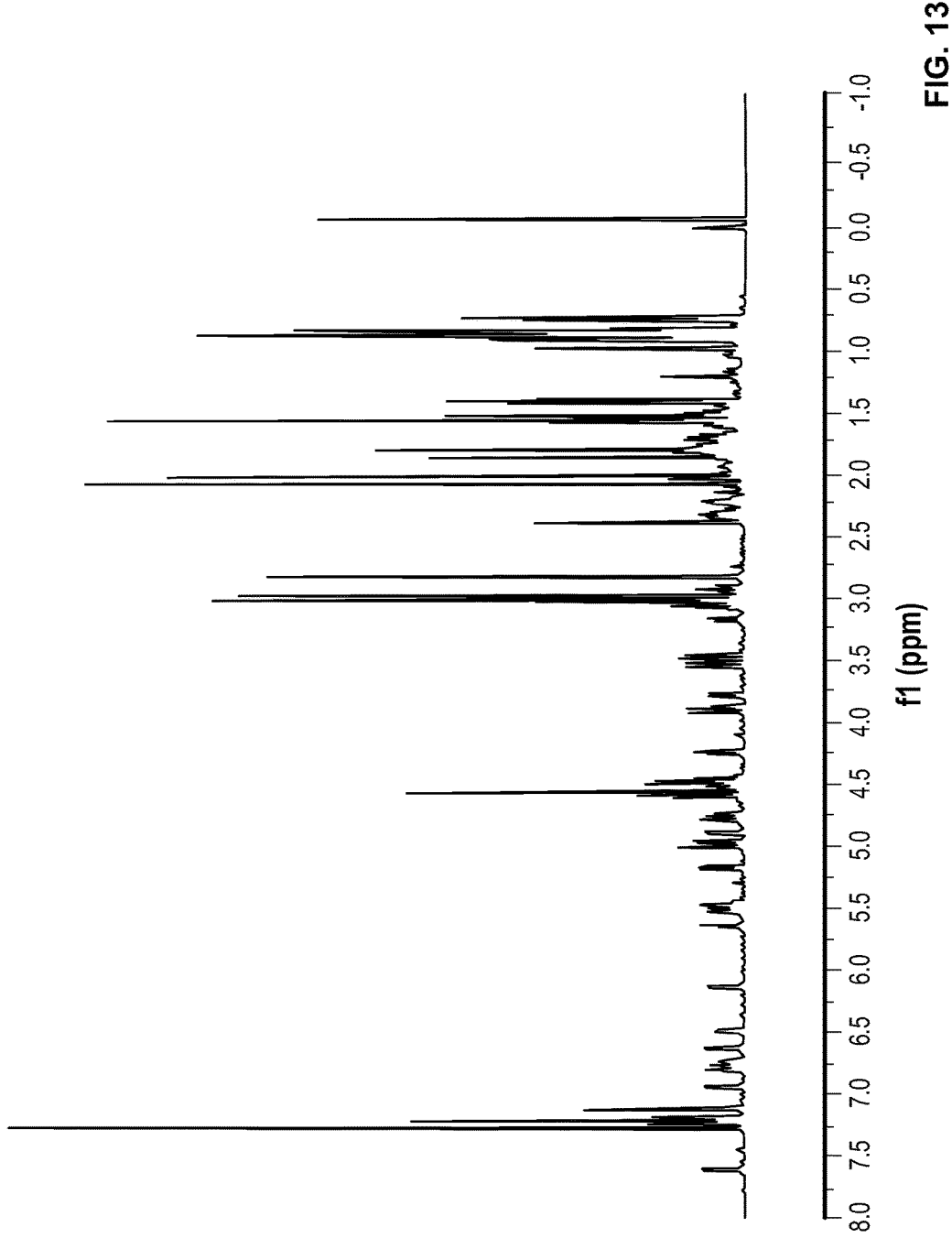
FIG. 13 is a $^1$H NMR spectrum of Compound 61 in $CDCl_3$.

Compound 61 was prepared in accordance with the procedure described in Umehara et al. (Bioorg. Med. Chem. Lett. 2012, 22, 7422). Observed ESI HRMS: m/z 920.4621 [M+H]$^+$. The $^1$H NMR spectrum is shown in FIG. 13.

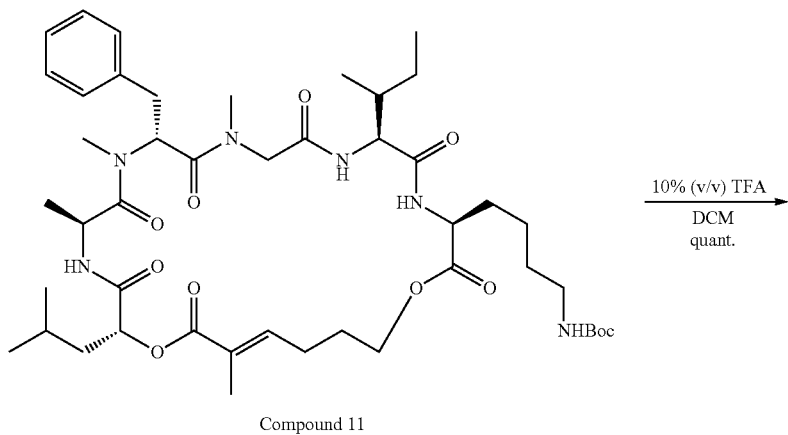

Compound 11

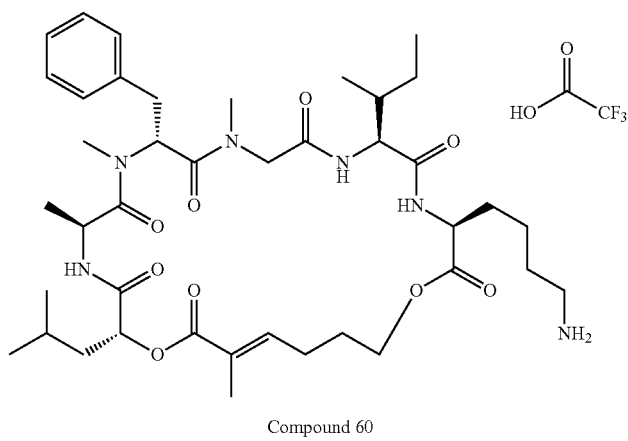

Compound 60

Example 9

Synthesis of Compound L8

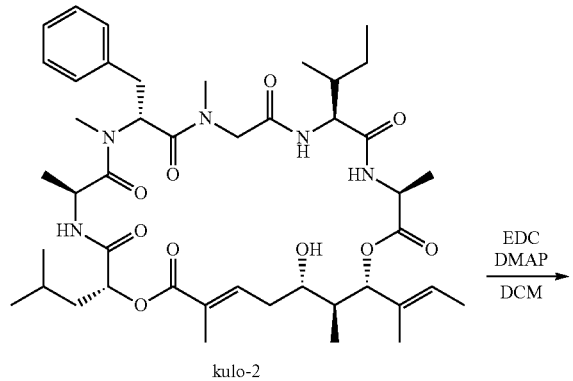

kulo-2

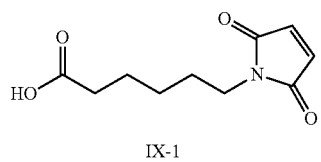

IX-1

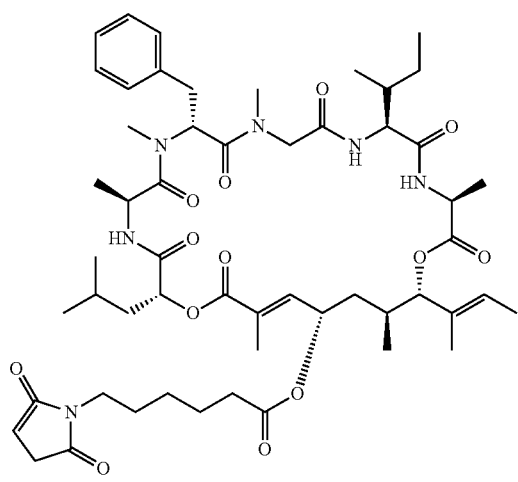

L8

Kulo-2 (100 μg) and compound IX-1 (acid; 1 mg) were dissolved in DCM (50 μL). DMAP (1 mg) and EDC (1 mg) were added at 0° C., and the mixture was allowed to warm up to room temperature. The reaction mixture was stirred overnight, and the volatile components were removed. The crude mixture was purified by HPLC to yield compound L8 (20 μg). ESI MS: m/z 1041.5505 [M+Na]$^+$.

Example 10

Synthesis of Compound 69

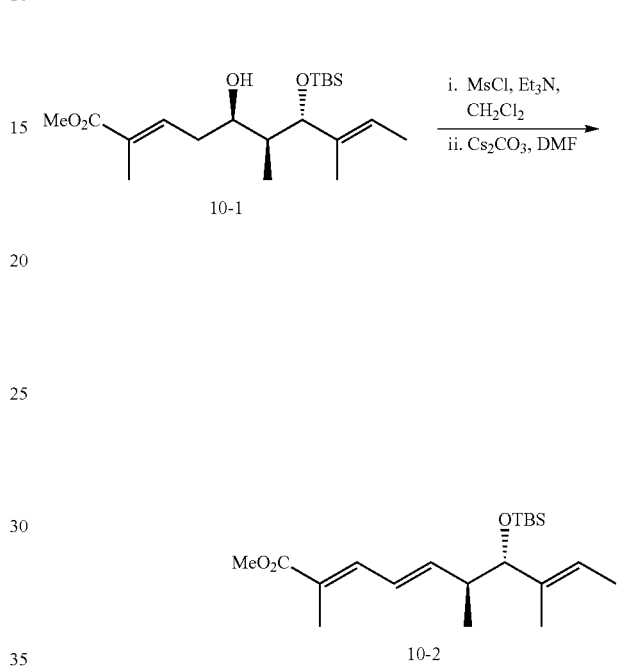

470 mg of the starting alcohol 10-1 was dissolved in 6.4 mL of $CH_2Cl_2$, and cooled to 0° C. $Et_3N$ (2.6 mL, 1.5 equiv) was added followed by MsCl (0.1 mL, 1.1 equiv). After 30 min the reaction was diluted with EtOAc, and quenched with ammonium chloride. The aqueous layer was extrected with EtOAc (3×20 mL). The combined organic layers were washed with brine (50 mL) and dried over $Na_2SO_4$. The crude product was taken to the next step without further purification.

The mesylate was dissolved in 6.3 mL of DMF. $Cs_2CO_3$ (1.23 g, 3 equiv) was added and the reaction was heated to 40° C. for 5 h. The reaction was removed from heat and diluted with EtOAC (20 mL) and water (20 mL). The layers were separated and the aqueous layer was extracted with EtOAc (3×30 mL). The combined organic layers were washed with brine (30 mL) dried over $Na_2SO_4$. The crude product was purified by flash chromotography (10% EtOAc in hexanes) to afford 100 mgs of 10-2 (20% yield).

Figure 14:
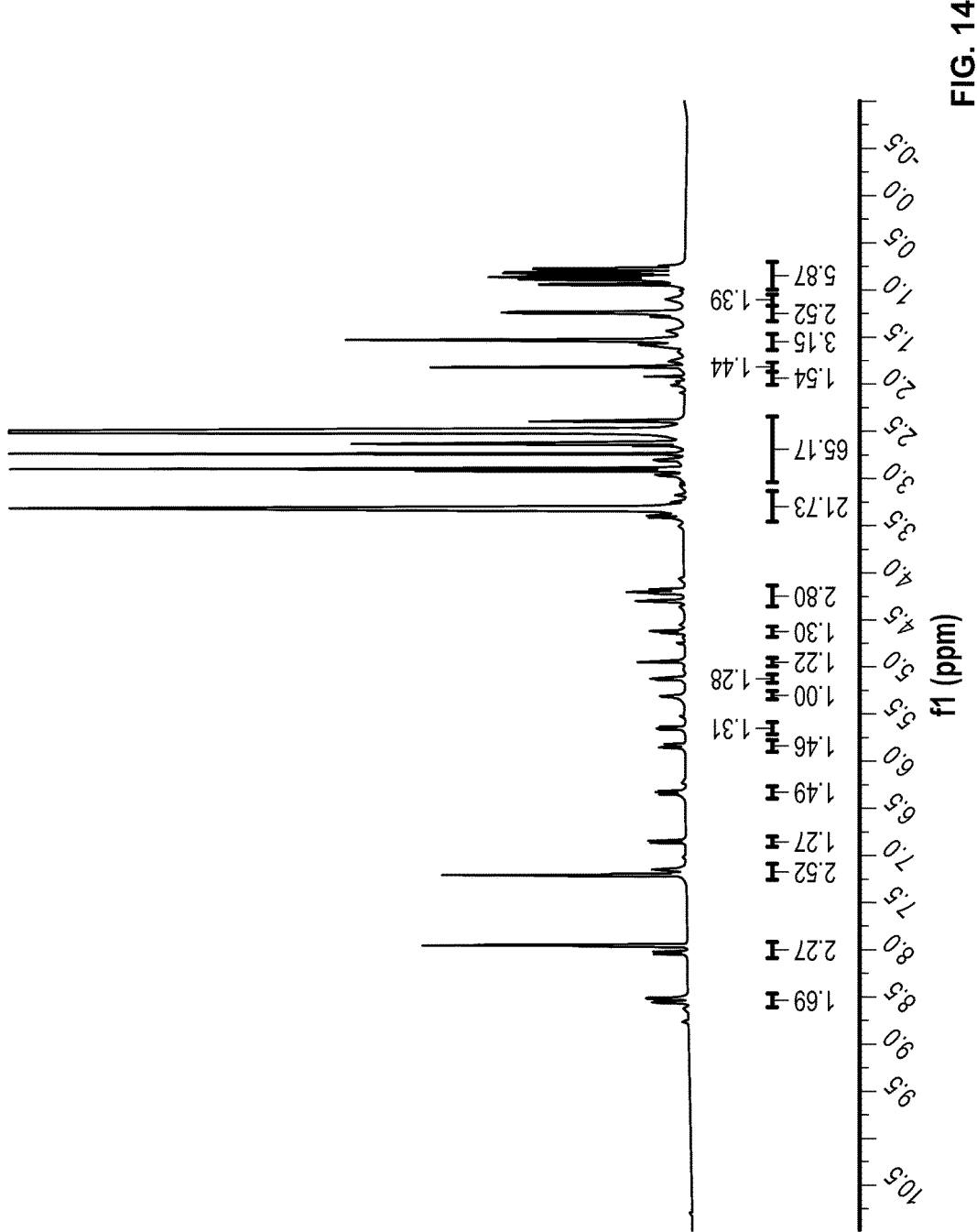
FIG. 14 is a $^1$H NMR spectrum of Compound 69 in DMSO-d6.

Compound 69 was otherwise synthesized according to a procedure similar to Example 2. $^1$H NMR of the final product is shown in FIG. 14.

Example 11

Synthesis of Conjugate L10

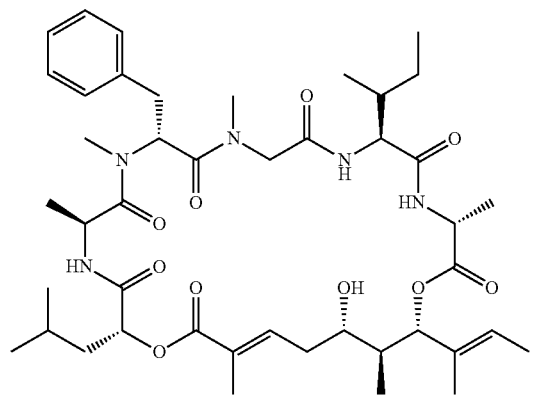

kulo-2

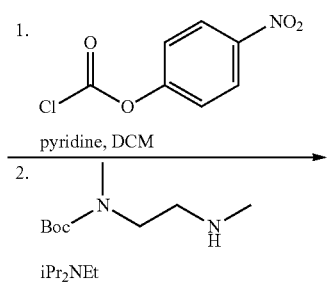

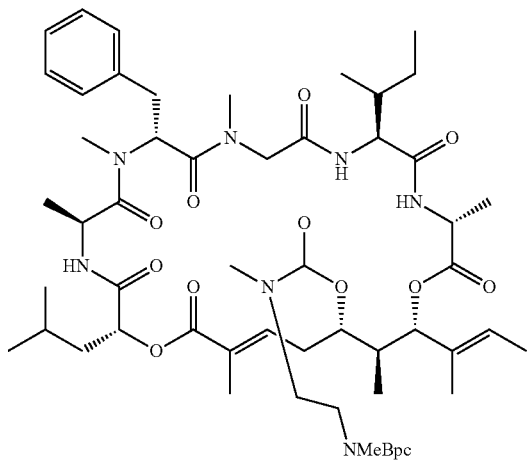

Compound 93

Figure 15:
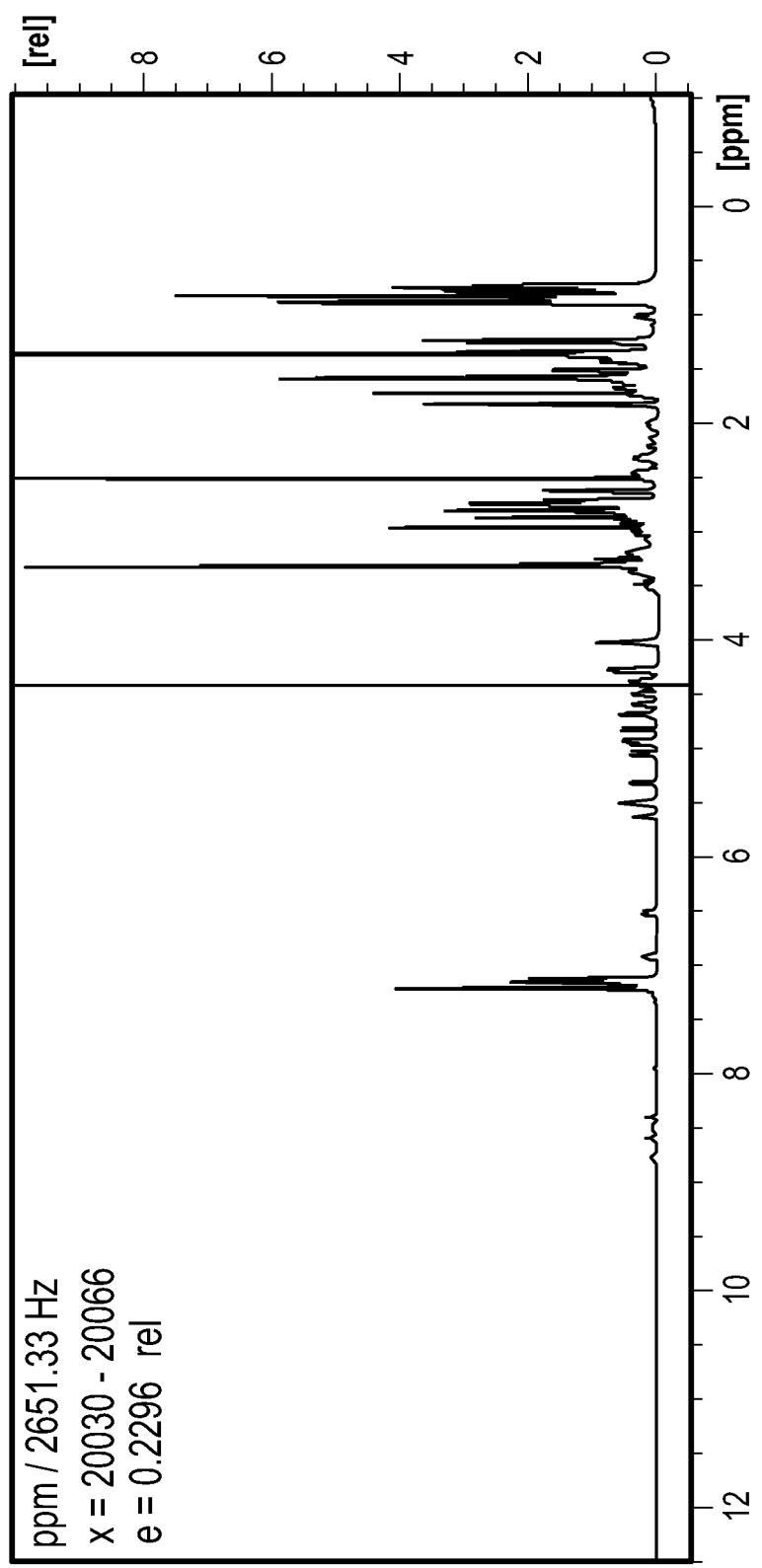
FIG. 15 is a $^1$H NMR spectrum Compound 93 in $d_6$-DMSO.

To a solution of kulo-2 (48 mg, 58 µmol) in DCM (5 mL) was added DMAP (6 mg, 50 µmol), chloro p-nitrophenyl-formate (160 mg, 793 µmol) and diisopropylethylamine (0.5 mL). The reaction mixture was stirred for 4 h at rt, then diluted with ethyl acetate and washed with 10% citric acid solution. The aqueous layer was extracted with ethyl acetate and the combined organic layer was washed with sodium bicarbonate solution and brine, then dried over $NaSO_4$ and concentrated in vacuo. The crude material was subjected to column chromatography to yield an intermediate carbonate (intermediate carbonate 1B, also used in Example 22). The intermediate carbonate (40 mg, 37.8 µmol) was then dissolved in DCM (1 mL) and added 26 mg of tert-butyl methyl(2-(methylamino)ethyl)carbamate and diisopropyl-ethylamine (50 µL). After stirring overnight, the reaction mixture was diluted with ethyl acetate, washed with 10% citric acid solution, $NaHCO_3$ solution and brine, then dried over NaSO$_4$ and concentrated in vacuo. The crude material was subjected to column chromatography to isolate 32 mg (31 μmol) of Compound 93 as a white solid. HRMS (ESI): m/z 1040.6387 [M+H]$^+$. Compound 93 was characterized by $^1$H NMR, as shown in FIG. 15.

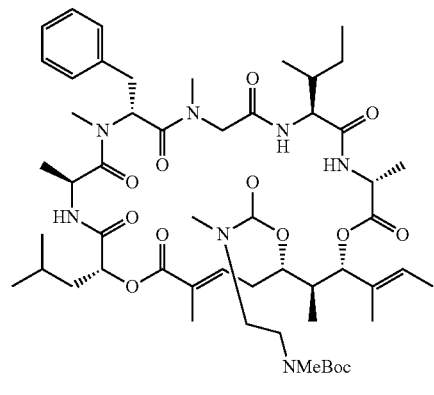

Compound 93

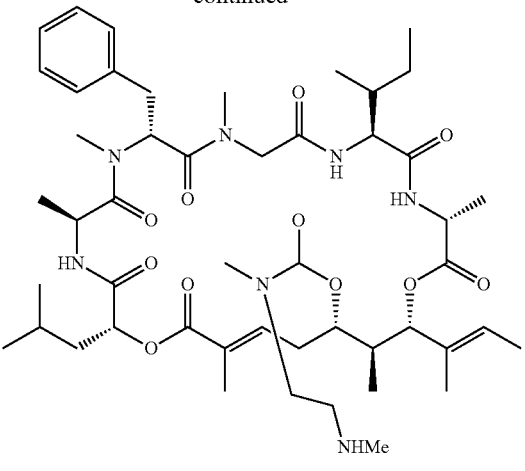

VI-2

To a solution of Compound 93 (48 mg, 46 μmol) in DCM (3 mL) was added trifluoroacetic acid (0.3 mL) at 0° C., and the reaction mixture was stirred overnight at the same temperature. The volatile material was removed by blowing with air to afford compound 75 (VI-2), which is directly subject to the next step.

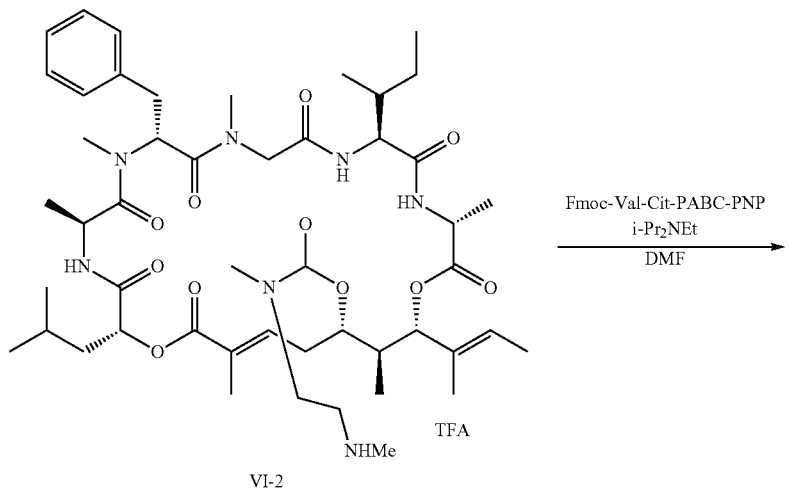

VI-2

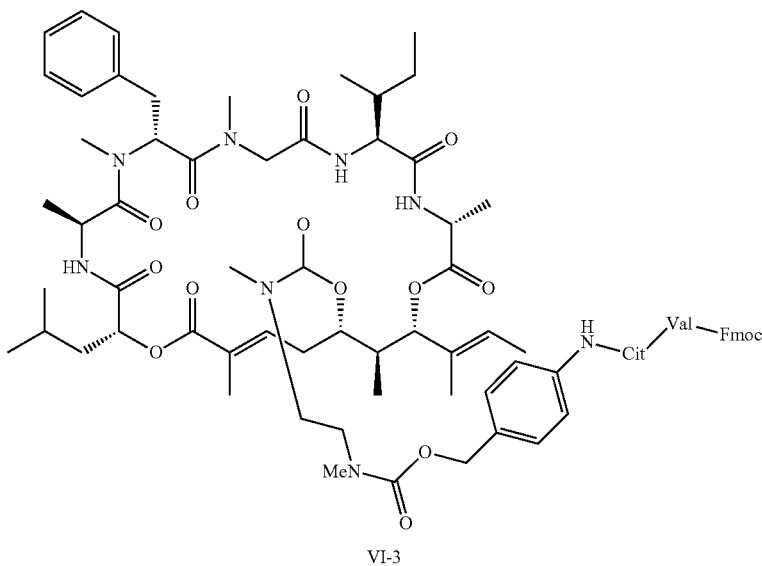

VI-3

The crude material from the previous step (46 µmol) was dissolved in DMF (5 mL). To the solution was added 35 mg (46 µmol) of Fmoc-Val-Cit-PABC-PNP and diisopropylethylamine (0.1 mL). The reaction mixture was stirred for overnight and 2 ml of 10% citric acid solution was added. The volatile material was removed in vacuo, and the residue was dissolved in ethyl acetate and 10% citric acid solution. The aqueous phase was extracted in ethyl acetate and the combined organic phase was washed with $NaHCO_3$ solution and brine, then dried over $NaSO_4$ and concentrated in vacuo. The residue was subjected to column chromatography to afford 57 mg of compound VI-3 (36 µmol, 78% yield over 2 steps) as a white solid.

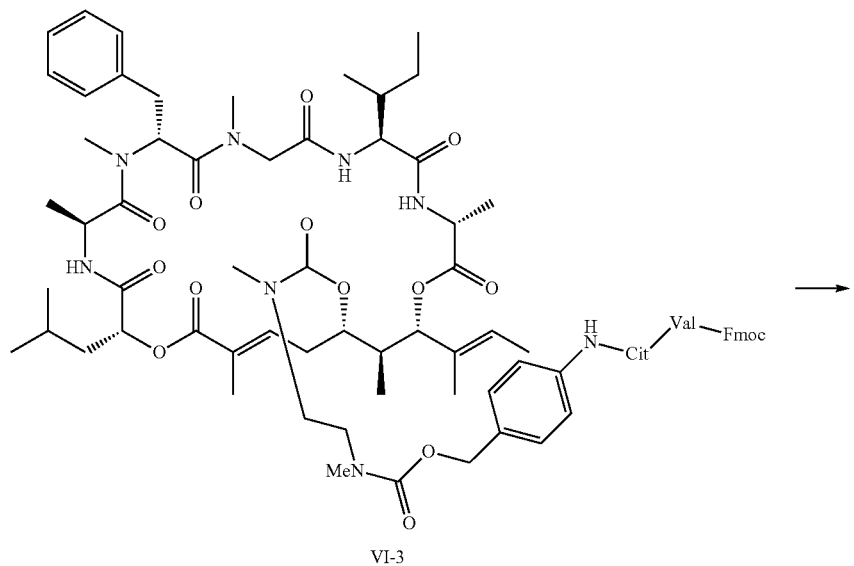

VI-3

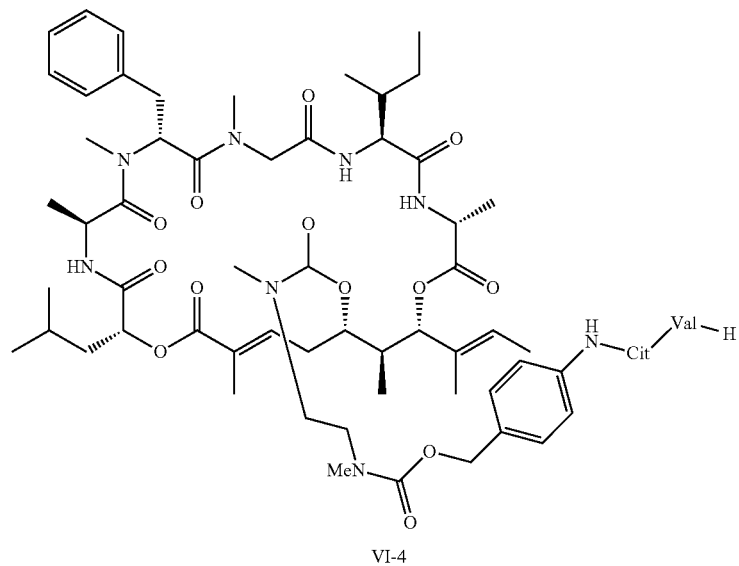

VI-4

To compound VI-3 (56 mg, 36 µmol) in MeCN (1 mL) was added diethylamine (0.1 mL), and the reaction was stirred for 6 h. The volatile material was removed in vacuo, and the residue was subjected to column chromatography to afford 22 mg of compound VI-4 (16 µmol, 44% yield) as a white solid.

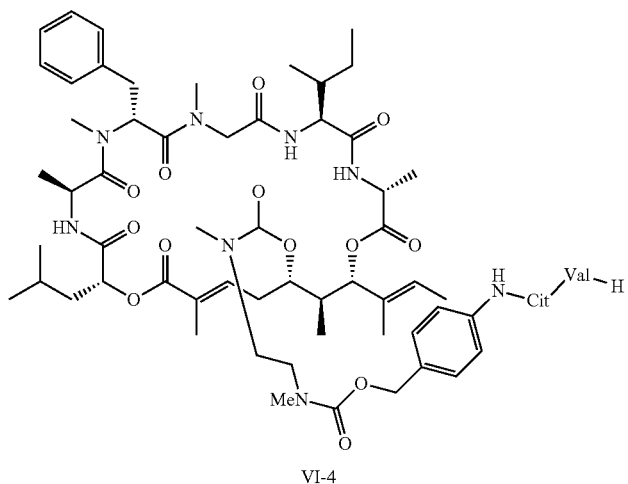

VI-4

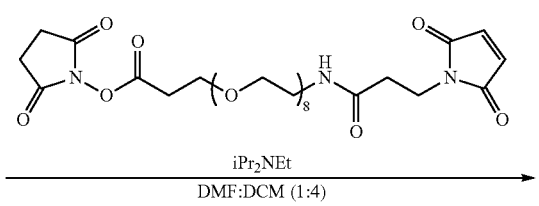

Conjugate L10

Figure 16:
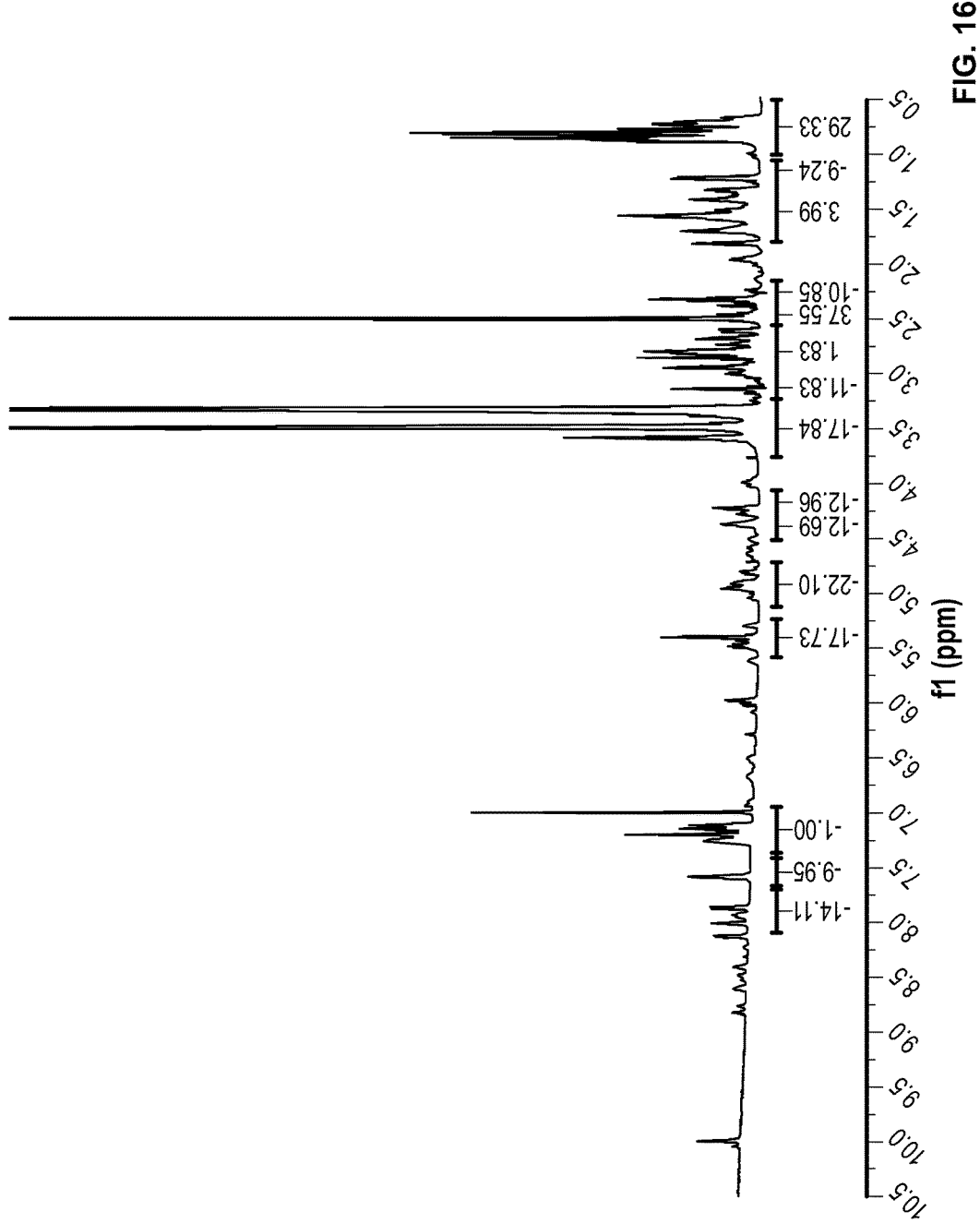
FIG. 16 is a $^1$H NMR spectrum Conjugate L10 in DMSO-d6.
Figure 17:
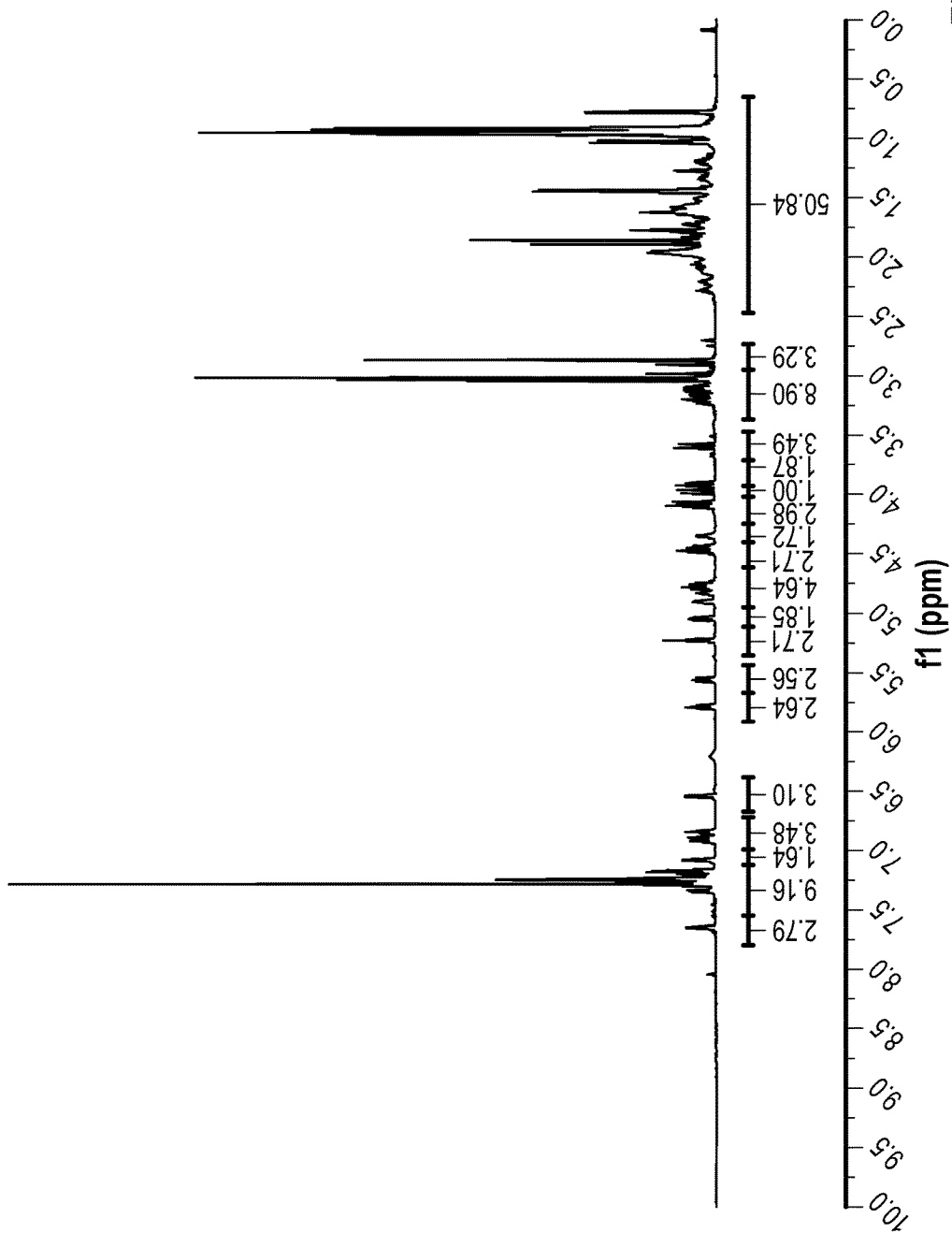
FIG. 17 is a $^1$H NMR spectrum of Compound 86 in $CDCl_3$.
Figure 18:
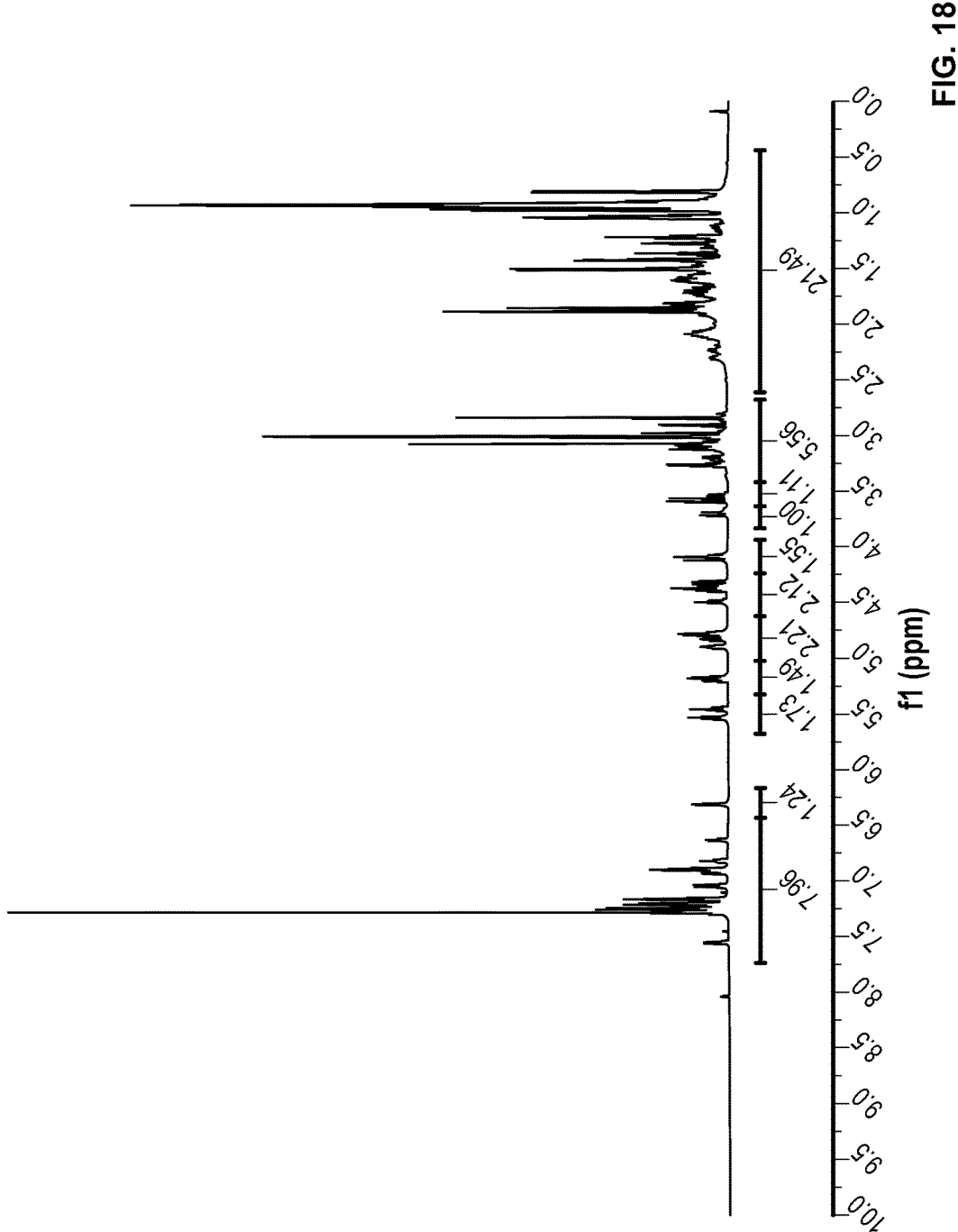
FIG. 18 is a $^1$H NMR spectrum of Compound 87 in $CDCl_3$.
Figure 19:
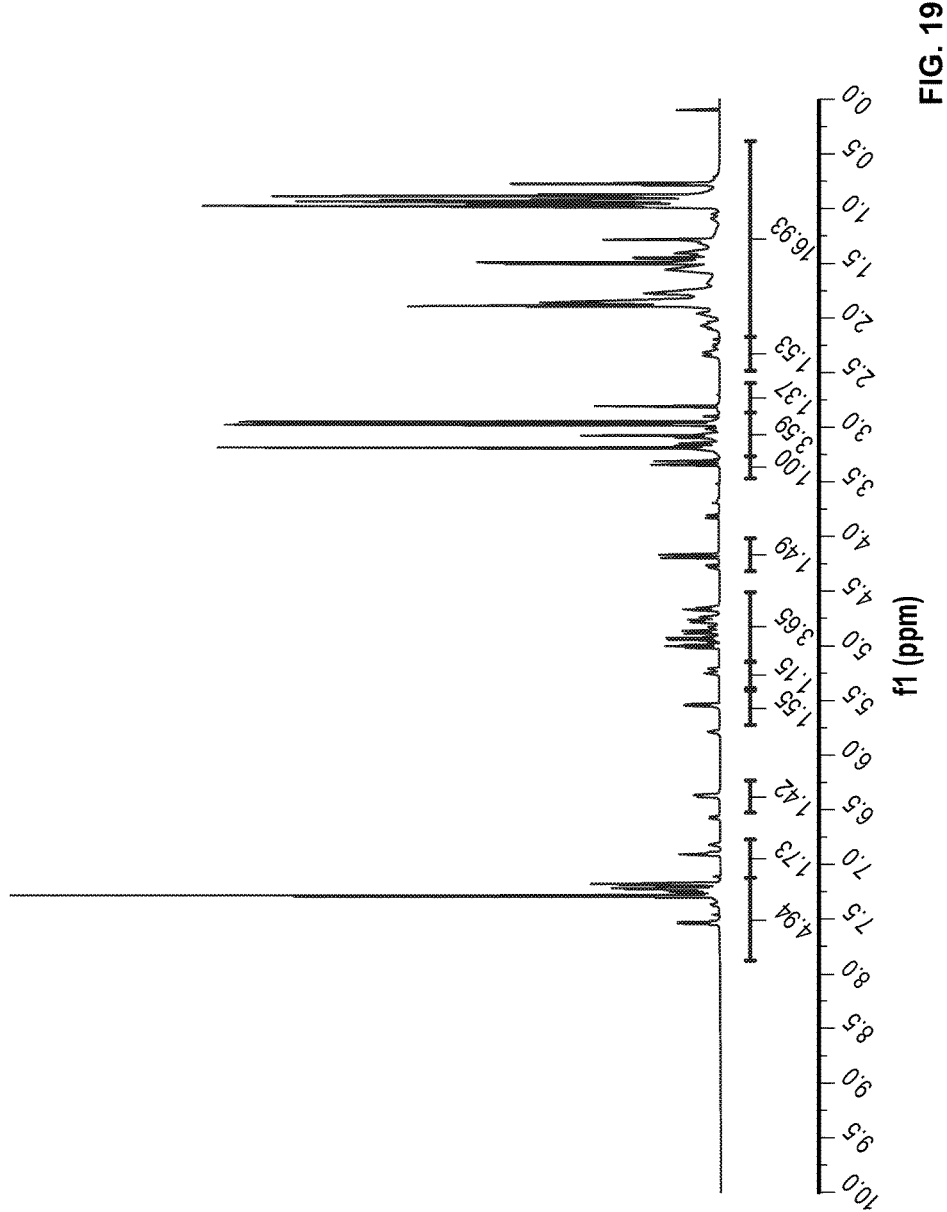
FIG. 19 is a $^1$H NMR spectrum of Compound 88 in $CDCl_3$.
Figure 20:
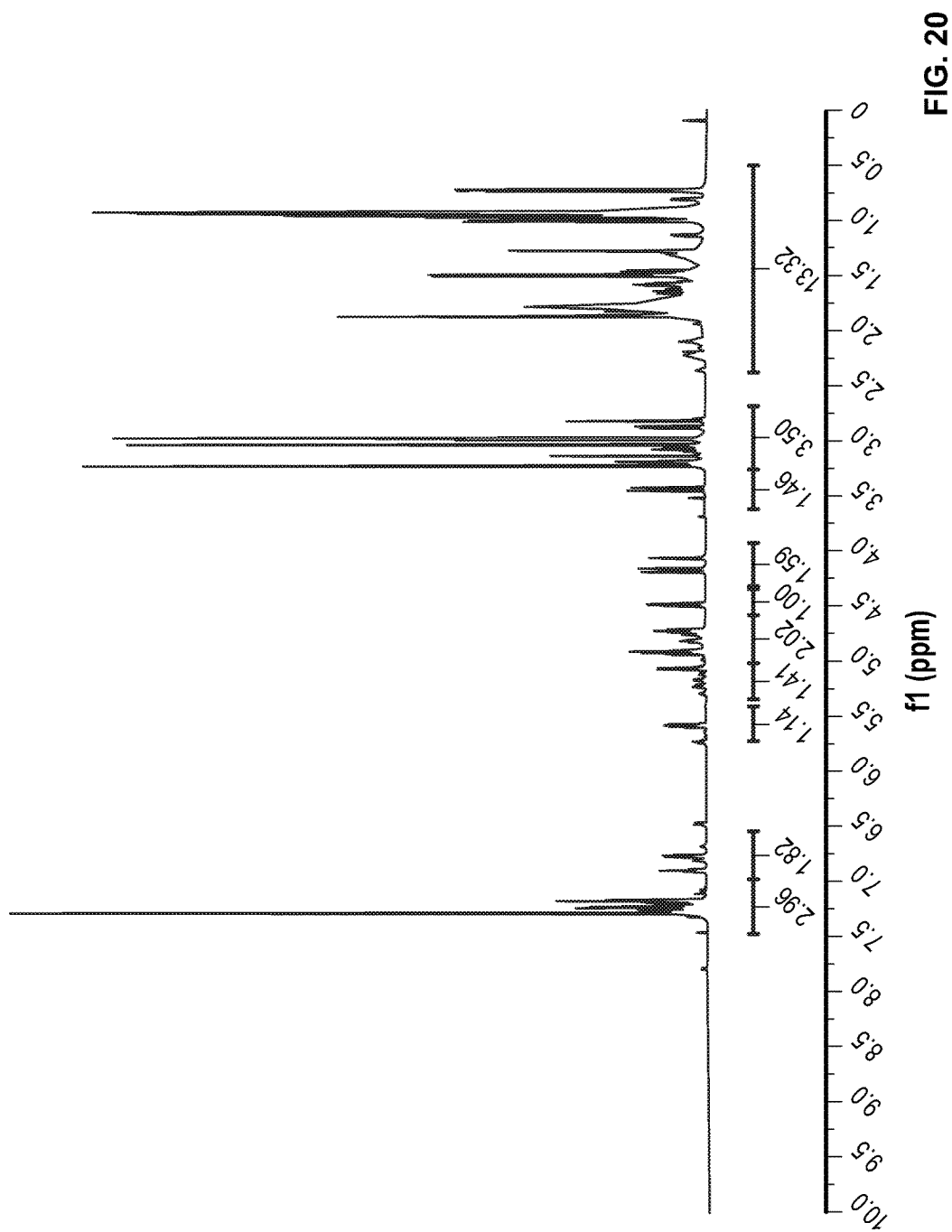
FIG. 20 is a $^1$H NMR spectrum of Compound 89 in $CDCl_3$.
Figure 21:
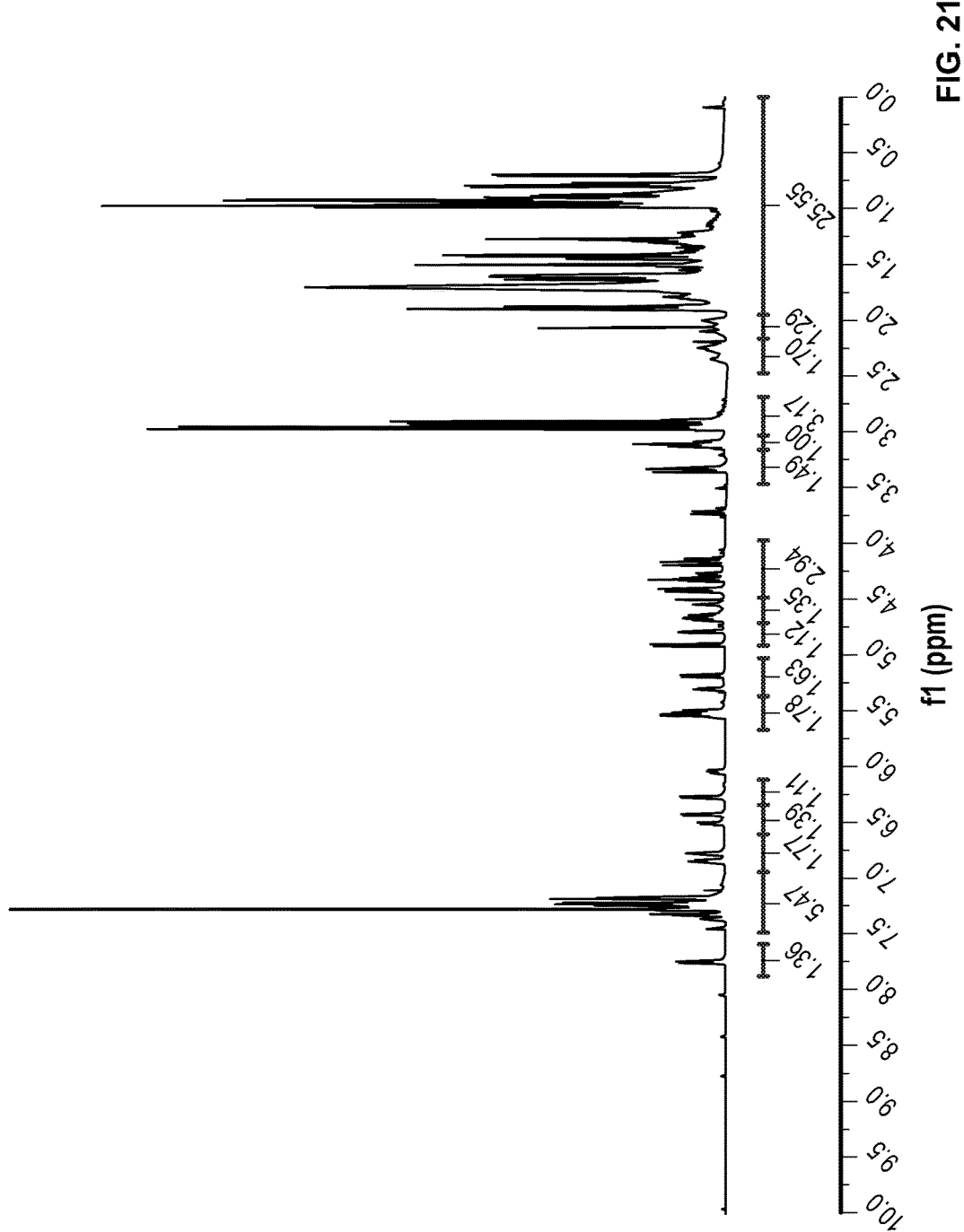
FIG. 21 is a $^1$H NMR spectrum of Compound 90 in $CDCl_3$.
Figure 22:
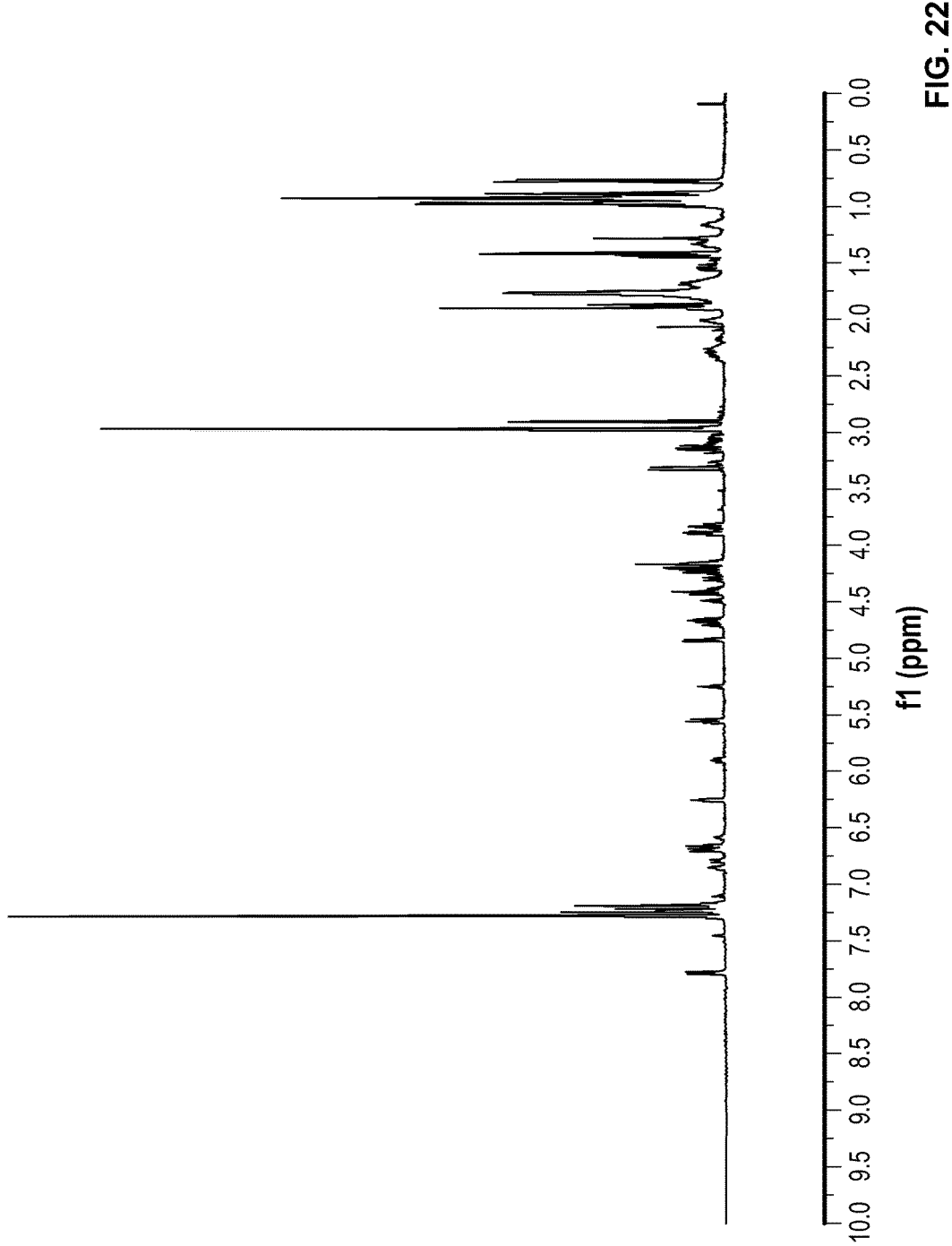
FIG. 22 is a $^1$H NMR spectrum of Compound 91 in $CDCl_3$.

To a solution of compound VI-4 (22 mg, 16 μmol) in DCM:DMF (1:4, 1 mL) was added 22 mg of maleimide (33 μmol) and diisopropylethylamine (30 μl, 160 μmol) at rt. The reaction mixture was stirred for 48 h at rt, and the volatile material was removed in vacuo. The residue was dissolved in MeCN/H$_2$O (10 mL) and subjected to reverse phase HPLC followed by lyophilization to afford two isomers F1 (1.6 mg, 0.83 μmol) and F2 (Conjugate L10, 1.3 mg, 0.67 μmol) as a white solid. Conjugate L10 was characterized by $^1$H NMR, as shown in FIG. 16.

Example 12

Synthesis of Compounds 82-84

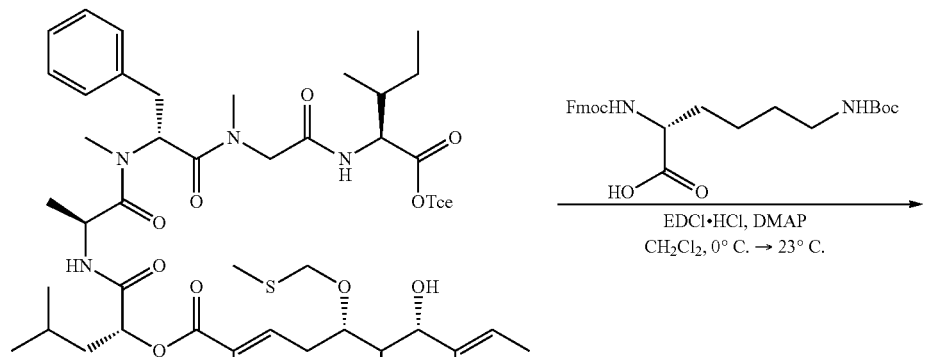

VII-1

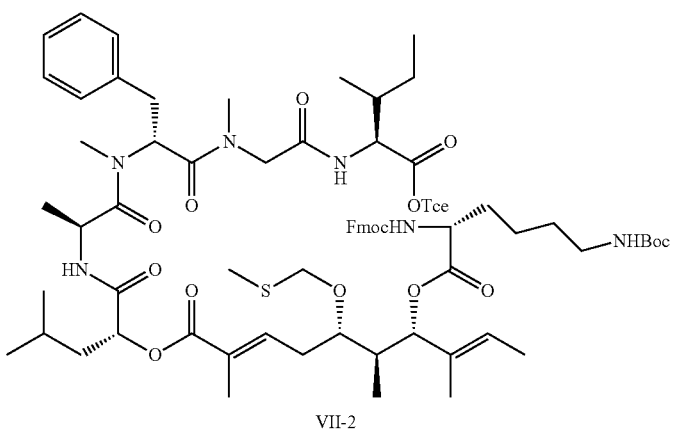

VII-2

A vial was charged with 20 mg of VII-1, and CH$_2$Cl$_2$ (0.21 mL) and N(α)-Fmoc-D-N(β)-Boc-lysine (19.6 mg, 2 equiv) were added. DMAP (2.6 mg, 1.0 equiv) was added, followed by EDCI.HCl (8.1 mg, 2.0 equiv). The reaction mixture was stirred for 12 h. The reaction was then diluted with EtOAc (5 mL) and quenched with 1 M HCl (5 mL). The aqueous layer was extracted with EtOAc (3×10 mL). The combined organic layers were washed with sat. aq. NaHCO$_3$ and brine and dried over Na$_2$SO$_4$ to afford compound VII-2.

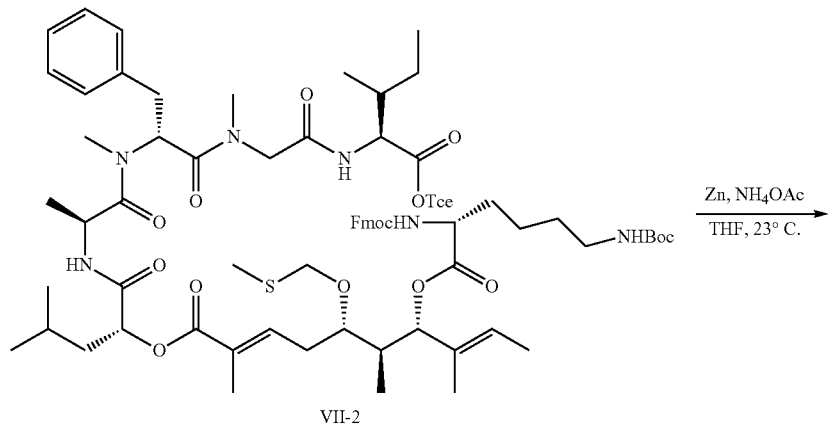

VII-2

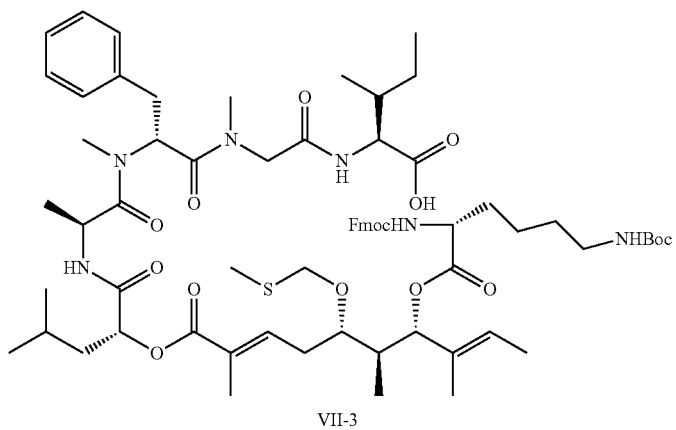

VII-3

TCE ester VII-2 (22.6 mg) was dissolved in THF (0.8 mL) and 1 M NH$_4$Ac (0.16 mL). Zn (73 mg) was then added and the reaction was stirred for 12 hours. The reaction was filtered over celite, and the organics were washed with 10% citric acid, water and brine, and dried over Na$_2$SO$_4$ to afford compound VII-3.

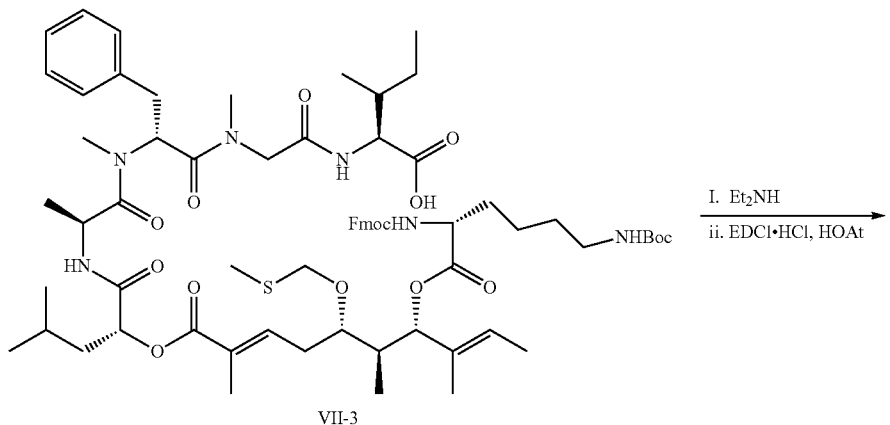

VII-3

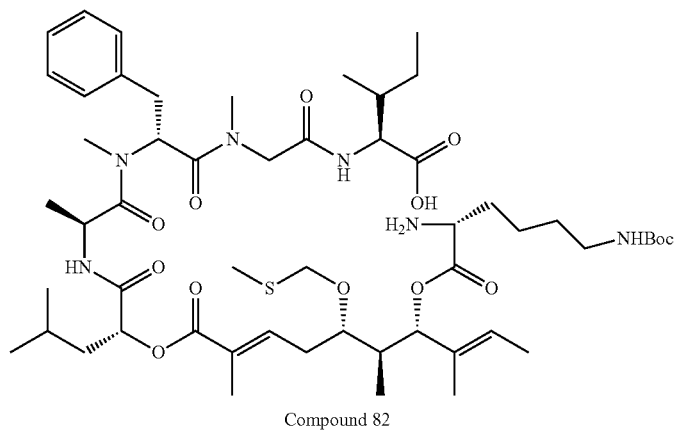

Compound 82

The resulting residue from the previous step was dissolved in CH$_3$CN (0.750 mL), and diethyl amine was added (0.08 mL). After three hours, the reaction was concentrated, and the non-polar compounds were washed away with pentanes. The resulting residue was then dissolved in CH$_2$Cl$_2$ (15.3 mL) and DMF (1.7 mL). HOAt (23.2 mg) was added, followed by EDCI.HCl (33 mg). The reaction was stirred for 22 hours and quenched with NH$_4$Cl. The aqueous layer was extracted with EtOAC and the combined organics were washed with brine and dried over Na$_2$SO$_4$. The product was purified by Prep TLC using EtOAC to afford 1 mg of Compound 82. ESI HRMS: m/z 1043.6108 [M+H]$^+$.

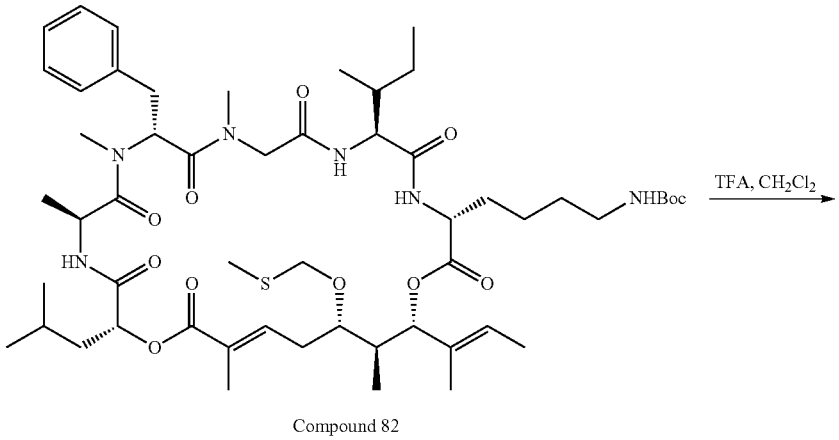

Compound 82

-continued

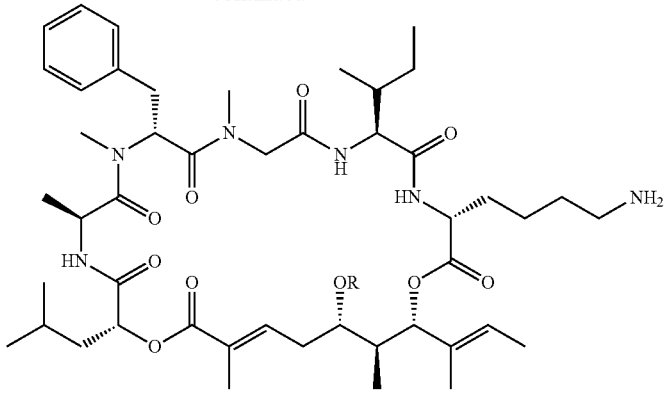

Compound 83: R = MTM
Compound 84: R = H

Compound 82 was dissolved in CH₂Cl₂ (0.1 mL), and TFA (0.007 mL) was added. After 2 h, the reaction was concentrated and the residue was purified via HPLC to afford Compound 83 and Compound 84.

Example 13

Synthesis of Various Compounds

Certain compounds were synthesized using a procedure similar to that described in Example 5 (compounds V-10 through V-13).

Table 6 shows the structures of certain TCE-protected hydroxyl acid starting materials. Table 7 shows combinations of protected hydroxyl acid and amino acid for various compounds. Table 8 shows the quantity of the final macro-crystallization products and the observed MS (ESI HRMS) data. FIGS. 17-22, 24, 25, and 28 show $^1$H NMR spectra for certain compounds.

TABLE 6

| Name | Structure |
|------|-----------|
| TCE-1 | 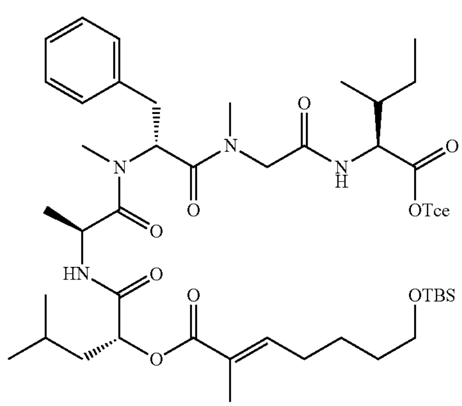 |

TABLE 6-continued

| Name | Structure |
|---|---|
| TCE-2 | 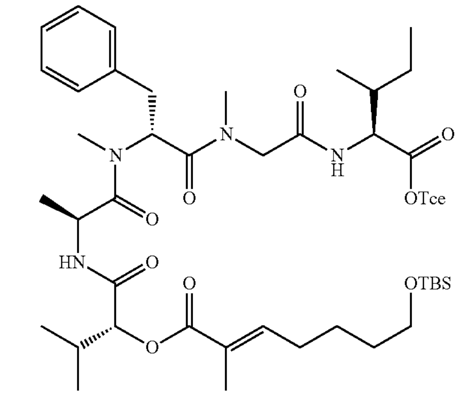 |
| TCE-3 | 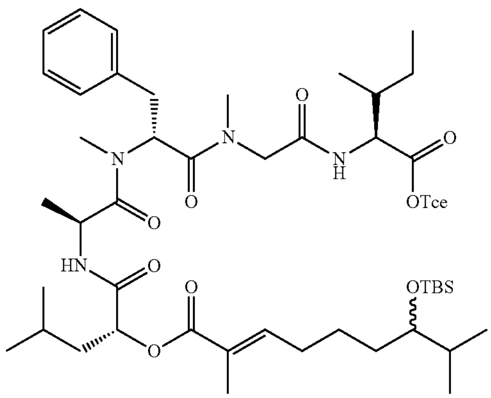 |
| TCE-4 | 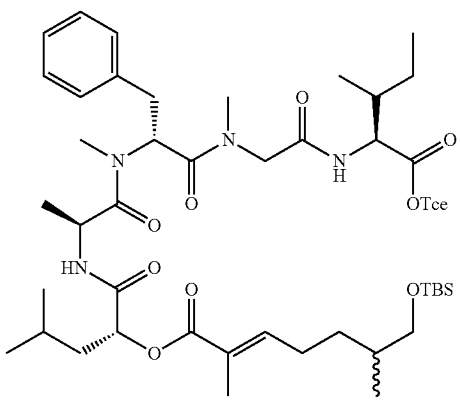 |
| TCE-5 | 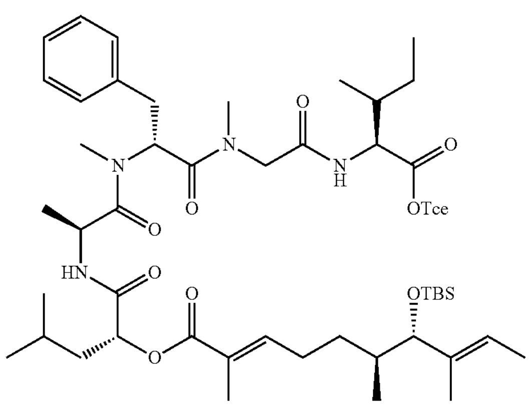 |

TABLE 6-continued

| Name | Structure |
|---|---|
| TCE-6 | (structure shown) |

TABLE 7

| Amino Acids | TCE-1 | TCE-2 | TCE-3 | TCE-4 | TCE-5 | TCE-6 |
|---|---|---|---|---|---|---|
| D-Abu | Cmpd. 77 | Cmpd. 80 | | | | |
| L-Abu | Cmpd. 78 | | | | | |
| Gly | Cmpd. 79 | | | | | |
| Aib | | Cmpd. 81 | | | | |
| D-Ala | | | Cmpd. 86 | Cmpd. 91 | Cmpd. 90 | Cmpd. 96 |
| | | | Cmpd. 87 | Cmpd. 92 | | |
| N-Me-D-Ala | | | Cmpd. 88 | | | |
| | | | Cmpd. 89 | | | |
| L-Ala | | | | | | Cmpd. 97 |
| N-Me-L-Ala | | | | | Cmpd. 100 | |

Cmpd. = Compound;
D-Abu = D-2-aminobutyric acid;
L-Abu = L-2-aminobutyric acid;
Gly = glycine;
Aib = 2-aminoisobutyric acid;
D-ala = D-alanine;
N-Me-D-Ala = N-methyl-D-alanine;
L-Ala = L-alanine;
N-Me-L-Al = N-methyl-L-alanine

TABLE 8

| Compound | Quantity (mg) | ESI HRMS m/z ([M + H]$^+$) |
|---|---|---|
| 77 | 0.99 | 756.46 |
| 78 | 0.63 | 756.46 |
| 79 | 2.85 | 728.43 |
| 80 | 1.28 | 742.45 |
| 81 | 0.56 | 742.44 |
| 86 | 0.58 | 784.48 |
| 87 | 0.92 | 784.48 |
| 88 | 0.72 | 798.49 |
| 89 | 0.54 | 798.49 |
| 90 | 1.25 | 810.49 |
| 91 | 0.52 | 756.45 |
| 92 | 0.49 | 756.44 |
| 96 | 0.30 | 965.60 |
| 97 | 0.20 | 983.61 |
| 100 | 0.80 | 824.52 |

Example 14

Synthesis of Compound 98

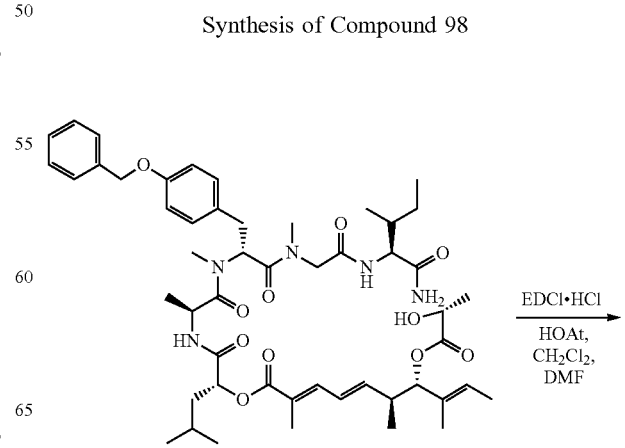

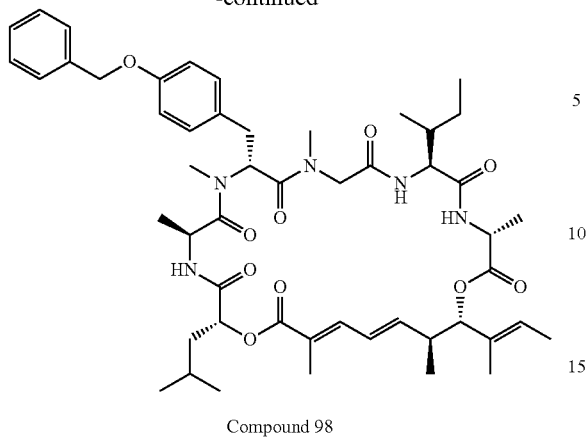

Compound 98

Figure 26:
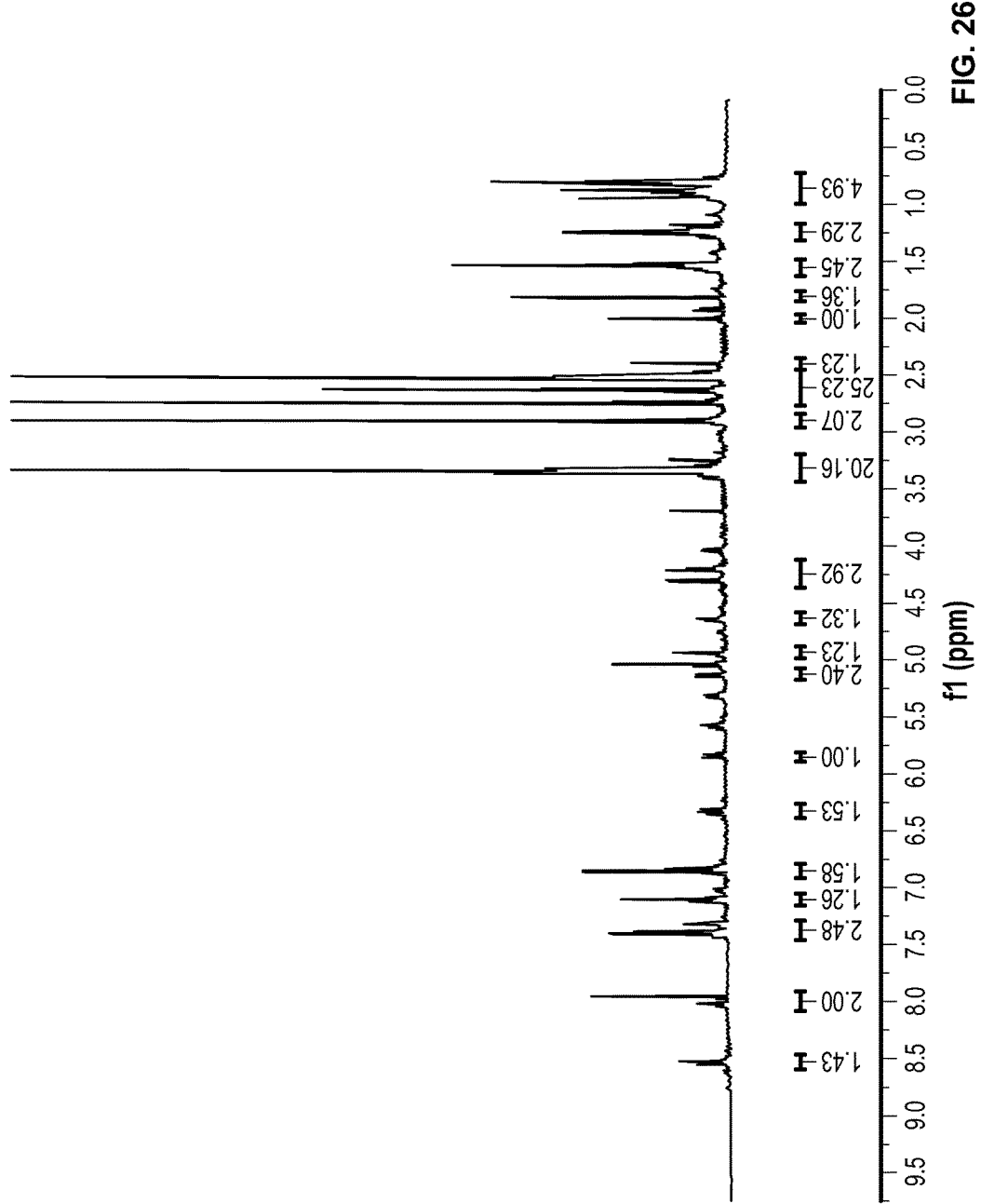
FIG. 26 is a $^1$H NMR spectrum of Compound 98 in DMSO-d6.

Compound 98 was synthesized using the procedure described in Examples 2 and 10. The compound was characterized by $^1$H NMR (FIG. 26) and MS. HRMS (ESI): m/z 914.5332 [M+H]$^+$.

Example 15

Synthesis of Compound 99

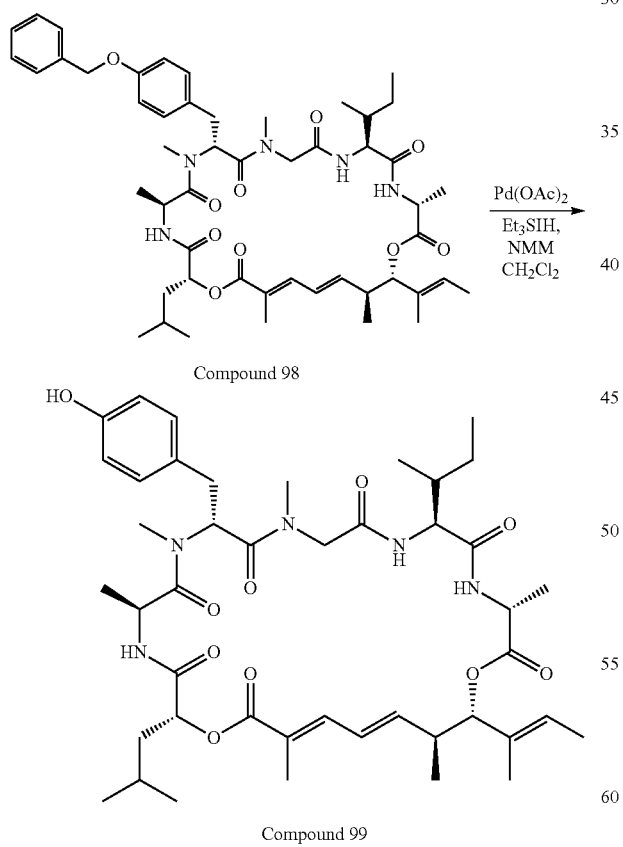

Compound 99

Figure 27:
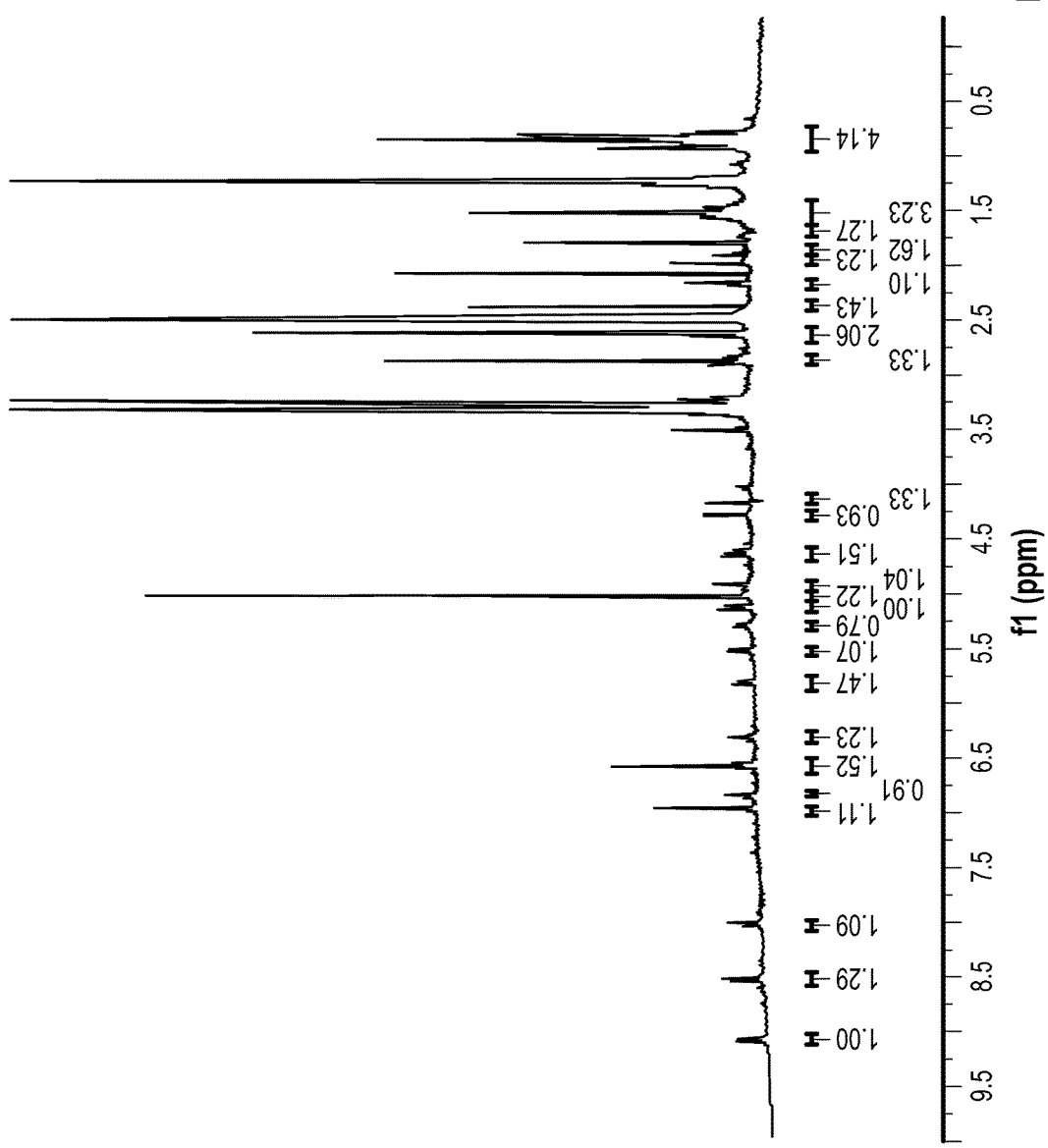
FIG. 27 is a $^1$H NMR spectrum of Compound 99 in DMSO-d6.
Figure 28:
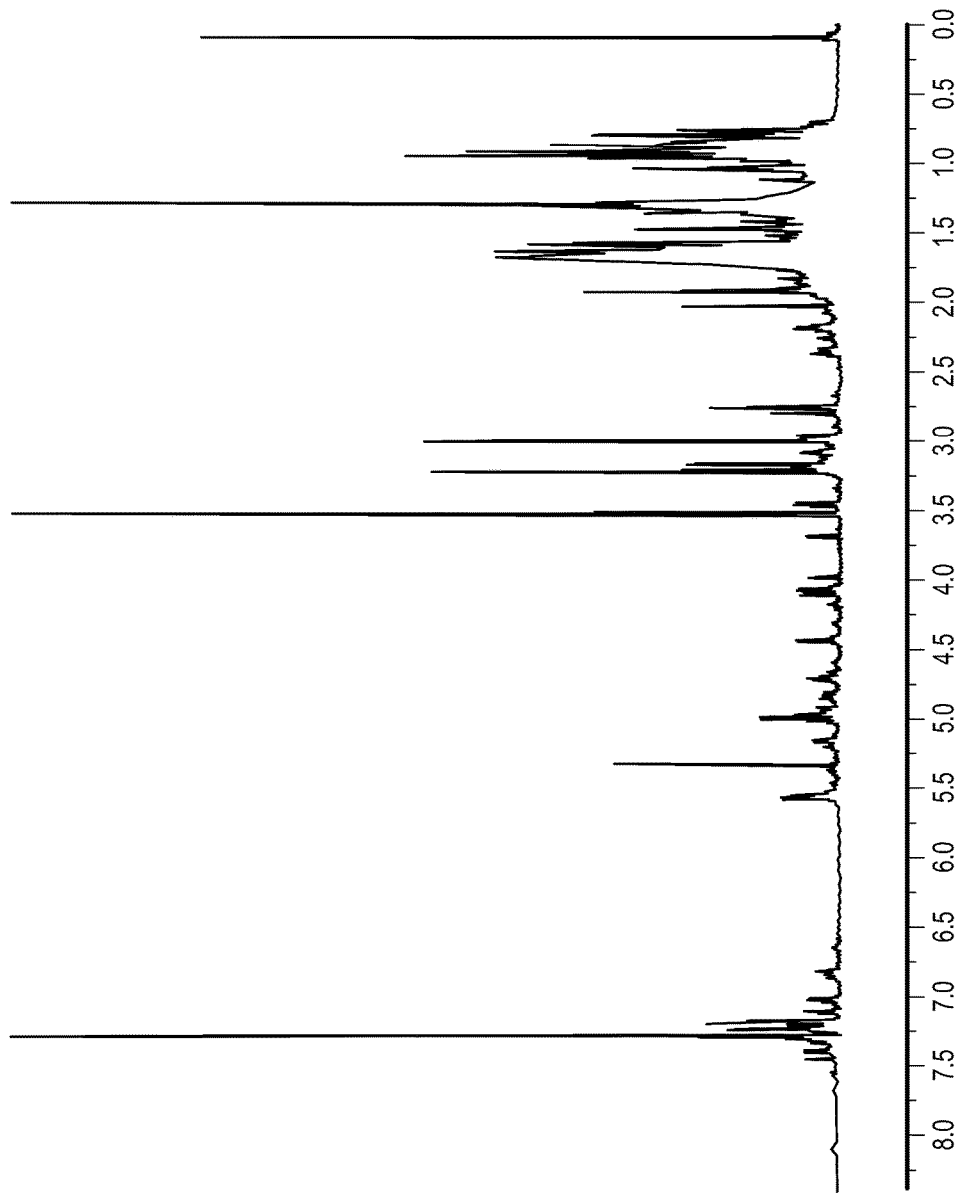
FIG. 28 is a $^1$H NMR spectrum of Compound 100 in $CDCl_3$.

A flame dried vial was charged with palladium(II) acetate (1 mg) and was dissolved in 0.1 mL of degassed dichloromethane. N-methylmorpholine (7.5 µL) was added followed by 1.3 µL of triethylsilane. The mixture was stirred for 15 minutes, and 5.0 mgs of benzyl ether in 0.1 mL of degassed dichloromethane was added. The mixture was tightly sealed with a Teflon cap and stirred over 16 h. The reaction mixture was then diluted with EtOAc and filtered over celite. The mixture was then washed with sat. aq. sodium bicarbonate (10 mL). The aqueous layer was extracted with EtOAc (3×15 mL), washed with brine (20 mL), and dried over sodium sulfate. Purification by HPLC (EtOAc) afforded phenol (1.0 mg). HRMS (ESI): m/z 824.4853 [M+H]$^+$. $^1$H NMR is shown in FIG. 27.

Example 16

Synthesis of Compound 75

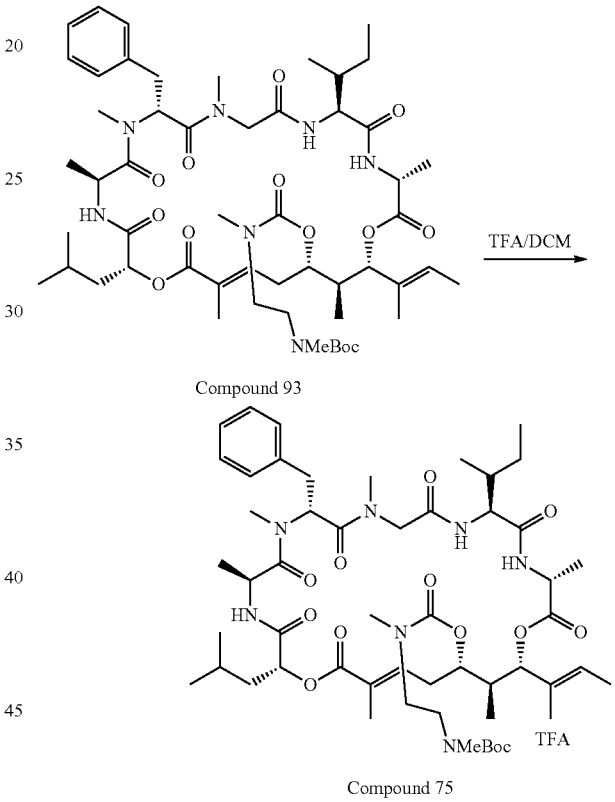

Figure 23:
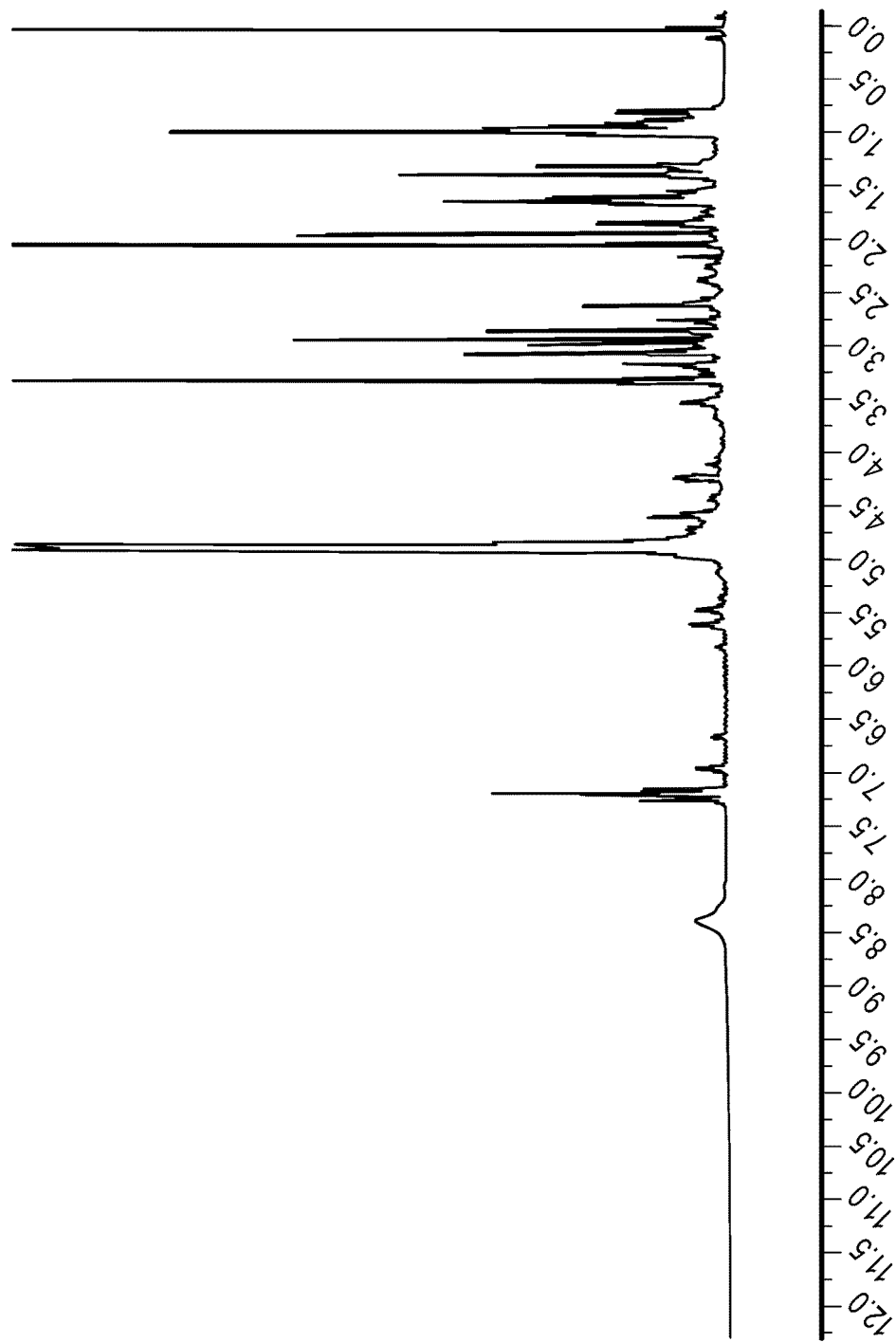
FIG. 23 is a $^1$H NMR spectrum of Compound 75 in $CD_3OD$.
Figure 24:
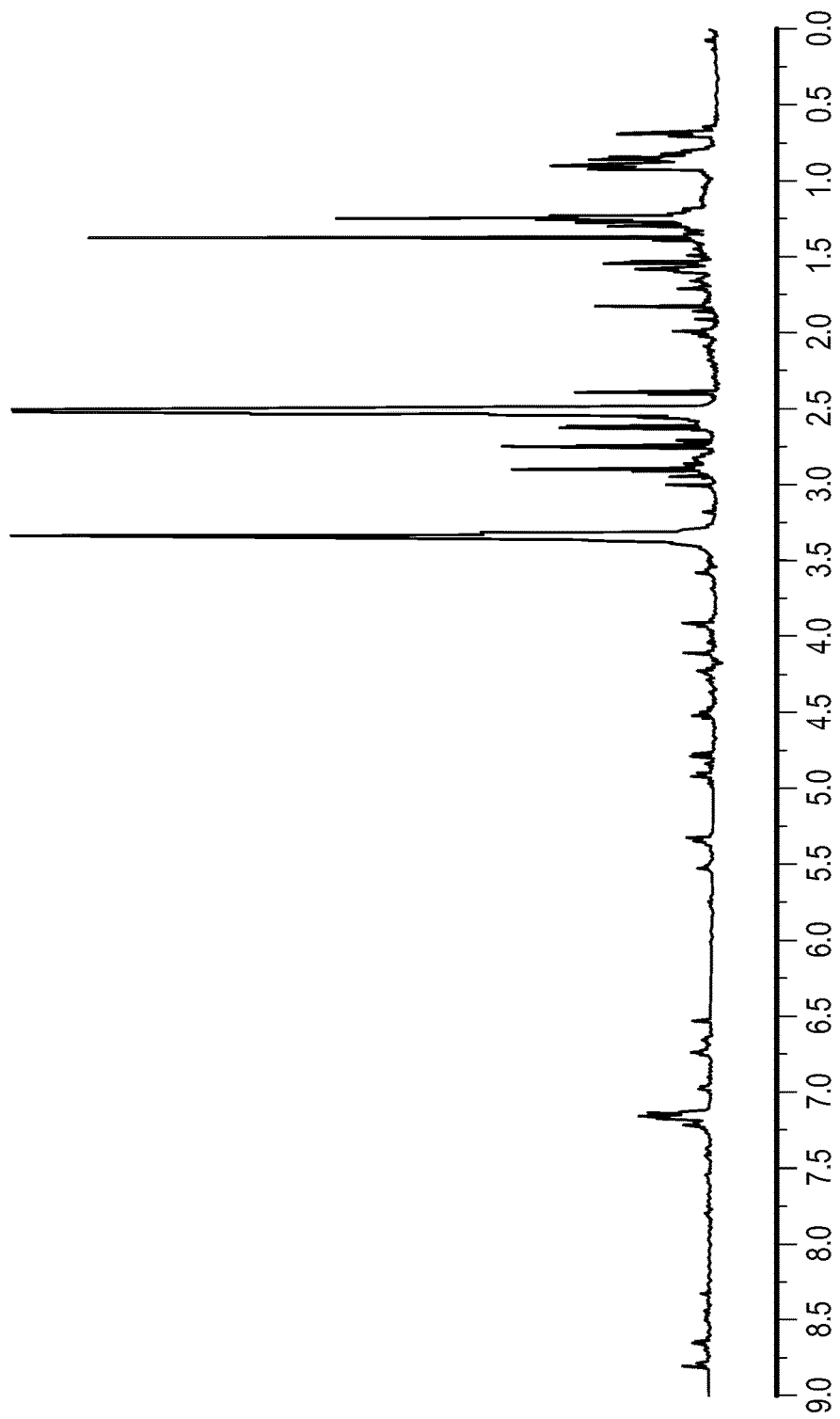
FIG. 24 is a $^1$H NMR spectrum of Compound 96 in DMSO-d6.
Figure 25:
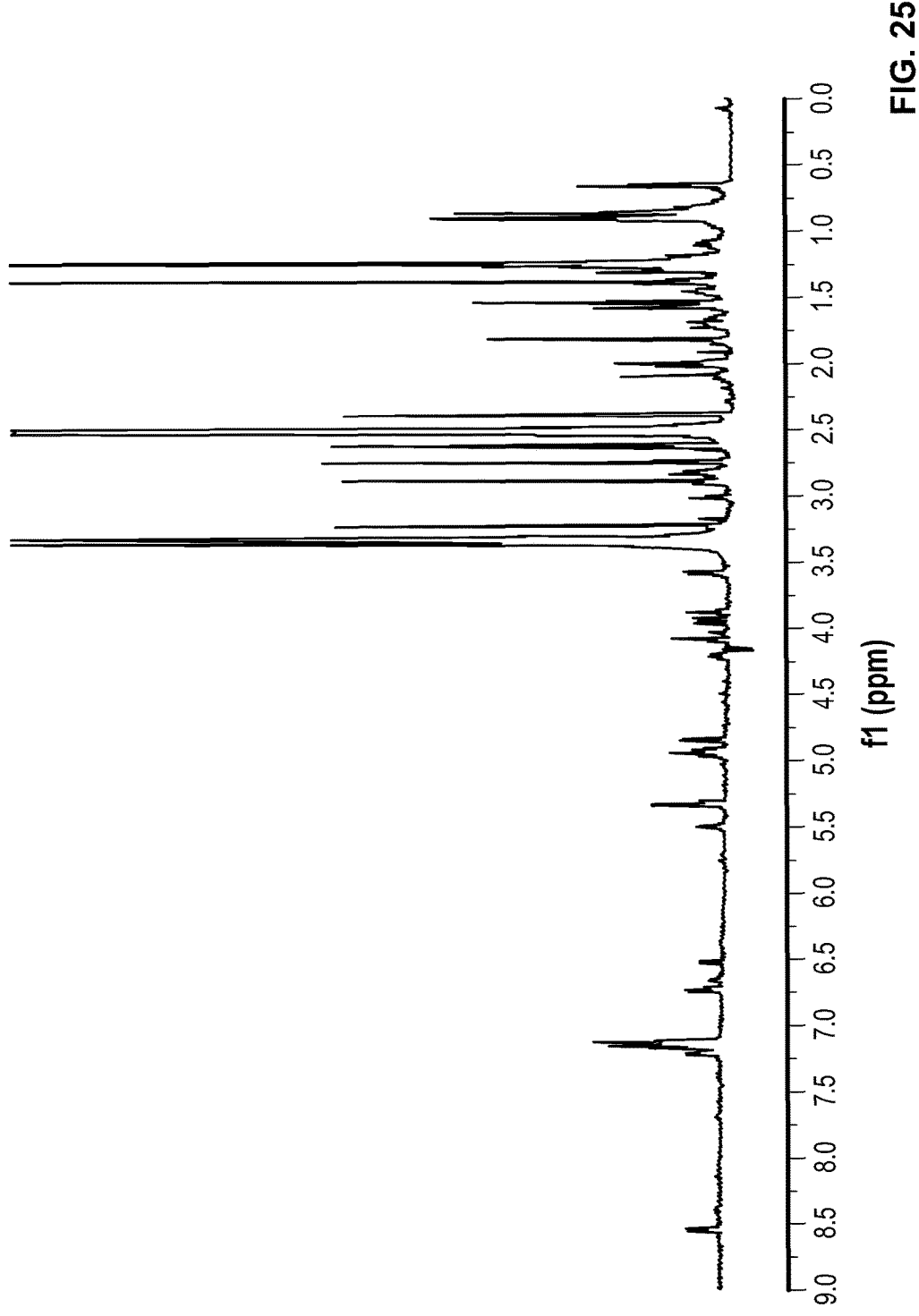
FIG. 25 is a $^1$H NMR spectrum of Compound 97 in DMSO-d6.

To a solution of Compound 93 (32 mg, 31 µmol) in DCM (1 mL) was added trifluoroacetic acid (0.2 mL) at 0° C., and then the reaction mixture was stirred overnight at the temperature. The volatile was removed by blowing with air and the crude material was subjected to RP HPLC to afford 4.0 mg of Compound 75. HRMS (ESI): m/z 940.5714 [M+H]$^+$. The structure was confirmed by $^1$H NMR (FIG. 23).

Example 17

Synthesis of Compounds 105-108

Figure 29:
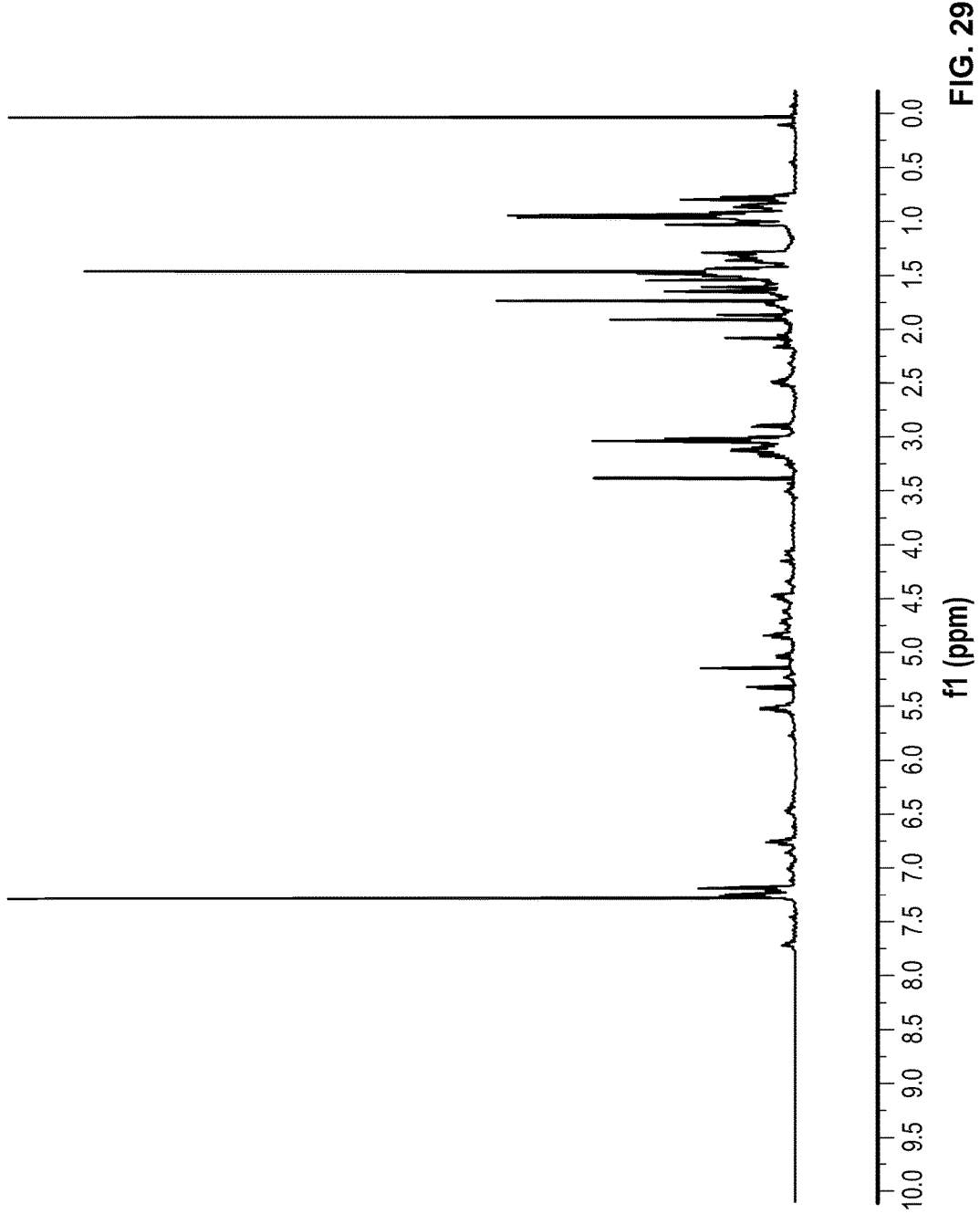
FIG. 29 is a $^1$H NMR spectrum of Compound 105 in $CDCl_3$.
Figure 30:
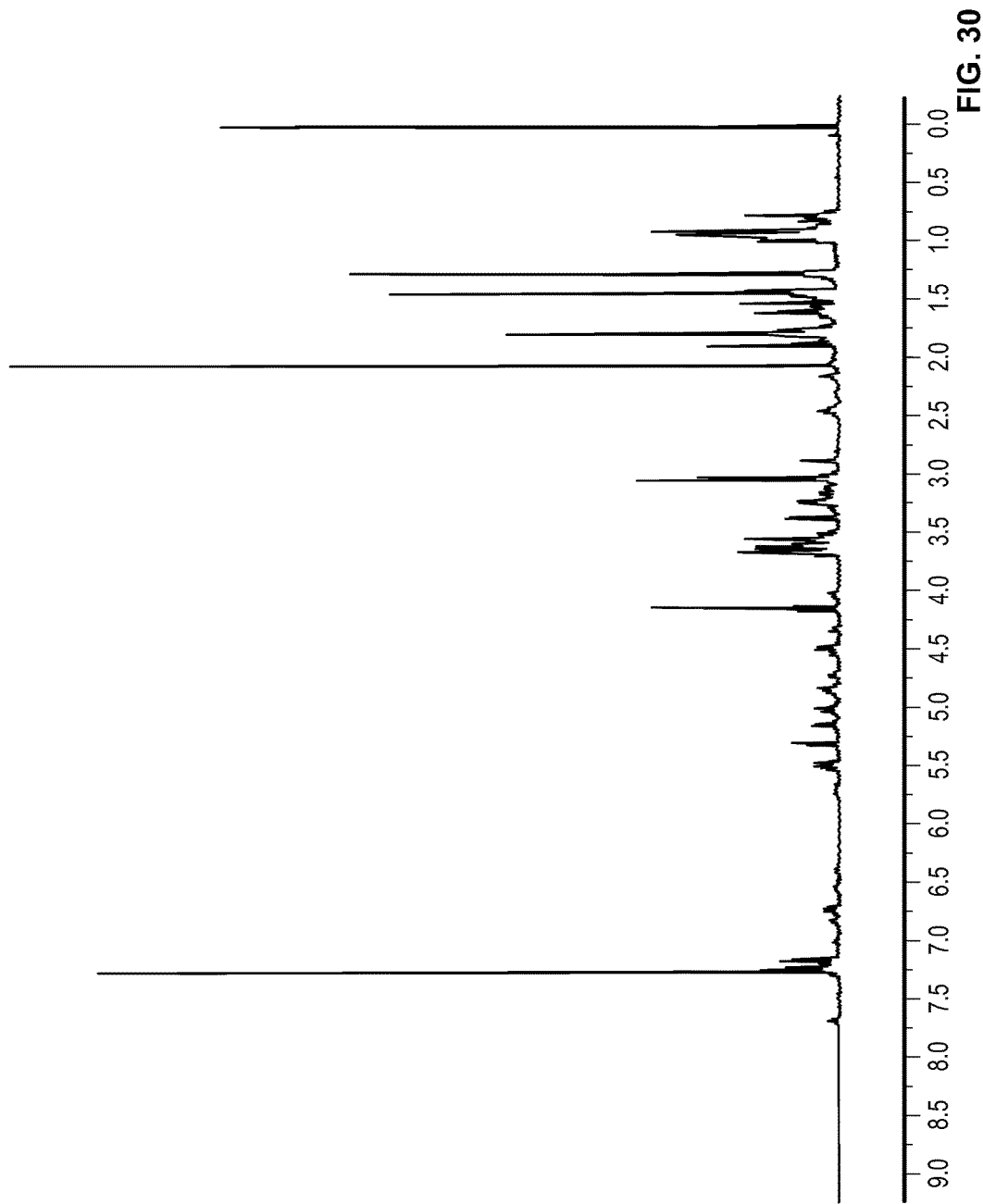
FIG. 30 is a $^1$H NMR spectrum of Compound 106 in $CDCl_3$.
Figure 31:
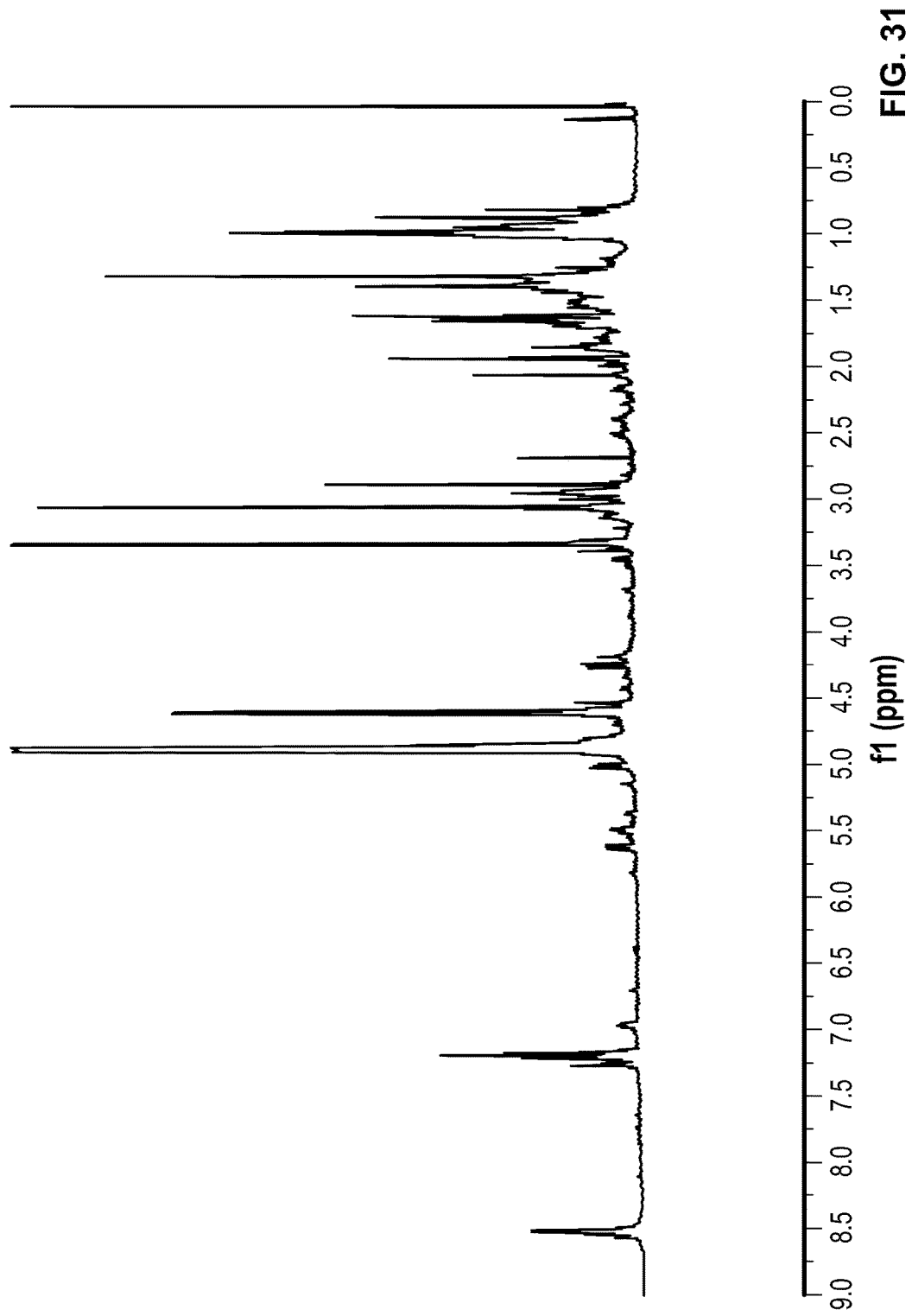
FIG. 31 is a $^1$H NMR spectrum of Compound 107 in $CD_3OD$.
Figure 32:
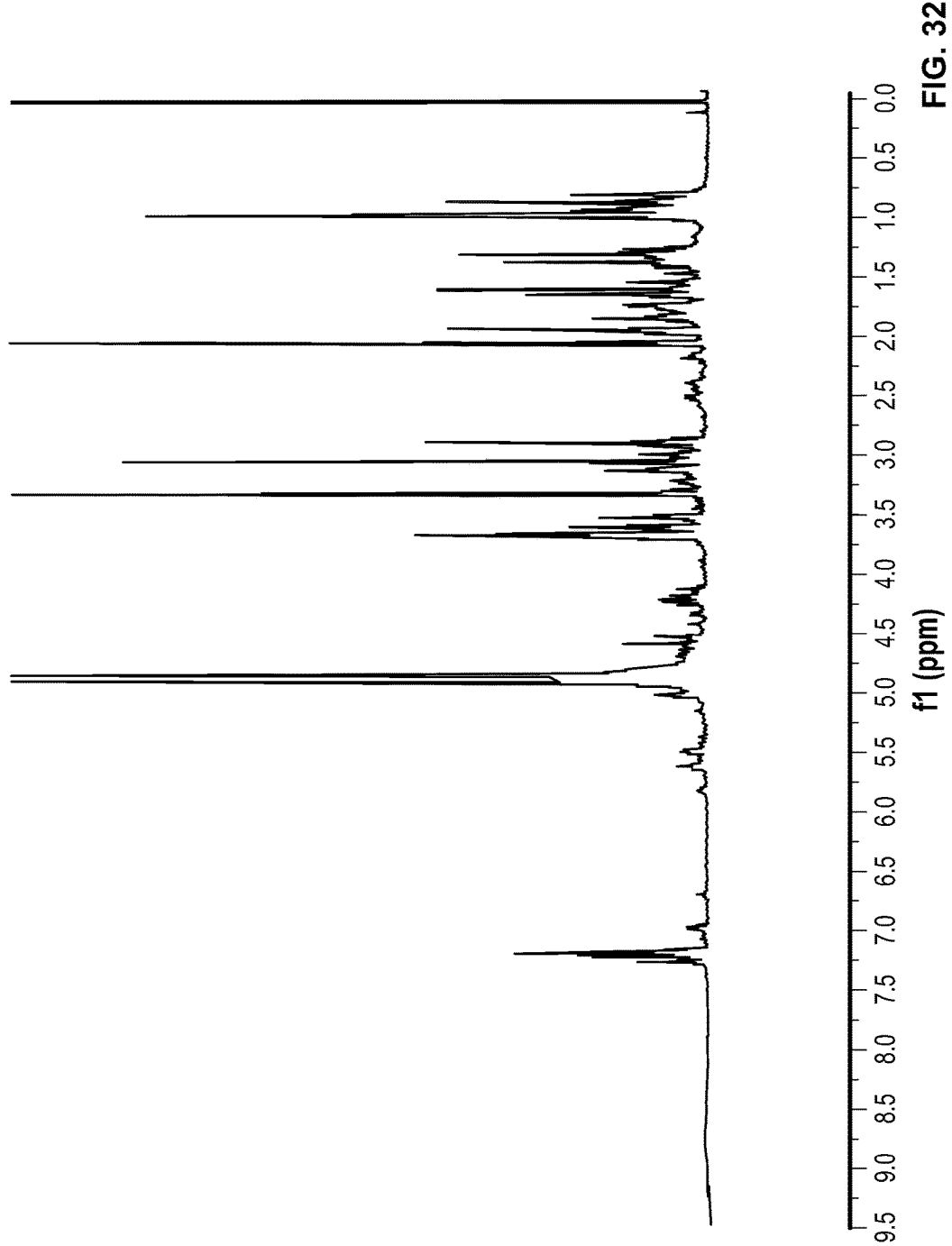
FIG. 32 is a $^1$H NMR spectrum of Compound 108 in $CD_3OD$.

Compounds 105 and 106 were prepared according to the procedure described for Compound 93 (example 11), using the appropriate amino carbamate substrates. $^1$H NMR spectra are shown in FIGS. 29 and 30. HRMS (ESI): m/z 1068.652 [M+H]+ for Compound 105, 1172.699 [M+H]+ for Compound 106.
Compounds 107 and 108 were synthesized from Compounds 105 and 106, respectively, using the procedure described for synthesis of Compound 75. ¹H NMR spectra are shown in FIGS. 31 and 32. HRMS (ESI): m/z 968.6028 [M+H]+ for Compound 107, 1072.648 [M+H]+ for Compound 108.
Example 18
Synthesis of Compound 101
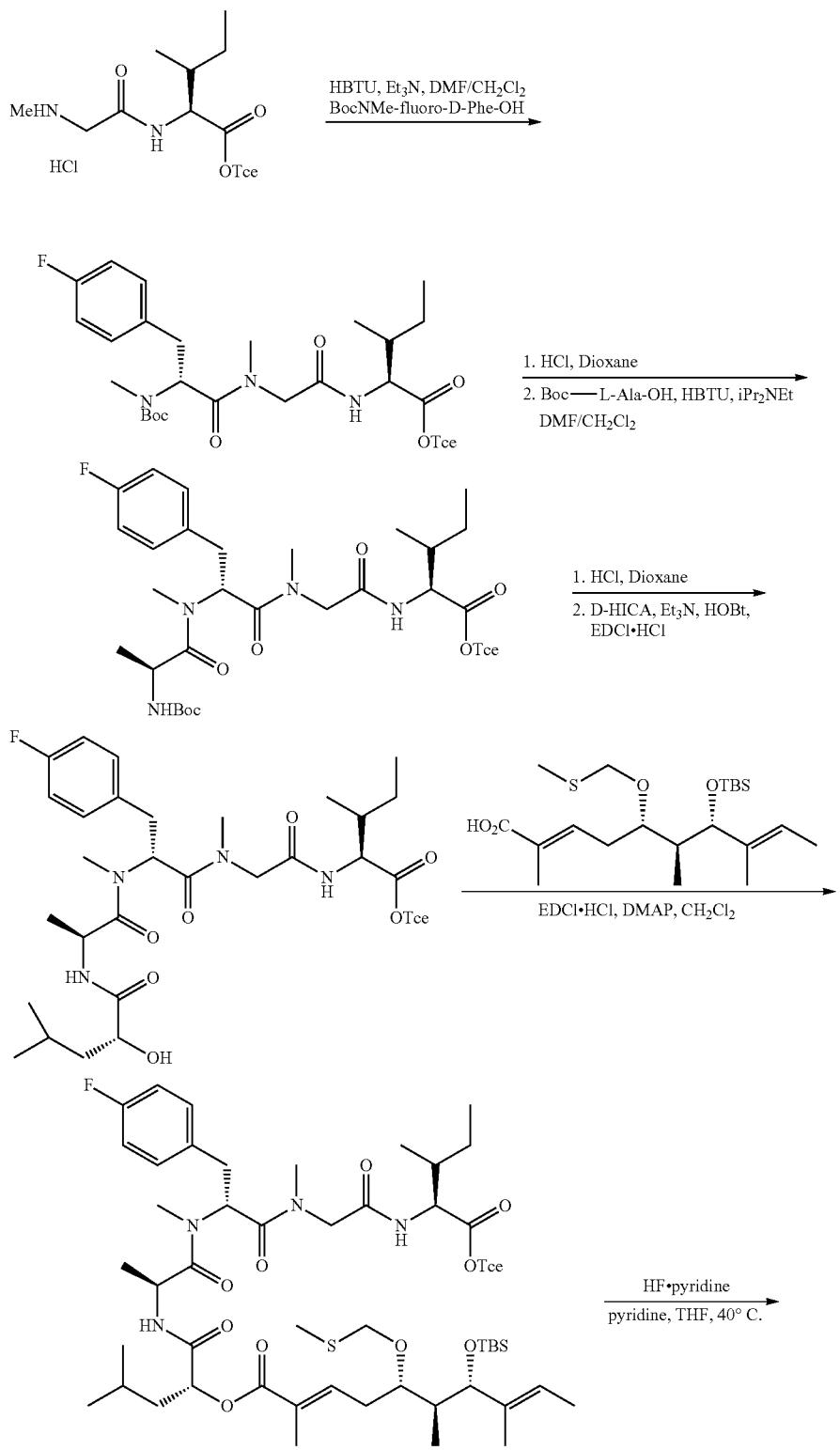

-continued

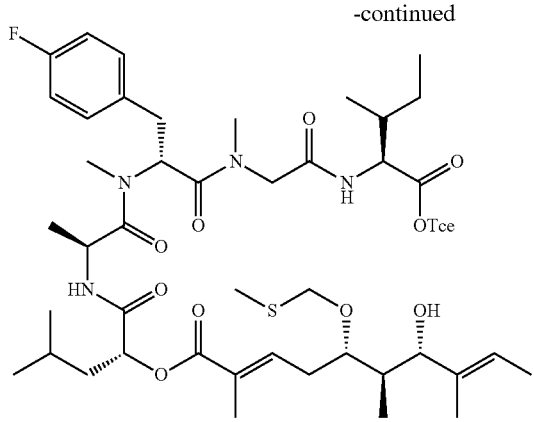 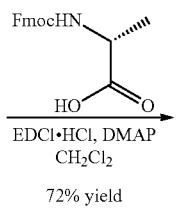

EDCl·HCl, DMAP
CH$_2$Cl$_2$

72% yield

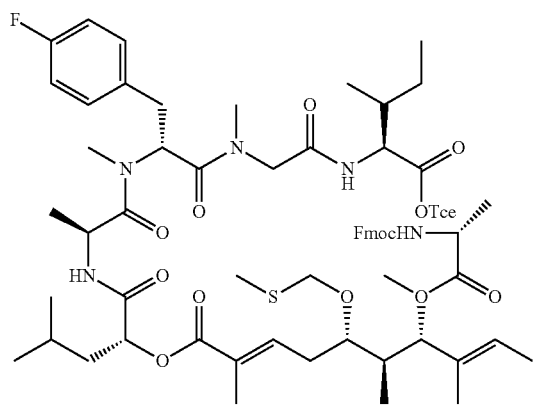 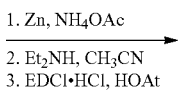

1. Zn, NH$_4$OAc
2. Et$_2$NH, CH$_3$CN
3. EDCl·HCl, HOAt

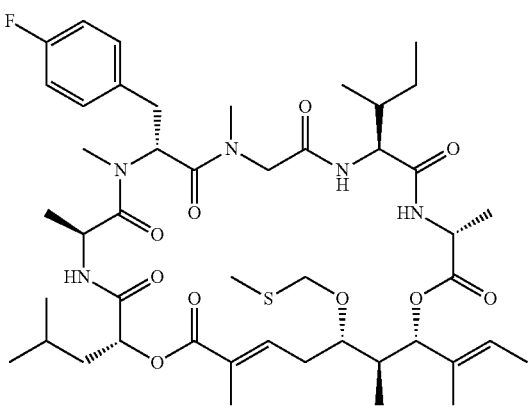

Compound 101

Figure 33:
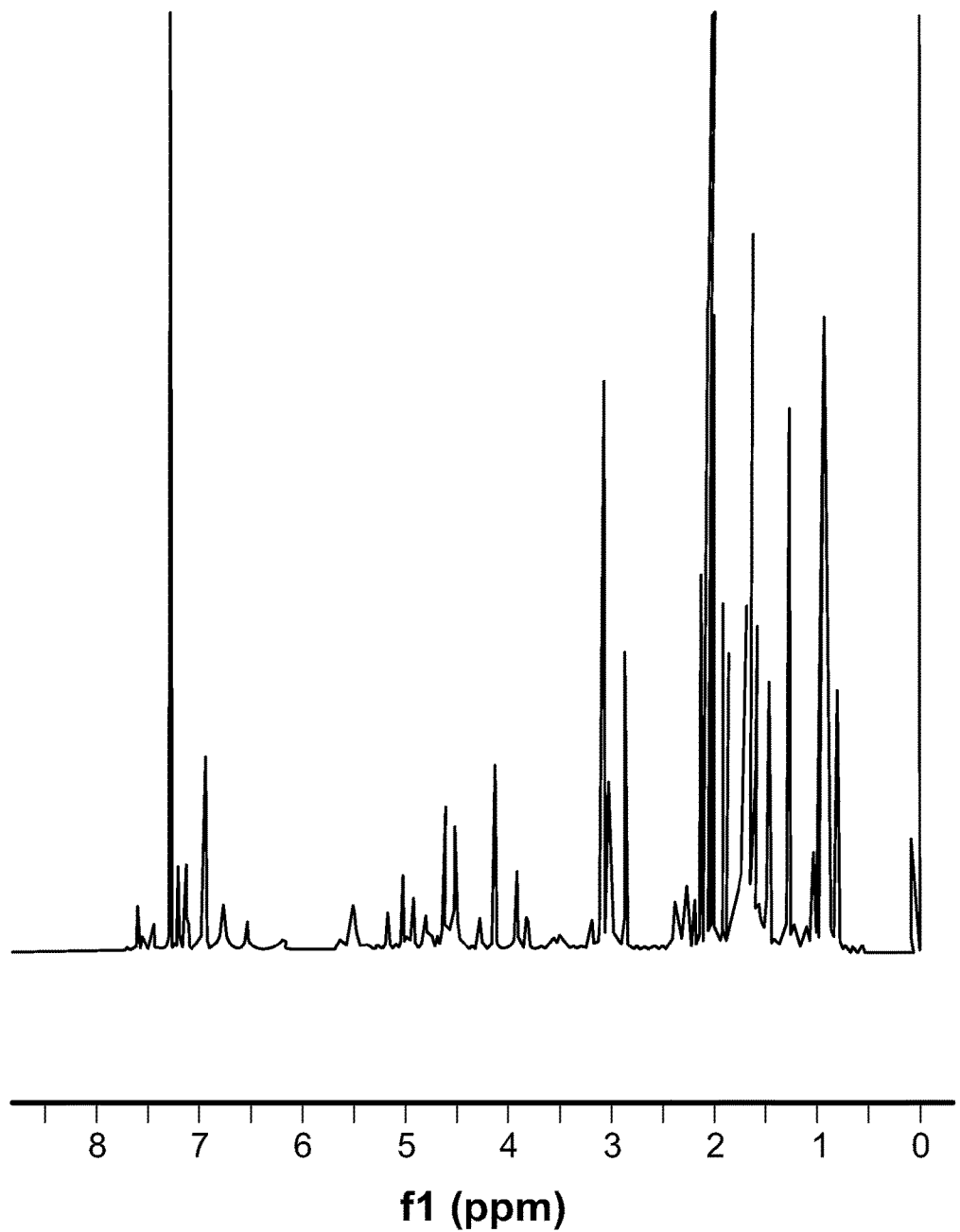
FIG. 33 is a $^1$H NMR spectrum of Compound 101 in $CDCl_3$.

Compound 101 was synthesized according to the method described in *Tetrahedron*, 68, 2012, 659-669, with modifications as shown in the above scheme. Modifications to the scheme include the use of BocNMe-Fluoro-D-Phe-OH in place of BocNMe-D-Phe-OH. Observed ESI HRMS: m/z 904.4915 [M+H]$^+$. The $^1$H NMR spectrum of Compound 101 is shown in FIG. 33.

Example 19

Synthesis of Compound 110

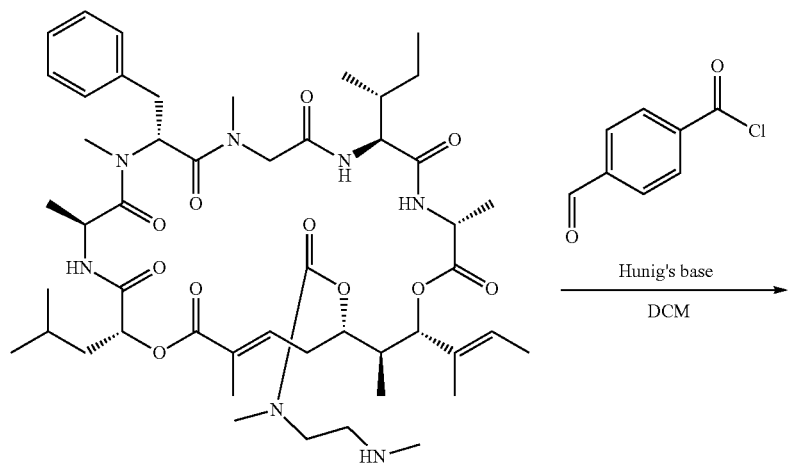

Compound 75

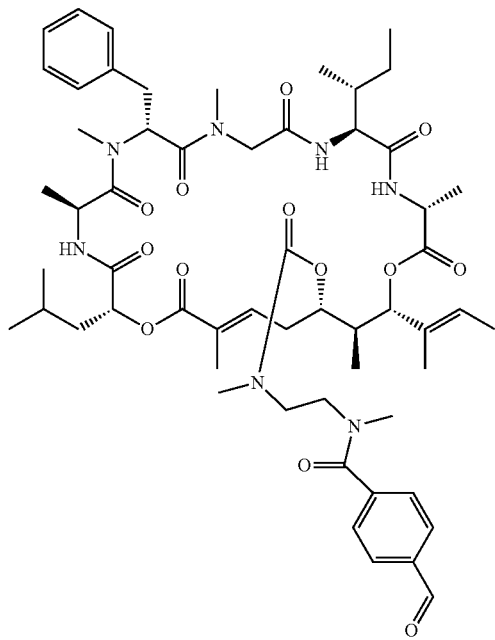

Compound 110

Figure 34:
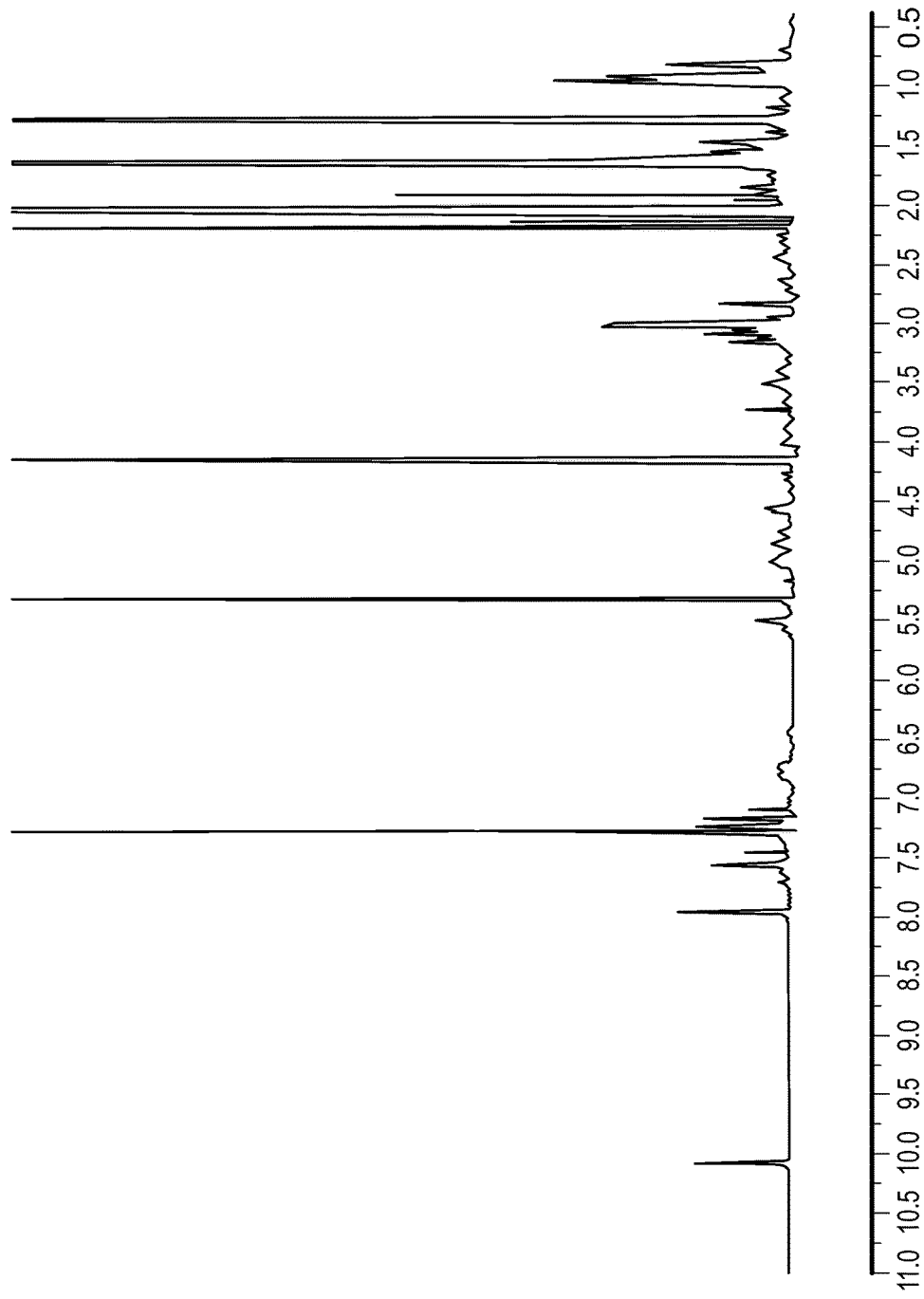
FIG. 34 is a $^1$H NMR spectrum of Compound 110 in CDCl$_3$.

To a solution of Compound 75 (5.32 μmol, 5 mg) and 4-formylbenzoyl chloride (0.030 mmol, 5 mg) in DCM (7.77 mmol, 0.5 mL) was added Hunig's base (0.053 mmol, 9.29 μL) at rt. The reaction mixture was stirred for 3 h and the volatiles were removed. The crude mixture was purified by RP-column chromatography to provide Compound 110 (2 mg, 35.1%) as a white solid. Observed HRMS (ESI): m/z 1072.596 [M+H]$^+$. The $^1$H NMR spectrum of Compound 110 is shown in FIG. 34.

Example 20
Synthesis of Compound 111
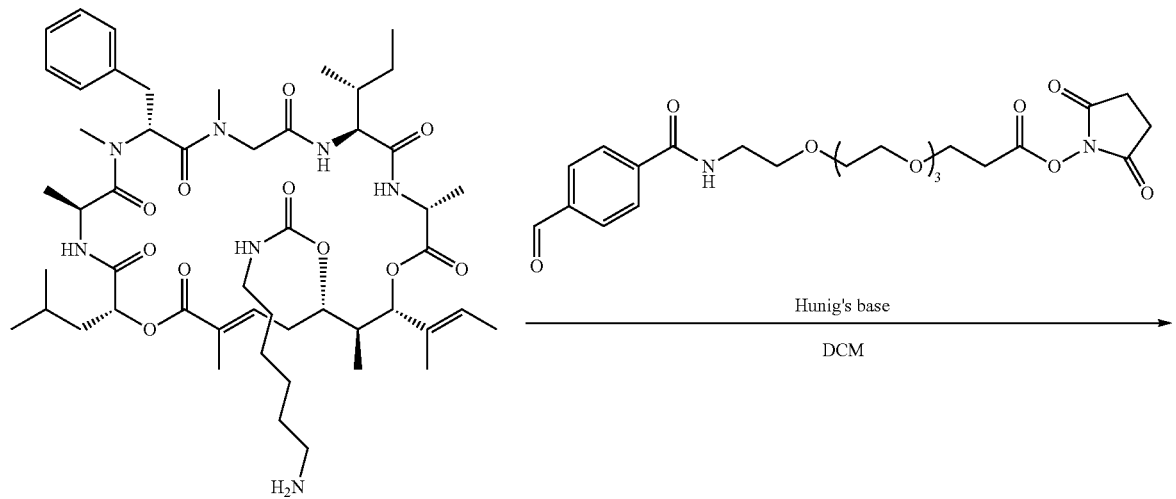
Compound 107
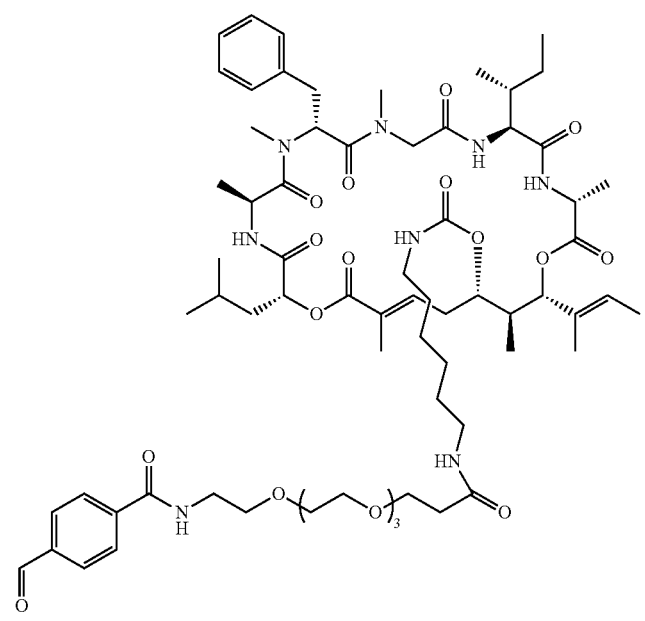
Compound 111

Figure 35:
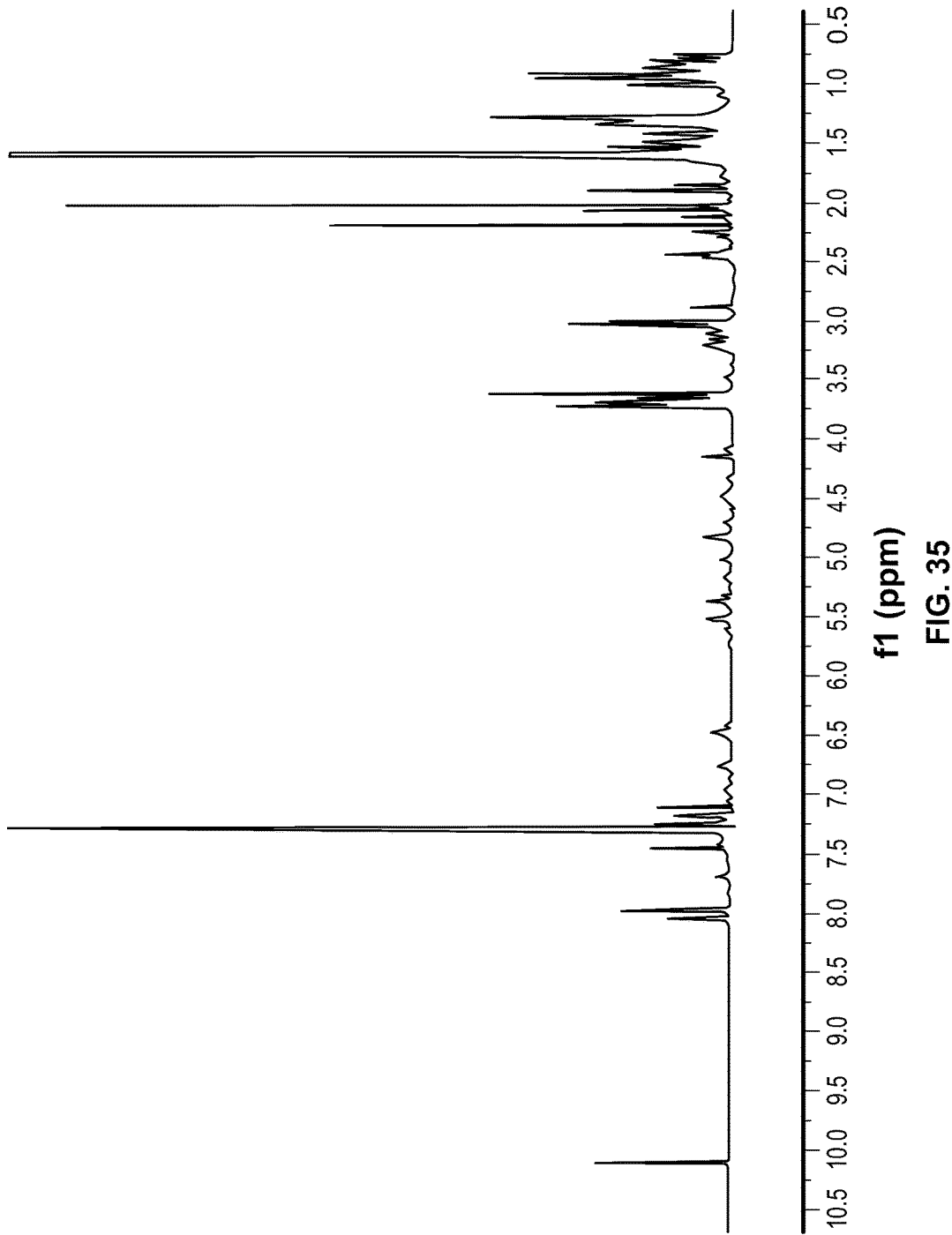
FIG. 35 is a $^1$H NMR spectrum of Compound 111 in CDCl$_3$.

To a solution of Compound 107 (2.066 μmol, 2 mg) and 2,5-dioxopyrrolidin-1-yl 1-(4-formylphenyl)-1-oxo-5,8,11,14-tetraoxa-2-azaheptadecan-17-oate (4.04 μmol, 2 mg) in DCM (7.77 mmol, 0.5 mL) was added Hunig's base (0.021 mmol, 3.61 μL). The reaction mixture was stirred overnight and the volatiles were removed. The crude mixture was purified by RP-column chromatography to afford Compound 111 (1.3 mg, 46.7%) as a white solid. Observed ESI HRMS: m/z 1347.767 [M+H]$^+$. The $^1$H NMR spectrum of Compound 111 is shown in FIG. 35.

Example 21

Synthesis of Compound 102

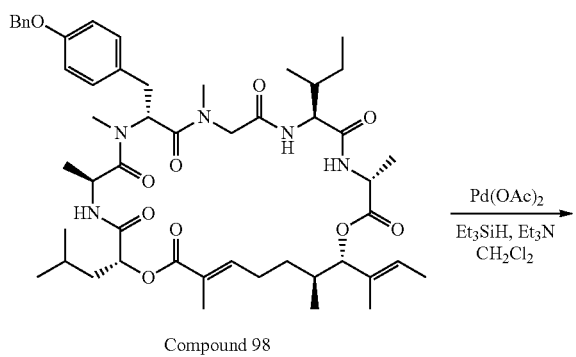

Compound 98

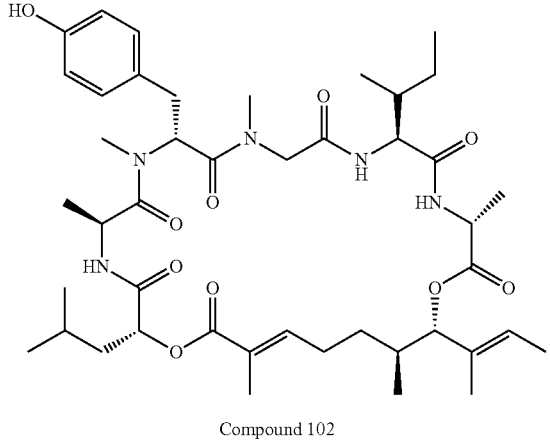

Compound 102

Figure 36:
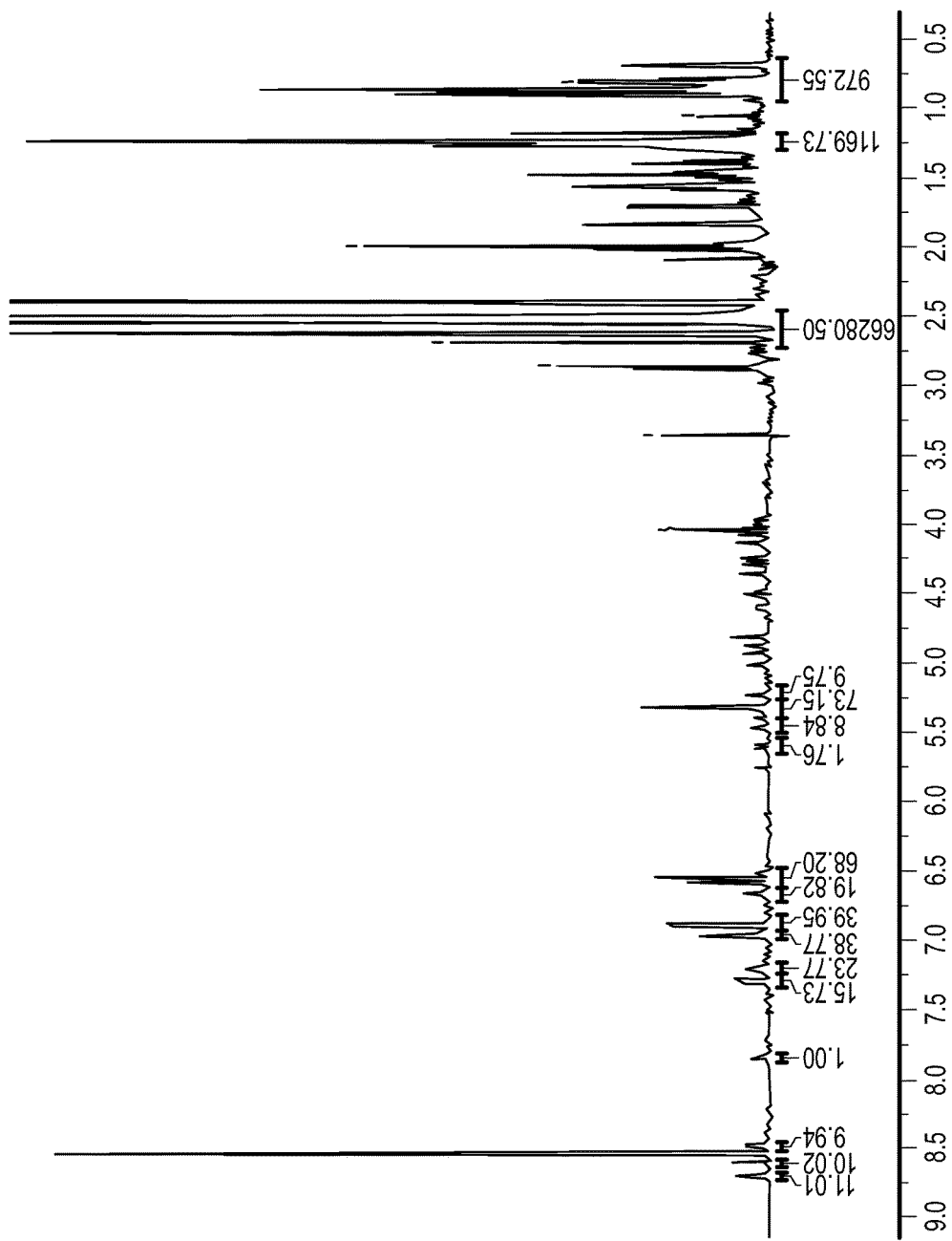
FIG. 36 is a $^1$H NMR spectrum of Compound 102 in DMSO-d6.

To a flame dried vial was added 3 mg (0.5 equiv) of Pd(OAc)$_2$ and 270 μL of freshly distilled CH$_2$Cl$_2$ (150 μL) followed by freshly distilled Et$_3$N (37 μL, 10 equiv). The mixture was stirred vigorously and 9 μL (2 equiv) of Et$_3$SiH were added dropwise. The mixture was stirred under Argon for 15 minutes. Then Compound 98 (20 μmol, 20 mg) in 120 μL of CH$_2$Cl$_2$ was added at once. The reaction mixture was capped and stirred. After 16 h, the reaction mixture was filtered over celite, and concentrated. Purification by reverse phase HPLC gave Compound 102 (1 mg, 5% yield). Observed ESI HRMS: m/z 826.5015 [M+H]$^+$. The $^1$H NMR spectrum of Compound 102 is shown in FIG. 36.

Example 22

Synthesis of Compounds 113, 115, and 117

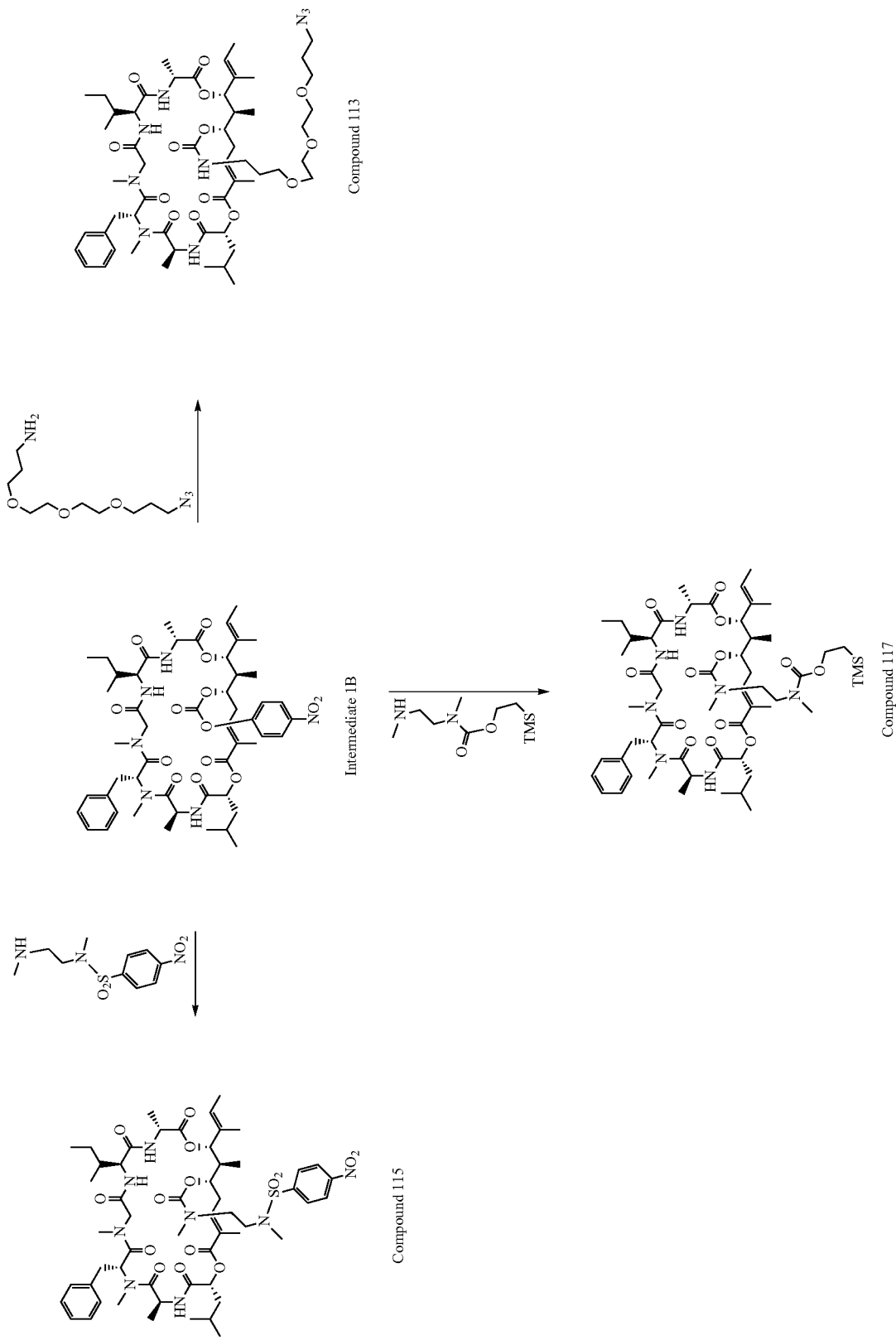

Compound 113

Figure 37:
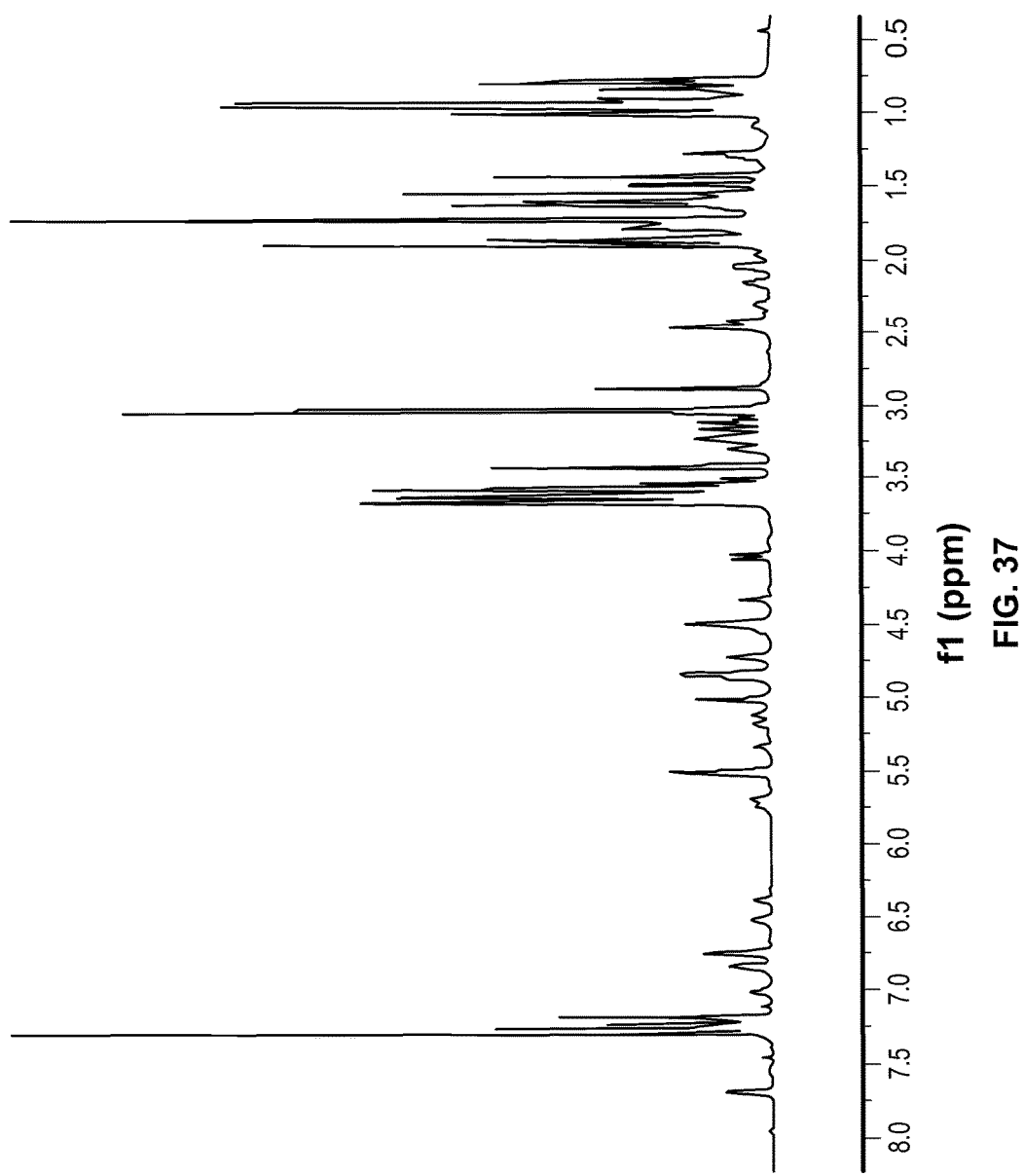
FIG. 37 is a $^1$H NMR spectrum of Compound 113 in CDCl$_3$.

To a solution of intermediate carbonate 1B (5.04 μmol, 0.5 mL) obtained as described in Example 11 was added N-ethyl-N-isopropylpropan-2-amine (0.050 mmol, 6.52 mg). The reaction mixture was stirred overnight, and the volatiles were removed. The crude mixture was purified by RP-column chromatography to afford Compound 113 (3 mg, 54.1%) as a white solid. Observed ESI HRMS: m/z 1098.652 [M+H]$^+$. The $^1$H NMR spectrum of Compound 113 is shown in FIG. 37.

Compound 115

Figure 39:
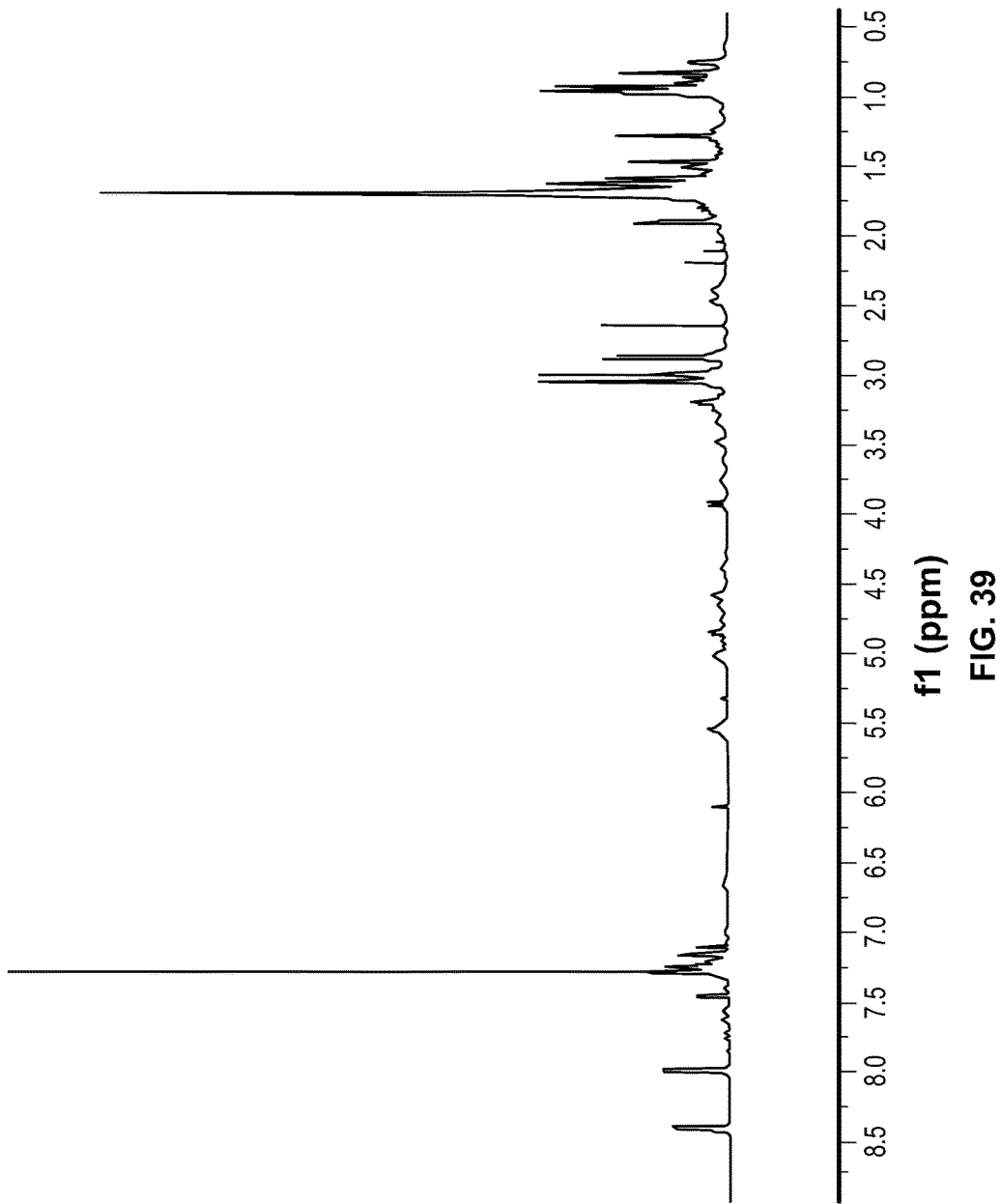
FIG. 39 is a $^1$H NMR spectrum of Compound 115 in CDCl$_3$.

To a solution of intermediate 1B (5.04 μmol, 5 mg) and N-(2-(methylamino)ethyl)-4-nitrobenzenesulfonamide (0.019 mmol, 5 mg) in dichloromethane (5.04 μmol, 0.428 mg) was added N-ethyl-N-isopropylpropan-2-amine (0.050 mmol, 6.52 mg) at rt. The reaction mixture was stirred overnight. The volatiles were removed, and the crude mixture was purified by RP-column chromatography to afford Compound 115 (2.4 mg, 42.3%) as a white solid. Observed ESI HRMS: m/z 1125.559 [M+H]$^+$. The $^1$H NMR spectrum of Compound 115 is shown in FIG. 39.

Compound 117

Figure 41:
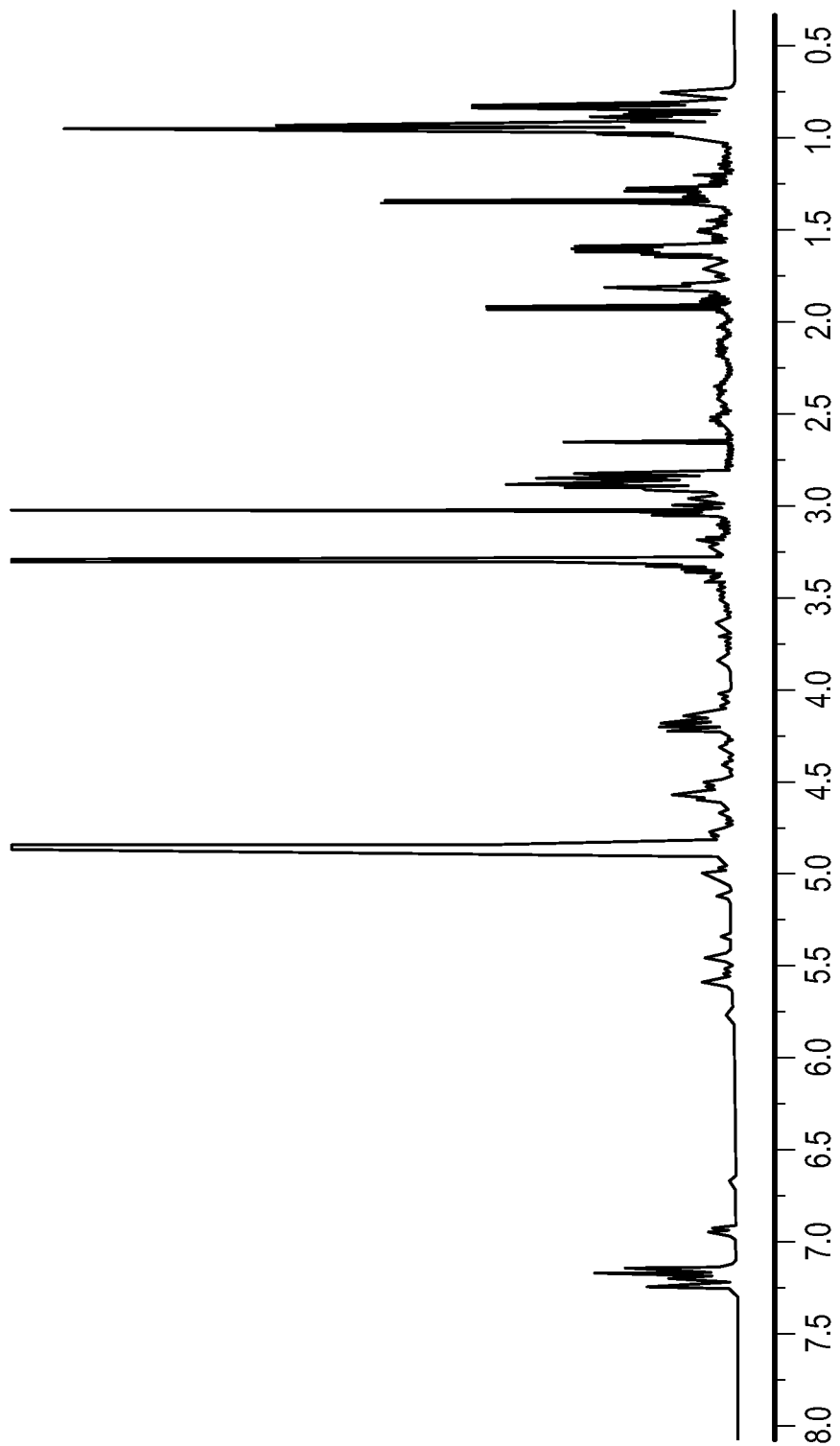
FIG. 41 is a $^1$H NMR spectrum of Compound 117 in CD$_3$OD.

To a solution of intermediate 1B (5.04 μmol, 5 mg) and 2-(trimethylsilyl)ethyl(2-(methylamino)ethyl)carbamate (0.023 mmol, 5 mg) in dichloromethane (5.04 μmol, 0.5 mL) was added N-ethyl-N-isopropylpropan-2-amine (0.050 mmol, 6.52 mg). The reaction mixture was stirred overnight. The volatiles were removed, and the crude mixture was purified by RP-column chromatography to afford Compound 117 (3.2 mg, 58.5%) as a white solid. Observed ESI HRMS: m/z 1101.66 [M+NH$_4$]$^+$. The $^1$H NMR spectrum of Compound 117 is shown in FIG. 41.

Example 23

Synthesis of Compound 114

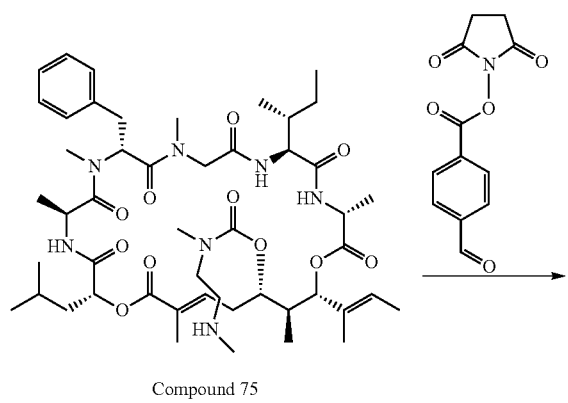

Compound 75

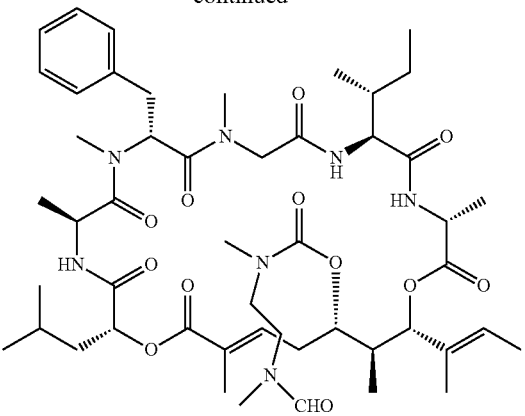

Compound 114

Figure 38:
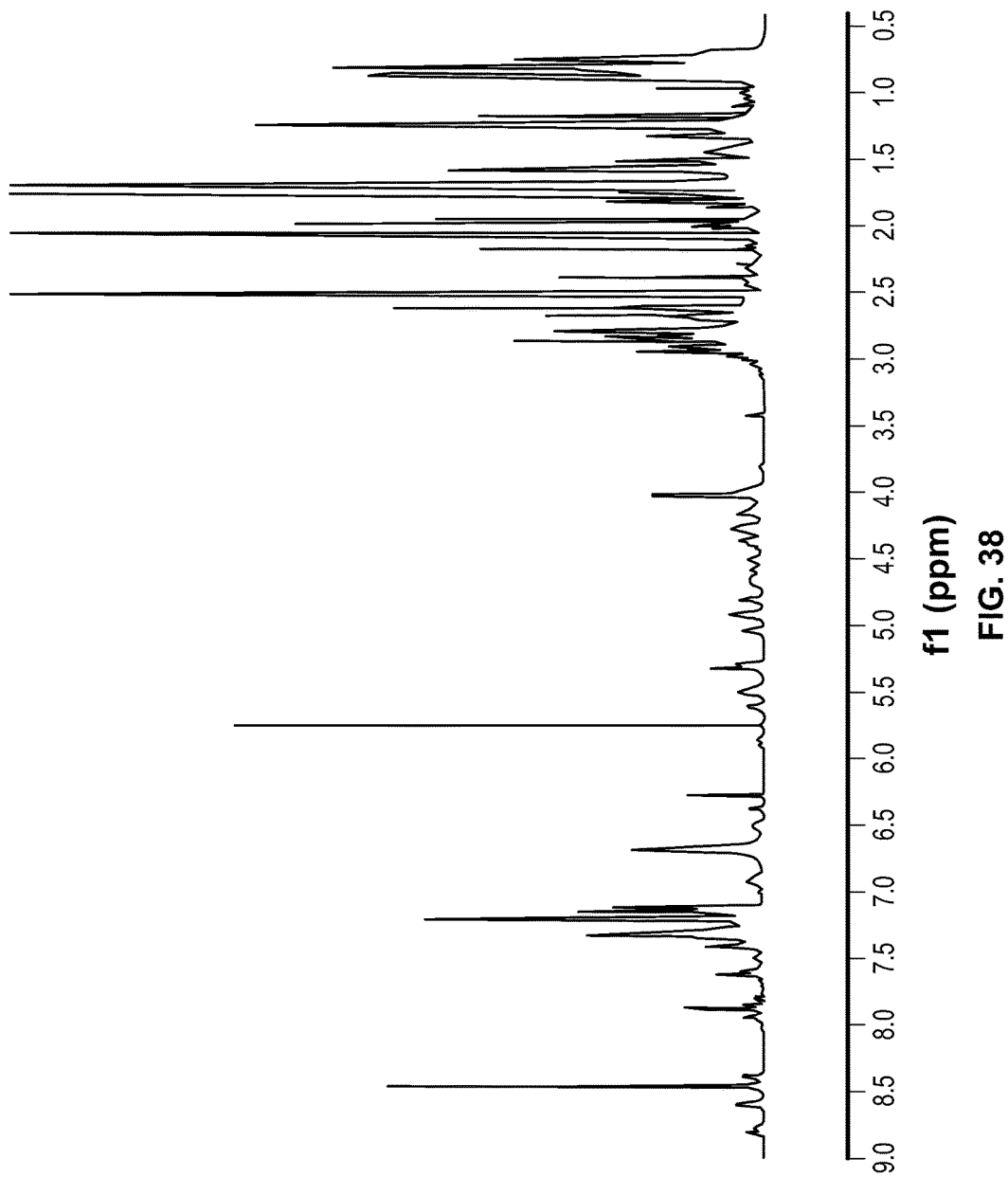
FIG. 38 is a $^1$H NMR spectrum of Compound 114 in DMSO-d6.

To a solution of compound 75 (5.32 μmol, 5 mg) and 2,5-dioxopyrrolidin-1-yl 4-formylbenzoate (0.020 mmol, 5 mg) in dichloromethane (5.32 μmol, 0.5 mL) was added N-ethyl-N-isopropylpropan-2-amine (0.053 mmol, 6.87 mg). The reaction mixture was stirred overnight. The volatiles were removed, and the crude mixture was purified by RP-column chromatography to afford Compound 114 (3 mg, 58.3%) as a white solid. Observed ESI HRMS: m/z 968.5699 [M+H]$^+$. The 1H NMR spectrum of Compound 114 is shown in FIG. 38.

Example 24

Synthesis of Compound 118

A. Synthesis of Intermediate A6

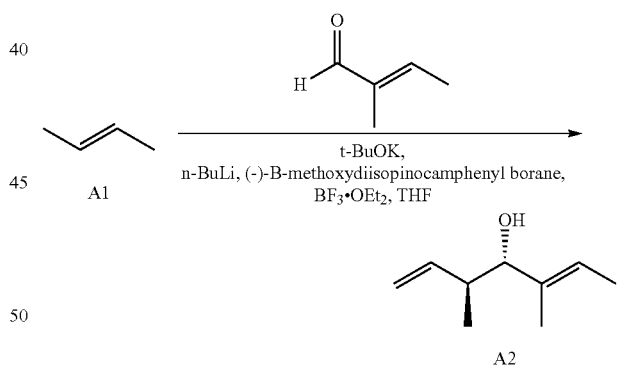

To a stirring solution of t-BuOK (3.4 g, 30.3 mmol) in THF (9.5 mL) at −78° C. was added trans-2-butene (3.39 g, 37.1783 mmol) followed by the addition of n-BuLi (12.625 mL, 2.5 M in hexanes). The resultant yellow suspension was stirred at −78° C. for 30 min, subsequently at −45° C. for 60 min, and cooled to −78° C. again. (−)-β-methoxydiisopinocamphenyl borane (11.52 g, 36.41 mmol) in THF (21.1615 mL) was added slowly. The mixture was stirred at −78° C. for 1 h, and boron trifluoride etherate (10.67 mL, 48%) was added dropwise. Immediately afterwards, a solution of tiglic aldehyde (7.178 mL, 74 mmol) was added dropwise. The mixture was kept at −78° C. for 3 h. The reaction was then quenched with saturated NaOAc and 30% H$_2$O$_2$. The resulting solution was stirred at −78° C. for 30 min and warmed to room temperature over 12 h. The aqueous layer was extracted with Et₂O, and the combined organic layers were dried over MgSO₄, concentrated under reduced pressure, and purified by flash chromatography (EtOAc/n-hexane) to yield alcohol A2 as a colorless liquid. (3.2 g, 72%) (Ref. Organic Letters, 2008, 10(15); 3223-3226).

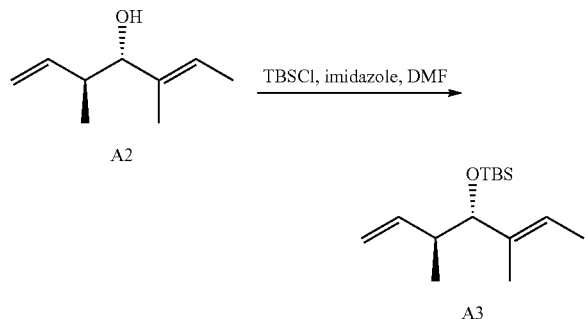

To a stirring solution of alcohol A2 (3.2 g, 22.82 mmol) in DMF (46 mL) were added imidazole (6.21 g, 91 mmol) and TBSCl (45.6 mmol). The reaction was stirred at room temperature for 8 h. The reaction was then quenched with water and extracted with Et₂O. The combined organic extracts were dried over Na₂SO₄, concentrated under reduced pressure and purified by flash chromatography (EtOAc/n-hexane) to yield alkene A3 as a colorless liquid (5 g, 86%).

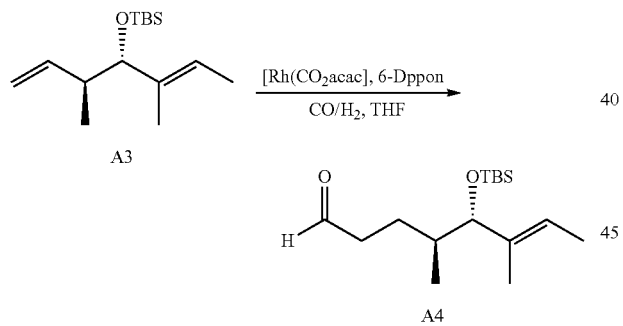

To a stirring solution of [Rh(CO)₂acac] (0.034 g, 0.132 mmol) and 6-Dppon (0.182 g, 0.654 mmol) in THF (10.2 mL) was added alkene A3 (2.5 g, 9.82 mmol) and a 1:1 ratio of carbon monoxide and hydrogen gas. The reaction was stirred for 20 h. The crude reaction was carried to the next step without purification (Ref. Adv. Synth. Catal. 2005, 347, 1488-1494).

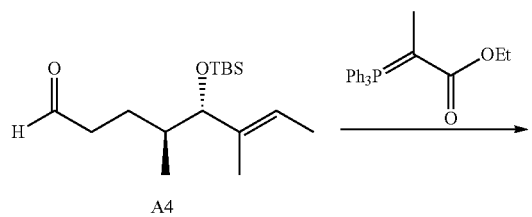

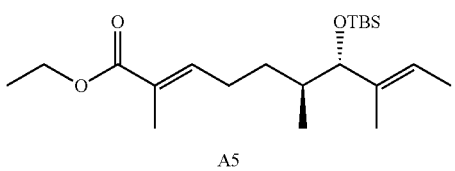

To a crude mixture of aldehyde A4 (2.5 g, 8.78 mmol) in THF (10.20 mL) was added Wittig reagent (4.14 g, 8.78 mmol). The mixture was stirred for 30 min. The reaction mixture was concentrated and purified by flash chromatography using EtOAc/n-hexane to yield ethyl ester A5 as a colorless oil (1.7 g, 52% over two steps). The compound was characterized by ¹H NMR (CDCl₃): δ 6.75 (ddd, J=1.5, 6.8 Hz, 1H), 5.32 (q, J=6.8 Hz, 1H), 4.18 (q, J=7 Hz, 2H), 3.56 (d, J=8 Hz, 1H)), 2.25 and 2.15 (m, 2H), 1.84 (brs, 3H), 1.82 (m, 1H), 1.58 (brd, J=6.6 Hz, 3H), 1.58 (m, 1H), 1.50 (brs, 3H), 1.39 (t, J=7 Hz, 3H), 1.15 (m, 1H), 0.87 (s, 9H), 0.72 (d, J=8 Hz, 3H), 0.1 (s, 3H), −0.06 (s, 3H).

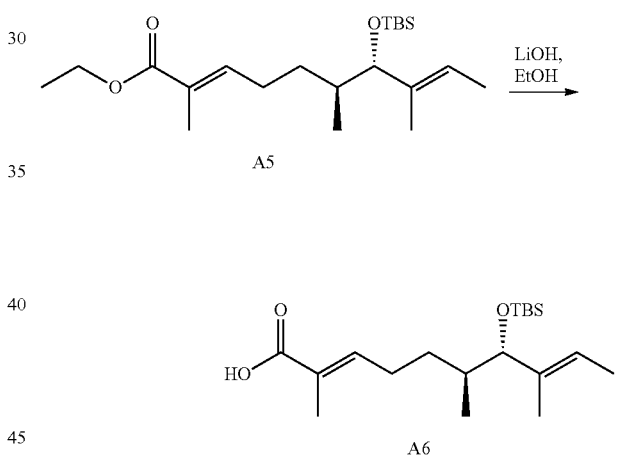

To a stirring solution of ethyl ester A5 (1.7 g, 4.61 mmol) in ethanol (57 mL) was added a 5 N LiOH solution (57 mL). The reaction mixture was stirred at 50° C. for 8 h. The reaction was quenched with 10% aqueous citric acid solution and extracted with Et₂O. The combined organic extracts were washed with H₂O, brine, and dried over Na₂SO₄ and then purified by flash chromatography using EtOAc/n-hexane to yield Intermediate A6 as a colorless oil (1.3 g, 83%). The compound was characterized by ¹H NMR (CDCl₃): δ 6.91 (ddd, J=1.5, 6.8 Hz, 1H), 5.32 (q, J=6.8 Hz, 1H), 3.56 (d, J=8 Hz, 1H)), 2.25 and 2.15 (m, 2H), 1.84 (brs, 3H), 1.82 (m, 1H), 1.58 (brd, J=6.6 Hz, 3H), 1.58 (m, 1H) 1.50 (brs, 3H), 1.15 (m, 1H), 0.87 (s, 9H), 0.72 (d, J=8 Hz, 3H), 0.1 (s, 3H), −0.06 (s, 3H).

Figure 42:
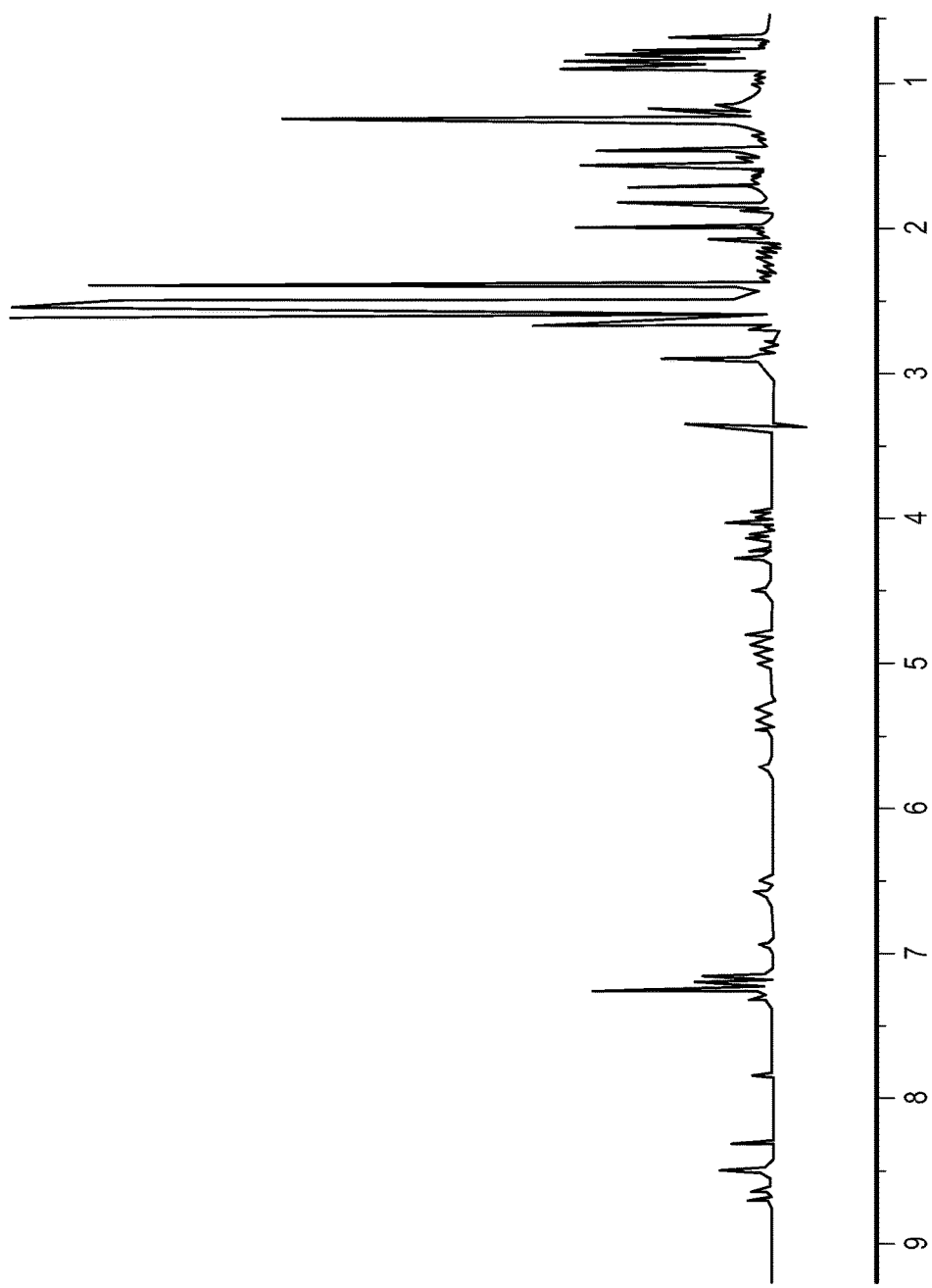
FIG. 42 is a $^1$H NMR spectrum of Compound 118 in DMSO-d6.
Figure 42A:
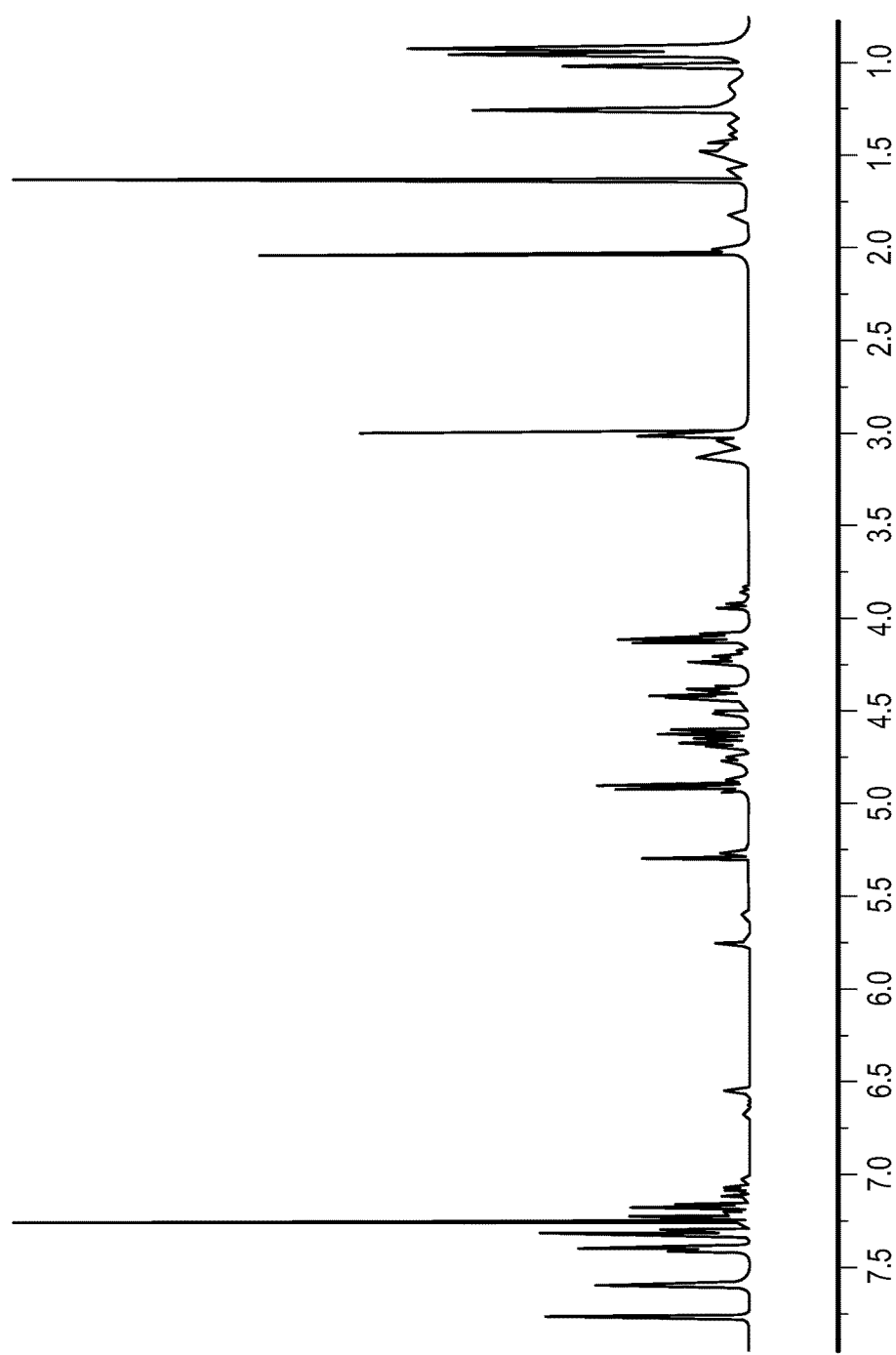
FIG. 42a is a $^1$H NMR spectrum of Intermediate B5 in CDCl$_3$.

B. Synthesis of Intermediate B5
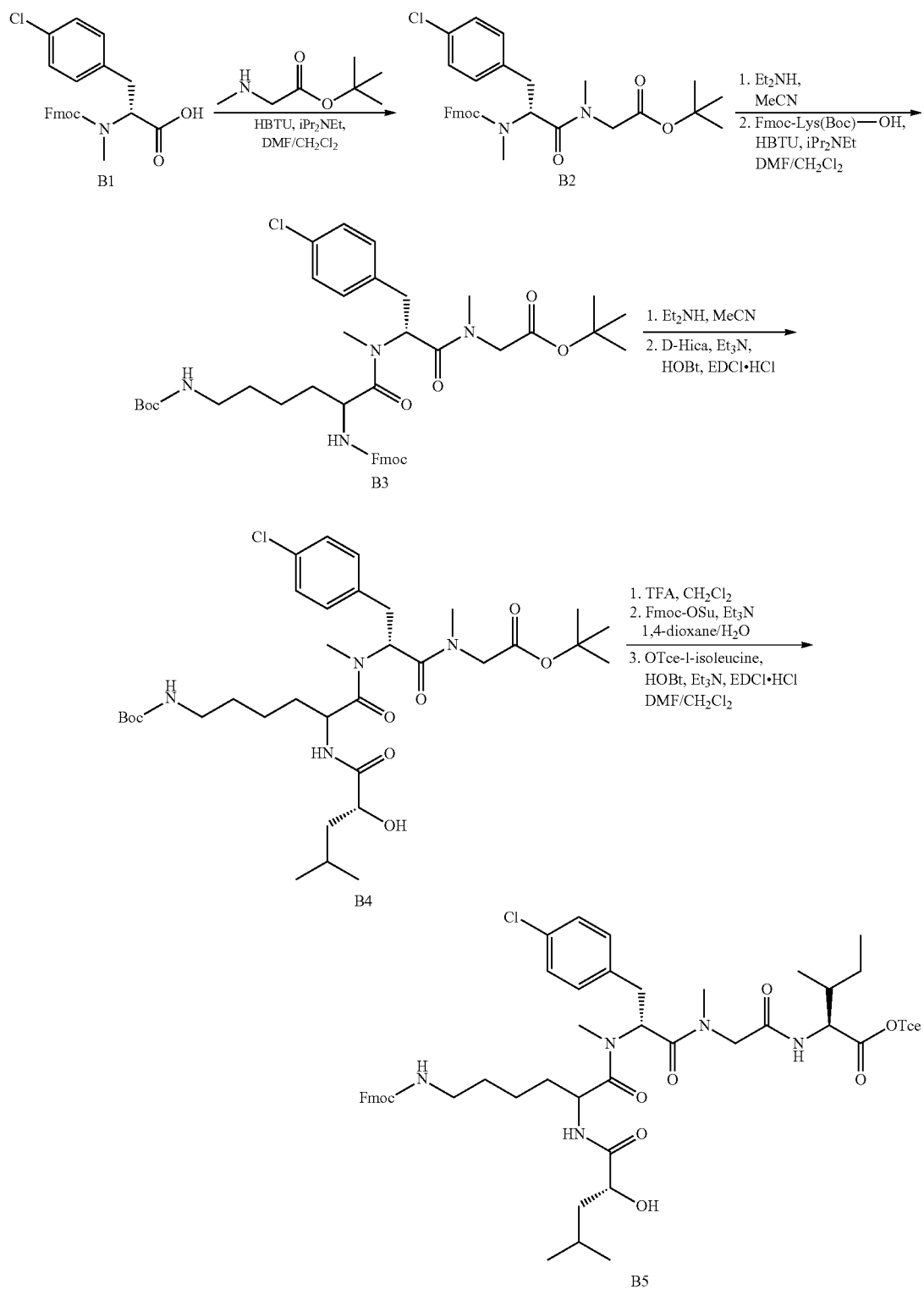
Intermediate B5 was synthesized using the method reported in Bioorganic & Medicinal Chemistry Letters 2008, 18, 3902-3905, with modifications as shown in the above scheme. Observed ESI HRMS: m/z 992.3193 [M+H]$^+$. The $^1$H NMR spectrum of B5 is shown in FIG. 42a.

C. Synthesis of Compound 118
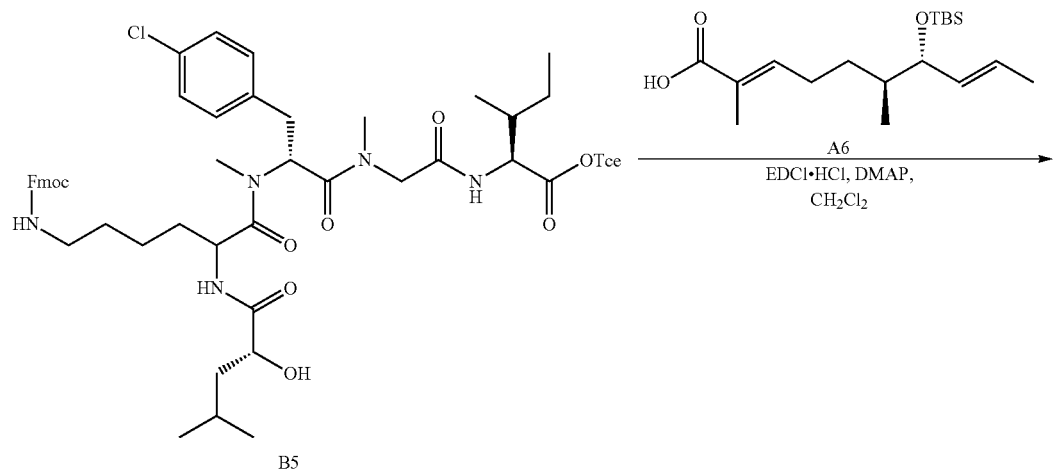
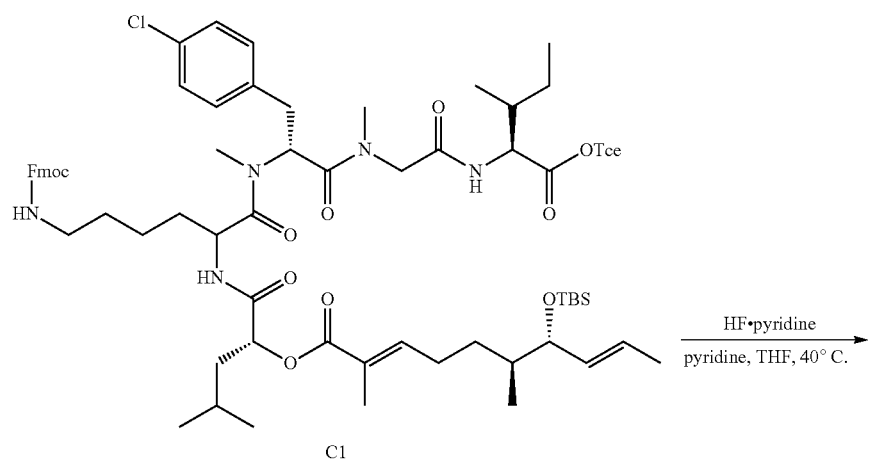
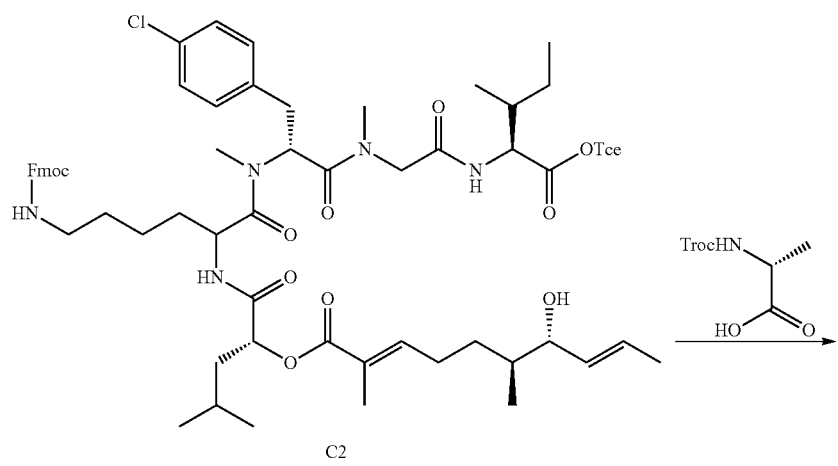

-continued
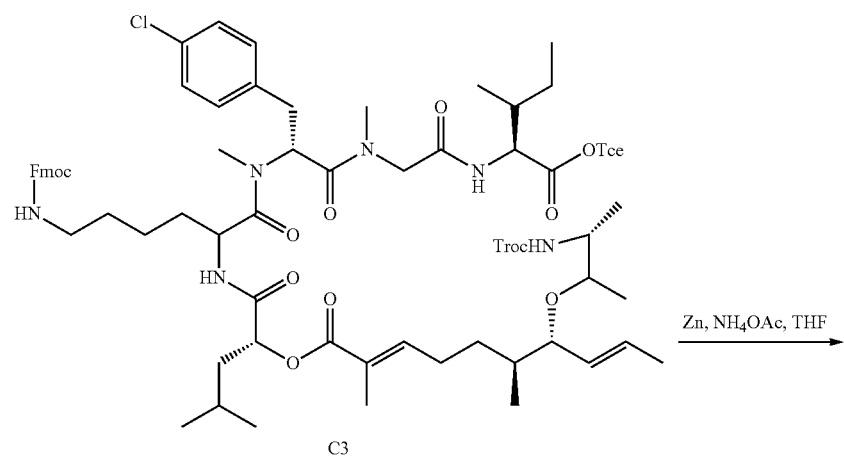
C3
Zn, NH₄OAc, THF →
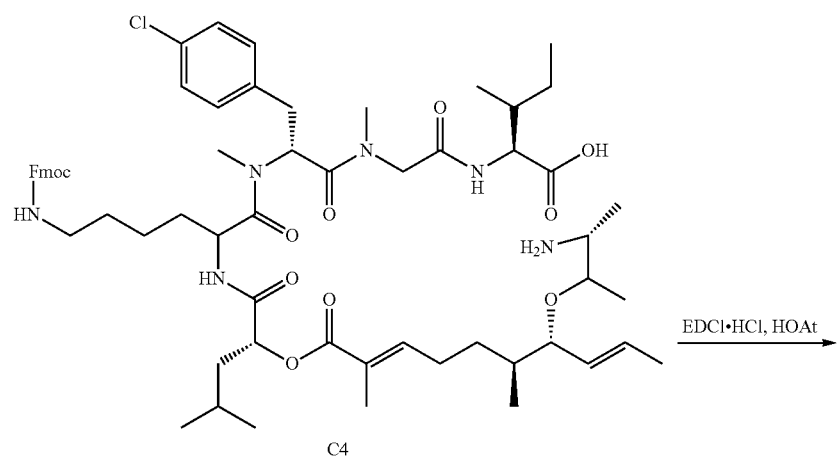
C4
EDCl·HCl, HOAt →
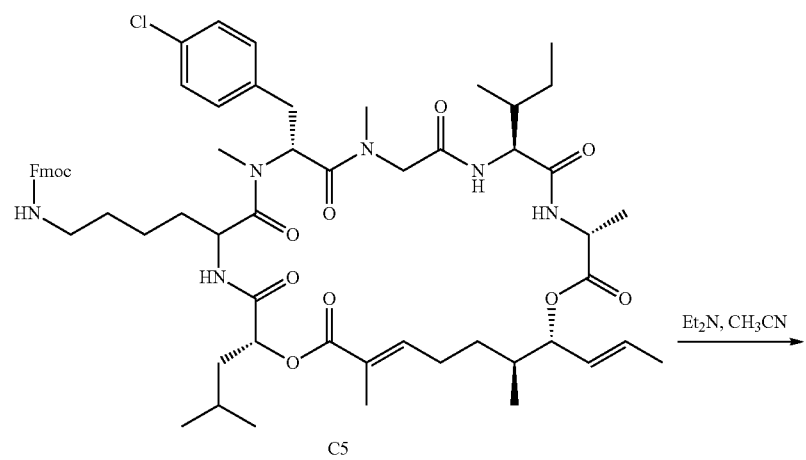
C5
Et₂N, CH₃CN →

-continued

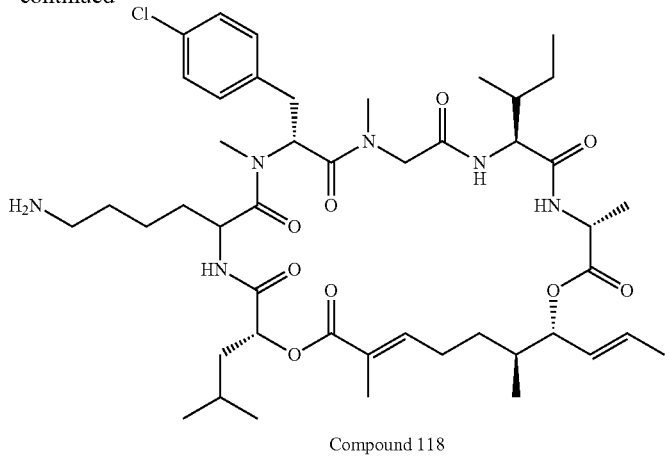

Compound 118

Figure 42B:
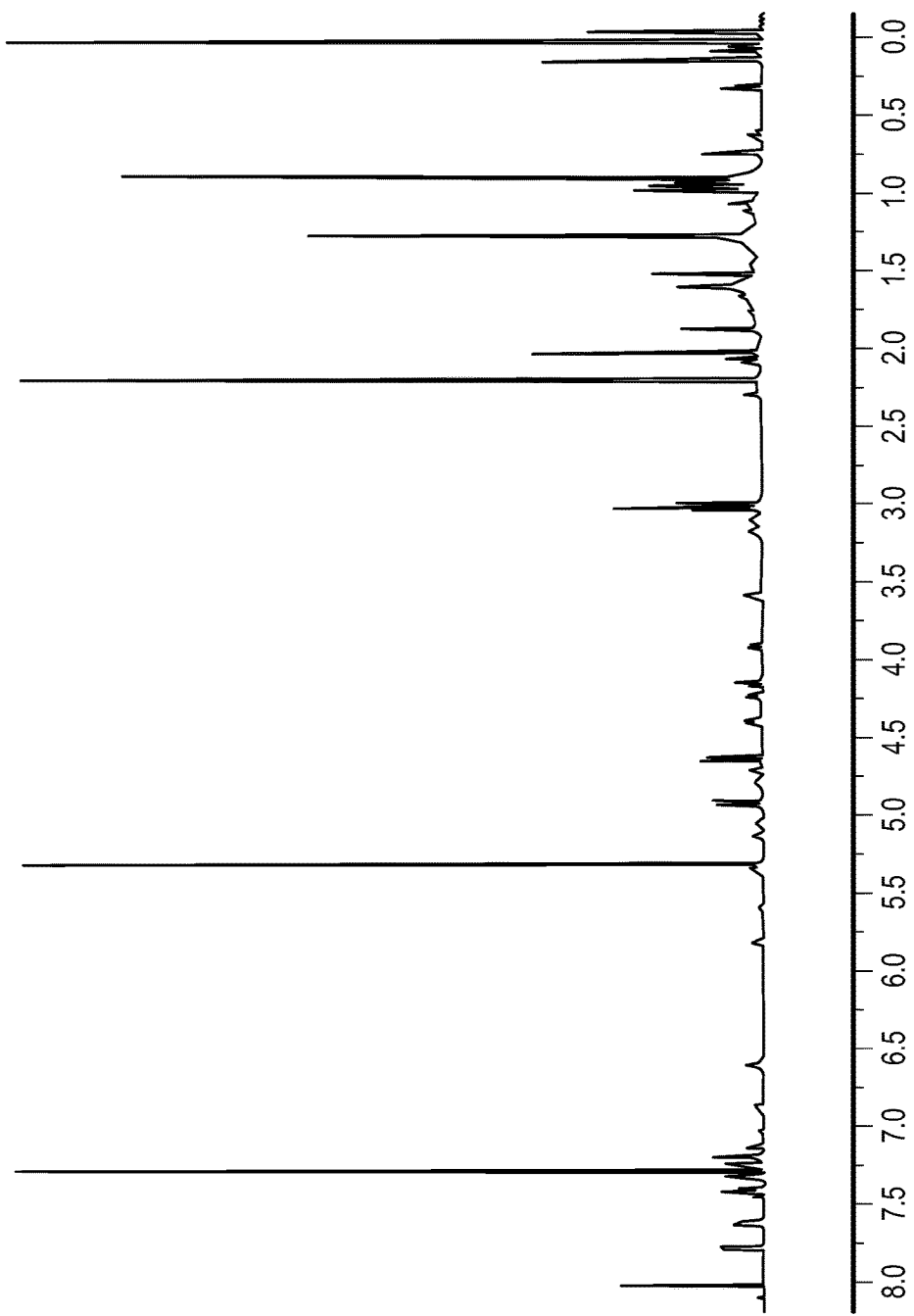
FIG. 42b is a $^1$H NMR spectrum of compound C1 in CDCl$_3$.

To a stirred solution of carboxylic acid A6 (0.15 g, 0.440 mmol) and pentapeptide B5 (0.328 g, 0.330 mmol) in CH$_2$Cl$_2$ (1.76 mL) were added 4-(dimethyl-amino)pyridine (0.054 g, 0.440 mmol) and 1-ethyl-3-(3' dimethylaminopropyl)carbodiimide hydrochloride (0.253 g, 1.321 mmol). The mixture was stirred at room temperature for 13 h. The mixture was diluted with CH$_2$Cl$_2$, washed with 1 N hydrochloric acid solution, saturated aqueous NaHCO$_3$ and brine, and dried over Na$_2$SO$_4$. The resulting solution was concentrated and purified on a C18 column to yield ester C1 (0.2 g, 34%) as a solid. The $^1$H NMR spectrum of compound C1 is shown in FIG. 42b.

Figure 42C:
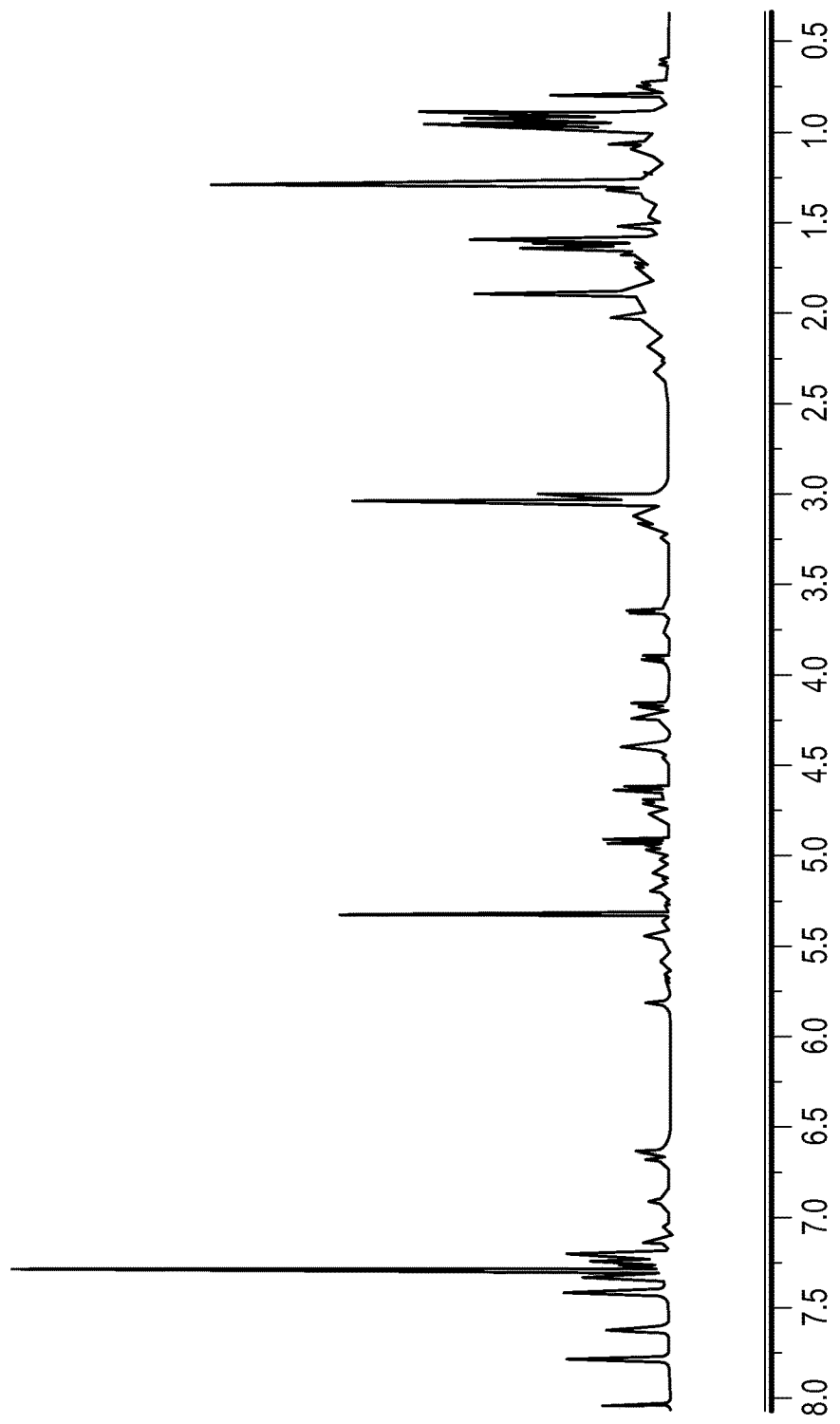
FIG. 42c is a $^1$H NMR spectrum of compound C2 in CDCl$_3$.

Ester C1 (0.200 g, 0.152 mmol) was dissolved in a 1:1:4 mixture of THF, pyridine, and HF Pyridine (4 mL). The mixture was stirred at 60° C. for 12 h. Workup was performed by diluting the reaction with EtOAc and pouring it into saturated NaHCO$_3$ at 0° C. The mixture was extracted with EtOAc, and the combined organic extracts were washed with brine and dried over Na$_2$SO$_4$. The resulting solution was concentrated under vacuum and purified by RP HPLC on a C18 column to yield alcohol C2 (0.138 g, 75%) as a solid. The $^1$H NMR spectrum of compound C2 is shown in FIG. 42c.

Figure 42D:
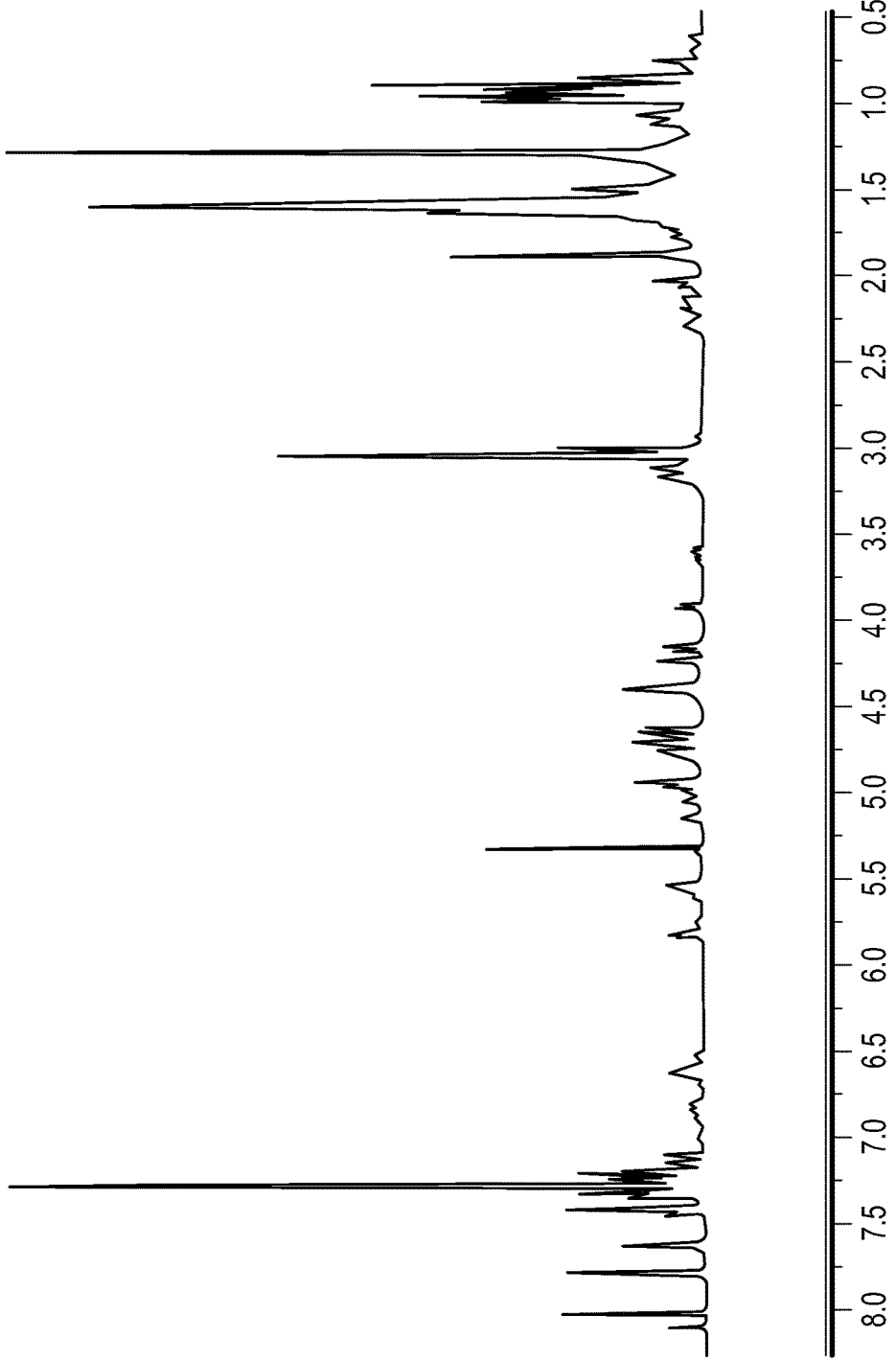
FIG. 42d is a $^1$H NMR spectrum of compound C3 in CDCl$_3$.

A stirred solution of alcohol C2 (0.138 g, 0.115 mmol) in CH$_2$Cl$_2$ (0.575 mL) was cooled to 0° C. Troc-D-Ala (0.061 g, 0.270 mmol), 4-(Dimethylamino)pyridine (0.014 g, 0.115 mmol), and 1-ethyl-3-(3'-dimethylaminopropyl) carbodiimide hydrochloride (0.044 g, 0.230 mmol) were added, and the mixture was stirred at rt for 12 h. The mixture was diluted with CH$_2$Cl$_2$, washed with 1 N HCl, saturated aqueous NaHCO$_3$, and brine, and dried over Na$_2$SO$_4$. The resulting solution was concentrated and purified by RP-HPLC on a C18 RP column using H$_2$O and acetonitrile with 0.1% formic acid gradient to yield compound C3 (0.141 g. 85%) as a solid. The $^1$H NMR spectrum of compound C3 is shown in FIG. 42d.

To a stirred solution of Ester-Troc-D-Ala C3 (0.141 g, 0.097 mmol) in THF (3.55 mL) and 1 M NH$_4$OAc (0.858 mL) was added activated Zn powder (1.273 g, 19.47 mmol). The reaction mixture was stirred for 4 h. The mixture was then filtered through celite, washed with EtOAC and concentrated to yield a crude residue. The residue was then diluted with CH$_2$Cl$_2$, washed with 1 N HCl and brine, and dried over sodium sulfate. The resulting solution was concentrated and purified by RP-HPLC on a C18 column using H$_2$O and acetonitrile with 0.1% formic acid gradient to yield free amino acid C4 (0.064 g, 58%) as a solid.

To a stirring solution of amino acid C4 (0.064 g, 0.056 mmol) in 175 mL of 1:10 (DMF:CH$_2$Cl$_2$) were added 1-hydroxy-7-azabenzotriazole (0.076 g, 0.56 mmol) and 1-ethyl-3-(3'-dimethylaminopropyl) carbodiimide hydrochloride (0.107 g, 0.56 mmol). The reaction mixture was stirred for 16 h. The reaction was then evaporated, diluted with CH$_2$Cl$_2$, washed with 1 N HCl, saturated aqueous NaHCO$_3$, and brine, and dried over Na$_2$SO$_4$. The resulting solution was concentrated and purified by RP-HPLC on a C18 column using H$_2$O and acetonitrile with 0.1% formic acid gradient to yield cyclized product C5 (0.024 g, 38%).

To a stirring solution of cyclized product C5 (0.024 g, 0.021 mmol) in acetonitrile (1.05 mL) was added diethylamine (0.112 mL). The mixture was stirred for 4 h. The resulting reaction mixture was then purified by flash chromatography to yield Compound 118 (0.011 g, 58%) as a clean solid. Observed ESI HRMS: m/z 901.526 [M+H]$^+$. The $^1$H NMR spectrum of Compound 118 is shown in FIG. 42.

Example 25

Synthesis of Compound 119

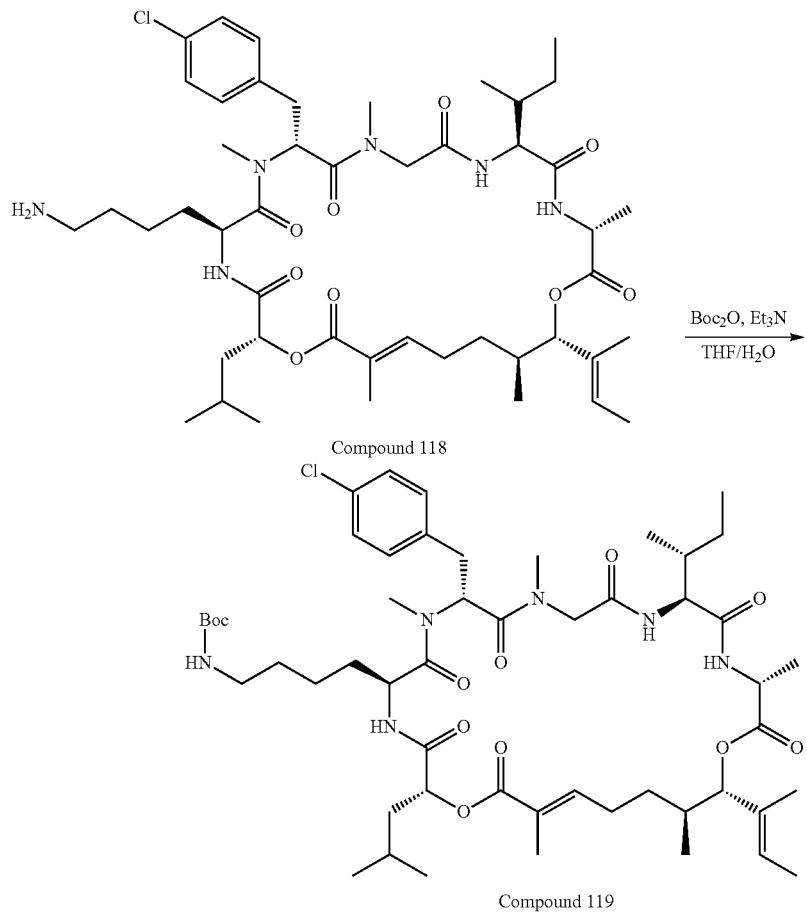

Compound 118

Compound 119

Figure 43:
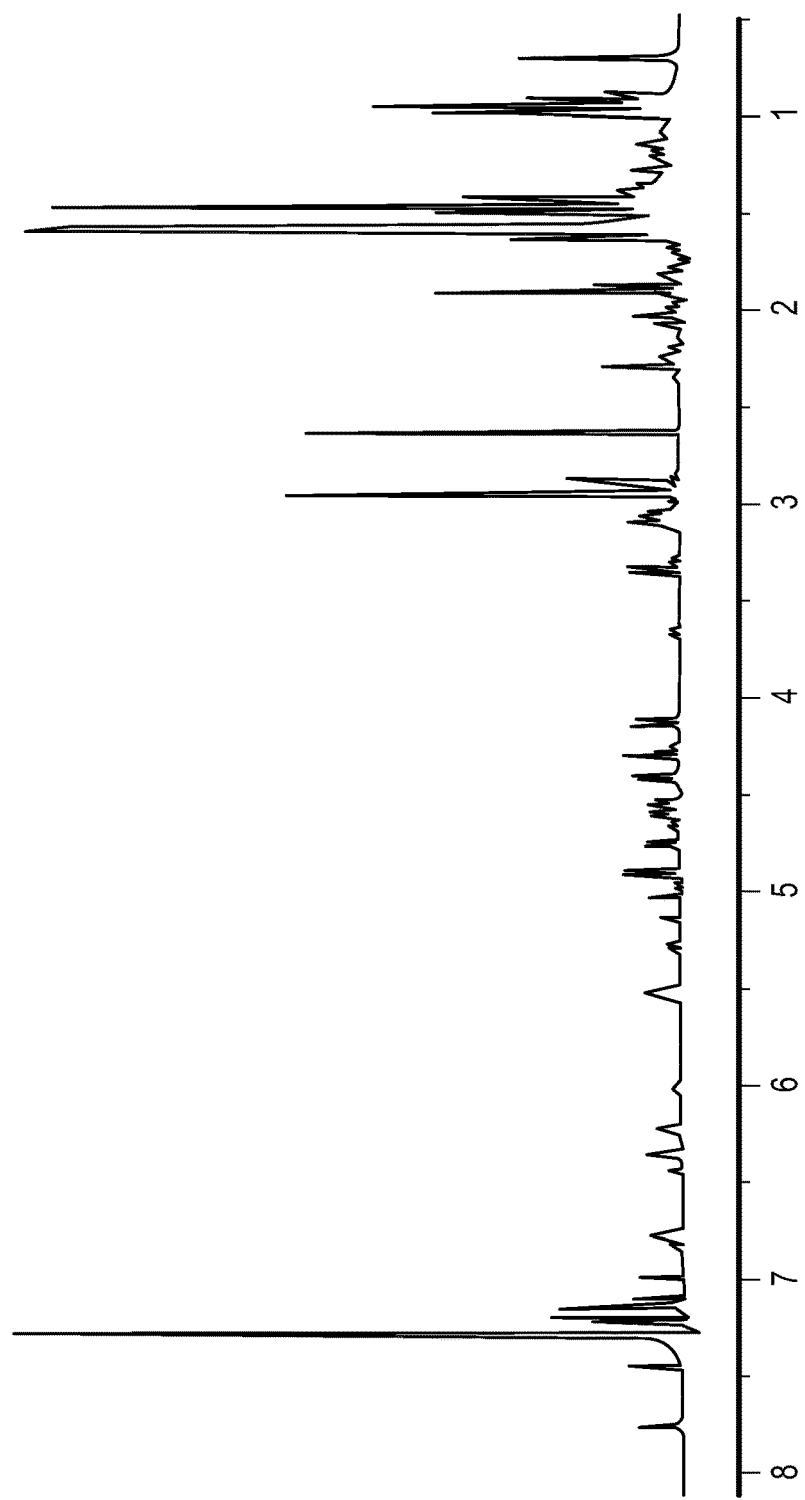
FIG. 43 is a $^1$H NMR spectrum of Compound 119 in CDCl$_3$.

To a stirring solution of Compound 118 (0.003 g, 3.3 μmol) in 1:1 $H_2O$ and THF (66 μL) were added triethylamine (0.464 μL, 3.3 μmol) and di-tert-butyl dicarbonate (0.799 mg, 3.66 μmol). The mixture was stirred at room temperature for 1 hour. The reaction mixture was concentrated and purified by HPLC using water and acetonitrile with 0.1% formic acid gradient to yield the pure Compound 119 (0.8 mg, yield 24%). Observed ESI HRMS: m/z 1001.573 [M+H]$^+$. The $^1$H NMR spectrum of Compound 119 is shown in FIG. 43.

Example 26

Synthesis of Compound 120

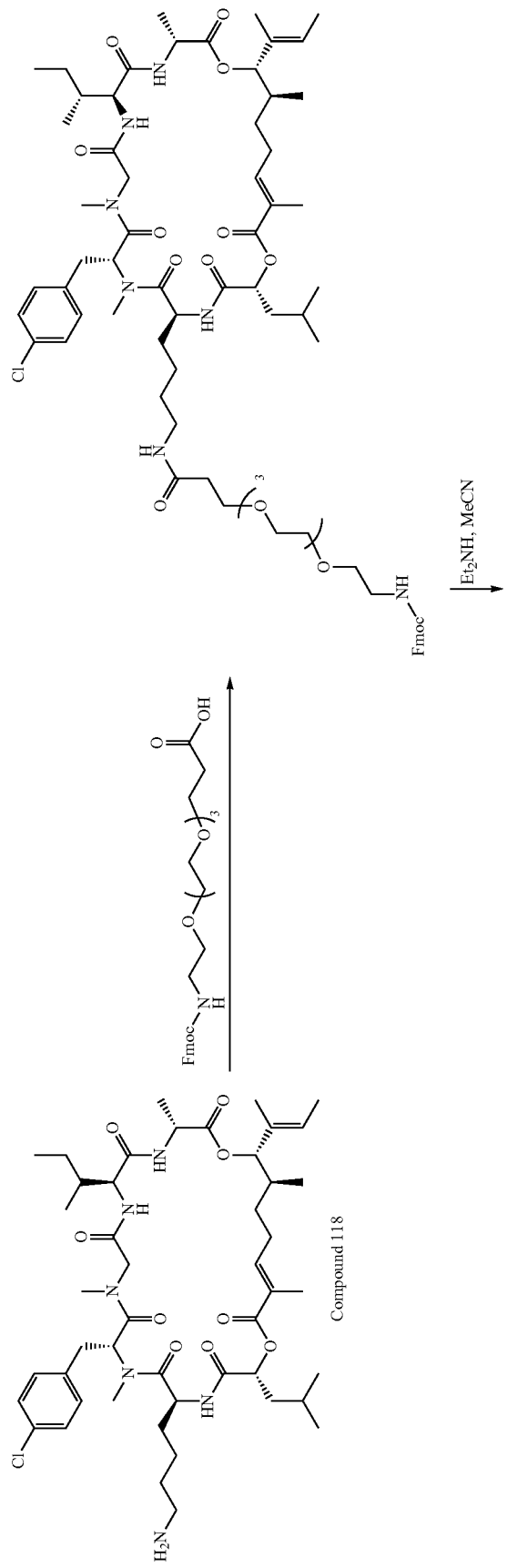

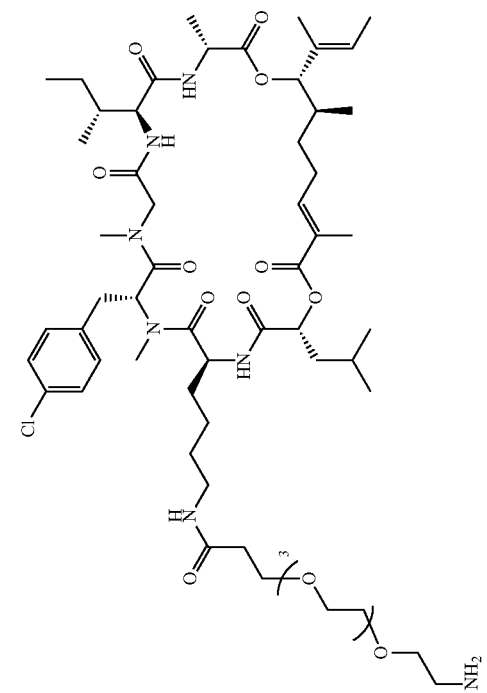
Intermediate 1C
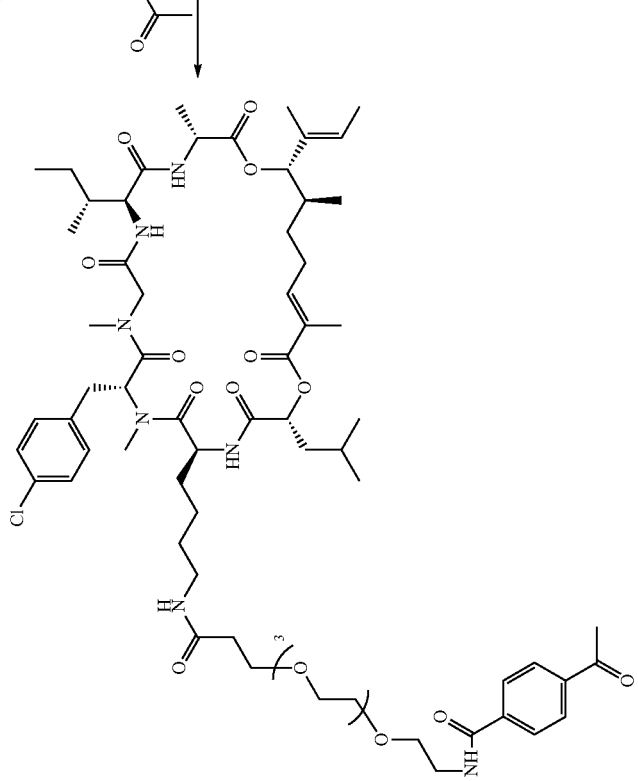
Compound 120

To a solution of Compound 118 (0.0005 g, 0.555 μmol) in CH$_2$Cl$_2$ (0.1 mL) were added Fmoc-dPeg$_4$-amino acid (0.270 mg, 0.555 μmol), diisopropylethylamine (0.484 μL, 0.555 μmol), and HATU (0.211 mg, 0.555 μmol). The mixture was stirred overnight. The solvent was removed and the residue was purified by flash chromatography using water/acetonitrile with 0.1% formic acid gradient to yield the Fmoc-dPeg4-amino acid derivative of Compound 118 (0.490 mg, 64%). Observed ESI HRMS: m/z 1370.7120 [M+H]$^+$.

To a stirring solution of the Fmoc-dPeg4-amino acid derivative of Compound 118 (0.00490 g, 3.65 μmol) in acetonitrile (0.1823 mL) was added diethylamine (20 μL). The reaction mixture was stirred for 6 h. The volatile material was removed in vacuo, and the resulting intermediate 1C was used in the next step without purification. Observed ESI HRMS: m/z 1148.6530 [M+H]$^+$.

To a stirring solution of intermediate 1C (0.0029 g, 2.52 μmol) in CH$_2$Cl$_2$ (0.15 mL) were added 4-acetylbenzoyl chloride (0.461 mg, 2.52 μmol) and diisopropylethylamine (2.2 μL, 0.013 mmol). The solution was stirred for 1 h. The volatiles were removed, and the remaining residue was purified by HPLC using water and acetonitrile with 0.1% formic acid to afford Compound 120 (0.490 mg, 89%) as a white powder. Observed ESI HRMS: m/z 1294.6999 [M+H]$^+$.

Example 27

Synthesis of Compound 121

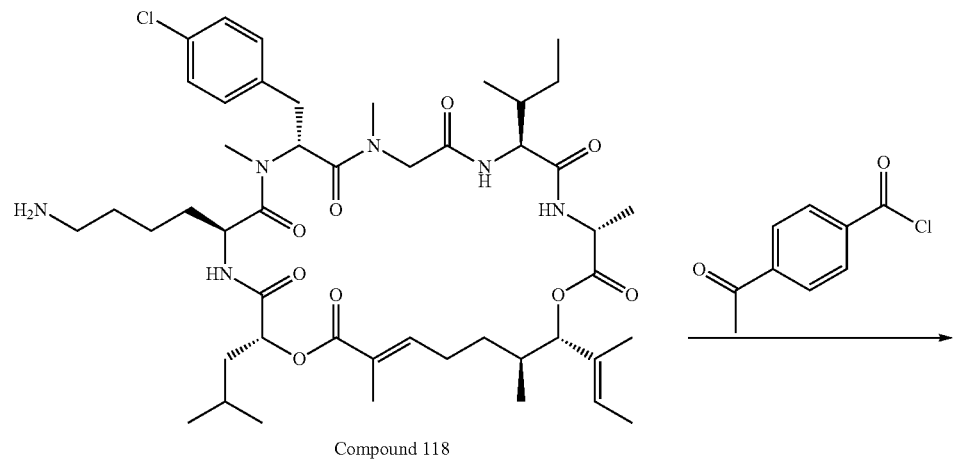

Compound 118

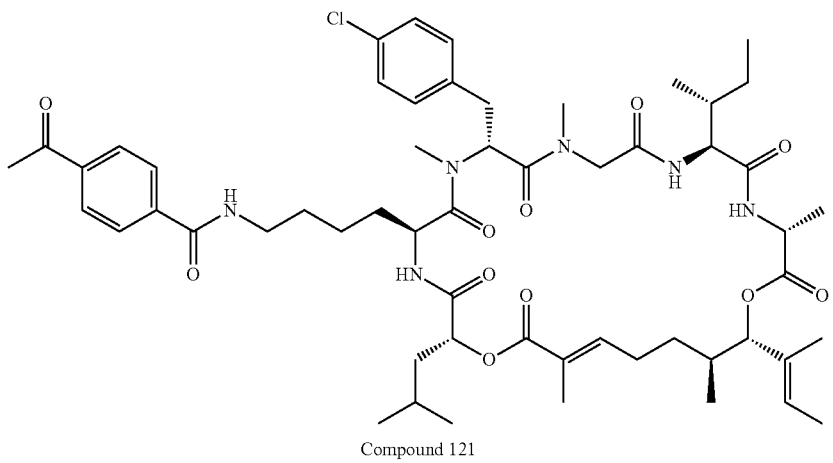

Compound 121

To a stirring solution of Compound 118 (0.0007 g, 0.776 μmol) in CH$_2$Cl$_2$ (0.1 mL) were added 4-acetylbenzoyl chloride (0.354 mg, 1.941 μmol) and diisopropylethylamine (0.678 μL, 3.88 μmol). The mixture was stirred for 3 h. The volatiles were removed, and the remaining residue was purified by HPLC using water and acetonitrile with 0.1% formic acid to afford Compound 121 (0.2 mg, 25%) as a white powder. Observed ESI HRMS: m/z 1047.5608 [M+H]+.

Example 28

Synthesis of Compound 122

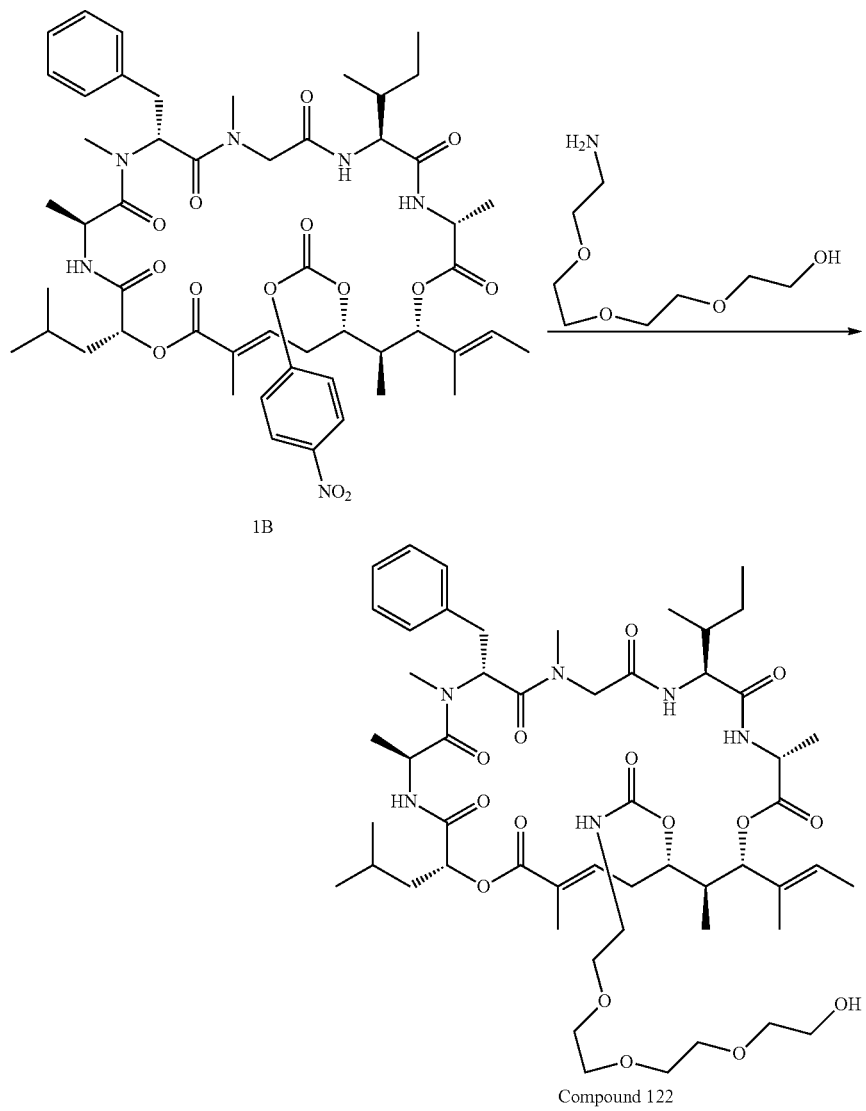

Figure 44:
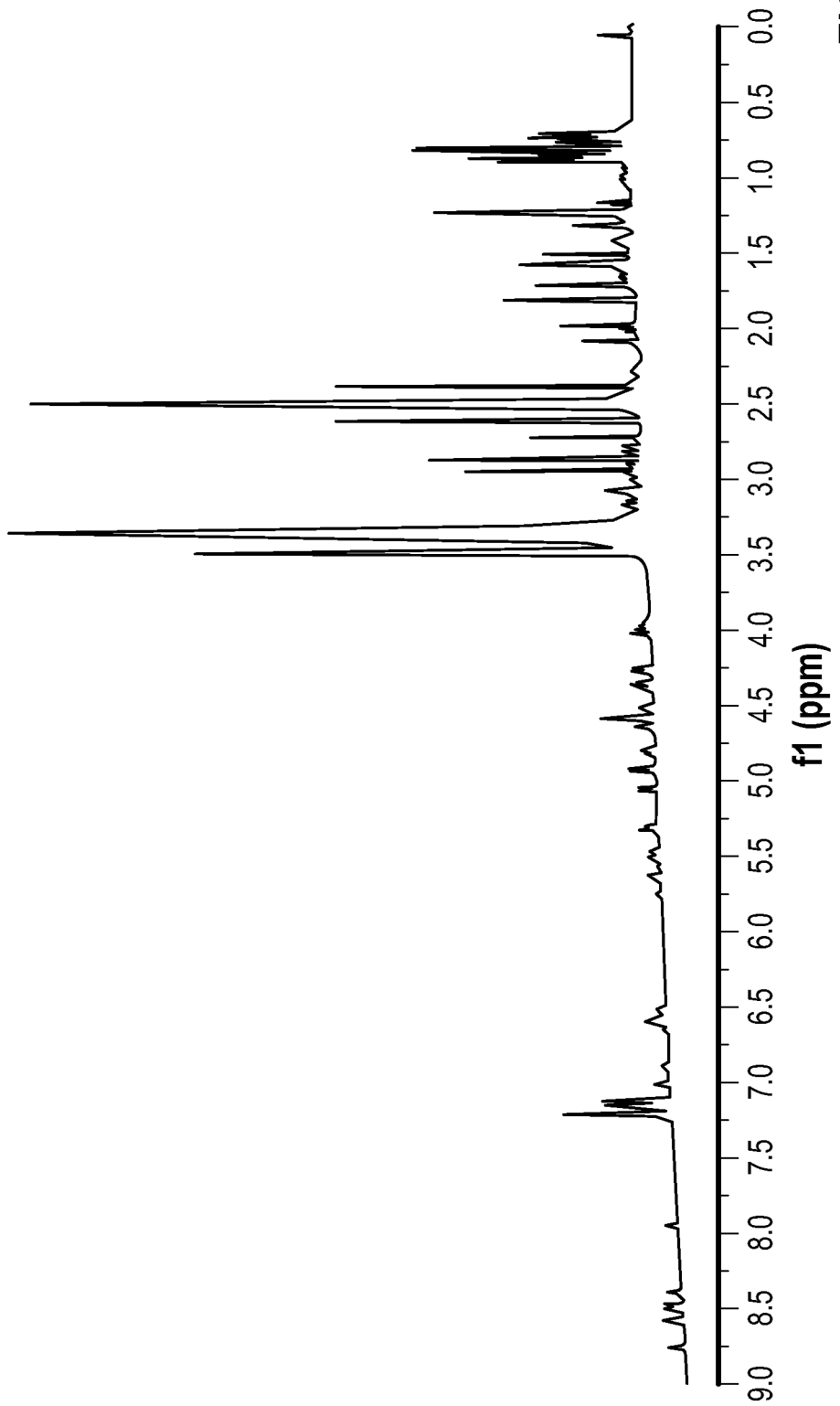
FIG. 44 is a $^1$H NMR spectrum of Compound 122 in DMSO-d6.

To the solution of intermediate carbonate 1B obtained in Example 11 (5.04 μmol, 5 mg) in DCM (7.77 mmol, 0.5 mL) was added 2-(2-(2-(2-aminoethoxy)ethoxy)ethoxy)ethan-1-ol (0.050 mmol, 9.75 mg) and Hunig's base (0.050 mmol, 8.81 μL). The reaction mixture was stirred overnight at rt and the volatiles were removed. The crude material was purified by RP-column chromatography to afford Compound 122 (3.1 mg, 58.8%) as a white solid. Observed ESI HRMS: m/z 1045.6173 [M+H]$^+$. The $^1$H NMR spectrum of Compound 122 is shown in FIG. 44.

Example 29

Synthesis of Compound 123

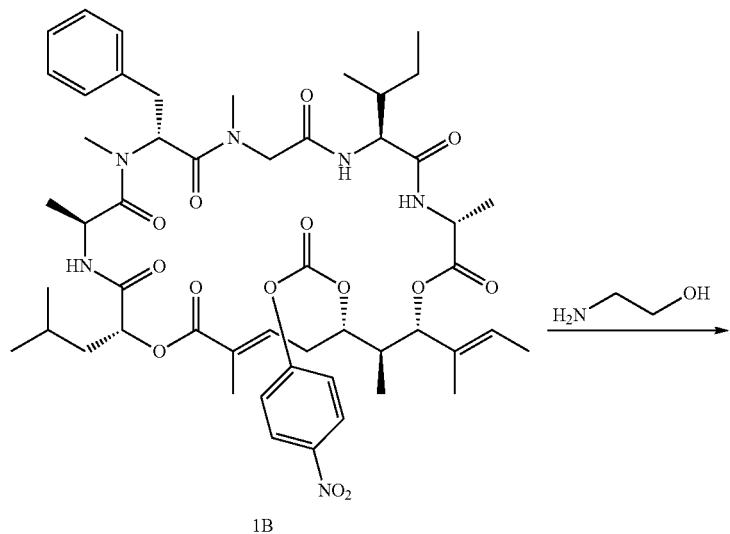

1B

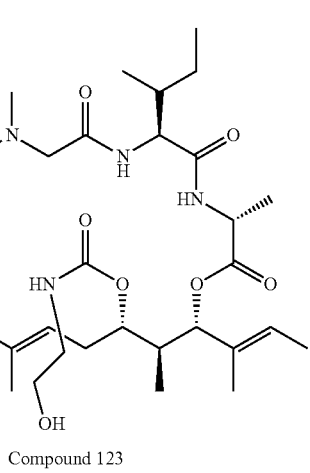

Compound 123

Figure 45:
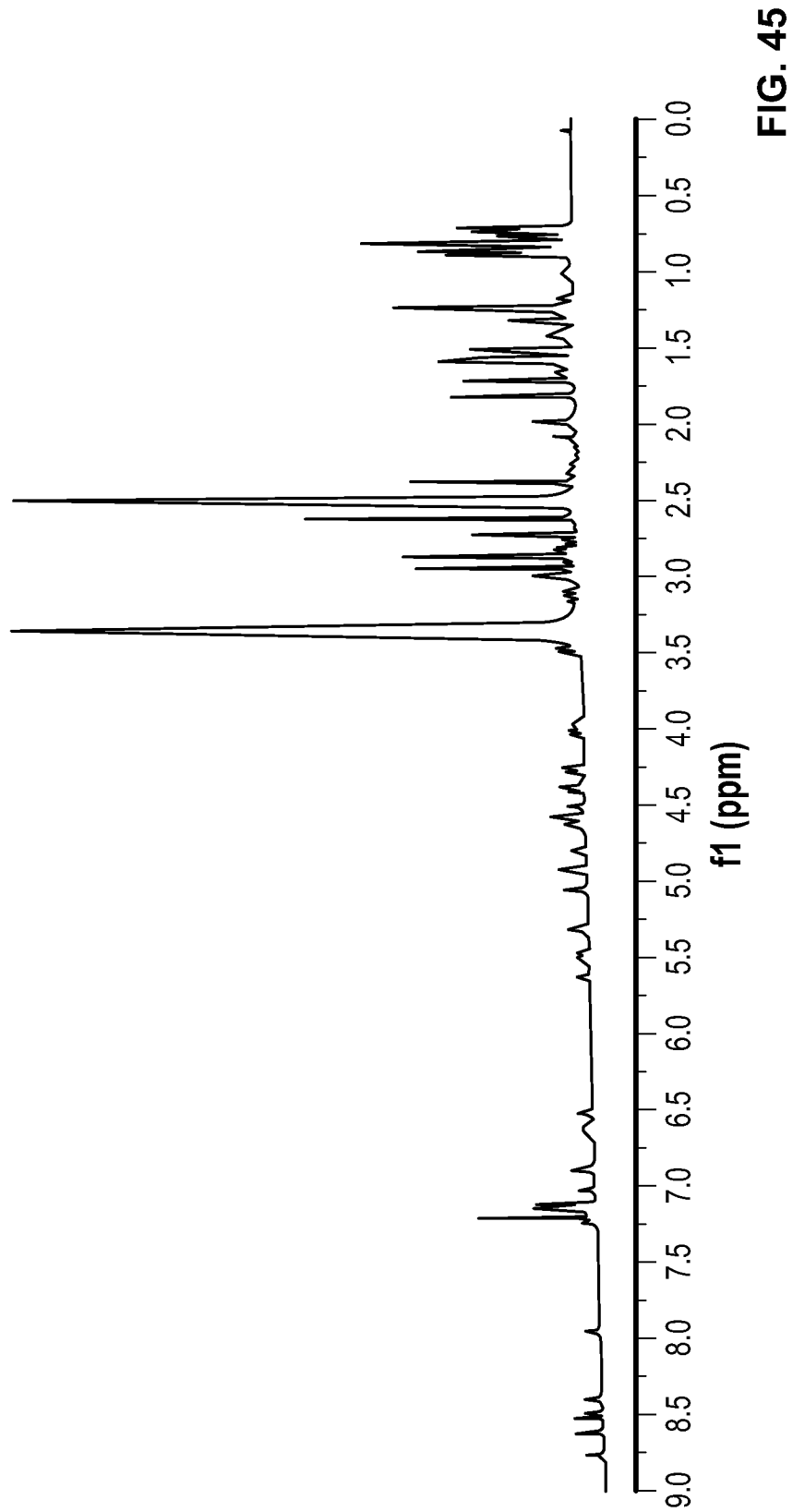
FIG. 45 is a $^1$H NMR spectrum of Compound 123 in DMSO-d6.

To the solution of intermediate carbonate 1B obtained in Example 11 (5.04 µmol, 5 mg) in DCM (7.77 mmol, 0.5 mL) was added 2-aminoethane-1-ol (0.050 mmol, 3.08 mg) and Hunig's base (0.050 mmol, 8.81 µL). The reaction mixture was stirred overnight at rt, and the volatiles were removed. The crude material was purified by column chromatography to yield Compound 123 (2.1 mg, 45.6%) as a white solid. Observed ESI HRMS: m/z 913.5393 [M+H]$^+$. The $^1$H NMR spectrum of Compound 123 is shown in FIG. 45.

Example 30

Synthesis of Compound 124

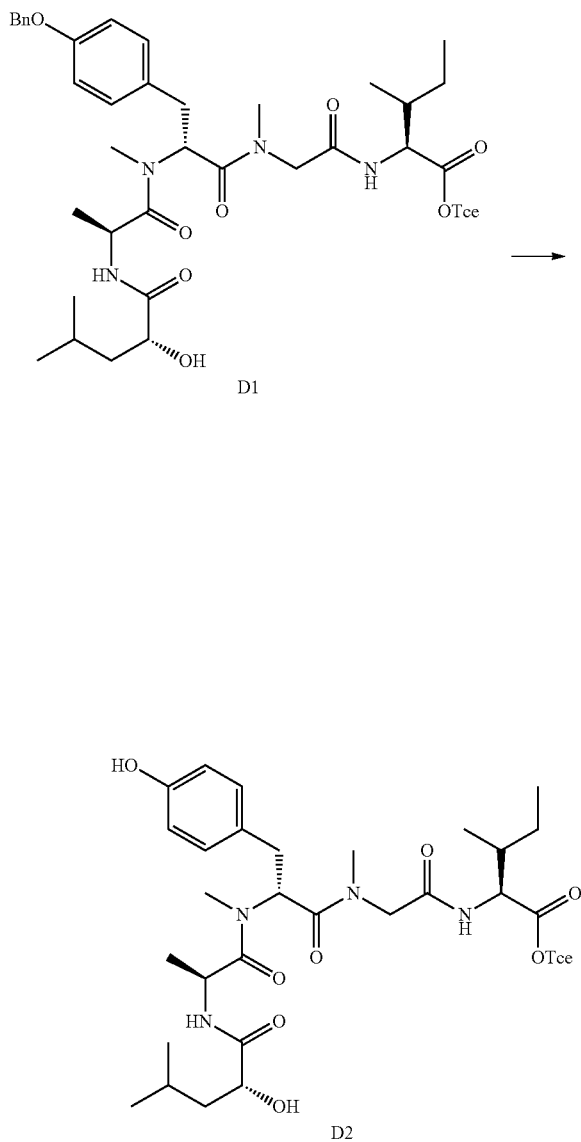

D1

D2

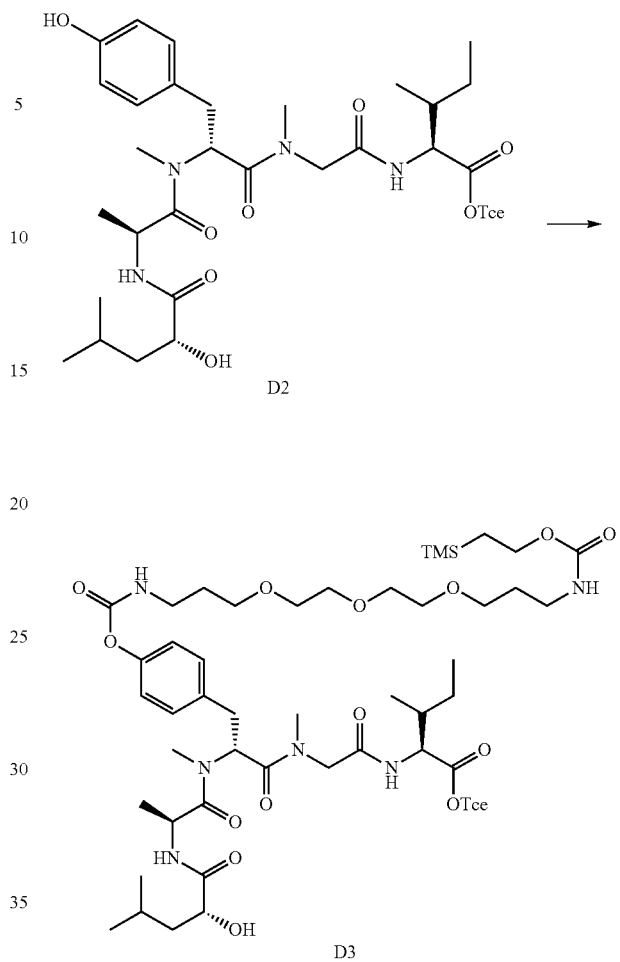

D2

D3

To the solution of 2,2,2-trichloroethyl N—((R)-3-(4-(benzyloxy)phenyl)-2-((S)-2-((R)-2-hydroxy-4-methylpentanamido)-N-methylpropanamido)propanoyl)-N-methylglycyl-L-alloisoleucinate (0.509 mmol, 400 mg) in ethyl acetate (102 mmol, 10 mL) was added Pd/C (0.051 mmol, 108 mg). The reaction mixture was stirred under atmospheric H$_2$ pressure for 6 h. The reaction mixture was filtered over Celite®, and the filtrate was concentrated in vacuo to provide 2,2,2-trichloroethyl N—(N—(((R)-2-hydroxy-4-methylpentanoyl)-L-alanyl)-N-methyl-D-tyrosyl)-N-methylglycyl-L-alloisoleucinate (300 mg, 85%) as a pale gum.

To the solution of 2,2,2-trichloroethyl N—(N—(((R)-2-hydroxy-4-methylpentanoyl)-L-alanyl)-N-methyl-D-tyrosyl)-N-methylglycyl-L-alloisoleucinate (0.503 mmol, 350 mg) and DMAP (0.503 mmol, 0.061 g) in DCM (78 mmol, 5 mL) was added 4-nitrophenyl carbonochloridate (0.503 mmol, 0.101 g) at rt. The reaction mixture was stirred for 2 h. 2-(trimethylsilyl)ethyl(3-(2-(2-(3-aminopropoxy)ethoxy)ethoxy)propyl)carbamate (0.503 mmol, 0.183 g) and Hunig's base (0.503 mmol, 0.088 mL) were added, and the reaction mixture was stirred for another 2 h. Citric acid (10%) was added to the mixture, and the resulting solution was extracted with ethyl acetate (×3) and washed with saturated NaHCO$_3$ (aq) and brine, dried with NaSO$_4$ and concentrated in vacuo. The crude mixture was purified with column chromatography to afford 2,2,2-trichloroethyl N—((R)-3-(4-(((2,2-dimethyl-6-oxo-5,11,14,17-tetraoxa-7-aza-2-silaicosan-20-yl)carbamoyl)oxy)phenyl)-2-((S)-2-((R)-2-hydroxy-4-methylpentanamido)-N-methylpropanamido)propanoyl)-N-methylglycyl-L-alloisoleucinate (320 mg, 58.6%) as a pale oil.

417

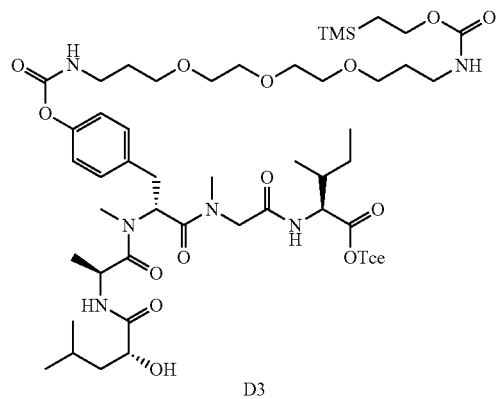

D3

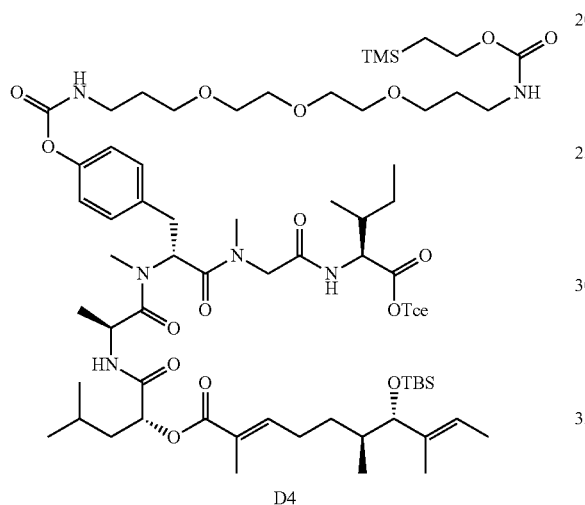

D4

418

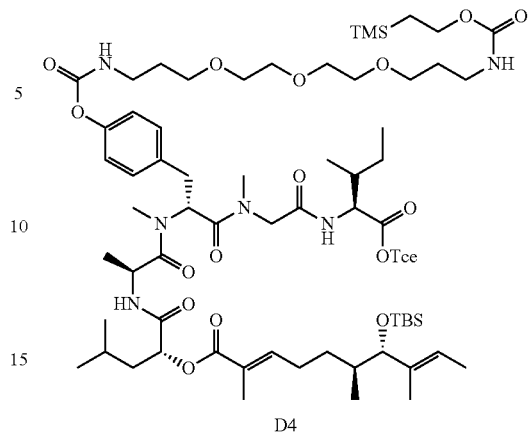

D4

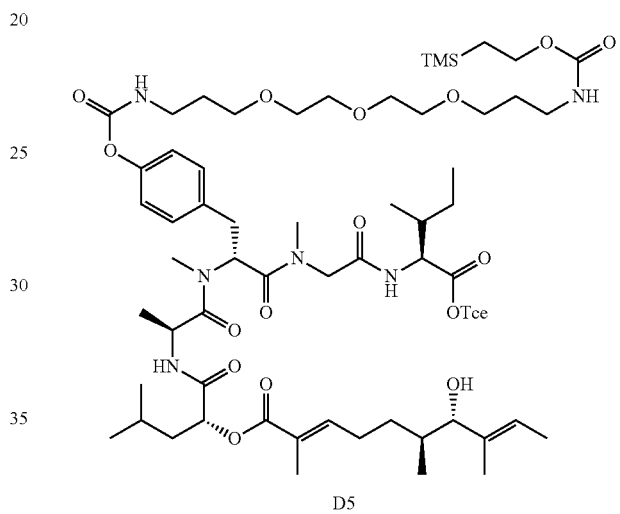

D5

To the solution of 2,2,2-trichloroethyl N—((R)-3-(4-(((2,2-dimethyl-6-oxo-5,11,14,17-tetraoxa-7-aza-2-silaicosan-20-yl)carbamoyl)oxy)phenyl)-2-((S)-2-((R)-2-hydroxy-4-methylpentanamido)-N-methylpropanamido)propanoyl)-N-methylglycyl-L-alloisoleucinate (0.294 mmol, 320 mg), (2E,6S,7S,8E)-7-((tert-butyldimethylsilyl)oxy)-2,6,8-trimethyldeca-2,8-dienoic acid (0.442 mmol, 0.150 g) and DMAP (0.294 mmol, 0.036 g) in DCM (15.54 mmol, 1 mL) was added EDC (0.883 mmol, 0.169 g) at 0° C. After stirring for 15 min at the same temperature, the reaction mixture was warmed to rt and stirred further overnight. Citric acid solution (10%) was added to the mixture, and the mixture was extracted with ethyl acetate (×3), washed with NaHCO₃ solution and brine, dried over NaSO₄, and concentrated in vacuo. The crude mixture was purified by column chromatography to afford 2,2,2-trichloroethyl(2S,8R,11S,14R)-2-((R)-sec-butyl)-14-(((2E,6S,7S,8E)-7-((tert-butyldimethylsilyl)oxy)-2,6,8-trimethyldeca-2,8-dienoyl)oxy)-8-(4-(((2,2-dimethyl-6-oxo-5,11,14,17-tetraoxa-7-aza-2-silaicosan-20-yl)carbamoyl)oxy)benzyl)-6,9,11,16-tetramethyl-4,7,10,13-tetraoxo-3,6,9,12-tetraazaheptadecanoate (152 mg, 36.6%) as a white solid.

The solution of 2,2,2-trichloroethyl(2S,8R,11S,14R)-2-((R)-sec-butyl)-14-(((2E,6S,7S,8E)-7-((tert-butyldimethylsilyl)oxy)-2,6,8-trimethyldeca-2,8-dienoyl)oxy)-8-(4-(((2,2-dimethyl-6-oxo-5,11,14,17-tetraoxa-7-aza-2-silaicosan-20-yl)carbamoyl)oxy)benzyl)-6,9,11,16-tetramethyl-4,7,10,13-tetraoxo-3,6,9,12-tetraazaheptadecanoate (0.108 mmol, 152 mg) in THF (54.9 mmol, 4.5 mL), pyridine (9.27 mmol, 0.75 mL) and HF-pyridine (0.108 mmol, 0.75 mL) was heated at 60° C. overnight. Saturated NaHCO₃ solution was added to the reaction mixture, and the mixture was extracted with ethyl acetate (×3), washed with brine, dried over NaSO₄, and concentrated in vacuo. The crude material was purified by column chromatography to provide 2,2,2-trichloroethyl(2S,8R,11S,14R)-2-((R)-sec-butyl)-8-(4-(((2,2-dimethyl-6-oxo-5,11,14,17-tetraoxa-7-aza-2-silaicosan-20-yl)carbamoyl)oxy)benzyl)-14-(((2E,6S,7S,8E)-7-hydroxy-2,6,8-trimethyldeca-2,8-dienoyl)oxy)-6,9,11,16-tetramethyl-4,7,10,13-tetraoxo-3,6,9,12-tetraazaheptadecanoate (70 mg, 50.1%) as a white solid.

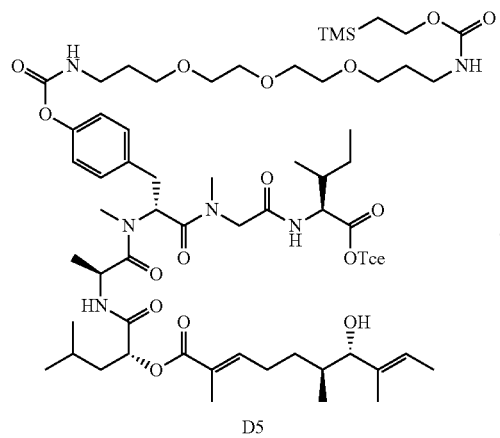

D5

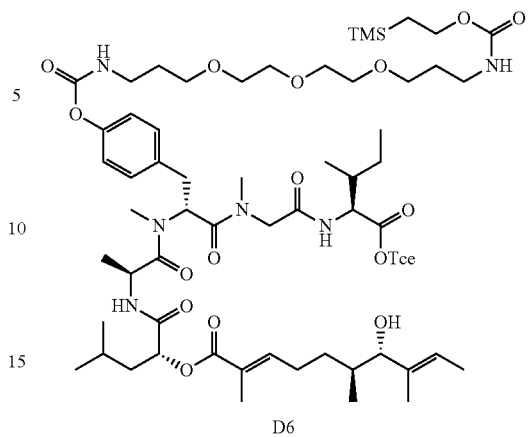

D6

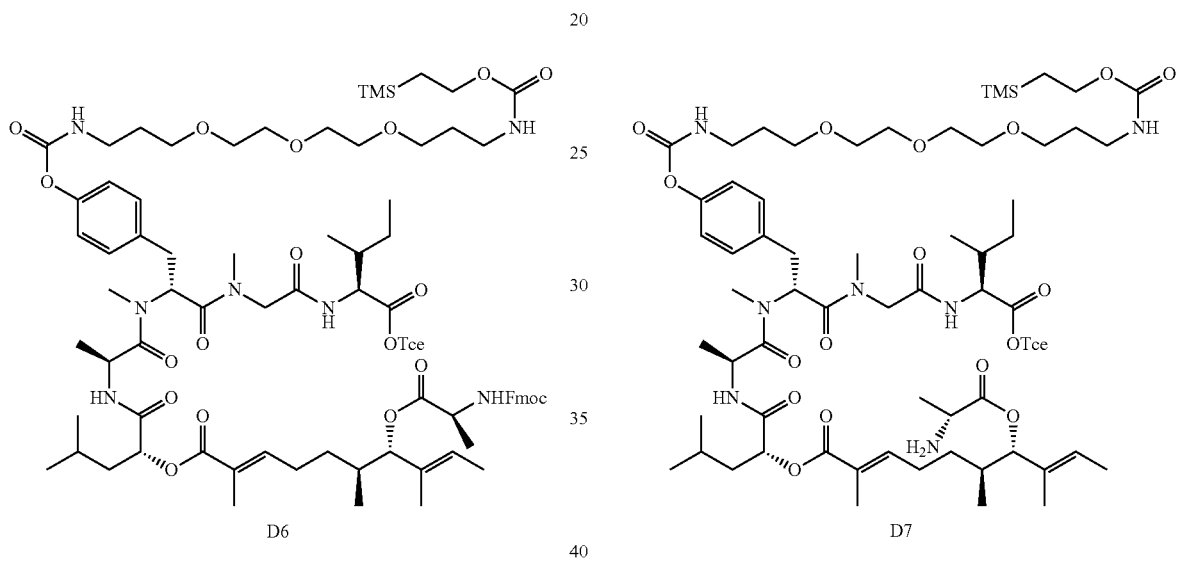

D6

D7

To the solution of 2,2,2-trichloroethyl(2S,8R,11S,14R)-2-((R)-sec-butyl)-8-(4-(((2,2-dimethyl-6-oxo-5,11,14,17-tetraoxa-7-aza-2-silaicosan-20-yl)carbamoyl)oxy)benzyl)-14-(((2E,6S,7S,8E)-7-hydroxy-2,6,8-trimethyldeca-2,8-dienoyl)oxy)-6,9,11,16-tetramethyl-4,7,10,13-tetraoxo-3,6,9,12-tetraazaheptadecanoate (0.054 mmol, 70 mg), (((9H-fluoren-9-yl)methoxy)carbonyl)-D-alanine (0.162 mmol, 0.050 g), and DMAP (0.054 mmol, 6.60 mg) in DCM (7.77 mmol, 0.5 mL) was added EDC (0.324 mmol, 0.062 g) at 0° C. The reaction mixture was stirred overnight. Citric acid solution (10%) was added to the reaction mixture, and the mixture was extracted with ethyl acetate, washed with NaHCO₃ (aq) and brine, dried over NaSO₄, and concentrated in vacuo. The crude material was purified by column chromatography to provide 2,2,2-trichloroethyl(2S,8R,11S,14R)-14-(((2E,6S,7S,8E)-7-(((((9H-fluoren-9-yl)methoxy)carbonyl)-D-alanyl)oxy)-2,6,8-trimethyldeca-2,8-dienoyl)oxy)-2-((R)-sec-butyl)-8-(4-(((2,2-dimethyl-6-oxo-5,11,14,17-tetraoxa-7-aza-2-silaicosan-20-yl)carbamoyl)oxy)benzyl)-6,9,11,16-tetramethyl-4,7,10,13-tetraoxo-3,6,9,12-tetraazaheptadecanoate (70 mg, 82%) as a white solid.

To the solution of 2,2,2-trichloroethyl(2S,8R,11S,14R)-14-(((2E,6S,7S,8E)-7-(((((9H-fluoren-9-yl)methoxy)carbonyl)-D-alanyl)oxy)-2,6,8-trimethyldeca-2,8-dienoyl)oxy)-2-((R)-sec-butyl)-8-(4-(((2,2-dimethyl-6-oxo-5,11,14,17-tetraoxa-7-aza-2-silaicosan-20-yl)carbamoyl)oxy)benzyl)-6,9,11,16-tetramethyl-4,7,10,13-tetraoxo-3,6,9,12-tetraazaheptadecanoate (0.044 mmol, 70 mg) in THF (61.0 mmol, 5 mL) and 1M AcOH (1.000 mmol, 1 mL) was added zinc (8.81 mmol, 0.576 g), and the reaction mixture was stirred for 3 h. The reaction mixture was filtered over Celite®, and the filterate was concentrated in vacuo. MeCN (38.3 mmol, 2 mL) and diethylamine (1.914 mmol, 0.2 mL) were added to the crude material, and the mixture was stirred for 2 h. The volatiles were removed, and the crude material was purified by RP-column chromatography to provide N—((R)-2-((S)-2-((R)-2-(((2E,6S,7S,8E)-7-((D-alanyl)oxy)-2,6,8-trimethyldeca-2,8-dienoyl)oxy)-4-methylpentanamido)-N-methylpropanamido)-3-(4-(((2,2-dimethyl-6-oxo-5,11,14,17-tetraoxa-7-aza-2-silaicosan-20-yl)carbamoyl)oxy)phenyl)propanoyl)-N-methylglycyl-L-alloisoleucine (10 mg, 18.38%) as a white solid.

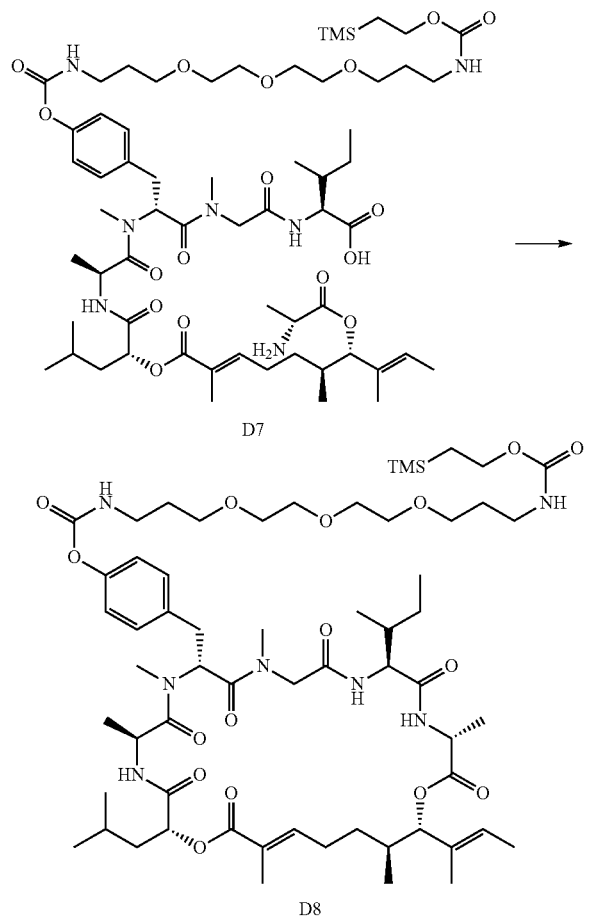

D7

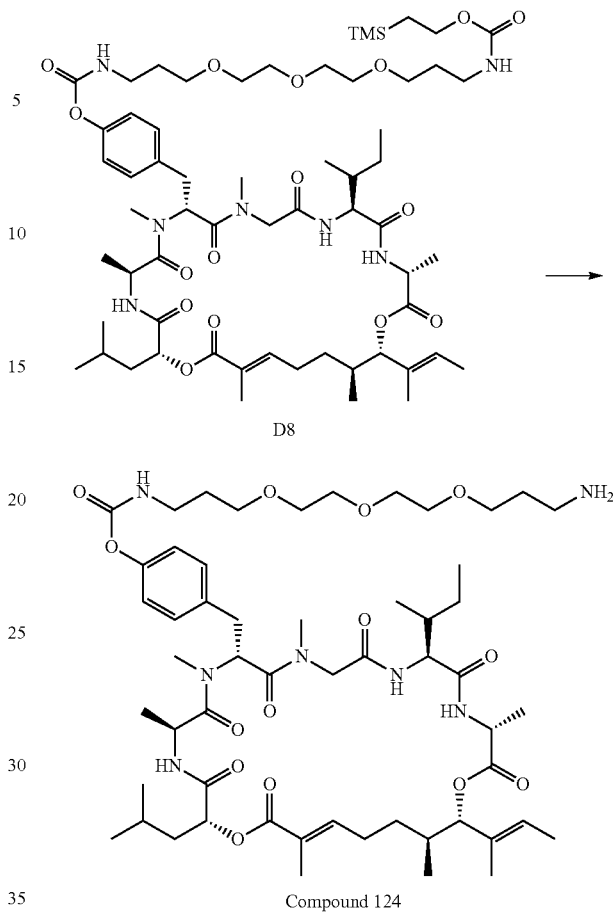

D8

D8

Compound 124

To the solution of N—((R)-2-((S)-2-((R)-2-(((2E,6S,7S,8E)-7-((D-alanyl)oxy)-2,6,8-trimethyldeca-2,8-dienoyl)oxy)-4-methylpentanamido)-N-methylpropanamido)-3-(4-(((2,2-dimethyl-6-oxo-5,11,14,17-tetraoxa-7-aza-2-silaicosan-20-yl)carbamoyl)oxy)phenyl)propanoyl)-N-methylglycyl-L-alloisoleucine (8.10 µmol, 10 mg) and HOAt (0.096 mmol, 13 mg) in DCM (155 mmol, 10 mL) and DMF (12.91 mmol, 1 mL) was added EDC (0.104 mmol, 20 mg) at 0° C. The reaction mixture was stirred for 2 h at the same temperature, warmed up to rt, and stirred overnight. Citric acid solution (10%) was added to the reaction mixture, and the mixture was extracted with ethyl acetate, washed with NaHCO₃ solution and brine, dried over NaSO₄, and concentrated in vacuo. The crude material was purified with RP-column chromatography to afford 4-(((2R,5S,8R,14S,17R,20S,21S,E)-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-8-yl)methyl)phenyl(2,2-dimethyl-6-oxo-5,11,14,17-tetraoxa-7-aza-2-silaicosan-20-yl)carbamate (7 mg, 71.0%) as a white solid.

Figure 46:
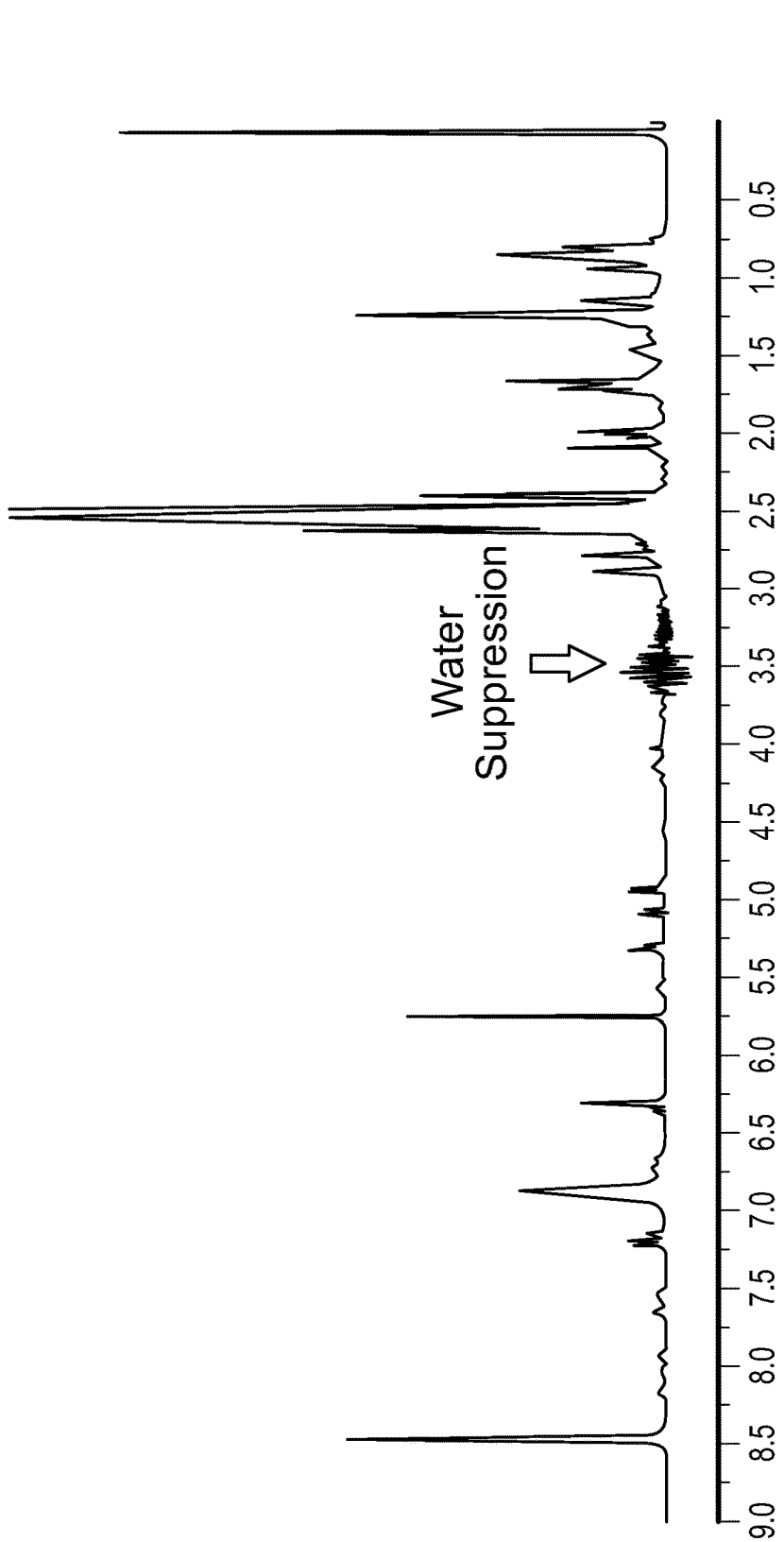
FIG. 46 is a $^1$H NMR spectrum of Compound 124 in DMSO-d6.

To the solution of 4-(((2R,5S,8R,14S,17R,20S,21S,E)-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-8-yl)methyl)phenyl(2,2-dimethyl-6-oxo-5,11,14,17-tetraoxa-7-aza-2-silaicosan-20-yl)carbamate (3.29 µmol, 4 mg) in DCM (6.22 mmol, 0.4 mL) was added 2,6-lutidine (0.033 mmol, 3.83 µL) and trimethylsilyl trifluoromethanesulfonate (0.049 mmol, 8.91 µL) at rt. The reaction mixture was stirred for 12 h, and sat NaHCO₃ solution was added. The reaction mixture was extracted with DCM/MeOH (10:1), washed with brine, dried over NaSO₄ and concentrated in vacuo. The crude material was purified by RP-HPLC to afford 4-(((2R,5S,8R,14S,17R,20S,21S,E)-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-8-yl)methyl)phenyl(3-(2-(2-(3-aminopropoxy)ethoxy)ethoxy)propyl)carbamate (Compound 124) (0.8 mg, 22.69%) as a white solid. Observed ESI HRMS: m/z 1072.6633 [M+H]⁺. The ¹H NMR spectrum of Compound 124 is shown in FIG. 46.

Example 31

Synthesis of Conjugate L14

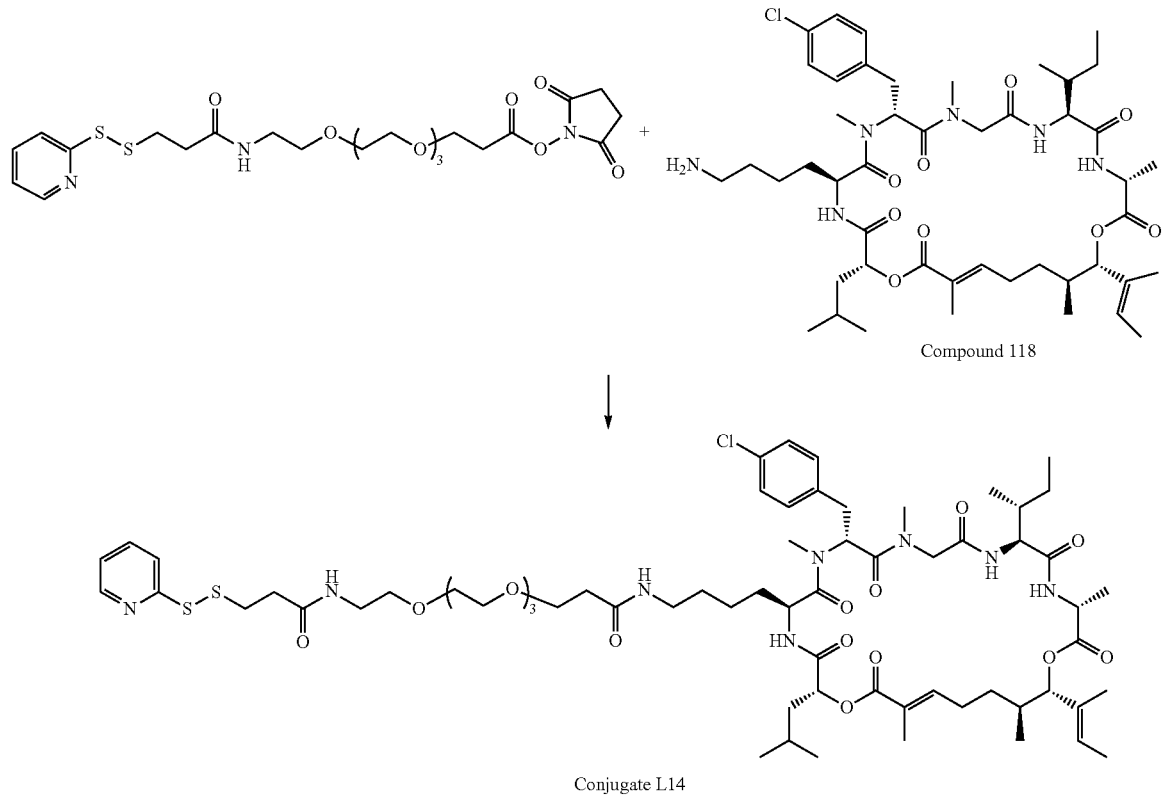

Compound 118

Conjugate L14

To a stirring solution of the free drug Compound 118 in CH$_2$Cl$_2$ (0.5 mL) were added 6.21 mg of 2,5-dioxopyrrolidin-1-yl 3-oxo-1-(pyridine-2-yl disulfonal), 7, 10, 13, 16-tetraoxa-4-azanonadecan-19-oate (6.21 mg. 0.011 mmol) and 1-hydroxy-7-azabenzotriazole (1.5 mg, 0.011 mmol). The mixture was stirred for 3 h. The volatiles were removed, and the remaining residue was purified by HPLC using water and acetonitrile with 0.1% formic acid to afford Conjugate L14 (1.58 mg, 21%) as a white powder. Observed ESI HRMS: m/z 1345.6625 [M+H]$^+$.

Example 32

Synthesis of Conjugate L15

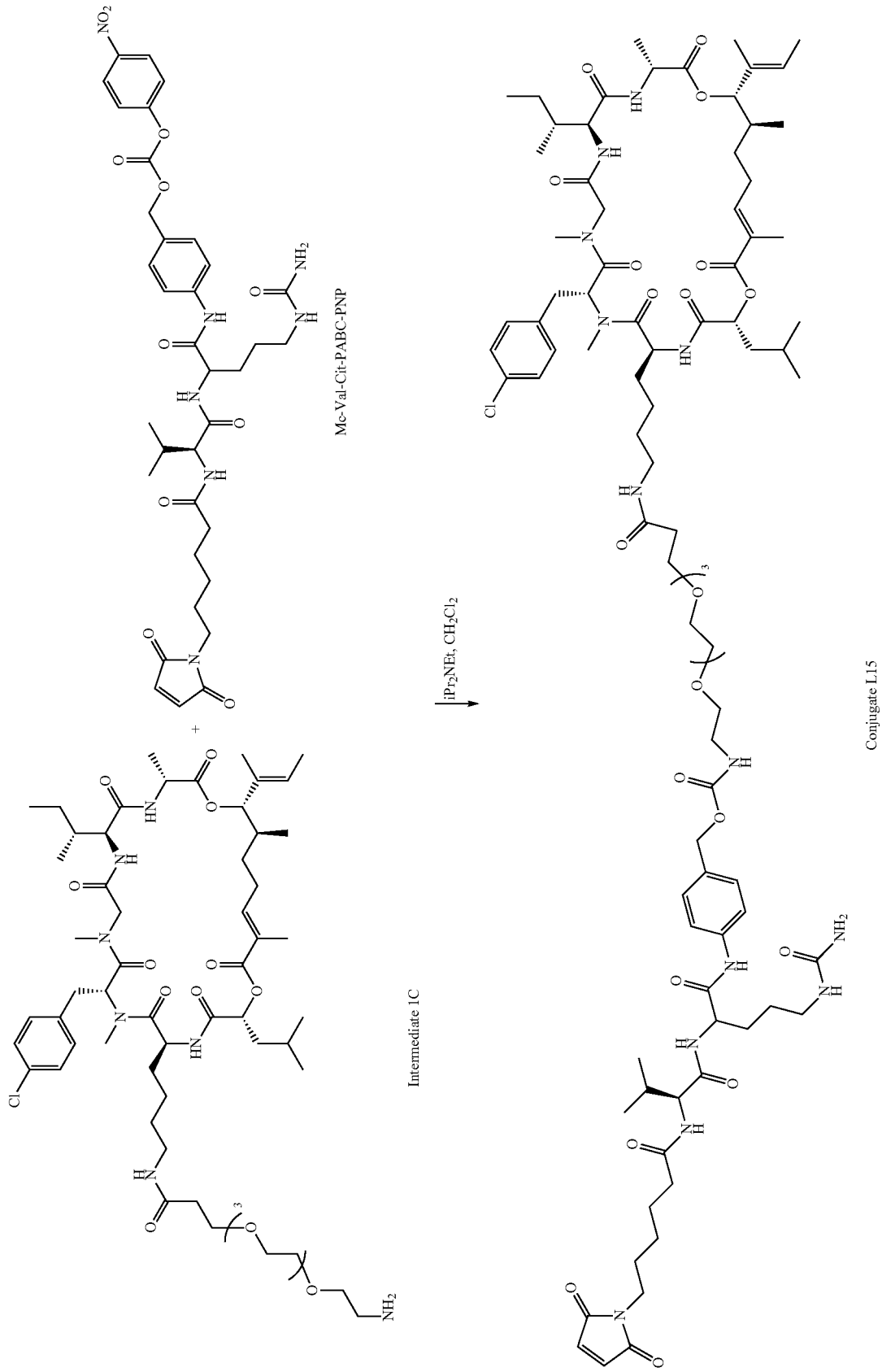

427

To a stirring solution of Intermediate 1C (0.005 g, 4.35 μmol) in $CH_2Cl_2$ (0.15 mL) were added Mc-Val-Cit-PABC-PNP (3.21 mg, 4.35 μmol) and diisopropylethylamine (3.80 uL, 0.022 mmol). The mixture was stirred for 3 h. The volatiles were removed, and the remaining residue was purified by HPLC using water and acetonitrile with 0.1% formic acid to afford Conjugate L15 (1.99 mg, 26%) as a white powder. Observed ESI HRMS: m/z 873.9756 [M/2+H]$^{2+}$.

Example 33

Synthesis of Conjugate L11

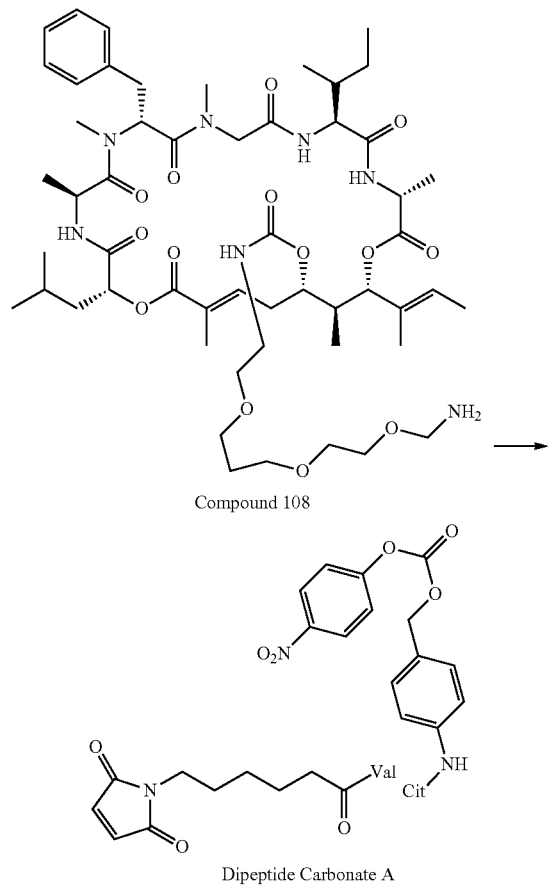

Compound 108

Dipeptide Carbonate A

428

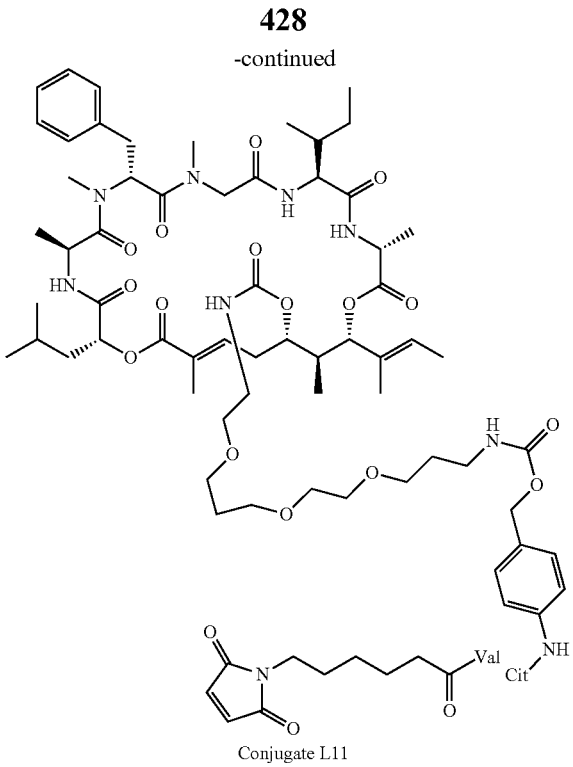

Conjugate L11

Figure 47:
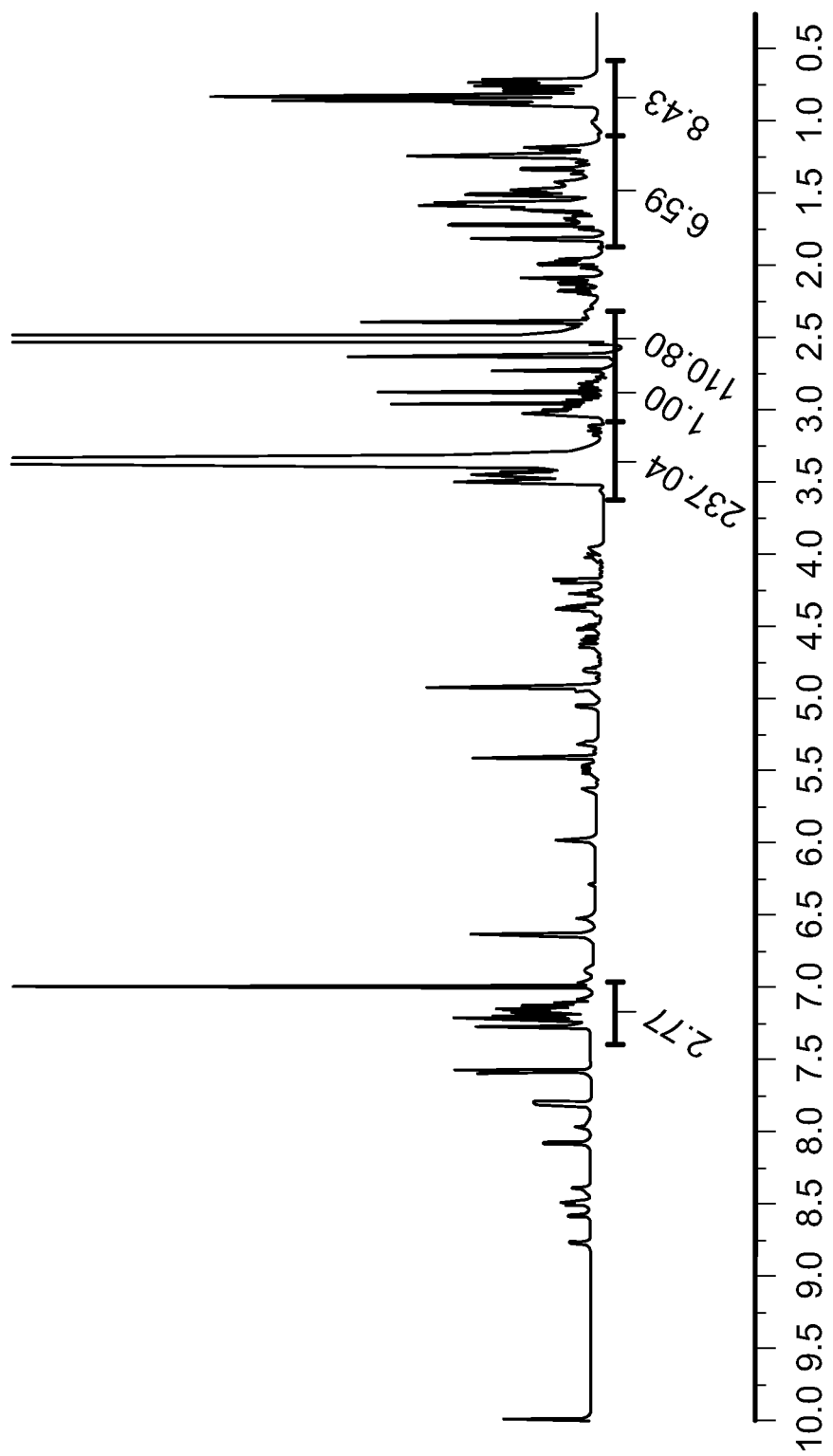
FIG. 47 is a $^1$H NMR spectrum of Conjugate L11 in DMSO-d6.

To the solution of Compound 108 (9.33 μmol, 10 mg) in DCM (6.22 mmol, 0.4 mL) and DMF (0.517 mmol, 0.04 mL) was added dipeptide carbonate A (0.01 mmol, 7.38 mg). The solution was stirred overnight. The solvent was removed by blowing air, and the residue was purified by RP-column chromatography to afford Conjugate L11 (6.8 mg, 43.6%) as a white powder. Observed ESI HRMS: m/z 1670.9297 [M+H]$^+$. The $^1$H NMR spectrum of Conjugate L11 is shown in FIG. 47.

Example 34

Synthesis of Conjugate L12

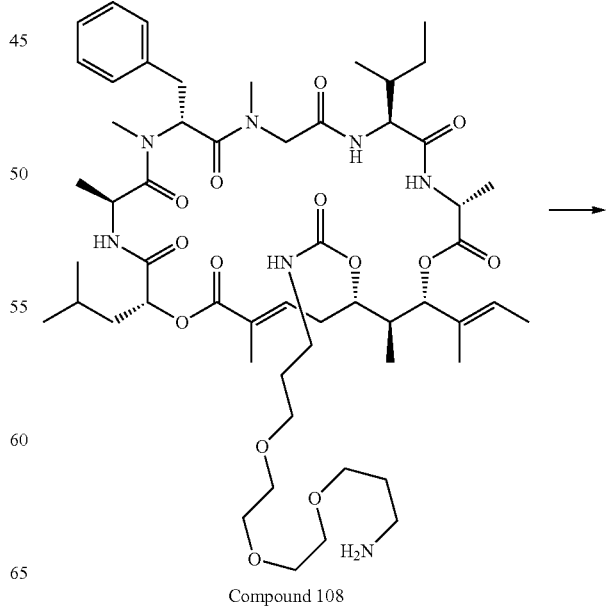

Compound 108

429
-continued

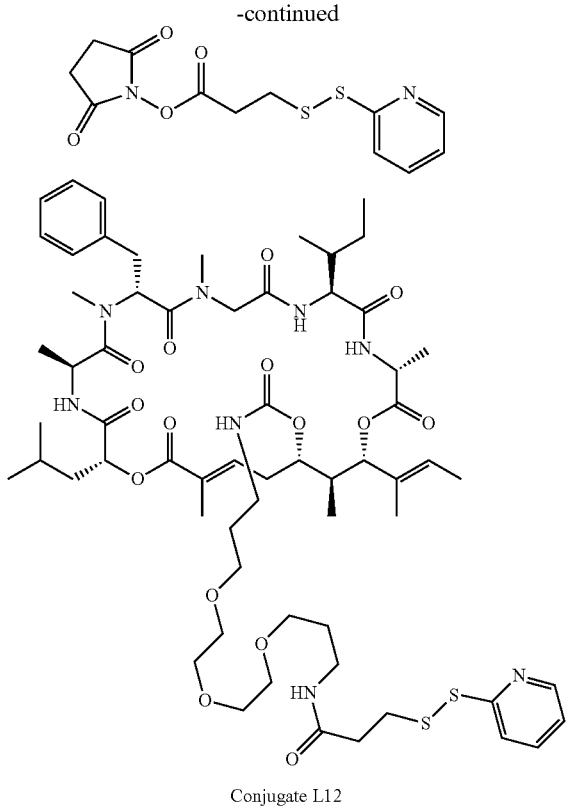

Conjugate L12

Figure 48:
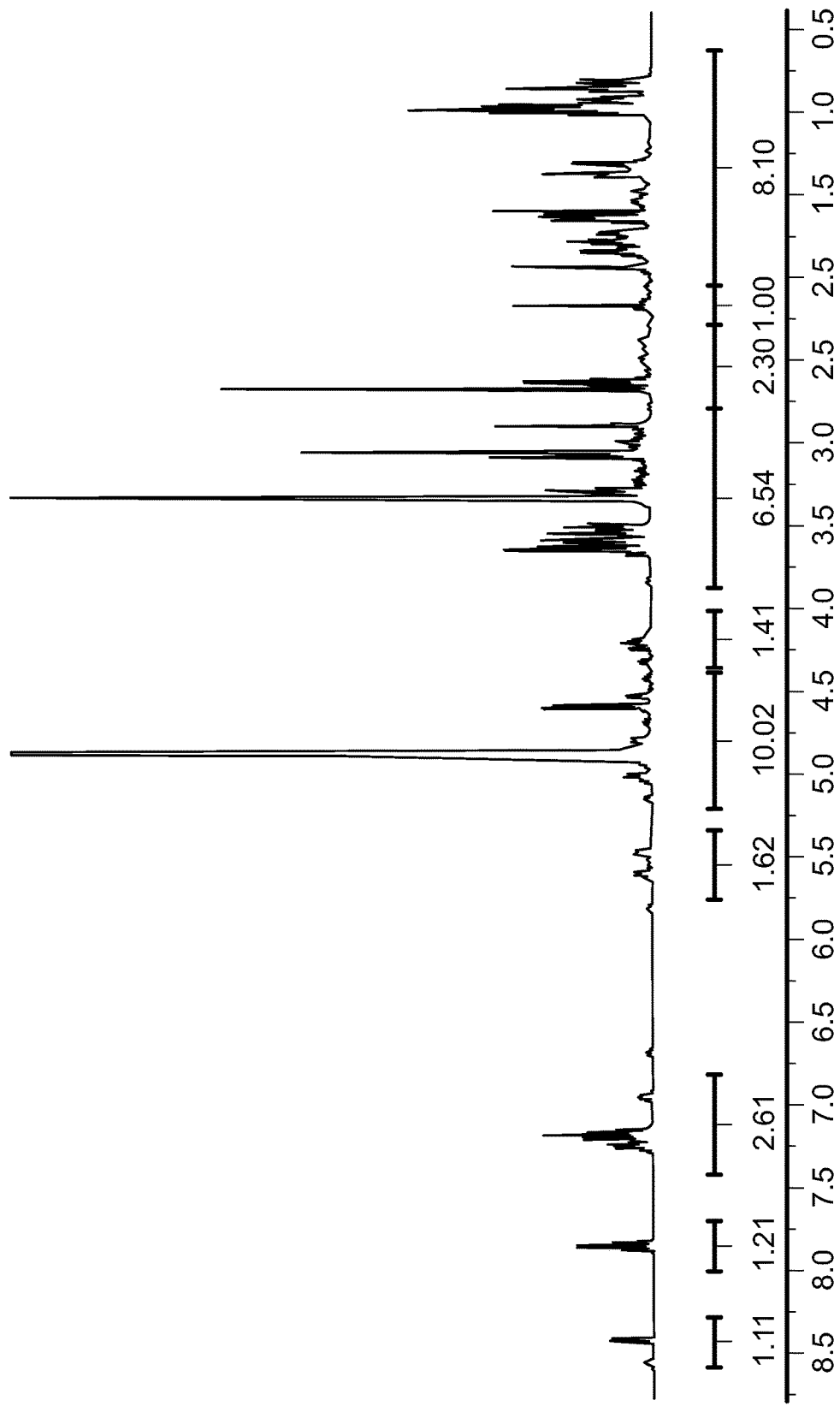
FIG. 48 is a $^1$H NMR spectrum of Conjugate L12 in CD$_3$OD.
Figure 49:
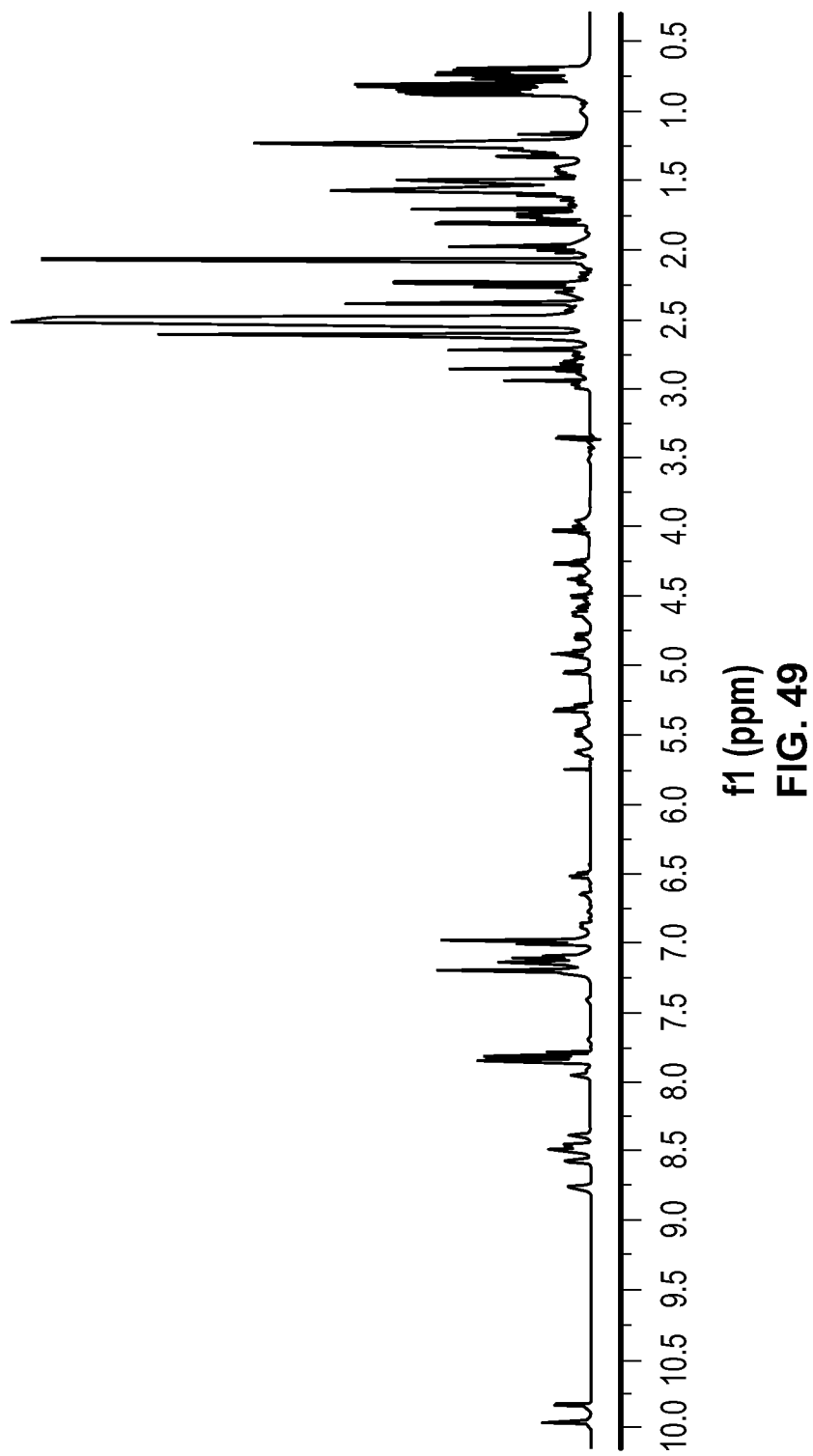
FIG. 49 is a $^1$H NMR spectrum of Conjugate L13 in DMSO-d6.

To a solution of Compound 108 (3.73 μmol, 4 mg) in DCM (7.77 mmol, 0.5 mL) was added 2,5-dioxopyrrolidin-1-yl-3-(pyridin-2-yldisulfanyl)propanoate (0.013 mmol, 4 mg). The mixture was stirred overnight. The solvent was removed, and the residue was purified with RP-column chromatography to afford Conjugate L12 (3.4 mg, 71.8%) as a white powder. Observed ESI HRMS: m/z 1269.651 [M+H]$^+$. The $^1$H NMR spectrum of Conjugate L12 is shown in FIG. 48.

Example 35

Synthesis of Compound 116 and Conjugate L13

A. Acyl Intermediate

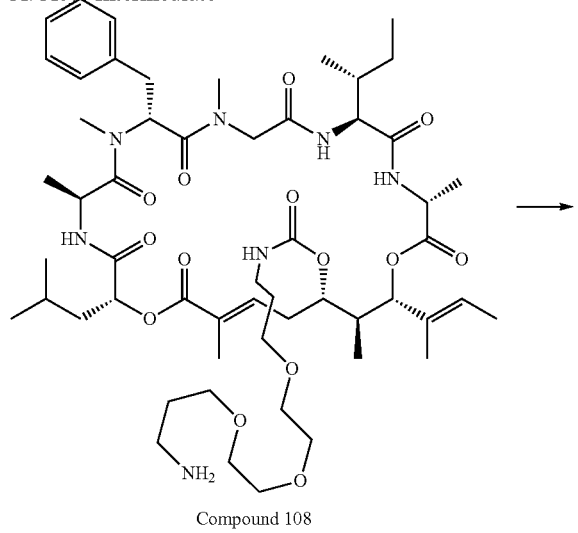

Compound 108

430
-continued

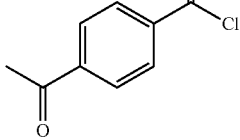

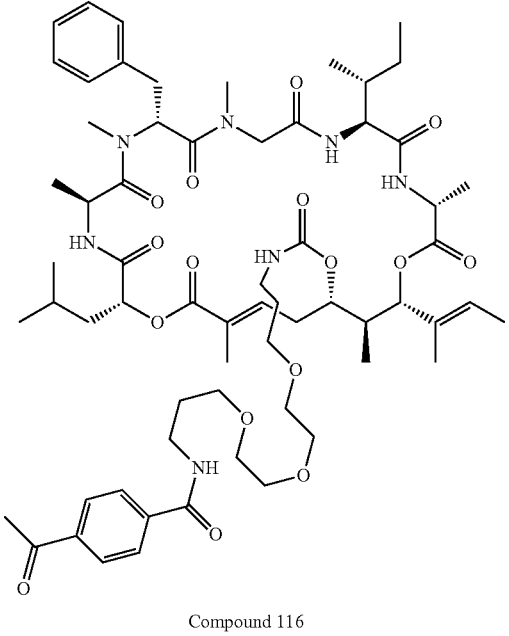

Compound 116

Figure 40:
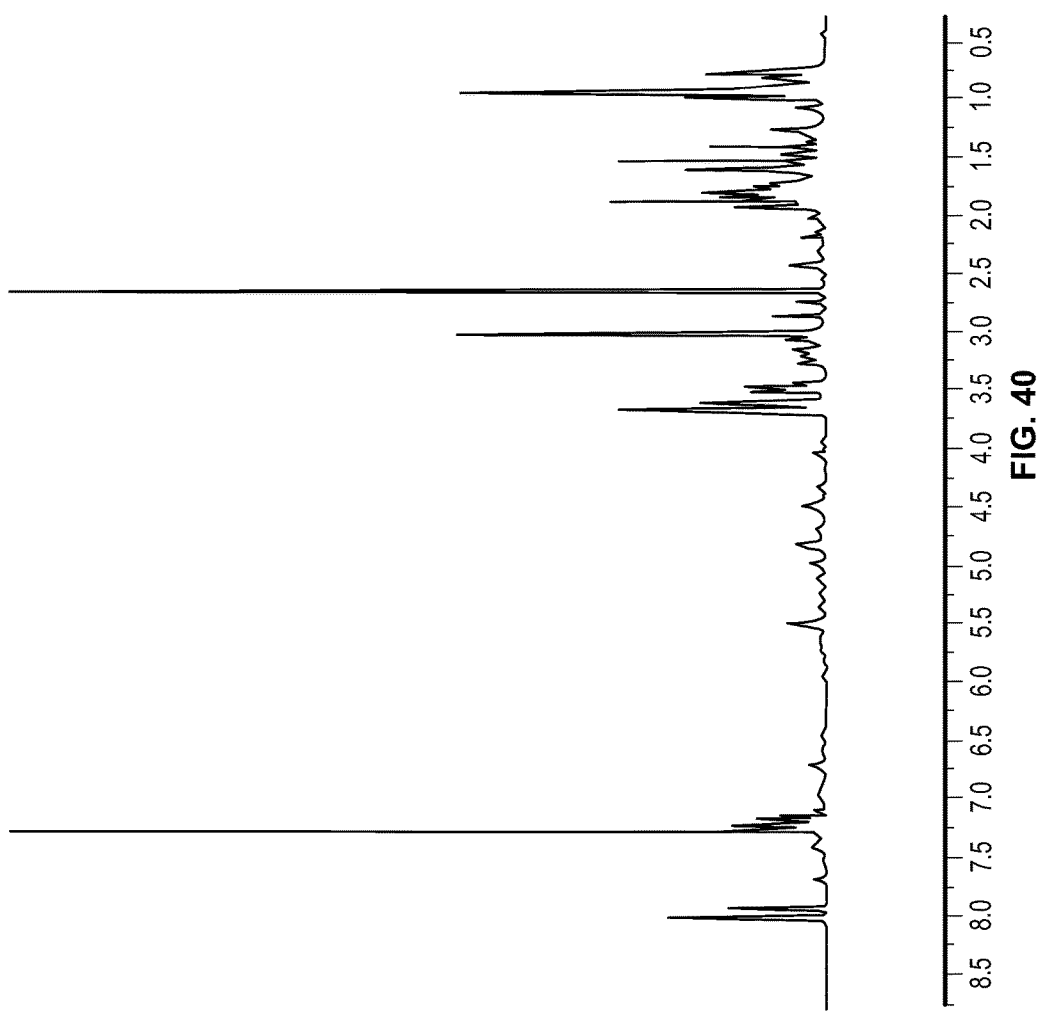
FIG. 40 is a $^1$H NMR spectrum of Compound 116 in CDCl$_3$.

To the solution of Compound 108 (0.012 mmol, 13 mg) and N-ethyl-N-isopropylpropan-2-amine (0.271 mmol, 35 mg) in DCM (7.77 mmol, 0.5 mL) was added 4-acetylbenzoyl chloride (0.071 mmol, 13 mg). The solution was stirred for 1 h. The volatiles were removed, and the remaining residue was purified by RP-column chromatography to afford Compound 116 (13 mg, 88%) as a white powder. Observed ESI HRMS: m/z 1218.6914 [M+H]$^+$. The $^1$H NMR spectrum of Compound 116 is shown in FIG. 40.

B. Conjugate L13

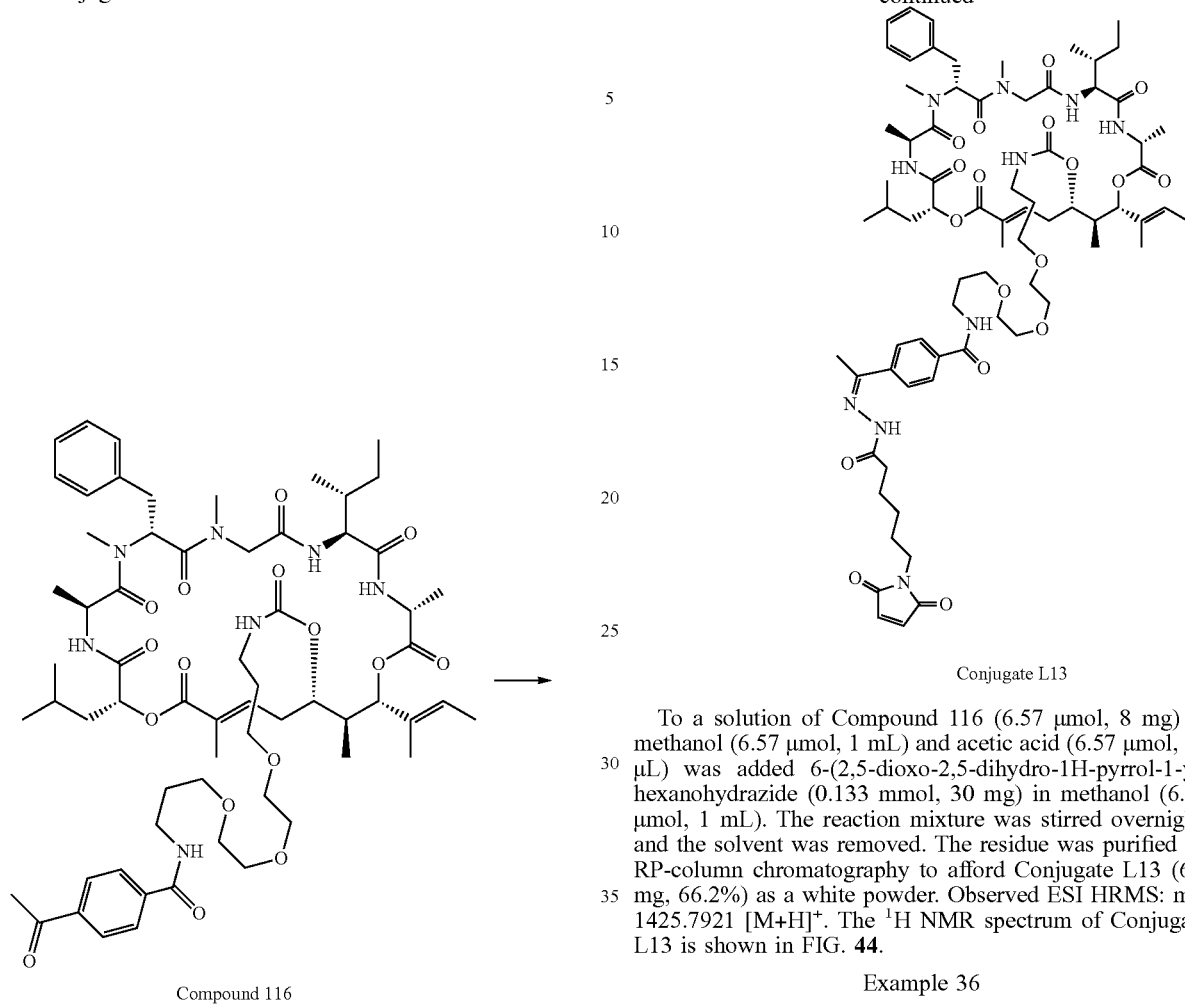

Compound 116

Conjugate L13

To a solution of Compound 116 (6.57 µmol, 8 mg) in methanol (6.57 µmol, 1 mL) and acetic acid (6.57 µmol, 10 µL) was added 6-(2,5-dioxo-2,5-dihydro-1H-pyrrol-1-yl)hexanohydrazide (0.133 mmol, 30 mg) in methanol (6.57 µmol, 1 mL). The reaction mixture was stirred overnight, and the solvent was removed. The residue was purified by RP-column chromatography to afford Conjugate L13 (6.2 mg, 66.2%) as a white powder. Observed ESI HRMS: m/z 1425.7921 [M+H]$^+$. The $^1$H NMR spectrum of Conjugate L13 is shown in FIG. 44.

Example 36

Synthesis of Conjugate L22

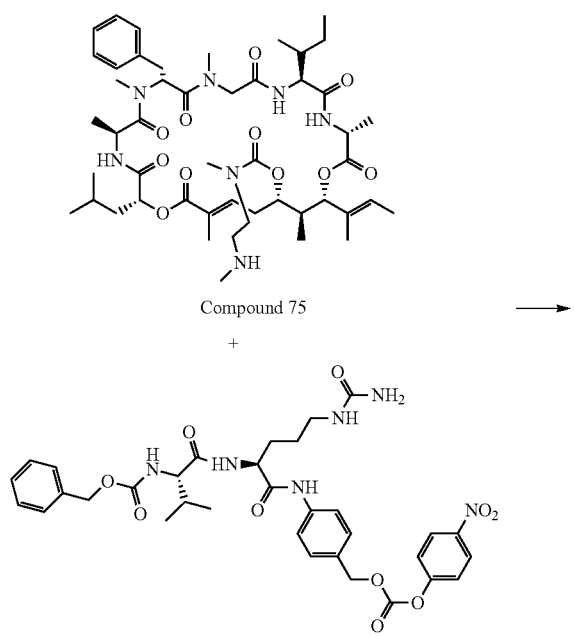

Compound 75

+

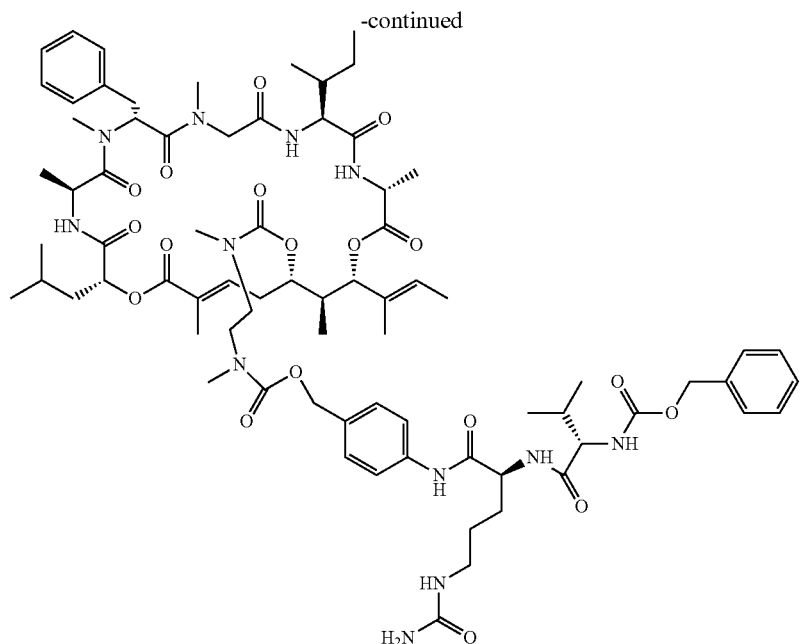

Conjugate L22

Figure 50:
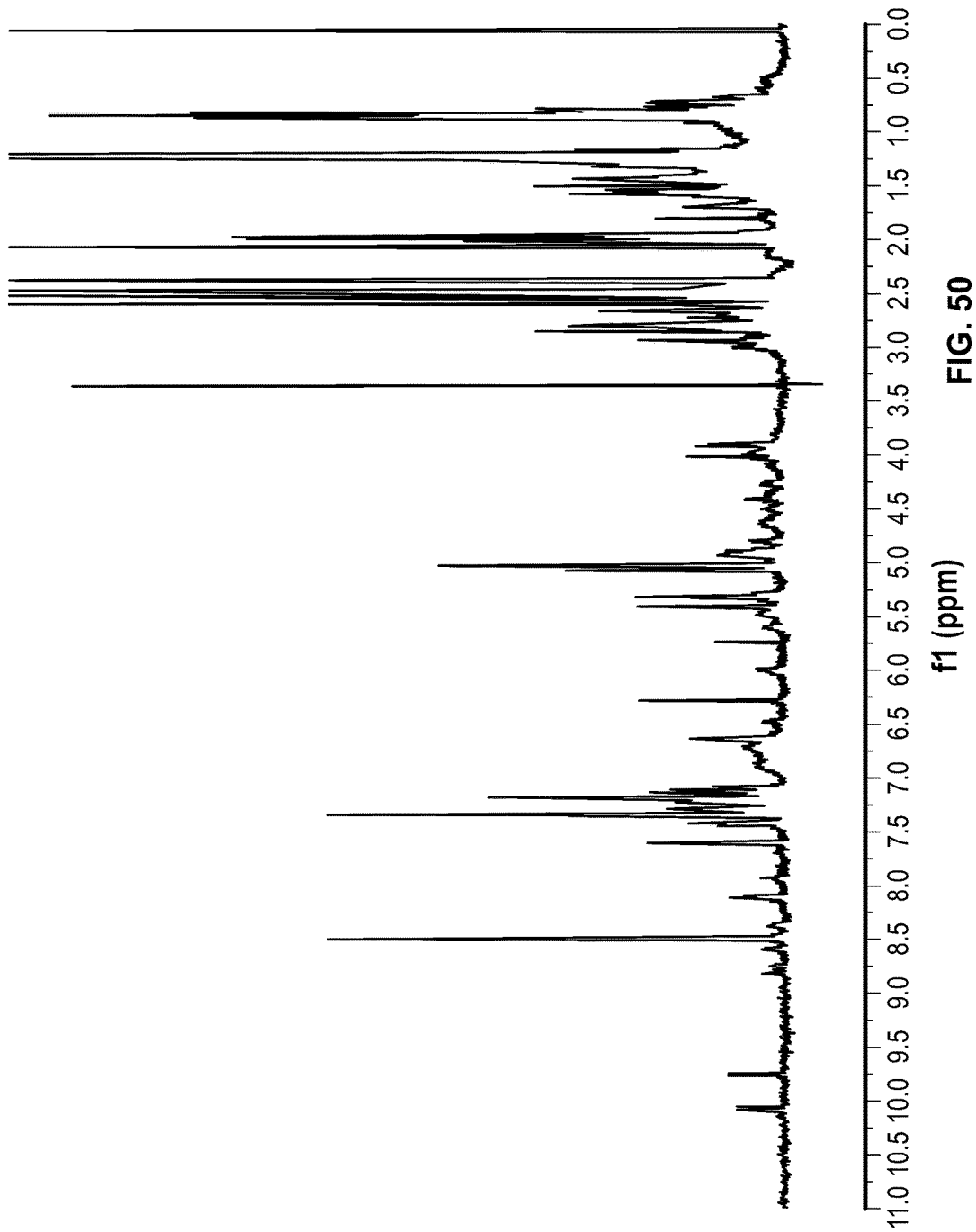
FIG. 50 is a $^1$H NMR spectrum of Conjugate L22 in DMSO-d6.

To a solution of Compound 75 (1.064 μmol, 1 mg) and benzyl((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (2.127 μmol, 1.444 mg) in DCM (1.554 mmol, 0.1 mL) was added HOBt (1.064 μmol, 0.163 mg) and Hunig's base (0.0106 mmol, 1.858 μL) at rt. The reaction mixture was stirred overnight and citiric acid solution (10%) was added. The reaction mixture was extracted with ethyl acetate, washed with NaHCO₃ solution and brine, dried over Na₂SO₄, and concentrated in vacuo. The crude mixture was subjected to RP-purification to provide Conjugate L22 (0.6 mg, 38.1%) as white solid. Observed ESI HRMS: m/z 1479.8190 [M+H]$^+$. The $^1$H NMR spectrum of Conjugate L22 is shown in FIG. 50.

Example 37

Synthesis of Conjugate L23

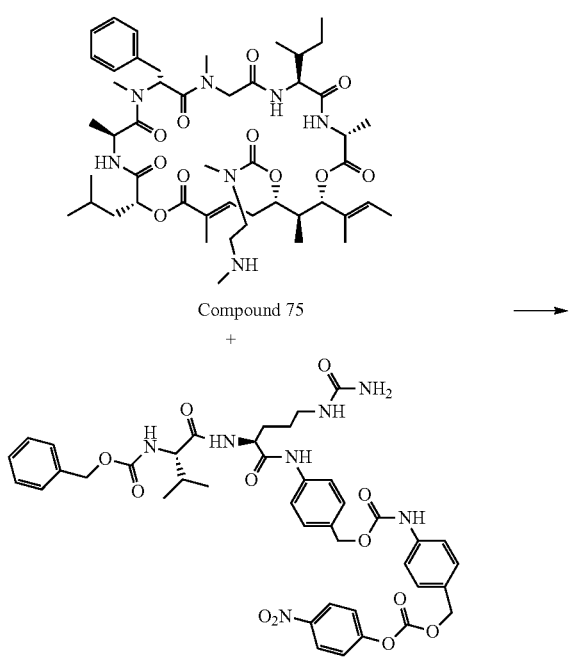

Compound 75
+

-continued

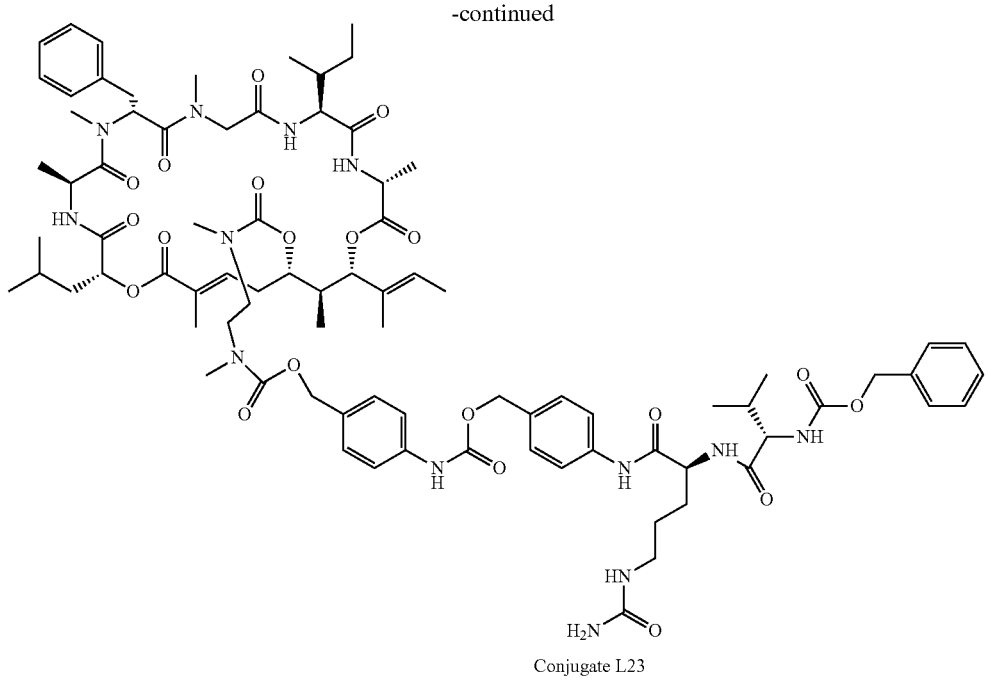

Conjugate L23

Figure 51:
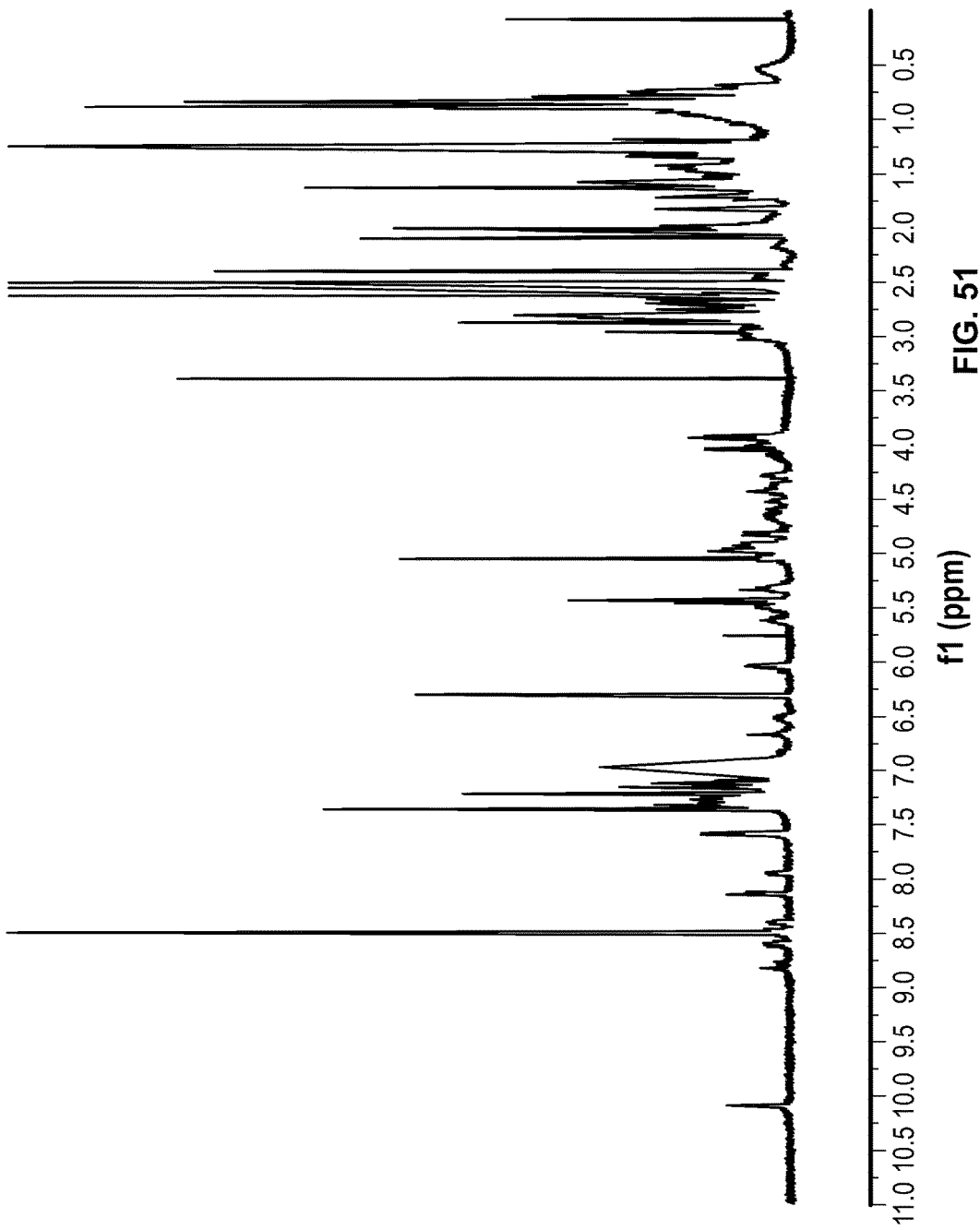
FIG. 51 is a $^1$H NMR spectrum of Conjugate L23 in DMSO-d6.

To a solution of Compound 75 (1.383 µmol, 1.3 mg) and benzyl((S)-3-methyl-1-(((S)-1-((4-(((((4-(((((4-nitrophenoxy)carbonyl)oxy)methyl)phenyl)carbamoyl)oxy)methyl)phenylamino)-1-oxo-5-ureidopentan-2-yl)amino)-1-oxobutan-2-yl)carbamate (2.416 µmol, 2 mg) in DCM (3.11 mmol, 0.2 mL) and DMF (1.291 mmol, 0.1 mL) was added HOBt (6.53 µmol, 1 mg) and Hunig's base (0.014 mmol, 2.415 µL) at rt. The reaction mixture was stirred overnight, and citric acid solution (10%) was added. The reaction mixture was extracted with ethyl acetate, washed with NaHCO$_3$ solution and brine, dried over Na$_2$SO$_4$, and concentrated in vacuo. The crude material was purified with RP-column chromatography to provide Conjugate L23 (0.7 mg, 31.1%) as a white solid. Observed ESI HRMS: m/z 1628.8657 [M+H]$^+$. The $^1$H NMR spectrum of Conjugate L23 is shown in FIG. 51.

Example 38

Synthesis of Conjugate L16

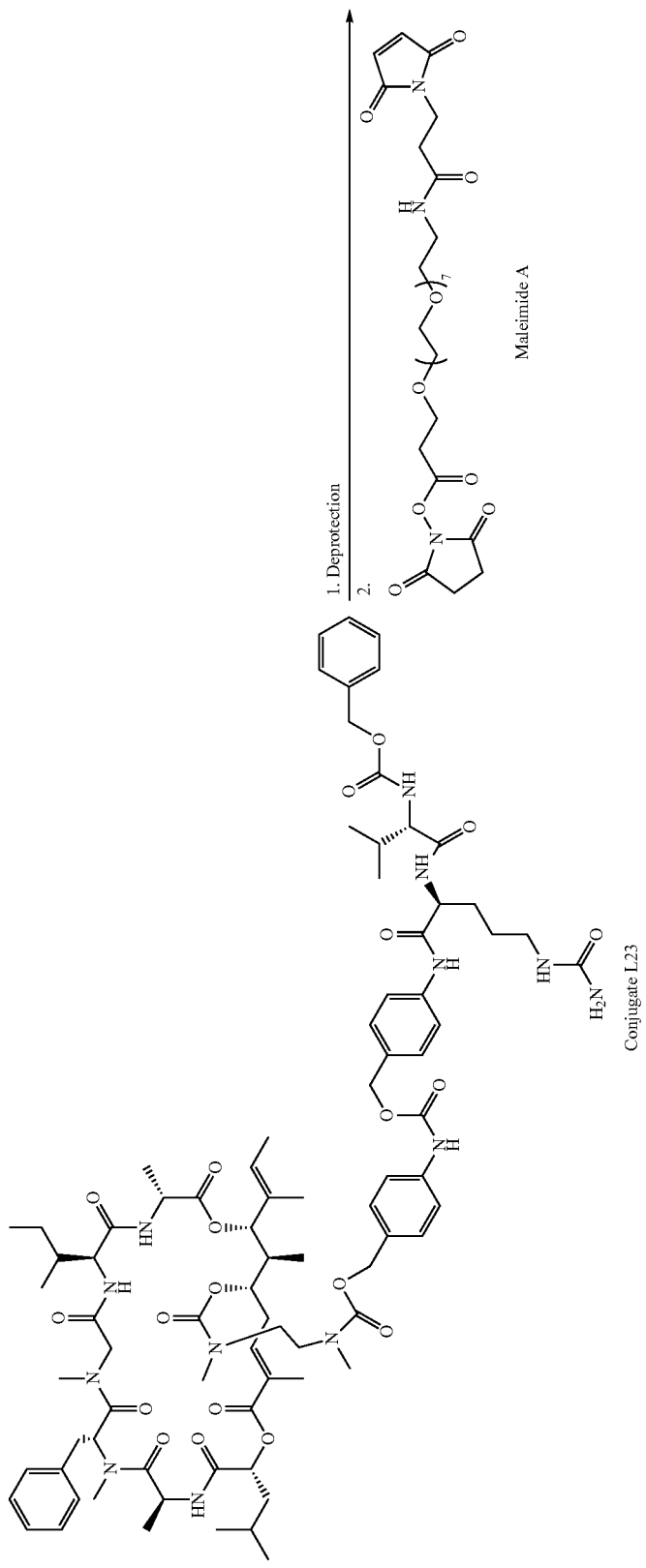

-continued
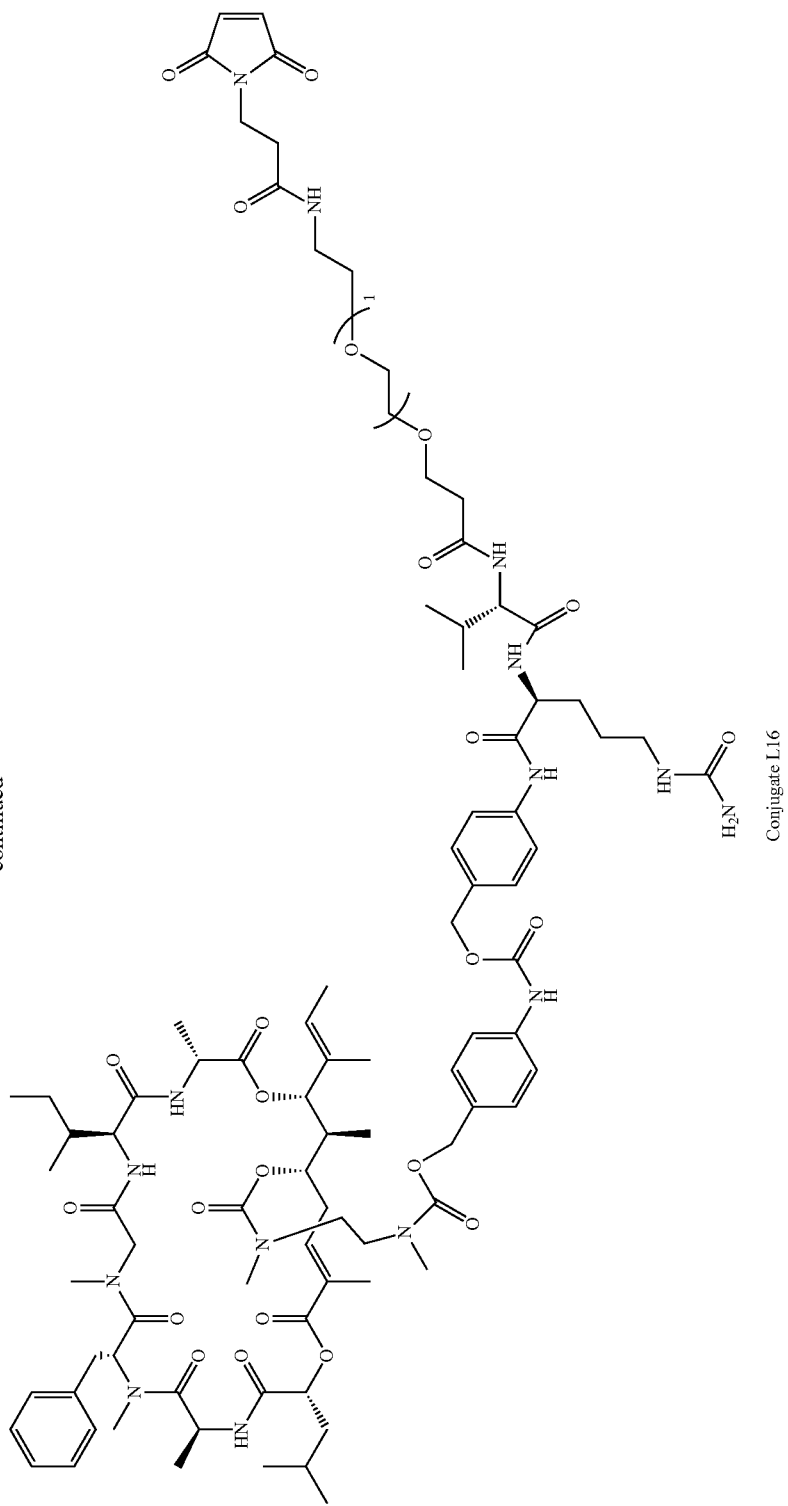
Conjugate L16

The benzyloxy carbamate (CBz) of Conjugate L23 is deprotected using a suitable deprotecting agent such as, $H_2/Pd(OH)_2$, $Pd/HCO_2NH_4$ or $H_2/Pd/C$ and then coupled with Maleimide A using suitable peptide coupling reagents as in example 11 to get the Conjugate L16.

Example 39

Synthesis of Conjugate L24

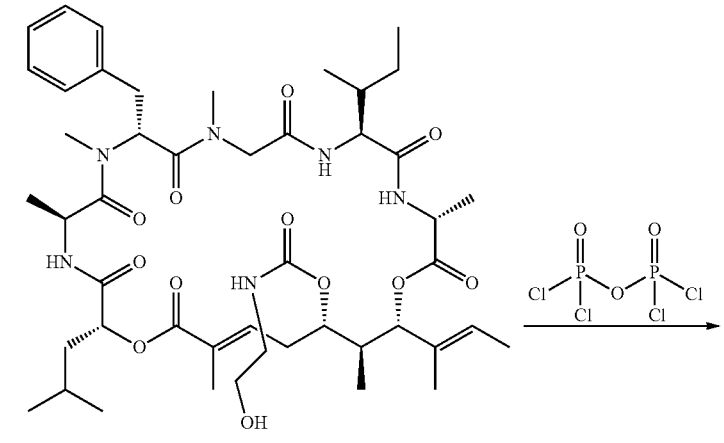

Compound 123

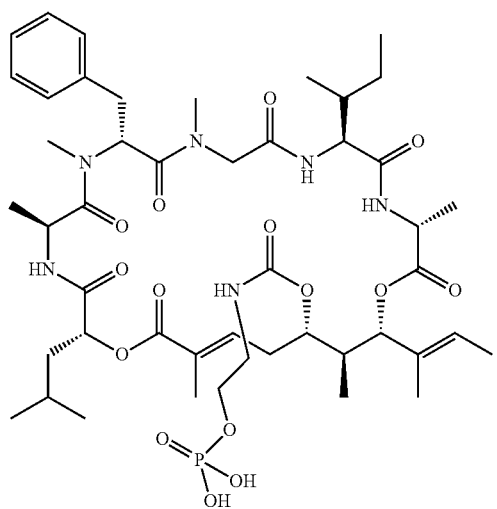

Conjugate L24

To a solution of Compound 123 (0.657 μmol, 0.6 mg) in THF (2.441 mmol, 0.2 mL) was added diphosphoryl chloride (4.77 μmol, 1.2 mg) at −40° C. The reaction mixture was stirred for 15 min and warmed up to rt. The reaction mixture was stirred for 6 h, sat. $NaHCO_3$ aq. was added, and the reaction mixture was acidified with citric acid solution (10%). The aqueous phase was subjected to RP-column chromatography to provide Conjugate L24 (0.2 mg, 30.6%) as a film. Observed LRMS (ESI) m/z: 993.4 $[M+H]^+$.

Example 40

Synthesis of Conjugates C10-TBS and C11-TBS

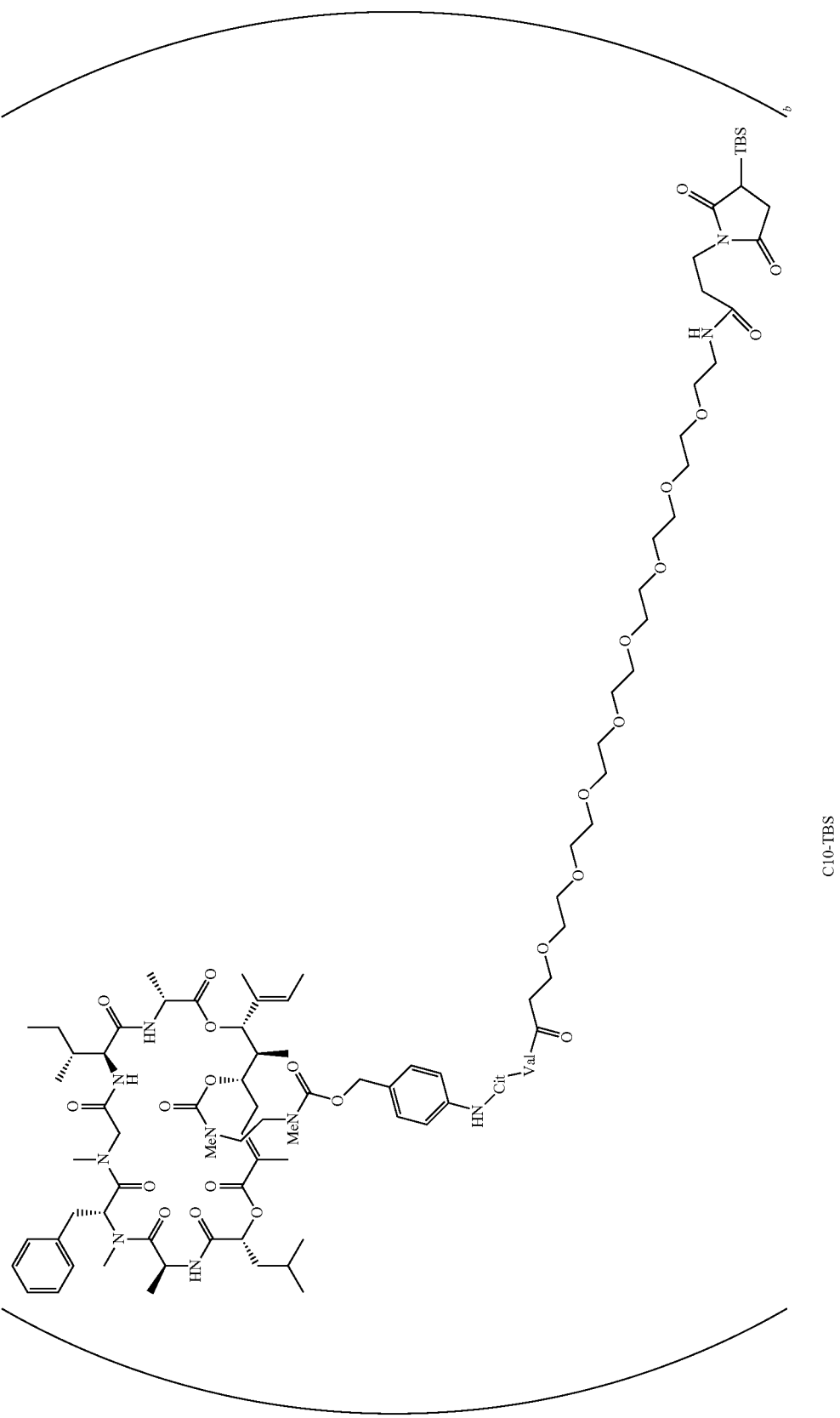

-continued
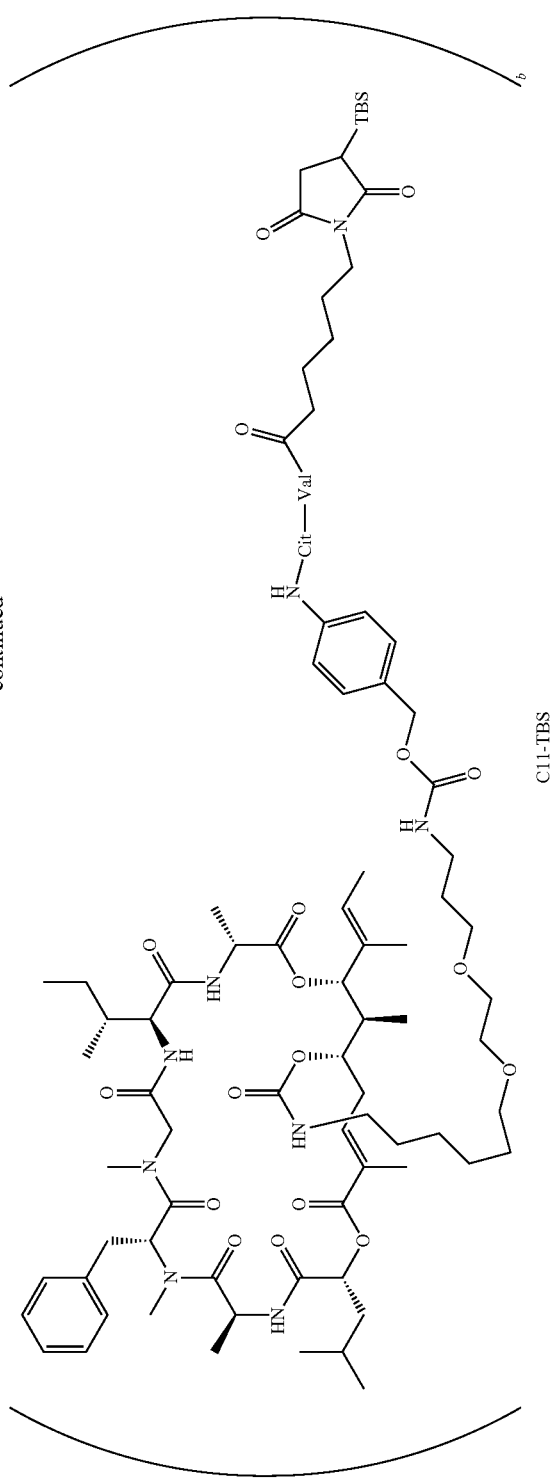

Figure 52A:
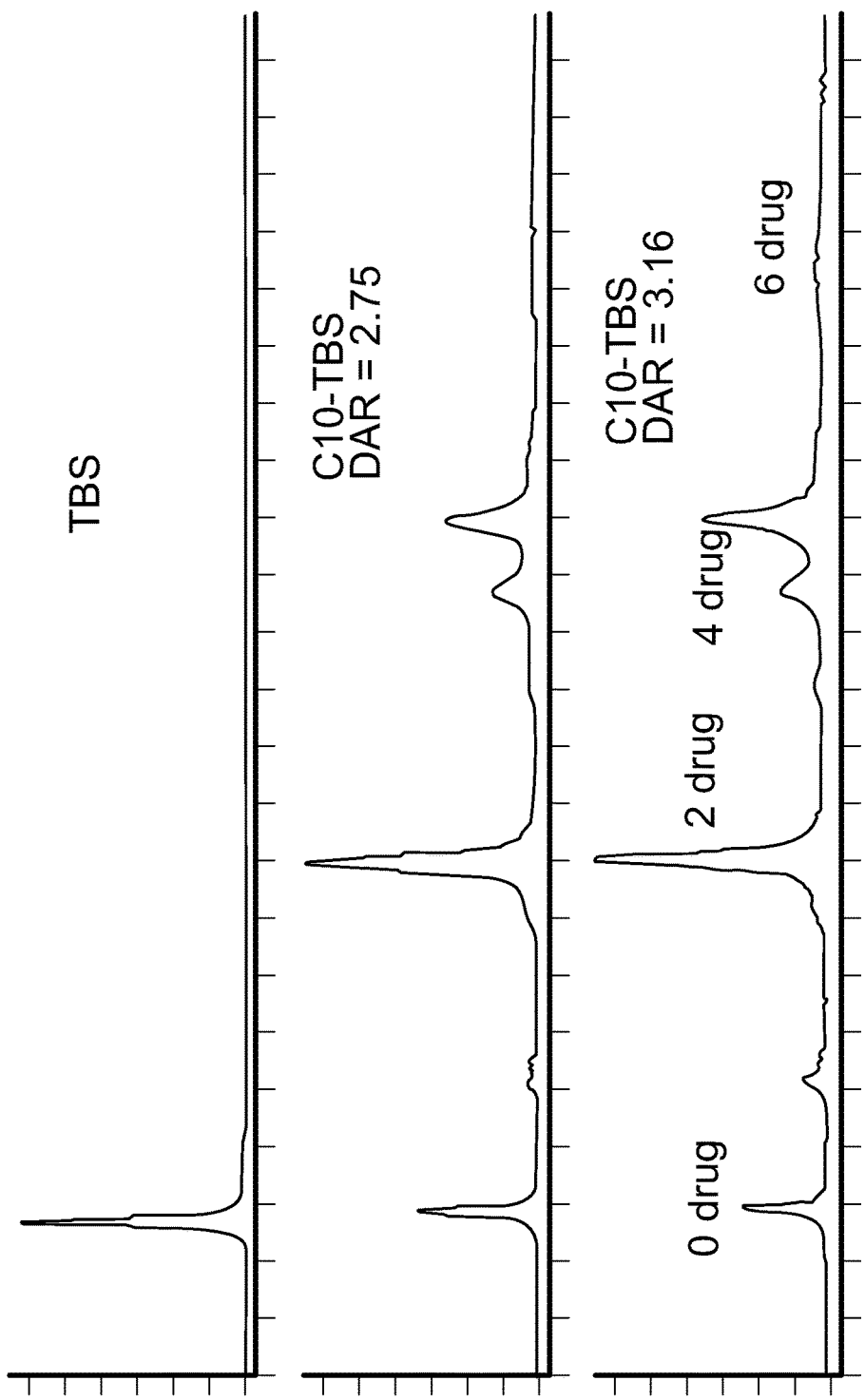
FIG. 52A shows the Hydrophobic Interaction Chromatographs (HICs) for Trastuzumab Biosimilar (TBS) and Conjugate C10-TBS.
Figure 52B:
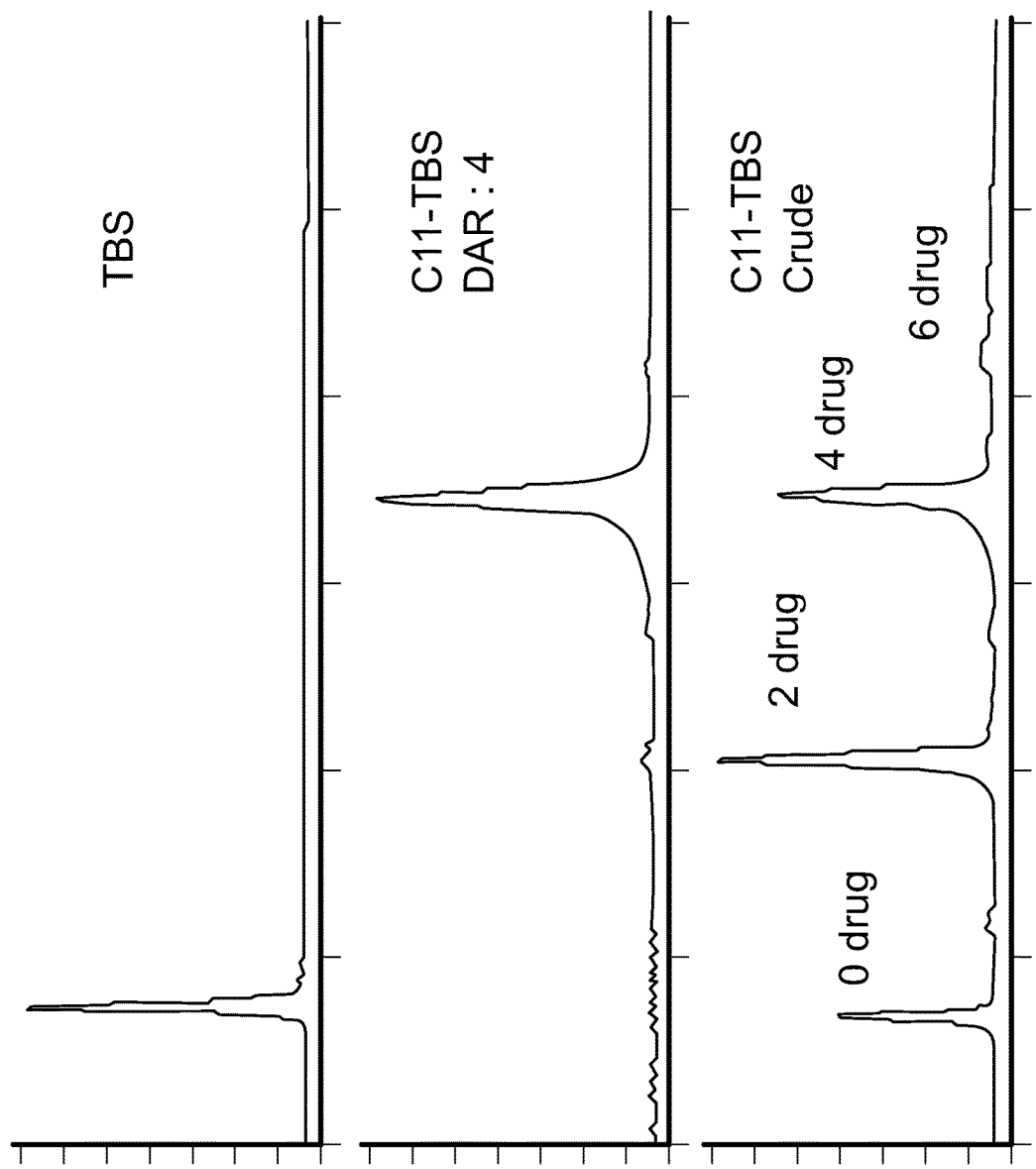
FIG. 52B shows the HICs for TBS and Conjugate C11-TBS.
Figure 53A:
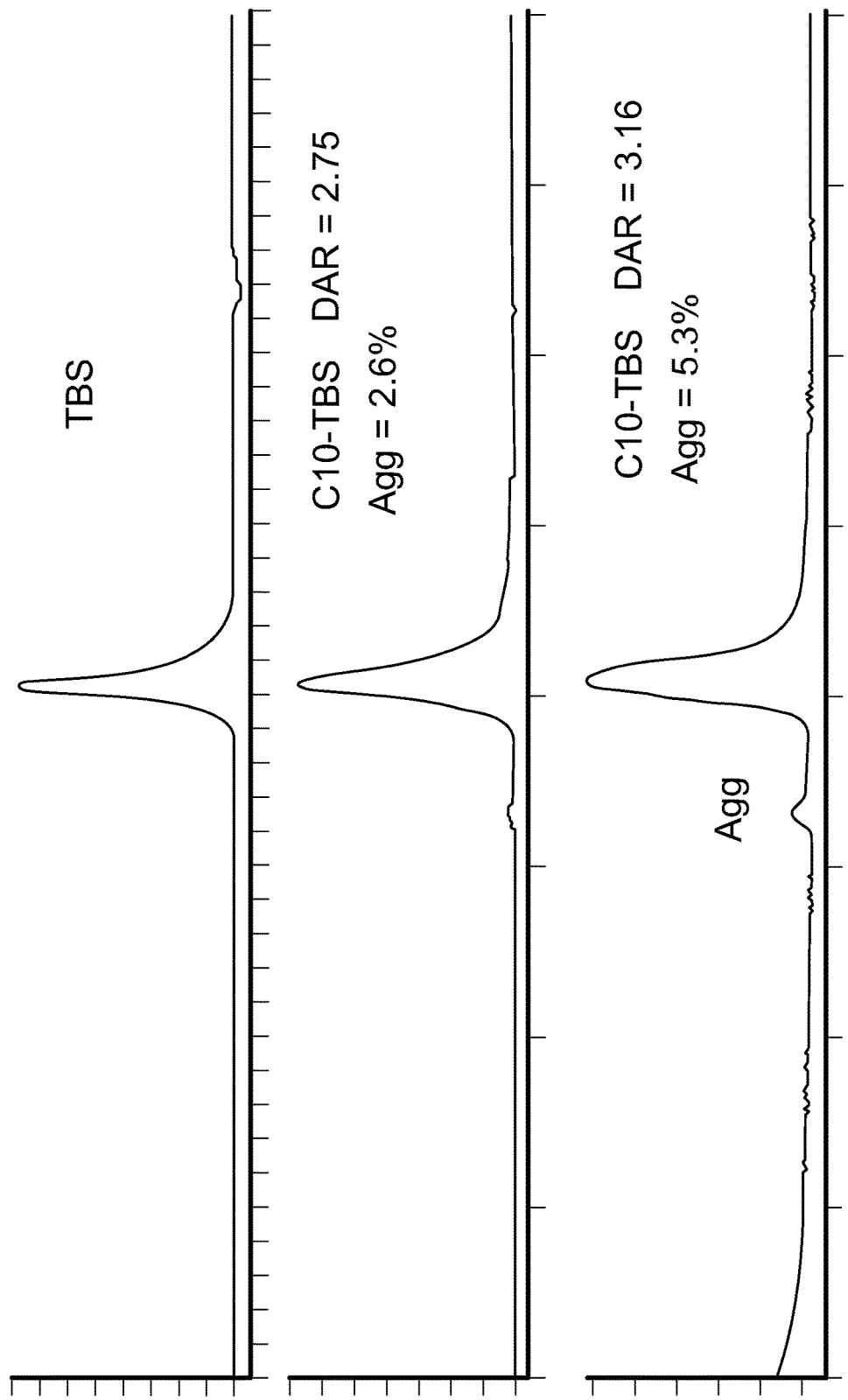
FIG. 53A shows the Size Exclusion Chromatographs (SECs) for Trastuzumab Biosimilar (TBS) and Conjugate C10-TBS.
Figure 53B:
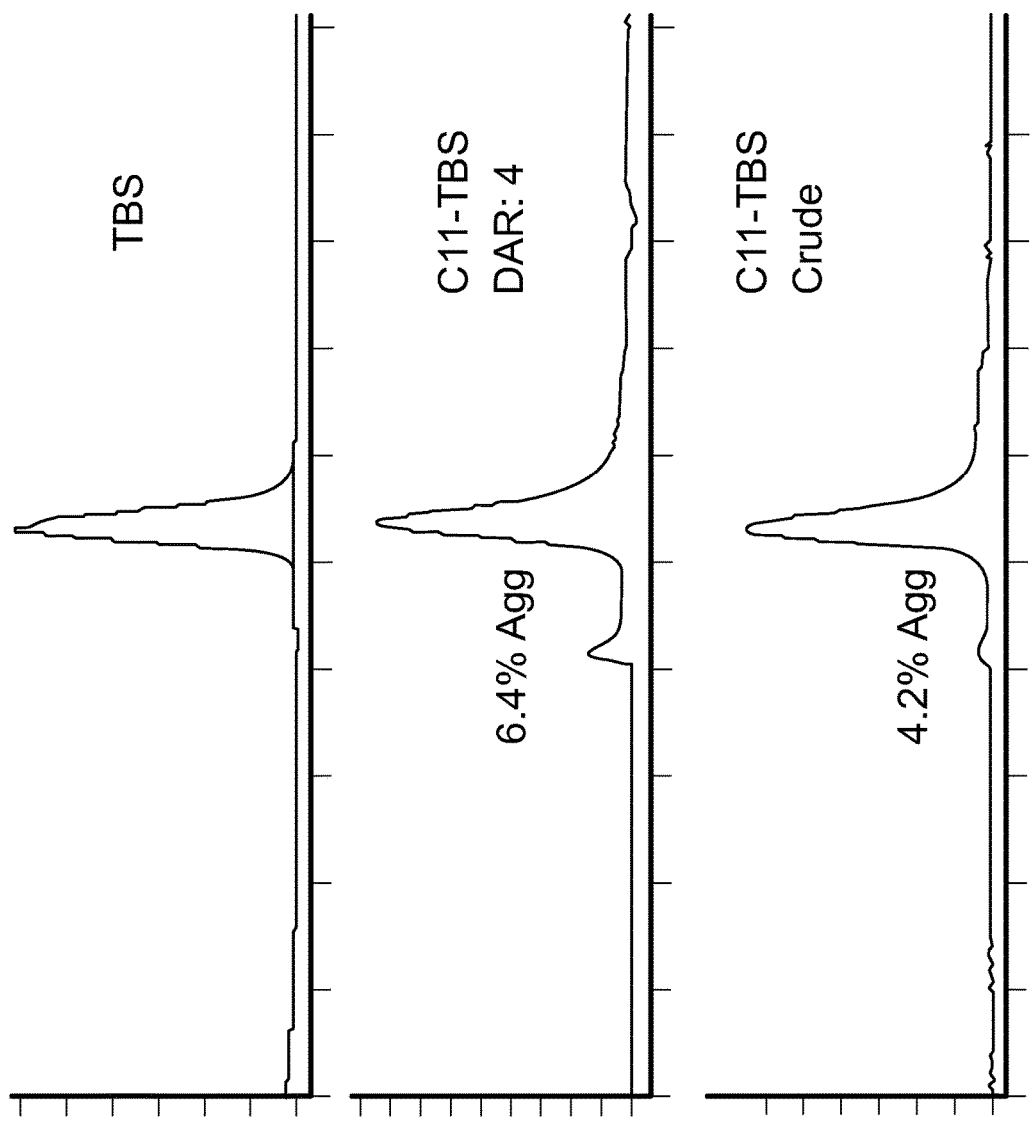
FIG. 53B shows the SECs for TBS and Conjugate CU-TBS.

The antibody-drug conjugates C10-TBS and C11-TBS, which correspond, respectively, to conjugates C10 and 11 wherein Ab is Trastuzumab Biosimilar (TBS) antibody, were synthesized using protocols similar to methods described previously (Ref: Doronina, S. O. et al, *Bioconjugate Chem.* 2008, 19 (10), 1960-1963). Briefly, the purified antibody, Trastuzumab Biosimilar (TBS) was buffer exchanged into PBS (pH 7.4). The antibody was diluted to a final concentration of 5 mg/mL in PBS and warmed to 37° C. in a heat block. A stock solution of TCEP (50 mM) was freshly prepared in water, and 2.5 molar equiv (relative to the antibody concentration) was added. After 2 h, the partially reduced antibody was removed from the heat block and cooled to room temperature. A stock solution of Conjugate L10 or L11 (2 mM in DMSO) was freshly prepared, and 2-5 molar equiv was added to the antibody. After 1 h, the reaction mixture was buffer exchanged into PBS using PD10 spin columns to remove small MW reagents and stored at 4° C. until needed. The drug to antibody ratio (DAR) was measured by Hydrophobic Interaction Chromatography (HIC) and aggregation was measured by Size Exclusion Chromatography (SEC). Various lots were prepared with DAR ranging from 2-4. In some cases, the individual DARs were purified by HIC chromatography. The HIC chromatographs for Conjugates C10-TBS and C11-TBS are shown in FIGS. 52A and 52B, respectively. The SEC chromatographs for Conjugates C10-TBS and C11-TBS are shown in FIGS. 53A and 53B, respectively.

Example B1

Inhibitory Response of Test Compounds Against BT-474 Cells

BT-474 human mammary gland ductal carcinoma cells were seeded in a clear polystyrene 96-well microculture plate (Corning® Costar® 96-well flat bottom plate, Cat.#3997) in a total volume of 90 µL/well. After 24 hours of incubation in a humidified incubator at 37° C. with 5% $CO_2$ and 95% air, 10 µL of 10×, serially diluted test agents in growth medium were added to each well (10 pt dose response curve, highest concentration 10 µM of test agent). After 72 hours of culture in a humidified incubator at 37° C., in an atmosphere of 5% $CO_2$ and 95% air, the plated cells and Cell Titer-Glo® (Promega G7571) reagents were brought to room temperature to equilibrate for 30 minutes. 100 µL of Cell Titer-Glo® reagent was added to each well. The plate was shaken for two minutes and then left to equilibrate for ten minutes. The media/Cell Titer-Glo® reagent was transferred to a white polystyrene 96-well microculture plate (Corning® Costar® 96-well flat bottom plate, Cat.#3917) before reading luminescence on a Tecan GENios microplate reader.

Percent inhibition of cell growth was calculated relative to untreated control wells. The $IC_{50}$ value for the test agents was determined using Prism 6.05 by curve-fitting of the data using the following four parameter-logistic equation:

$$Y = \frac{Top - Bottom}{1 + (X/IC_{50})^n} + Bottom,$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve. Data for various test agents is shown in Table 6.

TABLE 6

| Compound | BT-474 $IC_{50}$ |
| --- | --- |
| kulo-2 | 1.761 nM |
| 19 | >10 µM |
| 20 | 389.1 nM |

Inhibitory response of test compounds against HCC1954 cells was determined using a method analogous to that used for BT-474 cells. $IC_{50}$ values for various test agents in HCC1954 and/or BT-474 cells are shown in Table 7.

TABLE 7

| Compound/Conjugate | HCC1954 $IC_{50}$ | BT-474 $IC_{50}$ |
| --- | --- | --- |
| kulo-2 | ++++ | ++++ |
| 4 |  | + |
| 5 |  | + |
| 9 |  | + |
| 10 |  | + |
| 11 |  | + |
| 12 |  | + |
| 13 |  | + |
| 14 |  | + |
| 16 |  | + |
| 17 |  | ++ |
| 18 |  | ++ |
| 19 |  | + |
| 20 |  | ++ |
| 21 | ++++ | ++++ |
| 60 |  | + |
| 61 |  | ++++ |
| 63 | +++ | ++++ |
| 64 | +++ | ++++ |
| 69 | ++++ | ++++ |
| 75 | ++++ | ++++ |
| 77 |  | + |
| 78 |  | ++ |
| 79 |  | + |
| 80 |  | + |
| 81 |  | ++ |
| 82 | +++ | ++++ |
| 83 | + | + |
| 84 | ++ | ++ |
| 86 | ++ | ++ |
| 87 | ++ | ++ |
| 88 | ++ | ++ |
| 89 | ++ | +++ |
| 90 | ++++ | ++++ |
| 91 | ++ | ++ |
| 92 | ++ | ++ |
| 93 | ++++ | ++++ |
| 94 | ++++ | ++++ |
| 95 | +++ | ++++ |
| 96 | ++++ | ++++ |
| 97 | ++++ | ++++ |
| 98 | ++++ | ++++ |
| 99 | ++ | +++ |
| 100 | +++ | ++++ |
| 101 | ++++ | ++++ |
| 102 | +++ | ++++ |
| 105 | ++++ | ++++ |
| 106 | ++++ | ++++ |
| 107 | +++ | ++++ |
| 108 | ++ | +++ |
| 110 | +++ | ++++ |
| 111 | + | + |
| 113 | ++++ | ++++ |
| 114 | +++ | ++++ |
| 115 | ++++ | ++++ |
| 116 | +++ | ++++ |
| 117 | +++ | +++ |

TABLE 7-continued

| Compound/Conjugate | HCC1954 IC$_{50}$ | BT-474 IC$_{50}$ |
|---|---|---|
| 118 | ++ | ++ |
| 119 | ++++ | ++++ |
| 121 |  | ++ |
| 122 | +++ | ++++ |
| 123 | ++++ | ++++ |
| 125 | +++ | ++++ |
| L11 | +++ | +++ |
| L12 | + | ++ |
| L13 |  | +++ |

+ denotes >10,000 nM;
++ denotes 200-10,000 nM;
+++ denotes 20-200 nM;
++++ denotes <20 nM Example B2

Inhibitory Response of Test Conjugates Against BT-474 Cells

BT-474 human mammary gland ductal carcinoma cells were seeded in a clear polystyrene 96-well microculture plate in a total volume of 90 μL/well. After 24 hours of incubation in a humidified incubator at 37° C. with 5% CO$_2$ and 95% air, 10 μL of 10×, serially diluted test agents (e.g., conjugates, such as compounds bound to an antibody via a linker) in growth medium were added to each well. After 72 hours of culture in a humidified incubator at 37° C., in an atmosphere of 5% CO$_2$ and 95% air, the plated cells and Cell Titer-Glo® (Promega G7571) reagents were brought to room temperature to equilibrate for 30 minutes. 100 μL of Cell Titer-Glo® reagent were added to each well. The plate was shaken for two minutes and then left to equilibrate for ten minutes. The media/Cell Titer-Glo® reagent was transferred to a polystyrene 96-well microculture plate before reading luminescence on a Tecan GENios microplate reader.

Percent inhibition of cell growth was calculated relative to untreated control wells. The IC$_{50}$ value for the test agents was determined using Prism 6.05 by curve-fitting of the data using the following four parameter-logistic equation:

$$Y = \frac{\text{Top} - \text{Bottom}}{1 + (X/\text{IC}_{50})^n} + \text{Bottom},$$

where Top is the maximal % of control absorbance, Bottom is the minimal % of control absorbance at the highest agent concentration, Y is the % of control absorbance, X is the agent concentration, IC$_{50}$ is the concentration of agent that inhibits cell growth by 50% compared to the control cells, and n is the slope of the curve. Data for antibody-drug conjugates tested is shown in Table 8.

TABLE 8

| Test Agent | Antibody | DAR | BT-474 IC$_{50}$ (nM) |
|---|---|---|---|
| C10 | Trastuzumab Biosimilar | 4 | 0.7379 |
| C10 | Trastuzumab Biosimilar | 2 | 16.92 |
| C10 | Trastuzumab Biosimilar | 2.75 | 0.4376 |
| C10 | Trastuzumab Biosimilar | 3.16 | 0.4805 |
| C11 | Trastuzumab Biosimilar | 4 | 0.7621 |

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:

1. A conjugate comprising a compound, or a salt thereof, bonded to a ligand, wherein the ligand is a polypeptide or a targeting moiety, and wherein the compound is a compound of Formula (I):

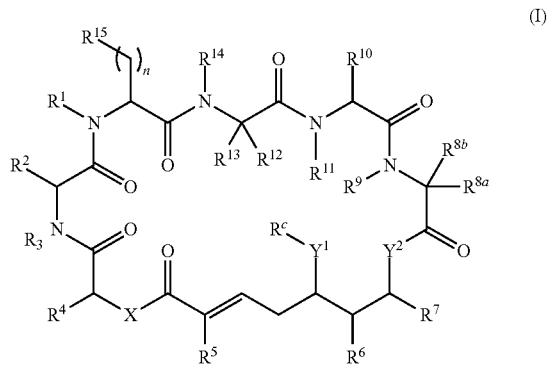

wherein
R$^1$, R$^2$, R$^3$, R$^{8a}$, R$^{8b}$, R$^9$, R$^{10}$, R$^{12}$, R$^{13}$, and R$^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

R$^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

R$^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

R$^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

R$^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, or substituted or unsubstituted heterocyclyl;

n is 0, 1, or 2;

X is —N($R^d$)— or —O—;

$Y^1$ is —N($R^d$)—, —O—, or —S—;

$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl, or —C(O)$R^c$;

or, alternatively, the (—$Y^1$—$R^c$) group is H or halo;

$Y^2$ is —N($R^d$)—, —O—, or —S—;

each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —O$R^d$, —N$R^d R^d$, or —S$R^d$.

2. The conjugate of claim 1, wherein the ligand is an antibody.

3. The conjugate of claim 1, wherein the compound, or salt thereof, is bonded to the ligand via a linker.

4. The conjugate of claim 3, wherein the linker is a cleavable linker.

5. The conjugate of claim 3, wherein the linker is a non-cleavable linker.

6. The conjugate of claim 3, wherein the linker is selected from the group consisting of i) through xiv):

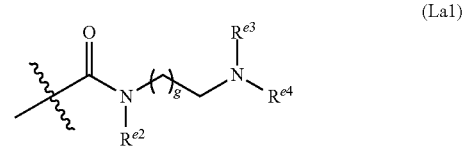
(La1)

wherein g is 1, 2, 3, 4, or 5; $R^{e2}$ and $R^{e3}$ are each independently H or substituted or unsubstituted alkyl; and $R^{e4}$ is H, substituted or unsubstituted alkyl,

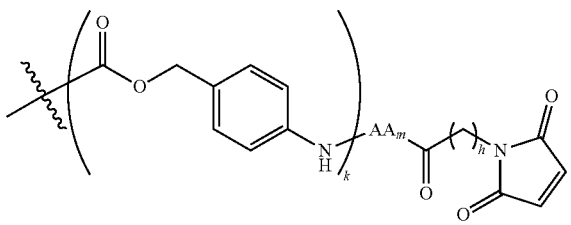

wherein AA is an amino acid, m is an integer from 0-12, h is an integer from 0-12, and k is 0 or 1, or

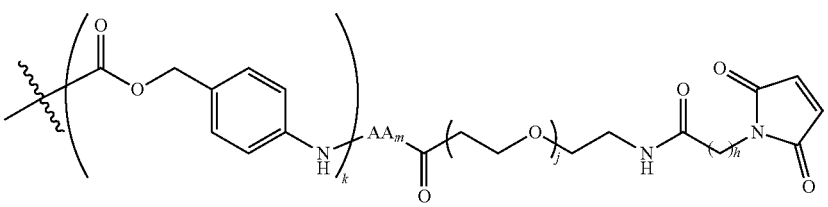

wherein AA is an amino acid; m, h, and j are each independently an integer from 0-12; and k is 0 or 1;

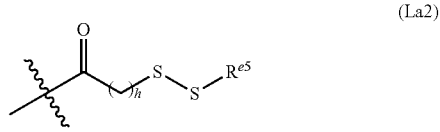
(La2)

wherein $R^{e5}$ is aryl or heteroaryl, and h is an integer from 1-12;

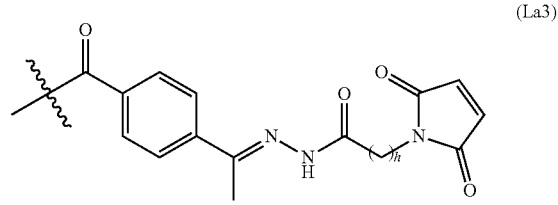
(La3)

wherein h is an integer from 1-12;

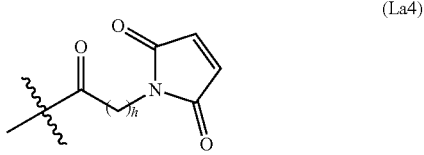
(La4)

wherein h is an integer from 0-12;

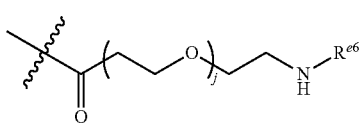
(La5)

wherein j is an integer from 1-12, and $R^{e6}$ is substituted or unsubstituted alkyl,

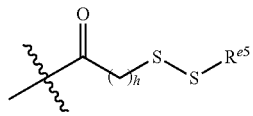

wherein $R^{e5}$ is aryl or heteroaryl, and h is an integer from 1-12, or

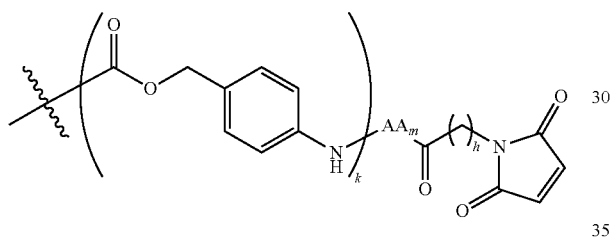

wherein AA is an amino acid, m is an integer from 0-12, h is an integer from 0-12, and k is 0 or 1;

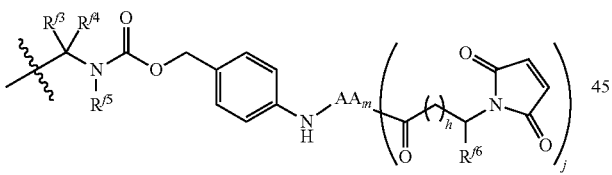
(La6)

wherein $R^{f3}$, $R^{f4}$, $R^{f5}$, and $R^{f6}$ are each independently H or substituted or unsubstituted alkyl; AA is an amino acid; m and h are each independently an integer from 0-12; and j is 0 or 1;

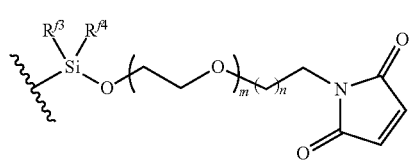
(La7)

wherein $R^{f3}$ and $R^{f4}$ are each independently H or substituted or unsubstituted alkyl; and m and n are each independently an integer from 0-12;

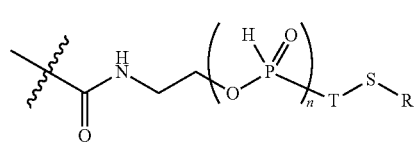
(La8)

wherein n is an integer from 1-4; T is —O— or —NH—; S is aryl or —$(CH_2)_m NH$— where m is an integer from 1-6; and R is

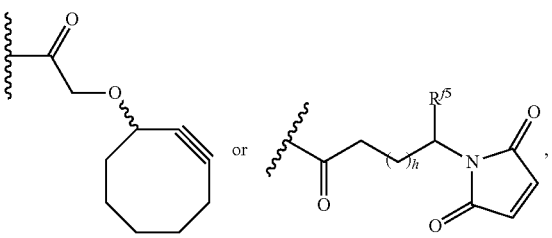

where $R^{f5}$ is H or substituted or unsubstituted alkyl, and h is an integer from 0-6;

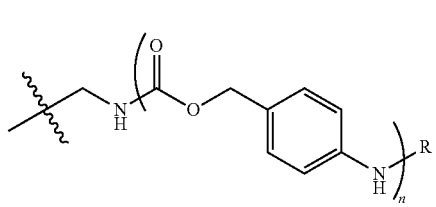
(La9)

wherein n is and integer from 2-4, and R is substituted or unsubstituted alkyl;

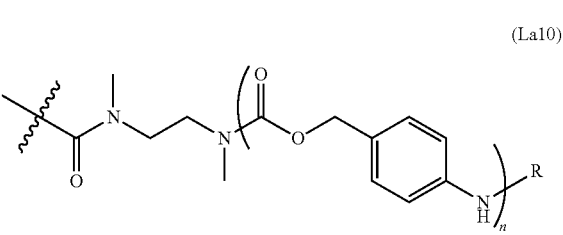
(La10)

wherein n is and integer from 2-4, and R is substituted or unsubstituted alkyl;

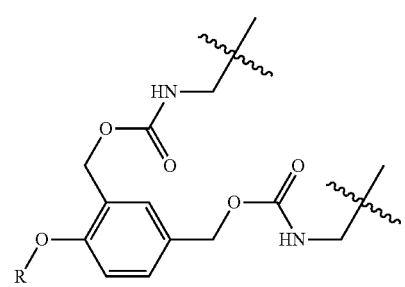
(La11)

wherein R is a moiety capable of forming a bond with a ligand;

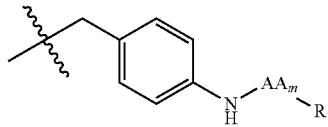
(La12)

wherein AA is an amino acid, m is an integer from 1-12, and R is a moiety capable of forming a bond with a ligand;

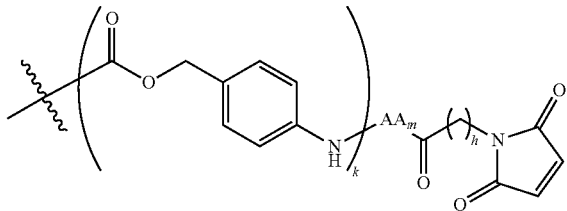
(La13)

wherein AA is an amino acid, m is an integer from 0-12, h is an integer from 0-12, and k is 0 or 1; and

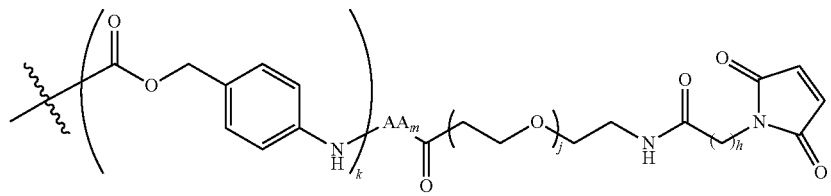
(La14)

wherein AA is an amino acid; m, h, and j are each independently an integer from 0-12; and k is 0 or 1.

7. A conjugate selected from the group consisting of conjugates of the following table, or a salt thereof:

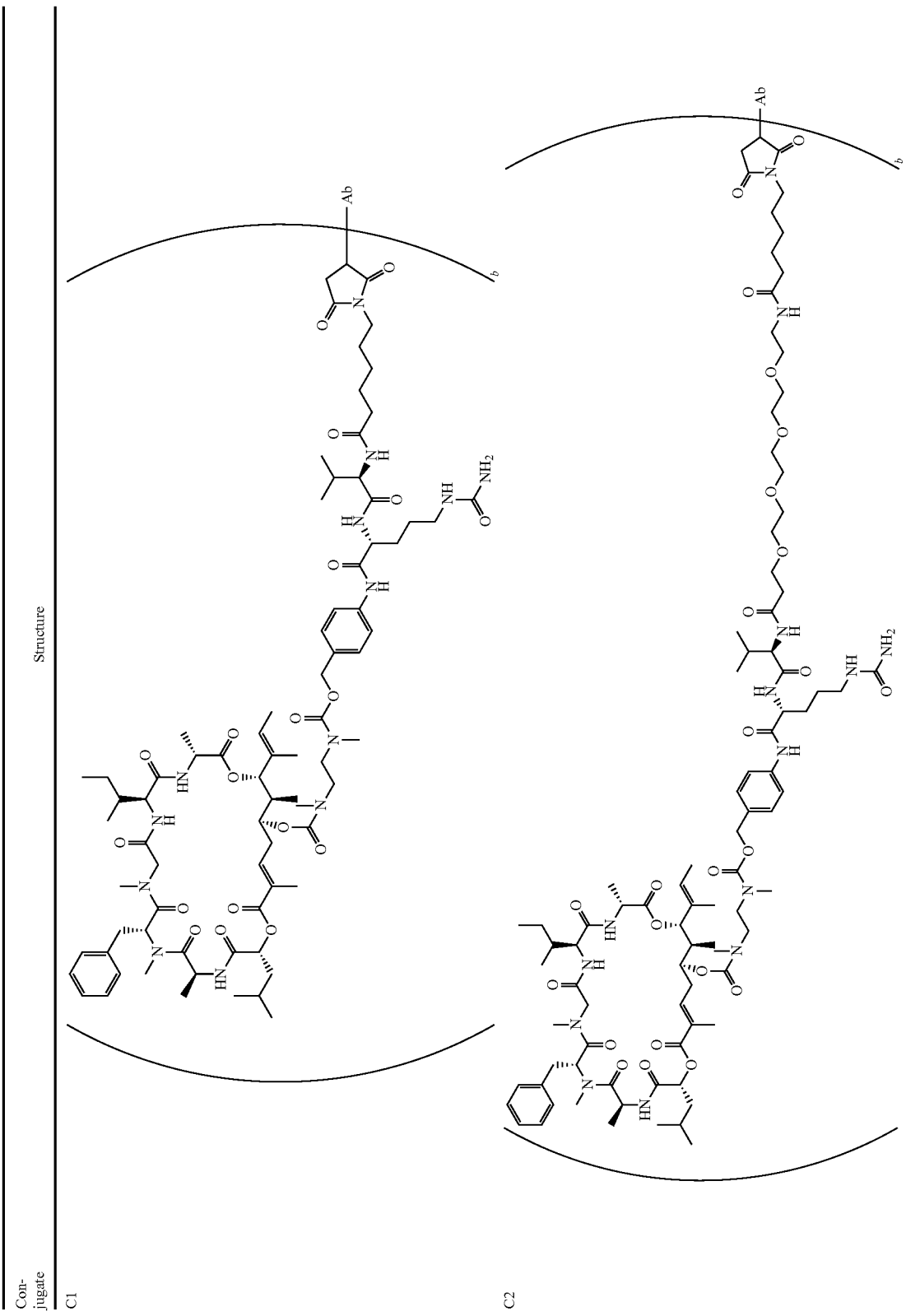

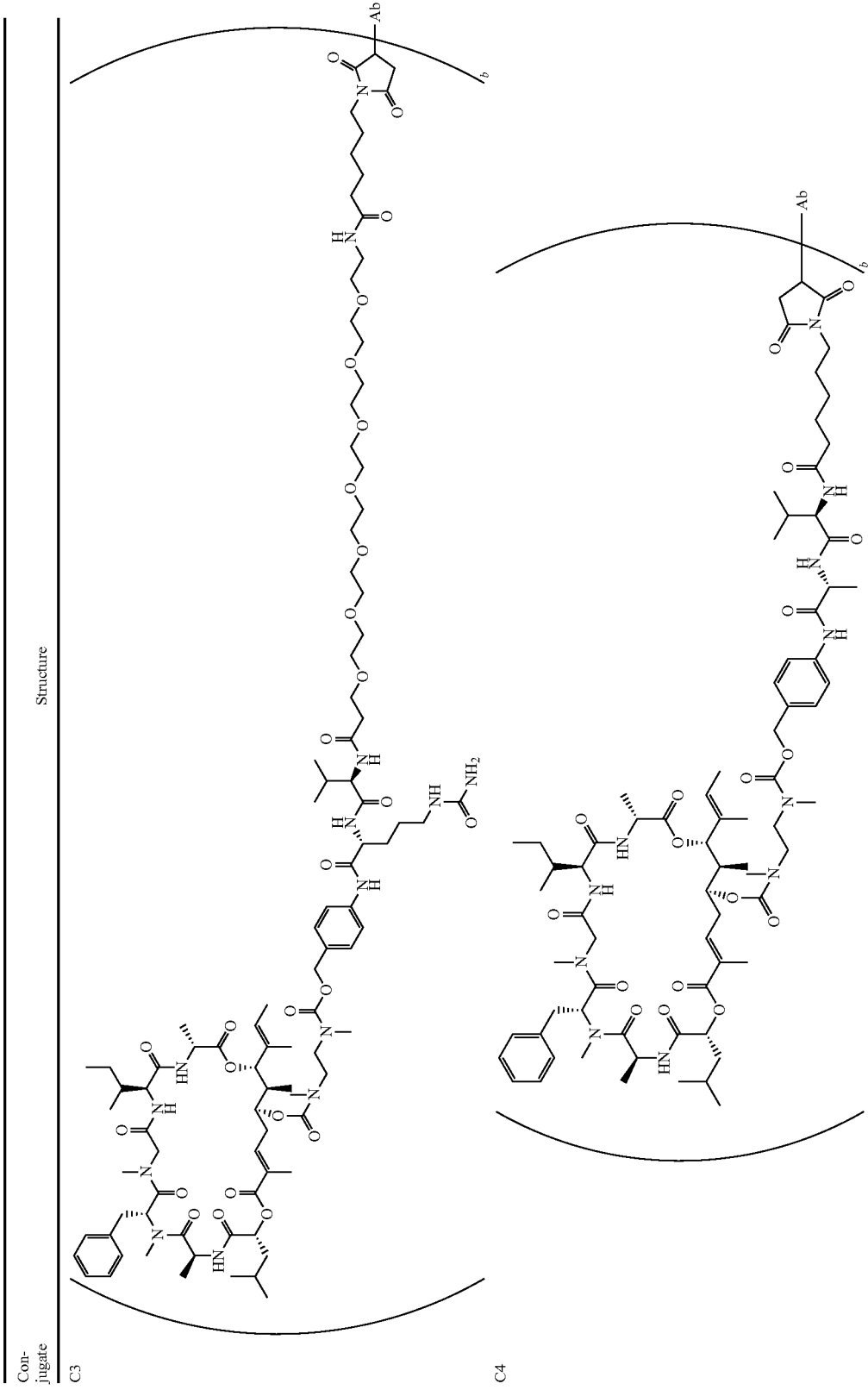

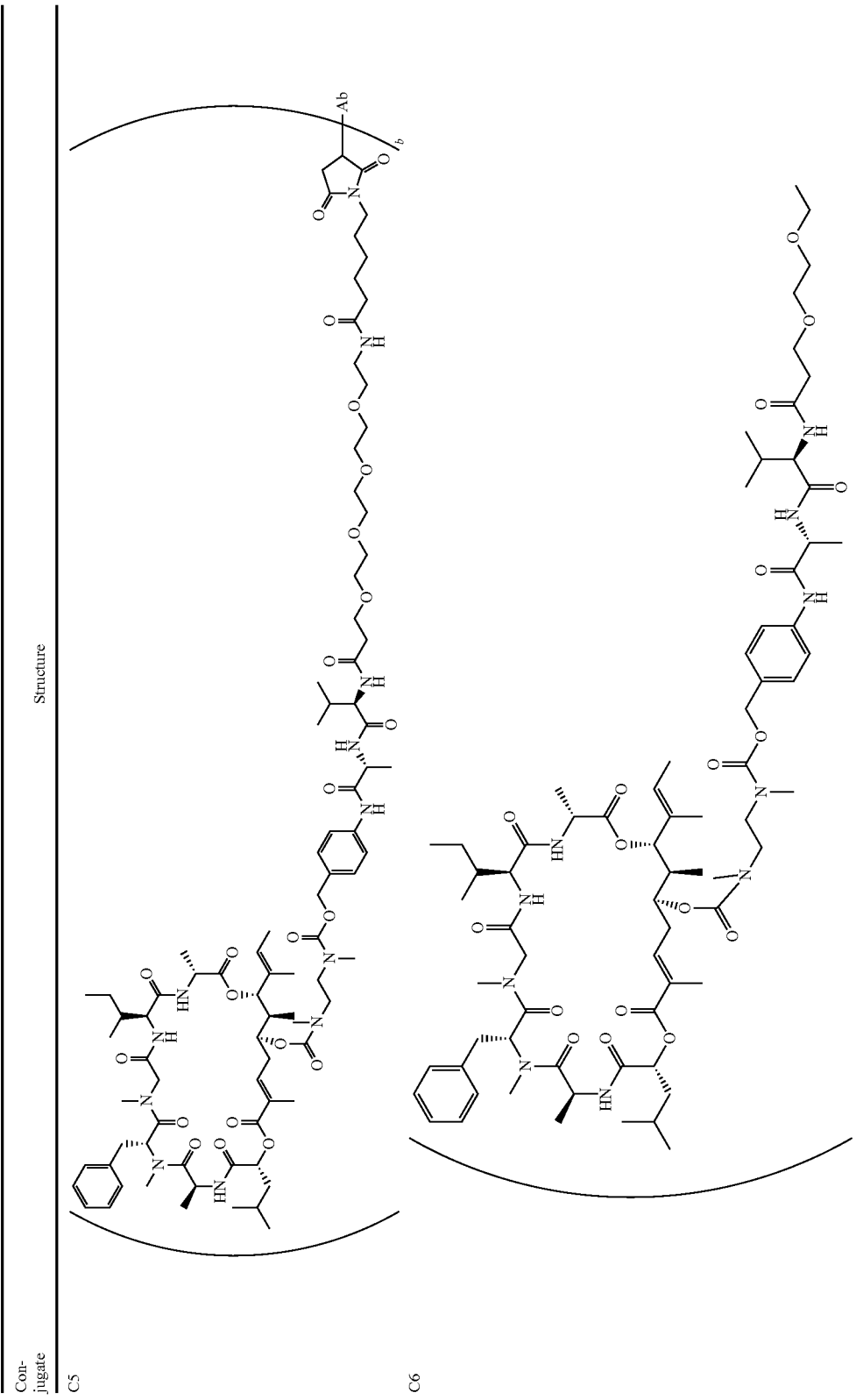

| Conjugate | Structure |
|---|---|
| C7 | 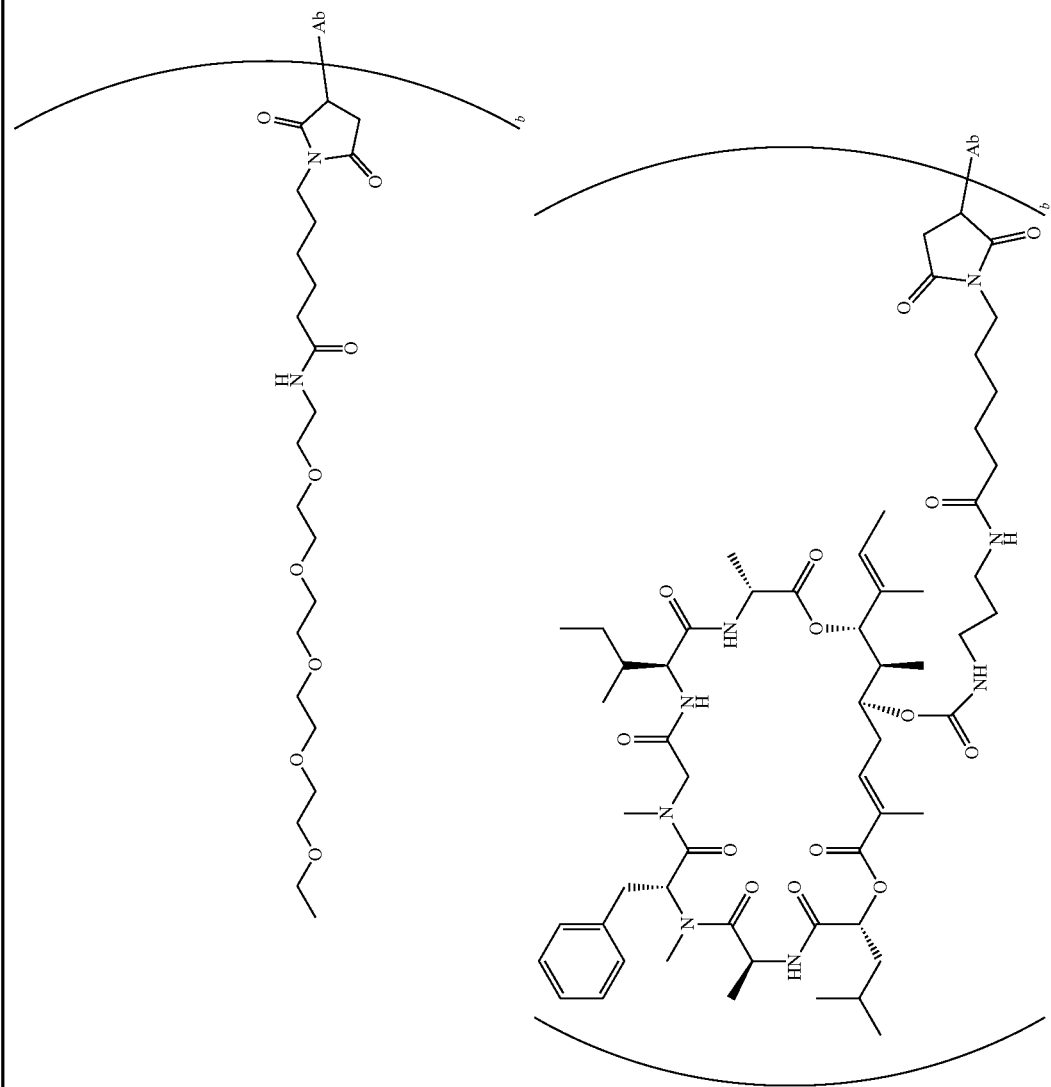 |

| Conjugate | Structure |
|---|---|
| C8 | 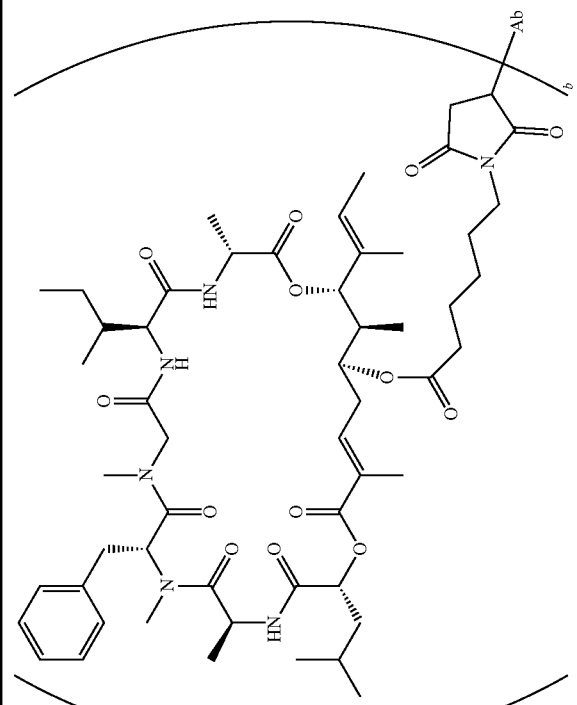 |
| C9 | 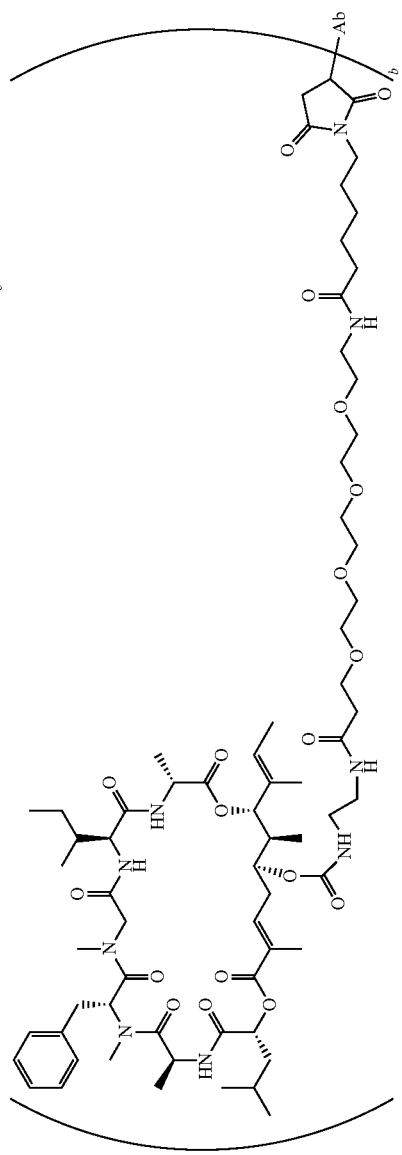 |

-continued
| Con-jugate | Structure |
|---|---|
| C10 | 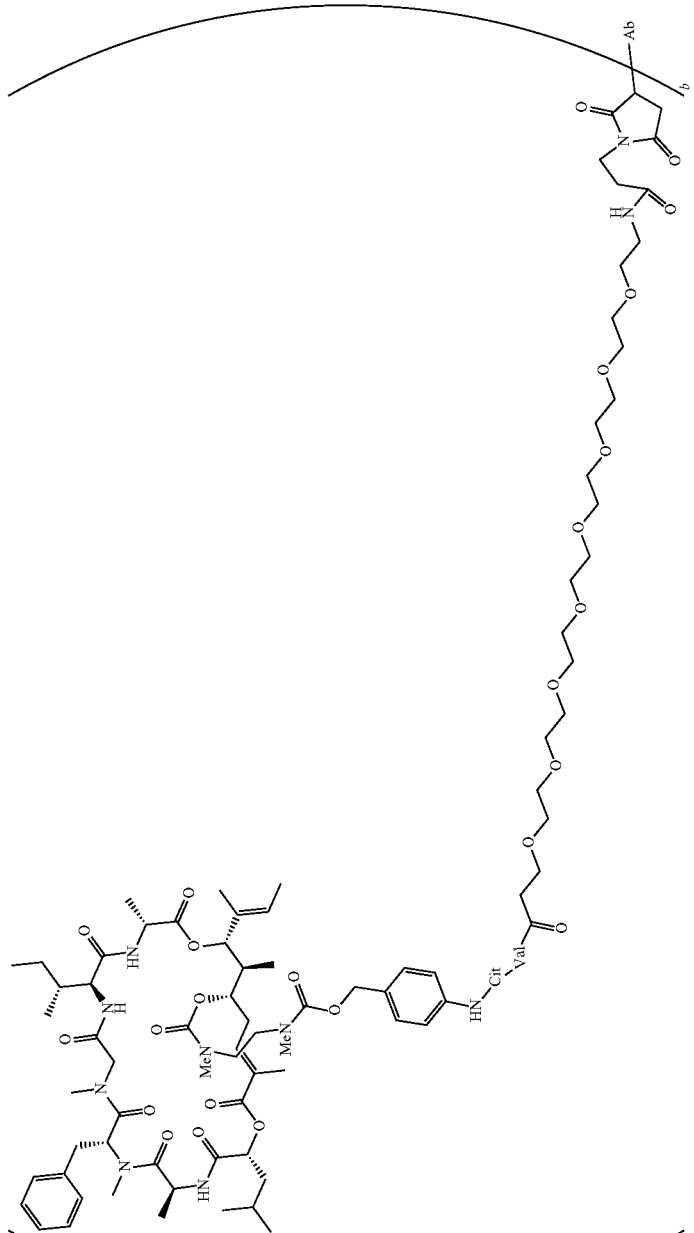 |

-continued

| Conjugate | Structure |
|---|---|
| C11 | 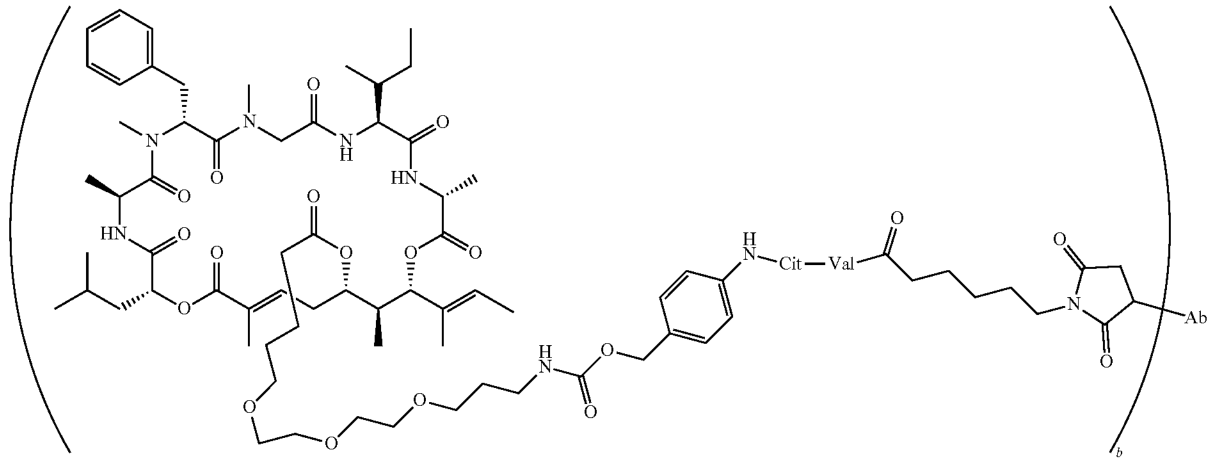 |
| C12 | 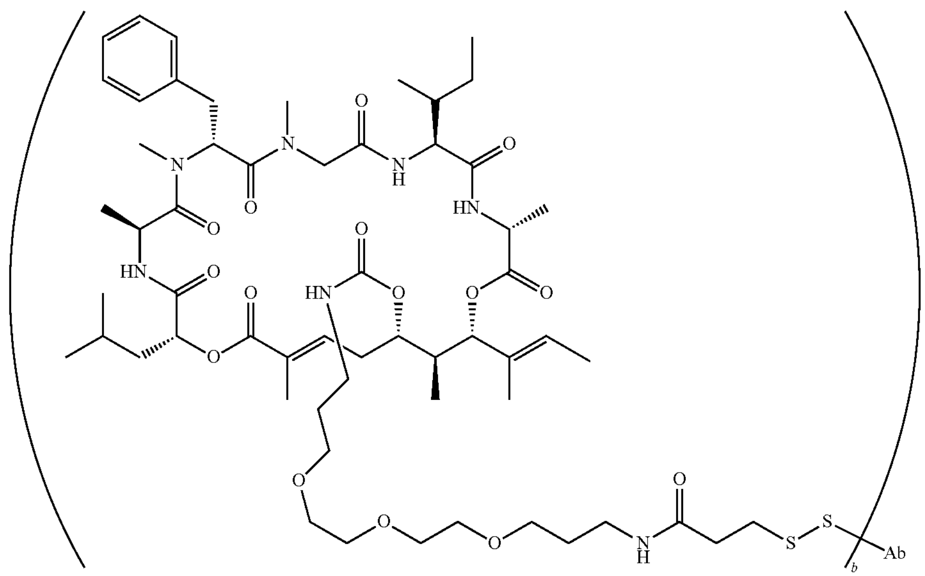 |

-continued
| Conjugate | Structure |
|---|---|
| C13 | 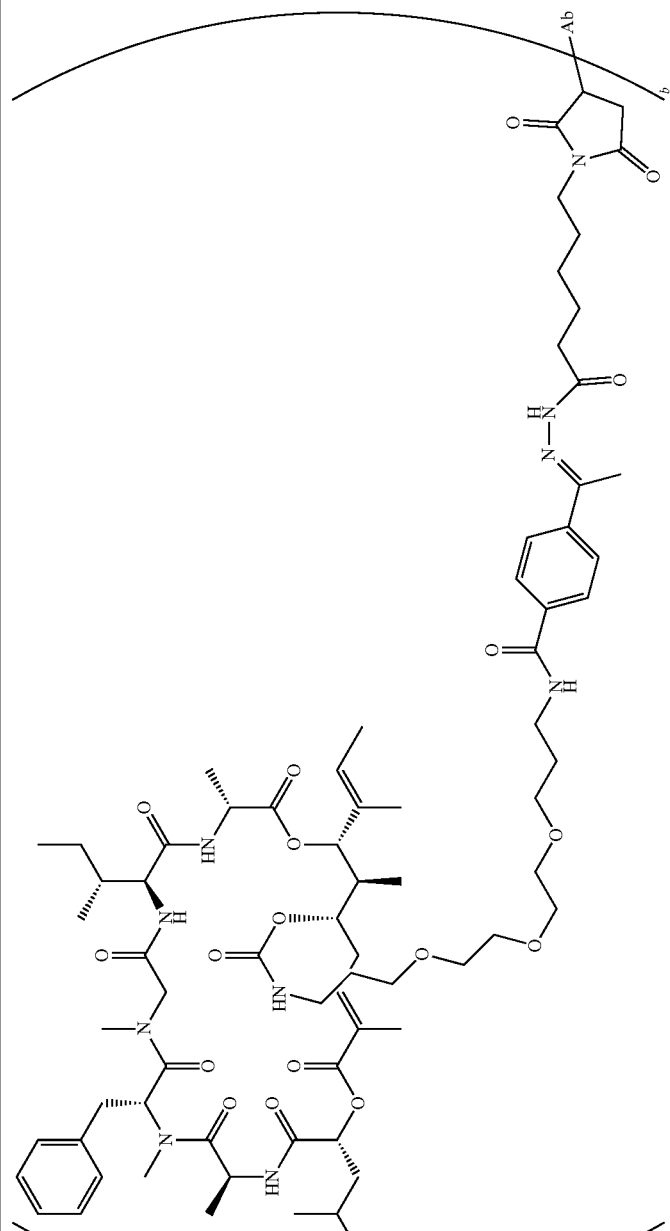 |

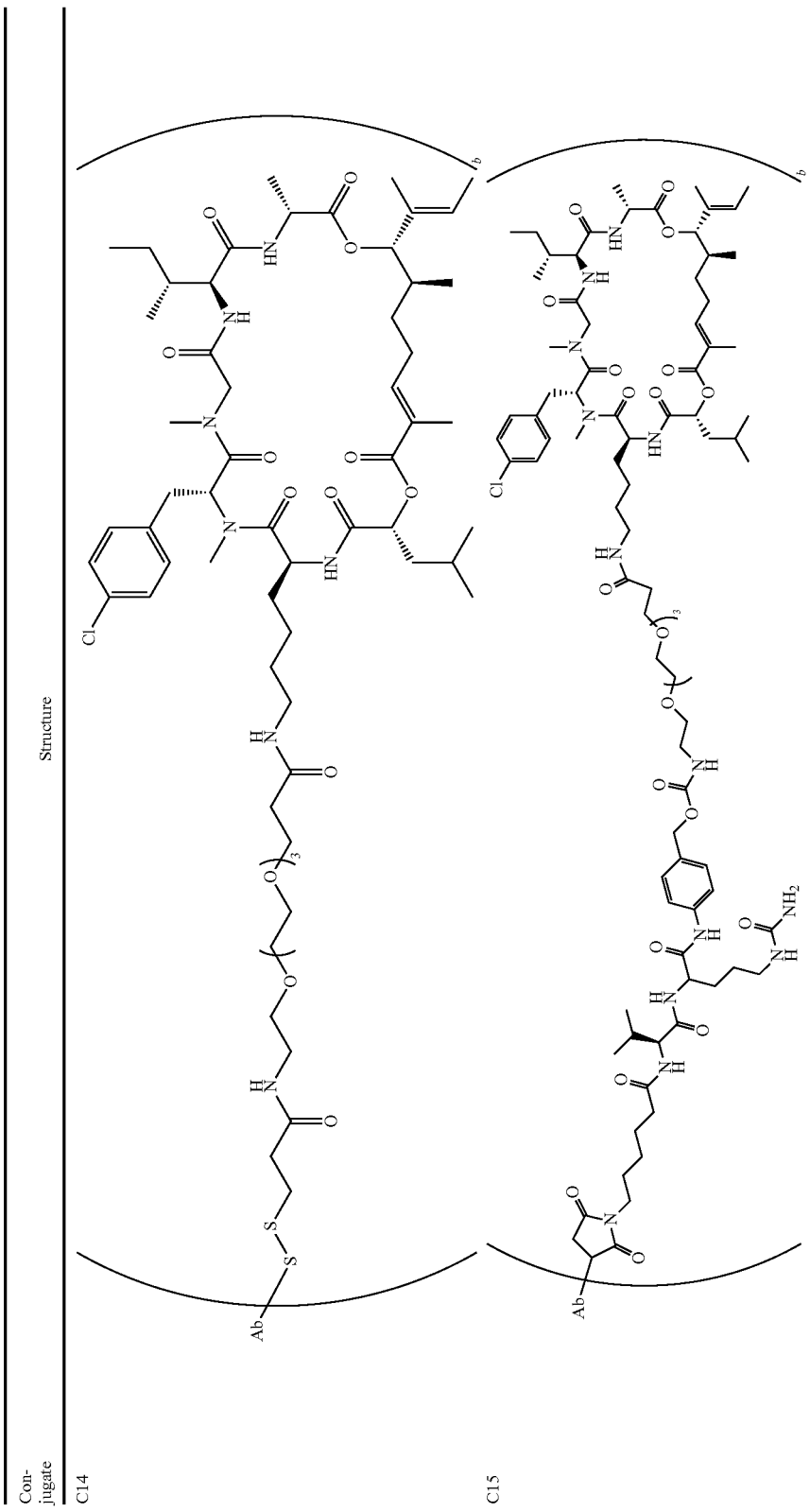

| Conjugate | Structure |
|---|---|
| C16 | 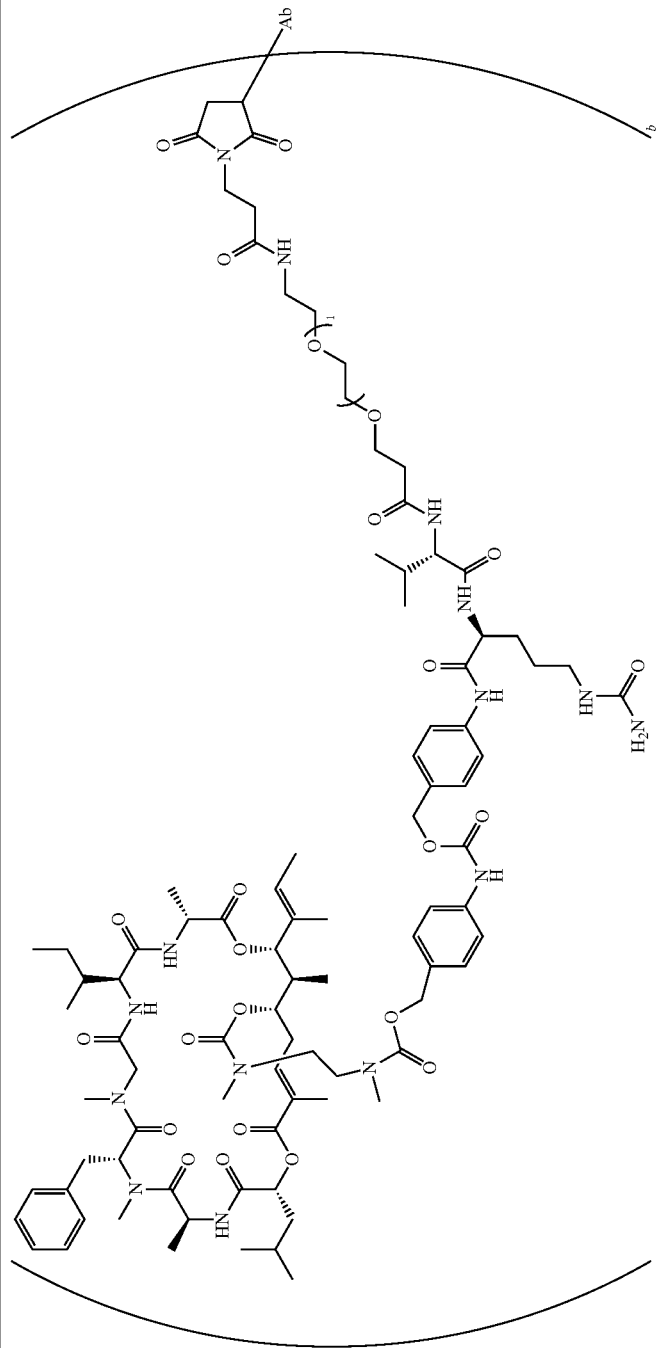 |

| Conjugate | Structure |
|---|---|
| C17 | 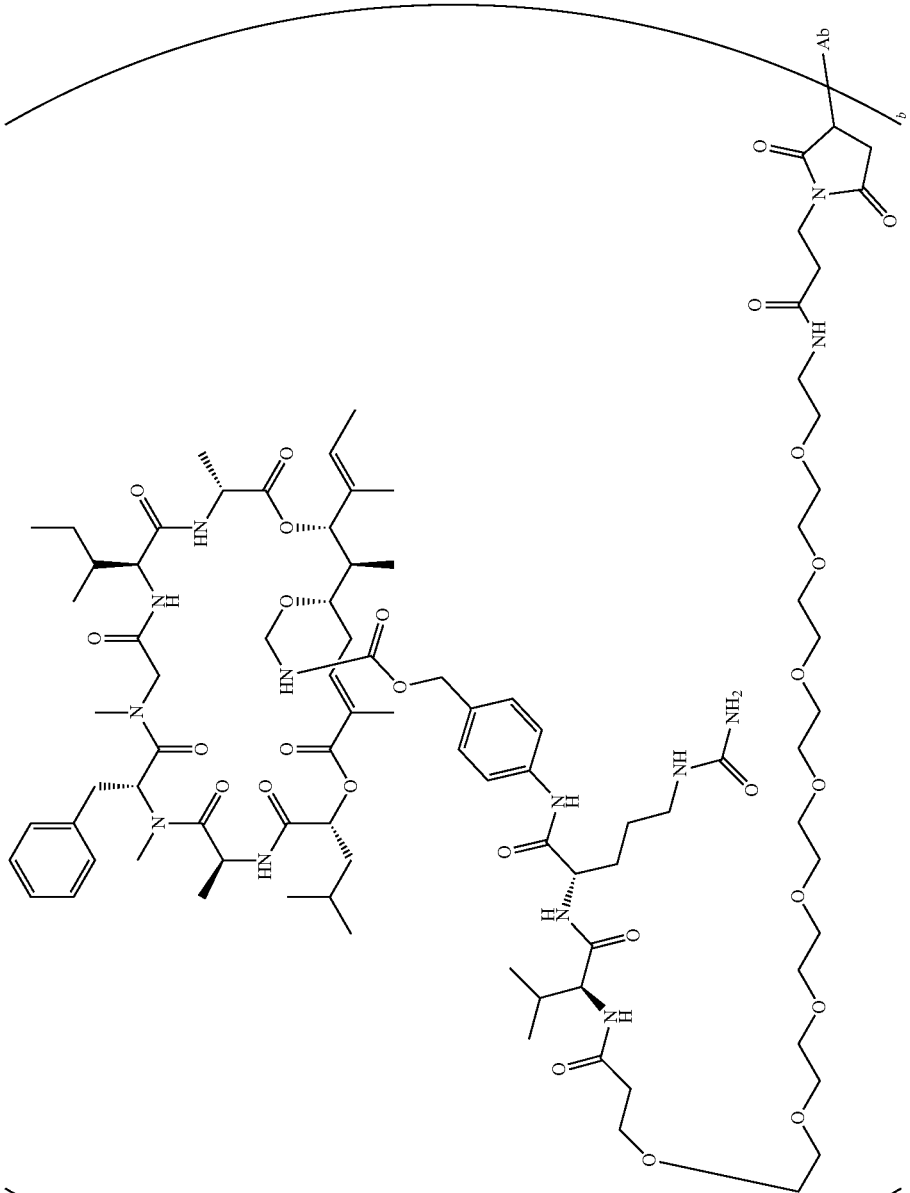 |

| Conjugate | Structure |
|---|---|
| C18 | 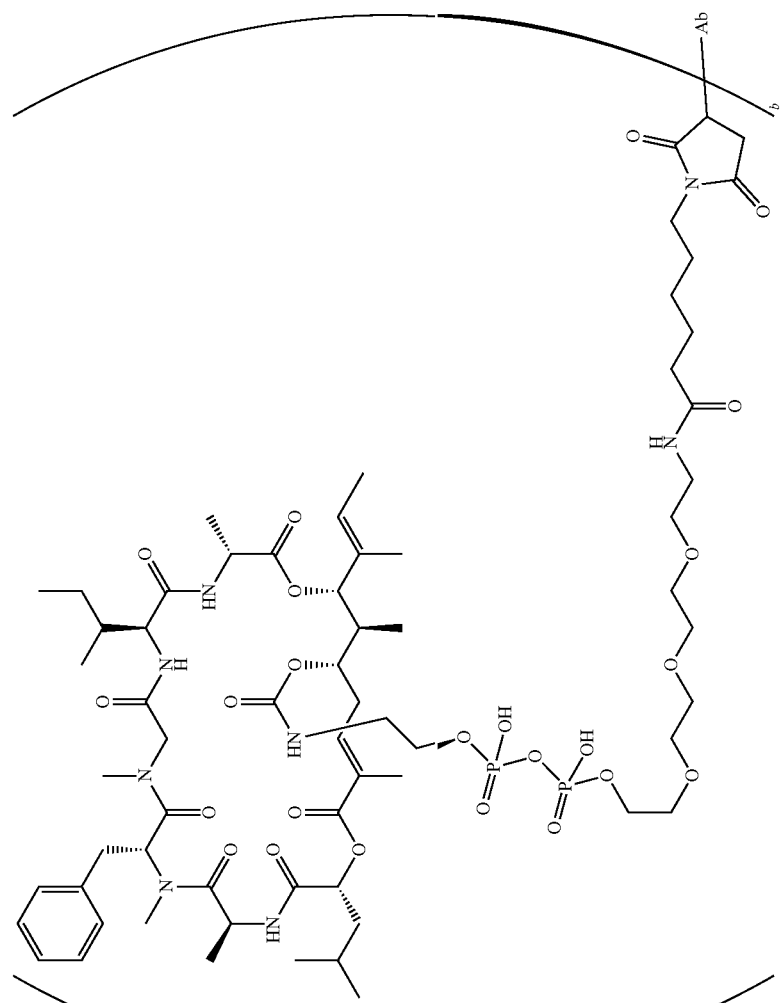 |

| Conjugate | Structure |
|---|---|
| C19 | 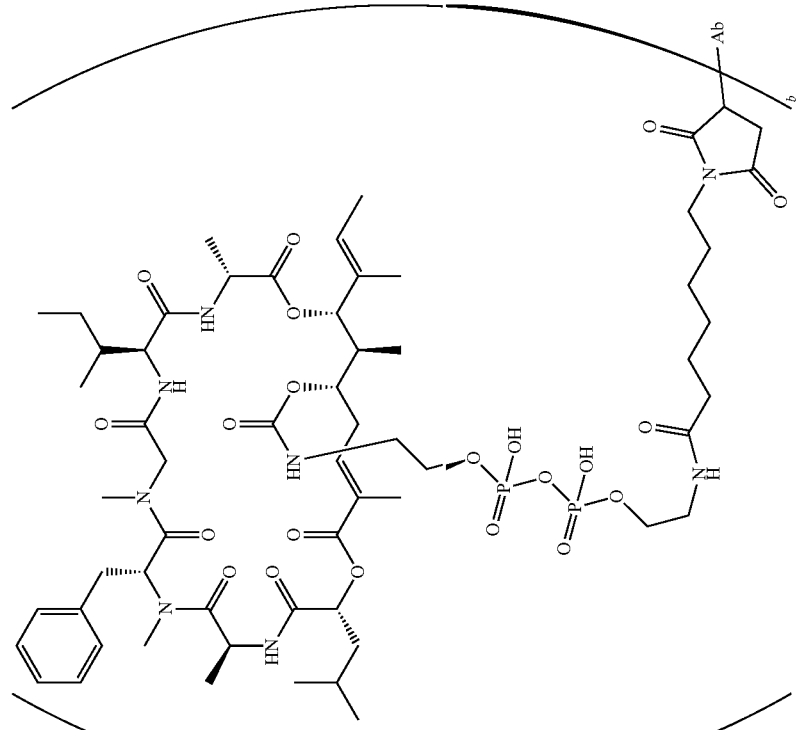 |

| Conjugate | Structure |
|---|---|
| C20 | 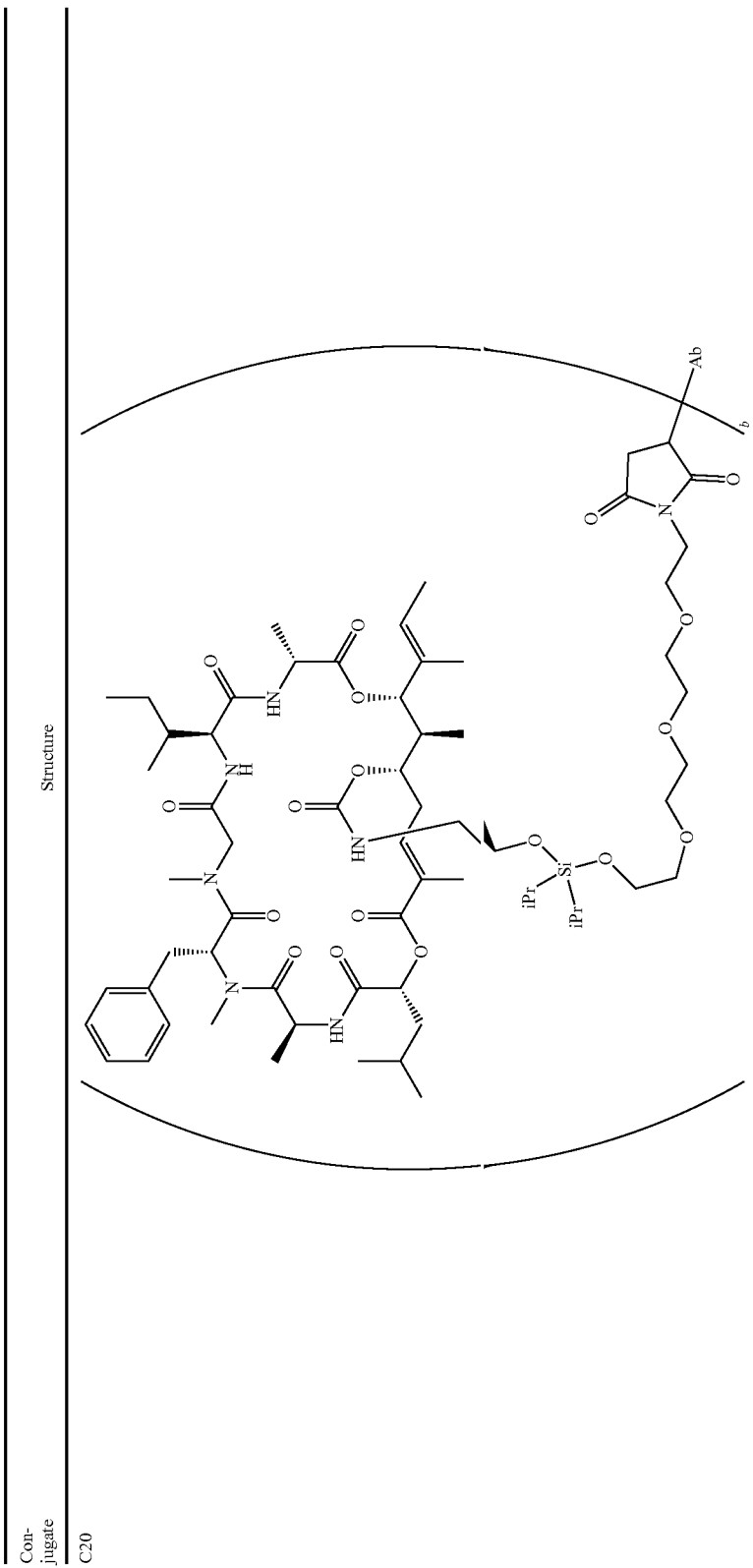 |

-continued
| Conjugate | Structure |
|---|---|
| C21 | 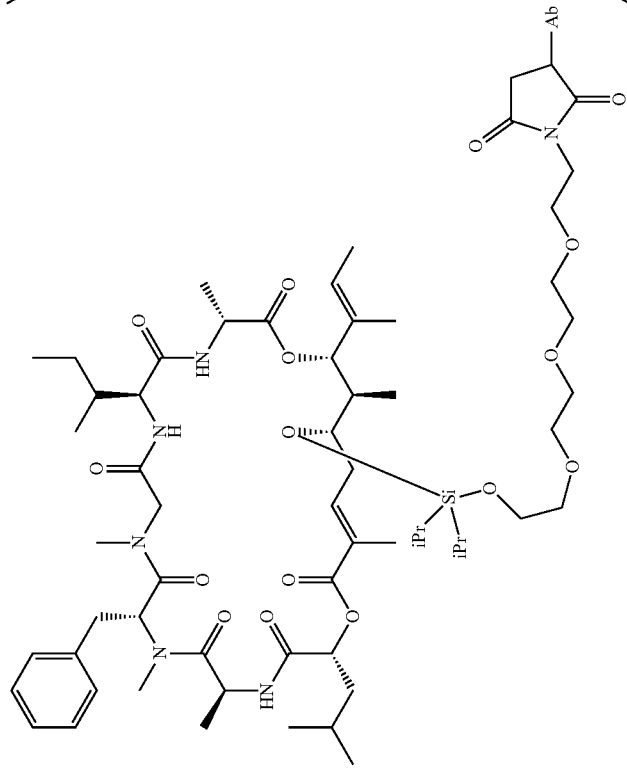 |

| Conjugate | Structure |
|---|---|
| C25 | 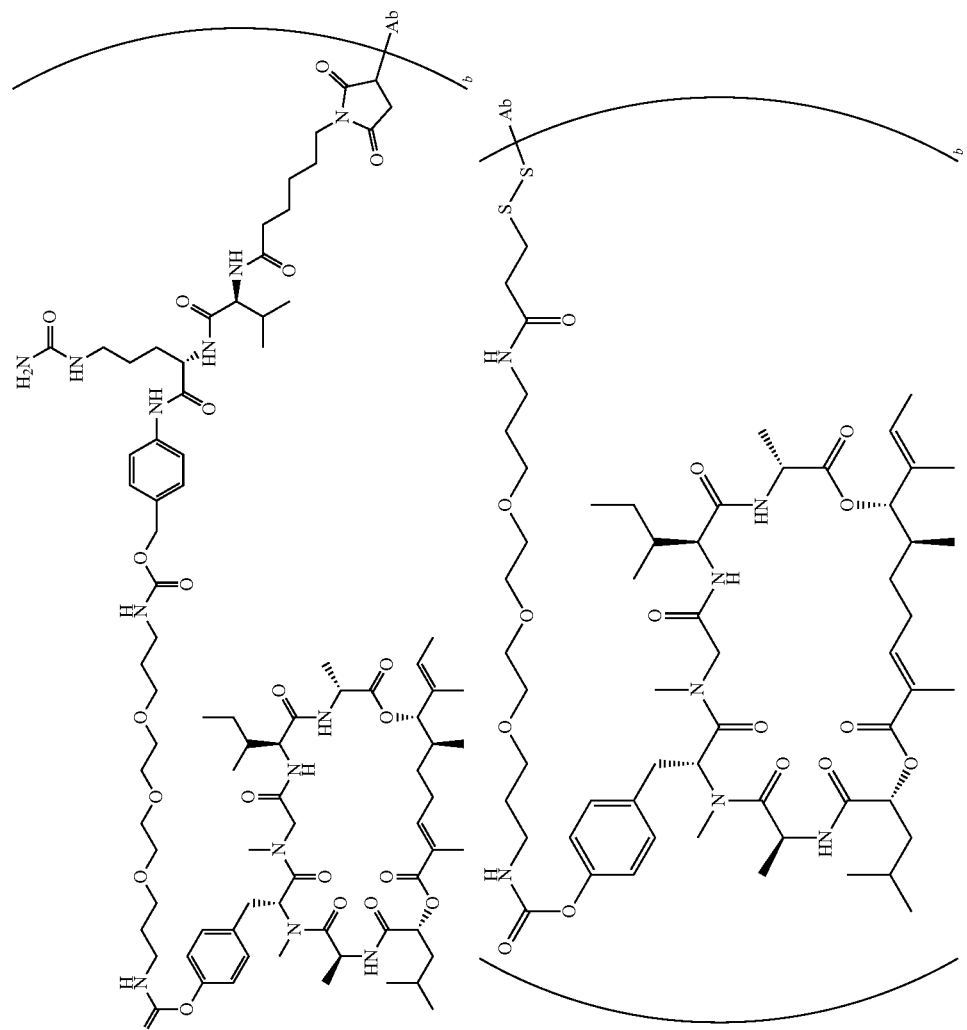 |
| C26 | 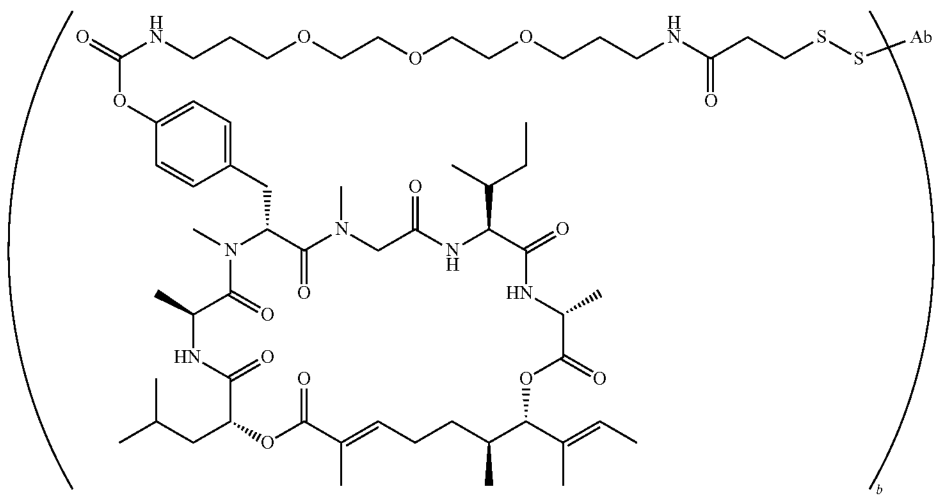 |

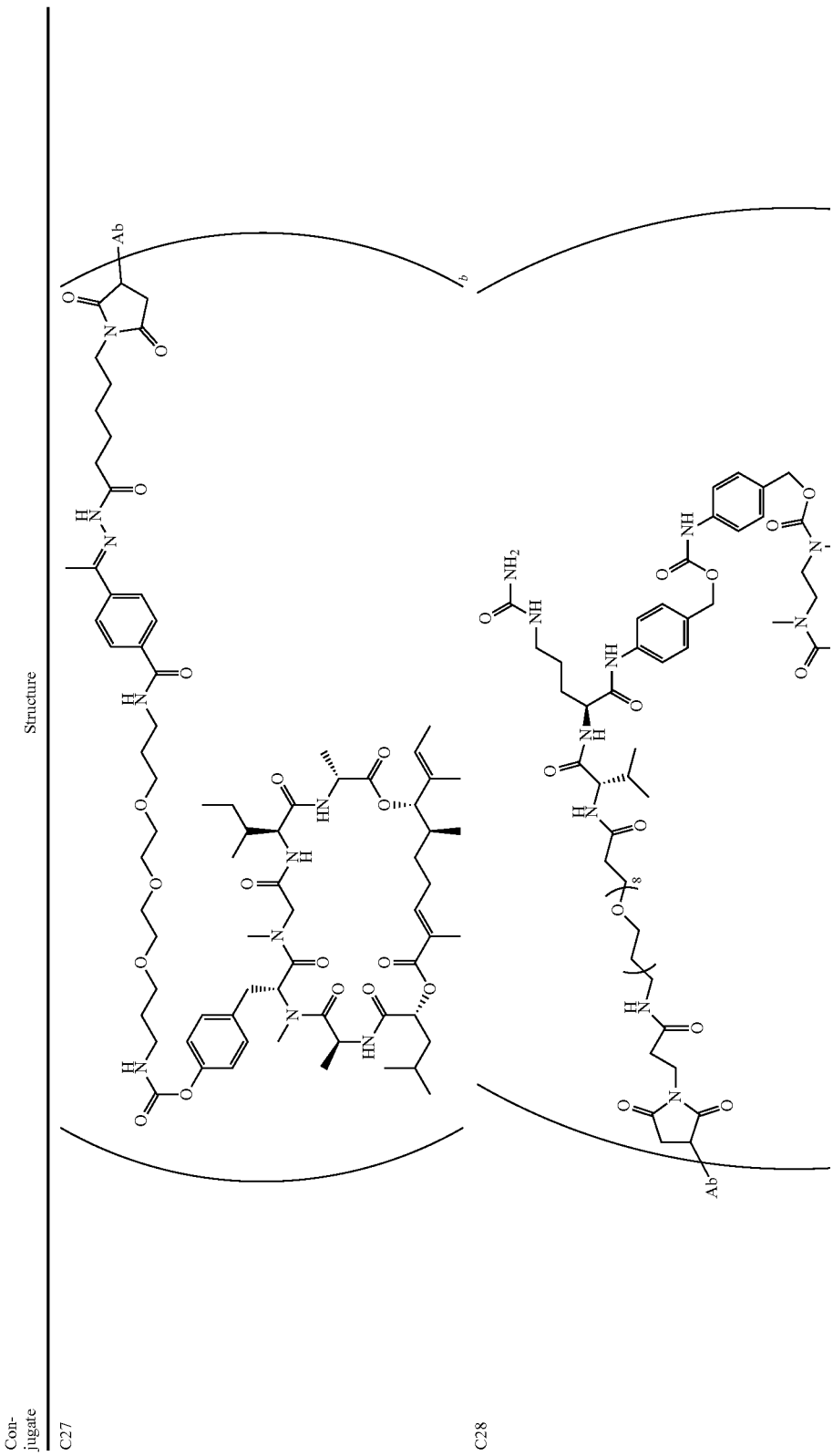

| Conjugate | Structure |
|---|---|
| C29 | 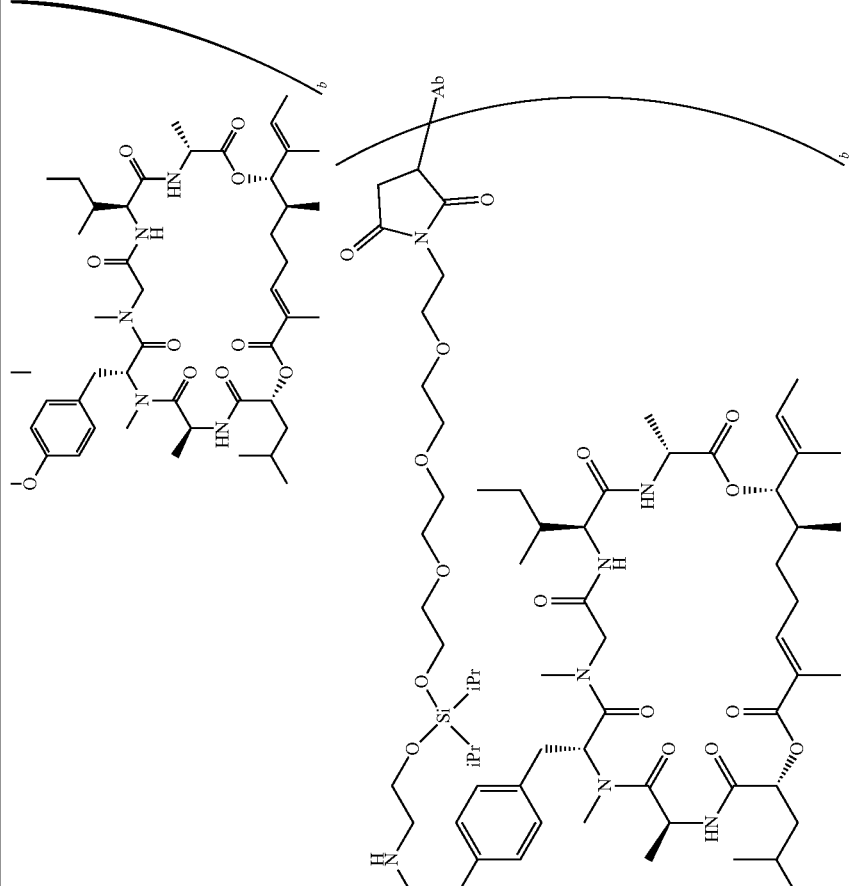 |

| Conjugate | Structure |
|---|---|
| C30 | 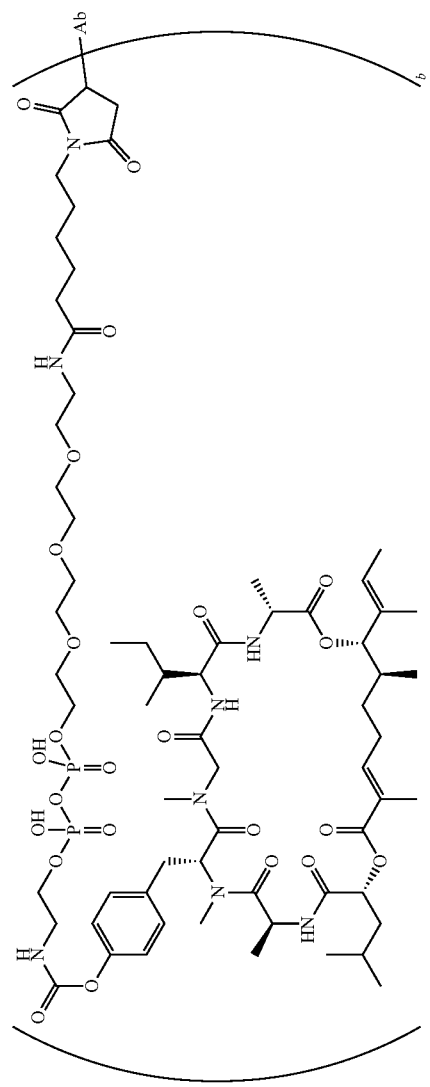 |
| C31 | 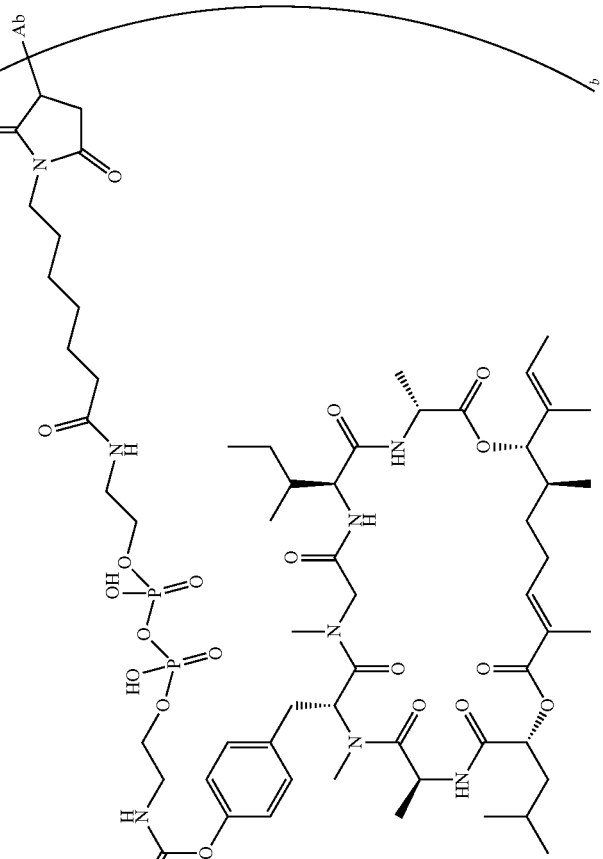 |

| Conjugate | Structure |
|---|---|
| C32 | 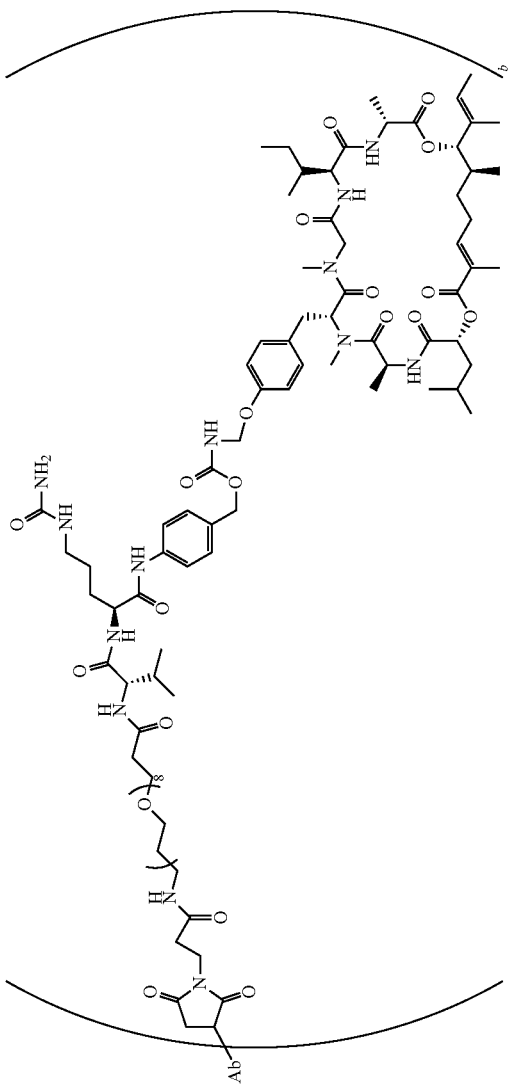 |

| Conjugate | Structure |
|---|---|
| C33 | 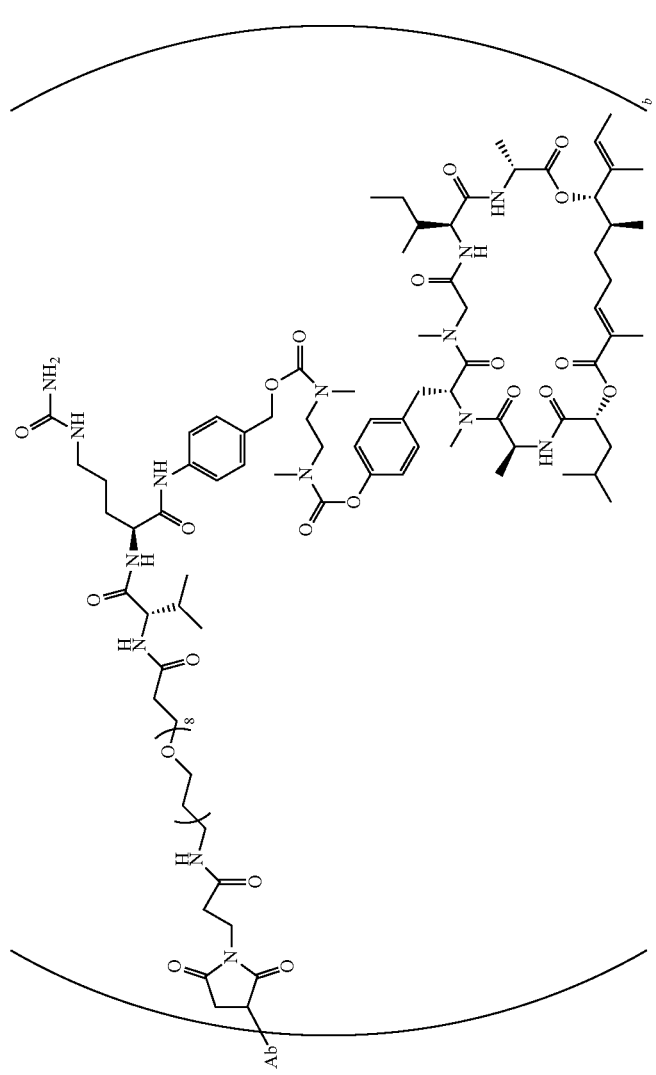 | wherein b is an integer from 1-12, inclusive, and Ab is an antibody.

8. A pharmaceutical composition comprising a conjugate of claim 1, or a pharmaceutically acceptable salt thereof, and a pharmaceutically acceptable carrier.

9. A kit comprising a conjugate of claim 1 and instructions for use.

10. The conjugate of claim 1, wherein $Y^1$ is $-N(R^d)-$.

11. The conjugate of claim 1, wherein $Y^1$ is $-O-$.

12. The conjugate of claim 1, wherein $R^c$ is H or substituted or unsubstituted $C_1$-$C_6$ alkyl.

13. The conjugate of claim 1, wherein $R^c$ is

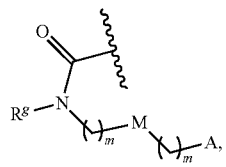

wherein
A is OH, $-NR^fR^h$ or $-N_3$;
M is $-(CH_2)_k-$ or $-(OCH_2-CH_2)_k-$, where k is an integer from 1-12, inclusive;
each m is independently an integer from 0 to 3,
$R^f$ is H, substituted or unsubstituted alkyl, or optionally substituted $-C(O)O$-alkyl;
$R^g$ is H or substituted or unsubstituted alkyl;
$R^h$ is H, substituted or unsubstituted alkyl, $-C(O)R^i$, or $-S(O)_2R^i$;
$R^i$ is H, OH, substituted or unsubstituted alkyl, substituted or unsubstituted aryl, substituted or unsubstituted heteroaryl, or

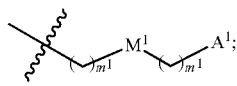

$A^1$ is $-NR^{f1}R^{h1}$;
$M^1$ is $-(CH_2)_j-$ or $-(OCH_2-CH_2)_j-$, where j is an integer from 1-12, inclusive;
each $m^1$ is independently an integer from 0 to 3;
$R^{f1}$ is H, or substituted or unsubstituted alkyl;
$R^{h1}$ is H, substituted or unsubstituted alkyl, or $-C(O)R^{i1}$; and
$R^{i1}$ is H, OH, substituted or unsubstituted alkyl, substituted or unsubstituted aryl, or substituted or unsubstituted heteroaryl.

14. The conjugate of claim 1, wherein $Y^2$ is $-N(R^d)-$.

15. The conjugate of claim 1, wherein $Y^2$ is $-O-$.

16. The conjugate of claim 1, wherein $R^1$, $R^3$, $R^5$, $R^{8a}$, $R^{8b}$, $R^9$, $R^{10}$, $R^{11}$, $R^{12}$, $R^{13}$ and $R^{14}$ are each independently H or $C_1$-$C_6$ alkyl.

17. The conjugate of claim 1, wherein $R^2$ is H or $C_1$-$C_6$ alkyl optionally substituted with $NH_2$.

18. The conjugate of claim 1, wherein $R^4$ is $C_1$-$C_6$ alkyl or $C_3$-$C_8$ cycloalkyl.

19. The conjugate of claim 1, wherein
$R^1$, $R^5$, $R^{8a}$, and $R^{14}$ are each methyl;
$R^2$ is methyl or $-(CH_2)_4NH_2$;
$R^3$, $R^{8b}$, $R^9$, $R^{11}$, $R^{12}$, and $R^{13}$ are each H;
$R^4$ is iso-butyl; and
$R^{10}$ is sec-butyl.

20. The conjugate of claim 1, wherein $R^{15}$ is substituted or unsubstituted aryl.

21. The conjugate of claim 1, wherein $R^{15}$ is phenyl optionally substituted with halo, hydroxy, $C_1$-$C_6$ alkoxy, $C_1$-$C_6$ alkyl, or $C_1$-$C_6$ perhaloalkyl.

22. The conjugate of claim 1, wherein n is 1.

23. The conjugate of claim 1, wherein X is $-O-$.

24. The conjugate of claim 1, wherein X is $-N(R^d)-$, and $R^d$ is H or $C_1$-$C_6$ alkyl.

25. The conjugate of claim 1, wherein $R^6$ is H or $C_1$-$C_6$ alkyl.

26. The conjugate of claim 1, wherein $R^7$ is H, $C_1$-$C_6$ alkyl, $C_1$-$C_6$ alkenyl, or $C_1$-$C_6$ alkynyl.

27. The conjugate of claim 1, wherein the compound is kulokekahilide-2 or a salt thereof.

28. The conjugate of claim 1, wherein the compound is selected from the group consisting of the compounds of the following table, or a salt thereof:

| Compound No. | Structure |
|---|---|
| 1 | <img of macrocyclic structure> |

-continued
| Compound No. | Structure |
|---|---|
| 2 | 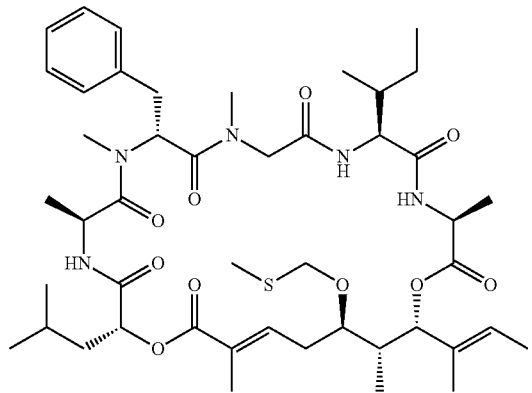 |
| 3 | 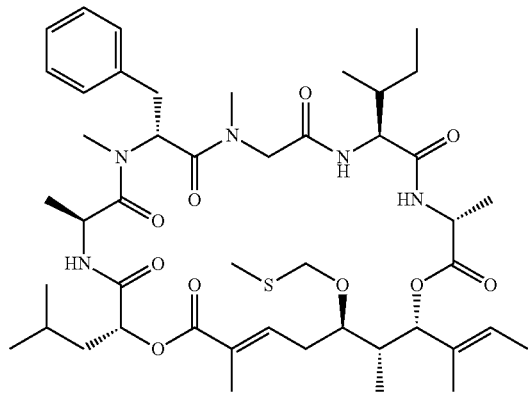 |
| 6 | 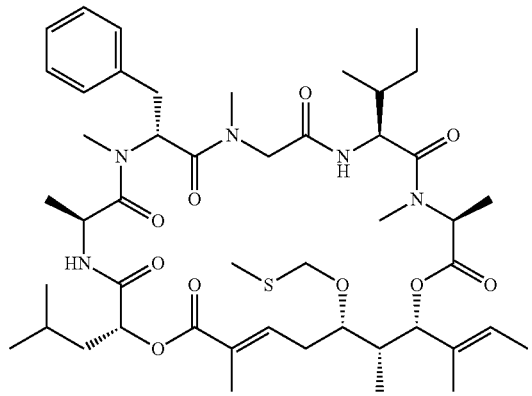 |

| Compound No. | Structure |
|---|---|
| 7 | 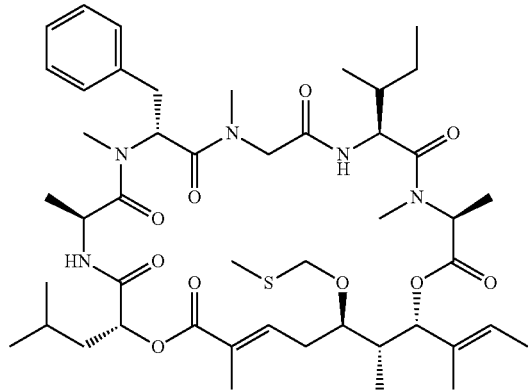 |
| 8 | 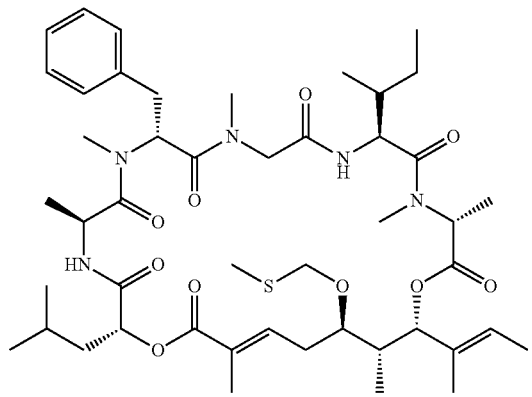 [SMILES: C/C=C(\C)[C@H]1OC(=O)[C@@H](C)N(C)C(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@@H](OCSC)[C@H]1C] |
| 13 | 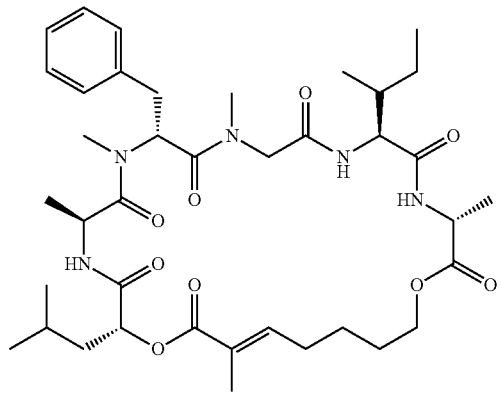 |

| Compound No. | Structure |
|---|---|
| 14 | 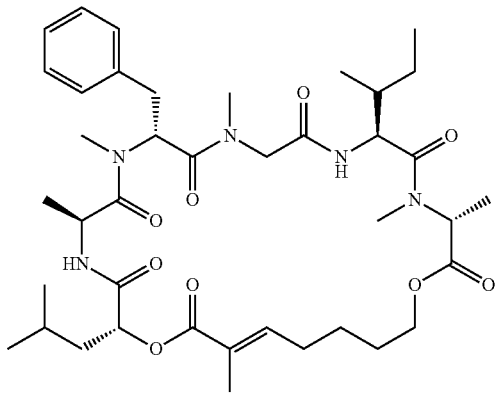 |
| 17 | 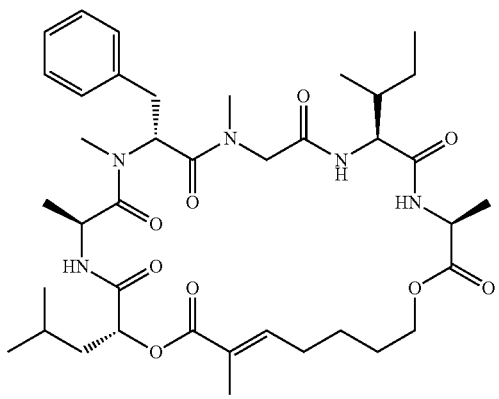 |
| 18 | 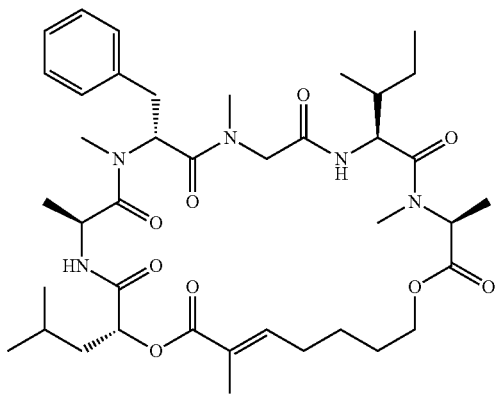 |

| Compound No. | Structure |
|---|---|
| 19 | 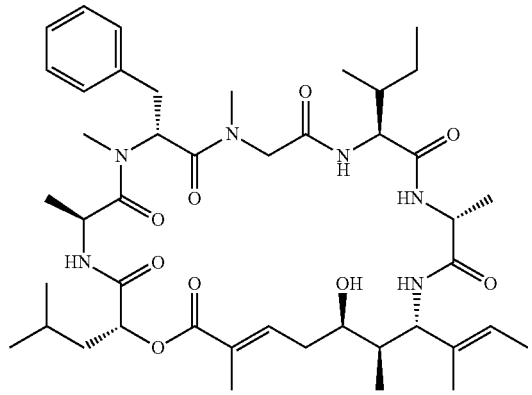 |
| 20 | 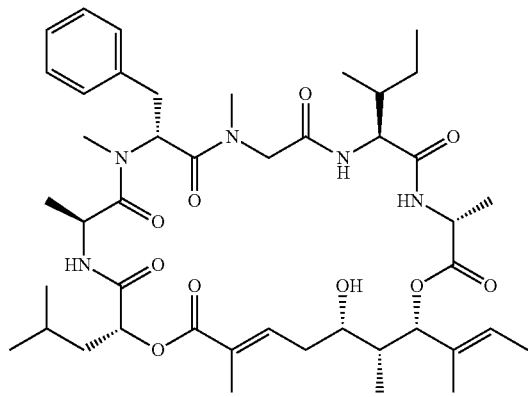 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@H]1C] |
| 21 | 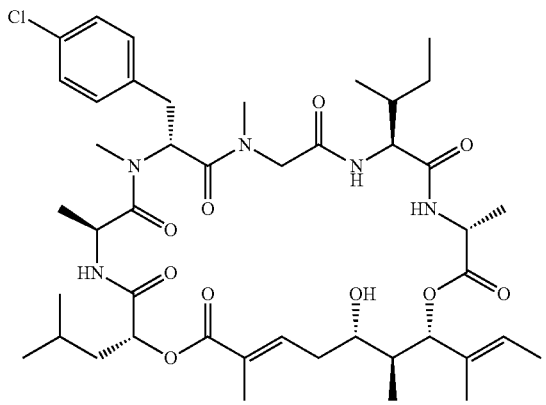 |

| Compound No. | Structure |
|---|---|
| 22 | 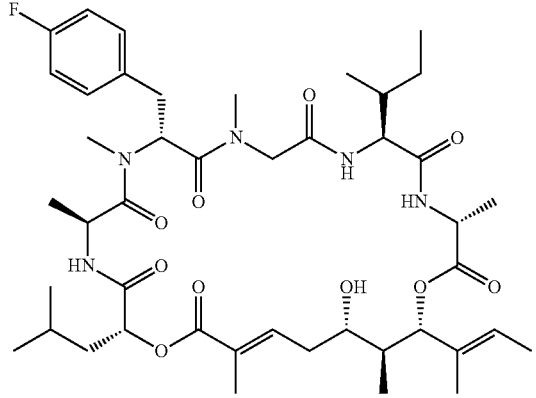 [SMILES: C/C=C(\C)[C@H]1OC(=O)[C@@H](C)NC(=O)[C@H](C(C)CC)NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@@H]1C] |
| 23 | 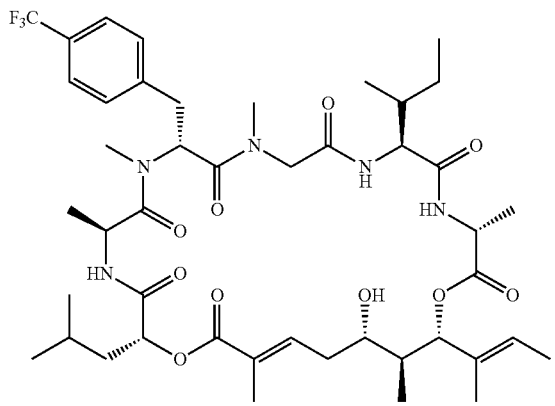 |
| 24 | 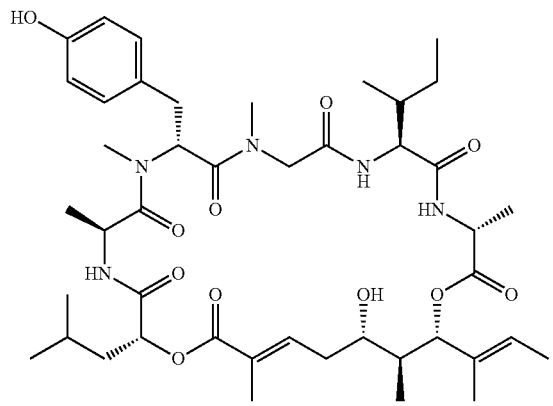 [SMILES: C/C=C(\C)[C@H]1OC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](O)[C@@H]1C] |

| Compound No. | Structure |
|---|---|
| 25 | 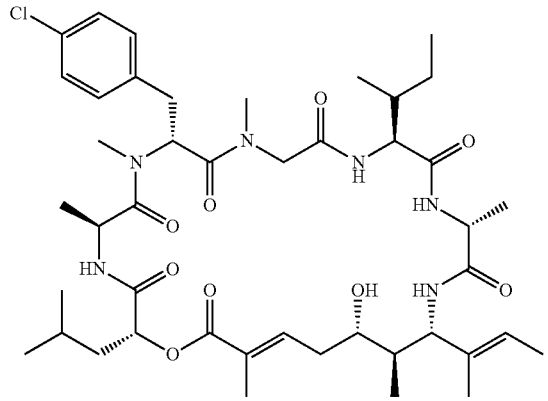 [SMILES: C/C=C(\C)[C@H]1NC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](O)[C@@H]1C] |
| 26 | 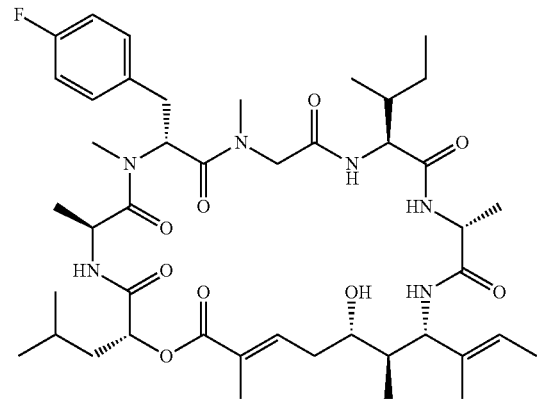 [SMILES: C/C=C(\C)[C@H]1NC(=O)[C@@H](C)NC(=O)[C@H](C(C)CC)NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@@H]1C] |
| 27 | 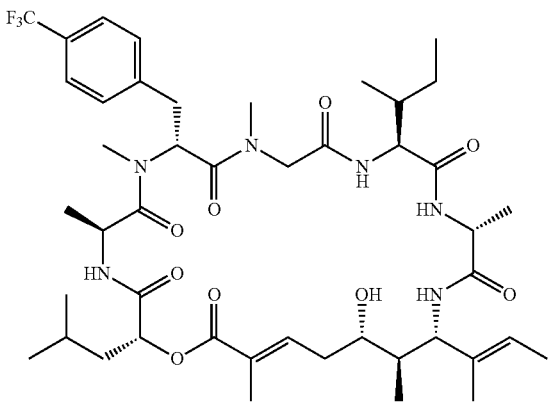 |

| Compound No. | Structure |
|---|---|
| 28 | 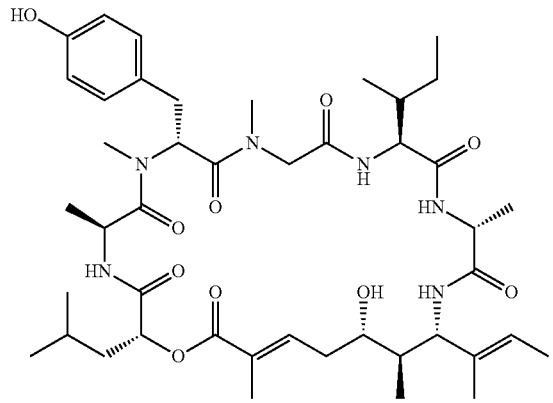 |
| 29 | 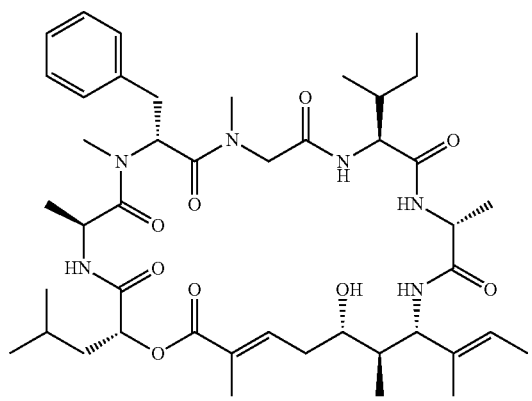 [SMILES: C/C=C(\C)[C@H]1NC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@@H]1C] |
| 30 | 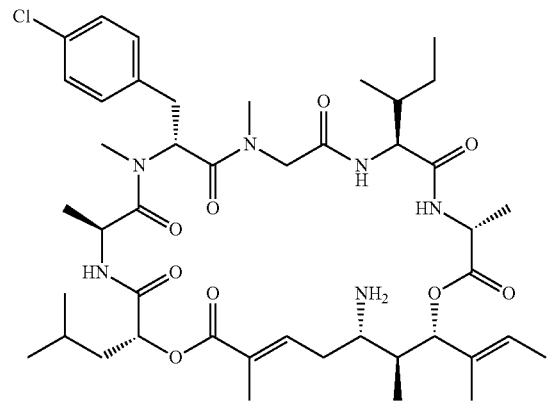 |

| Compound No. | Structure |
|---|---|
| 31 | 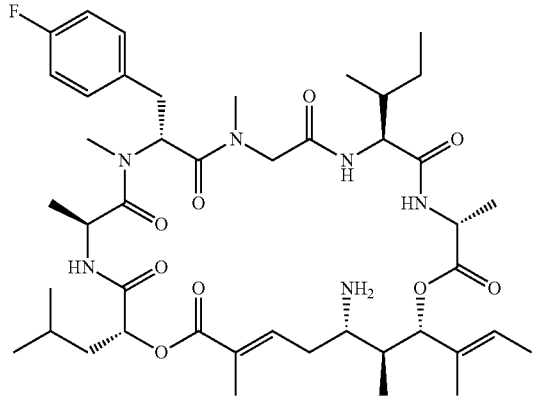 |
| 32 | 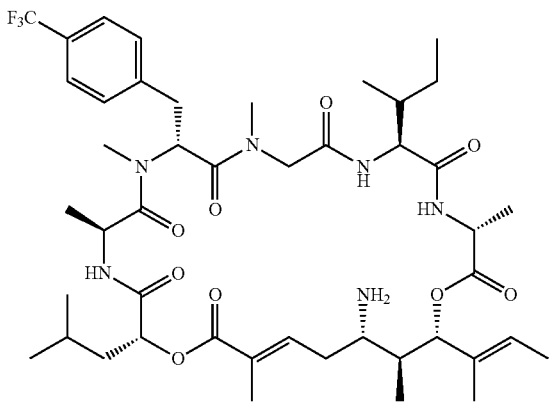 |
| 33 | 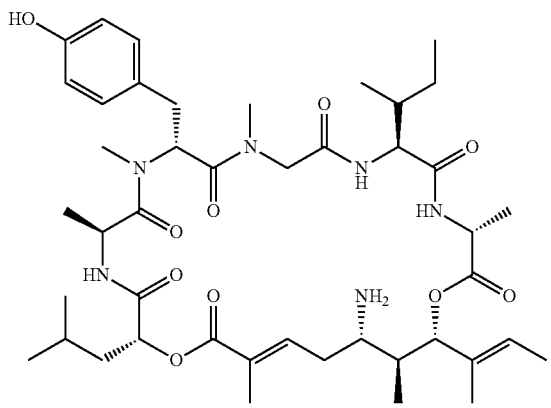 |

| Compound No. | Structure |
|---|---|
| 34 | 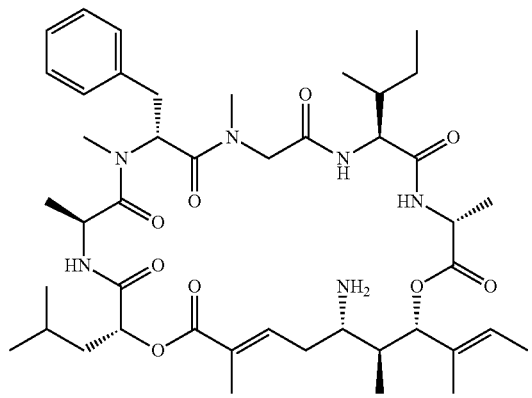 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](N)[C@@H]1C] |
| 35 | 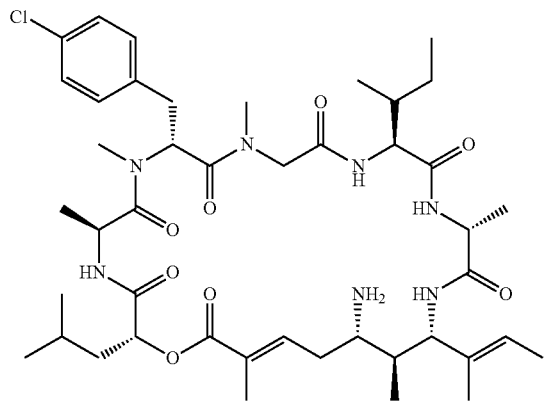 |
| 36 | 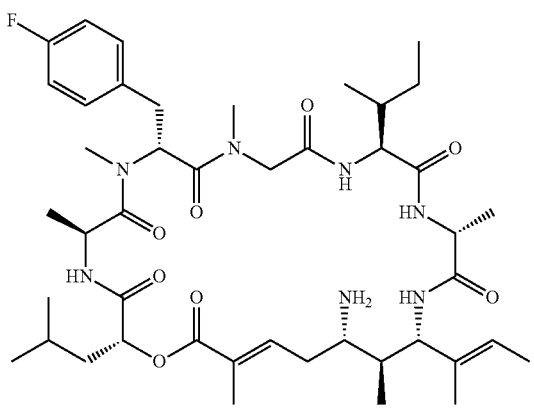 |

| Compound No. | Structure |
|---|---|
| 37 | 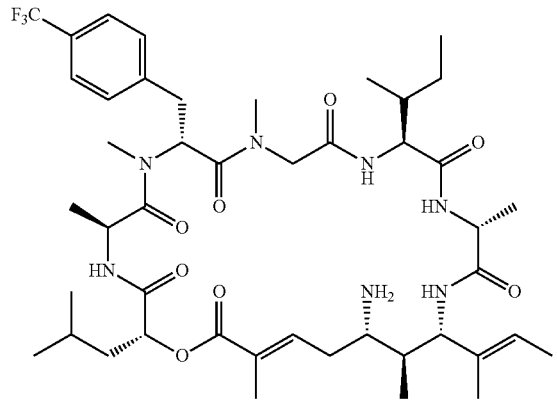 [SMILES: C/C=C(\C)[C@H]1NC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](N)[C@@H]1C] |
| 38 | 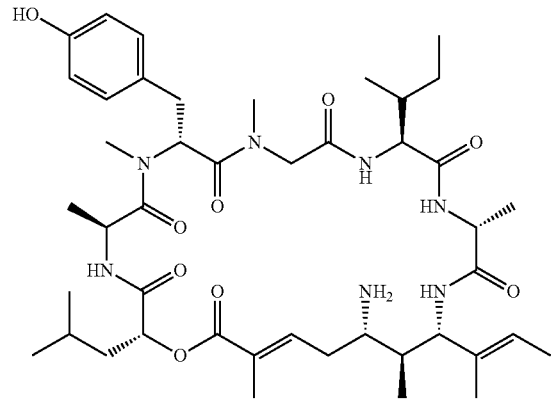 |
| 39 | 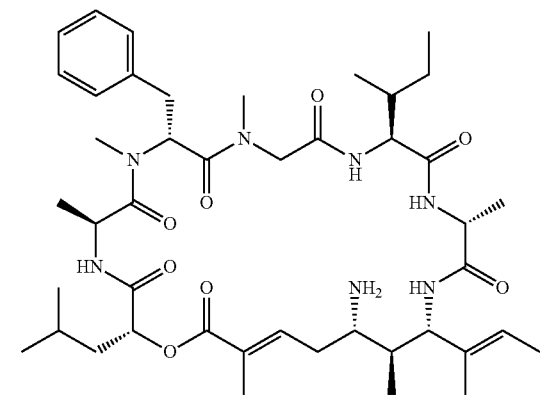 |

-continued
| Compound No. | Structure |
|---|---|
| 40 | 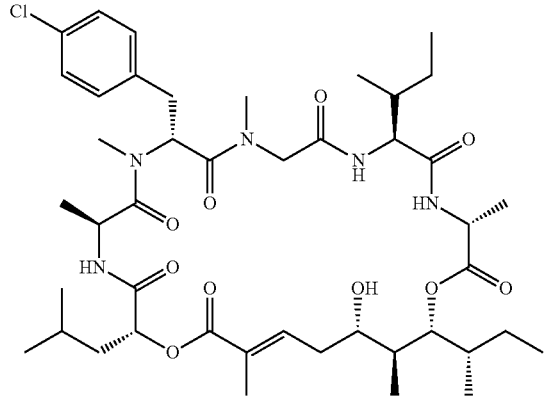 |
| 41 | 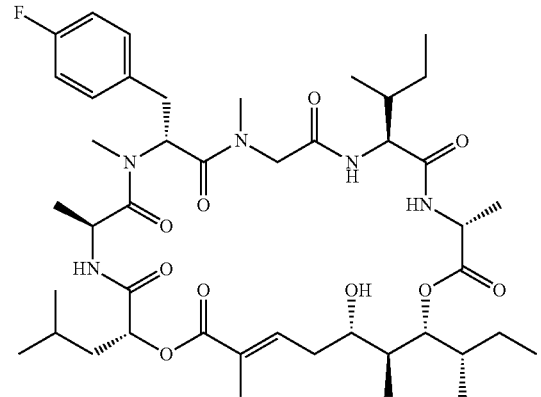 [SMILES: CCC(C)[C@@H]1NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](O)[C@H](C)[C@@H]([C@@H](C)CC)OC(=O)[C@@H](C)NC1=O] |
| 42 | 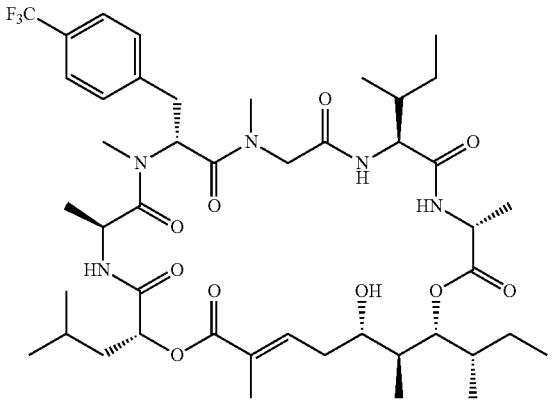 |

| Compound No. | Structure |
|---|---|
| 43 | 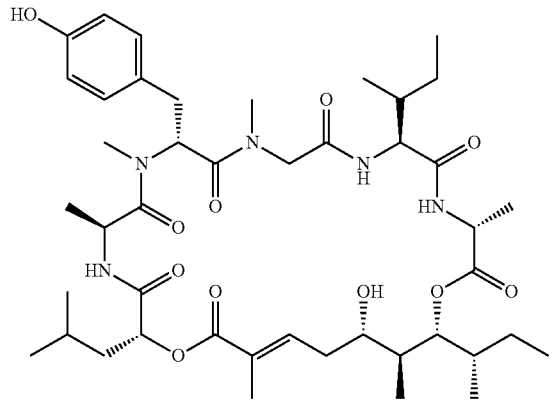 [SMILES: CCC(C)[C@@H]1NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](O)[C@H](C)[C@@H]([C@@H](C)CC)OC(=O)[C@@H](C)NC1=O] |
| 44 | 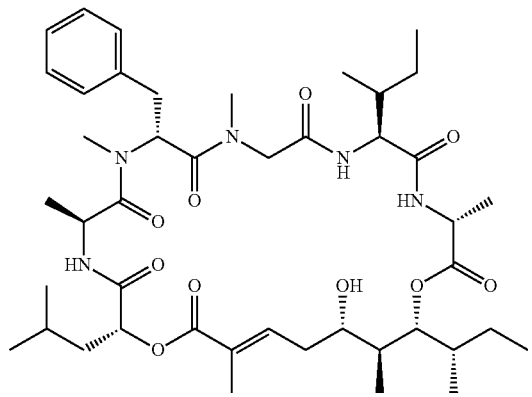 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@H](C)[C@@H]([C@@H](C)CC)OC(=O)[C@@H](C)NC1=O] |
| 45 | 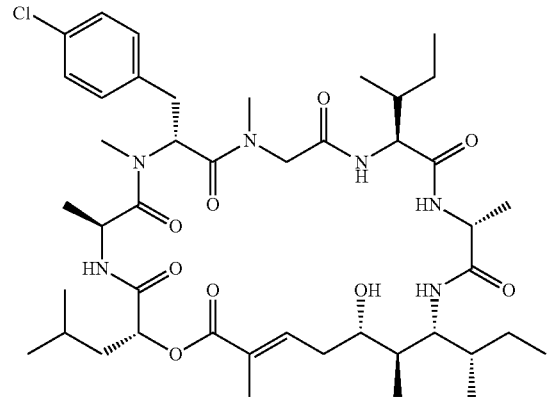 [SMILES: CCC(C)[C@@H]1NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](O)[C@H](C)[C@@H]([C@@H](C)CC)NC(=O)[C@@H](C)NC1=O] |

| Compound No. | Structure |
|---|---|
| 46 | 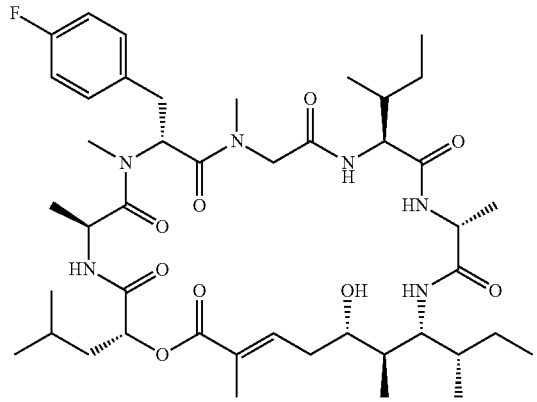 |
| 47 | 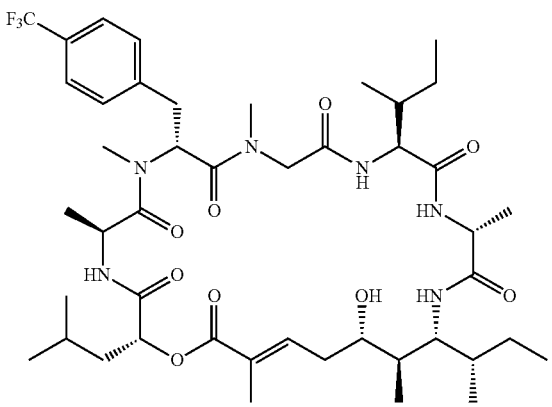 [SMILES: CCC(C)[C@@H]1NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](O)[C@H](C)[C@@H]([C@@H](C)CC)NC(=O)[C@@H](C)NC1=O] |
| 48 | 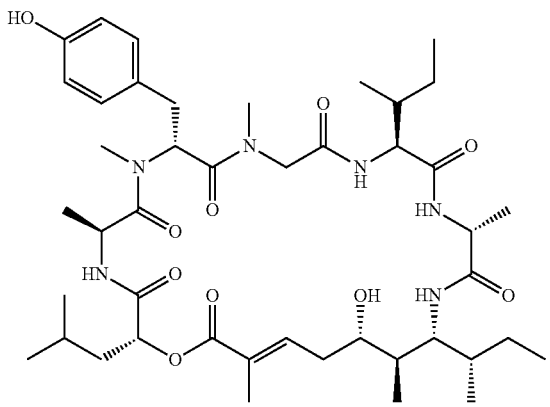 |

| Compound No. | Structure |
|---|---|
| 49 | 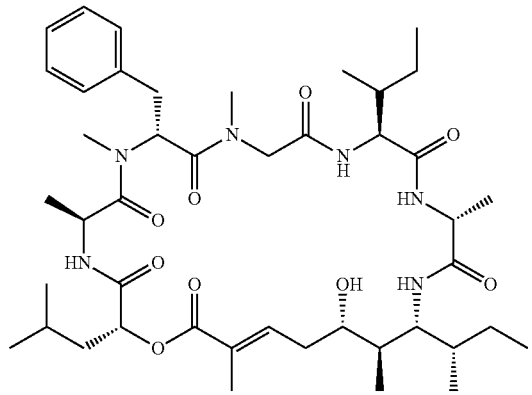 |
| 50 | 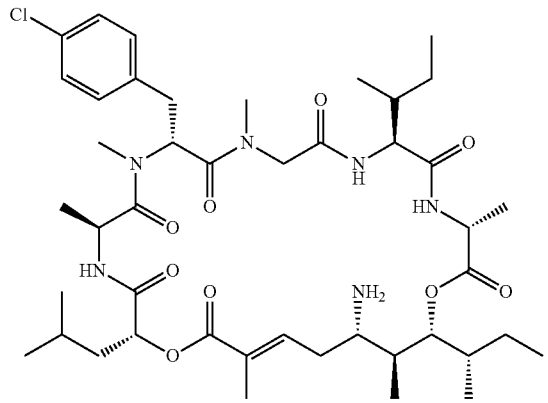 [SMILES: CCC(C)[C@@H]1NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](N)[C@H](C)[C@@H]([C@@H](C)CC)OC(=O)[C@@H](C)NC1=O] |
| 51 | 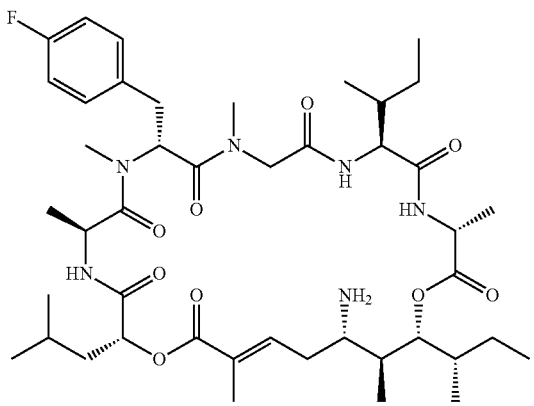 |

| Compound No. | Structure |
|---|---|
| 52 | 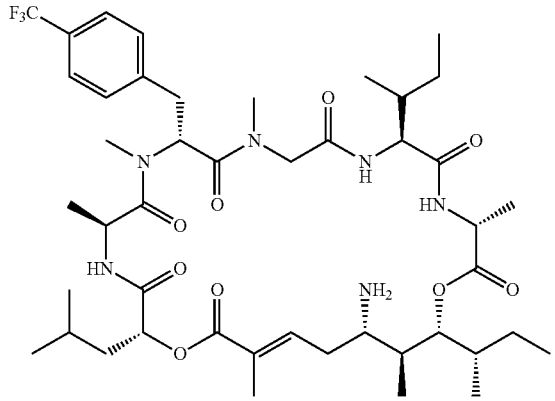 |
| 53 | 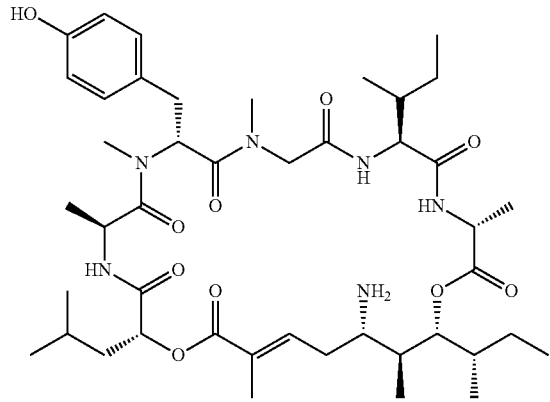 [SMILES: CCC(C)[C@@H]1NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](N)[C@H](C)[C@@H]([C@@H](C)CC)OC(=O)[C@@H](C)NC1=O] |
| 54 | 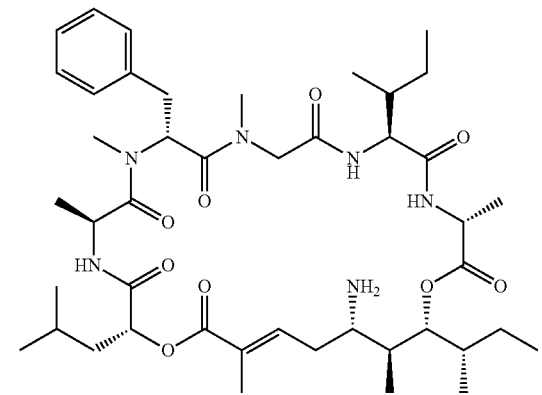 |

| Compound No. | Structure |
|---|---|
| 55 | 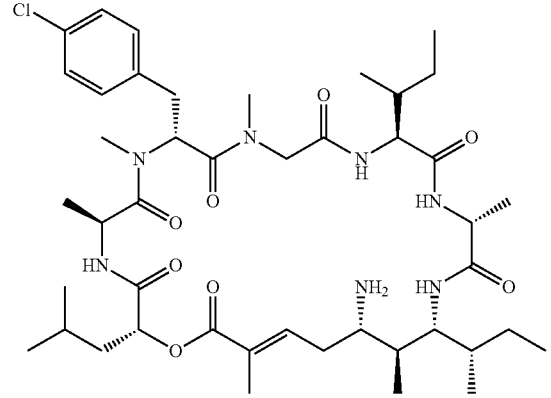 [SMILES: CCC(C)[C@@H]1NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](N)[C@H](C)[C@@H]([C@@H](C)CC)NC(=O)[C@@H](C)NC1=O] |
| 56 | 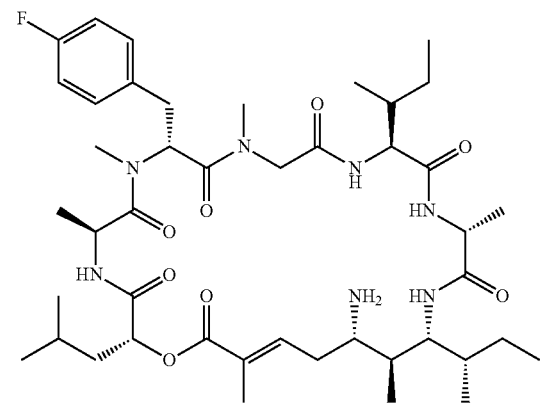 |
| 57 | 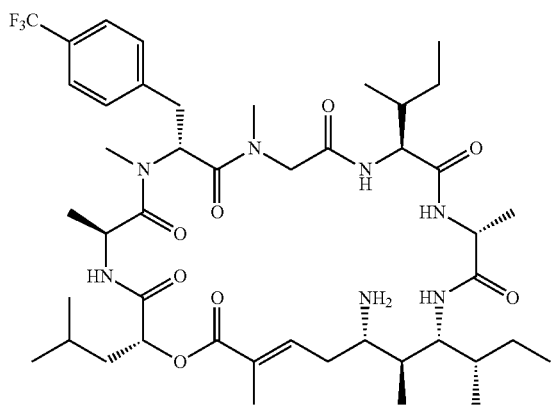 |

-continued
| Compound No. | Structure |
|---|---|
| 58 | 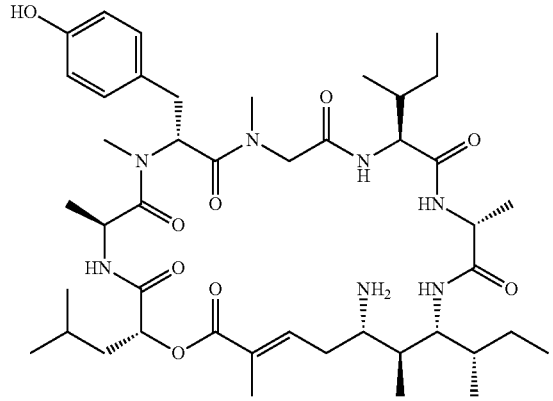 [SMILES: CCC(C)[C@@H]1NC(=O)CN(C)C(=O)[C@@H](Cc2ccc(O)cc2)N(C)C(=O)[C@H](C)NC(=O)[C@@H](CC(C)C)OC(=O)/C(C)=C/C[C@H](N)[C@H](C)[C@@H]([C@@H](C)CC)NC(=O)[C@@H](C)NC1=O] |
| 59 | 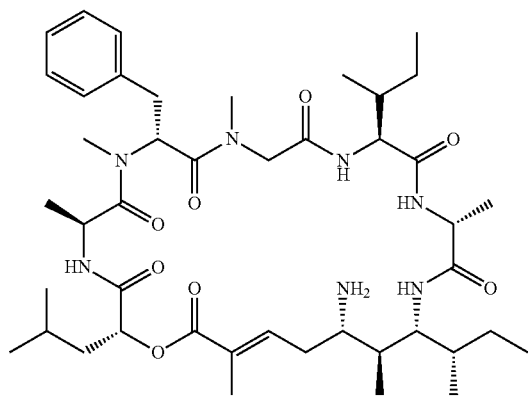 |
| 61 | 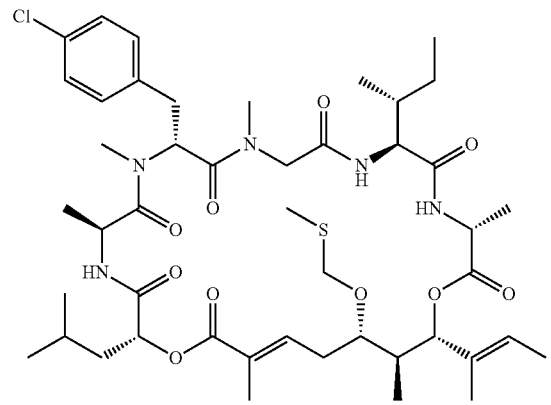 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OCSC)[C@@H]1C] |

| Compound No. | Structure |
|---|---|
| 62 | 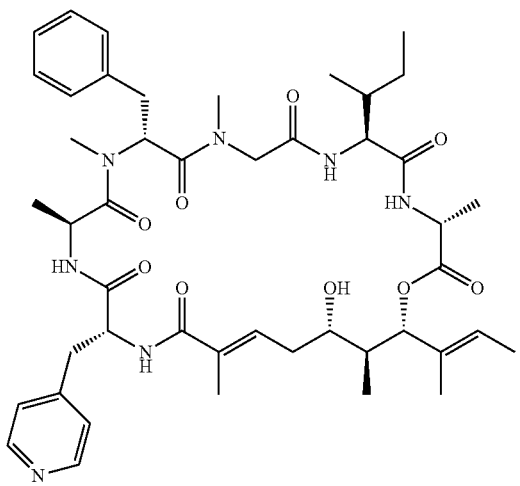 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](Cc2ccncc2)NC(=O)/C(C)=C/C[C@H](O)[C@@H]1C] |
| 63 | 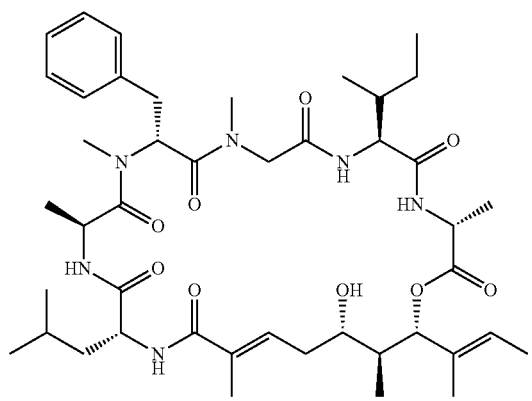 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)NC(=O)/C(C)=C/C[C@H](O)[C@@H]1C] |
| 64 | 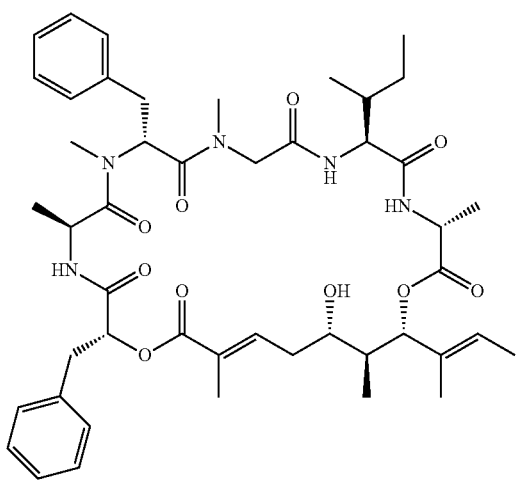 |

| Compound No. | Structure |
|---|---|
| 65 | 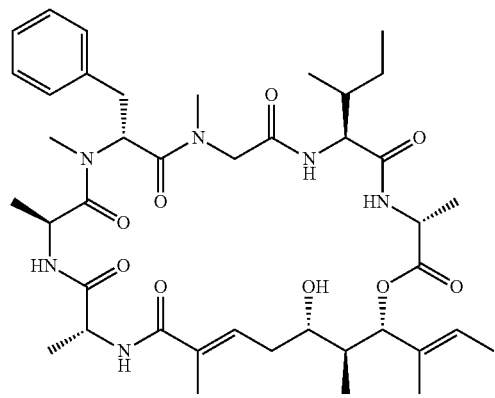 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](C)NC(=O)/C(C)=C/C[C@H](O)[C@@H]1C] |
| 66 | 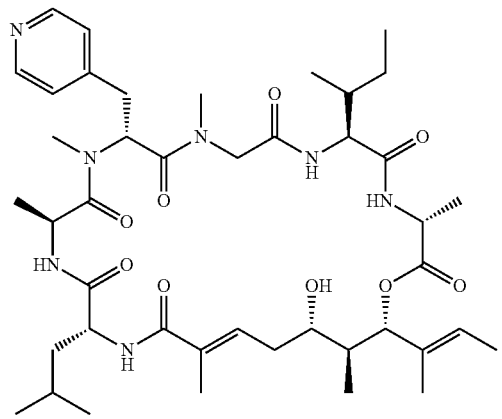 [SMILES: C/C=C(\C)[C@H]1OC(=O)[C@@H](C)NC(=O)[C@H](C(C)CC)NC(=O)CN(C)C(=O)[C@@H](Cc2ccncc2)N(C)C(=O)[C@H](C)NC(=O)[C@@H](CC(C)C)NC(=O)/C(C)=C/C[C@H](O)[C@@H]1C] |
| 67 | 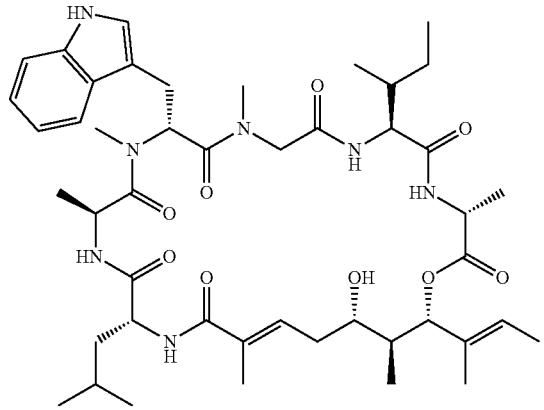 [SMILES: C/C=C(\C)[C@H]1OC(=O)[C@@H](C)NC(=O)[C@H](C(C)CC)NC(=O)CN(C)C(=O)[C@@H](Cc2c[nH]c3ccccc23)N(C)C(=O)[C@H](C)NC(=O)[C@@H](CC(C)C)NC(=O)/C(C)=C/C[C@H](O)[C@@H]1C] |

-continued
| Compound No. | Structure |
|---|---|
| 70 | 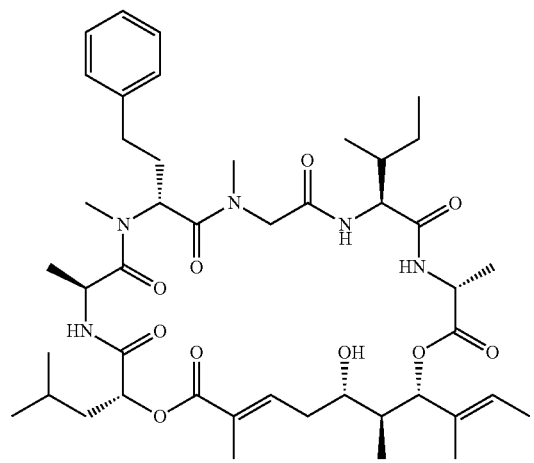 [SMILES: C/C=C(\C)[C@H]1OC(=O)[C@@H](C)NC(=O)[C@H](C(C)CC)NC(=O)CN(C)C(=O)[C@@H](CCc2ccccc2)N(C)C(=O)[C@H](C)NC(=O)[C@@H](CC(C)C)OC(=O)/C(C)=C/C[C@H](O)[C@@H]1C] |
| 71 | 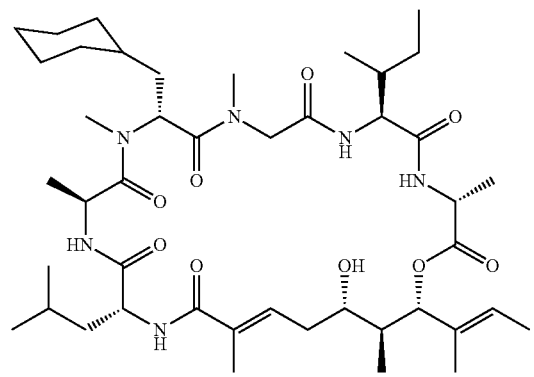 [SMILES: C/C=C(\C)[C@H]1OC(=O)[C@@H](C)NC(=O)[C@H](C(C)CC)NC(=O)CN(C)C(=O)[C@@H](CC2CCCCC2)N(C)C(=O)[C@H](C)NC(=O)[C@@H](CC(C)C)NC(=O)/C(C)=C/C[C@H](O)[C@@H]1C] |
| 72 | 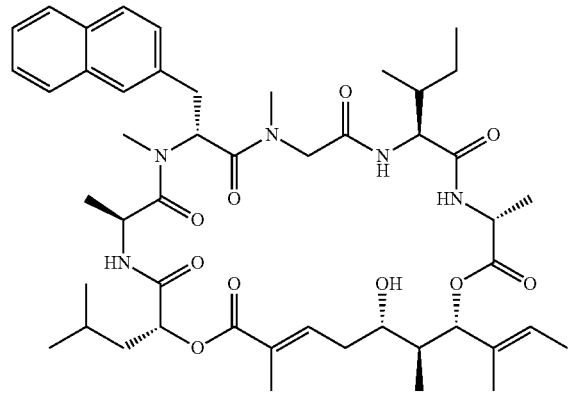 [SMILES: C/C=C(\C)[C@H]1OC(=O)[C@@H](C)NC(=O)[C@H](C(C)CC)NC(=O)CN(C)C(=O)[C@@H](Cc2ccc3ccccc3c2)N(C)C(=O)[C@H](C)NC(=O)[C@@H](CC(C)C)OC(=O)/C(C)=C/C[C@H](O)[C@@H]1C] |

| Compound No. | Structure |
|---|---|
| 73 | 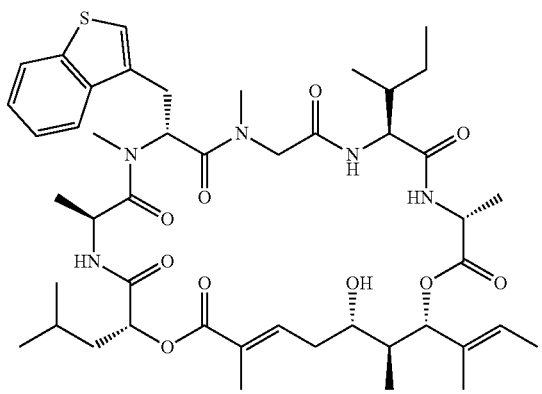 [SMILES: C/C=C(\C)[C@H]1OC(=O)[C@@H](C)NC(=O)[C@H](C(C)CC)NC(=O)CN(C)C(=O)[C@@H](Cc2csc3ccccc23)N(C)C(=O)[C@H](C)NC(=O)[C@@H](CC(C)C)OC(=O)/C(C)=C/C[C@H](O)[C@@H]1C] |
| 74 | 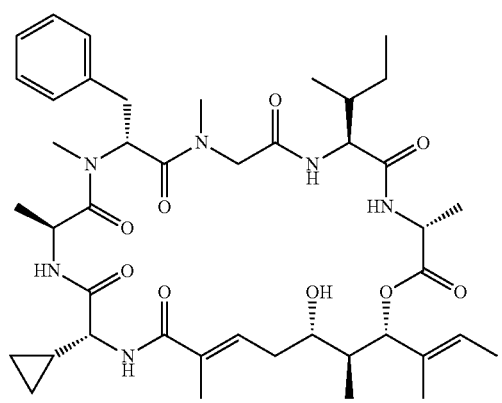 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](C2CC2)NC(=O)/C(C)=C/C[C@H](O)[C@@H]1C] |
| 75 | 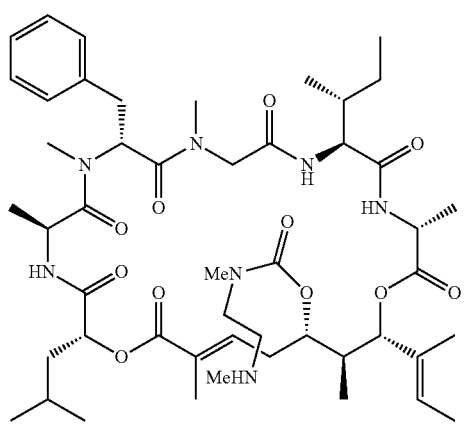 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCNC)[C@@H]1C] |

US 10,472,395 B2
543                                                         544
-continued
| Compound No. | Structure |
|---|---|
| 77 | 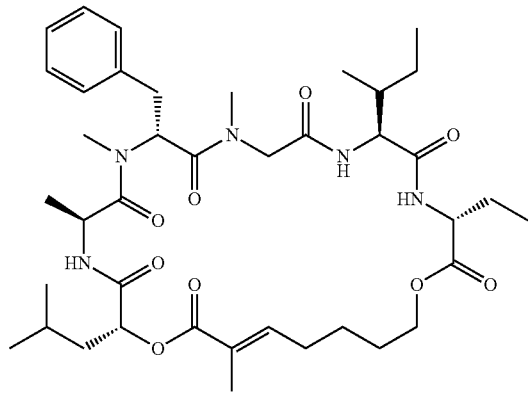 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@@H](CC)NC1=O] |
| 78 | 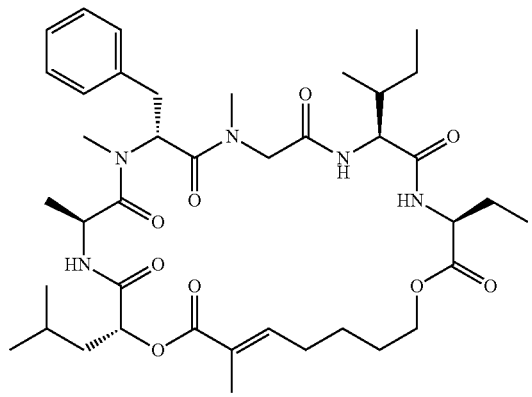 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCCCOC(=O)[C@H](CC)NC1=O] |
| 79 | 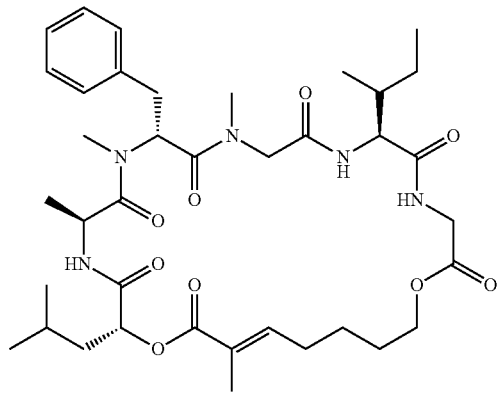 |

| Compound No. | Structure |
|---|---|
| 80 | 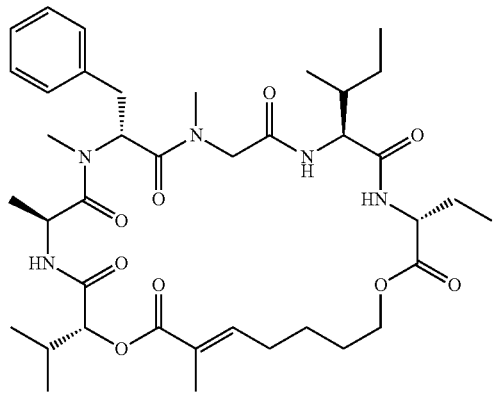 [SMILES: CCC(C)[C@@H]1NC(=O)CN(C)C(=O)[C@@H](Cc2ccccc2)N(C)C(=O)[C@H](C)NC(=O)[C@@H](C(C)C)OC(=O)/C(C)=C/CCCCOC(=O)[C@@H](CC)NC1=O] |
| 81 | 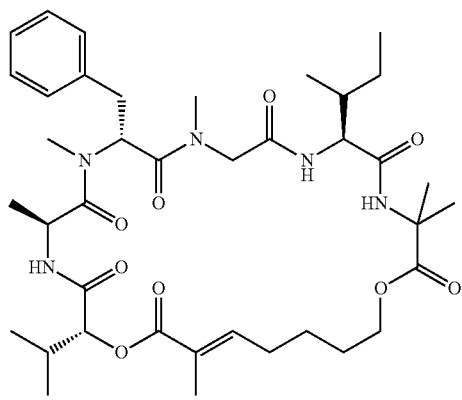 [SMILES: CCC(C)[C@@H]1NC(=O)CN(C)C(=O)[C@@H](Cc2ccccc2)N(C)C(=O)[C@H](C)NC(=O)[C@@H](C(C)C)OC(=O)/C(C)=C/CCCCOC(=O)C(C)(C)NC1=O] |
| 82 | 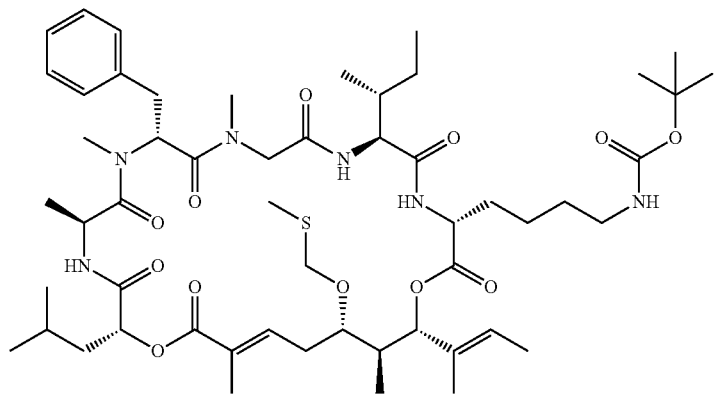 [SMILES: C/C=C(\C)[C@H]1OC(=O)[C@@H](CCCCNC(=O)OC(C)(C)C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@@H]1C] |

|Compound No.|Structure|
|---|---|
|83|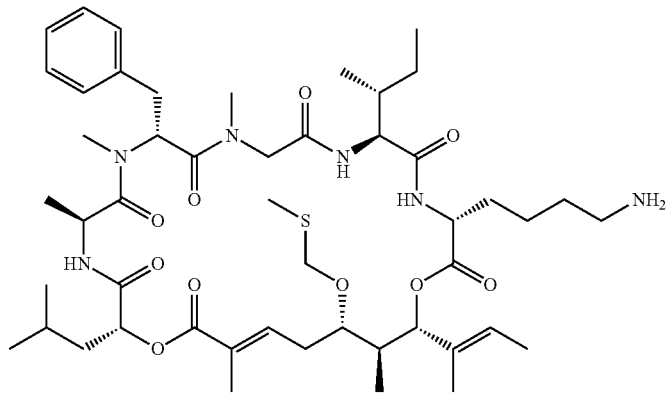 [SMILES: C/C=C(\C)[C@H]1OC(=O)[C@@H](CCCCN)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@@H]1C]|
|84|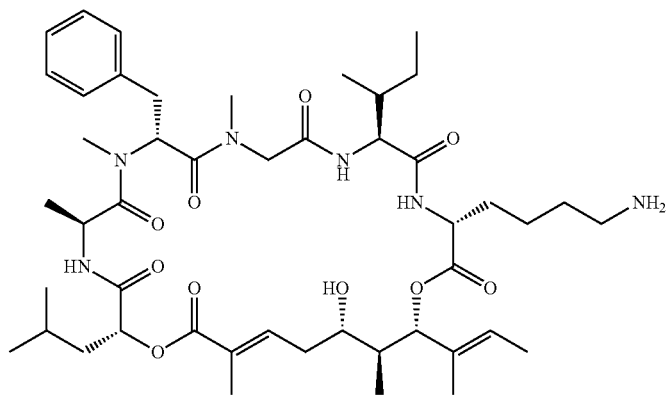 [SMILES: C/C=C(\C)[C@H]1OC(=O)[C@@H](CCCCN)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](O)[C@@H]1C]|
|85|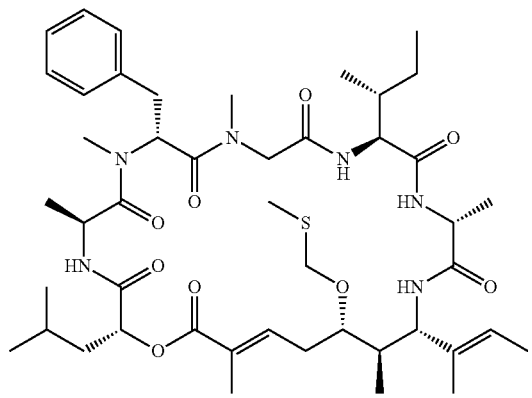 [SMILES: C/C=C(\C)[C@H]1NC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@@H]1C]|

| Compound No. | Structure |
|---|---|
| 86 | 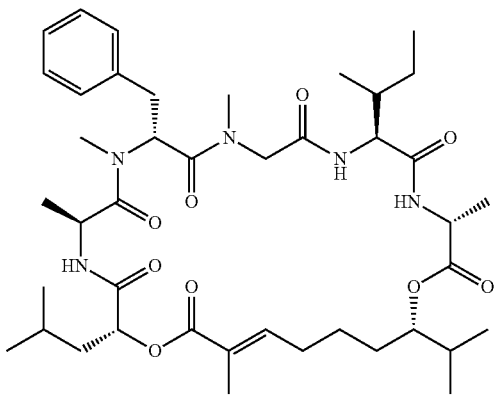 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@@H](C(C)C)OC(=O)[C@@H](C)NC1=O] |
| 87 | 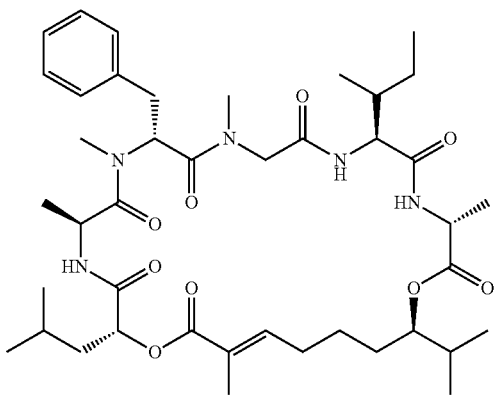 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@H](C(C)C)OC(=O)[C@@H](C)NC1=O] |
| 88 | 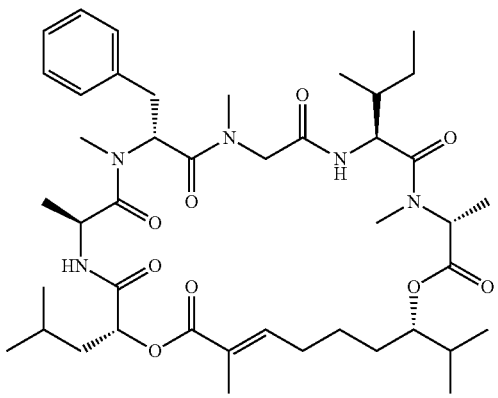 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@@H](C(C)C)OC(=O)[C@@H](C)N(C)C1=O] |

| Compound No. | Structure |
|---|---|
| 89 | 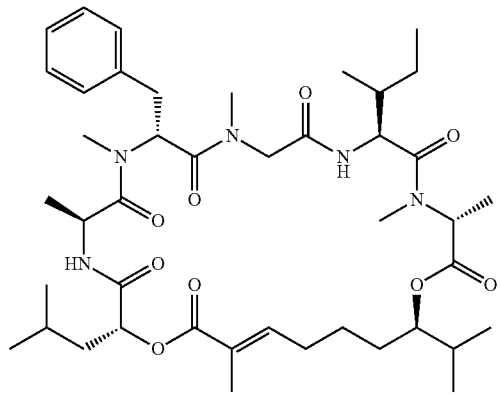 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CCC[C@H](C(C)C)OC(=O)[C@@H](C)N(C)C1=O] |
| 90 | 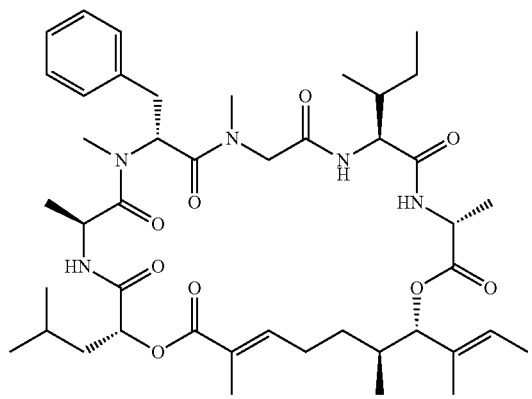 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/CC[C@@H]1C] |
| 91 | 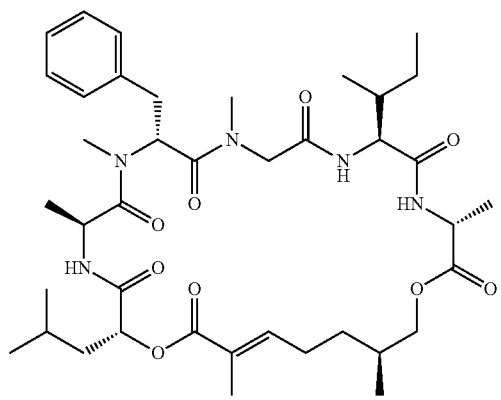 |

| Compound No. | Structure |
|---|---|
| 92 | 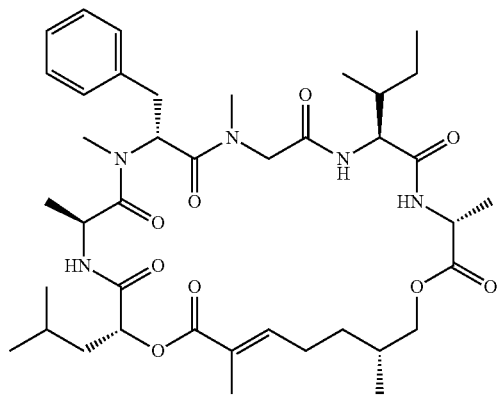 |
| 93 | 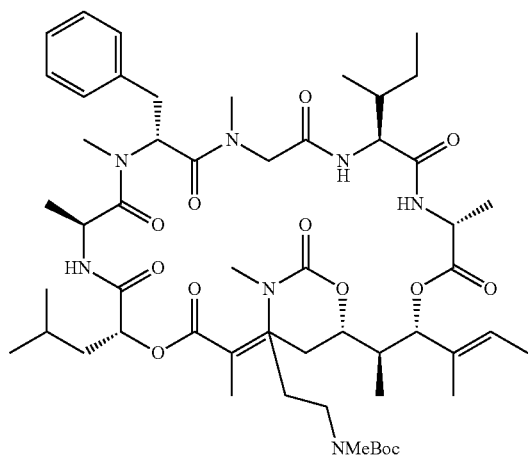 |
| 94 | 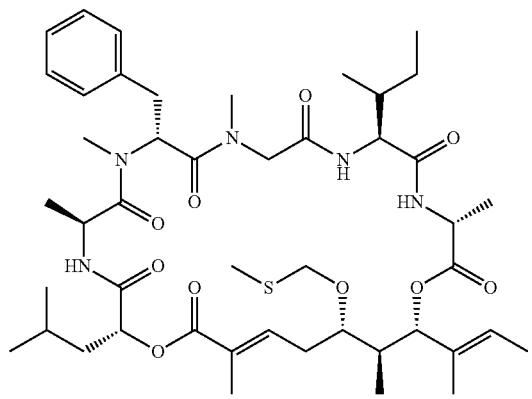 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OCSC)[C@@H]1C] |

| Compound No. | Structure |
|---|---|
| 96 | 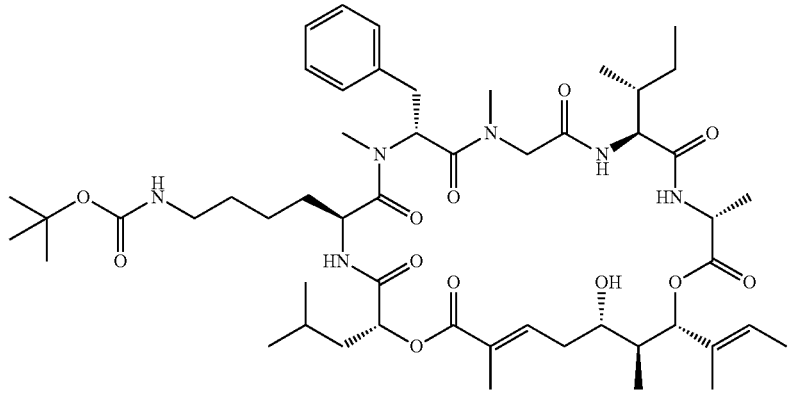 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](CCCCNC(=O)OC(C)(C)C)NC(=O)[C@@H](CC(C)C)OC(=O)/C(C)=C/C[C@H](O)[C@@H]1C] |
| 97 | 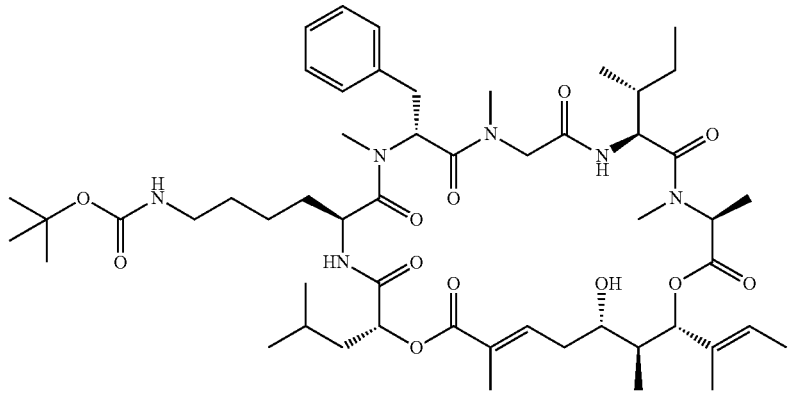 [SMILES: C/C=C(\C)[C@H]1OC(=O)[C@H](C)N(C)C(=O)[C@H]([C@H](C)CC)NC(=O)CN(C)C(=O)[C@@H](Cc2ccccc2)N(C)C(=O)[C@H](CCCCNC(=O)OC(C)(C)C)NC(=O)[C@@H](CC(C)C)OC(=O)/C(C)=C/C[C@H](O)[C@@H]1C] |
| 100 | 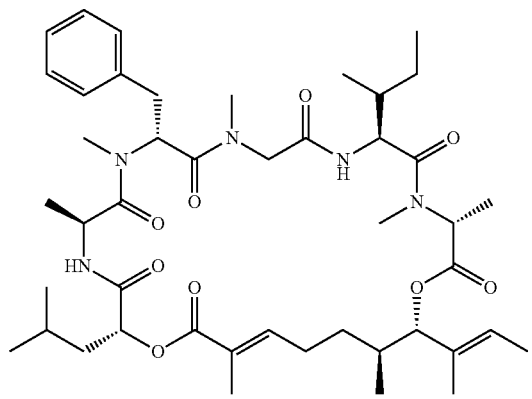 [SMILES: C/C=C(\C)[C@H]1OC(=O)[C@@H](C)N(C)C(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/CC[C@@H]1C] |

| Compound No. | Structure |
|---|---|
| 101 | 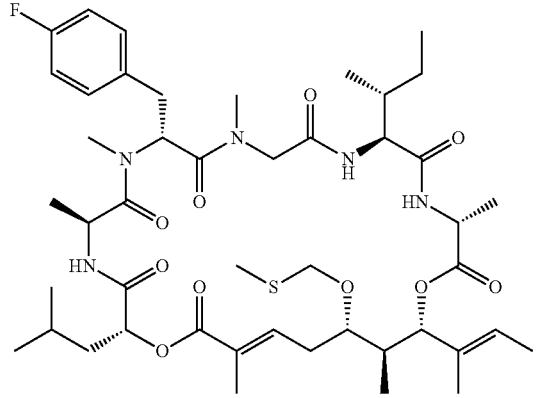 [SMILES: C/C=C(\C)[C@H]1OC(=O)[C@@H](C)NC(=O)[C@H]([C@H](C)CC)NC(=O)CN(C)C(=O)[C@@H](Cc2ccc(F)cc2)N(C)C(=O)[C@H](C)NC(=O)[C@@H](CC(C)C)OC(=O)/C(C)=C/C[C@H](OCSC)[C@@H]1C] |
| 102 | 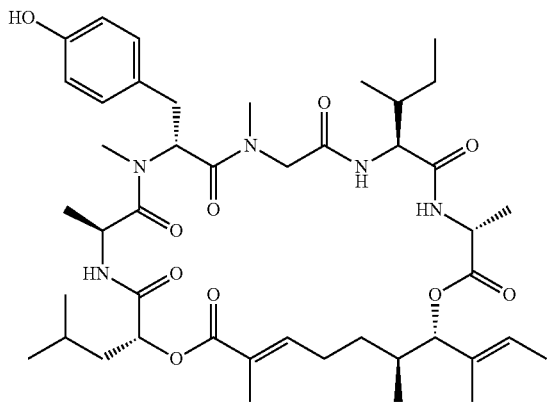 [SMILES: C/C=C(\C)[C@H]1OC(=O)[C@@H](C)NC(=O)[C@H](C(C)CC)NC(=O)CN(C)C(=O)[C@@H](Cc2ccc(O)cc2)N(C)C(=O)[C@H](C)NC(=O)[C@@H](CC(C)C)OC(=O)/C(C)=C/CC[C@@H]1C] |
| 103 | 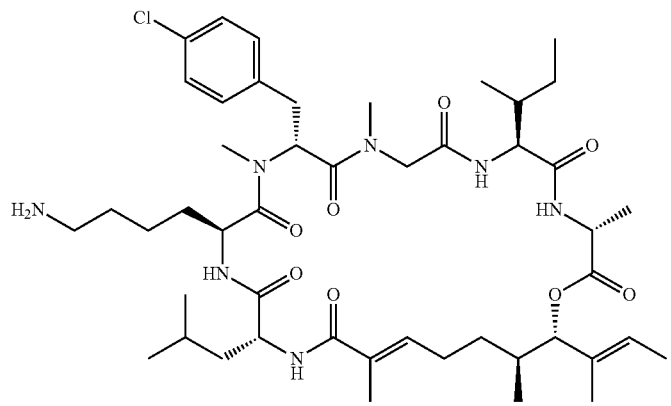 |

| Compound No. | Structure |
|---|---|
| 104 | 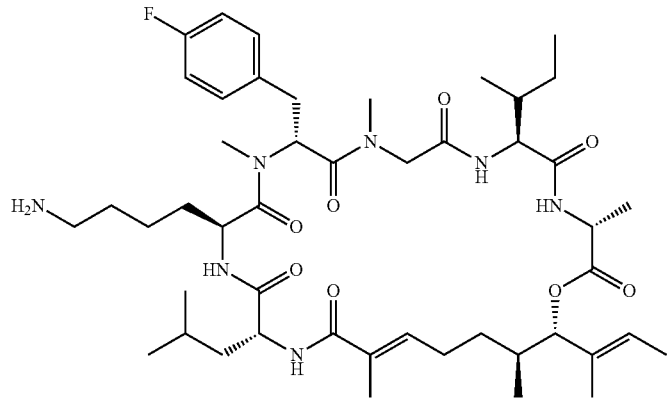 |
| 105 | 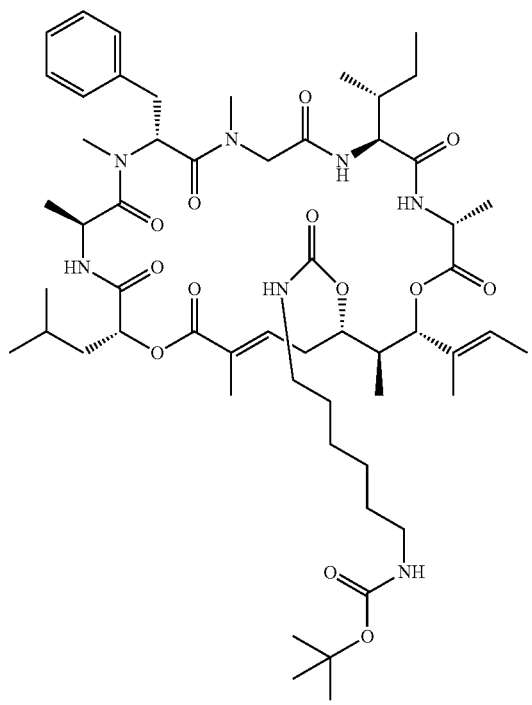 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCNC(=O)OC(C)(C)C)[C@@H]1C] |
| 106 | 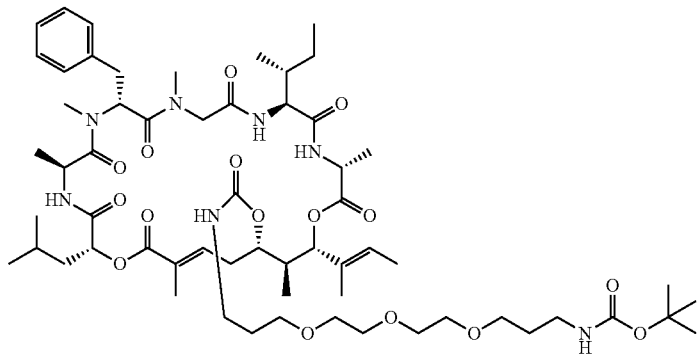 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCNC(=O)OC(C)(C)C)[C@@H]1C] |

-continued
| Compound No. | Structure |
|---|---|
| 107 | 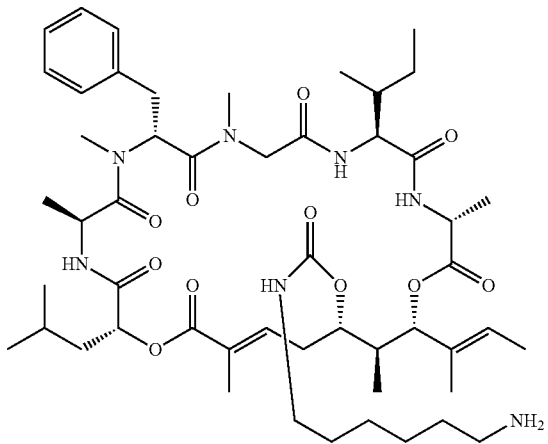 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCN)[C@@H]1C] |
| 108 | 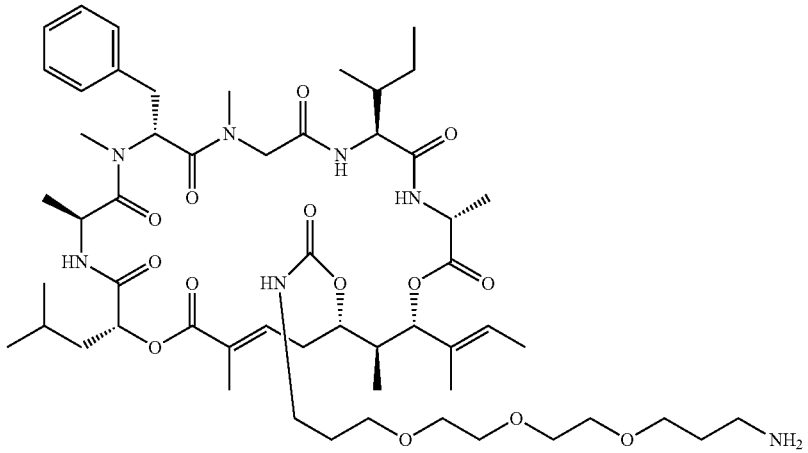 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCN)[C@@H]1C] |
| 109 | 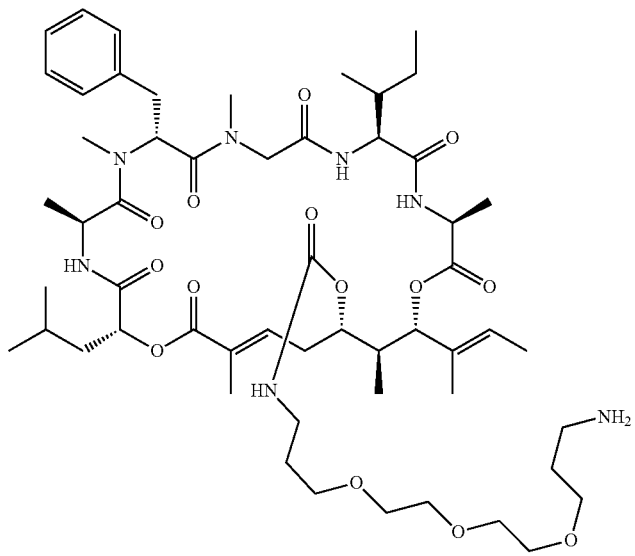 [SMILES: C/C=C(\C)[C@H]1OC(=O)[C@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCN)[C@@H]1C] |

| Compound No. | Structure |
|---|---|
| 110 | 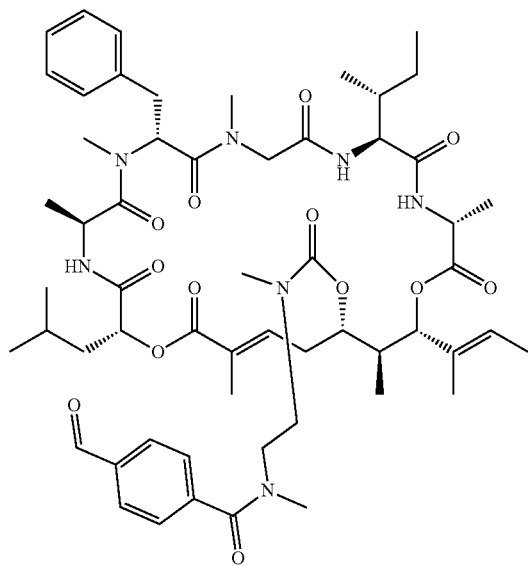 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)C(=O)c2ccc(C=O)cc2)[C@@H]1C] |
| 111 | 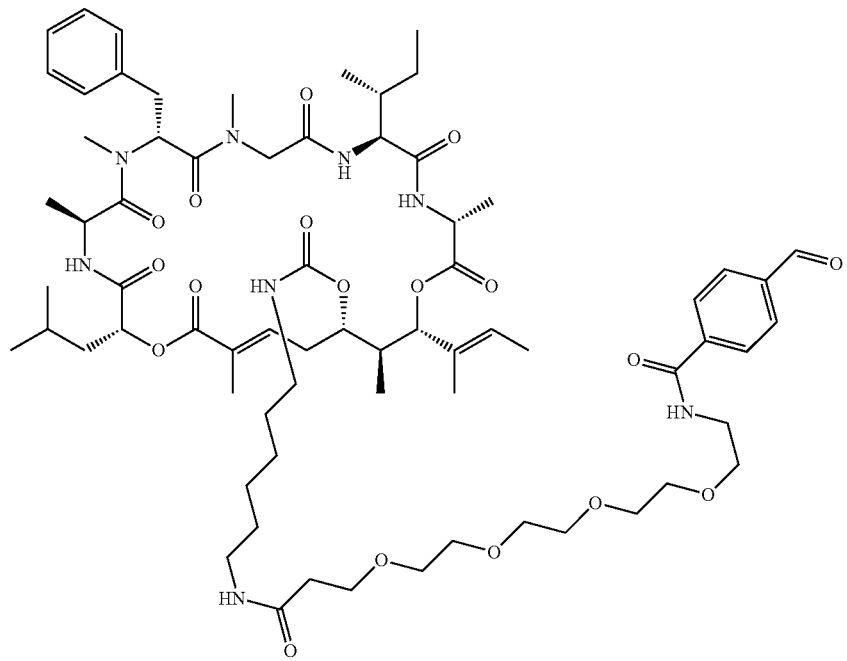 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCNC(=O)CCOCCOCCOCCOCCNC(=O)c2ccc(C=O)cc2)[C@@H]1C] |

| Compound No. | Structure |
|---|---|
| 112 | 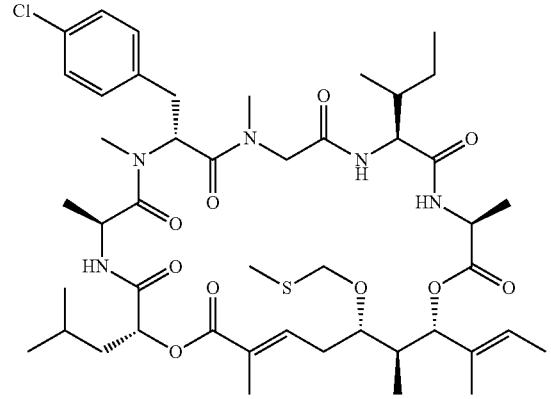 [SMILES: C/C=C(\C)[C@H]1OC(=O)[C@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OCSC)[C@@H]1C] |
| 113 | 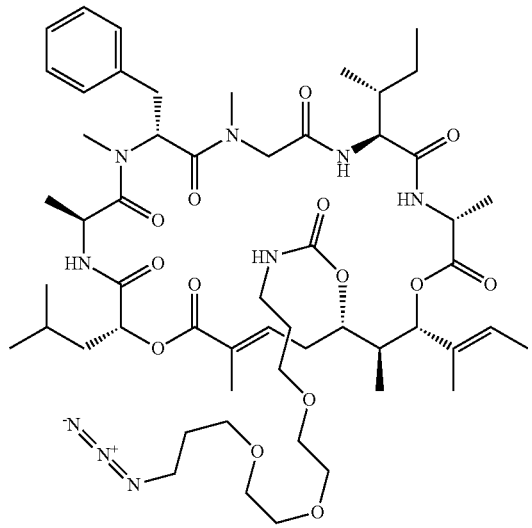 |
| 114 | 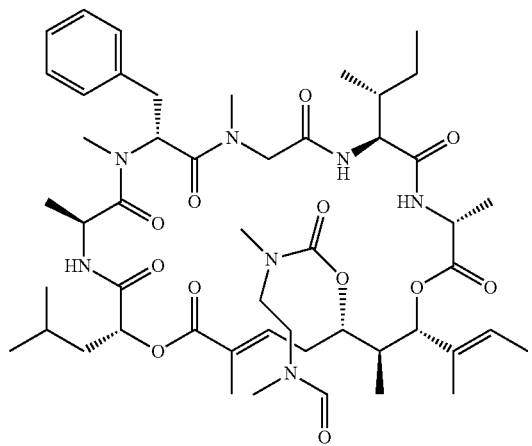 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)C=O)[C@@H]1C] |

| Compound No. | Structure |
|---|---|
| 115 | 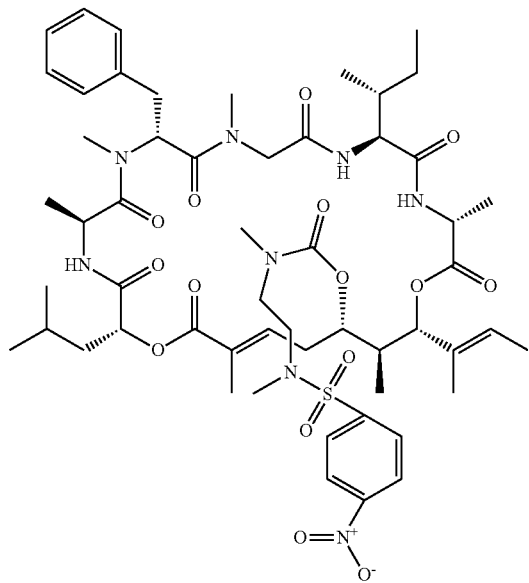 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)S(=O)(=O)c2ccc([N+](=O)[O-])cc2)[C@@H]1C] |
| 116 | 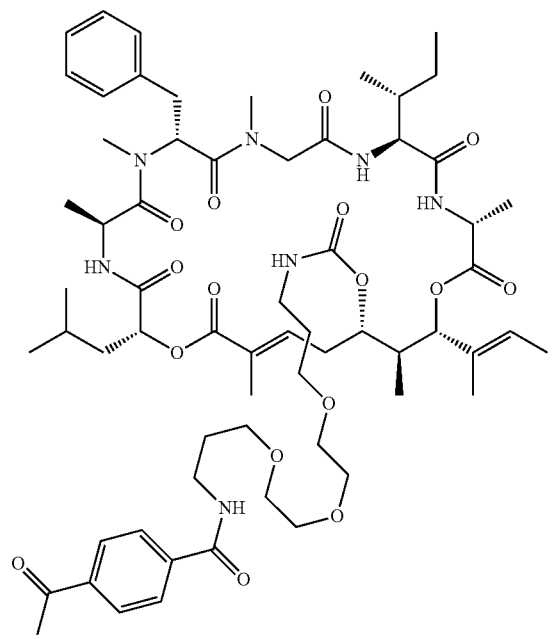 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCOCCOCCOCCCNC(=O)c2ccc(C(C)=O)cc2)[C@@H]1C] |

| Compound No. | Structure |
|---|---|
| 117 | 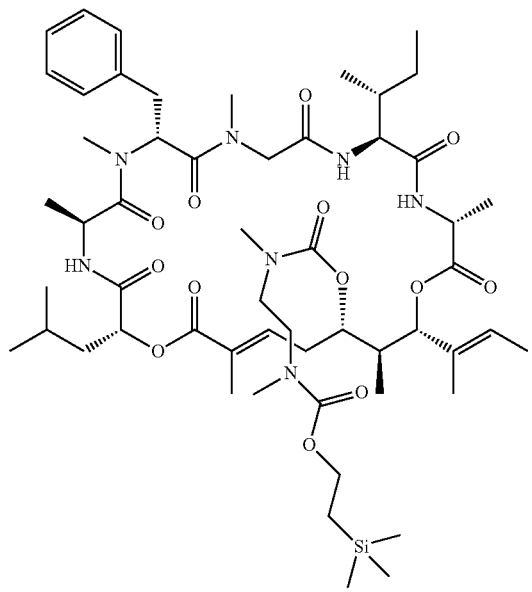 [SMILES: C/C=C(\C)[C@H]1OC(=O)[C@@H](C)NC(=O)[C@H]([C@H](C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)N(C)CCN(C)C(=O)OCC[Si](C)(C)C)[C@@H]1C] |
| 118 | 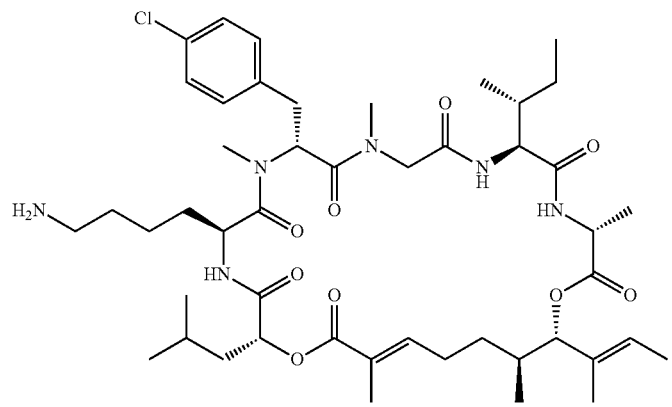 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCN)NC(=O)[C@@H](CC(C)C)OC(=O)/C(C)=C/CC[C@@H]1C] |
| 119 | 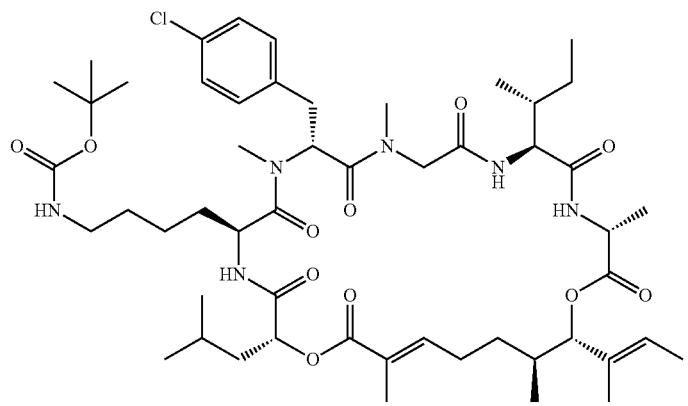 [SMILES: C/C=C(\C)[C@H]1OC(=O)[C@@H](C)NC(=O)[C@H]([C@H](C)CC)NC(=O)CN(C)C(=O)[C@@H](Cc2ccc(Cl)cc2)N(C)C(=O)[C@H](CCCCNC(=O)OC(C)(C)C)NC(=O)[C@@H](CC(C)C)OC(=O)/C(C)=C/CC[C@@H]1C] |

| Compound No. | Structure |
|---|---|
| 120 | 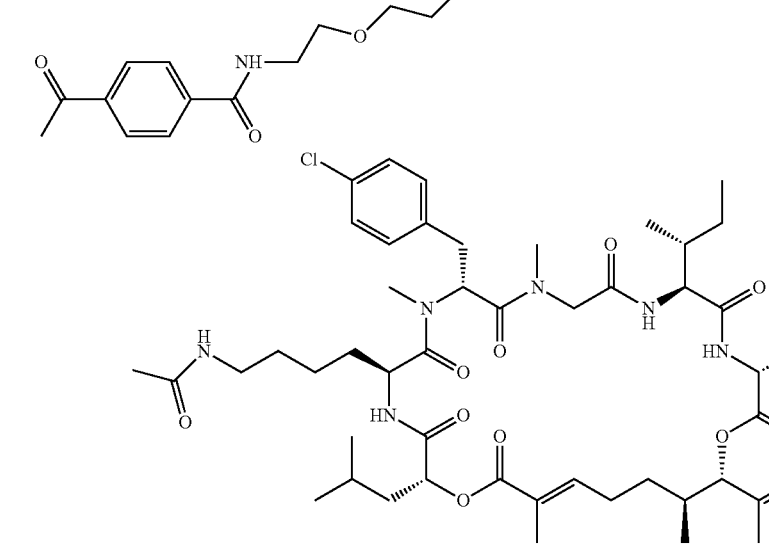 |
| 121 | 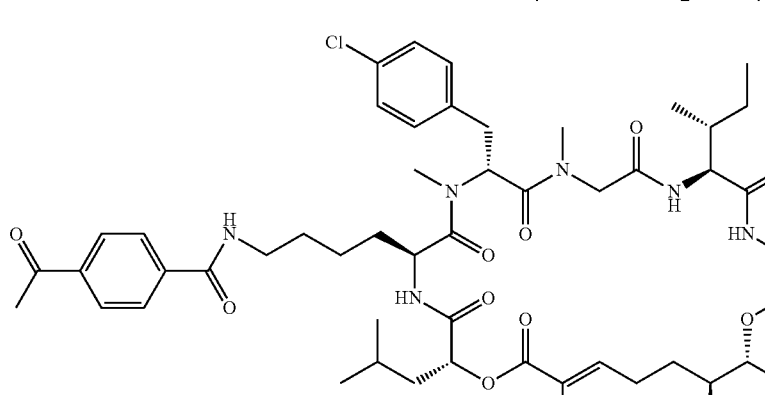 |
| 122 | 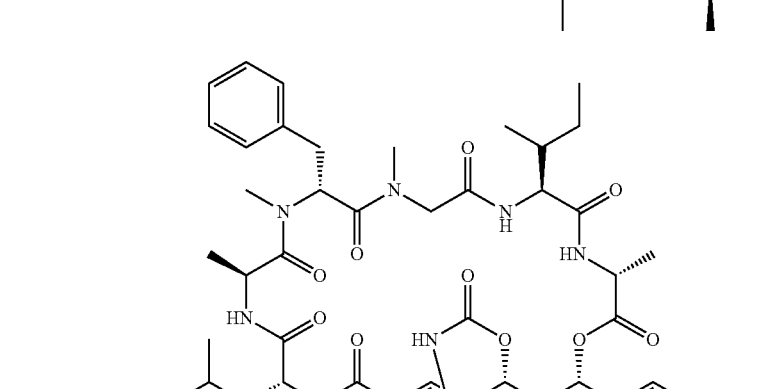 |

| Compound No. | Structure |
|---|---|
| 123 | 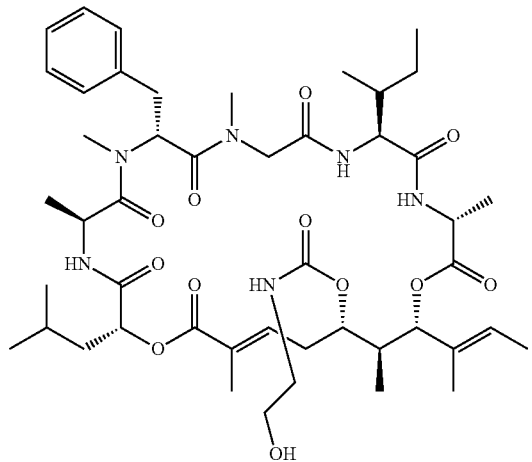 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCO)[C@@H]1C] |
| 124 | 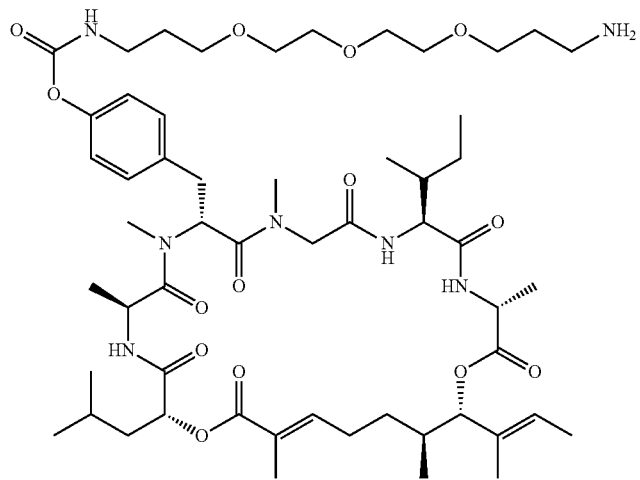 [SMILES: C/C=C(\C)[C@H]1OC(=O)[C@@H](C)NC(=O)[C@H](C(C)CC)NC(=O)CN(C)C(=O)[C@@H](Cc2ccc(OC(=O)NCCCOCCOCCOCCCN)cc2)N(C)C(=O)[C@H](C)NC(=O)[C@@H](CC(C)C)OC(=O)/C(C)=C/CC[C@@H]1C] |
| 125 | 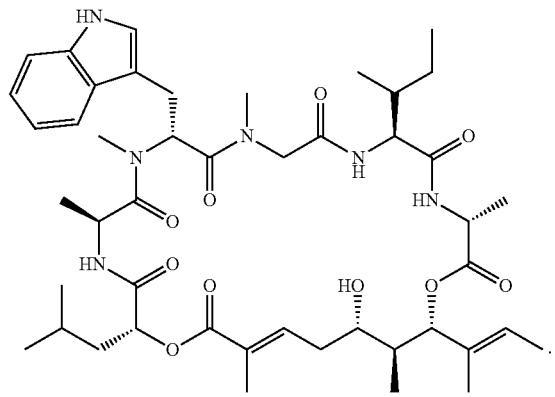 [SMILES: C/C=C(\C)[C@H]1OC(=O)[C@@H](C)NC(=O)[C@H](C(C)CC)NC(=O)CN(C)C(=O)[C@@H](Cc2c[nH]c3ccccc23)N(C)C(=O)[C@H](C)NC(=O)[C@@H](CC(C)C)OC(=O)/C(C)=C/C[C@H](O)[C@@H]1C] |

29. The conjugate of claim 1, wherein the ligand is a polypeptide.

30. A conjugate comprising a compound, or a salt thereof, bonded to a ligand, wherein the ligand is a nucleic acid, and wherein the compound is a compound of Formula (I):

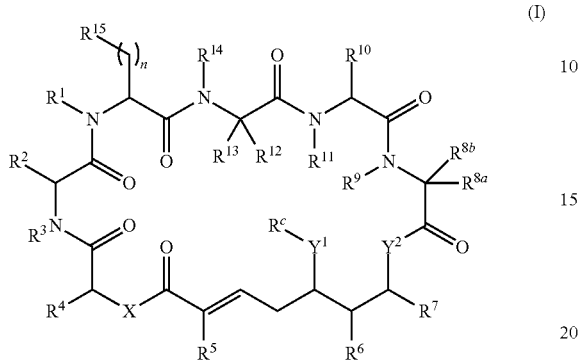

(I)

wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, or substituted or unsubstituted heterocyclyl;

n is 0, 1, or 2;

X is —N($R^d$)— or —O—;

$Y^1$ is —N($R^d$)—, —O—, or —S—;

$R^c$ is H, substituted or unsubstituted alkyl, substituted or unsubstituted alkenyl, substituted or unsubstituted alkynyl, substituted or unsubstituted cycloalkyl, or substituted or unsubstituted cycloalkenyl, or —C(O)$R^e$;

or, alternatively, the (—$Y^1$—$R^c$) group is H or halo;

$Y^2$ is —N($R^d$)—, —O—, or —S—;

each $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl; and $R^e$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heterocyclyl, substituted or unsubstituted heteroaryl, —O$R^d$, —N$R^d R^d$, or —S$R^d$.

* * * * *